(12) United States Patent
Aissaoui et al.

(10) Patent No.: US 11,306,078 B2
(45) Date of Patent: Apr. 19, 2022

(54) PIPERIDINE CXCR7 RECEPTOR MODULATORS

(71) Applicant: IDORSIA PHARMACEUTICALS LTD., Allschwil (CH)

(72) Inventors: Hamed Aissaoui, Allschwil (CH); Philippe Guerry, Allschwil (CH); Francois Lehembre, Allschwil (CH); Julien Pothier, Allschwil (CH); Laetitia Pouzol, Allschwil (CH); Sylvia Richard-Bildstein, Allschwil (CH); Shuguang Yuan, Allschwil (CH)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 16/928,787

(22) Filed: Jul. 14, 2020

(65) Prior Publication Data

US 2020/0385373 A1    Dec. 10, 2020

Related U.S. Application Data

(62) Division of application No. 16/320,906, filed as application No. PCT/EP2017/068990 on Jul. 27, 2017, now Pat. No. 10,752,620.

(30) Foreign Application Priority Data

Jul. 28, 2016    (WO) ................ PCT/EP2016/068052

(51) Int. Cl.
| | | |
|---|---|---|
| *C07D 413/14* | (2006.01) | |
| *C07D 413/12* | (2006.01) | |
| *C07D 401/12* | (2006.01) | |
| *C07D 401/14* | (2006.01) | |
| *C07D 417/14* | (2006.01) | |
| *A61P 35/00* | (2006.01) | |

(52) U.S. Cl.
CPC ............ *C07D 413/14* (2013.01); *A61P 35/00* (2018.01); *C07D 401/12* (2013.01); *C07D 401/14* (2013.01); *C07D 413/12* (2013.01); *C07D 417/14* (2013.01); *C07B 2200/07* (2013.01); *C07B 2200/09* (2013.01)

(58) Field of Classification Search
CPC ... C07D 413/14; C07D 401/12; C07D 401/14
USPC .................................................. 514/210.18
See application file for complete search history.

(56) References Cited

U.S. PATENT DOCUMENTS

| | | | |
|---|---|---|---|
| 7,560,564 B2 * | 7/2009 | Annis .................... | A01N 43/10 544/333 |
| 9,428,456 B2 | 8/2016 | Fretz et al. | |
| 9,920,010 B2 | 3/2018 | Fretz et al. | |
| 10,202,368 B2 | 2/2019 | Guerry et al. | |
| 2013/0345199 A1 | 12/2013 | Fretz et al. | |
| 2015/0336893 A1 | 11/2015 | Fretz et al. | |
| 2016/0107997 A1 | 4/2016 | Fretz et al. | |
| 2017/0327493 A1 | 11/2017 | Guerry et al. | |

FOREIGN PATENT DOCUMENTS

| | | |
|---|---|---|
| WO | 2004050024 A2 | 6/2004 |
| WO | 2005026149 A1 | 3/2005 |
| WO | 2005032490 A2 | 4/2005 |
| WO | 2006087543 A1 | 8/2006 |
| WO | 2012168315 A1 | 12/2012 |
| WO | 2013084241 A1 | 6/2013 |
| WO | 2013190508 A2 | 12/2013 |
| WO | 2014191929 A1 | 12/2014 |
| WO | 2015033299 A1 | 3/2015 |
| WO | 2015034820 A1 | 3/2015 |
| WO | 2015044900 A1 | 4/2015 |
| WO | 2016040515 A1 | 3/2016 |

(Continued)

OTHER PUBLICATIONS

Hung-Chih Chang et al, Critical involvement of atypical chemokine receptor CXCR7 in allergic airway inflammation. (Year: 2017).*

(Continued)

*Primary Examiner* — Timothy R Rozof

(74) *Attorney, Agent, or Firm* — Jeff B. Vockrodt; Culhane Meadow, PLLC

(57) ABSTRACT

The present invention relates to piperidine derivatives of formula (I)

Formula (I)

wherein $Ar^1$, $Ar^2$, $R^{Ar1}$, $R^1$, $R^2$, and $R^3$ are as described in the description, their preparation, to pharmaceutically acceptable salts thereof, and to their use as pharmaceuticals, to pharmaceutical compositions containing one or more compounds of formula (I), and especially to their use as CXCR7 receptor modulators.

29 Claims, No Drawings

(56) References Cited

FOREIGN PATENT DOCUMENTS

| WO | 2016087370 A1 | 6/2016 |
|---|---|---|
| WO | 2019145460 A1 | 8/2019 |

OTHER PUBLICATIONS

Shuhong Guan et al CXCR& attenuates the TGF-Beta-induced endothelial-to-mesenchymal transition and pulmonary fibrosis. (Year: 2017).*

Liu et al., "Targeting Chemokine Receptor CXCR7 Inhibits Glioma Cell Proliferation and Mobility," Anticancer Research, vol. 35, 2015, pp. 53-64.

Liu et al., "The Involvement of CXCR7 in Modulating the Progression of Papillary Thyroid Carcinoma," Journal of Surgical Research, vol. 191, 2014, pp. 379-388.

Liu et al., "The Role of SDF-1-CXCR4/CXCR7 Axis in the Therapeutic Effects of Hypoxia-Preconditioned Mesenchymal Stem Cells for Renal Ischemia/Reperfusion Injury," PLOS ONE, vol. 7, No. 4, Apr. 2012, e34608, pp. 1-13.

Lu et al., "CXCR4, CXCR7, and CXCL 12 are Associated with Trophoblastic Cells Apoptosis and Linked to Pathophysiology of Severe Preeclampsia," Experimental and Molecular Pathology, vol. 100, 2016, pp. 184-191.

Lukacs et al., "AMD3100, a CXCR4 Antagonist, Attenuates Allergic Lung Inflammation and Airway Hyperreactivity," American Journal of Pathology, vol. 160, No. 4, Apr. 2002, pp. 1353-1360.

Ma et al., "Atorvastatin Inhibits CXCR7 Induction to Reduce Macrophage Migration," Biochemical Pharmacology, vol. 69, 2014, pp. 99-108.

Maussang et al., "Llama-derived Single Variable Domains (Nanobodies) Directed against Chemokine Receptor CXCR7 Reduce Head and Neck Cancer Cell Growth in Vivo," The Journal of Biological Chemistry, vol. 288, No. 41, Oct. 2013, pp. 29562-29572.

McCandless et al., "Pathological Expression of CXCL 12 at the Blood-Brain Barrier Correlates with Severity of Multiple Sclerosis," The American Journal of Pathology, vol. 172, No. 3, Mar. 2008, pp. 799-808.

McConnell et al., "Significant impact of the CXCR4/CXCR7/ CXCL 12 axis in primary melanoma," British Journal of Dermatology, 2016, 27 pages.

Miao et al., "CXCR7 (RDC1) Promotes Breast and Lung Tumor Grown in vivo and is Expressed on Tumor-Associated vasculature," PNAS, vol. 104, No. 40, Oct. 2007, pp. 15735-15740.

Mikami et al., "Blockade of CXCL 12/CXCR4 Axis Ameliorates Murine Experimental Colitis," The Journal of Pharmacology and Experimental Therapeutics, vol. 327, 2008, pp. 383-392.

Monnier et al., "CXCR7 is Up-regulated in Human and Murine Hepatocellular Carcinoma and is Specifically Expressed by Endothelial Cells," European Journal of Cancer, vol. 48, 2012, pp. 138-148.

Nanki et al., "Stromal Cell-Derived Factor-1-CXC Chemokine Receptor 4 Interactions Play a Central Role in CD4 + T Cell Accumulation in Rheumatoid Arthritis Synovium," The Journal of Immunology, 2000, vol. 165, No. 11, pp. 6590-6598.

Naumann et al., "CXCR7 Functions as a Scavenger for CXCL 12 and CXCL 11," PLOS ONE, vol. 5, No. 2, 2010, e9175, pp. 1-11.

Patadia et al., "Evaluation of the Presence of B-cell Attractant Chemokines in Chronic Rhinosinusitis," American Journal of Rhinology & Allergy, vol. 24, No. 1, 2010, pp. 11-16.

Petty et al., "Pulmonary Stromal-Derived Factor-1 Expression and Effect on Neutrophil Recruitment During Acute Lung Injury," The Journal of Immunology, vol. 178, No. 12, pp. 8148-8157.

Phillips et al., "Circulating Fibrocytes Traffic to the Lungs in Response to CXCL 12 and Mediate Fibrosis," The Journal of Clinical Investigation, vol. 114, No. 3, Aug. 2004, pp. 438-446.

Porter et al., "Polarized Localization of Epithelial CXCL 11 in Chronic Obstructive Pulmonary Disease and Mechanisms of T Cell Egression 1," J. Immunol. vol. 180, No. 3, 2008, pp. 1866-1877.

Rafii et al., "Platelet-derived SDF1 Primes Pulmonary Capillary Vascular Niche to Drive Lung Alveolar Regeneration," Nat Cell. Biol., vol. 17, No. 2, Feb. 2015, pp. 123-136.

Raggo et al., "Novel Cellular Genes Essential for Transformation of Endothelial Cells by Kaposi's Sarcoma-Associated Herpesvirus," Cancer Res., vol. 65, No. 12, Jun. 2005, pp. 5084-5095.

Rankin et al., "Chemokines and Adult Bone Marrow Stem Cells," Immunology Letters, vol. 145, 2012, pp. 47-54.

Remington, The Science and Practice of Pharmacy, 21st Edition, 2005, pp. 1-5.

Rupertus et al., "Interaction of the Chemokines I-TAC (CXCL 11) and SDF-1 (CXCL 12) in the Regulation of Tumor Angiogenesis of Colorectal Cancer," Clin. Exp. Metastasis, vol. 31, 2014, pp. 447-459.

S.Y. Sit et al., "Oxime Carbamate-Discovery of a Series of Novel FMH Inhibitors," Bioorganic & Medicinal Chemistry Letters, vol. 20, 2010, pp. 1272-1277.

Salmaggi et al., "CXCL12, CXCR4 and CXCR7 Expression in Brain Metastases," Cancer Biology & Therapy, vol. 8, No. 17, 2009, pp. 1-7.

Sanchez-Martin et al., "CXCR7 Impacton CXCL12 Biology and Disease," Trends in Molecular Medicine, vol. 19, No. 1, Jan. 2013, pp. 12-22.

Sartina et al., "Antagonism of CXCR7 Attenuates Chronic Hypoxia-Induced Pulmonary Hypertension," Pediatric Research, vol. 71, No. 6, 2012, pp. 682-688.

Schinnerl et al., "Asymmetric Synthesis of a New Helix-Forming beta-Amino Acid: trans-4-Aminopiperidine-3-carboxylic Acid," Eur. J. Chem., 2003, pp. 721-726.

Shakir et al., "The Chemokine Receptors CXCR4/CXCR7 and Their Primary Heterodimeric Ligands CXCL 12 and CXCL 12/High Mobility Group Box 1 in Pancreatic Cancer Growth and Development," Pancreas, vol. 44, No. 4, May 2015, pp. 528-534.

Stahl et al., Handbook of Pharmaceutical Salts, 2008, pp. 329-350.

Sun et al., "CXCL 12/CXCR4/CXCR7 Chemokine Axis and Cancer Progression," Cancer Metastasis Rev., vol. 29, No. 4, 2010, pp. 709-722.

Teicher et al., "CXCL12 (SDF-1 )/CXCR4 Pathway in Cancer," Clin. Cancer Res., vol. 16, No. 11, 2010, pp. 2927-2931.

Thomas et al., "SDF-1/CXCR4/CXCR7 is Pivotal for Vascular Smooth Muscle Cell Proliferation and Chronic Allograft Vasculopathy," Transplant International, vol. 28, No. 12, 2015, pp. 1426-1435.

Villalvilla et al., "SDF-1 Signaling: A Promising Target in Rheumatic Diseases," Expert. Opin. Ther. Targets, vol. 18, No. 9, 2014, pp. 1077-1087.

Walters et al., "Inhibition of CXCR7 Extends Survival Following Irradiation of Brain Tumors in Mice and Rats," British Journal of Cancer, vol. 110, 2014, pp. 1179-1188.

Wang et al., "CXCR4/CXCL12 Hyperexpression Plays a Pivotal Role in the Pathogenesis of Lupus," J. Immunol., vol. 182, No. 7, 2009, pp. 4448-4458.

Wang et al., "Role of CXC Chemokine Receptor Type 7 in Carcinogenesis and Lymph Node Metastasis of Colon Cancer," Molecular and Clinical Oncology, vol. 3, 2015, pp. 1229-1232.

Wang et al., "The Role of CXCR7/RDC1 as a Chemokine Receptor for CXCL 12/SDF-1 in Prostate Cancer," The Journal of Biological Chemistry, vol. 283, No. 7, Feb. 2008, pp. 4283-4294.

Watanabe et al., "Pathogenic Role of CXCR7 in Rheumatoid Arthritis," Arthritis & Rheumatism, vol. 62, No. 1, Nov. 2010, pp. 3211-3220.

Werner et al., "Involvement of CXCR4/CXCR7/CXCL 12 Interactions in Inflammatory Bowel Disease," Theranostics, vol. 3, No. 1, 2013, pp. 40-46.

Werner et al., "Reciprocal Regulation of CXCR4 and CXCR7 in Intestinal Mucosal Homeostasis and Inflammatory Bowel Disease," Journal of Leukocyte Biology, vol. 90, Sep. 2011, pp. 583-590.

Williams et al., "Targeting CXCR7/ACKR3 as a Therapeutic Strategy to Promote Remyelination in the Adult Central Nervous System," J. Exp. Med., vol. 211, No. 5, 2014, pp. 791-799.

Wouters et al., Pharmaceutical Salts and Co-crystals, 2012, pp. vii-xiv.

Xian-Ming et al., "CXCR4 Antagonist AMD3100 Modulates Claudin Expression and Intestinal Barrier Function in Experimental Colitis," PLOS ONE, vol. 6, No. 11, Nov. 2011, e27282, pp. 1-11.

(56) References Cited

OTHER PUBLICATIONS

Xue et al., "Down-regulation of CXCR7 Inhibits the Growth and Lung Metastasis of Human Hepatocellular Carcinoma Cells with Highly Metastatic Potential," Experimental and Therapeutic Medicine, vol. 3, No. 1, 2012, pp. 117-123.
Zeng et al., "Efficient Synthesis and Utilization of Phenyl-substituted Heteroaromatic Carboxylic Acids as Aryl Diketo Acid Isosteres in the Design of Novel HIV-1 Integrase Inhibitors," Bioorganic & Medicinal Chemistry Letters, vol. 18, 2008, pp. 4521-4524.
Zgraggen et al., "An Important Role of the SDF-1/CXCR4 Axis in Chronic Skin Inflammation," PLOS ONE, vol. 9, No. 4, e93665, Apr. 2014, pp. 1-12.
Zhang et al., "Knockdown of CXCR7 Inhibits Proliferation and Invasion of Osteosarcoma Cells Through Inhibition of he PI3K/Akt and beta-arrestin pathways," Oncology Reports, vol. 32, 2014, pp. 965-972.
Zhang et al., "The Chemokine Receptor CXCR7 is a Critical Regulator for the Tumoigenesis and Development of Papillary Thyroid Carcinoma by Inducing Angiogenesis in Vitro and in Vivo," Tumor Biol., vol. 37, 2016, pp. 2415-2423.
Antonelli et al., "Increase of Interferon-v Inducible CXCL9 and CXCL 11 Serum Levels in Patients with Active Graves' Disease and Modulation by Methimazole Therapy," Thyroid, vol. 23, No. 11, 2013, pp. 1461-1470.
Azab et al., "CXCR7-dependent angiogenic mononuclear cell trafficking regulates tumor progression in multiple myeloma," Blood, Sep. 2014, vol. 124, No. 12, pp. 1905-1914.
Banisadr et al., "Pattern of CXCR7 Gene Expression in Mouse Brain Under Normal and Inflammatory Conditions," J. Neuroimmune Pharmacol., vol. 11, No. 1, Mar. 2016, pp. 26-35.
Bao et al., "CXCR7 suppression modulates microglial chemotaxis to ameliorate experimentally-induced autoimmune encephalomyelitis," Biochemical and Biophysical Research Communications, vol. 469, 2016, pp. 1-7.
Basarab et al., "Optimization of Pyrrolamide Topoisomerase II Inhibitors Toward Identification of an Antibacterial Clinical Candidate (AZD5099)," Journal of Medicinal Chemistry, vol. 57, 2014, pp. 6060-6082.
Berahovich et al., "Endothelial expression of CXCR7 and the regulation of systemic CXCL 12 levels," Immunology, vol. 141, 2013, pp. 111-122.
Biajoux et al., "Expression of CXCL 12 receptors in B cells from Mexican Mestizos patients with systemic lupus erythematosus," Journal of Transnational Medicine, vol. 10, No. 251, 2012, pp. 1-16.
Blades et al., "Stromal Cell-Derived Factor 1 (CXCL12) Induces Monocyte Migration Into Human Synovium Transplanted Onto SCID Mice," Arthritis & Rheumatism, vol. 46, No. 3, Mar. 2002, pp. 824-836.
Brunn et al., "Differential effects of CXCR4 CXCL 12- and CXCR7 CXCL 12-mediated immune reactions on murine PO106-125-induced experimental autoimmune neuritis," Neuropathology and Applied Neurobiology, 2013, vol. 39, pp. 772-787.
Burns et al., "A Novel Chemokine Receptor for SDF-1 and I-TAC involved in cell survival, cell adhesion, and tumor development," The Journal of Experimental Medicine, vol. 203, No. 9, Sep. 2006, pp. 2201-2213.
Calatozzolo et al., "Expression of the New CXCL12 receptor, CXCR7, in gliomas," Cancer Biology & Therapy, vol. 11, No. 2, Jan. 2011, pp. 1-12.
Cao et al., "Targeting of the pulmonary capillary vascular niche promotes lung alveolar repair and ameliorates fibrosis," Nat. Med., vol. 22, No. 2, Feb. 2016, pp. 154-162.
Cecchi et al., "1,4-Diazabicyclo[2-2.2]octane (DABCO) as an Efficient Reagent for the Synthesis of Isoxazole Derivatives from Primary Nitro Compounds and Dipolarophiles: The Role of the Base," Eur. J. Chem., 2006, pp. 4852-4860.
Chen et al., "Crosstalk between SDF-1/CXCR4 and SDF-1/CXCR7 in cardiac stem cell migration," www.nature.com/scientificreports/, Scientific Reports, 2015, pp. 1-9.

Chen et al., "CXCL 12-CXCR4/CXCR7 axis contributes to cell motilities of oral squamous cell carcinoma," Tumor Biol., vol. 37, 2016, pp. 567-575.
Chen et al., "Expression of Chemokine Receptor CXCR3 by lymphocytes and plasmacytoid dendritic cells in human psoriatic lesions," Arch Dermatol Res., vol. 302, 2010, pp. 113-123.
Cruz-Orengo et al., "CXCR7 influences leukocyte entry into CNS parenchyma by controlling abluminal CXCL 12 abundance during autoimmunity," The Journal of Experimental Medicine, 2011, pp. 1-18.
Ding et al., "Divergent angriocrine signals from vascular niche balance liver regeneration and fibrosis," Nature, vol. 605,2014, pp. 97-102.
Domanska et al., "A Review on CXCR4/CXCL12 axis in oncology: No Place to Hide," European Journal of Cancer, vol. 49, 2013, pp. 219-230.
Duda et al., "CXCL 12 (SDF1alpha)-CXCR4/CXCR7 Pathway Inhibition: An Emerging Sensitizer for Anti-Cancer Therapies?" Clin. Cancer Res. Apr. 2011, vol. 17, No. 8. pp. 2074-2080.
Ebsworth et al., "ET-023. The CXCR7 Inhibitor CCX650 Significantly Prolongs Survival in the C6 Rat Model of Glioblastoma," Neuro-Oncology, 2013, pp. iii37-iii61.
Ebsworth et al., "The Effect of the CXCR7 Inhibitor CCX662 on Survival in the ENU Rat Model of Glioblastoma," Journal of Clinical Oncology, 2012, vol. 30, No. 15, 1 page.
Ellanova Laboratories Product List, SciFinder, Chemical Name: 5-(2,4-Difluorophenyl)-1,3,4-Thiadiazole-2-Carboxylic Acid, American Chemical Society, 2018, 1 page.
Feig et al., "Targeting CXCL 12 from FAP-expressing Carcinoma-associated Fibroblasts Synergizes with anti-PD-L1 Immunotherapy in Pancreatic Cancer," PNAS, Dec. 2013, vol. 110, No. 50, pp. 20212-20217.
Gasparik et al., "Prodrugs of a CXC Chemokine-12 (CXCL 12) Neutraligand Prevent Inflammatory Reactions in an Asthma Model in Vivo," ACS Medicinal Chemistry Letters, vol. 3, 2012, pp. 10-14.
Goguet-Surmenian et al., "CXCR7-mediated Progression of Osteosarcoma in the Lungs," British Journal of Cancer, vol. 109, 2013, pp. 1579-1585.
Göttle et al., "Activation of CXCR7 Receptor Promotes Oligodendroglial Cell Maturation," Annals of Neurology, vol. 68, No. 6, Dec. 2010, pp. 915-924.
Greene et al., Protective Groups in Organic Synthesis, Third Edition, Wiley-Interscience, 1999, pp. 1-3.
Grymula et al., "Overlapping and Distinct Role of CXCR7-SDF-1/ITAC and CXCR4-SDF-1 Axes in Regulating Metastatic Behavior of Human Rhabdomyosarcomas," Int. J. Cancer., vol. 127, No. 11, Dec. 2010, pp. 2554-2568.
Guillemot et al., "CXCR7 Receptors Facilitate the Progression of Colon Carcinoma within Lung not within Liver," British Journal of Cancer, vol. 107, 2012, pp. 1944-1949.
Hartmann et al., "A Crosstalk between Intracellular CXCR7 and CXCR4 involved in rapid CXCL 12-triggered integrin Activation but not in Chemokine-triggered Motility of Human T Lymphocytes and CD34+ cells," Journal of Leukocyte Biology, vol. 84, Oct. 2008, pp. 1130-1140.
Hattermann et al., "CXCL 12 Mediates Apoptosis Resistance in Rat C6 Glioma Cells," Oncology Reports, vol. 27, 2012, pp. 1348-1352.
Hattermann et al., "The Chemokine Receptor CXCR7 Is Highly Expressed in Human Glioma Cells and Mediates Antiapoptotic Effects," Cancer Res., vol. 70, No. 8, Apr. 2010, pp. 3299-3308.
Heinrich et al., "Chemokine CXCL 12 Activates Dual CXCR4 and CXCR7-mediated Signaling Pathways in Pancreatic Cancer Cells," Journal of Translation Medicine, vol. 10, No. 68, 2012, pp. 1-9.
Huguet et al., "Hydroxamic Acids as Potent Inhibitors of Fe and Mn E. coli Methionine Aminopeptidase: Biological Activities and X-ray Structures of Oxazole Hydroxamate-EcMetAp-Mn Complexes," ChemMedChem, vol. 7, 2012, pp. 1020-1030.
Ikeda et al., "Modulation of Circadian Glucocorticoid Oscillation via Adrenal Opiod-CXCR7 Signaling Alters Emotional Behavior," Cell, vol. 155, No. 6, 2013, pp. 1323-1336.
International Search Report as cited in the International Application No. PCT/EP2017/008990 dated Sep. 21, 2017.

(56) References Cited

OTHER PUBLICATIONS

Iwakiri et al., "Higher Expression of Chemokine Receptor CXCR7 Is Linked to Early and Metastatic Recurrence in Pathological Stage I Nonsmall Cell Lunch Cancer," Cancer, vol. 115, No. 11, 2009, pp. 2580-2593.

Jeno et al., "The Production of CXCR3-Agonistic Chemokines by Synovial Fibroblasts from Patients with Rheumatoid Arthritis," Rheumatol Int., vol. 25, 2005, pp. 361-367.

Jin et al., "CXCR7 is Inducible by HTLV-1 Tax and Promotes Growth and Survival of HTLV-1-infected T Cells," Int. J. Cancer, vol. 125, 2009, pp. 2229-2235.

Koelink et al., "Targeting Chemokine Receptors in Chronic Inflammatory Diseases: An Extensive Review," Pharmacology & Therapeutics, vol. 133, 2012, pp. 1-18.

Kryczek et al., "CXCL 12 and Vascular Endothelial Growth Factor Synergistically Induce Neoangiogenesis in Human Ovarian Cancers," Cancer Res., vol. 65, No. 2, Jan. 2005, pp. 465-472.

Kumar et al., "CXCR7 Mediated Gi alpha Independent Activation of ERK and Aki Promotes Cell Survival and Chemotaxis in T Cells," Cellular Immunology, vol. 272, 2012, pp. 230-241.

Lewellis et al., "Precise SDF1-mediated Cell Guidance is Achieved though Ligand Clearance and MicroRNA-mediated Decay," J. Cell Biol., vol. 200, No. 3, 2013, pp. 337-355.

Liberman et al., "Involvement of the CXCR7/CXCR4/CXCL 12 Axis in the Malignant Progression of Human Neuroblastoma," PLOS One, vol. 7, No. 8, Aug. 2012, pp. 1-14.

Linder et al., "Telomestatin: Formal Total Synthesis and Cation-Mediated Interaction of Its seco-Derivatives with G-Quadruplexes," Journal of the American Chemical Society,J. Am. Chem. Soc. vol. 133, 2011, pp. 1044-1051.

Liu et al., "Blockade of SDF-1 After Irradiation Inhibits Tumor Recurrences of Autochthonous Brain Tumors in Rats," Neuro-Oncology, vol. 16, No. 1, 2014, pp. 21-28.

Liu et al., "Decreased Expression of miR-430 Promotes the Development of Bladder Cancer via the Upregulation of CXCR7," Molecular Medicine Reports, vol. 8, 2013, pp. 140-146.

Liu et al., "Expression of Stromal Cell-Derived Factor 1 and CXCR7 Ligand Receptor System in Pancreatic Adenocarcinoma," World Journal of Surgical Oncology, vol. 12, No. 348, 2014, pp. 1-6.

Zhao et al., "Pioglitazone Suppresses CXCR7 Expression To Inhibit Human Macrophage Chemotaxis through Peroxisome Proliferator-Activated Receptor v," Biochemstry, vol. 54, 2015, pp. 6806-6814.

Zheng et al., "Chemokine Receptor CXCR7 Regulates the Invasion, Angiogenesis and Tumor Growth of Human Hepatocellular Carcinoma Cells," Journal of Experimental and Clinical Cancer Research, vol. 29, No. 31, 2010, pp. 1-14.

Zheng et al., "Chemokine Receptor CXCR7 Regulates the Invasion, Angiogenesis and Tumor Growth of Human Hepatocellular Carcinoma Cells," Journal of Experimental & Clinical Cancer Research, vol. 29, No. 31, 2010, pp. 1-14.

Zhou et al., "miR-100 Suppresses the Proliferation and Tumor Growth of Esophageal Squamous Cancer Cells via Targeting CXCR7," Oncology Reports, vol. 35, 2016, pp. 3453-3459.

Zhu et al., "Expression and Function of CXCL 12/CXCR4/CXCR7 in Thyroid Cancer," International Journal of Oncology, vol. 48, 2016, pp. 2321-2329.

Zohar et al., "CXCL 11-dependent Induction of FOXP3-nagative regulatory T cells suppresses autoimmune encephalomyelitis," The Journal of Clinical Investigation, vol. 124, No. 5, May 2014, pp. 2009-2022.

\* cited by examiner

PIPERIDINE CXCR7 RECEPTOR MODULATORS

CROSS REFERENCE TO REPLATED APPLICATIONS

This application is a divisional of U.S. patent application Ser. No. 16/320,906, filed Jan. 25, 2019, which is a filing under 35 U.S.C. § 371 of international application number PCT/EP2017/068990, filed Jul. 27, 2017, which claims priority to application number PCT/EP2016/068052 filed on Jul. 28, 2016, the entire disclosures of each of which are hereby incorporated by reference.

The present invention relates to novel piperidine derivatives of formula (I) which are suited as pharmaceuticals which are modulators of the CXCL11/CXCL12 receptor CXCR7, and to related aspects including processes for the preparation of the compounds of formula (I), pharmaceutical compositions containing one or more compounds of formula (I), and to the use of the compounds of formula (I) as modulators of the CXCL11/CXCL12 receptor CXCR7. The invention further relates to the compounds of formula (I) and their use as pharmaceuticals in combination with one or more therapeutic agents and/or radiotherapy and/or targeted therapy in the treatment of cancers (especially brain tumors including malignant gliomas, glioblastoma multiforme; neuroblastoma; pancreatic cancer including pancreatic adenocarcinoma/pancreatic ductal adenocarcinoma; gastro-intestinal cancers including colon carcinoma, hepatocellular carcinoma; Kaposi's sarcoma; leukemias including adult T-cell leukemia; lymphoma; lung cancer; breast cancer; rhabdomyosarcoma; prostate cancer; esophageal squamous cancer; oral squamous cell carcinoma; endometrial cancer; thyroid carcinoma including papillary thyroid carcinoma; metastatic cancers; lung metastasis; skin cancer including melanoma and metastatic melanoma; bladder cancer; multiple myelomas; osteosarcoma; head and neck cancer; and renal carcinomas including renal clear cell carcinoma, metastatic renal clear cell carcinoma).

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

CXCR7 (alias ACKR3, alias RDC1, alias CMKOR1, alias GPR159) has two known chemokine ligands: CXCL12 (alias stromal cell-derived factor 1, SDF-1; alias Pre-B cell growth stimulating factor, PBSF) and CXCL11 (alias I-TAC, alias INF-y-inducible T cell a chemo-attractant).

CXCL12, a stroma-derived chemo-attractant participates in the immune surveillance and in the regulation of inflammatory responses. CXCL12 is secreted by bone marrow stromal cells, endothelial cells, heart, skeletal muscle, liver, brain, kidney, parenchymal cells and play an essential role in stem cell proliferation, survival, and homing of hematopoietic/progenitor to the bone marrow (Rankin S M et al.; Chemokine and adult bone marrow stem cells; Immunol let. 2012, 145(1-2):47-54). CXCL12 also recruits bone-marrow derived progenitor cells to sites of vasculature formation. Moreover, it plays a prominent role in carcinogenesis. CXCL12 promotes the recruitment of endothelial progenitor cells and of myeloid derived suppressor cells to the tumor sites as well as other bone marrow derived cells. Furthermore, CXCL12 regulates angiogenesis/vasculogenesis linked to tumor progression and plays a key role in seeding circulating tumor cells to metastatic sites. Besides its chemotactic functions, CXCL12 has been shown to regulate tumor cell proliferation, motility and survival (Kryczek I et al.; CXCL12 and vascular endothelial growth factor synergistically induce neoangiogenesis in human ovarian cancers; Cancer Res. 2005, 65(2):465-72; Teicher B A et al.; CXCL12 (SDF-1)/CXCR4 pathway in cancer; Clin Can Res. 2010, 16(11):2927-31; Domanska U M et al.; A review on CXCR4/CXCL12 axis in oncology: no place to hide; European J of cancer. 2013, 49(1):219-30).

In addition to CXCR7, CXCL12 binds and activates CXCR4 (alias Fusin, alias Leukocyte-derived seven-transmembrane-domain receptor; LESTR, alias D2S201E, alias seven-transmembrane-segment receptor, alias HM89, alias lipopolysaccharide-associated protein 3; lap3, alias LPS-associated protein 3) while CXCL11 binds and activate CXCR3 (alias GPR9, alias CD183).

The interaction of CXCR7 and its ligands CXCL12 and CXCL11 (henceforth referred to as the CXCR7 axis) is thus involved in guiding receptor bearing cells to specific locations in the body, particularly to sites of inflammation, immune injury and immune dysfunction and is also associated with tissue damage, the induction of apoptosis, cell growth and angiostasis. CXCR7 and its ligands are upregulated and highly expressed in diverse pathological situations including cancer, autoimmune disorders, inflammation, infection, transplant rejection, fibrosis and neurodegeneration.

Cancers figure among the leading causes of death worldwide. Tumors are comprised of abnormally proliferating malignant cancer cells but also of a functionally supportive microenvironment. This tumor microenvironment is comprised of a complex array of cells, extracellular matrix components, and signaling molecules and is established by the altered communication between stromal and tumor cells. As tumors expand in size, they elicit the production of diverse factors that can help the tumor to grow such as angiogenic factors (promoting ingrowth of blood vessels) or that can help to evade the attack of the host immune response. CXCL12 is such an angiogenic and immunomodulatory factor produced in tumors.

The present CXCR7 modulators may be useful, alone, or in combination in cancers where the expression of the CXCL11/CXCL12 receptor CXCR7 correlates with disease progression in cancer (among others in pancreas cancer, pancreatic adenocarcinoma, breast cancer, hormone refractory prostate cancer, renal cell carcinoma, cervical cancer, cervical intra-epithelial neoplasia, papillary thyroid carcinoma, bladder cancer, Ewing's sarcoma, colon cancer, colorectal cancers, lung cancer, lung adenocarcinoma, non-small cell lung cancer, meningiomas, MALT lymphoma, cutaneous squamous cell carcinoma, neuro-endocrine tumors, nasopharyngeal carcinoma, glioblastoma multiforme, astrocytomas, gliomas, hepatocellular carcinoma, oestrogen positive breast cancer, osteosarcoma, gallbladder cancer, kidney tumors, and renal cell carcinoma). CXCR7 is also expressed in leukemias, adenocarcinomas, brain metastases, multiple myelomas, head and neck cancer, primary cutaneous melanoma, melanoma, metastatic melanoma, rhabdomyosarcoma, pituitary adenoma, oral squamous cell carcinoma, oral tumors, lymphoplasmacytic lymphoma, adult T-cell leukemia, brain tumors, esophageal squamous cancer, esophageal cancer, ovarian carcinoma, lymphoma, viral-induced tumors, otorhinolaryngologic neoplasm, Burkitt's lymphoma, Hodgkin's lymphoma, thyroid cancers, cervical squamous cell carcinoma, endometrial cancer, neuroblastoma, gastro-intestinal cancer, lymphoproliferative disease, acute myeloid leukemia, acute lymphoid leukemia, gastric cancer, nerve sheath tumors and choriocarcinoma, malignant pleural mesothelioma, neurilemnoma, meningioma, diffuse large B cell lymphoma, oral leukoplakia, Kaposi sarcoma, and alveolar rhabdomyosarcoma (for review see Sun et al.; CXCL12/CXCR4/CXCR7 Chemokine Axis and Cancer Progression; Cancer Metastasis Rev. 2010, 29(4), 709-722).

The present CXCR7 modulators may be useful, alone, or in combination, in diseases where CXCR7 modulation using siRNA, shRNA, microRNAs, overexpression, CXCR7 knock-out animals, CXCR7 agonists, CXCR7 antagonists, antibodies or nanobodies have been shown to alter tumor growth in experimental disease models as single agents, or in combination with cytotoxic therapies in including among others hepatocellular carcinoma (Xue T C et al.; Down-regulation of CXCR7 inhibits the growth and lung metastasis of human hepatocellular carcinoma cells with highly metastatic potential; Exp Ther Med. 2012, 3(1):117-123; Zheng et al.; Chemokine receptor CXCR7 regulates the invasion, angiogenesis and tumor growth of human hepatocellular carcinoma cells; Journal of Experimental and Clinical Cancer Research. 2010, 11; 29:31), Kaposi's sarcoma (Raggo C et al.; Novel cellular genes essential for transformation of endothelial cells by Kaposi's sarcoma-associated herpesvirus; Cancer Res. 2005, 65(12):5084-95), T cell leukemia (Jin Z et al.; CXCR7 is inducible by HTLV-1 Tax and promotes growth and survival of HTLV-1-infected T cells; Int J Cancer. 2009, 125(9):2229-35), lymphoma (Burns J M et al.; A novel chemokine receptor for SDF-1 and I-TAC involved in cell survival, cell adhesion, and tumor development; J Exp Med. 2006, 203(9):2201-13), lung carcinomas, breast cancer (Miao Z et al.; CXCR7 (RDC1) promotes breast and lung tumor growth in vivo and is expressed on tumor-associated vasculature. PNAS. 2007, 104(40):15735-40), rhabdomyosarcoma (Grymula K et al.; Overlapping and distinct role of CXCR7-SDF-1/ITAC and CXCR4-SDF-1 axes in regulating metastatic behavior of human rhabdomyosarcomas; Int J cancer. 2010, 127(11):2554-68), prostate cancer (Wang J et al.; The role of CXCR7/RDC1 as a chemokine receptor for CXCL12/SDF-1 in prostate cancer; J biol Chem. 2008, 283(7):4283-94), pancreatic cancer (Shakir M et al.; The chemokine receptors CXCR4/CXCR7 and their primary heterodimeric ligands CXCL12 and CXCL12/high mobility group box 1 in pancreatic cancer growth and development: finding flow; Pancreas. 2015, 44(4):528-34), esophageal squamous cancer (Zhou S M et al.; miR-100 suppresses the proliferation and tumor growth of esophageal squamous cancer cells via targeting CXCR7; Oncol Rep. 2016, 35(6):3453-9), endometrial cancer (Long P et al.; Inhibition of CXCR4 and CXCR7 for reduction of cell proliferation and invasion in human endometrial cancer; Tumour boil. 2016, 37(6):7473-80), papillary thyroid carcinoma (Zhang H et al.; The chemokine receptor CXCR7 is a critical regulator for the tumorigenesis and development of papillary thyroid carcinoma by inducing angiogenesis in vitro and in vivo; Tumour boil. 2016, 37(2):2415-23), oral squamous cell carcinoma (Chen N et al.; CXCL12-CXCR4/CXCR7 axis contributes to cell motilities of oral squamous cell carcinoma; Tumour boil. 2016, 37(1):567-75), lung metastasis (Goguet-Surmenian et al.; CXCR7-mediated progression of osteosarcoma in the lungs; Br J Cancer. 2013, 109(6):1579-85), melanoma (McConnell A T et al.; The prognostic significance and impact of the CXCR4/CXCR7/CXCL12 axis in primary cutaneous melanoma; Br J Dermatol. 2016, doi: 10.1111/bjd.14720), bladder cancer (Liu L et al.; Decreased expression of miR-430 promotes the development of bladder cancer via the upregulation of CXCR7; Mol Med Rep. 2013, 8(1):140-6), multiple myeloma (Azab A K et al.; CXCR7-dependent angiogenic mononuclear cell trafficking regulates tumor progression in multiple myeloma; Blood. 2014, 124 (12):1905-14), osteosarcoma (Zhang Y et al.; Knockdown of CXCR7 inhibits proliferation and invasion of osteosarcoma cells through inhibition of the PI3K/Akt and 8-arrestin pathways; Oncol Rep. 2014, 32(3):965-72), colon cancer (Wang H X et al.; Role of CXC chemokine receptor type 7 in carcinogenesis and lymph node metastasis of colon cancer; Mol Clin Oncol. 2015, 3(6):1229-1232), grade IV astrocytomas (Walters M J et al.; Inhibition of CXCR7 extends survival following irradiation of brain tumours in mice and rats; Br J Cancer. 2014, 110(5):1179-88), head and neck cancers (Maussang D et al.; Llama-derived single variable domains (nanobodies) directed against chemokine receptor CXCR7 reduce head and neck cancer cell growth in vivo; J biol Chem. 2013, 288(41):29562-72), neuroblastoma (Liberman J et al.; Involvement of the CXCR7/CXCR4/CXCL12 axis in the malignant progression of human neuroblastoma; Plos One. 2012, 7(8):e43665) and glioblastoma (Liu Y; Targeting chemokine receptor CXCR7 inhibits glioma cell proliferation and mobility; Anticancer Res. 2015, 35(1):53-64; Walters M J et al.; Inhibition of CXCR7 extends survival following irradiation of brain tumours in mice and rats; Br J Cancer. 2014, 110(5):1179-88; Ebsworth K et al.; The effect of the CXCR7 inhibitor CCX662 on survival in the ENU rat model of glioblastoma; J Clin Oncol. 2012, 30(15) e13580); to alter tumor-associated blood vessels (Miao Z et al.; CXCR7 (RDC1) promotes breast and lung tumor growth in vivo and is expressed on tumor-associated vasculature. PNAS. 2007, 104(40):15735-40); to reduce tumor cell seeding (Grymula K et al.; Overlapping and distinct role of CXCR7-SDF-1/ITAC and CXCR4-SDF-1 axes in regulating metastatic behavior of human rhabdomyosarcomas; Int J cancer. 2010, 127(11):2554-68); to regulate leucocyte migration (Berahovich R D et al.; Endothelial expression of CXCR7 and the regulation of systemic CXCL12 levels; Immunology. 2014, 141(1):111-22); to reduce rheumatoid arthritis clinical scores in mice with collagen induced arthritis (Watanabe K et al.; Pathogenic role of CXCR7 in rheumatoid arthritis; Arthritis Rheum. 2010, 62(11):3211-20); to decrease the clinical severity of experimental autoimmune encephalomyelitis influencing leucocytes infiltration and microglial chemotaxis (Cruz-Orengo L et al.; CXCR7 antagonism prevents axonal injury during experimental autoimmune encephalomyelitis as revealed by in vivo axial diffusivity; J Neuroinflammation. 2011, 6; 8:170; Bao J et al.; CXCR7 suppression modulates microglial chemotaxis to ameliorate experimentally-induced autoimmune encephalomyelitis; Biochem Biophys Res Commun. 2016 Jan. 1; 469(1):1-7); to reduce disease activity of experimental autoimmune neuritis (Brunn A et al.; Differential effects of CXCR4-CXCL12- and CXCR7-CXCL12-mediated immune reactions on murine P0106-125-induced experimental autoimmune neuritis; Neuropathol Appl Neurobiol. 2013, 39(7):772-87); to promote remyelination in a cuprizone model, promoting oligodendroglial cell maturation (Williams J L et al.; Targeting CXCR7/ACKR3 as a therapeutic strategy to promote remyelination in the adult central nervous system; J Exp Med. 2014, 5; 211(5):791-9; Gottle P et al.; Activation of CXCR7 receptor promotes oligodendroglial cell maturation; Ann Neurol. 2010, 68(6):915-24); to attenuate chronic hypoxia-induced pulmonary hypertension (Sartina E et al.; Antagonism of CXCR7 attenuates chronic hypoxia-induced pulmonary hypertension; Pediatr Res. 2012, 71(6):682-8); to induce anxiolytic-like behaviour (Ikeda Y et al.; Modulation of circadian glucocorticoid oscillation via adrenal opioid-CXCR7 signaling alters emotional behaviour; Cell. 2013, 5; 155(6):1323-36); to trigger an angiocrine response to initiate liver regeneration and resolve fibrosis, to promote alveolar repair and reduce lung fibrosis (Cao Z et al.; Targeting of the pulmonary capillary vascular niche promotes lung alveolar repair and ameliorates fibrosis; Nat Med. 2016; 22(2):154-62); to limit atherosclerosis reducing macrophages migration (Zhao D et al.; Pioglitazone Suppresses CXCR7 Expression To Inhibit Human Macrophage Chemotaxis through Peroxisome Proliferator-Activated Receptor γ; Biochemistry. 2015, 17; 54(45):6806-14; Ma W. et al.; Atorvastatin inhibits CXCR7 induction to reduce macrophage migration. Biochem Pharmacol. 2014, 1; 89(1):99-108); and to improve beneficial effects of mesenchymal stem cells based therapies for renal ischemia/reperfusion injury (Liu H et al.; The role of SDF-1-CXCR4/CXCR7 axis in the therapeutic effects of hypoxia-preconditioned mesenchymal stem cells for renal ischemia/reperfusion injury; Plos One. 2012, 7(4):e34608).

Furthermore, CXCR7 has been proposed to be involved in cardiac stem cell migration (Chen D et al.; Crosstalk between SDF-1/CXCR4 and SDF-1/CXCR7 in cardiac stem cell migration; Sci Rep. 2015, 5:16813), chronic allograft vasculopathy (Thomas M N et al; SDF-1/CXCR4/CXCR7 is pivotal for vascular smooth muscle cell proliferation and chronic allograft vasculopathy; Transpl Int. 2015, 28(12): 1426-35), inflammatory bowel disease (Werner L et al.; Involvement of CXCR4/CXCR7/CXCL12 Interactions in Inflammatory bowel disease; Theranostics. 2013, 3(1):40-6), chronic rhinosinusitis (Patadia M et al.; Evaluation of the presence of B-cell attractant chemokines in chronic rhinosinusitis; Am J Rhinol Allergy. 2010, 24(1):11-6), human pulmonary vascular diseases (Rafii S et al.; Platelet-derived SDF-1 primes the pulmonary capillary vascular niche to drive lung alveolar regeneration; Nat Cell Biol. 2015, 17(2): 123-36) and development of severe preeclampsia (Lu J et al.; CXCR4, CXCR7, and CXCL12 are associated with trophoblastic cells apoptosis and linked to pathophysiology of severe preeclampsia; Exp Mol Pathol. 2016, 100(1):184-91). In addition to the above mentioned diseases CXCR7 modulators may be useful in the treatment of renal allograft rejection, systemic lupus erythematosus, osteoarthritis, pulmonary vascular diseases, acute renal failure, ischemia, chronic allograft rejection, acute coronary syndrome, injured central nervous system; hyperlipidemia, HSCs transplantation, cerebral ischemia, hypertension, pulmonary hypertension, Shiga-toxin-associated heomolytic uremic syndrome, HIV/AIDS; acute lung injury, asthma, cirrhosis, stress-related disorders, proliferative diabetic retinopathy, West Nile virus encephalitis, vascular injury and pulmonary fibrosis.

Mechanistically, recent studies have provided increasing evidence that activation of the CXCL12 pathway is a potential mechanism of tumor resistance to both conventional therapies and biological agents via multiple complementary actions: (i) by directly promoting cancer cell survival, invasion, and the cancer stem and/or tumor-initiating cell phenotype; (ii) by recruiting "distal stroma" (i.e., myeloid bone marrowderived cells) to facilitate immune-suppression, tumor recurrence, and metastasis; and (iii) by promoting angiogenesis directly or in a paracrine manner (Duda D G et al: CXCL12 (SDF1alpha)-CXCR4/CXCR7 pathway inhibition: an emerging sensitizer for anticancer therapies?; *Clin Cancer Res;* 2011, 17(8); 2074-80) recently discussed preclinical and clinical data that support the potential use of anti-CXCL12 agents including CXCR7 modulators as sensitizers to currently available therapies in cancer treatments. In addition, the enhancement in CXCR7 expression on endothelium seems to be critical for the inflammatory infiltration in autoimmune diseases. CXCL12 and CXCL11 are key ligands in inflammatory immune response: (i) by acting on cell migration, on cell adhesion and cell survival (Kumar R et al.; CXCR7 mediated Gia independent activation of ERK and Akt promotes cell survival and chemotaxis in T cells; Cell Immunol. 2012, 272(2):230-41); (ii) by driving differentiation and polarization of cell i.e., macrophages (Ma W. et al.; Atorvastatin inhibits CXCR7 induction to reduce macrophage migration. Biochem Pharmacol. 2014, 1; 89(1):99-108), CD4+ T cells/ Zohar Y et al.; CXCL11-dependent induction of FOXP3-negative regulatory T cells suppresses autoimmune encephalomyelitis; J Clin Invest. 2014, 124(5):2009-22), oligodendrocytes progenitors (Gottle P et al.; Activation of CXCR7 receptor promotes oligodendroglial cell maturation; Ann Neurol. 2010, 68(6):915-24); (iii) by participating in homing processes (Lewellis S W et al.; Precise SDF1-mediated cell guidance is achieved through ligand clearance and microRNA-mediated decay. J Cell Biol. 2013, 4; 200 (3):337-55). Therefore, targeting CXCR7 and thus regulating the level of its ligands would have a decisive role in the pathogenesis of a wide variety of autoimmune and inflammatory diseases. Sanchez-Martin et al (Sanchez-Martin et al.; CXCR7 impact on CXCL12 biology and disease; Trends Mol Med. 2013, 19(1):12-22) recently discussed dysregulation of CXCR7 in disease and highlighted the fact that this receptor is an attractive therapeutic target for the treatment of autoimmune diseases and inflammation.

Thus, the present CXCR7 antagonists may be useful, alone, or in combination with one or more therapeutic agents and/or chemotherapy and/or radiotherapy and/or immunotherapy; in particular in combination with chemotherapy, radiotherapy, EGFR inhibitors, aromatase inhibitors, immunotherapy such as especially PD1 and/or PDL1 blockade and/or CTLA4 blockade, or other targeted therapies; for the prevention/prophylaxis or treatment of cancers such as carcinomas; adenocarcinomas; neuroendocrine tumors; skin cancer including melanoma and metastatic melanoma; lung cancer including non-small cell lung cancer; metastatic cancer; lung metastasis; bladder cancer including urinary bladder cancer; urothelial cell carcinoma; renal carcinomas including renal cell carcinoma; metastatic renal cell carcinoma, metastatic renal clear cell carcinoma; gastro-intestinal cancers including colon carcinoma, colorectal adenoma, colorectal adenocarcinoma, colorectal cancer, metastatic colorectal cancer, familial adenomatous polyposis (FAP), oesophageal cancer, oral squamous cell carcinoma; gastric cancer, gallbladder cancer, cholangiocarcinoma, hepatocellular carcinoma; pancreatic cancer such as pancreatic adenocarcinoma or pancreatic ductal (adeno)carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; primary intra-ocular B-Cell lymphoma, multiple myelomas and virally induced tumors; and diseases involving CXCR7 and/or CXCL12 and/or CXCL11 mediated metastasis, chemotaxis, cell adhesion, trans-endothelial migration, cell proliferation and/or survival.

Specifically, the potential role of CXCR7 in brain tumors, malignant glioma and in glioblastoma multiforme is known from the literature. Modulators of the CXCL12 pathway including CXCR7 modulators have been mentioned as potential therapeutic agents for treating brain cancer in combination with chemotherapeutic agents or radiotherapy. For example, Hattermann et al (Hattermann et al.; The chemokine receptor CXCR7 is highly expressed in human glioma cells and mediates antiapoptotic effects; Cancer research 2010, 70 (8):3299-3308) teach that CXCL12 "stimulation prevented camptothecin- and temozolomide-induced apoptosis and that a CXCR7 antagonist reduced the antiapoptotic effect of CXCL12". The authors concluded that "CXCR7 is a functional receptor for CXCL12 in astrocytomas/glioblastomas and mediates resistance to drug-induced apoptosis". Furthermore, Hattermann et al (Hattermann et al.; CXCL12 mediates apoptosis resistance in rat C6 glioma cells; Oncol Rep. 2012, 27: 1348-1352) teach that "CXCL12 abrogates the antiproliferative effect of temozolomide". The authors also teach that this effect could be almost completely abolished by a CXCR7 specific antagonist, "indicating that the antiapoptotic effect of CXCL12 is mainly mediated via CXCR7". Ebsworth et al (Ebsworth et al.; Neuro Oncol (2013) 15 (suppl 3):iii37-iii61. ET-023) teach that a CXCR7 antagonist significantly prolongs survival when administered in combination with radiotherapy in a rat model of glioblastoma. This finding is supported by other studies (e.g. Ebsworth K et al.; The effect of the CXCR7 inhibitor CCX662 on survival in the ENU rat model of glioblastoma; J Clin Oncol. 2012, 30(15) e13580; Walters M J et al.; Inhibition of CXCR7 extends survival following irradiation of brain tumours in mice and rats; Br J Cancer. 2014, 110(5):1179-88) disclosing that in vivo inhibition of CXCR7 in concert with radiotherapy results in a significant extension of survival time in another rat model of glioblastoma. In addition, Liu S C et al (Liu S C et al.; Neuro-Oncology 2014; 16(1):21-28) teach that inhibition of CXCL12 after irradiation inhibits tumor recurrence in autochtonous brain tumors in rats. Liu S C et al (Liu S C et al.; Blockade of SDF-1 after irradiation inhibits tumor recurrences of autochthonous brain tumors in rats; Neuro Oncol. 2013, 16(1):21-8) also teach that inhibition of CXCL12 in a brain metastasis model after irradiation produced a marked inhibition of tumor growth and prolongation of lifespan compared to irradiation alone. Calatozzolo C et al (Calatozzolo C et al.; Expression of the new CXCL12 receptor, CXCR7, in gliomas; Cancer Biol Ther. 2011, 11(2), 1-12) teach in in vitro experiments that CXCR7 antagonists showed complete inhibition of glioma proliferation.

Specifically, a role for CXCR7 in pancreas tumors, has been described in the literature. Shakir et al. (Shakir M et al.; The chemokine receptors CXCR4/CXCR7 and their primary heterodimeric ligands CXCL12 and CXCL12/high mobility group box 1 in pancreatic cancer growth and development: finding flow; Pancreas. 2015, 44(4):528-34) observed that CXCR4 and CXCR7, upon interaction with CXCL12, activate downstream protein kinases that promote a more aggressive behaviour. Moreover, the expression of CXCR7 and CXCl12 correlates with tumors histological grades (Liu Z et al.; Expression of stromal cell-derived factor 1 and CXCR7 ligand receptor system in pancreatic adenocarcinoma. World J Surg Oncol. 2014, 12:348). These findings were confirmed by Heinrich E L et al. (Heinrich E L et al.; Chemokine CXCL12 activates dual CXCR4 and CXCR7-mediated signaling pathways in pancreatic cancer cells; J Transl Med. 2012, 10:68). Therefore, CXCR7 modulators may be useful in the treatment of pancreas cancers.

CXCR7 modulators may also be useful in the treatment of papillary thyroid carcinoma. Liu Z et al. (Liu Z et al.; The involvement of CXCR7 in modulating the progression of papillary thyroid carcinoma; J Surg Res. 2014, 191(2):379-88) described that CXCR7 messenger RNA and protein levels were markedly increased in papillary thyroid carcinoma and correlated with tumor progression. CXCR7 could regulate proliferation, cell cycle, apoptosis, invasion, and the expression of cell cycle regulatory proteins involved in the S-G2 phase transition. Knockdown of CXCR7 in papillary thyroid carcinoma cells suppressed cell proliferation and invasion, induced S phase arrest, and promoted apoptosis. Zhang H et al further demonstrated that CXCR7 affects the growth of papillary thyroid carcinoma cells and participates in the tumorigenesis of papillary thyroid carcinoma, probably through regulating angiogenesis by the proangiogenic VEGF or IL-8. (Zhang H et al.; The chemokine receptor CXCR7 is a critical regulator for the tumorigenesis and development of papillary thyroid carcinoma by inducing angiogenesis in vitro and in vivo; Tumor Biol. 2016, 37(2): 2415-23). The expression and function of the CXCR7 axis in thyroid cancer was confirmed by Zhu X et al. (by Zhu X et al.; Expression and function of CXCL12/CXCR4/CXCR7 in thyroid cancer; Int J Oncol. 2016, 48(6):2321-9)

CXCR7 modulators may also be useful in the treatment of lung cancer: Using a combination of overexpression and RNA interference, Miao Z et al (Miao Z et al.; CXCR7 (RDC1) promotes breast and lung tumor growth in vivo and is expressed on tumor-associated vasculature. PNAS. 2007, 104(40):15735-40) established that CXCR7 promotes growth of tumors formed from breast and lung cancer cells and enhances experimental lung metastases. Iwakiri S et al. (Iwakiri S et al.; Higher expression of chemokine receptor CXCR7 is linked to early and metastatic recurrence in pathological stage I nonsmall cell lung cancer; Cancer. 2009, 115(11):2580-93) observed that higher expression of CXCR7 is linked to early and metastatic recurrence in pathological stage I non small cell lung cancer.

CXCR7 modulators may also be useful in the treatment of hepatocellular carcinoma: it was reported that CXCR7 expression is increased in hepatocellular carcinoma tissues. Knockdown of CXCR7 expression significantly inhibited hepatocellular carcinoma cells invasion, adhesion and angiogenesis. In addition, down-regulation of CXCR7 expression lead to a reduction of tumor growth in a xenograft model of hepatocellular carcinoma (Zheng K et al.; Chemokine receptor CXCR7 regulates the invasion, angiogenesis and tumor growth of human hepatocellular carcinoma cells; J Exp Clin Cancer Res. 2010, 29:31). Monnier J et al. also observed in a cohort of 408 human hepatocellular carcinoma, that CXCR7 was significantly higher in tumours compared to normal liver controls (Monnier J et al.; CXCR7 is up-regulated in human and murine hepatocellular carcinoma and is specifically expressed by endothelial cells; Eur J Cancer. 2012, 48(1):138-48). Immunohistochemical staining on human hepatocellular carcinoma sections confirmed that CXCR7 expression was much higher in cancer tissues. Using RNAi of CXCR7 in an hepatocellular carcinoma cell line, Xue T C et all observed that CXCR7 downregulation decreased the growth of tumors and the number of lung metastases in nude mice. Moreover, tissue microarray showed that HCCs with high expression of CXCR7 were prone to metastasize to the lung. Down-regulation of CXCR7 inhibits the growth and lung metastasis of human hepatocellular carcinoma cells with highly metastatic potential (Xue T C et al.; Down-regulation of CXCR7 inhibits the growth and lung metastasis of human hepatocellular carcinoma cells with highly metastatic potential; Exp Ther Med. 2012, 3(1):117-123).

CXCR7 modulators may also be useful in the treatment of metastatic colon cancer: Guillemot et al. (Guillemot et al.; CXCR7 receptors facilitate the progression of colon carcinoma within lung not within liver; Br J Cancer. 2012, 107(12):1944-9) observed that following injection of colorectal cancer cells, mice treated with a CXCR7 antagonists exhibited a significant reduction in lung metastasis. Wang H X et al studied CXCR7 expression in colon cancer specimen and observed that CXCR7 levels were significantly higher in colon tumors compared with those in normal colon tissue. In addition, lymph node metastatic colon tumors exhibited significantly higher CXCR7 expression compared with non-metastatic tumors (Wang H X et al.; Role of CXC chemokine receptor type 7 in carcinogenesis and lymph node metastasis of colon cancer; Mol Clin Oncol. 2015, 3(6): 1229-1232).

CXCR7 modulators may also be useful in the treatment of head and neck cancer: A nanobody directed against CXCR7 reduced head and neck cancer growth in vivo (Maussang D et al.; Llama-derived single variable domains (nanobodies) directed against chemokine receptor CXCR7 reduce head and neck cancer cell growth in vivo; J biol Chem. 2013, 288(41):29562-72). Moreover, the same authors analysed a wide variety of tumor biopsies and showed high expression of CXCR7 in head and neck cancer.

CXCR7 is also reported to be expressed in brain metastases (Salmaggi et al.; CXCL12, CXCR4 and CXCR7 expression in brain metastases. Cancer Biol Ther. 2009, 8:17, 1-7). The authors concluded that the CXCL12/CXCR4/CXCR7 pathway could be an interesting target for further researches investigating the role of these molecules in invasion and proliferation of metastatic cells.

Specifically, the impact of CXCR7 on inflammatory demyelinating diseases is known from the literature. CXCR7 is expressed in various regions throughout the adult mouse brain and its expression is upregulated in mouse model for multiple sclerosis (Banisadr G et al.; Pattern of CXCR7 Gene Expression in Mouse Brain Under Normal and Inflammatory Conditions; J Neuroimmune Pharmacol. 2016 March; 11(1):26-35). Altered expression patterns of CXCL12 at the blood-brain barrier (BBB) is involved in multiple sclerosis and correlate with severity of the disease (McCandless E E et al.; Pathological expression of CXCL12 at the blood-brain barrier correlates with severity of multiple sclerosis; Am J Pathol. 2008, 172(3):799-808). CXCR7 antagonism have been shown to be effective in experimental autoimmune encephalomyelitis in mice. Those recent studies strongly implicate CXCR7 as a disease-modifying molecule in multiple sclerosis via complementary mechanisms: (i) by facilitating leucocytes entry into the perivascular space via CXCL12 redistribution at the BBB (Cruz-Orengo L et al.; CXCR7 antagonism prevents axonal injury during experimental autoimmune encephalomyelitis as revealed by in vivo axial diffusivity; J Neuroinflammation. 2011, 6; 8:170; Cruz-Orengo L et al.; CXCR7 influences leukocyte entry into the CNS parenchyma by controlling abluminal CXCL12 abundance during autoimmunity; J Exp Med. 2011, 14; 208(2):327-39) and regulating the CXCR4-mediated activation of integrins (Hartmann T N et al.; A crosstalk between intracellular CXCR7 and CXCR4 involved in rapid CXCL12-triggered integrin activation but not in chemokine-triggered motility of human T lymphocytes and CD34+ cells; J Leukoc Biol. 2008; 84(4):1130-40) (ii) by direct effect on microglial chemotaxis (Bao J et al.; CXCR7 suppression modulates microglial chemotaxis to ameliorate experimentally-induced autoimmune encephalomyelitis; Biochem Biophys Res Commun. 2016 Jan. 1; 469(1):1-7) (iii) by promoting remyelination via increase levels of CXCL12 enhancing CXCR4-mediated oligodendrocytes progenitor cells maturation (Williams J L et al.; Targeting CXCR7/ACKR3 as a therapeutic strategy to promote remyelination in the adult central nervous system; J Exp Med. 2014, 5; 211(5):791-9; Gottle P et al.; Activation of CXCR7 receptor promotes oligodendroglial cell maturation; Ann Neurol. 2010, 68(6):915-24). Thus CXCR7 antagonism could therapeutically prevent inflammation and enhance myelin repair in the demyelinated adult CNS.

Moreover, CXCR7 antagonism have been shown to be effective in a mouse model for Guillain-Barré syndrome. Indeed, Brunn et al (Brunn A et al.; Differential effects of CXCR4-CXCL12- and CXCR7-CXCL12-mediated immune reactions on murine P0106-125-induced experimental autoimmune neuritis; Neuropathol Appl Neurobiol. 2013, 39(7):772-87) teach that "antagonization of CXCR7 reduced disease prevalence to 75% and impressively minimized disease activity" in a mouse model of experimental autoimmune neuritis. The authors conclude that "CXCR7/CXCL12-interaction is a gatekeeper for pathogenic cells".

Specifically, the potential role of CXCR7 in rheumatoid arthritis is known from the literature. CXCR7 is reported to be expressed on endothelial cells in the synovium. Also, elevated levels of CXCL12 and CXCL11 mRNA were found in synovial tissue of rheumatoid arthritis patients (Ueno et al.; The production of CXCR3-agonistic chemokines by synovial fibroblasts from patients with rheumatoid arthritis; Rheumatol Int. 2005, 25(5):361-7). CXCL12 was shown to play a central role in CD4+ T cell and monocytes accumulation in the synovium (Nanki T et al.; Stromel cell-derived factor-1-CXC chemokine receptor 4 interactions play a central role in CD4+ T cell accumulation in rheumatoid arthritis synovium; J Immunol. 2000, 165(11):6590-8; Blades M C et al.; Stromel cell-derived factor 1 (CXCL12) induces monocyte migration into human synovium transplanted onto SCID Mice; Arthritis Rheum. 2002 March; 46(3):824-36). In addition CXCL12 participates in the rheumatoid arthritis process via its proangiogenic functions and its action on osteoclast recruitment and differentiation. Therefore, modulators of the CXCL12 pathway including CXCR7 modulators have been proposed as potential therapeutic agents to treat rheumatoid arthritis. Villalvilla et al (Villalvilla A et al.; SDF-1 signaling: a promising target in rheumatic diseases; Expert Opin Ther Targets. 2014, 18(9): 1077-87) recently discussed preclinical and clinical data that support the potential use of anti-CXCL12 agents in rheumatoid arthritis treatments. Watanabe et al (Watanabe K et al.; Pathogenic role of CXCR7 in rheumatoid arthritis; Arthritis Rheum. 2010, 62(11):3211-20) teach that a CXCR7 inhibitor prophylactically and therapeutically reduces disease clinical signs and angiogenesis in a mouse collagen-induced arthritis model.

Specifically, CXCR7 is involved in several inflammatory disorders. For example, CXCL12 and CXCL11 are involved in chronic lung inflammatory processes (Petty J M et al.; Pulmonary stromal-derived factor-1 expression and effect on neutrophil recruitment during acute lung injury; J Immunol. 2007, 178(12):8148-57; Porter J C et al.; Polarized localization of epithelial CXCL11 in chronic obstructive pulmonary disease and mechanisms of T cell egression; J Immunol. 2008, 180(3):1866-77). CXCL12 was found upregulated in the lung in both humans and animals models (Phillips R J et al.; Circulating fibrocytes traffic to the lungs in response to CXCL12 and mediate fibrosis; J Clin Invest. 2004, 114(3):438-46). Anti-CXCL12 agents have been shown to attenuate lung inflammation and airway hyperreactivity in asthma models (Gasparik V et al.; Prodrugs of a CXC Chemokine-12 (CXCL12) Neutraligand Prevent Inflammatory Reactions in an Asthma Model in Vivo; ACS Med Chem Lett. 2012 Jan. 12; 3(1):10-4; Lukacs N W et al.; AMD3100, a CXCR4 antagonist, attenuates allergic lung inflammation and airway hyperreactivity; Am J Pathol. 2002, 160(4):1353-60). Petty et al. (Petty J M et al.; Pulmonary stromal-derived factor-1 expression and effect on neutrophil recruitment during acute lung injury. J Immunol. 2007, 178(12):8148-57) teach that CXCL12 blockade attenuates late neutrophilia in the acute lung injury in mice. Cao et al (Cao Z et al.; Targeting of the pulmonary capillary vascular niche promotes lung alveolar repair and ameliorates fibrosis; Nat Med. 2016; 22(2):154-62) teach that CXCR7 modulator after lung injury "promotes alveolar repair and reduces fibrosis" in a mouse model of lung fibrosis. CXCL12 and CXCL11 are also reported to be upregulated in Inflammatory bowel diseases (Koelink P J et al.; Targeting chemokine receptors in chronic inflammatory diseases: an extensive review; Pharmacol Ther. 2012, 133(1):1-18). CXCR7 was found upregulated on peripheral blood T cells in Inflammatory bowel diseases (Werner L et al.; Reciprocal regulation of CXCR4 and CXCR7 in intestinal mucosal homeostasis and inflammatory bowel disease; J Leukoc Biol. 2011, 90(3):583-90). The author hypothetise that "the increased expression of CXCR7 in the peripheral blood of Inflammatory bowel diseases patients could foster increased influx of T cells to sites of mucosal inflammation" (Werner L et al.; Involvement of CXCR4/CXCR7/CXCL12 Interactions in Inflammatory bowel disease; Theranostics. 2013, 3(1):40-6). In mouse models for Inflammatory bowel disease, modulators of the CXCL12 pathway could decrease infiltration of T cells and reduce tissue damage (Mikami S et al.; Blockade of CXCL12/CXCR4 axis ameliorates murine experimental colitis; J Pharmacol Exp Ther. 2008, 327(2):383-92; Xia X M et al.; CXCR4 antagonist AMD3100 modulates claudin expression and intestinal barrier function in experimental colitis; PLoS One. 2011, 6(11): e27282).

Elevated levels of CXCL12 and CXCL11 have also been found in lesional psoriatic skin (Chen S C et al.; Expression of chemokine receptor CXCR3 by lymphocytes and plasmacytoid dendritic cells in human psoriatic lesions; Arch Dermatol Res. 2010, 302(2):113-23; Zgraggen S et al.; An important role of the SDF-1/CXCR4 axis in chronic skin inflammation; PLoS One. 2014, 9(4):e93665). Zgraggen et al teach that blockade of CXCL12 improved the course of chronic skin inflammation in two different models of psoriasis-like skin inflammation.

Several other auto-immune disorders like systemic lupus erythematosus (SLE) display altered CXCR7/CXCR4 expression correlated with an impaired CXCL12-promoted migration of SLE B cells (Biajoux V et al.; Expression of CXCL12 receptors in B cells from Mexican Mestizos patients with systemic Lupus erythematosus; J Transl Med. 2012, 18; 10:251). In addition, CXCL12 was significantly up-regulated in the nephritic kidneys in multiple murine models of lupus. Wang et al. (Wang A et al.; CXCR4/CXCL12 hyperexpression plays a pivotal role in the pathogenesis of lupus; J Immunol. 2009, 182(7):4448-58) teach that acting on the CXCL12 axis is a good therapeutic target in lupus, as a CXCR4 antagonist significantly ameliorates the disease, prolonging survival and reducing nephritis and lymphoproliferation.

CXCR7 modulators may also be useful in the treatment of fibrosis: Cao Z et al (Cao Z. et al; Targeting of the pulmonary capillary vascular niche promotes lung alveolar repair and ameliorates fibrosis. Nat Med. 2016, 22(2):154-62) demonstrated that the administration of a CXCR7 modulator after lung injury promotes alveolar repair and reduces fibrosis. A role for CXCR7 in liver fibrosis was also described (Ding B S et al.; Divergent angiocrine signals from vascular niche balance liver regeneration and fibrosis; Nature. 2014, 505 (7481):97-102).

The biological properties of CXCR7 modulators also include, but are not limited to, any physiological function and/or cellular function linked and/or controlled by its ligands CXCL11, CXCL12, BAM22 and its related peptides. Hence, CXCL12 depletion sensitizes cancer cells to chemotherapy in vivo and CXCL12 treatment blocks colonic carcinoma metastasis (Duda et al.; CXCL12 (SDF1alpha)-CXCR4/CXCR7 pathway inhibition: an emerging sensitizer for anticancer therapies?; Clin. Cancer Res. 2011 17(8) 2074-2080; Naumann et al.; CXCR7 function as a scavenger for CXCL12 and CXCL11; Plos One. 2010, 5(2) e9175). CXCR7 is also a receptor for CXCL11 (alias small inducible cytokine subfamily b, member 11; scyb11, alias interferon-gamma-inducible protein 9; ip9, alias small inducible cytokine subfamily b, member 9b; scyb9b) and therefore modulators of CXCR7 activity can also be used in indications with CXCL11-associated pathology (Rupertus K et al.; Interaction of the chemokines I-TAC (CXCL11) and SDF-1 (CXCL12) in the regulation of tumor angiogenesis of colorectal cancer; Clin Exp Metastasis. 2014, 31(4):447-59; Zohar Y et al.; CXCL11-dependent induction of FOXP3-negative regulatory T cells suppresses autoimmune encephalomyelitis; J Clin Invest. 2014, 124(5): 2009-22; Antonelli A et al.; Increase of interferon-γ inducible CXCL9 and CXCL11 serum levels in patients with active Graves' disease and modulation by methimazole therapy; Thyroid. 2013, 23(11):1461-9). CXCR7 functions also as a receptor for the opioid peptide BAM22 and its related peptides (peptide E, peptides BAM12, BAM14, BAM18) and therefore modulators of CXCR7 activity possibly may also be used in indications with opioid peptides associated pathologies (Ikeda et al.; Modulation of circadian glucocorticoid oscillation via adrenal opioid-CXCR7 signaling alters emotional behaviour; Cell. 2013, 155, 1323-1336). CXCR7 has also been shown to function as a scavenger receptor for CXCl11 and CXCL12. Thus, CXCR7 targeting has been shown to alter CXCl11 and CXCL12 local concentration leading to a deregulation of the CXCl11 and CXCL12 concentration gradients.

Certain isoxazole compounds which are SMYD protein blockers are known from WO2016/040515, wherein in the compounds of WO2016/040515, the isoxazole ring is substituted with certain (cyclo-)alkyl substituents instead of the present phenyl substituent $Ar^2$; and the piperidine moiety does not carry a carboxamide substituent $R^1$—CO—. Certain pyrrole compounds are known as antibacterial agents from WO2006/087543, WO2005/026149 and J. Med. Chem 2014, 57(14), 6060-6082. Cyclic diamines as Factor Xa inhibitors are known from WO2005/032490. WO2004/050024 discloses pyrrolidine compounds as chemokine receptor modulators.

The present invention provides novel trans-3,4-di-substituted piperidine derivatives of formula (I) which are modulators of the CXCR7 receptor, i.e. they act as CXCR7 receptor antagonists, and are useful for the prevention or treatment of diseases which respond to the activation of the CXCL12 receptors and/or CXCL11 receptors, especially cancer. In the prevention or treatment of cancers the compounds of formula (I) may also be used in combination with one or more chemotherapy agents and/or radiotherapy and/or targeted therapy.

1) A first aspect of the invention relates to novel piperidine derivatives of formula (I);

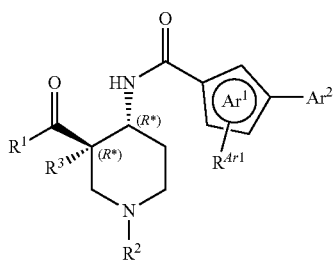

Formula (I)

wherein
the two substituents of the piperidine ring: $R^1$—CO— and —NH—CO—$Ar^1$—$Ar^2$, are in relative trans-configuration (i.e. the relative configuration of the two chiral carbon atoms in position 3 and 4 of the piperidine ring is (3R*,4R*));
$Ar^1$ represents a 5-membered heteroarylene group (especially a 5-membered heteroarylene containing one to a maximum of three heteroatoms, each independently selected from oxygen, nitrogen, and sulfur; notably oxazol-diyl, isoxazol-diyl, oxadiazol-diyl, triazol-diyl, isothiazol-diyl, or thiadiazol-diyl), wherein the —NH—CO— group and $Ar^2$ are attached in meta arrangement to ring atoms of $Ar^1$; wherein said 5-membered heteroarylene is unsubstituted, or mono-substituted with $R^{Ar1}$; wherein $R^{Ar1}$ represents $(C_{1-4})$ alkyl, $(C_{1-4})$alkoxy, halogen, $(C_{1-3})$fluoroalkyl, or $(C_{1-3})$ fluoroalkoxy (especially said 5-membered heteroarylene is unsubstituted);
$Ar^2$ represents phenyl (preferred) or 6-membered heteroaryl; wherein said phenyl or 6-membered heteroaryl independently is mono-, di- or tri-substituted, wherein the substituents are independently selected from fluoro, chloro, methyl, cyano, methoxy, or $(C_1)$fluoroalkyl;
  [notably one or two of said substituents is/are independently selected from fluoro, chloro, and methyl, and the remaining, if present, is/are fluoro; especially $Ar^2$ represents phenyl which is mono-, di- or tri-substituted, wherein the substituents are independently fluoro or chloro; in particular $Ar^2$ represents phenyl which is mono-, di- or tri-substituted with fluoro];
$R^1$ represents $R^{N1}R^{N2}N$—, wherein
  $R^{N1}$ represents
    hydrogen;
    $(C_{1-6})$alkyl (especially methyl, ethyl, isopropyl, isobutyl, tert.-butyl, 1,2,2-trimethyl-propyl);
    $(C_{1-6})$alkyl which is mono-substituted with
      hydroxy;
      $(C_{1-3})$alkoxy (especially methoxy, ethoxy);
      2-hydroxy-ethoxy;
      —CO—$NH_2$;
      —$SO_2$—$(C_{1-3})$alkyl (especially methanesulfonyl);
      cyano;
      $(C_{1-3})$fluoroalkoxy (especially trifluoromethoxy);
      —$NR^{N3}R^{N4}$, wherein $R^{N3}$ and $R^{N4}$ independently represent hydrogen or $(C_{1-4})$alkyl (especially —$NR^{N3}R^{N4}$ represents dimethylamino);
    (especially such group $R^{N1}$ being mono-substituted $(C_{1-6})$alkyl is 2-hydroxy-ethyl, 2-hydroxy-1-methyl-ethyl, 2-hydroxy-1,1-dimethyl-ethyl, 2-methoxy-ethyl, 3-methoxy-propyl, 2-ethoxy-ethyl, 2-ethoxy-1-methyl-ethyl, 2-methoxy-1,1-dimethyl-ethyl, 3-methoxy-1,1-dimethyl-propyl, 2-(2-hydroxy-ethoxy)-ethyl, carbamoyl-methyl, 2-methanesulfonyl-1,1-dimethyl-ethyl, 1-cyano-1-methyl-ethyl, 2-dimethylamino-ethyl, 2-trifluoromethoxy-ethyl);
    $(C_{2-6})$alkynyl (especially 1-methyl-prop-2-ynyl);
    $(C_{2-5})$fluoroalkyl (especially 2-fluoro-ethyl, 2,2-difluoro-ethyl, 2-fluoro-1-methyl-ethyl, 2-fluoro-1,1-dimethyl-ethyl, 2,2-difluoro-1-methyl-ethyl, 3,3,3-trifluoro-1,1-dimethyl-propyl);
    $(C_{1-4})$alkoxy (especially methoxy);
    2-(2-oxo-pyrrolidin-1-yl)-ethyl;
    a group -$L^1$-$Cy^1$; wherein
      $L^1$ represents a direct bond, —$(C_{1-3})$alkylene-, or —$(C_{3-5})$cycloalkylene-; and
      $Cy^1$ represents $(C_{3-6})$cycloalkyl; wherein said $(C_{3-6})$ cycloalkyl optionally contains one ring oxygen atom; wherein said $(C_{3-6})$cycloalkyl independently is unsubstituted; or mono-substituted with fluoro, methyl, hydroxy, —CO—$(C_{1-4})$alkoxy, or cyano; or di-substituted with fluoro, or tri-substituted with methyl and two fluoro;
    (especially such group -$L^1$-$Cy^1$ is cyclopropyl, cyclopentyl, 1-methyl-cyclopropyl, 1-methyl-cyclobutyl, 1-cyclopropyl-cyclopropan-1-yl, 1-cyclobutyl-ethyl, 3-methyl-tetrahydrofuran-3-yl, tetrahydrofuran-3-yl-methyl, tetrahydrofuran-2-yl-methyl, 1-tetrahydrofuran-2-yl-ethyl, oxetan-3-yl-methyl, 3,3-difluoro-1-methyl-cyclobutyl, 1-(ethoxycarbonyl)-cyclopropyl, or 1-cyano-cyclobutyl);
    a group -$L^2$-$Ar^3$, wherein
      $L^2$ represents a direct bond; —$(C_{1-4})$alkylene-; *—$(C_{3-5})$cycloalkylene-$(C_{0-2})$alkylene- wherein said $(C_{3-5})$cycloalkylene optionally contains one ring oxygen atom, wherein the asterisk indicates the bond to which $Ar^3$ is attached; *—$(C_{1-2})$ alkylene-$(C_{3-5})$cycloalkylene- wherein said $(C_{3-5})$ cycloalkylene optionally contains one ring oxygen atom, wherein the asterisk indicates the bond to which $Ar^3$ is attached; or —$(C_{1-3})$alkylene- which is mono-substituted with hydroxy, trifluoromethyl, or —CO—$(C_{1-4})$alkoxy; and
      $Ar^3$ represents phenyl, or 5- or 6-membered heteroaryl; wherein said phenyl or 5- or 6-membered heteroaryl independently is unsubstituted, or mono-, or di-substituted; wherein the substituents are independently selected from $(C_{1-4})$alkyl, $(C_{1-4})$alkoxy, halogen, hydroxy, $(C_{1-3})$fluoroalkyl, or $(C_{1-3})$fluoroalkoxy; wherein, in case $Ar^3$ represents 6-membered heteroaryl which is pyridyl or pyrimidinyl, such pyridyl or pyrimidinyl may additionally be present in form of the respective N-oxide (for avoidance of doubt, it is understood that the term 6-membered heteroaryl comprises the groups 1-oxy-pyridinyl, and 1-oxy-pyrimidinyl);
    (especially such group -$L^2$-$Ar^3$ is phenyl, benzyl, 1-phenyl-ethyl, 2-phenyl-ethyl, 2-(2-chloro-phenyl)-ethyl, 2-(4-fluoro-phenyl)-ethyl, 2-(2-methyl-phenyl)-ethyl, 2-(3-methyl-phenyl)-ethyl, 2-(4-methyl-phenyl)-ethyl, 2-(2-methoxy-phenyl)-ethyl, 2-phenyl-propyl, 2-hydroxy-1-phenyl-ethyl, 2-hydroxy-2-phenyl-ethyl, 2-phenyl-cyclopropyl; or 1-(3-bromo-phenyl)-ethyl, 1-phenyl-cyclopropyl, 1-phenyl-cyclobutyl, 2-phenyl-cyclobutyl, 1-(3-chloro-phenyl)-cyclopropyl, 1-(4-fluoro-phenyl)-cyclopropyl, 1-(3-fluoro-phenyl)-cyclopropyl, 1-(2-fluoro-phenyl)-cyclopropyl, 1-(2-methyl-phenyl)-cyclopropyl, 1-(2-hydroxy-phenyl)-cyclopropyl, 1-(2-methoxy-phenyl)-ethyl, 2-methyl-2-(2-chloro-phenyl)-propyl, 1-(4-chloro-phenyl)-cyclopropyl-methyl, 3-(3-chloro-phenyl)-oxetan-3-yl, 3-(4-fluoro-phenyl)-oxetan-3-yl, 3-(phenyl)-oxetan-3-yl-methyl, 3-(benzyl)-oxetan-3-yl, 1-(2-methoxy-phenyl)-cyclopropyl, 1-(3-methoxy-phenyl)-cyclopropyl, 1-(2-trifluoromethyl-phenyl)-cyclopropyl, 2-ethoxy-2-oxo-1-phenylethyl; or 4,5-dimethyl-thiazol-2-yl, 1H-imidazol-4-yl-methyl, thiazol-2-yl-methyl, 4-methyl-thiazol-5-yl-methyl, 4-methyl-thiazol-2-yl-methyl, 5-methyl-thiazol-2-yl-methyl, 2-methyl-thiazol-4-yl-methyl, oxazol-5-yl-methyl, 1-(2H-pyrazol-3-yl)-ethyl, (1-methyl-1H-pyrazol-3-yl)-methyl, 1-([1,2,4]oxadiazol-3-yl)-ethyl, 1-(isoxazol-3-yl)-ethyl, 3-methyl-isoxazol-5-yl-methyl, 5-methyl-isoxazol-3-yl-methyl, 1-(1H-[1,2,4]triazol-3-yl)-ethyl, (1,5-dimethyl-1H-pyrazol-3-yl)-methyl, (2,5-dimethyl-2H-pyrazol-3-yl)-methyl, (3-ethyl-([1,2,4]oxadiazol-5-yl)-methyl, 1-(5-methyl-([1,3,4]oxadiazol-2-yl)-ethyl, 1-methyl-1-(1-methyl-1H-pyrazol-4-yl)-ethyl, 1-methyl-1-(5-methyl-[1,2,4]oxadiazol-3-yl)-ethyl, or 1-(4-methyl-thiazol-2-yl)-cyclobutyl; or pyridin-3-yl, pyridin-2-yl-methyl, pyridin-3-yl-methyl, pyridin-4-yl-methyl, pyrimidin-2-yl-methyl, pyrimidin-4-yl-methyl, pyrazin-2-yl-methyl, 1-(pyridin-2-yl)-ethyl, 1-(pyridin-3-yl)-ethyl, 2-(pyridin-2-yl)-ethyl, 1-methyl-1-(pyridin-2-yl)-ethyl, 1-(pyrazin-2-yl)-ethyl, 1-(pyrimidin-4-yl)-ethyl, 1-(5-fluoro-pyrimidin-2-yl)-ethyl, 1-(3-fluoro-pyridin-2-yl)-ethyl, 1-(5-fluoro-pyridin-2-yl)-ethyl, 1-(6-methyl-pyridin-2-yl)-ethyl, 2-hydroxy-1-(pyridin-2-yl)-ethyl, 1-(1-oxy-pyridin-2-yl)-ethyl, 1-(pyridin-2-yl)-cyclopropyl, 1-(pyridin-4-yl)-cyclopropyl, 1-(pyrazin-2-yl)-cyclopropyl, 1-(pyridazin-3-yl)-cyclopropyl, 1-(pyrimidin-2-yl)-cyclopropyl, 1-(5-fluoro-pyridin-2-yl)-cyclopropyl, 1-(3,5-difluoro-pyridin-2-yl)-ethyl, 2,2,2-trifluoro-1-(pyridin-2-yl)-ethyl, 1-(4,6-dimethyl-pyrimidin-2-yl)-cyclopropyl; or (6-methyl-pyridin-2-yl)-methyl, 1-(pyrimidin-2-yl)-ethyl, 1-methyl-1-(pyrimidin-2-yl)-ethyl, 1-(pyrimidin-4-yl)-cyclopropyl, 2-(pyrimidin-2-yl)-cyclobutyl, 2-(pyrimidin-2-yl)-cyclopentyl, 1-(1-oxy-pyrimidin-2-yl)-cyclopropyl, 1-(3-fluoro-pyridin-2-yl)-cyclopropyl, [1-(pyridin-2-yl)-cyclopropyl]-methyl, 1-(pyridin-2-yl)-cyclobutyl, 1-(1-oxy-pyridin-2-yl)-cyclopropyl, 2-methyl-2-(pyridin-2-yl)-propyl, 2-methyl-2-(3-methyl-pyridin-2-yl)-propyl);

and $R^{N2}$ independently represents hydrogen, $(C_{1-4})$alkyl (especially methyl, ethyl, isopropyl) or $(C_{2-3})$fluoroalkyl (especially 2-fluoro-ethyl);

or $R^{N1}$ and $R^{N2}$ together with the nitrogen atom to which they are attached to form a 4- to 6-membered ring selected from azetidinyl, pyrrolidinyl or piperidinyl; each independently unsubstituted;

or mono-substituted with fluoro, methyl, or hydroxy;

or di-substituted with fluoro;

or mono-substituted with $Ar^4$, wherein $Ar^4$ represents phenyl, or 5- or 6-membered heteroaryl (especially pyridinyl); wherein said phenyl or 5- or 6-membered heteroaryl independently is (especially) unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; or morpholinyl;

(especially such cyclic group $R^{N1}R^{N2}N$— is azetidin-1-yl, pyrrolidin-1-yl, morpholin-4-yl, 3-fluoro-azetidin-1-yl, 3,3-difluoro-azetidin-1-yl, 3-hydroxy-pyrrolidin-1-yl, 3-phenyl-pyrrolidin-1-yl, 3-(pyridin-2-yl)-pyrrolidin-1-yl);

$R^2$ represents hydrogen;

$(C_{1-6})$alkyl (especially ethyl, isopropyl, isobutyl, tert.-butyl, 2,2-dimethylpropyl, 3-methyl-butyl, 3,3-dimethylbutyl);

$(C_{2-6})$alkyl which is mono-substituted with $(C_{1-3})$alkoxy (especially methoxy), or hydroxy (especially 2-hydroxyethyl, 2-methoxy-ethyl, 2-hydroxy-1-methyl-propyl);

$(C_{3-5})$alkenyl (especially allyl);

cyano-methyl;

$(C_{2-3})$fluoroalkyl (especially 3-fluoro-propyl);

$(C_{3-8})$cycloalkyl-$(C_{0-3})$alkyl; wherein the $(C_{3-8})$cycloalkyl is unsubstituted, or mono- or di-substituted wherein the substituents are independently selected from $(C_{1-3})$alkyl (especially methyl), fluoro, hydroxy, hydroxy-$(C_{1-3})$alkyl (especially hydroxy-methyl), $(C_{1-3})$alkoxy (especially methoxy), or $(C_{1-3})$fluoroalkyl (especially difluoromethyl);

(especially cyclobutyl, 2-methylcyclobutyl, 2,2-dimethylcyclobutyl, 3,3-dimethylcyclobutyl, cyclopentyl, cyclohexyl, spiro[2.4]hept-4-yl, spiro[3.3]hept-2-yl, bicyclo[2.2.1]hept-2-yl, 2-methylcyclopentyl, 2-(hydroxymethyl)-cyclopentyl, 3,3-dimethylcyclopentyl, 2-ethylcyclopentyl, 3,3-dimethylcyclohexyl, 2-fluoro-cyclohexyl, 4-fluoro-cyclohexyl, 4,4-difluoro-cyclohexyl, 2-hydroxy-cyclohexyl, 2-methoxy-cyclohexyl, 3-methoxy-cyclohexyl, cyclopropylmethyl, cyclobutylmethyl, cyclopentylmethyl, 1-cyclopropyl-ethyl, (1-methyl-cyclopropyl)-methyl, (1-methyl-cyclobutyl)-methyl, 2-cyclopropyl-ethyl; or (1-fluoro-cyclopropyl)-methyl, spiro[2.3]hex-5-yl, bicyclo[3.1.0]hex-3-yl, 3,3-difluorocyclobutyl, (2,2-difluorocyclopropyl)-methyl, (3,3-difluorocyclobutyl)-methyl, (1-difluoromethyl-cyclopropyl)-methyl);

thietan-3-yl;

$(C_{3-8})$cycloalkenyl-$(C_{1-3})$alkyl (especially cyclopenten-1-yl-methyl); or $Ar^5$—$CH_2$— wherein $Ar^5$ represents phenyl, or 5- or 6-membered heteroaryl (especially pyrrolyl), wherein the phenyl or 5- or 6-membered heteroaryl independently is unsubstituted, or mono- or di-substituted wherein the substituents are independently selected from $(C_{1-4})$alkyl, $(C_{1-4})$alkoxy, halogen, $(C_{1-3})$fluoroalkyl, or $(C_{1-3})$fluoroalkoxy; [especially such group $Ar^5$—$CH_2$— is benzyl wherein the phenyl ring of said benzyl is unsubstituted, or mono- or di-substituted wherein the substituents are independently selected from $(C_{1-4})$alkyl, $(C_{1-4})$alkoxy, halogen, $(C_{1-3})$fluoroalkyl, or $(C_{1-3})$fluoroalkoxy; in particular benzyl wherein the phenyl ring of said benzyl is unsubstituted, or mono-substituted with halogen (especially benzyl, 2-chloro-benzyl, 2-fluoro-benzyl, 4-fluoro-benzyl)]; and $R^3$ represents hydrogen, or methyl (especially hydrogen).

The compounds of formula (I) contain at least two stereogenic centers which are situated in position 3 and 4 of the piperidine moiety. It is understood that the two substituents of the piperidine ring: $R^1$—CO— and —NH—CO—$Ar^1$—$Ar^2$, are in relative trans-configuration (i.e. the relative configuration of said two chiral carbon atoms in position 3 and 4 of the piperidine ring is (3R*,4R*)). Thus, a compound of formula (I) represents either a compound of formula ($I_R$), or a compound of formula ($I_S$), or any mixture thereof:

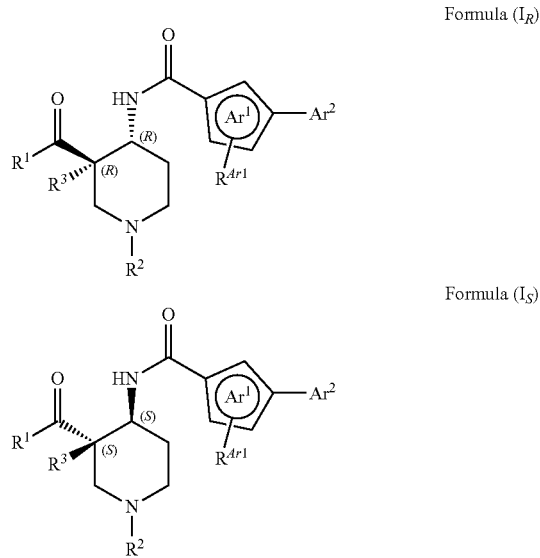

Formula ($I_R$)

Formula ($I_S$)

The relative configuration of stereoisomers is thus denoted as follows:
for example (3R*,4R*)-1-cyclohexyl-4-{[5-(2,4-difluoro-phenyl)-isoxazole-3-carbonyl]-amino}-piperidine-3-carboxylic acid [2-(2-chloro-phenyl)-ethyl]-amide denominates
(3R,4R)-1-Cyclohexyl-4-{[5-(2,4-difluoro-phenyl)-isoxazole-3-carbonyl]-amino}-piperidine-3-carboxylic acid [2-(2-chloro-phenyl)-ethyl]-amide,
(3S,4S)-1-Cyclohexyl-4-{[5-(2,4-difluoro-phenyl)-isoxazole-3-carbonyl]-amino}-piperidine-3-carboxylic acid [2-(2-chloro-phenyl)-ethyl]-amide,
or any mixture of these two enantiomers including the racemate.

In addition, the compounds of formulae (I), ($I_R$), and ($I_S$) may contain one or more further stereogenic or asymmetric centers, such as one or more additional asymmetric carbon atoms. The compounds of formulae (I), ($I_R$), and ($I_S$) may thus be present as mixtures of stereoisomers or preferably as pure stereoisomers. Mixtures of stereoisomers may be separated in a manner known to a person skilled in the art.

In case a particular compound (or generic structure) is designated as (R)- or (S)-enantiomer/as having an absolute (R)- or (S)-configuration, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations (or (R*,R*) designations) are to be understood as referring to the respective stereoisomer of the respective relative configuration in enriched form, especially in essentially pure form.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

In some instances, the compounds of formula (I) may contain tautomeric forms. Such tautomeric forms are encompassed in the scope of the present invention. For example, in case the present compounds contain heteroaromatic aromatic rings containing unsubstituted ring nitrogen atoms having a free valency such as imidazol-2,4-diyl, or [1,2,4]-triazol-3,5-diyl, such rings may be present in tautomeric forms. For example, the group imidazol-2,4-diyl represents the tautomeric forms 1H-imidazol-2,4-diyl and 3H-imidazol-2,4-diyl; and the group [1,2,4]triazol-3,5-diyl represents the tautomeric forms 1H-[1,2,4]triazol-3,5-diyl, 2H-[1,2,4]triazol-3,5-diyl and 4H-[1,2,4]triazol-3,5-diyl.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Deuterated groups are denominated as follows: for example the group (1,1,2,2,2-d$_5$-ethyl) denominates the residue

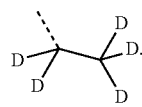

In this patent application, a bond drawn as a dotted line shows the point of attachment of the radical drawn. For example, the radical drawn below

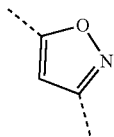

is an isoxazol-3,5-diyl group.

Where the plural form is used for compounds, salts, pharmaceutical compositions, diseases and the like, this is intended to mean also a single compound, salt, or the like.

Any reference to compounds of formula (I) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 19), and 27), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. If not explicitly defined otherwise in the respective embodiment or claim, groups defined herein are unsubstituted.

The term "halogen" means fluorine, chlorine, bromine, or iodine, preferably fluorine or chlorine, especially fluorine.

The term "alkyl", used alone or in combination, refers to a saturated straight or branched chain hydrocarbon group containing one to six (especially one to four) carbon atoms. The term "$(C_{x-y})$alkyl" (x and y each being an integer), refers to an alkyl group as defined before, containing x to y carbon atoms. For example a $(C_{1-6})$alkyl group contains from one to six carbon atoms. Examples of alkyl groups are methyl, ethyl, propyl, isopropyl, n-butyl, isobutyl, sec.-butyl, tert.-butyl, n-pentyl, 1,1-dimethyl-propyl, 2,2-dimethyl-propyl, 3-methyl-butyl, and 1,1,2-trimethyl-propyl. Particular examples of $(C_{1-6})$alkyl groups as used for $R^2$ are ethyl, isopropyl, 2,2-dimethyl-propyl, 3-methyl-butyl and 3,3-dimethyl-butyl. Particular examples of $(C_{1-6})$alkyl groups as used for $R^{N1}$ are methyl, ethyl, isopropyl, isobutyl, tert.-butyl and 1,1,2-trimethyl-propyl. Particular examples of $(C_{1-4})$alkyl groups as used for $R^{N2}$ are methyl, ethyl, and isopropyl, especially methyl. Particular examples of $(C_{1-4})$ alkyl groups which are substituents of $Ar^1$, $Ar^3$ or $Ar^4$ are methyl and ethyl, especially methyl.

Examples of "$(C_{1-6})$alkyl which is mono-substituted with $(C_{1-3})$alkoxy, or hydroxy" as used for $R^2$ are 2-hydroxy-ethyl, 2-hydroxy-propyl, 2-hydroxy-1-methyl-propyl, and 2-methoxy-ethyl.

The term "—$(C_{x-y})$alkylene-", used alone or in combination, refers to bivalently bound alkyl group as defined before containing x to y carbon atoms. Preferably, the points of attachment of any bivalently bound alkyl group are in 1,1-diyl, or in 1,2-diyl arrangement. In case a $(C_{0-y})$alkylene group is used in combination with another substituent, the term means that either said substituent is directly attached to the rest of the molecule (i.e. the $(C_0)$alkyl group represents a direct bond linking said substituent to the rest of the molecule), or it is linked through a $(C_{1-y})$alkylene group to the rest of the molecule. Examples of —$(C_{1-4})$alkylene- are the —$(C_{1-3})$alkylene- groups methylene, ethylene, ethan-1,1-diyl, propan-1,2-diyl, and propan-2,2-diyl, as well as the —$(C_4)$alkylene- group 2-methyl-propan-1,2-diyl. In case a linker group is a —$(C_0)$alkylene- group, such group refers to a direct bond.

Examples of "—$(C_{1-3})$alkylene- which is mono-substituted with hydroxy or trifluoromethyl" as used for $L^2$ are 1-trifluoromethyl-ethan-1,1-diyl, 2-hydroxy-ethan-1,2-diyl, and 2-hydroxy-ethan-1,1-diyl.

The term "alkynyl", used alone or in combination, refers to a straight or branched chain hydrocarbon group containing one to six (especially one to four) carbon atoms wherein said hydrocarbon group contains at least one carbon-carbon triple bond. The term "$(C_{x-y})$alkynyl" (x and y each being an integer), refers to an alkynyl group as defined before, containing x to y carbon atoms. For example a $(C_{2-6})$alkynyl group contains from two to six carbon atoms. An example of an alkynyl group is 1-methyl-prop-2-ynyl.

The term "alkenyl", used alone or in combination, refers to a straight or branched chain hydrocarbon group containing one to six (especially one to four) carbon atoms wherein said hydrocarbon group contains at least one carbon-carbon double bond. The term "$(C_{x-y})$alkenyl" (x and y each being an integer), refers to an alkenyl group as defined before, containing x to y carbon atoms. For example a $(C_{2-6})$alkenyl group contains from two to six carbon atoms. An example of an alkenyl group is allyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. A preferred example is methoxy.

The term "fluoroalkyl" refers to an alkyl group as defined before containing one to five carbon atoms in which one or more (especially 1, 2, or 3; and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include the $(C_1)$fluoroalkyl groups difluoromethyl and trifluoromethyl, as well as the $(C_{2-5})$ fluoroalkyl groups 2-fluoro-ethyl, 2,2-difluoro-ethyl, 2,2,2-trifluoroethyl, 2,2-difluoropropyl, 3,3,3-trifluoropropyl, 2-fluoro-1-methyl-ethyl, 2-fluoro-1,1-dimethyl-ethyl, 2,2-difluoro-1-methyl-ethyl, and 3,3,3-trifluoro-1,1-dimethyl-propyl.

The term "$(C_{x-y})$fluoroalkylene", used alone or in combination, refers to bivalently bound fluoroalkyl group as defined before containing x to y carbon atoms. Preferably, the points of attachment of any bivalently bound fluoroalkyl group are in 1,1-diyl arrangement. An example is 2,2,2-trifluoro-ethan-1,1-diyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. A preferred example is trifluoromethoxy.

The term "cyano" refers to a group —CN.

The term "cycloalkyl", used alone or in combination, refers to a saturated mono- or bicyclic carbocyclic ring containing three to eight carbon atoms, wherein the term "bicyclic cycloalkyl" includes fused, bridged, and spiro-bicyclic cycloalkyl groups. The term "$(C_{x-y})$cycloalkyl" (x and y each being an integer), refers to a cycloalkyl group as defined before containing x to y carbon atoms. For example a $(C_{3-8})$cycloalkyl group contains from three to eight carbon atoms. Examples of cycloalkyl groups are the mono-cyclic cycloalkyl groups cyclopropyl, cyclobutyl, cyclopentyl, cyclohexyl, cycloheptyl and cyclooctyl; as well as bicyclic cycloalkyl groups such as spiro[2.4]hept-4-yl, spiro[3.3]hept-2-yl, bicyclo[2.2.1]hept-2-yl, spiro[2.3]hex-5-yl, and bicyclo[3.1.0]hex-3-yl. Preferred are cyclopropyl, cyclobutyl, cyclopentyl and cyclohexyl.

The term "—$(C_{x-y})$cycloalkylene-", used alone or in combination, refers to bivalently bound cycloalkyl group as defined before containing x to y carbon atoms. Preferably, the points of attachment of any bivalently bound cycloalkyl group are in 1,1-diyl, or in 1,2-diyl arrangement. Examples are cyclopropan-1,1-diyl, cyclopropan-1,2-diyl, cyclobutan-1,1-diyl, and cyclopentan-1,3-diyl; preferred are cyclopropan-1,1-diyl, and cyclobutan-1,1-diyl.

The term "$(C_{x-y})$cycloalkyl, wherein said $(C_{x-y})$cycloalkyl optionally contains one ring oxygen atom", refers to a $(C_{x-y})$cycloalkyl group containing x to y carbon atoms, especially a mono-cyclic $(C_{3-6})$cycloalkyl group, as defined before. In addition, one ring carbon atom of said $(C_{x-y})$cycloalkyl may be replaced by an oxygen atom. Such groups are unsubstituted or substituted as explicitly defined. Examples are especially the $(C_{3-6})$cycloalkyl groups cyclopropyl, cyclobutyl, cyclopentyl, cyclohexyl; as well as oxetanyl, tetrahydrofuranyl, and tetrahydropyranyl. A preferred "$(C_{x-y})$cycloalkylene, wherein said $(C_{x-y})$cycloalkylene optionally contains one ring oxygen atom" is oxetan-3,3-diyl.

The term "$(C_{3-8})$cycloalkyl-$(C_{0-3})$alkyl" refers to a $(C_{3-8})$cycloalkyl group as defined before (i.e. such group may optionally contain ring a oxygen atom as explicitly defined) which group is linked to the rest of the molecule through a $(C_{0-3})$alkylene group as defined before. The $(C_{3-8})$cycloalkyl group part of $(C_{3-8})$cycloalkyl-$(C_{0-3})$alkyl is unsubstituted or substituted as explicitly defined. The $(C_{0-3})$alkylene group part of $(C_{3-8})$cycloalkyl-$(C_{0-3})$alkyl is unsubstituted, or substituted as explicitly defined.

The term "cycloalkenyl", used alone or in combination, refers to a non-aromatic, unsaturated (i.e. containing at least one ring carbon-carbon-double bond) mono- or bicyclic carbocyclic ring containing three to eight carbon atoms, wherein the term "bicyclic cycloalkenyl" includes fused, bridged, and spiro-bicyclic cycloalkenyl groups. The term "$(C_{x-y})$cycloalkenyl" (x and y each being an integer), refers to a cycloalkenyl group as defined before containing x to y carbon atoms. For example a $(C_{3-8})$cycloalkenyl group contains from three to eight carbon atoms. Examples of cycloalkenyl groups are cyclopentenyl, cyclohexenyl, cycloheptenyl and cyclooctenyl; especially cyclopenten-1-yl.

The term "aryl", used alone or in combination, means phenyl or naphthyl, preferably phenyl. Likewise, an arylene group is an aryl group as defined before having two points of attachment to the respective rests of the molecule. The above-mentioned aryl/arylene groups are unsubstituted or substituted as explicitly defined.

For the substituent $Ar^2$ representing "phenyl, wherein said phenyl is mono-, di- or tri-substituted, wherein the substituents are independently selected from fluoro, chloro, methyl, cyano, methoxy, or $(C_1)$fluoroalkyl" particular groups are those where one or two of said substituents is/are independently selected from fluoro, chloro, and methyl, and the remaining, if present, is/are fluoro. Especially $Ar^2$ represents phenyl which is mono-, di- or tri-substituted, wherein the substituents are independently fluoro or chloro; in particular $Ar^2$ represents phenyl which is mono-, di- or tri-substituted with fluoro, or phenyl which is mono-, di- or tri-substituted wherein one substituent is chloro and the remaining substituents, if present, are fluoro. Examples of $Ar^2$ are 2-fluoro-phenyl, 4-fluoro-phenyl, 2,4-difluoro-phenyl, 2,4,6-trifluoro-phenyl, 4-chloro-2-fluoro-phenyl, 2-chloro-4-fluoro-phenyl, 2,4-dichlorophenyl, 2,3,4-trifluoro-phenyl, 2,4-dimethylphenyl, 2-methylphenyl, 3,4-dimethylphenyl, 2,3-difluoro-phenyl, 3,4-difluoro-phenyl, 4-cyano-phenyl, 4-trifluoromethyl-phenyl, 3-trifluoromethyl-phenyl, 2-trifluoromethyl-phenyl, and 2-fluoro-4-methoxy-phenyl. Preferred examples are 2,4-difluoro-phenyl, 2,4,6-trifluoro-phenyl, 2,4-dichlorophenyl, 2,3,4-trifluoro-phenyl, and 2,4-dimethylphenyl (especially 2,4-difluoro-phenyl).

For the substituent $Ar^3$ representing phenyl, the phenyl is unsubstituted, or substituted as explicitly defined. Examples are phenyl, 2-chloro-phenyl, 4-fluoro-phenyl, 2-methyl-phenyl, 3-methyl-phenyl, 4-methyl-phenyl, and 2-methoxy-phenyl; as well as 3-bromo-phenyl, 3-chloro-phenyl, 4-fluoro-phenyl, 3-fluoro-phenyl, 2-fluoro-phenyl, 2-hydroxy-phenyl, 2-methoxy-phenyl, 4-chloro-phenyl, 3-methoxy-phenyl, and 2-trifluoromethyl-phenyl.

The term "aryl-$(C_{x-y})$alkyl" refers to an aryl group as defined before which is linked to the rest of the molecule through a $(C_{x-y})$alkylene group as defined before. The aryl group part of aryl-$(C_{x-y})$alkyl is unsubstituted or substituted as explicitly defined. The $(C_{x-y})$alkylene group part of aryl-$(C_{x-y})$alkyl is unsubstituted, or substituted as explicitly defined.

The term "aryl-$(C_{x-y})$cycloalkyl" refers to an aryl group as defined before which is linked to the rest of the molecule through a $(C_{x-y})$cycloalkylene group as defined before. The aryl group part of aryl-$(C_{x-y})$cycloalkyl is unsubstituted or substituted as explicitly defined. The $(C_{x-y})$cycloalkylene group part of aryl-$(C_{x-y})$cycloalkyl is unsubstituted, or substituted as explicitly defined.

The term "heteroaryl", used alone or in combination, means a 5- to 10-membered monocyclic or bicyclic aromatic ring containing one to a maximum of four heteroatoms (notably containing one to a maximum of three heteroatoms), each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. Likewise, a heteroarylene group is a heteroaryl group as defined before having two points of attachment to the respective rests of the molecule. The above-mentioned heteroaryl/heteroarylene groups are unsubstituted or substituted as explicitly defined.

For the group $Ar^1$ representing a 5-membered heteroarylene, the term means a 5-membered heteroarylene group as defined above (wherein said 5-membered heteroarylene notably contains one to a maximum of three heteroatoms); which is bound to the rest of the molecule as explicitly defined. The term "meta arrangement" in the context of a heteroarylene group such as $Ar^1$ means that the respective substituents are attached in a relative 1,3-arrangement. Examples of $Ar^1$ representing 5-membered heteroarylene are especially 5-membered heteroarylene groups containing one to a maximum of three heteroatoms, each independently selected from oxygen, nitrogen and sulfur (especially 5-membered heteroarylene containing one to a maximum of three heteroatoms, each independently selected from oxygen and nitrogen; or 5-membered heteroarylene containing one sulfur ring atom and one to a maximum of two nitrogen ring atoms); notably oxazol-diyl, isoxazol-diyl, oxadiazol-diyl, or triazol-diyl; or thiadiazol-diyl, or isothiazol-diyl; in particular oxazol-2,5-diyl, oxazol-2,4-diyl, isoxazol-3,5-diyl, [1,3,4]oxadiazol-2,5-diyl, [1,2,4]oxadiazol-3,5-diyl, or 1H-[1,2,3]triazol-1,4-diyl; or [1,3,4]thiadiazol-2,5-diyl, or isothiazol-3,5-diyl. Preferred examples of $Ar^1$ representing a 5-membered heteroarylene group are oxazol-2,5-diyl wherein the substituent $Ar^2$ is attached to the carbon atom in position 5; oxazol-2,4-diyl wherein the substituent $Ar^2$ is attached to the carbon atom in position 4; isoxazol-3,5-diyl wherein the substituent $Ar^2$ is attached to the carbon atom in position 5; isoxazol-3,5-diyl wherein the substituent $Ar^2$ is attached to the carbon atom in position 3; [1,3,4]oxadiazol-2,5-diyl; [1,2,4]oxadiazol-3,5-diyl wherein the substituent $Ar^2$ is attached to the carbon atom in position 5; 1H-[1,2,3]triazol-1,4-diyl wherein the substituent $Ar^2$ is attached to the nitrogen atom in position 1; [1,3,4]thiadiazol-2,5-diyl; and isothiazol-3,5-diyl wherein the substituent $Ar^2$ is attached to the carbon atom in position 5.

For the substituent $Ar^2$ representing "6-membered heteroaryl, wherein said 6-membered heteroaryl independently is mono-, di- or tri-substituted, wherein two of said the substituents are independently selected from fluoro, chloro, methyl, cyano, methoxy, or $(C_1)$fluoroalkyl; and the remaining substituent, if present, is fluoro", examples are especially pyridinyl groups which are mono-, or di-substituted with fluoro. An example is 5-fluoro-pyridin-2-yl.

For the substituent $Ar^3$ representing 5- or 6-membered heteroaryl, the term means 5- or 6-membered heteroaryl groups as defined above. Examples of $Ar^3$ representing 6-membered heteroaryl are pyrimidinyl, pyridinyl, pyridazinyl, and pyrazinyl. For avoidance of doubt, the term 6-membered heteroaryl as used for the substituent $Ar^3$ in addition comprises the groups 1-oxy-pyridinyl, and 1-oxy-pyrimidinyl. Particular examples are pyrazin-2-yl, pyridazin-3-yl, pyrimidin-2-yl, pyrimidin-4-yl, pyridin-2-yl, pyridin-3-yl, and pyridin-4-yl; as well as the N-oxides 1-oxy-pyrimidin-2-yl and 1-oxy-pyridin-2-yl. The 6-membered heteroaryl groups as used for the substituent $Ar^3$ are preferably unsubstituted; or said groups are substituted as explicitly defined (especially mono- or disubstituted wherein the substituents are independently selected from fluoro or methyl). Examples of $Ar^3$ representing 5-membered heteroaryl are oxazolyl, isoxazolyl, thiazolyl, imidazolyl, pyrazolyl, oxadiazolyl, and triazolyl; in particular oxazol-5-yl, isoxazol-3-yl, isoxazol-5-yl, thiazol-2-yl, thiazol-5-yl, thiazol-4-yl, imidazol-4-yl, 2H-pyrazol-3-yl, 1H-pyrazol-3-yl, 2H-pyrazol-3-yl, 1H-pyrazol-4-yl, [1,2,4]oxadiazol-3-yl, [1,2,4]oxadiazol-5-yl, [1,3,4]oxadiazol-2-yl, and 1H-[1,2,4]triazol-3-yl. The 5-membered heteroaryl groups as used for the substituent $Ar^3$ are unsubstituted; or said groups are substituted as explicitly defined (especially mono- or disubstituted wherein the substituents are independently selected from methyl or ethyl).

An example of $Ar^4$ representing 5- or 6-membered heteroaryl is pyridinyl.

An example of $Ar^5$—$CH_2$— wherein $Ar^5$ represents 5- or 6-membered heteroaryl is (1-methyl-pyrrol-3-yl)-methyl.

The term "heteroaryl-$(C_{x-y})$alkyl" refers to a heteroaryl group as defined before which is linked to the rest of the molecule through a $(C_{x-y})$alkylene group as defined before. The heteroaryl group part of heteroaryl-$(C_{x-y})$alkyl is unsubstituted or substituted as explicitly defined. The $(C_{x-y})$alkylene group part of heteroaryl-$(C_{x-y})$alkyl is unsubstituted, or substituted as explicitly defined.

The term "heteroaryl-$(C_{x-y})$cycloalkyl" refers to a heteroaryl group as defined before which is linked to the rest of the molecule through a $(C_{x-y})$cycloalkylene group as defined before. The heteroaryl group part of heteroaryl-$(C_{x-y})$cycloalkyl is unsubstituted or substituted as explicitly defined. The $(C_{x-y})$cycloalkylene group part of heteroaryl-$(C_{x-y})$cycloalkyl is unsubstituted, or substituted as explicitly defined.

Further embodiments of the invention are presented hereinafter:

2) A further embodiment relates to the compounds of formula (I) according to embodiment 1) which are also compounds of Formula ($I_R$), wherein the two substituents of the piperidine ring: $R^1$—CO— and —NH—CO—$Ar^1$—$Ar^2$, are in relative trans-configuration, wherein the absolute configuration of the two chiral carbon atoms in position 3 and 4 of the piperidine ring is (3R,4R):

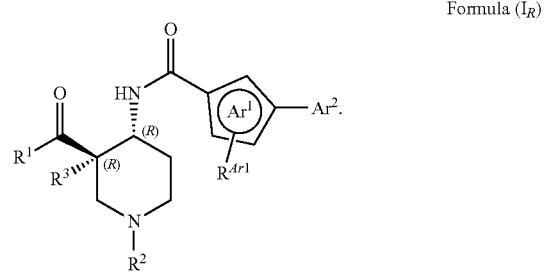

Formula ($I_R$)

3) A further embodiment relates to the compounds of formula (I) according to embodiment 1) which are also compounds of Formula ($I_S$), wherein the two substituents of the piperidine ring: $R^1$—CO— and —NH—CO—$Ar^1$—$Ar^2$, are in relative trans-configuration, wherein the absolute configuration of the two chiral carbon atoms in position 3 and 4 of the piperidine ring is (3S,4S):

Formula (I_S)

[Chemical structure diagram showing Formula (I_S) with R¹, R³, Ar¹, R^Ar1, Ar², R², and stereochemistry markers (S)]

4) A further embodiment relates to the compounds according to any one of embodiments 1) to 3), wherein $R^3$ represents hydrogen.

5) A further embodiment relates to the compounds of formula (I) according to any one of embodiments 1) to 4), wherein $Ar^1$ represents a 5-membered heteroarylene group (especially a 5-membered heteroarylene containing one to a maximum of three heteroatoms, each independently selected from oxygen and nitrogen (notably oxazol-diyl, isoxazol-diyl, oxadiazol-diyl, or triazol-diyl); or a 5-membered heteroarylene containing one sulfur ring atom and one or two nitrogen ring atoms (notably isothiazolyl, or thiadiazol-diyl)), wherein the —NH—CO— group and $Ar^2$ are attached in meta arrangement to ring atoms of $Ar^1$; wherein said 5-membered heteroarylene is unsubstituted.

6) A further embodiment relates to the compounds of formula (I) according to any one of embodiments 1) to 4), wherein $Ar^1$ represents a 5-membered heteroarylene group selected from oxazol-diyl, isoxazol-diyl, oxadiazol-diyl, or triazol-diyl, wherein the —NH—CO— group and $Ar^2$ are attached in meta arrangement to ring atoms of $Ar^1$; wherein said 5-membered heteroarylene is unsubstituted, or mono-substituted with $R^{Ar1}$; wherein $R^{Ar1}$ represents methyl, methoxy, fluorine, chlorine, trifluoromethyl, or trifluoromethoxy (especially said 5-membered heteroarylene is unsubstituted).

7) A further embodiment relates to the compounds of formula (I) according to any one of embodiments 1) to 4), wherein $Ar^1$ represents a 5-membered heteroarylene group selected from oxazol-2,5-diyl, oxazol-2,4-diyl, isoxazol-3,5-diyl, [1,3,4]oxadiazol-2,5-diyl, [1,2,4]oxadiazol-3,5-diyl, 1H-[1,2,3]triazol-1,4-diyl, [1,3,4]thiadiazol-2,5-diyl, or isothiazol-3,5-diyl; wherein said 5-membered heteroarylene is unsubstituted [especially $Ar^1$ represents a 5-membered heteroarylene group selected from oxazol-2,5-diyl wherein the substituent $Ar^2$ is attached to the carbon atom in position 5; oxazol-2,4-diyl wherein the substituent $Ar^2$ is attached to the carbon atom in position 4; isoxazol-3,5-diyl wherein the substituent $Ar^2$ is attached to the carbon atom in position 5; isoxazol-3,5-diyl wherein the substituent $Ar^2$ is attached to the carbon atom in position 3; [1,3,4]oxadiazol-2,5-diyl; [1,2,4]oxadiazol-3,5-diyl wherein the substituent $Ar^2$ is attached to the carbon atom in position 5; 1H-[1,2,3]triazol-1,4-diyl wherein the substituent $Ar^2$ is attached to the nitrogen atom in position 1; [1,3,4]thiadiazol-2,5-diyl; or isothiazol-3,5-diyl wherein the substituent $Ar^2$ is attached to the carbon atom in position 5].

8) A further embodiment relates to the compounds of formula (I) according to any one of embodiments 1) to 4), wherein $Ar^1$ represents (preferably) unsubstituted isoxazol-3,5-diyl, wherein the substituent $Ar^2$ is attached to the carbon atom in position 5; or $Ar^1$ represents [1,3,4]thiadiazol-2,5-diyl.

9) A further embodiment relates to the compounds of formula (I) according to any one of embodiments 1) to 8), wherein $Ar^2$ represents phenyl which is mono-, di- or tri-substituted; wherein one or two of said substituents is/are independently selected from fluoro, chloro, and methyl, and the remaining, if present, is/are fluoro (especially 2,4-difluoro-phenyl).

In a sub-embodiment, $Ar^2$ represents phenyl which is mono-, di- or tri-substituted, wherein the substituents are independently fluoro or chloro; in particular $Ar^2$ represents phenyl which is mono-, di- or tri-substituted with fluoro (especially 2,4-difluoro-phenyl).

10) A further embodiment relates to the compounds of formula (I) according to any one of embodiments 1) to 8), wherein $Ar^2$ represents 2-fluoro-phenyl, 4-fluoro-phenyl, 2,4-difluoro-phenyl, 2,4,6-trifluoro-phenyl, 4-chloro-2-fluoro-phenyl, 2-chloro-4-fluoro-phenyl, 2,4-dichlorophenyl, 2,3,4-trifluoro-phenyl, 2,4-dimethylphenyl, 2-methylphenyl, 3,4-dimethylphenyl, 2,3-difluoro-phenyl, 3,4-difluoro-phenyl, 4-cyano-phenyl, 4-trifluoromethyl-phenyl, 3-trifluoromethyl-phenyl, 2-trifluoromethyl-phenyl, or 2-fluoro-4-methoxy-phenyl. In a sub-embodiment, $Ar^2$ represents 2-fluoro-phenyl, 4-fluoro-phenyl, 2,4-difluoro-phenyl, 2,4,6-trifluoro-phenyl, 4-chloro-2-fluoro-phenyl, or 2-chloro-4-fluoro-phenyl (especially $Ar^2$ represents 2,4-difluoro-phenyl).

11) A further embodiment relates to the compounds of formula (I) according to any one of embodiments 1) to 10), wherein $R^1$ represents $R^{N1}R^{N2}N—$, wherein
$R^{N1}$ represents
  $(C_{1-6})$alkyl (especially methyl, ethyl, isopropyl, isobutyl, tert.-butyl, 1,2,2-trimethyl-propyl);
  $(C_{1-6})$alkyl which is mono-substituted with
    hydroxy;
    $(C_{1-3})$alkoxy (especially methoxy, ethoxy);
    2-hydroxy-ethoxy;
    —CO—NH$_2$;
    —SO$_2$—$(C_{1-3})$alkyl (especially methanesulfonyl);
    cyano;
    $(C_{1-3})$fluoroalkoxy (especially trifluoromethoxy);
    —NR$^{N3}$R$^{N4}$, wherein R$^{N3}$ and R$^{N4}$ independently represent hydrogen or $(C_{1-4})$alkyl (especially —NR$^{N3}$R$^{N4}$ represents dimethylamino);
  (especially such group RN' being mono-substituted $(C_{1-6})$alkyl is 2-hydroxy-ethyl, 2-hydroxy-1-methyl-ethyl, 2-hydroxy-1,1-dimethyl-ethyl, 2-methoxy-ethyl, 3-methoxy-propyl, 2-ethoxy-ethyl, 2-ethoxy-1-methyl-ethyl, 2-methoxy-1,1-dimethyl-ethyl, 3-methoxy-1,1-dimethyl-propyl, 2-(2-hydroxy-ethoxy)-ethyl, carbamoyl-methyl, 2-methanesulfonyl-1,1-dimethyl-ethyl, 1-cyano-1-methyl-ethyl, 2-dimethylamino-ethyl, 2-trifluoromethoxy-ethyl);
  $(C_{2-6})$alkynyl (especially 1-methyl-prop-2-ynyl);
  $(C_{2-5})$fluoroalkyl (especially 2-fluoro-ethyl, 2,2-difluoro-ethyl, 2-fluoro-1-methyl-ethyl, 2-fluoro-1,1-dimethyl-ethyl, 2,2-difluoro-1-methyl-ethyl, 3,3,3-trifluoro-1,1-dimethyl-propyl);
  2-(2-oxo-pyrrolidin-1-yl)-ethyl;
  a group -L$^1$-Cy$^1$; wherein
    L$^1$ represents a direct bond, —$(C_{1-3})$alkylene-, or —$(C_{3-5})$cycloalkylene-; and
    Cy$^1$ represents $(C_{3-6})$cycloalkyl, wherein said $(C_{3-6})$cycloalkyl optionally contains one ring oxygen atom; wherein said $(C_{3-6})$cycloalkyl independently is unsubstituted; or mono-substituted with fluoro, methyl, hydroxy, —CO—$(C_{1-4})$alkoxy, or cyano; or di-substituted with fluoro, or tri-substituted with methyl and two fluoro;
(especially such group -L$^1$-Cy$^1$ is cyclopropyl, cyclopentyl, 1-methyl-cyclopropyl, 1-methyl-cyclobutyl, 1-cyclopropyl-cyclopropan-1-yl, 1-cyclobutyl-ethyl, 3-methyl-tetrahydrofuran-3-yl, tetrahydrofuran-3-yl-methyl, tetrahydrofuran-2-yl-methyl, 1-tetrahydrofuran-2-yl-ethyl, oxetan-3-yl-methyl, 3,3-difluoro-1-methyl-cyclobutyl, 1-(ethoxycarbonyl)-cyclopropyl, or 1-cyano-cyclobutyl);

a group -L$^2$-Ar$^3$, wherein
  L$^2$ represents a —(C$_{1-4}$)alkylene-; —(C$_{3-5}$)cycloalkylene- wherein said (C$_{3-5}$)cycloalkylene optionally contains one ring oxygen atom; *—(C$_{3-5}$)cycloalkylene-(C$_{1-2}$)alkylene- wherein said (C$_{3-5}$)cycloalkylene optionally contains one ring oxygen atom, wherein the asterisk indicates the bond to which Ar$^3$ is attached; *—(C$_{1-2}$)alkylene-(C$_{3-5}$)cycloalkylene- wherein said (C$_{3-5}$)cycloalkylene optionally contains one ring oxygen atom, wherein the asterisk indicates the bond to which Ar$^3$ is attached; or —(C$_{1-3}$)alkylene- which is mono-substituted with hydroxy or trifluoromethyl; and
  Ar$^3$ represents phenyl, or 5-membered heteroaryl containing one oxygen atom and one or two nitrogen atoms, or 6-membered heteroaryl containing one or two nitrogen atoms; wherein said phenyl or 5- or 6-membered heteroaryl independently is unsubstituted, or mono-, or di-substituted; wherein the substituents are independently selected from (C$_{1-4}$)alkyl, (C$_{1-4}$)alkoxy, halogen, (C$_{1-3}$)fluoroalkyl, or (C$_{1-3}$)fluoroalkoxy; wherein, in case Ar$^3$ represents 6-membered heteroaryl which is pyridyl or pyrimidinyl, such pyridyl or pyrimidinyl may additionally be present in form of the respective N-oxide;
(especially such group -L$^2$-Ar$^3$ is benzyl, 1-phenyl-ethyl, 2-phenyl-ethyl, 2-(2-chloro-phenyl)-ethyl, 2-(4-fluoro-phenyl)-ethyl, 2-(2-methyl-phenyl)-ethyl, 2-(3-methyl-phenyl)-ethyl, 2-(4-methyl-phenyl)-ethyl, 2-(2-methoxy-phenyl)-ethyl, 2-phenyl-propyl, 2-hydroxy-1-phenyl-ethyl, 2-hydroxy-2-phenyl-ethyl, 2-phenyl-cyclopropyl; or 1-(3-bromo-phenyl)-ethyl, 1-phenyl-cyclopropyl, 1-phenyl-cyclobutyl, 2-phenyl-cyclobutyl, 1-(3-chloro-phenyl)-cyclopropyl, 1-(4-fluoro-phenyl)-cyclopropyl, 1-(3-fluoro-phenyl)-cyclopropyl, 1-(2-fluoro-phenyl)-cyclopropyl, 1-(2-methyl-phenyl)-cyclopropyl, 1-(2-hydroxy-phenyl)-cyclopropyl, 1-(2-methoxy-phenyl)-ethyl, 2-methyl-2-(2-chloro-phenyl)-propyl, 1-(4-chloro-phenyl)-cyclopropyl-methyl, 3-(3-chloro-phenyl)-oxetan-3-yl, 3-(4-fluoro-phenyl)-oxetan-3-yl, 3-(phenyl)-oxetan-3-yl-methyl, 3-(benzyl)-oxetan-3-yl, 1-(2-methoxy-phenyl)-cyclopropyl, 1-(3-methoxy-phenyl)-cyclopropyl, 1-(2-trifluoromethyl-phenyl)-cyclopropyl; or
oxazol-5-yl-methyl, 1-([1,2,4]oxadiazol-3-yl)-ethyl, 1-(isoxazol-3-yl)-ethyl, 3-methyl-isoxazol-5-yl-methyl, 5-methyl-isoxazol-3-yl-methyl, (3-ethyl-([1,2,4]oxadiazol-5-yl)-methyl, 1-(5-methyl-([1,3,4]oxadiazol-2-yl)-ethyl, 1-methyl-1-(5-methyl-[1,2,4]oxadiazol-3-yl)-ethyl;
pyridin-2-yl-methyl, pyridin-3-yl-methyl, pyridin-4-yl-methyl, pyrimidin-2-yl-methyl, pyrimidin-4-yl-methyl, pyrazin-2-yl-methyl, 1-(pyridin-2-yl)-ethyl, 1-(pyridin-3-yl)-ethyl, 2-(pyridin-2-yl)-ethyl, 1-methyl-1-(pyridin-2-yl)-ethyl, 1-(pyrazin-2-yl)-ethyl, 1-(pyrimidin-4-yl)-ethyl, 1-(5-fluoro-pyrimidin-2-yl)-ethyl, 1-(3-fluoro-pyridin-2-yl)-ethyl, 1-(5-fluoro-pyridin-2-yl)-ethyl, 1-(6-methyl-pyridin-2-yl)-ethyl, 2-hydroxy-1-(pyridin-2-yl)-ethyl, 1-(1-oxy-pyridin-2-yl)-ethyl, 1-(pyridin-2-yl)-cyclopropyl, 1-(pyridin-4-yl)-cyclopropyl, 1-(pyrazin-2-yl)-cyclopropyl, 1-(pyridazin-3-yl)-cyclopropyl, 1-(pyrimidin-2-yl)-cyclopropyl, 1-(5-fluoro-pyridin-2-yl)-cyclopropyl, 1-(3,5-difluoro-pyridin-2-yl)-ethyl, 2,2,2-trifluoro-1-(pyridin-2-yl)-ethyl, 1-(4,6-dimethyl-pyrimidin-2-yl)-cyclopropyl; or (6-methyl-pyridin-2-yl)-methyl, 1-(pyrimidin-2-yl)-ethyl, 1-methyl-1-(pyrimidin-2-yl)-ethyl, 1-(pyrimidin-4-yl)-cyclopropyl, 2-(pyrimidin-2-yl)-cyclobutyl, 2-(pyrimidin-2-yl)-cyclopentyl, 1-(1-oxy-pyrimidin-2-yl)-cyclopropyl, 1-(3-fluoro-pyridin-2-yl)-cyclopropyl, [1-(pyridin-2-yl)-cyclopropyl]-methyl, 1-(pyridin-2-yl)-cyclobutyl, 1-(1-oxy-pyridin-2-yl)-cyclopropyl, 2-methyl-2-(pyridin-2-yl)-propyl, 2-methyl-2-(3-methyl-pyridin-2-yl)-propyl);

and R$^{N2}$ independently represents hydrogen, or (C$_{1-4}$) alkyl (especially methyl, ethyl, isopropyl).

12) A further embodiment relates to the compounds of formula (I) according to any one of embodiments 1) to 10), wherein R$^1$ represents R$^{N1}$R$^{N2}$N—, wherein
  R$^{N1}$ represents
    (C$_{3-6}$)cycloalkyl, wherein said (C$_{3-6}$)cycloalkyl optionally contains one ring oxygen atom; wherein said (C$_{3-6}$)cycloalkyl independently is unsubstituted, or mono-substituted with fluoro, methyl, or hydroxy, or di-substituted with fluoro, or tri-substituted with methyl and two fluoro (especially cyclopropyl, cyclopentyl, 1-methyl-cyclopropyl, 1-methyl-cyclobutyl, 3-methyl-tetrahydrofuran-3-yl, 3,3-difluoro-1-methyl-cyclobutyl);
    (C$_{3-6}$)cycloalkyl-(C$_{1-3}$)alkylene-, wherein said (C$_{3-6}$)cycloalkyl optionally contains one ring oxygen atom (especially 1-cyclobutyl-ethyl, tetrahydrofuran-3-yl-methyl, tetrahydrofuran-2-yl-methyl, 1-tetrahydrofuran-2-yl-ethyl, oxetan-3-yl-methyl);
    (C$_{3-6}$)cycloalkyl-(C$_{3-5}$)cycloalkylene- (especially 1-cyclopropyl-cyclopropan-1-yl);
    phenyl-(C$_{1-4}$)alkylene- wherein said phenyl is unsubstituted, or mono-, or di-substituted; wherein the substituents are independently selected from (C$_{1-4}$) alkyl, (C$_{1-4}$)alkoxy, halogen, (C$_{1-3}$)fluoroalkyl, or (C$_{1-3}$)fluoroalkoxy; (especially such group is benzyl, 1-phenyl-ethyl, 2-phenyl-ethyl, 2-(2-chloro-phenyl)-ethyl, 2-(4-fluoro-phenyl)-ethyl, 2-(2-methyl-phenyl)-ethyl, 2-(3-methyl-phenyl)-ethyl, 2-(4-methyl-phenyl)-ethyl, 2-(2-methoxy-phenyl)-ethyl, 2-phenyl-propyl; or 1-(3-bromo-phenyl)-ethyl, 1-(2-methoxy-phenyl)-ethyl, 2-methyl-2-(2-chloro-phenyl)-propyl);
    phenyl-(C$_{1-3}$)alkylene- wherein said —(C$_{1-3}$)alkylene- is mono-substituted with hydroxy (especially 2-hydroxy-2-phenyl-ethyl, 2-hydroxy-1-phenyl-ethyl);
    phenyl-(C$_{3-5}$)cycloalkylene- wherein said (C$_{3-5}$)cycloalkylene optionally contains one ring oxygen atom, and wherein said phenyl is unsubstituted, or mono-, or di-substituted; wherein the substituents are independently selected from (C$_{1-4}$)alkyl, (C$_{1-4}$) alkoxy, halogen, hydroxy, (C$_{1-3}$)fluoroalkyl, or (C$_{1-3}$)fluoroalkoxy; (especially 2-phenyl-cyclopropyl, 1-phenyl-cyclopropyl, 1-phenyl-cyclobutyl, 2-phenyl-cyclobutyl, 1-(3-chloro-phenyl)-cyclopropyl, 1-(4-fluoro-phenyl)-cyclopropyl, 1-(3-fluoro-phenyl)-cyclopropyl, 1-(2-fluoro-phenyl)-cyclopropyl, 1-(2-methyl-phenyl)-cyclopropyl, 1-(2-hydroxy-phenyl)-cyclopropyl, 3-(3-chloro-phenyl)-oxetan-3-yl, 3-(4-fluoro-phenyl)-oxetan-3-yl, 1-(2-methoxy-phenyl)-cyclopropyl, 1-(3-methoxy-phenyl)-cyclopropyl, 1-(2-trifluoromethyl-phenyl)-cyclopropyl);

phenyl-($C_{3-5}$)cycloalkylene-($C_{1-2}$)alkylene- wherein said ($C_{3-5}$)cycloalkylene optionally contains one ring oxygen atom, and wherein said phenyl is unsubstituted, or mono-substituted with halogen (especially 1-(4-chloro-phenyl)-cyclopropyl-methyl, 3-(phenyl)-oxetan-3-yl-methyl);

phenyl-($C_{1-2}$)alkylene-($C_{3-5}$)cycloalkylene- wherein said ($C_{3-5}$)cycloalkylene optionally contains one ring oxygen atom (especially 3-(benzyl)-oxetan-3-yl);

5-membered heteroaryl-($C_{1-3}$)alkylene-, wherein said 5-membered heteroaryl contains one oxygen atom and one or two nitrogen atoms; and wherein said 5-membered heteroaryl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; (especially oxazol-5-yl-methyl, 1-([1,2,4]oxadiazol-3-yl)-ethyl, 1-(isoxazol-3-yl)-ethyl, 3-methyl-isoxazol-5-yl-methyl, 5-methyl-isoxazol-3-yl-methyl, (3-ethyl-([1,2,4]oxadiazol-5-yl)-methyl, 1-(5-methyl-([1,3,4]oxadiazol-2-yl)-ethyl, 1-methyl-1-(5-methyl-[1,2,4]oxadiazol-3-yl)-ethyl);

6-membered heteroaryl-($C_{1-4}$)alkylene-, wherein said 6-membered heteroaryl contains one or two nitrogen atoms; and wherein said 6-membered heteroaryl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; wherein, in case Ar$^3$ represents pyridyl or pyrimidinyl, such pyridyl or pyrimidinyl may additionally be present in form of the respective N-oxide; (especially pyridin-2-yl-methyl, pyridin-3-yl-methyl, pyridin-4-yl-methyl, pyrimidin-2-yl-methyl, pyrimidin-4-yl-methyl, pyrazin-2-yl-methyl, 1-(pyridin-2-yl)-ethyl, 1-(pyridin-3-yl)-ethyl, 2-(pyridin-2-yl)-ethyl, 1-methyl-1-(pyridin-2-yl)-ethyl, 1-(pyrazin-2-yl)-ethyl, 1-(pyrimidin-4-yl)-ethyl, 1-(5-fluoro-pyrimidin-2-yl)-ethyl, 1-(3-fluoro-pyridin-2-yl)-ethyl, 1-(5-fluoro-pyridin-2-yl)-ethyl, 1-(6-methyl-pyridin-2-yl)-ethyl, 1-(3,5-difluoro-pyridin-2-yl)-ethyl, (6-methyl-pyridin-2-yl)-methyl, 1-(pyrimidin-2-yl)-ethyl, 1-methyl-1-(pyrimidin-2-yl)-ethyl, 2-methyl-2-(pyridin-2-yl)-propyl, 2-methyl-2-(3-methyl-pyridin-2-yl)-propyl);

6-membered heteroaryl-($C_{1-3}$)alkylene-, wherein said —($C_{1-3}$)alkylene- is mono-substituted with hydroxy or trifluoromethyl; wherein said 6-membered heteroaryl contains one or two nitrogen atoms; (especially 2-hydroxy-1-(pyridin-2-yl)-ethyl, 2,2,2-trifluoro-1-(pyridin-2-yl)-ethyl);

6-membered heteroaryl-($C_{3-5}$)cycloalkylene-, wherein said 6-membered heteroaryl contains one or two nitrogen atoms; and wherein said 6-membered heteroaryl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; wherein, in case Ar$^3$ represents pyridyl or pyrimidinyl, such pyridyl or pyrimidinyl may additionally be present in form of the respective N-oxide (especially 1-(pyridin-2-yl)-cyclopropyl, 1-(pyridin-4-yl)-cyclopropyl, 1-(pyrazin-2-yl)-cyclopropyl, 1-(pyridazin-3-yl)-cyclopropyl, 1-(pyrimidin-2-yl)-cyclopropyl, 1-(5-fluoro-pyridin-2-yl)-cyclopropyl, 1-(4,6-dimethyl-pyrimidin-2-yl)-cyclopropyl, 1-(pyrimidin-4-yl)-cyclopropyl, 2-(pyrimidin-2-yl)-cyclobutyl, 2-(pyrimidin-2-yl)-cyclopentyl, 1-(1-oxy-pyrimidin-2-yl)-cyclopropyl, 1-(3-fluoro-pyridin-2-yl)-cyclopropyl, 1-(pyridin-2-yl)-cyclobutyl, 1-(1-oxy-pyridin-2-yl)-cyclopropyl);

6-membered heteroaryl-($C_{3-5}$)cycloalkylene-($C_{1-2}$)alkylene- wherein said 6-membered heteroaryl contains one or two nitrogen atoms; and wherein said 6-membered heteroaryl is unsubstituted; (especially [1-(pyridin-2-yl)-cyclopropyl]-methyl);

and $R^{N2}$ independently represents hydrogen (preferred), or ($C_{1-4}$)alkyl (especially methyl, ethyl, isopropyl);

or $R^{N1}$ represents ($C_{1-3}$)alkyl (especially methyl, ethyl); and $R^{N2}$ represents hydrogen, or methyl.

13) A further embodiment relates to the compounds of formula (I) according to any one of embodiments 1) to 10), wherein $R^1$ represents $R^{N1}R^{N2}N$—, wherein $R^{N1}$ represents ($C_{3-6}$)cycloalkyl-($C_{1-3}$)alkylene-, wherein said ($C_{3-6}$)cycloalkyl optionally contains one ring oxygen atom (especially 1-cyclobutyl-ethyl, tetrahydrofuran-3-yl-methyl, tetrahydrofuran-2-yl-methyl, 1-tetrahydrofuran-2-yl-ethyl, oxetan-3-yl-methyl);

phenyl-($C_{1-4}$)alkylene- wherein said phenyl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; (especially such group is benzyl, 1-phenyl-ethyl, 2-phenyl-ethyl, 2-(2-chloro-phenyl)-ethyl, 2-(4-fluoro-phenyl)-ethyl, 2-(2-methyl-phenyl)-ethyl, 2-(3-methyl-phenyl)-ethyl, 2-(4-methyl-phenyl)-ethyl, 2-(2-methoxy-phenyl)-ethyl, 2-phenyl-propyl; or 1-(3-bromo-phenyl)-ethyl, 1-(2-methoxy-phenyl)-ethyl, 2-methyl-2-(2-chloro-phenyl)-propyl);

phenyl-($C_{3-5}$)cycloalkylene- wherein said ($C_{3-5}$)cycloalkylene optionally contains one ring oxygen atom, and wherein said phenyl is unsubstituted, or mono-, or di-substituted; wherein the substituents are independently selected from ($C_{1-4}$)alkyl, ($C_{1-4}$)alkoxy, halogen, hydroxy, ($C_{1-3}$)fluoroalkyl, or ($C_{1-3}$)fluoroalkoxy; (especially 2-phenyl-cyclopropyl, 1-phenyl-cyclopropyl, 1-phenyl-cyclobutyl, 2-phenyl-cyclobutyl, 1-(3-chloro-phenyl)-cyclopropyl, 1-(4-fluoro-phenyl)-cyclopropyl, 1-(3-fluoro-phenyl)-cyclopropyl, 1-(2-fluoro-phenyl)-cyclopropyl, 1-(2-methyl-phenyl)-cyclopropyl, 1-(2-hydroxy-phenyl)-cyclopropyl, 3-(3-chloro-phenyl)-oxetan-3-yl, 3-(4-fluoro-phenyl)-oxetan-3-yl, 1-(2-methoxy-phenyl)-cyclopropyl, 1-(3-methoxy-phenyl)-cyclopropyl, 1-(2-trifluoromethyl-phenyl)-cyclopropyl);

6-membered heteroaryl-($C_{1-4}$)alkylene-, wherein said 6-membered heteroaryl contains one or two nitrogen atoms; and wherein said 6-membered heteroaryl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; wherein, in case Ar$^3$ represents pyridyl or pyrimidinyl, such pyridyl or pyrimidinyl may additionally be present in form of the respective N-oxide; (especially pyridin-2-yl-methyl, pyridin-3-yl-methyl, pyridin-4-yl-methyl, pyrimidin-2-yl-methyl, pyrimidin-4-yl-methyl, pyrazin-2-yl-methyl, 1-(pyridin-2-yl)-ethyl, 1-(pyridin-3-yl)-ethyl, 2-(pyridin-2-yl)-ethyl, 1-methyl-1-(pyridin-2-yl)-ethyl, 1-(pyrazin-2-yl)-ethyl, 1-(pyrimidin-4-yl)-ethyl, 1-(5-fluoro-pyrimidin-2-yl)-ethyl, 1-(3-fluoro-pyridin-2-yl)-ethyl, 1-(5-fluoro-pyridin-2-yl)-ethyl, 1-(6-methyl-pyridin-2-yl)-ethyl, 1-(3,5-difluoro-pyridin-2-yl)-ethyl, (6-methyl-pyridin-2-yl)-methyl, 1-(pyrimidin-2-yl)-ethyl, 1-methyl-1-(pyrimidin-2-yl)-ethyl, 2-methyl-2-(pyridin-2-yl)-propyl, 2-methyl-2-(3-methyl-pyridin-2-yl)-propyl);

6-membered heteroaryl-($C_{3-5}$)cycloalkylene-, wherein said 6-membered heteroaryl contains one or two nitrogen atoms; and wherein said 6-membered heteroaryl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; wherein, in case $Ar^3$ represents pyridyl or pyrimidinyl, such pyridyl or pyrimidinyl may additionally be present in form of the respective N-oxide (especially 1-(pyridin-2-yl)-cyclopropyl, 1-(pyridin-4-yl)-cyclopropyl, 1-(pyrazin-2-yl)-cyclopropyl, 1-(pyridazin-3-yl)-cyclopropyl, 1-(pyrimidin-2-yl)-cyclopropyl, 1-(5-fluoro-pyridin-2-yl)-cyclopropyl, 1-(4,6-dimethyl-pyrimidin-2-yl)-cyclopropyl, 1-(pyrimidin-4-yl)-cyclopropyl, 2-(pyrimidin-2-yl)-cyclobutyl, 2-(pyrimidin-2-yl)-cyclopentyl, 1-(1-oxy-pyrimidin-2-yl)-cyclopropyl, 1-(3-fluoro-pyridin-2-yl)-cyclopropyl, 1-(pyridin-2-yl)-cyclobutyl, 1-(1-oxy-pyridin-2-yl)-cyclopropyl);

and $R^{N2}$ independently represents hydrogen, or ($C_{1-4}$) alkyl (especially methyl, ethyl, isopropyl).

14) A further embodiment relates to the compounds of formula (I) according to any one of embodiments 1) to 10), wherein $R^1$ represents $R^{N1}R^{N2}N$—, wherein $R^{N1}$ represents 6-membered heteroaryl-($C_{1-4}$)alkylene-, wherein said 6-membered heteroaryl contains one or two nitrogen atoms; and wherein said 6-membered heteroaryl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; wherein, in case $Ar^3$ represents pyridyl or pyrimidinyl, such pyridyl or pyrimidinyl may additionally be present in form of the respective N-oxide; (especially pyridin-2-yl-methyl, pyridin-3-yl-methyl, pyridin-4-yl-methyl, pyrimidin-2-yl-methyl, pyrimidin-4-yl-methyl, pyrazin-2-yl-methyl, 1-(pyridin-2-yl)-ethyl, 1-(pyridin-3-yl)-ethyl, 2-(pyridin-2-yl)-ethyl, 1-methyl-1-(pyridin-2-yl)-ethyl, 1-(pyrazin-2-yl)-ethyl, 1-(pyrimidin-4-yl)-ethyl, 1-(5-fluoro-pyrimidin-2-yl)-ethyl, 1-(3-fluoro-pyridin-2-yl)-ethyl, 1-(5-fluoro-pyridin-2-yl)-ethyl, 1-(6-methyl-pyridin-2-yl)-ethyl, 1-(3,5-difluoro-pyridin-2-yl)-ethyl, (6-methyl-pyridin-2-yl)-methyl, 1-(pyrimidin-2-yl)-ethyl, 1-methyl-1-(pyrimidin-2-yl)-ethyl, 2-methyl-2-(pyridin-2-yl)-propyl, 2-methyl-2-(3-methyl-pyridin-2-yl)-propyl);

6-membered heteroaryl-($C_{3-5}$)cycloalkylene-, wherein said 6-membered heteroaryl contains one or two nitrogen atoms; and wherein said 6-membered heteroaryl is unsubstituted, or mono-, or di-substituted; wherein the substituents are independently selected from ($C_{1-4}$)alkyl, ($C_{1-4}$)alkoxy, halogen, ($C_{1-3}$)fluoroalkyl, or ($C_{1-3}$)fluoroalkoxy; wherein, in case $Ar^3$ represents pyridyl or pyrimidinyl, such pyridyl or pyrimidinyl may additionally be present in form of the respective N-oxide (especially 1-(pyridin-2-yl)-cyclopropyl, 1-(pyridin-4-yl)-cyclopropyl, 1-(pyrazin-2-yl)-cyclopropyl, 1-(pyridazin-3-yl)-cyclopropyl, 1-(pyrimidin-2-yl)-cyclopropyl, 1-(5-fluoro-pyridin-2-yl)-cyclopropyl, 1-(4,6-dimethyl-pyrimidin-2-yl)-cyclopropyl, 1-(pyrimidin-4-yl)-cyclopropyl, 2-(pyrimidin-2-yl)-cyclobutyl, 2-(pyrimidin-2-yl)-cyclopentyl, 1-(1-oxy-pyrimidin-2-yl)-cyclopropyl, 1-(3-fluoro-pyridin-2-yl)-cyclopropyl, 1-(pyridin-2-yl)-cyclobutyl, 1-(1-oxy-pyridin-2-yl)-cyclopropyl);

and $R^{N2}$ independently represents hydrogen or methyl.

15) A further embodiment relates to the compounds of formula (I) according to any one of embodiments 1) to 10), wherein $R^1$ represents $R^{N1}R^{N2}N$—, wherein $R^{N1}$ represents hydrogen;

methyl, ethyl, isopropyl, isobutyl, tert.-butyl, or 1,2,2-trimethyl-propyl;

2-hydroxy-ethyl, 2-hydroxy-1-methyl-ethyl, 2-hydroxy-1,1-dimethyl-ethyl, 2-methoxy-ethyl, 3-methoxy-propyl, 2-ethoxy-ethyl, 2-ethoxy-1-methyl-ethyl, 2-methoxy-1,1-dimethyl-ethyl, 3-methoxy-1,1-dimethyl-propyl, 2-(2-hydroxy-ethoxy)-ethyl carbamoyl-methyl, 2-methanesulfonyl-1,1-dimethyl-ethyl, 1-cyano-1-methyl-ethyl, 2-dimethylamino-ethyl, or 2-trifluoromethoxy-ethyl;

1-methyl-prop-2-ynyl;

2-fluoro-ethyl, 2,2-difluoro-ethyl, 2-fluoro-1-methyl-ethyl, 2-fluoro-1,1-dimethyl-ethyl, 2,2-difluoro-1-methyl-ethyl, or 3,3,3-trifluoro-1,1-dimethyl-propyl;

methoxy;

2-(2-oxo-pyrrolidin-1-yl)-ethyl;

cyclopropyl, cyclopentyl, 1-methyl-cyclopropyl, 1-methyl-cyclobutyl, 1-cyclopropyl-cyclopropan-1-yl, 1-cyclobutyl-ethyl, 3-methyl-tetrahydrofuran-3-yl, tetrahydrofuran-3-yl-methyl, tetrahydrofuran-2-yl-methyl, 1-tetrahydrofuran-2-yl-ethyl, oxetan-3-yl-methyl, or 3,3-difluoro-1-methyl-cyclobutyl, 1-(ethoxycarbonyl)-cyclopropyl, or 1-cyano-cyclobutyl;

phenyl, benzyl, 1-phenyl-ethyl, 2-(2-chloro-phenyl)-ethyl, 2-(4-fluoro-phenyl)-ethyl, 2-(2-methyl-phenyl)-ethyl, 2-(3-methyl-phenyl)-ethyl, 2-(4-methyl-phenyl)-ethyl, 2-(2-methoxy-phenyl)-ethyl, 2-phenyl-propyl, 2-hydroxy-1-phenyl-ethyl, 2-hydroxy-2-phenyl-ethyl, or 2-phenyl-cyclopropyl, 1-(3-bromo-phenyl)-ethyl, 1-phenyl-cyclopropyl, 1-phenyl-cyclobutyl, 2-phenyl-cyclobutyl, 1-(3-chloro-phenyl)-cyclopropyl, 1-(4-fluoro-phenyl)-cyclopropyl, 1-(3-fluoro-phenyl)-cyclopropyl, 1-(2-fluoro-phenyl)-cyclopropyl, 1-(2-methyl-phenyl)-cyclopropyl, 1-(2-hydroxy-phenyl)-cyclopropyl, 1-(2-methoxy-phenyl)-ethyl, 2-methyl-2-(2-chloro-phenyl)-propyl, 1-(4-chloro-phenyl)-cyclopropyl-methyl, 3-(3-chloro-phenyl)-oxetan-3-yl, 3-(4-fluoro-phenyl)-oxetan-3-yl, 3-(phenyl)-oxetan-3-yl-methyl, 3-(benzyl)-oxetan-3-yl, 1-(2-methoxy-phenyl)-cyclopropyl, 1-(3-methoxy-phenyl)-cyclopropyl, 1-(2-trifluoromethyl-phenyl)-cyclopropyl, or 2-ethoxy-2-oxo-1-phenylethyl;

4,5-dimethyl-thiazol-2-yl, 1H-imidazol-4-yl-methyl, thiazol-2-yl-methyl, 4-methyl-thiazol-5-yl-methyl, 4-methyl-thiazol-2-yl-methyl, 5-methyl-thiazol-2-yl-methyl, 2-methyl-thiazol-4-yl-methyl, oxazol-5-yl-methyl, 1-(2H-pyrazol-3-yl)-ethyl, (1-methyl-1H-pyrazol-3-yl)-methyl, 1-([1,2,4]oxadiazol-3-yl)-ethyl, 1-(isoxazol-3-yl)-ethyl, 3-methyl-isoxazol-5-yl-methyl, 5-methyl-isoxazol-3-yl-methyl, 1-(1H-[1,2,4]triazol-3-yl)-ethyl, (1,5-dimethyl-1H-pyrazol-3-yl)-methyl, (2,5-dimethyl-2H-pyrazol-3-yl)-methyl, (3-ethyl-([1,2,4]oxadiazol-5-yl)-methyl, 1-(5-methyl-([1,3,4]oxadiazol-2-yl)-ethyl, 1-methyl-1-(1-methyl-1H-pyrazol-4-yl)-ethyl, or 1-methyl-1-(5-methyl-[1,2,4]oxadiazol-3-yl)-ethyl; or pyridin-3-yl, pyridin-2-yl-methyl, pyridin-3-yl-methyl, pyridin-4-yl-methyl, pyrimidin-2-yl-methyl, pyrimidin-4-yl-methyl, pyrazin-2-yl-methyl, 1-(pyridin-2-yl)-ethyl, 1-(pyridin-3-yl)-ethyl, 2-(pyridin-2-yl)-ethyl, 1-methyl-1-(pyridin-2-yl)-ethyl, 1-(pyrazin-2-yl)-ethyl, 1-(pyrimidin-4-yl)-ethyl, 1-(5-fluoro-pyrimidin-2-yl)-ethyl, 1-(3-fluoro-pyridin-2-yl)-ethyl, 1-(5-fluoro-pyridin-2-yl)-ethyl, 1-(6-methyl-pyridin-2-yl)-ethyl, 2-hydroxy-1-(pyridin-2-yl)-ethyl, 1-(1-oxy-pyridin-2-yl)-ethyl, 1-(pyridin-2-yl)-cyclopropyl, 1-(pyridin-4-yl)-cyclopropyl, 1-(pyrazin-2-yl)-cyclopropyl, 1-(pyridazin-3-yl)-cyclopropyl, 1-(pyrimidin-2-yl)-cyclopropyl, 1-(5-fluoro-pyridin-2-yl)-cyclopropyl, 1-(3,5-difluoro-pyridin-2-yl)-ethyl, 2,2,2-trifluoro-1-(pyridin-2-yl)-ethyl, or 1-(4,6-dimethyl-pyrimidin-2-yl)-cyclopropyl; or (6-methyl-pyridin-2-yl)-methyl, 1-(pyrimidin-2-yl)-ethyl, 1-methyl-1-(pyrimidin-2-yl)-ethyl, 1-(pyrimidin-4-yl)-cyclopropyl, 2-(pyrimidin-2-yl)-cyclobutyl, 2-(pyrimidin-2-yl)-cyclopentyl, 1-(1-oxy-pyrimidin-2-yl)-cyclopropyl, 1-(3-fluoro-pyridin-2-yl)-cyclopropyl, [1-(pyridin-2-yl)-cyclopropyl]-methyl, 1-(pyridin-2-yl)-cyclobutyl, 1-(1-oxy-pyridin-2-yl)-cyclopropyl, 2-methyl-2-(pyridin-2-yl)-propyl, or 2-methyl-2-(3-methyl-pyridin-2-yl)-propyl;

and $R^{N2}$ independently represents hydrogen, methyl, ethyl, isopropyl, or 2-fluoro-ethyl;

or $R^{N1}$ and $R^{N2}$ together with the nitrogen atom to which they are attached to form a 4- to 6-membered ring selected from azetidin-1-yl, pyrrolidin-1-yl, morpholin-4-yl, 3-fluoro-azetidin-1-yl, 3,3-difluoro-azetidin-1-yl, 3-hydroxy-pyrrolidin-1-yl, 3-phenyl-pyrrolidin-1-yl, 3-(pyridin-2-yl)-pyrrolidin-1-yl.

16) A further embodiment relates to the compounds of formula (I) according to any one of embodiments 1) to 15), wherein $R^2$ represents hydrogen;

$(C_{1-6})$alkyl (especially ethyl, isopropyl, isobutyl, tert.-butyl, 2,2-dimethylpropyl, 3-methyl-butyl, 3,3-dimethylbutyl);

$(C_{2-6})$alkyl which is mono-substituted with $(C_{1-3})$alkoxy (especially methoxy), or hydroxy; (especially 2-hydroxyethyl, 2-methoxy-ethyl, 2-hydroxy-1-methyl-propyl);

$(C_{3-8})$cycloalkyl-$(C_{1-3})$alkyl, wherein the $(C_{3-8})$cycloalkyl is unsubstituted; or mono-substituted wherein the substituent is $(C_{1-3})$alkyl (especially methyl), fluoro, or $(C_{1-3})$fluoroalkyl (especially difluoromethyl); or di-substituted with fluoro;

(especially cyclopropylmethyl, cyclobutylmethyl, cyclopentylmethyl, 1-cyclopropyl-ethyl, (1-methyl-cyclopropyl)-methyl, (1-methyl-cyclobutyl)-methyl, 2-cyclopropyl-ethyl, (1-fluoro-cyclopropyl)-methyl, (2,2-difluorocyclopropyl)-methyl, (3,3-difluorocyclobutyl)-methyl, (1-difluoromethyl-cyclopropyl)-methyl);

$(C_{3-8})$cycloalkyl, wherein the $(C_{3-8})$cycloalkyl is unsubstituted, or mono- or di-substituted wherein the substituents are independently selected from $(C_{1-3})$alkyl (especially methyl), fluoro, hydroxy, hydroxy-$(C_{1-3})$alkyl (especially hydroxy-methyl), or $(C_{1-3})$alkoxy (especially methoxy);

(especially cyclobutyl, 2-methylcyclobutyl, 2,2-dimethylcyclobutyl, 3,3-dimethylcyclobutyl, cyclopentyl, cyclohexyl, spiro[2.4]hept-4-yl, spiro[3.3]hept-2-yl, bicyclo[2.2.1]hept-2-yl, 2-methylcyclopentyl, 2-(hydroxymethyl)-cyclopentyl, 3,3-dimethylcyclopentyl, 2-ethylcyclopentyl, 3,3-dimethylcyclohexyl, 2-fluoro-cyclohexyl, 4-fluoro-cyclohexyl, 4,4-difluoro-cyclohexyl, 2-hydroxy-cyclohexyl, 2-methoxy-cyclohexyl, 3-methoxy-cyclohexyl, spiro[2.3]hex-5-yl, bicyclo[3.1.0]hex-3-yl, 3,3-difluorocyclobutyl);

$(C_{3-8})$cycloalkenyl-$(C_{1-3})$alkyl (especially cyclopenten-1-ylmethyl); or benzyl wherein the phenyl ring of said benzyl is unsubstituted, or mono-substituted with halogen (especially benzyl, 2-chloro-benzyl, 2-fluoro-benzyl, 4-fluoro-benzyl).

17) A further embodiment relates to the compounds of formula (I) according to any one of embodiments 1) to 15), wherein $R^2$ represents $(C_{3-8})$cycloalkyl-$(C_{1-3})$alkyl, wherein the $(C_{3-8})$cycloalkyl is unsubstituted; or mono-substituted wherein the substituent is $(C_{1-3})$alkyl (especially methyl), fluoro, or $(C_{1-3})$fluoroalkyl (especially difluoromethyl); or di-substituted with fluoro; (especially cyclopropylmethyl, cyclobutylmethyl, cyclopentylmethyl, 1-cyclopropyl-ethyl, (1-methyl-cyclopropyl)-methyl, (1-methyl-cyclobutyl)-methyl, 2-cyclopropyl-ethyl, (1-fluoro-cyclopropyl)-methyl, (2,2-difluorocyclopropyl)-methyl, (3,3-difluorocyclobutyl)-methyl, (1-difluoromethyl-cyclopropyl)-methyl); or $(C_{3-8})$cycloalkyl, wherein the $(C_{3-8})$cycloalkyl is unsubstituted, or mono- or di-substituted wherein the substituents are independently selected from $(C_{1-3})$alkyl (especially methyl), or fluoro; (especially cyclobutyl, 2-methylcyclobutyl, 2,2-dimethylcyclobutyl, 3,3-dimethylcyclobutyl, cyclopentyl, cyclohexyl, spiro[2.4]hept-4-yl, spiro[3.3]hept-2-yl, bicyclo[2.2.1]hept-2-yl, 2-methylcyclopentyl, 3,3-dimethylcyclopentyl, 2-ethylcyclopentyl, 3,3-dimethylcyclohexyl, 2-fluoro-cyclohexyl, 4-fluoro-cyclohexyl, 4,4-difluoro-cyclohexyl, spiro[2.3]hex-5-yl, bicyclo[3.1.0]hex-3-yl, 3,3-difluorocyclobutyl).

18) A further embodiment relates to the compounds of formula (I) according to any one of embodiments 1) to 15), wherein $R^2$ represents unsubstituted $(C_{3-8})$cycloalkyl-$(C_{1-3})$alkyl (especially cyclopropylmethyl, cyclobutylmethyl, cyclopentylmethyl, 1-cyclopropyl-ethyl, 2-cyclopropyl-ethyl); or unsubstituted $(C_{3-6})$cycloalkyl (especially cyclobutyl, cyclopentyl, cyclohexyl); or $(C_{3-8})$cycloalkyl, wherein the $(C_{3-8})$cycloalkyl is di-substituted with fluoro (especially 3,3-difluorocyclobutyl); or $(C_{3-8})$cycloalkyl-$(C_{1-3})$alkyl; wherein the $(C_{3-8})$cycloalkyl is mono-substituted with methyl, fluoro, or $(C_1)$fluoroalkyl (especially difluoromethyl); or di-substituted with fluoro (especially (1-methyl-cyclopropyl)- methyl, (1-methyl-cyclobutyl)-methyl, (1-fluoro-cyclopropyl)-methyl, (2,2-difluorocyclopropyl)-methyl, (3,3-difluorocyclobutyl)-methyl, (1-difluoromethyl-cyclopropyl)-methyl).

19) A further embodiment relates to the compounds of formula (I) according to any one of embodiments 1) to 15), wherein $R^2$ represents hydrogen;

ethyl, isopropyl, 2,2-dimethylpropyl, 3-methyl-butyl, 3,3-dimethylbutyl;

isobutyl, tert.-butyl;

2-hydroxyethyl, 2-methoxy-ethyl, 2-hydroxy-1-methyl-propyl;

allyl;

cyano-methyl;

3-fluoro-propyl;

cyclopropylmethyl, cyclobutylmethyl, cyclopentylmethyl, 1-cyclopropyl-ethyl, (1-methyl-cyclopropyl)-methyl, (1-methyl-cyclobutyl)-methyl, 2-cyclopropyl-ethyl;

(1-fluoro-cyclopropyl)-methyl, (2,2-difluorocyclopropyl)-methyl, (3,3-difluorocyclobutyl)-methyl, (1-difluoromethyl-cyclopropyl)-methyl;

cyclobutyl, cyclopentyl, cyclohexyl;

2-methylcyclobutyl, 2,2-dimethylcyclobutyl, 3,3-dimethylcyclobutyl;

2-methylcyclopentyl, 2-(hydroxymethyl)-cyclopentyl, 3,3-dimethylcyclopentyl, 2-ethylcyclopentyl, 3,3-dimethylcyclohexyl, 2-fluoro-cyclohexyl, 4-fluoro-cyclohexyl, 4,4-difluoro-cyclohexyl, 2-hydroxy-cyclohexyl, 2-methoxy-cyclohexyl, 3-methoxy-cyclohexyl;

3,3-difluorocyclobutyl;

spiro[2.4]hept-4-yl, spiro[3.3]hept-2-yl, bicyclo[2.2.1]hept-2-yl;

spiro[2.3]hex-5-yl, bicyclo[3.1.0]hex-3-yl;

thietan-3-yl;

cyclopenten-1-ylmethyl; or benzyl, 2-chloro-benzyl, 2-fluoro-benzyl, or 4-fluoro-benzyl.

20) The invention, thus, especially relates to compounds of the formula (I) as defined in embodiment 1), and to such compounds further limited by the characteristics of any one of embodiments 2) to 19), under consideration of their respective dependencies; to pharmaceutically acceptable salts thereof; and to the use of such compounds as medicaments especially in the prevention/prophylaxis or treatment of disorders relating to the CXCR7 receptor or its ligands as described herein, alone, or, as for example in the case of cancer (especially in the case of malignant glioma, in particular a glioblastoma multiforme; pancreatic cancer, in particular pancreatic ductal adenocarcinoma; papillary thyroid carcinoma; lung metastasis; melanoma; lung cancer; metastatic cancers; hepatocellular carcinoma; breast cancer; colon cancer; head and neck cancer), optionally in combination with one or more therapeutic agents and/or radiotherapy and/or targeted therapy. For avoidance of any doubt, especially the following embodiments relating to the compounds of formula (I) are thus possible and intended and herewith specifically disclosed in individualized form:

1, 3+1, 4+1, 4+3+1, 5+1, 5+3+1, 5+4+1, 5+4+3+1, 7+1, 7+3+1, 7+4+1, 7+4+3+1, 8+1, 8+3+1, 8+4+1, 8+4+3+1, 9+1, 9+3+1, 9+4+1, 9+4+3+1, 9+5+1, 9+5+3+1, 9+5+4+1, 9+5+4+3+1, 9+7+1, 9+7+3+1, 9+7+4+1, 9+7+4+3+1, 9+8+1, 9+8+3+1, 9+8+4+1, 9+8+4+3+1, 10+1, 10+3+1, 10+4+1, 10+4+3+1, 10+5+1, 10+5+3+1, 10+5+4+1, 10+5+4+3+1, 10+7+1, 10+7+3+1, 10+7+4+1, 10+7+4+3+1, 10+8+1, 10+8+3+1, 10+8+4+1, 10+8+4+3+1, 11+1, 11+3+1, 11+4+1, 11+4+3+1, 11+5+1, 11+5+3+1, 11+5+4+1, 11+5+4+3+1, 11+7+1, 11+7+3+1, 11+7+4+1, 11+7+4+3+1, 11+8+1, 11+8+3+1, 11+8+4+1, 11+8+4+3+1, 11+9+1, 11+9+3+1, 11+9+4+1, 11+9+4+3+1, 11+9+5+1, 11+9+5+3+1, 11+9+5+4+1, 11+9+5+4+3+1, 11+9+7+1, 11+9+7+3+1, 11+9+7+4+1, 11+9+7+4+3+1, 11+9+8+1, 11+9+8+3+1, 11+9+8+4+1, 11+9+8+4+3+1, 11+10+1, 11+10+3+1, 11+10+4+1, 11+10+4+3+1, 11+10+5+1, 11+10+5+3+1, 11+10+5+4+1, 11+10+5+4+3+1, 11+10+7+1, 11+10+7+3+1, 11+10+7+4+1, 11+10+7+4+3+1, 11+10+8+1, 11+10+8+3+1, 11+10+8+4+1, 11+10+8+4+3+1, 12+1, 12+3+1, 12+4+1, 12+4+3+1, 12+5+1, 12+5+3+1, 12+5+4+1, 12+5+4+3+1, 12+7+1, 12+7+3+1, 12+7+4+1, 12+7+4+3+1, 12+8+1, 12+8+3+1, 12+8+4+1, 12+8+4+3+1, 12+9+1, 12+9+3+1, 12+9+4+1, 12+9+4+3+1, 12+9+5+1, 12+9+5+3+1, 12+9+5+4+1, 12+9+5+4+3+1, 12+9+7+1, 12+9+7+3+1, 12+9+7+4+1, 12+9+7+4+3+1, 12+9+8+1, 12+9+8+3+1, 12+9+8+4+1, 12+9+8+4+3+1, 12+10+1, 12+10+3+1, 12+10+4+1, 12+10+4+3+1, 12+10+5+1, 12+10+5+3+1, 12+10+5+4+1, 12+10+5+4+3+1, 12+10+7+1, 12+10+7+3+1, 12+10+7+4+1, 12+10+7+4+3+1, 12+10+8+1, 12+10+8+3+1, 12+10+8+4+1, 12+10+8+4+3+1, 13+1, 13+3+1, 13+4+1, 13+4+3+1, 13+5+1, 13+5+3+1, 13+5+4+1, 13+5+4+3+1, 13+7+1, 13+7+3+1, 13+7+4+1, 13+7+4+3+1, 13+8+1, 13+8+3+1, 13+8+4+1, 13+8+4+3+1, 13+9+1, 13+9+3+1, 13+9+4+1, 13+9+4+3+1, 13+9+5+1, 13+9+5+3+1, 13+9+5+4+1, 13+9+5+4+3+1, 13+9+7+1, 13+9+7+3+1, 13+9+7+4+1, 13+9+7+4+3+1, 13+9+8+1, 13+9+8+3+1, 13+9+8+4+1, 13+9+8+4+3+1, 13+10+1, 13+10+3+1, 13+10+4+1, 13+10+4+3+1, 13+10+5+1, 13+10+5+3+1, 13+10+5+4+1, 13+10+5+4+3+1, 13+10+7+1, 13+10+7+3+1, 13+10+7+4+1, 13+10+7+4+3+1, 13+10+8+1, 13+10+8+3+1, 13+10+8+4+1, 13+10+8+4+3+1, 14+1, 14+3+1, 14+4+1, 14+4+3+1, 14+5+1, 14+5+3+1, 14+5+4+1, 14+5+4+3+1, 14+7+1, 14+7+3+1, 14+7+4+1, 14+7+4+3+1, 14+8+1, 14+8+3+1, 14+8+4+1, 14+8+4+3+1, 14+9+1, 14+9+3+1, 14+9+4+1, 14+9+4+3+1, 14+9+5+1, 14+9+5+3+1, 14+9+5+4+1, 14+9+5+4+3+1, 14+9+7+1, 14+9+7+3+1, 14+9+7+4+1, 14+9+7+4+3+1, 14+9+8+1, 14+9+8+3+1, 14+9+8+4+1, 14+9+8+4+3+1, 14+10+1, 14+10+3+1, 14+10+4+1, 14+10+4+3+1, 14+10+5+1, 14+10+5+3+1, 14+10+5+4+1, 14+10+5+4+3+1, 14+10+7+1, 14+10+7+3+1, 14+10+7+4+1, 14+10+7+4+3+1, 14+10+8+1, 14+10+8+3+1, 14+10+8+4+1, 14+10+8+4+3+1, 15+1, 15+3+1, 15+4+1, 15+4+3+1, 15+5+1, 15+5+3+1, 15+5+4+1, 15+5+4+3+1, 15+7+1, 15+7+3+1, 15+7+4+1, 15+7+4+3+1, 15+8+1, 15+8+3+1, 15+8+4+1, 15+8+4+3+1, 15+9+1, 15+9+3+1, 15+9+4+1, 15+9+4+3+1, 15+9+5+1, 15+9+5+3+1, 15+9+5+4+1, 15+9+5+4+3+1, 15+9+7+1, 15+9+7+3+1, 15+9+7+4+1, 15+9+7+4+3+1, 15+9+8+1, 15+9+8+3+1, 15+9+8+4+1, 15+9+8+4+3+1, 15+10+1, 15+10+3+1, 15+10+4+1, 15+10+4+3+1, 15+10+5+1, 15+10+5+3+1, 15+10+5+4+1, 15+10+5+4+3+1, 15+10+7+1, 15+10+7+3+1, 15+10+7+4+1, 15+10+7+4+3+1, 15+10+8+1, 15+10+8+3+1, 15+10+8+4+1, 15+10+8+4+3+1, 17+1, 17+3+1, 17+4+1, 17+4+3+1, 17+5+1, 17+5+3+1, 17+5+4+1, 17+5+4+3+1, 17+7+1, 17+7+3+1, 17+7+4+1, 17+7+4+3+1, 17+8+1, 17+8+3+1, 17+8+4+1, 17+8+4+3+1, 17+9+1, 17+9+3+1, 17+9+4+1, 17+9+4+3+1, 17+9+5+1, 17+9+5+3+1, 17+9+5+4+1, 17+9+5+4+3+1, 17+9+7+1, 17+9+7+3+1, 17+9+7+4+1, 17+9+7+4+3+1, 17+9+8+1, 17+9+8+3+1, 17+9+8+4+1, 17+9+8+4+3+1, 17+10+1, 17+10+3+1, 17+10+4+1, 17+10+4+3+1, 17+10+5+1, 17+10+5+3+1, 17+10+5+4+1, 17+10+5+4+3+1, 17+10+7+1, 17+10+7+3+1, 17+10+7+4+1, 17+10+7+4+3+1, 17+10+8+1, 17+10+8+3+1, 17+10+8+4+1, 17+10+8+4+3+1, 17+11+1, 17+11+3+1, 17+11+4+1, 17+11+4+3+1, 17+11+5+1, 17+11+5+3+1, 17+11+5+4+1,

17+11+5+4+3+1, 17+11+7+1, 17+11+7+3+1, 17+11+7+4+1, 17+11+7+4+3+1, 17+11+8+1, 17+11+8+3+1, 17+11+8+4+1, 17+11+8+4+3+1, 17+11+9+1, 17+11+9+3+1, 17+11+9+4+1, 17+11+9+4+3+1, 17+11+9+5+1, 17+11+9+5+3+1, 17+11+9+5+4+1, 17+11+9+5+4+3+1, 17+11+9+7+1, 17+11+9+7+3+1, 17+11+9+7+4+1, 17+11+9+7+4+3+1, 17+11+9+8+1, 17+11+9+8+3+1, 17+11+9+8+4+1, 17+11+9+8+4+3+1, 17+11+10+1, 17+11+10+3+1, 17+11+10+4+1, 17+11+10+4+3+1, 17+11+10+5+1, 17+11+10+5+3+1, 17+11+10+5+4+1, 17+11+10+5+4+3+1, 17+11+10+7+1, 17+11+10+7+3+1, 17+11+10+7+4+1, 17+11+10+7+4+3+1, 17+11+10+8+1, 17+11+10+8+3+1, 17+11+10+8+4+1, 17+11+10+8+4+3+1, 17+12+1, 17+12+3+1, 17+12+4+1, 17+12+4+3+1, 17+12+5+1, 17+12+5+3+1, 17+12+5+4+1, 17+12+5+4+3+1, 17+12+7+1, 17+12+7+3+1, 17+12+7+4+1, 17+12+7+4+3+1, 17+12+8+1, 17+12+8+3+1, 17+12+8+4+1, 17+12+8+4+3+1, 17+12+9+1, 17+12+9+3+1, 17+12+9+4+1, 17+12+9+4+3+1, 17+12+9+5+1, 17+12+9+5+3+1, 17+12+9+5+4+1, 17+12+9+5+4+3+1, 17+12+9+7+1, 17+12+9+7+3+1, 17+12+9+7+4+1, 17+12+9+7+4+3+1, 17+12+9+8+1, 17+12+9+8+3+1, 17+12+9+8+4+1, 17+12+9+8+4+3+1, 17+12+10+1, 17+12+10+3+1, 17+12+10+4+1, 17+12+10+4+3+1, 17+12+10+5+1, 17+12+10+5+3+1, 17+12+10+5+4+1, 17+12+10+5+4+3+1, 17+12+10+7+1, 17+12+10+7+3+1, 17+12+10+7+4+1, 17+12+10+7+4+3+1, 17+12+10+8+1, 17+12+10+8+3+1, 17+12+10+8+4+1, 17+12+10+8+4+3+1, 17+13+1, 17+13+3+1, 17+13+4+1, 17+13+4+3+1, 17+13+5+1, 17+13+5+3+1, 17+13+5+4+1, 17+13+5+4+3+1, 17+13+7+1, 17+13+7+3+1, 17+13+7+4+1, 17+13+7+4+3+1, 17+13+8+1, 17+13+8+3+1, 17+13+8+4+1, 17+13+8+4+3+1, 17+13+9+1, 17+13+9+3+1, 17+13+9+4+1, 17+13+9+4+3+1, 17+13+9+5+1, 17+13+9+5+3+1, 17+13+9+5+4+1, 17+13+9+5+4+3+1, 17+13+9+7+1, 17+13+9+7+3+1, 17+13+9+7+4+1, 17+13+9+7+4+3+1, 17+13+9+8+1, 17+13+9+8+3+1, 17+13+9+8+4+1, 17+13+9+8+4+3+1, 17+13+10+1, 17+13+10+3+1, 17+13+10+4+1, 17+13+10+4+3+1, 17+13+10+5+1, 17+13+10+5+3+1, 17+13+10+5+4+1, 17+13+10+5+4+3+1, 17+13+10+7+1, 17+13+10+7+3+1, 17+13+10+7+4+1, 17+13+10+7+4+3+1, 17+13+10+8+1, 17+13+10+8+3+1, 17+13+10+8+4+1, 17+13+10+8+4+3+1, 17+14+1, 17+14+3+1, 17+14+4+1, 17+14+4+3+1, 17+14+5+1, 17+14+5+3+1, 17+14+5+4+1, 17+14+5+4+3+1, 17+14+7+1, 17+14+7+3+1, 17+14+7+4+1, 17+14+7+4+3+1, 17+14+8+1, 17+14+8+3+1, 17+14+8+4+1, 17+14+8+4+3+1, 17+14+9+1, 17+14+9+3+1, 17+14+9+4+1, 17+14+9+4+3+1, 17+14+9+5+1, 17+14+9+5+3+1, 17+14+9+5+4+1, 17+14+9+5+4+3+1, 17+14+9+7+1, 17+14+9+7+3+1, 17+14+9+7+4+1, 17+14+9+7+4+3+1, 17+14+9+8+1, 17+14+9+8+3+1, 17+14+9+8+4+1, 17+14+9+8+4+3+1, 17+14+10+1, 17+14+10+3+1, 17+14+10+4+1, 17+14+10+4+3+1, 17+14+10+5+1, 17+14+10+5+3+1, 17+14+10+5+4+1, 17+14+10+5+4+3+1, 17+14+10+7+1, 17+14+10+7+3+1, 17+14+10+7+4+1, 17+14+10+7+4+3+1, 17+14+10+8+1, 17+14+10+8+3+1, 17+14+10+8+4+1, 17+14+10+8+4+3+1, 17+15+1, 17+15+3+1, 17+15+4+1, 17+15+4+3+1, 17+15+5+1, 17+15+5+3+1, 17+15+5+4+1, 17+15+5+4+3+1, 17+15+7+1, 17+15+7+3+1, 17+15+7+4+1, 17+15+7+4+3+1, 17+15+8+1, 17+15+8+3+1, 17+15+8+4+1, 17+15+8+4+3+1, 17+15+9+1, 17+15+9+3+1, 17+15+9+4+1, 17+15+9+4+3+1, 17+15+9+5+1, 17+15+9+5+3+1, 17+15+9+5+4+1, 17+15+9+5+4+3+1, 17+15+9+7+1, 17+15+9+7+3+1, 17+15+9+7+4+1, 17+15+9+7+4+3+1, 17+15+9+8+1, 17+15+9+8+3+1, 17+15+9+8+4+1, 17+15+9+8+4+3+1, 17+15+10+1, 17+15+10+3+1, 17+15+10+4+1, 17+15+10+4+3+1, 17+15+10+5+1, 17+15+10+5+3+1, 17+15+10+5+4+1, 17+15+10+5+4+3+1, 17+15+10+7+1, 17+15+10+7+3+1, 17+15+10+7+4+1, 17+15+10+7+4+3+1, 17+15+10+8+1, 17+15+10+8+3+1, 17+15+10+8+4+1, 17+15+10+8+4+3+1, 18+1, 18+3+1, 18+4+1, 18+4+3+1, 18+5+1, 18+5+3+1, 18+5+4+1, 18+5+4+3+1, 18+7+1, 18+7+3+1, 18+7+4+1, 18+7+4+3+1, 18+8+1, 18+8+3+1, 18+8+4+1, 18+8+4+3+1, 18+9+1, 18+9+3+1, 18+9+4+1, 18+9+4+3+1, 18+9+5+1, 18+9+5+3+1, 18+9+5+4+1, 18+9+5+4+3+1, 18+9+7+1, 18+9+7+3+1, 18+9+7+4+1, 18+9+7+4+3+1, 18+9+8+1, 18+9+8+3+1, 18+9+8+4+1, 18+9+8+4+3+1, 18+10+1, 18+10+3+1, 18+10+4+1, 18+10+4+3+1, 18+10+5+1, 18+10+5+3+1, 18+10+5+4+1, 18+10+5+4+3+1, 18+10+7+1, 18+10+7+3+1, 18+10+7+4+1, 18+10+7+4+3+1, 18+10+8+1, 18+10+8+3+1, 18+10+8+4+1, 18+10+8+4+3+1, 18+11+1, 18+11+3+1, 18+11+4+1, 18+11+4+3+1, 18+11+5+1, 18+11+5+3+1, 18+11+5+4+1, 18+11+5+4+3+1, 18+11+7+1, 18+11+7+3+1, 18+11+7+4+1, 18+11+7+4+3+1, 18+11+8+1, 18+11+8+3+1, 18+11+8+4+1, 18+11+8+4+3+1, 18+11+9+1, 18+11+9+3+1, 18+11+9+4+1, 18+11+9+4+3+1, 18+11+9+5+1, 18+11+9+5+3+1, 18+11+9+5+4+1, 18+11+9+5+4+3+1, 18+11+9+7+1, 18+11+9+7+3+1, 18+11+9+7+4+1, 18+11+9+7+4+3+1, 18+11+9+8+1, 18+11+9+8+3+1, 18+11+9+8+4+1, 18+11+9+8+4+3+1, 18+11+10+1, 18+11+10+3+1, 18+11+10+4+1, 18+11+10+4+3+1, 18+11+10+5+1, 18+11+10+5+3+1, 18+11+10+5+4+1, 18+11+10+5+4+3+1, 18+11+10+7+1, 18+11+10+7+4+1, 18+11+10+7+4+3+1, 18+11+10+8+1, 18+11+10+8+3+1, 18+11+10+8+4+1, 18+11+10+8+4+3+1, 18+12+1, 18+12+3+1, 18+12+4+1, 18+12+4+3+1, 18+12+5+1, 18+12+5+3+1, 18+12+5+4+1, 18+12+5+4+3+1, 18+12+7+1, 18+12+7+3+1, 18+12+7+4+1, 18+12+7+4+3+1, 18+12+8+1, 18+12+8+3+1, 18+12+8+4+1, 18+12+8+4+3+1, 18+12+9+1, 18+12+9+3+1, 18+12+9+4+1, 18+12+9+4+3+1, 18+12+9+5+1, 18+12+9+5+3+1, 18+12+9+5+4+1, 18+12+9+5+4+3+1, 18+12+9+7+1, 18+12+9+7+3+1, 18+12+9+7+4+1, 18+12+9+7+4+3+1, 18+12+9+8+1, 18+12+9+8+3+1, 18+12+9+8+4+1, 18+12+9+8+4+3+1, 18+12+10+1, 18+12+10+3+1, 18+12+10+4+1, 18+12+10+4+3+1, 18+12+10+5+1, 18+12+10+5+3+1, 18+12+10+5+4+1, 18+12+10+5+4+3+1, 18+12+10+7+1, 18+12+10+7+3+1, 18+12+10+7+4+1, 18+12+10+7+4+3+1, 18+12+10+8+1, 18+12+10+8+3+1, 18+12+10+8+4+1, 18+12+10+8+4+3+1, 18+13+1, 18+13+3+1, 18+13+4+1, 18+13+4+3+1, 18+13+5+1, 18+13+5+3+1, 18+13+5+4+1, 18+13+5+4+3+1, 18+13+7+1, 18+13+7+3+1, 18+13+7+4+1, 18+13+7+4+3+1, 18+13+8+1, 18+13+8+3+1, 18+13+8+4+1, 18+13+8+4+3+1, 18+13+9+1, 18+13+9+3+1, 18+13+9+4+1, 18+13+9+4+3+1, 18+13+9+5+1, 18+13+9+5+3+1, 18+13+9+5+4+1, 18+13+9+5+4+3+1, 18+13+9+7+1, 18+13+9+7+3+1, 18+13+9+7+4+1, 18+13+9+7+4+3+1, 18+13+9+8+1, 18+13+9+8+3+1, 18+13+9+8+4+1, 18+13+9+8+4+3+1, 18+13+10+1, 18+13+10+3+1, 18+13+10+4+1, 18+13+10+4+3+1, 18+13+10+5+1, 18+13+10+5+3+1, 18+13+10+5+4+1, 18+13+10+5+4+3+1, 18+13+10+7+1, 18+13+10+7+3+1, 18+13+10+7+4+1, 18+13+10+7+4+3+1, 18+13+10+8+1, 18+13+10+8+3+1, 18+13+10+8+4+1, 18+13+10+8+4+3+1, 18+14+1, 18+14+3+1, 18+14+4+1, 18+14+4+3+1, 18+14+5+1, 18+14+5+3+1, 18+14+5+4+1, 18+14+5+4+3+1, 18+14+7+1, 18+14+7+3+1, 18+14+7+4+1, 18+14+7+4+3+1, 18+14+8+1, 18+14+8+3+1, 18+14+8+4+1, 18+14+8+4+3+1, 18+14+9+1, 18+14+9+3+1, 18+14+9+4+1, 18+14+9+4+3+1, 18+14+9+5+1, 18+14+9+5+3+1, 18+14+9+5+4+1, 18+14+9+5+4+3+1, 18+14+9+7+1, 18+14+9+7+3+1, 18+14+9+7+4+1, 18+14+9+7+4+3+1, 18+14+9+8+1, 18+14+9+8+3+1, 18+14+9+8+4+1, 18+14+9+8+4+3+1, 18+14+10+1, 18+14+10+3+1, 18+14+10+4+1, 18+14+10+4+3+1, 18+14+10+5+1, 18+14+10+5+3+1, 18+14+10+5+4+1, 18+14+10+5+4+3+1, 18+14+10+7+1, 18+14+10+7+3+1, 18+14+10+7+4+1, 18+14+10+7+4+3+1,

18+14+10+8+1, 18+14+10+8+3+1, 18+14+10+8+4+1, 18+14+10+8+4+3+1, 18+15+1, 18+15+3+1, 18+15+4+1, 18+15+4+3+1, 18+15+5+1, 18+15+5+3+1, 18+15+5+4+1, 18+15+5+4+3+1, 18+15+7+1, 18+15+7+3+1, 18+15+7+4+1, 18+15+7+4+3+1, 18+15+8+1, 18+15+8+3+1, 18+15+8+4+1, 18+15+8+4+3+1, 18+15+9+1, 18+15+9+3+1, 18+15+9+4+1, 18+15+9+4+3+1, 18+15+9+5+1, 18+15+9+5+3+1, 18+15+9+5+4+1, 18+15+9+5+4+3+1, 18+15+9+7+1, 18+15+9+7+3+1, 18+15+9+7+4+1, 18+15+9+7+4+3+1, 18+15+9+8+1, 18+15+9+8+3+1, 18+15+9+8+4+1, 18+15+9+8+4+3+1, 18+15+10+1, 18+15+10+3+1, 18+15+10+4+1, 18+15+10+4+3+1, 18+15+10+5+1, 18+15+10+5+3+1, 18+15+10+5+4+1, 18+15+10+5+4+3+1, 18+15+10+7+1, 18+15+10+7+3+1, 18+15+10+7+4+1, 18+15+10+7+4+3+1, 18+15+10+8+1, 18+15+10+8+3+1, 18+15+10+8+4+1, 18+15+10+8+4+3+1, 19+1, 19+3+1, 19+4+1, 19+4+3+1, 19+5+1, 19+5+3+1, 19+5+4+1, 19+5+4+3+1, 19+7+1, 19+7+3+1, 19+7+4+1, 19+7+4+3+1, 19+8+1, 19+8+3+1, 19+8+4+1, 19+8+4+3+1, 19+9+1, 19+9+3+1, 19+9+4+1, 19+9+4+3+1, 19+9+5+1, 19+9+5+3+1, 19+9+5+4+1, 19+9+5+4+3+1, 19+9+7+1, 19+9+7+3+1, 19+9+7+4+1, 19+9+7+4+3+1, 19+9+8+1, 19+9+8+3+1, 19+9+8+4+1, 19+9+8+4+3+1, 19+10+1, 19+10+3+1, 19+10+4+1, 19+10+4+3+1, 19+10+5+1, 19+10+5+3+1, 19+10+5+4+1, 19+10+5+4+3+1, 19+10+7+1, 19+10+7+3+1, 19+10+7+4+1, 19+10+7+4+3+1, 19+10+8+1, 19+10+8+3+1, 19+10+8+4+1, 19+10+8+4+3+1, 19+11+1, 19+11+3+1, 19+11+4+1, 19+11+4+3+1, 19+11+5+1, 19+11+5+3+1, 19+11+5+4+1, 19+11+5+4+3+1, 19+11+7+1, 19+11+7+3+1, 19+11+7+4+1, 19+11+7+4+3+1, 19+11+8+1, 19+11+8+3+1, 19+11+8+4+1, 19+11+8+4+3+1, 19+11+9+1, 19+11+9+3+1, 19+11+9+4+1, 19+11+9+4+3+1, 19+11+9+5+1, 19+11+9+5+3+1, 19+11+9+5+4+1, 19+11+9+5+4+3+1, 19+11+9+7+1, 19+11+9+7+3+1, 19+11+9+7+4+1, 19+11+9+7+4+3+1, 19+11+9+8+1, 19+11+9+8+3+1, 19+11+9+8+4+1, 19+11+9+8+4+3+1, 19+11+10+1, 19+11+10+3+1, 19+11+10+4+1, 19+11+10+4+3+1, 19+11+10+5+1, 19+11+10+5+3+1, 19+11+10+5+4+1, 19+11+10+5+4+3+1, 19+11+10+7+1, 19+11+10+7+3+1, 19+11+10+7+4+1, 19+11+10+7+4+3+1, 19+11+10+8+1, 19+11+10+8+3+1, 19+11+10+8+4+1, 19+11+10+8+4+3+1, 19+12+1, 19+12+3+1, 19+12+4+1, 19+12+4+3+1, 19+12+5+1, 19+12+5+3+1, 19+12+5+4+1, 19+12+5+4+3+1, 19+12+7+1, 19+12+7+3+1, 19+12+7+4+1, 19+12+7+4+3+1, 19+12+8+1, 19+12+8+3+1, 19+12+8+4+1, 19+12+8+4+3+1, 19+12+9+1, 19+12+9+3+1, 19+12+9+4+1, 19+12+9+4+3+1, 19+12+9+5+1, 19+12+9+5+3+1, 19+12+9+5+4+1, 19+12+9+5+4+3+1, 19+12+9+7+1, 19+12+9+7+3+1, 19+12+9+7+4+1, 19+12+9+7+4+3+1, 19+12+9+8+1, 19+12+9+8+3+1, 19+12+9+8+4+1, 19+12+9+8+4+3+1, 19+12+10+1, 19+12+10+3+1, 19+12+10+4+1, 19+12+10+4+3+1, 19+12+10+5+1, 19+12+10+5+3+1, 19+12+10+5+4+1, 19+12+10+5+4+3+1, 19+12+10+7+1, 19+12+10+7+3+1, 19+12+10+7+4+1, 19+12+10+7+4+3+1, 19+12+10+8+1, 19+12+10+8+3+1, 19+12+10+8+4+1, 19+12+10+8+4+3+1, 19+13+1, 19+13+3+1, 19+13+4+1, 19+13+4+3+1, 19+13+5+1, 19+13+5+3+1, 19+13+5+4+1, 19+13+5+4+3+1, 19+13+7+1, 19+13+7+3+1, 19+13+7+4+1, 19+13+7+4+3+1, 19+13+8+1, 19+13+8+3+1, 19+13+8+4+1, 19+13+8+4+3+1, 19+13+9+1, 19+13+9+3+1, 19+13+9+4+1, 19+13+9+4+3+1, 19+13+9+5+1, 19+13+9+5+3+1, 19+13+9+5+4+1, 19+13+9+5+4+3+1, 19+13+9+7+1, 19+13+9+7+3+1, 19+13+9+7+4+1, 19+13+9+7+4+3+1, 19+13+9+8+1, 19+13+9+8+3+1, 19+13+9+8+4+1, 19+13+9+8+4+3+1, 19+13+10+1, 19+13+10+3+1, 19+13+10+4+1, 19+13+10+4+3+1, 19+13+10+5+1, 19+13+10+5+3+1, 19+13+10+5+4+1, 19+13+10+5+4+3+1, 19+13+10+7+1, 19+13+10+7+3+1, 19+13+10+7+4+1, 19+13+10+7+4+3+1, 19+13+10+8+1, 19+13+10+8+3+1, 19+13+10+8+4+1, 19+13+10+8+4+3+1, 19+14+1, 19+14+3+1, 19+14+4+1, 19+14+4+3+1, 19+14+5+1, 19+14+5+3+1, 19+14+5+4+1, 19+14+5+4+3+1, 19+14+7+1, 19+14+7+3+1, 19+14+7+4+1, 19+14+7+4+3+1, 19+14+8+1, 19+14+8+3+1, 19+14+8+4+1, 19+14+8+4+3+1, 19+14+9+1, 19+14+9+3+1, 19+14+9+4+1, 19+14+9+4+3+1, 19+14+9+5+1, 19+14+9+5+3+1, 19+14+9+5+4+1, 19+14+9+5+4+3+1, 19+14+9+7+1, 19+14+9+7+3+1, 19+14+9+7+4+1, 19+14+9+7+4+3+1, 19+14+9+8+1, 19+14+9+8+3+1, 19+14+9+8+4+1, 19+14+9+8+4+3+1, 19+14+10+1, 19+14+10+3+1, 19+14+10+4+1, 19+14+10+4+3+1, 19+14+10+5+1, 19+14+10+5+3+1, 19+14+10+5+4+1, 19+14+10+5+4+3+1, 19+14+10+7+1, 19+14+10+7+3+1, 19+14+10+7+4+1, 19+14+10+7+4+3+1, 19+14+10+8+1, 19+14+10+8+3+1, 19+14+10+8+4+1, 19+14+10+8+4+3+1, 19+15+1, 19+15+3+1, 19+15+4+1, 19+15+4+3+1, 19+15+5+1, 19+15+5+3+1, 19+15+5+4+1, 19+15+5+4+3+1, 19+15+7+1, 19+15+7+3+1, 19+15+7+4+1, 19+15+7+4+3+1, 19+15+8+1, 19+15+8+3+1, 19+15+8+4+1, 19+15+8+4+3+1, 19+15+9+1, 19+15+9+3+1, 19+15+9+4+1, 19+15+9+4+3+1, 19+15+9+5+1, 19+15+9+5+3+1, 19+15+9+5+4+1, 19+15+9+5+4+3+1, 19+15+9+7+1, 19+15+9+7+3+1, 19+15+9+7+4+1, 19+15+9+7+4+3+1, 19+15+9+8+1, 19+15+9+8+3+1, 19+15+9+8+4+1, 19+15+9+8+4+3+1, 19+15+10+1, 19+15+10+3+1, 19+15+10+4+1, 19+15+10+4+3+1, 19+15+10+5+1, 19+15+10+5+3+1, 19+15+10+5+4+1, 19+15+10+5+4+3+1, 19+15+10+7+1, 19+15+10+7+3+1, 19+15+10+7+4+1, 19+15+10+7+4+3+1, 19+15+10+8+1, 19+15+10+8+3+1, 19+15+10+8+4+1, 19+15+10+8+4+3+1.

In the list above the numbers refer to the embodiments according to their numbering provided hereinabove whereas "+" indicates the dependency from another embodiment. The different individualized embodiments are separated by commas. In other words, "18+14+8+1" for example refers to embodiment 18) depending on embodiment 14), depending on embodiment 8), depending on embodiment 1), i.e. embodiment "18+14+8+1" corresponds to the compounds of formula (I) according to embodiment 1) further limited by all the features of the embodiments 8), 14), and 18).

21) Another embodiment relates to compounds according to embodiment 1) which are selected from the following compounds:
(3R*,4R*)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide;
(3R,4R)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide;
(3R*,4R*)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide;
(3R,4R)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide;
(3R*,4R*)-1-Cyclohexyl-4-{[5-(2,4-difluoro-phenyl)-isoxazole-3-carbonyl]-amino}-piperidine-3-carboxylic acid cyclopentylamide;
5-(2,4-Difluoro-phenyl)-isoxazole-3-carboxylic acid[(3R*,4R*)-1-cyclohexyl-3-(pyrrolidine-1-carbonyl)-piperidin-4-yl]-amide;

(3R*,4R*)-1-Cyclohexyl-4-{[5-(2,4-difluoro-phenyl)-isoxazole-3-carbonyl]-amino}-piperidine-3-carboxylic acid (2-hydroxy-ethyl)-methyl-amide;
(3R*,4R*)-1-Cyclohexyl-4-{[5-(2,4-difluoro-phenyl)-isoxazole-3-carbonyl]-amino}-piperidine-3-carboxylic acid (2-methoxy-ethyl)-amide;
(3R*,4R*)-1-Cyclohexyl-4-{[5-(2,4-difluoro-phenyl)-isoxazole-3-carbonyl]-amino}-piperidine-3-carboxylic acid isobutyl-amide;
(3R*,4R*)-1-Cyclohexyl-4-{[5-(2,4-difluoro-phenyl)-isoxazole-3-carbonyl]-amino}-piperidine-3-carboxylic acid isopropylamide;
(3R*,4R*)-1-Cyclohexyl-4-{[5-(2,4-difluoro-phenyl)-isoxazole-3-carbonyl]-amino}-piperidine-3-carboxylic acid dimethylamide;
(3R*,4R*)-1-Cyclohexyl-4-{[5-(2,4-difluoro-phenyl)-isoxazole-3-carbonyl]-amino}-piperidine-3-carboxylic acid methylamide;
(3R*,4R*)-1-Cyclohexyl-4-{[5-(2,4-difluoro-phenyl)-isoxazole-3-carbonyl]-amino}-piperidine-3-carboxylic acid (2-fluoro-ethyl)-amide;
(3R*,4R*)-1-Cyclohexyl-4-{[5-(2,4-difluoro-phenyl)-isoxazole-3-carbonyl]-amino}-piperidine-3-carboxylic acid ethylamide;
(3R*,4R*)-1-Cyclohexyl-4-{[5-(2,4-difluoro-phenyl)-isoxazole-3-carbonyl]-amino}-piperidine-3-carboxylic acid cyclopropyl-methyl-amide;
(3R*,4R*)-1-Cyclohexyl-4-{[5-(2,4-difluoro-phenyl)-isoxazole-3-carbonyl]-amino}-piperidine-3-carboxylic acid carbamoylmethyl-amide;
(3R*,4R*)-1-Cyclohexyl-4-{[5-(2,4-difluoro-phenyl)-isoxazole-3-carbonyl]-amino}-piperidine-3-carboxylic acid (2-hydroxy-ethyl)-amide;
5-(2,4-Difluoro-phenyl)-isoxazole-3-carboxylic acid [(3R*,4R*)-1-cyclohexyl-3-(morpholine-4-carbonyl)-piperidin-4-yl]-amide;
(3R*,4R*)-1-Cyclohexyl-4-{[5-(2,4-difluoro-phenyl)-isoxazole-3-carbonyl]-amino}-piperidine-3-carboxylic acid isopropyl-methyl-amide;
(3R*,4R*)-1-Cyclohexyl-4-{[5-(2,4-difluoro-phenyl)-isoxazole-3-carbonyl]-amino}-piperidine-3-carboxylic acid (2-dimethylamino-ethyl)-methyl-amide;
(3R*,4R*)-1-Cyclohexyl-4-{[5-(2,4-difluoro-phenyl)-isoxazole-3-carbonyl]-amino}-piperidine-3-carboxylic acid (2-ethoxy-ethyl)-methyl-amide;
(3R*,4R*)-1-Cyclohexyl-4-{[5-(2,4-difluoro-phenyl)-isoxazole-3-carbonyl]-amino}-piperidine-3-carboxylic acid (5-methyl-thiazol-2-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (2-methoxy-ethyl)-methyl-amide;
(3R*,4R*)-1-Cyclohexyl-4-{[5-(2,4-difluoro-phenyl)-isoxazole-3-carbonyl]-amino}-piperidine-3-carboxylic acid (5-methyl-isoxazol-3-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (2-dimethylamino-ethyl)-amide;
(3R*,4R*)-1-Cyclohexyl-4-{[5-(2,4-difluoro-phenyl)-isoxazole-3-carbonyl]-amino}-piperidine-3-carboxylic acid ethyl-methyl-amide;
(3R*,4R*)-1-Cyclohexyl-4-{[5-(2,4-difluoro-phenyl)-isoxazole-3-carbonyl]-amino}-piperidine-3-carboxylic acid (pyridin-2-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (2,2-difluoro-ethyl)-amide;
(3R*,4R*)-1-Cyclohexyl-4-{[5-(2,4-difluoro-phenyl)-isoxazole-3-carbonyl]-amino}-piperidine-3-carboxylic acid (3-methoxy-propyl)-methyl-amide;
5-(2,4-Difluoro-phenyl)-isoxazole-3-carboxylic acid [(3R*,4R*)-1-cyclohexyl-3-(3-hydroxy-pyrrolidine-1-carbonyl)-piperidin-4-yl]-amide;
(3R*,4R*)-1-Cyclohexyl-4-{[5-(2,4-difluoro-phenyl)-isoxazole-3-carbonyl]-amino}-piperidine-3-carboxylic acid (3-methyl-isoxazol-5-ylmethyl)-amide;
5-(2,4-Difluoro-phenyl)-isoxazole-3-carboxylic acid [(3R*,4R*)-3-(azetidine-1-carbonyl)-1-cyclohexyl-piperidin-4-yl]-amide;
(3R*,4R*)-1-Cyclohexyl-4-{[5-(2,4-difluoro-phenyl)-isoxazole-3-carbonyl]-amino}-piperidine-3-carboxylic acid (2-methyl-thiazol-4-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (pyrimidin-2-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (4-methyl-thiazol-5-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (pyrimidin-4-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (oxazol-5-ylmethyl)-amide;
5-(2,4-Difluoro-phenyl)-isoxazole-3-carboxylic acid [(3R*,4R*)-1-cyclohexyl-3-(3-fluoro-azetidine-1-carbonyl)-piperidin-4-yl]-amide;
(3R*,4R*)-1-Cyclohexyl-4-{[5-(2,4-difluoro-phenyl)-isoxazole-3-carbonyl]-amino}-piperidine-3-carboxylic acid (pyrazin-2-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (2-trifluoromethoxy-ethyl)-amide;
(3R*,4R*)-1-Cyclohexyl-4-{[5-(2,4-difluoro-phenyl)-isoxazole-3-carbonyl]-amino}-piperidine-3-carboxylic acid methyl-oxetan-3-ylmethyl-amide;
(3R*,4R*)-1-Cyclohexyl-4-{[5-(2,4-difluoro-phenyl)-isoxazole-3-carbonyl]-amino}-piperidine-3-carboxylic acid (1-pyridin-2-yl-ethyl)-amide;
(3R*,4R*)-1-Cyclohexyl-4-{[5-(2,4-difluoro-phenyl)-isoxazole-3-carbonyl]-amino}-piperidine-3-carboxylic acid [2-(2-oxo-pyrrolidin-1-yl)-ethyl]-amide;
(3R*,4R*)-1-Cyclohexyl-4-{[5-(2,4-difluoro-phenyl)-isoxazole-3-carbonyl]-amino}-piperidine-3-carboxylic acid (1-methyl-1H-pyrazol-3-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (1H-imidazol-4-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (tetrahydro-furan-2-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (1,5-dimethyl-1H-pyrazol-3-ylmethyl)-amide;
(3R,4R)-1-Cyclohexyl-4-{[5-(2,4,6-trifluoro-phenyl)-isoxazole-3-carbonyl]-amino}-piperidine-3-carboxylic acid ((1S,2R)-2-phenyl-cyclopropyl)-amide;
(3R,4R)-1-Cyclohexyl-4-{[5-(2,4,6-trifluoro-phenyl)-isoxazole-3-carbonyl]-amino}-piperidine-3-carboxylic acid ((1R,2S)-2-phenyl-cyclopropyl)-amide;
(3S,4S)-1-Cyclohexyl-4-{[5-(2,4,6-trifluoro-phenyl)-isoxazole-3-carbonyl]-amino}-piperidine-3-carboxylic acid ((1S,2R)-2-phenyl-cyclopropyl)-amide;

(3S,4S)-1-Cyclohexyl-4-{[5-(2,4,6-trifluoro-phenyl)-isoxazole-3-carbonyl]-amino}-piperidine-3-carboxylic acid ((1R,2S)-2-phenyl-cyclopropyl)-amide;
(3R*,4R*)-1-Cyclohexyl-4-{[5-(2,4-difluoro-phenyl)-isoxazole-3-carbonyl]-amino}-piperidine-3-carboxylic acid (3-ethyl-[1,2,4]oxadiazol-5-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (pyridin-3-ylmethyl)-amide;
(3R*,4R*)-1-Cyclohexyl-4-{[5-(2,4-difluoro-phenyl)-isoxazole-3-carbonyl]-amino}-piperidine-3-carboxylic acid methyl-phenethyl-amide;
(3R*,4R*)-1-Cyclohexyl-4-{[5-(2,4-difluoro-phenyl)-isoxazole-3-carbonyl]-amino}-piperidine-3-carboxylic acid (pyridin-4-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (thiazol-2-ylmethyl)-amide;
5-(2,4-Difluoro-phenyl)-isoxazole-3-carboxylic acid [(3R*,4R*)-1-cyclohexyl-3-(3,3-difluoro-azetidine-1-carbonyl)-piperidin-4-yl]-amide;
(3R*,4R*)-1-Cyclohexyl-4-{[5-(2,4-difluoro-phenyl)-isoxazole-3-carbonyl]-amino}-piperidine-3-carboxylic acid (tetrahydro-furan-3-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (2,5-dimethyl-2H-pyrazol-3-ylmethyl)-amide;
(3R*,4R*)-1-Cyclohexyl-4-{[5-(2,4-difluoro-phenyl)-isoxazole-3-carbonyl]-amino}-piperidine-3-carboxylic acid [2-(2-hydroxy-ethoxy)-ethyl]-isopropyl-amide;
(3R*,4R*)-1-Cyclohexyl-4-{[5-(2,4-difluoro-phenyl)-isoxazole-3-carbonyl]-amino}-piperidine-3-carboxylic acid (2-o-tolyl-ethyl)-amide;
(3R*,4R*)-1-Cyclohexyl-4-{[5-(2,4-difluoro-phenyl)-isoxazole-3-carbonyl]-amino}-piperidine-3-carboxylic acid [2-(2-methoxy-phenyl)-ethyl]-amide;
(3R*,4R*)-1-Cyclohexyl-4-{[5-(2,4-difluoro-phenyl)-isoxazole-3-carbonyl]-amino}-piperidine-3-carboxylic acid [2-(2-chloro-phenyl)-ethyl]-amide;
(3R*,4R*)-1-Cyclohexyl-4-{[5-(2,4-difluoro-phenyl)-isoxazole-3-carbonyl]-amino}-piperidine-3-carboxylic acid [2-(4-fluoro-phenyl)-ethyl]-amide;
(3R*,4R*)-1-Cyclohexyl-4-{[5-(2,4-difluoro-phenyl)-isoxazole-3-carbonyl]-amino}-piperidine-3-carboxylic acid (2-phenyl-propyl)-amide;
(3R*,4R*)-1-Cyclohexyl-4-{[5-(2,4-difluoro-phenyl)-isoxazole-3-carbonyl]-amino}-piperidine-3-carboxylic acid ((1R*,2S*)-2-phenyl-cyclopropyl)-amide;
(3R*,4R*)-1-Cyclohexyl-4-{[5-(2,4-difluoro-phenyl)-isoxazole-3-carbonyl]-amino}-piperidine-3-carboxylic acid ((1S*,2R*)-2-phenyl-cyclopropyl)-amide;
(3R*,4R*)-1-Cyclohexyl-4-{[5-(2,4-difluoro-phenyl)-isoxazole-3-carbonyl]-amino}-piperidine-3-carboxylic acid (2-p-tolyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (1-(pyrimidin-4-yl)-ethyl)-amide;
(3R*,4R*)-1-Cyclohexyl-4-{[5-(2,4-difluoro-phenyl)-isoxazole-3-carbonyl]-amino}-piperidine-3-carboxylic acid phenylamide;
(3R*,4R*)-1-Cyclohexyl-4-{[5-(2,4-difluoro-phenyl)-isoxazole-3-carbonyl]-amino}-piperidine-3-carboxylic acid (4,5-dimethyl-thiazol-2-yl)-amide;
(3R*,4R*)-1-Cyclohexyl-4-{[5-(2,4-difluoro-phenyl)-isoxazole-3-carbonyl]-amino}-piperidine-3-carboxylic acid (2-m-tolyl-ethyl)-amide;
(3R*,4R*)-1-Cyclohexyl-4-{[5-(2,4-difluoro-phenyl)-isoxazole-3-carbonyl]-amino}-piperidine-3-carboxylic acid pyridin-3-ylamide;
(3R*,4R*)-1-Cyclohexyl-4-{[5-(2,4-difluoro-phenyl)-isoxazole-3-carbonyl]-amino}-piperidine-3-carboxylic acid (4-methyl-thiazol-2-ylmethyl)-amide;
(3R*,4R*)-1-Cyclohexyl-4-{[5-(2,4-difluoro-phenyl)-isoxazole-3-carbonyl]-amino}-piperidine-3-carboxylic acid (2,2,2-trifluoro-1-pyridin-2-yl-ethyl)-amide;
5-(2,4-Difluoro-phenyl)-isoxazole-3-carboxylic acid [(3R*,4R*)-1-cyclohexyl-3-(3-phenyl-pyrrolidine-1-carbonyl)-piperidin-4-yl]-amide;
(3R*,4R*)-1-Cyclohexyl-4-{[5-(2,4-difluoro-phenyl)-isoxazole-3-carbonyl]-amino}-piperidine-3-carboxylic acid (1-pyridin-2-yl-cyclopropyl)-amide;
(3R*,4R*)-1-Cyclohexyl-4-{[5-(2,4-difluoro-phenyl)-isoxazole-3-carbonyl]-amino}-piperidine-3-carboxylic acid ((R)-2-hydroxy-2-phenyl-ethyl)-amide;
(3R*,4R*)-1-Cyclohexyl-4-{[5-(2,4-difluoro-phenyl)-isoxazole-3-carbonyl]-amino}-piperidine-3-carboxylic acid ((S)-2-hydroxy-2-phenyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (2-pyridin-2-yl-ethyl)-amide;
(3R*,4R*)-1-Cyclohexyl-4-{[5-(2,4-difluoro-phenyl)-isoxazole-3-carbonyl]-amino}-piperidine-3-carboxylic acid methyl-(2-pyridin-2-yl-ethyl)-amide;
(3R*,4R*)-1-Cyclohexyl-4-{[5-(2,4-difluoro-phenyl)-isoxazole-3-carbonyl]-amino}-piperidine-3-carboxylic acid (2-hydroxy-1-methyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (2,2-difluoro-1-methyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (1-cyclobutyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (2-fluoro-1,1-dimethyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (3,3,3-trifluoro-1,1-dimethyl-propyl)-amide;
(3R*,4R*)-1-Cyclohexyl-4-{[5-(2,4-difluoro-phenyl)-isoxazole-3-carbonyl]-amino}-piperidine-3-carboxylic acid (2-methanesulfonyl-1,1-dimethyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (2-fluoro-1-methyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (2-ethoxy-1-methyl-ethyl)-amide;
(3R*,4R*)-1-Cyclohexyl-4-{[5-(2,4-difluoro-phenyl)-isoxazole-3-carbonyl]-amino}-piperidine-3-carboxylic acid (3-methyl-tetrahydro-furan-3-yl)-amide;
(3R*,4R*)-1-Cyclohexyl-4-{[5-(2,4-difluoro-phenyl)-isoxazole-3-carbonyl]-amino}-piperidine-3-carboxylic acid [1-(5-methyl-[1,3,4]oxadiazol-2-yl)-ethyl]-amide;
(3R*,4R*)-1-Cyclohexyl-4-{[5-(2,4-difluoro-phenyl)-isoxazole-3-carbonyl]-amino}-piperidine-3-carboxylic acid [1-(3,5-difluoro-pyridin-2-yl)-ethyl]-amide;
(3R*,4R*)-1-Cyclohexyl-4-{[5-(2,4-difluoro-phenyl)-isoxazole-3-carbonyl]-amino}-piperidine-3-carboxylic acid (3,3-difluoro-1-methyl-cyclobutyl)-amide;
(3R*,4R*)-1-Cyclohexyl-4-{[5-(2,4-difluoro-phenyl)-isoxazole-3-carbonyl]-amino}-piperidine-3-carboxylic acid (2-hydroxy-1,1-dimethyl-ethyl)-amide;

5-(2,4-Difluoro-phenyl)-isoxazole-3-carboxylic acid [(3R*,4R*)-1-cyclohexyl-3-(3-pyridin-2-yl-pyrrolidine-1-carbonyl)-piperidin-4-yl]-amide;

(3R*,4R*)-1-Cyclohexyl-4-{[5-(2,4-difluoro-phenyl)-isoxazole-3-carbonyl]-amino}-piperidine-3-carboxylic acid ((R)-1-pyrazin-2-yl-ethyl)-amide;

(3R*,4R*)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide;

(3R*,4R*)-1-Cyclohexyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide;

(3R*,4R*)-1-Cyclohexyl-4-{[5-(2,4-difluoro-phenyl)-isoxazole-3-carbonyl]-amino}-piperidine-3-carboxylic acid ((R)-1,2,2-trimethyl-propyl)-amide;

(3R*,4R*)-1-Cyclohexyl-4-{[5-(2,4-difluoro-phenyl)-isoxazole-3-carbonyl]-amino}-piperidine-3-carboxylic acid [(R)-1-(5-fluoro-pyrimidin-2-yl)-ethyl]-amide;

(3R,4R)-1-Cyclohexyl-4-{[1-(2,4-difluoro-phenyl)-1H-[1,2,3]triazole-4-carbonyl]-amino}-piperidine-3-carboxylic acid dimethylamide;

(3S,4S)-1-Cyclohexyl-4-{[1-(2,4-difluoro-phenyl)-1H-[1,2,3]triazole-4-carbonyl]-amino}-piperidine-3-carboxylic acid dimethylamide;

(3R*,4R*)-1-Cyclopentyl-4-{[1-(2,4-difluoro-phenyl)-1H-[1,2,3]triazole-4-carbonyl]-amino}-piperidine-3-carboxylic acid dimethylamide;

(3R*,4R*)-1-Cyclopropylmethyl-4-{[1-(2,4-difluoro-phenyl)-1H-[1,2,3]triazole-4-carbonyl]-amino}-piperidine-3-carboxylic acid dimethylamide;

(3R*,4R*)-4-{[1-(2,4-Difluoro-phenyl)-1H-[1,2,3]triazole-4-carbonyl]-amino}-1-(2-methyl-cyclopentyl)-piperidine-3-carboxylic acid dimethylamide;

(3R*,4R*)-1-Cyclopentyl-4-{[5-(2,4,6-trifluoro-phenyl)-isoxazole-3-carbonyl]-amino}-piperidine-3-carboxylic acid dimethylamide;

(3R*,4R*)-1-Cyclopropylmethyl-4-{[5-(2,4,6-trifluoro-phenyl)-isoxazole-3-carbonyl]-amino}-piperidine-3-carboxylic acid dimethylamide;

(3R*,4R*)-1-(2-Methyl-cyclopentyl)-4-{[5-(2,4,6-trifluoro-phenyl)-isoxazole-3-carbonyl]-amino}-piperidine-3-carboxylic acid dimethylamide;

(3R*,4R*)-1-Cyclohexyl-4-{[3-(2,4-difluoro-phenyl)-isoxazole-5-carbonyl]-amino}-piperidine-3-carboxylic acid dimethylamide;

(3R*,4R*)-1-Cyclopentyl-4-{[3-(2,4-difluoro-phenyl)-isoxazole-5-carbonyl]-amino}-piperidine-3-carboxylic acid dimethylamide;

1-(2,4-Difluoro-phenyl)-1H-[1,2,3]triazole-4-carboxylic acid [(3R*,4R*)-3-(azetidine-1-carbonyl)-1-cyclohexyl-piperidin-4-yl]-amide;

5-(2,4,6-Trifluoro-phenyl)-isoxazole-3-carboxylic acid [(3R*,4R*)-3-(azetidine-1-carbonyl)-1-cyclohexyl-piperidin-4-yl]-amide;

5-(2,4,6-Trifluoro-phenyl)-isoxazole-3-carboxylic acid [(3R*,4R*)-3-(azetidine-1-carbonyl)-1-cyclopentyl-piperidin-4-yl]-amide;

5-(2,4,6-Trifluoro-phenyl)-isoxazole-3-carboxylic acid [(3R*,4R*)-3-(azetidine-1-carbonyl)-1-cyclopropylmethyl-piperidin-4-yl]-amide;

5-(2,4,6-Trifluoro-phenyl)-isoxazole-3-carboxylic acid [(3R*,4R*)-3-(azetidine-1-carbonyl)-1-(2-methyl-cyclopentyl)-piperidin-4-yl]-amide;

(3R*,4R*)-1-Cyclopentyl-4-{[1-(2,4-difluoro-phenyl)-1H-[1,2,3]triazole-4-carbonyl]-amino}-piperidine-3-carboxylic acid (2-methoxy-1,1-dimethyl-ethyl)-amide;

(3R*,4R*)-1-Cyclopropylmethyl-4-{[1-(2,4-difluoro-phenyl)-1H-[1,2,3]triazole-4-carbonyl]-amino}-piperidine-3-carboxylic acid (2-methoxy-1,1-dimethyl-ethyl)-amide;

(3R,4R)-1-Cyclohexyl-4-{[5-(2,4,6-trifluoro-phenyl)-isoxazole-3-carbonyl]-amino}-piperidine-3-carboxylic acid (2-methoxy-1,1-dimethyl-ethyl)-amide;

(3S,4S)-1-Cyclohexyl-4-{[5-(2,4,6-trifluoro-phenyl)-isoxazole-3-carbonyl]-amino}-piperidine-3-carboxylic acid (2-methoxy-1,1-dimethyl-ethyl)-amide;

(3R*,4R*)-1-Cyclopentyl-4-{[5-(2,4,6-trifluoro-phenyl)-isoxazole-3-carbonyl]-amino}-piperidine-3-carboxylic acid (2-methoxy-1,1-dimethyl-ethyl)-amide;

(3R,4R)-1-Cyclopropylmethyl-4-{[5-(2,4,6-trifluoro-phenyl)-isoxazole-3-carbonyl]-amino}piperidine-3-carboxylic acid (2-methoxy-1,1-dimethyl-ethyl)-amide;

(3S,4S)-1-Cyclopropylmethyl-4-{[5-(2,4,6-trifluoro-phenyl)-isoxazole-3-carbonyl]-amino}-piperidine-3-carboxylic acid (2-methoxy-1,1-dimethyl-ethyl)-amide;

(3R*,4R*)-1-(2-Methyl-cyclopentyl)-4-{[5-(2,4,6-trifluoro-phenyl)-isoxazole-3-carbonyl]-amino}-piperidine-3-carboxylic acid (2-methoxy-1,1-dimethyl-ethyl)-amide;

(3R*,4R*)-1-Cyclohexyl-4-{[3-(2,4-difluoro-phenyl)-isoxazole-5-carbonyl]-amino}-piperidine-3-carboxylic acid (2-methoxy-1,1-dimethyl-ethyl)-amide;

(3R*,4R*)-1-Cyclopentyl-4-{[3-(2,4-difluoro-phenyl)-isoxazole-5-carbonyl]-amino}-piperidine-3-carboxylic acid (2-methoxy-1,1-dimethyl-ethyl)-amide;

(3R,4R)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;

(3S,4S)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;

(3R,4R)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;

(3S,4S)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;

(3R*,4R*)-1-Cyclopropylmethyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;

(3R*,4R*)-4-{[1-(2,4-Difluoro-phenyl)-1H-[1,2,3]triazole-4-carbonyl]-amino}-1-(2-methyl-cyclopentyl)-piperidine-3-carboxylic acid ((R)-1-pyridin-2-yl-ethyl)-amide;

(3R,4R)-1-Cyclohexyl-4-{[5-(2,4,6-trifluoro-phenyl)-isoxazole-3-carbonyl]-amino}-piperidine-3-carboxylic acid ((R)-1-pyridin-2-yl-ethyl)-amide;

(3S,4S)-1-Cyclohexyl-4-{[5-(2,4,6-trifluoro-phenyl)-isoxazole-3-carbonyl]-amino}-piperidine-3-carboxylic acid ((R)-1-pyridin-2-yl-ethyl)-amide;

(3R,4R)-1-Cyclopentyl-4-{[5-(2,4,6-trifluoro-phenyl)-isoxazole-3-carbonyl]-amino}-piperidine-3-carboxylic acid ((R)-1-pyridin-2-yl-ethyl)-amide;

(3S,4S)-1-Cyclopentyl-4-{[5-(2,4,6-trifluoro-phenyl)-isoxazole-3-carbonyl]-amino}-piperidine-3-carboxylic acid ((R)-1-pyridin-2-yl-ethyl)-amide;

(3R,4R)-1-Cyclopropylmethyl-4-{[5-(2,4,6-trifluoro-phenyl)-isoxazole-3-carbonyl]-amino}piperidine-3-carboxylic acid ((R)-1-pyridin-2-yl-ethyl)-amide;

(3S,4S)-1-Cyclopropylmethyl-4-{[5-(2,4,6-trifluoro-phenyl)-isoxazole-3-carbonyl]-amino}-piperidine-3-carboxylic acid ((R)-1-pyridin-2-yl-ethyl)-amide;

(3R*,4R*)-1-(2-Methyl-cyclopentyl)-4-{[5-(2,4,6-trifluoro-phenyl)-isoxazole-3-carbonyl]-amino}-piperidine-3-carboxylic acid ((R)-1-pyridin-2-yl-ethyl)-amide;

(3R,4R)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide;
(3S,4S)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide;
(3R*,4R*)-1-Cyclopentyl-4-{[3-(2,4-difluoro-phenyl)-isoxazole-5-carbonyl]-amino}-piperidine-3-carboxylic acid ((R)-1-pyridin-2-yl-ethyl)-amide;
(3R*,4R*)-1-Cyclohexyl-4-{[1-(2,4-difluoro-phenyl)-1H-[1,2,3]triazole-4-carbonyl]-amino}-piperidine-3-carboxylic acid ((R)-1-pyrazin-2-yl-ethyl)-amide;
(3R*,4R*)-1-Cyclopentyl-4-{[1-(2,4-difluoro-phenyl)-1H-[1,2,3]triazole-4-carbonyl]-amino}-piperidine-3-carboxylic acid ((R)-1-pyrazin-2-yl-ethyl)-amide;
(3R*,4R*)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3R,4R)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3S,4S)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3R*,4R*)-1-Cyclopentyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3R*,4R*)-1-Cyclopropylmethyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3R*,4R*)-1-(2-Methyl-cyclopentyl)-4-{[5-(2,4,6-trifluoro-phenyl)-isoxazole-3-carbonyl]-amino}-piperidine-3-carboxylic acid ((R)-1-pyrazin-2-yl-ethyl)-amide;
(3R*,4R*)-1-Cyclohexyl-4-{[3-(2,4-difluoro-phenyl)-isoxazole-5-carbonyl]-amino}-piperidine-3-carboxylic acid ((R)-1-pyrazin-2-yl-ethyl)-amide;
(3R*,4R*)-1-Cyclohexyl-4-{[1-(2,4-difluoro-phenyl)-1H-[1,2,3]triazole-4-carbonyl]-amino}-piperidine-3-carboxylic acid ((R)-1-cyclobutyl-ethyl)-amide;
(3R*,4R*)-1-Cyclopentyl-4-{[1-(2,4-difluoro-phenyl)-1H-[1,2,3]triazole-4-carbonyl]-amino}-piperidine-3-carboxylic acid ((R)-1-cyclobutyl-ethyl)-amide;
(3R*,4R*)-1-Cyclopropylmethyl-4-{[1-(2,4-difluoro-phenyl)-1H-[1,2,3]triazole-4-carbonyl]-amino}-piperidine-3-carboxylic acid ((R)-1-cyclobutyl-ethyl)-amide;
(3R*,4R*)-4-{[1-(2,4-Difluoro-phenyl)-1H-[1,2,3]triazole-4-carbonyl]-amino}-1-(2-methyl-cyclopentyl)-piperidine-3-carboxylic acid ((R)-1-cyclobutyl-ethyl)-amide;
(3R*,4R*)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide;
(3R,4R)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide;
(3S,4S)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide;
(3R*,4R*)-1-Cyclopropylmethyl-4-{[5-(2,4,6-trifluoro-phenyl)-isoxazole-3-carbonyl]-amino}-piperidine-3-carboxylic acid ((R)-1-cyclobutyl-ethyl)-amide;
(3R,4R)-1-Cyclopropylmethyl-4-{[5-(2,4,6-trifluoro-phenyl)-isoxazole-3-carbonyl]-amino}piperidine-3-carboxylic acid ((R)-1-cyclobutyl-ethyl)-amide;
(3S,4S)-1-Cyclopropylmethyl-4-{[5-(2,4,6-trifluoro-phenyl)-isoxazole-3-carbonyl]-amino}-piperidine-3-carboxylic acid ((R)-1-cyclobutyl-ethyl)-amide;
(3R*,4R*)-1-Cyclohexyl-4-{[3-(2,4-difluoro-phenyl)-isoxazole-5-carbonyl]-amino}-piperidine-3-carboxylic acid ((R)-1-cyclobutyl-ethyl)-amide;
(3R*,4R*)-1-Cyclopentyl-4-{[3-(2,4-difluoro-phenyl)-isoxazole-5-carbonyl]-amino}-piperidine-3-carboxylic acid ((R)-1-cyclobutyl-ethyl)-amide;
(3R*,4R*)-1-Cyclohexyl-4-{[1-(2,4-difluoro-phenyl)-1H-[1,2,3]triazole-4-carbonyl]-amino}-piperidine-3-carboxylic acid [1-(5-fluoro-pyridin-2-yl)-cyclopropyl]-amide;
(3R*,4R*)-1-Cyclohexyl-4-{[5-(2,4,6-trifluoro-phenyl)-isoxazole-3-carbonyl]-amino}-piperidine-3-carboxylic acid [1-(5-fluoro-pyridin-2-yl)-cyclopropyl]-amide;
(3R*,4R*)-1-Cyclopropylmethyl-4-{[5-(2,4,6-trifluoro-phenyl)-isoxazole-3-carbonyl]-amino}-piperidine-3-carboxylic acid [1-(5-fluoro-pyridin-2-yl)-cyclopropyl]-amide;
(3R*,4R*)-1-Cyclohexyl-4-{[1-(2,4-difluoro-phenyl)-1H-[1,2,3]triazole-4-carbonyl]-amino}-piperidine-3-carboxylic acid ((1R*,2S*)-2-phenyl-cyclopropyl)-amide;
(3R*,4R*)-1-Cyclohexyl-4-{[1-(2,4-difluoro-phenyl)-1H-[1,2,3]triazole-4-carbonyl]-amino}-piperidine-3-carboxylic acid ((1S*,2R*)-2-phenyl-cyclopropyl)-amide;
(3R*,4R*)-1-Cyclopentyl-4-{[1-(2,4-difluoro-phenyl)-1H-[1,2,3]triazole-4-carbonyl]-amino}-piperidine-3-carboxylic acid ((1R*,2S*)-2-phenyl-cyclopropyl)-amide;
(3R*,4R*)-1-Cyclopentyl-4-{[1-(2,4-difluoro-phenyl)-1H-[1,2,3]triazole-4-carbonyl]-amino}-piperidine-3-carboxylic acid ((1R*,2S*)-2-phenyl-cyclopropyl)-amide;
(3R*,4R*)-1-Cyclohexyl-4-{[3-(2,4-difluoro-phenyl)-isoxazole-5-carbonyl]-amino}-piperidine-3-carboxylic acid ((1S*,2R*)-2-phenyl-cyclopropyl)-amide;
(3R*,4R*)-1-Cyclohexyl-4-{[3-(2,4-difluoro-phenyl)-isoxazole-5-carbonyl]-amino}-piperidine-3-carboxylic acid ((1R*,2S*)-2-phenyl-cyclopropyl)-amide;
(3R*,4R*)-1-Cyclopentyl-4-{[3-(2,4-difluoro-phenyl)-isoxazole-5-carbonyl]-amino}-piperidine-3-carboxylic acid ((1S*,2R*)-2-phenyl-cyclopropyl)-amide;
(3R*,4R*)-1-Cyclopentyl-4-{[3-(2,4-difluoro-phenyl)-isoxazole-5-carbonyl]-amino}-piperidine-3-carboxylic acid ((1R*,2S*)-2-phenyl-cyclopropyl)-amide;
(3R*,4R*)-1-Cyclopropylmethyl-4-{[3-(2,4-difluoro-phenyl)-isoxazole-5-carbonyl]-amino}-piperidine-3-carboxylic acid dimethylamide;
(3R*,4R*)-4-{[3-(2,4-Difluoro-phenyl)-isoxazole-5-carbonyl]-amino}-1-(2-methyl-cyclopentyl)-piperidine-3-carboxylic acid dimethylamide;
(3R*,4R*)-1-Cyclopropylmethyl-4-{[3-(2,4-difluoro-phenyl)-isoxazole-5-carbonyl]-amino}-piperidine-3-carboxylic acid (2-methoxy-1,1-dimethyl-ethyl)-amide;
(3R*,4R*)-1-Cyclohexyl-4-{[5-(2,4-difluoro-phenyl)-[1,2,4]oxadiazole-3-carbonyl]-amino}-piperidine-3-carboxylic acid (2-methoxy-1,1-dimethyl-ethyl)-amide;
(3R*,4R*)-1-Cyclopropylmethyl-4-{[5-(2,4-difluoro-phenyl)-[1,2,4]oxadiazole-3-carbonyl]-amino}-piperidine-3-carboxylic acid (2-methoxy-1,1-dimethyl-ethyl)-amide;
(3R,4R)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide;
(3S,4S)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide;
(3R*,4R*)-4-{[3-(2,4-Difluoro-phenyl)-isoxazole-5-carbonyl]-amino}-1-(2-methyl-cyclopentyl)-piperidine-3-carboxylic acid ((R)-1-pyridin-2-yl-ethyl)-amide;
(3R,4R)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3S,4S)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3R*,4R*)-1-Cyclopentyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3R*,4R*)-1-Cyclopropylmethyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3R*,4R*)-1-Cyclopropylmethyl-4-{[3-(2,4-difluoro-phenyl)-isoxazole-5-carbonyl]-amino}-piperidine-3-carboxylic acid ((R)-1-pyrazin-2-yl-ethyl)-amide;

(3R*,4R*)-1-Cyclohexyl-4-{[5-(2,4-difluoro-phenyl)-[1,2,4]oxadiazole-3-carbonyl]-amino}-piperidine-3-carboxylic acid ((R)-1-pyrazin-2-yl-ethyl)-amide;

(3R*,4R*)-1-Cyclopropylmethyl-4-{[3-(2,4-difluoro-phenyl)-isoxazole-5-carbonyl]-amino}-piperidine-3-carboxylic acid ((R)-1-cyclobutyl-ethyl)-amide;

(3R*,4R*)-4-{[3-(2,4-Difluoro-phenyl)-isoxazole-5-carbonyl]-amino}-1-(2-methyl-cyclopentyl)-piperidine-3-carboxylic acid ((R)-1-cyclobutyl-ethyl)-amide;

(3R*,4R*)-1-Cyclopropylmethyl-4-{[3-(2,4-difluoro-phenyl)-isoxazole-5-carbonyl]-amino}-piperidine-3-carboxylic acid [1-(5-fluoro-pyridin-2-yl)-cyclopropyl]-amide;

(3R*,4R*)-1-Cyclopropylmethyl-4-{[3-(2,4-difluoro-phenyl)-isoxazole-5-carbonyl]-amino}-piperidine-3-carboxylic acid ((1S*,2R*)-2-phenyl-cyclopropyl)-amide;

(3R*,4R*)-1-Cyclopropylmethyl-4-{[3-(2,4-difluoro-phenyl)-isoxazole-5-carbonyl]-amino}-piperidine-3-carboxylic acid ((1R*,2S*)-2-phenyl-cyclopropyl)-amide;

(3R*,4R*)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3R,4R)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3R*,4R*)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3R*,4R*)-1-Cyclopropylmethyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3R*,4R*)-4-{[1-(2,4-Difluoro-phenyl)-1H-[1,2,3]triazole-4-carbonyl]-amino}-1-(2-methyl-cyclopentyl)-piperidine-3-carboxylic acid (1-pyridin-2-yl-cyclopropyl)-amide;

(3R*,4R*)-1-Cyclohexyl-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-Cyclopropylmethyl-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-Cyclopropylmethyl-4-{[5-(2,4,6-trifluoro-phenyl)-isoxazole-3-carbonyl]-amino}piperidine-3-carboxylic acid (1-pyridin-2-yl-cyclopropyl)-amide;

(3R*,4R*)-1-(2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3R*,4R*)-1-Cyclopentyl-4-{[3-(2,4-difluoro-phenyl)-isoxazole-5-carbonyl]-amino}-piperidine-3-carboxylic acid (1-pyridin-2-yl-cyclopropyl)-amide;

(3R*,4R*)-1-Cyclopropylmethyl-4-{[3-(2,4-difluoro-phenyl)-isoxazole-5-carbonyl]-amino}-piperidine-3-carboxylic acid (1-pyridin-2-yl-cyclopropyl)-amide;

(3R*,4R*)-4-{[3-(2,4-Difluoro-phenyl)-isoxazole-5-carbonyl]-amino}-1-(2-methyl-cyclopentyl)-piperidine-3-carboxylic acid (1-pyridin-2-yl-cyclopropyl)-amide;

(3R,4R)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide;

(3S,4S)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide;

(3R*,4R*)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide;

(3R*,4R*)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid (1-pyrazin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid (1-pyridazin-3-yl-cyclopropyl)-amide;

(3S,4S)-1-Cyclopentyl-4-{[5-(2,4-difluoro-phenyl)-isoxazole-3-carbonyl]-amino}-piperidine-3-carboxylic acid (1-pyrazin-2-yl-cyclopropyl)-amide;

(3S,4S)-1-Cyclopentyl-4-{[5-(2,4-difluoro-phenyl)-isoxazole-3-carbonyl]-amino}-piperidine-3-carboxylic acid (1-pyridazin-3-yl-cyclopropyl)-amide;

(3R*,4R*)-1-Cyclohexyl-4-{[5-(2,4-difluoro-phenyl)-isoxazole-3-carbonyl]-amino}-piperidine-3-carboxylic acid (cyano-dimethyl-methyl)-amide;

(3S,4S)-1-Cyclopentyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide;

(3R,4R)-1-Cyclohexyl-4-{[5-(2,4-difluoro-phenyl)-isoxazole-3-carbonyl]-amino}-piperidine-3-carboxylic acid dimethylamide;

(3R,4R)-1-Cyclohexyl-4-{[5-(2,4-difluoro-phenyl)-isoxazole-3-carbonyl]-amino}-piperidine-3-carboxylic acid ((S)-1-pyridin-2-yl-ethyl)-amide;

(3S,4S)-1-Cyclohexyl-4-{[5-(2,4-difluoro-phenyl)-isoxazole-3-carbonyl]-amino}-piperidine-3-carboxylic acid ((S)-1-pyridin-2-yl-ethyl)-amide;

(3S,4S)-1-Cyclohexyl-4-{[5-(2,4-difluoro-phenyl)-isoxazole-3-carbonyl]-amino}-piperidine-3-carboxylic acid ((R)-1-pyridin-2-yl-ethyl)-amide;

(3R,4R)-1-Cyclohexyl-4-{[5-(2,4-difluoro-phenyl)-isoxazole-3-carbonyl]-amino}-piperidine-3-carboxylic acid ((R)-1-pyridin-2-yl-ethyl)-amide;

(3S,4S)-1-Cyclohexyl-4-{[5-(2,4-difluoro-phenyl)-isoxazole-3-carbonyl]-amino}-piperidine-3-carboxylic acid [(R)-1-(6-methyl-pyridin-2-yl)-ethyl]-amide;

(3R,4R)-1-Cyclohexyl-4-{[5-(2,4-difluoro-phenyl)-isoxazole-3-carbonyl]-amino}-piperidine-3-carboxylic acid [(R)-1-(6-methyl-pyridin-2-yl)-ethyl]-amide;

(3S,4S)-1-Cyclohexyl-4-{[5-(2,4-difluoro-phenyl)-isoxazole-3-carbonyl]-amino}-piperidine-3-carboxylic acid [(S)-1-(6-methyl-pyridin-2-yl)-ethyl]-amide;

(3R,4R)-1-Cyclohexyl-4-{[5-(2,4-difluoro-phenyl)-isoxazole-3-carbonyl]-amino}-piperidine-3-carboxylic acid [(S)-1-(6-methyl-pyridin-2-yl)-ethyl]-amide;
(3R*,4R*)-4-{[5-(2,4-Difluoro-phenyl)-isoxazole-3-carbonyl]-amino}-1-isopropyl-piperidine-3-carboxylic acid dimethylamide;
(3R*,4R*)-4-{[5-(2,4-Difluoro-phenyl)-isoxazole-3-carbonyl]-amino}-1-ethyl-piperidine-3-carboxylic acid dimethylamide;
(3R*,4R*)-4-{[5-(2,4-Difluoro-phenyl)-isoxazole-3-carbonyl]-amino}-1-isopropyl-piperidine-3-carboxylic acid methyl-phenethyl-amide;
(3R*,4R*)-4-{[5-(2,4-Difluoro-phenyl)-isoxazole-3-carbonyl]-amino}-1-ethyl-piperidine-3-carboxylic acid methyl-phenethyl-amide;
(3R*,4R*)-1-Cyclopentyl-4-{[5-(2,4-difluoro-phenyl)-isoxazole-3-carbonyl]-amino}-piperidine-3-carboxylic acid methyl-phenethyl-amide;
(3R*,4R*)-1-Cyclopropylmethyl-4-{[5-(2,4-difluoro-phenyl)-isoxazole-3-carbonyl]-amino}-piperidine-3-carboxylic acid methyl-phenethyl-amide;
(3R*,4R*)-4-{[5-(2,4-Difluoro-phenyl)-isoxazole-3-carbonyl]-amino}1-isopropyl-piperidine-3-carboxylic acid (1-pyridin-2-yl-ethyl)-amide;
(3R*,4R*)-4-{[5-(2,4-Difluoro-phenyl)-isoxazole-3-carbonyl]-amino}-1-ethyl-piperidine-3-carboxylic acid (1-pyridin-2-yl-ethyl)-amide;
(3R*,4R*)-1-Cyclopentyl-4-{[5-(2,4-difluoro-phenyl)-isoxazole-3-carbonyl]-amino}-piperidine-3-carboxylic acid (1-pyridin-2-yl-ethyl)-amide;
(3R*,4R*)-1-Cyclopropylmethyl-4-{[5-(2,4-difluoro-phenyl)-isoxazole-3-carbonyl]-amino}-piperidine-3-carboxylic acid ((1-pyridin-2-yl-ethyl)-amide;
(3R*,4R*)-1-Cyclopropylmethyl-4-{[5-(2,4-difluoro-phenyl)-isoxazole-3-carbonyl]-amino}-piperidine-3-carboxylic acid [(R)-1-(1-oxy-pyridin-2-yl)-ethyl]-amide;
(3R*,4R*)-1-(1-Cyclopropyl-ethyl)-4-{[5-(2,4-difluoro-phenyl)-isoxazole-3-carbonyl]-amino}-piperidine-3-carboxylic acid dimethylamide;
(3R*,4R*)-4-{[5-(2,4-Difluoro-phenyl)-isoxazole-3-carbonyl]-amino}-1-(2-hydroxymethyl-cyclopentyl)-piperidine-3-carboxylic acid dimethylamide;
(3R*,4R*)-4-{[5-(2,4-Difluoro-phenyl)-isoxazole-3-carbonyl]-amino}-1-(2-ethyl-cyclopentyl)-piperidine-3-carboxylic acid dimethylamide;
(3R*,4R*)-4-{[5-(2,4-Difluoro-phenyl)-isoxazole-3-carbonyl]-amino}-1-(2-methyl-cyclobutyl)-piperidine-3-carboxylic acid dimethylamide;
(3R,4R)-4-{[5-(2,4-Difluoro-phenyl)-isoxazole-3-carbonyl]-amino}-1-(2-methyl-cyclobutyl)-piperidine-3-carboxylic acid dimethylamide;
(3R*,4R*)-4-{[5-(2,4-Difluoro-phenyl)-isoxazole-3-carbonyl]-amino}-1-(2,2-dimethyl-cyclobutyl)-piperidine-3-carboxylic acid dimethylamide;
(3R*,4R*)-4-{[5-(2,4-Difluoro-phenyl)-isoxazole-3-carbonyl]-amino}1-(3,3-dimethyl-cyclopentyl)-piperidine-3-carboxylic acid dimethylamide;
(3R,4R)-1-Cyclopentyl-4-{[5-(2,4-difluoro-phenyl)-isoxazole-3-carbonyl]-amino}-piperidine-3-carboxylic acid dimethylamide;
(3S,4S)-1-Cyclopentyl-4-{[5-(2,4-difluoro-phenyl)-isoxazole-3-carbonyl]-amino}-piperidine-3-carboxylic acid dimethylamide;
(3R*,4R*)-4-{[5-(2,4-Difluoro-phenyl)-isoxazole-3-carbonyl]-amino}1-(2,2-dimethyl-propyl)-piperidine-3-carboxylic acid dimethylamide;
(3R*,4R*)-4-{[5-(2,4-Difluoro-phenyl)-isoxazole-3-carbonyl]-amino}-1-(3-methyl-butyl)-piperidine-3-carboxylic acid dimethylamide;
(3R*,4R*)-4-{[5-(2,4-Difluoro-phenyl)-isoxazole-3-carbonyl]-amino}-1-(3,3-dimethyl-butyl)-piperidine-3-carboxylic acid dimethylamide;
(3R*,4R*)-4-{[5-(2,4-Difluoro-phenyl)-isoxazole-3-carbonyl]-amino}-1-(2-methyl-cyclopentyl)-piperidine-3-carboxylic acid dimethylamide;
(3R,4R)-4-{[5-(2,4-Difluoro-phenyl)-isoxazole-3-carbonyl]-amino}-1-(2-methyl-cyclopentyl)-piperidine-3-carboxylic acid dimethylamide;
(3R*,4R*)-4-{[5-(2,4-Difluoro-phenyl)-isoxazole-3-carbonyl]-amino}-1-(3,3-dimethyl-cyclohexyl)-piperidine-3-carboxylic acid dimethylamide;
(3R*,4R*)-4-{[5-(2,4-Difluoro-phenyl)-isoxazole-3-carbonyl]-amino}-1-spiro[3.3]hept-2-yl-piperidine-3-carboxylic acid dimethylamide;
(3R*,4R*)-4-{[5-(2,4-Difluoro-phenyl)-isoxazole-3-carbonyl]-amino}1-(4-fluoro-cyclohexyl)-piperidine-3-carboxylic acid dimethylamide;
(3R*,4R*)-1-(4,4-Difluoro-cyclohexyl)-4-{[5-(2,4-difluoro-phenyl)-isoxazole-3-carbonyl]-amino}-piperidine-3-carboxylic acid dimethylamide;
(3R*,4R*)-1-Cyclobutyl-4-{[5-(2,4-difluoro-phenyl)-isoxazole-3-carbonyl]-amino}-piperidine-3-carboxylic acid dimethylamide;
(3R*,4R*)-1-Cyclopropylmethyl-4-{[5-(2,4-difluoro-phenyl)-isoxazole-3-carbonyl]-amino}-piperidine-3-carboxylic acid dimethylamide;
(3R*,4R*)-1-Cyclopentylmethyl-4-{[5-(2,4-difluoro-phenyl)-isoxazole-3-carbonyl]-amino}-piperidine-3-carboxylic acid dimethylamide;
(3R*,4R*)-4-{[5-(2,4-Difluoro-phenyl)-isoxazole-3-carbonyl]-amino}-1-(3,3-dimethyl-cyclobutyl)-piperidine-3-carboxylic acid dimethylamide;
(3R*,4R*)-4-{[5-(2,4-Difluoro-phenyl)-isoxazole-3-carbonyl]-amino}-1-(3-methoxy-cyclohexyl)-piperidine-3-carboxylic acid dimethylamide;
(3R*,4R*)-4-{[5-(2,4-Difluoro-phenyl)-isoxazole-3-carbonyl]-amino}-1-(2-methoxy-cyclohexyl)-piperidine-3-carboxylic acid dimethylamide;
(3R*,4R*)-4-{[5-(2,4-Difluoro-phenyl)-isoxazole-3-carbonyl]-amino}-1-(1-methyl-cyclopropylmethyl)-piperidine-3-carboxylic acid dimethylamide;
(3R*,4R*)-4-{[5-(2,4-Difluoro-phenyl)-isoxazole-3-carbonyl]-amino}-1-(1-methyl-cyclobutylmethyl)-piperidine-3-carboxylic acid dimethylamide;
(3R*,4R*)-1-Cyclopent-1-enylmethyl-4-{[5-(2,4-difluoro-phenyl)-isoxazole-3-carbonyl]-amino}-piperidine-3-carboxylic acid dimethylamide;
(3R*,4R*)-1-Bicyclo[2.2.1]hept-2-yl-4-{[5-(2,4-difluoro-phenyl)-isoxazole-3-carbonyl]-amino}-piperidine-3-carboxylic acid dimethylamide;
(3R*,4R*)-1-Cyclobutylmethyl-4-{[5-(2,4-difluoro-phenyl)-isoxazole-3-carbonyl]-amino}-piperidine-3-carboxylic acid dimethylamide;
(3R*,4R*)-1-(2-Cyclopropyl-ethyl)-4-{[5-(2,4-difluoro-phenyl)-isoxazole-3-carbonyl]-amino}-piperidine-3-carboxylic acid dimethylamide;
(3R*,4R*)-4-{[5-(2,4-Difluoro-phenyl)-isoxazole-3-carbonyl]-amino}1-(2-fluoro-cyclohexyl)-piperidine-3-carboxylic acid dimethylamide;
(3R,4R)-1-Cyclopropylmethyl-4-{[5-(2,4-difluoro-phenyl)-isoxazole-3-carbonyl]-amino}-piperidine-3-carboxylic acid dimethylamide;

(3R,4R)-1-(1-Cyclopropyl-ethyl)-4-{[5-(2,4-difluoro-phenyl)-isoxazole-3-carbonyl]-amino}-piperidine-3-carboxylic acid dimethylamide;
(3R,4R)-4-{[5-(2,4-Difluoro-phenyl)-isoxazole-3-carbonyl]-amino}-1-spiro[2.4]hept-4-yl-piperidine-3-carboxylic acid dimethylamide;
(3R*,4R*)-4-{[5-(2,4-Difluoro-phenyl)-isoxazole-3-carbonyl]-amino}-1-(2-hydroxy-cyclohexyl)-piperidine-3-carboxylic acid dimethylamide;
(3R*,4R*)-4-{[5-(2,4-Difluoro-phenyl)-isoxazole-3-carbonyl]-amino}-1-(2-hydroxy-1-methyl-propyl)-piperidine-3-carboxylic acid dimethylamide;
(3R*,4R*)-4-{[5-(2,4-Difluoro-phenyl)-isoxazole-3-carbonyl]-amino}-1-(2-hydroxy-cyclohexyl)-piperidine-3-carboxylic acid methyl-phenethyl-amide;
(3R*,4R*)-4-{[5-(2,4-Difluoro-phenyl)-isoxazole-3-carbonyl]-amino}-1-(2-hydroxy-1-methyl-propyl)-piperidine-3-carboxylic acid methyl-phenethyl-amide;
(3R*,4R*)-4-{[5-(2,4-Difluoro-phenyl)-isoxazole-3-carbonyl]-amino}-1-(2-hydroxy-ethyl)-piperidine-3-carboxylic acid methyl-phenethyl-amide;
(3R*,4R*)-4-{[5-(2,4-Difluoro-phenyl)-isoxazole-3-carbonyl]-amino}-1-(2-hydroxy-cyclohexyl)-piperidine-3-carboxylic acid (1-pyridin-2-yl-ethyl)-amide;
(3R*,4R*)-4-{[5-(2,4-Difluoro-phenyl)-isoxazole-3-carbonyl]-amino}-1-(2-hydroxy-1-methyl-propyl)-piperidine-3-carboxylic acid (1-pyridin-2-yl-ethyl)-amide;
(3S,4S)-4-{[5-(2,4-Difluoro-phenyl)-isoxazole-3-carbonyl]-amino}-1-(2-methoxy-ethyl)-piperidine-3-carboxylic acid (1-pyrimidin-2-yl-cyclopropyl)-amide;
(3S,4S)-4-{[5-(2,4-Difluoro-phenyl)-isoxazole-3-carbonyl]-amino}-1-ethyl-piperidine-3-carboxylic acid (1-pyrimidin-2-yl-cyclopropyl)-amide;
(3S,4S)-4-{[5-(2,4-Difluoro-phenyl)-isoxazole-3-carbonyl]-amino}-1-(1,1,2,2,2-d-ethyl)-piperidine-3-carboxylic acid (1-pyrimidin-2-yl-cyclopropyl)-amide;
(3R*,4R*)-4-{[5-(2,4-Difluoro-phenyl)-isoxazole-3-carbonyl]-amino}-piperidine-3-carboxylic acid methyl-phenethyl-amide;
(3S,4S)-4-{[5-(2,4-Difluoro-phenyl)-isoxazole-3-carbonyl]-amino}-piperidine-3-carboxylic acid (1-pyrimidin-2-yl-cyclopropyl)-amide;
(3R*,4R*)-1-Cyclohexyl-4-{[5-(2,6-difluoro-phenyl)-isoxazole-3-carbonyl]-amino}-piperidine-3-carboxylic acid dimethylamide;
(3R*,4R*)-1-Cyclohexyl-4-{[5-(4-fluoro-phenyl)-isoxazole-3-carbonyl]-amino}-piperidine-3-carboxylic acid dimethylamide;
(3R*,4R*)-1-Cyclohexyl-4-{[5-(2,4-difluoro-phenyl)-[1,3,4]oxadiazole-2-carbonyl]-amino}-piperidine-3-carboxylic acid dimethylamide;
(3S,4S)-1-Cyclohexyl-4-{[5-(2,4-difluoro-phenyl)-[1,3,4]oxadiazole-2-carbonyl]-amino}-piperidine-3-carboxylic acid dimethylamide;
(3R,4R)-1-Cyclohexyl-4-{[5-(2,4-difluoro-phenyl)-[1,3,4]oxadiazole-2-carbonyl]-amino}-piperidine-3-carboxylic acid dimethylamide;
(3R*,4R*)-4-{[5-(2-Chloro-4-fluoro-phenyl)-isoxazole-3-carbonyl]-amino}-1-cyclohexyl-piperidine-3-carboxylic acid dimethylamide;
(3R*,4R*)-1-Cyclohexyl-4-{[5-(2,4,6-trifluoro-phenyl)-isoxazole-3-carbonyl]-amino}-piperidine-3-carboxylic acid dimethylamide;
(3R*,4R*)-4-{[5-(4-Chloro-2-fluoro-phenyl)-isoxazole-3-carbonyl]-amino}-1-cyclohexyl-piperidine-3-carboxylic acid dimethylamide;

(3R*,4R*)-1-Cyclohexyl-4-{[5-(2,4-difluoro-phenyl)-[1,2,4]oxadiazole-3-carbonyl]-amino}-piperidine-3-carboxylic acid dimethylamide;
(3R*,4R*)-1-Cyclohexyl-4-{[5-(2-fluoro-phenyl)-isoxazole-3-carbonyl]-amino}-piperidine-3-carboxylic acid (1-pyridin-2-yl-cyclopropyl)-amide;
(3R*,4R*)-1-Cyclohexyl-4-{[5-(2,4-difluoro-phenyl)-[1,2,4]oxadiazole-3-carbonyl]-amino}-piperidine-3-carboxylic acid (1-pyridin-2-yl-cyclopropyl)-amide;
(3R*,4R*)-1-Cyclohexyl-4-{[5-(2,4-difluoro-phenyl)-oxazole-2-carbonyl]-amino}-piperidine-3-carboxylic acid (1-pyridin-2-yl-cyclopropyl)-amide;
(3R*,4R*)-1-Cyclohexyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide;
(3R*,4R*)-1-Cyclopropylmethyl-4-{[5-(2-fluoro-phenyl)-isoxazole-3-carbonyl]-amino}-piperidine-3-carboxylic acid (1-pyridin-2-yl-cyclopropyl)-amide;
(3R*,4R*)-1-Cyclopropylmethyl-4-{[5-(4-fluoro-phenyl)-isoxazole-3-carbonyl]-amino}-piperidine-3-carboxylic acid (1-pyridin-2-yl-cyclopropyl)-amide;
(3R*,4R*)-1-Cyclopropylmethyl-4-{[5-(2,4-difluoro-phenyl)-oxazole-2-carbonyl]-amino}-piperidine-3-carboxylic acid (1-pyridin-2-yl-cyclopropyl)-amide;
(3R,4R)-1-Cyclopropylmethyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide;
(3S,4S)-1-Cyclopropylmethyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide;
(3R*,4R*)-1-Cyclopentyl-4-{[5-(2,4-difluoro-phenyl)-oxazole-2-carbonyl]-amino}-piperidine-3-carboxylic acid dimethylamide;
(3R*,4R*)-1-Cyclohexyl-4-{[5-(2,4-difluoro-phenyl)-oxazole-2-carbonyl]-amino}-piperidine-3-carboxylic acid dimethylamide;
(3R*,4R*)-1-Cyclohexyl-4-{[3-(2,4-difluoro-phenyl)-[1,2,4]oxadiazole-5-carbonyl]-amino}-piperidine-3-carboxylic acid dimethylamide;
(3R,4R)-1-Cyclopropylmethyl-4-{[5-(2,4,6-trifluoro-phenyl)-isoxazole-3-carbonyl]-amino}piperidine-3-carboxylic acid (1-pyrimidin-2-yl-cyclopropyl)-amide;
(3S,4S)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide;
(3S,4S)-1-Cyclohexyl-4-{[5-(2,4-difluoro-phenyl)-isoxazole-3-carbonyl]-amino}-piperidine-3-carboxylic acid (1-methyl-cyclopropyl)-amide;
(3S,4S)-1-Cyclohexyl-4-{[5-(2,4-difluoro-phenyl)-isoxazole-3-carbonyl]-amino}-piperidine-3-carboxylic acid (2-methoxy-1,1-dimethyl-ethyl)-amide;
(3S,4S)-1-Cyclohexyl-4-{[5-(2,4-difluoro-phenyl)-isoxazole-3-carbonyl]-amino}-piperidine-3-carboxylic acid (3-methoxy-1,1-dimethyl-propyl)-amide;
(3S,4S)-1-Cyclohexyl-4-{[5-(2,4-difluoro-phenyl)-isoxazole-3-carbonyl]-amino}-piperidine-3-carboxylic acid[1-(5-fluoro-pyridin-2-yl)-cyclopropyl]-amide;
(3S,4S)-1-Cyclohexyl-4-{[5-(2,4-difluoro-phenyl)-isoxazole-3-carbonyl]-amino}-piperidine-3-carboxylic acid dimethylamide;
(3S,4S)-1-Cyclohexyl-4-{[5-(2,4-difluoro-phenyl)-isoxazole-3-carbonyl]-amino}-piperidine-3-carboxylic acid (1-methyl-cyclobutyl)-amide;
(3S,4S)-1-Cyclohexyl-4-{[5-(2,4-difluoro-phenyl)-isoxazole-3-carbonyl]-amino}-piperidine-3-carboxylic acid (1-[1,2,4]oxadiazol-3-yl-ethyl)-amide;

(3S,4S)-1-Cyclohexyl-4-{[5-(2,4-difluoro-phenyl)-isoxazole-3-carbonyl]-amino}-piperidine-3-carboxylic acid[1-(5-fluoro-pyridin-2-yl)-ethyl]-amide;
(3R,4R)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide;
(3S,4S)-1-Cyclohexyl-4-{[5-(2,4-difluoro-phenyl)-isoxazole-3-carbonyl]-amino}-piperidine-3-carboxylic acid ((R)-1-phenyl-ethyl)-amide;
(3S,4S)-1-Cyclohexyl-4-{[5-(2,4-difluoro-phenyl)-isoxazole-3-carbonyl]-amino}-piperidine-3-carboxylic acid ((S)-2-hydroxy-1-phenyl-ethyl)-amide;
(3S,4S)-1-Cyclohexyl-4-{[5-(2,4-difluoro-phenyl)-isoxazole-3-carbonyl]-amino}-piperidine-3-carboxylic acid benzylamide;
(3S,4S)-1-Cyclohexyl-4-{[5-(2,4-difluoro-phenyl)-isoxazole-3-carbonyl]-amino}-piperidine-3-carboxylic acid (2-hydroxy-1-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide;
(3R,4R)-1-Cyclohexyl-4-{[5-(2,4-difluoro-phenyl)-isoxazole-3-carbonyl]-amino}-piperidine-3-carboxylic acid tert-butylamide;
(3R,4R)-1-Cyclohexyl-4-{[5-(2,4-difluoro-phenyl)-isoxazole-3-carbonyl]-amino}-piperidine-3-carboxylic acid (1-methyl-cyclobutyl)-amide;
(3R,4R)-1-Cyclohexyl-4-{[5-(2,4-difluoro-phenyl)-isoxazole-3-carbonyl]-amino}-piperidine-3-carboxylic acid amide;
(3R,4R)-1-Cyclohexyl-4-{[5-(2,4-difluoro-phenyl)-isoxazole-3-carbonyl]-amino}-piperidine-3-carboxylic acid (1-methyl-cyclopropyl)-amide;
(3R,4R)-1-Cyclohexyl-4-{[5-(2,4-difluoro-phenyl)-isoxazole-3-carbonyl]-amino}-piperidine-3-carboxylic acid (cyano-dimethyl-methyl)-amide;
(3R,4R)-1-Cyclohexyl-4-{[5-(2,4-difluoro-phenyl)-isoxazole-3-carbonyl]-amino}-piperidine-3-carboxylic acid ((S)-2-hydroxy-1-phenyl-ethyl)-amide;
(3R,4R)-1-Cyclohexyl-4-{[5-(2,4-difluoro-phenyl)-isoxazole-3-carbonyl]-amino}-piperidine-3-carboxylic acid ((R)-2-hydroxy-1-phenyl-ethyl)-amide;
(3R,4R)-1-Cyclohexyl-4-{[5-(2,4-difluoro-phenyl)-isoxazole-3-carbonyl]-amino}-piperidine-3-carboxylic acid ((R)-1-phenyl-ethyl)-amide;
(3S,4S)-1-Cyclopropylmethyl-4-{[5-(2,4-difluoro-phenyl)-isoxazole-3-carbonyl]-amino}-piperidine-3-carboxylic acid [1-(2H-pyrazol-3-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid ((R)-1-pyridin-3-yl-ethyl)-amide;
(3R,4R)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyridin-4-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyridin-4-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyridin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyridin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclopentyl-4-{[5-(2,4-difluoro-phenyl)-isoxazole-3-carbonyl]-amino}-piperidine-3-carboxylic acid [1-methyl-1-(1-methyl-1H-pyrazol-4-yl)-ethyl]-amide;
(3S,4S)-1-Cyclopentyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]-amide;
(3S,4S)-1-Cyclopentyl-4-{[5-(2,4-difluoro-phenyl)-isoxazole-3-carbonyl]-amino}-piperidine-3-carboxylic acid bicyclopropyl-1-ylamide;
(3S,4S)-1-Cyclopentyl-4-{[5-(2,4-difluoro-phenyl)-isoxazole-3-carbonyl]-amino}-piperidine-3-carboxylic acid [1-(tetrahydro-furan-2-yl)-ethyl]-amide;
(3S,4S)-1-Cyclopentyl-4-{[5-(2,4-difluoro-phenyl)-isoxazole-3-carbonyl]-amino}-piperidine-3-carboxylic acid [1-(1H-[1,2,4]triazol-3-yl)-ethyl]-amide;
(3S,4S)-1-Cyclopentyl-4-{[5-(2,4-difluoro-phenyl)-isoxazole-3-carbonyl]-amino}-piperidine-3-carboxylic acid (1-methyl-prop-2-ynyl)-amide;
(3S,4S)-1-Cyclopentyl-4-{[5-(2,4-difluoro-phenyl)-isoxazole-3-carbonyl]-amino}-piperidine-3-carboxylic acid (1-isoxazol-3-yl-ethyl)-amide;
(3S,4S)-1-Cyclopentyl-4-{[5-(2,4-difluoro-phenyl)-isoxazole-3-carbonyl]-amino}-piperidine-3-carboxylic acid [1-(2H-pyrazol-3-yl)-ethyl]-amide;
(3S,4S)-1-Cyclopentyl-4-{[5-(2,4-difluoro-phenyl)-isoxazole-3-carbonyl]-amino}-piperidine-3-carboxylic acid ((R)-1-pyridin-3-yl-ethyl)-amide;
(3S,4S)-1-Cyclopropylmethyl-4-{[5-(2,4-difluoro-phenyl)-isoxazole-3-carbonyl]-amino}-piperidine-3-carboxylic acid [1-methyl-1-(1-methyl-1H-pyrazol-4-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid bicyclopropyl-1-ylamide;
(3S,4S)-1-Cyclopropylmethyl-4-{[5-(2,4-difluoro-phenyl)-isoxazole-3-carbonyl]-amino}-piperidine-3-carboxylic acid [1-(tetrahydro-furan-2-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [1-(1H-[1,2,4]triazol-3-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid (1-methyl-prop-2-ynyl)-amide;
(3S,4S)-1-Cyclopropylmethyl-4-{[5-(2,4-difluoro-phenyl)-isoxazole-3-carbonyl]-amino}-piperidine-3-carboxylic acid (1-isoxazol-3-yl-ethyl)-amide;
(3R*,4R*)-1-Cyclohexyl-4-{[5-(2,4-difluoro-phenyl)-isoxazole-3-carbonyl]-amino}-3-methyl-piperidine-3-carboxylic acid ((R)-1-pyridin-2-yl-ethyl)-amide; and (3R*,4R*)-1-Cyclohexyl-4-{[5-(2,4-difluoro-phenyl)-isoxazole-3-carbonyl]-amino}-3-methyl-piperidine-3-carboxylic acid dimethylamide;

22) In addition to the compounds of embodiment 21), further compounds according to embodiment 1) are selected from the following compounds:

(3R*,4R*)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,3,4-trifluoro-phenyl)-isoxazole-3-carbonyl]-amino}piperidine-3-carboxylic acid (1-pyrimidin-2-yl-cyclopropyl)-amide;

(3S,4S)-1-Cyclopropylmethyl-4-{[5-(2,3,4-trifluoro-phenyl)-isoxazole-3-carbonyl]-amino}-piperidine-3-carboxylic acid (1-pyrimidin-2-yl-cyclopropyl)-amide;

(3R*,4R*)-1-Cyclopropylmethyl-4-{[5-(2,4-difluoro-phenyl)-isoxazole-3-carbonyl]-amino}-piperidine-3-carboxylic acid (1-pyridin-2-yl-cyclobutyl)-amide;

(3R*,4R*)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide;

(3R*,4R*)-4-{[5-(2,4-Difluoro-phenyl)-isoxazole-3-carbonyl]-amino}-1-(2-hydroxy-cyclohexyl)-piperidine-3-carboxylic acid (1-pyrimidin-2-yl-cyclopropyl)-amide;

(3R*,4R*)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3R*,4R*)-1-Cyclopentyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3S,4S)-1-Cyclopentyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3R*,4R*)-1-Cyclopentyl-4-{[5-(2,4-difluoro-phenyl)-isoxazole-3-carbonyl]-amino}-piperidine-3-carboxylic acid (1-cyano-cyclobutyl)-amide;

(3S,4S)-1-Cyclopentylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-(1-Difluoromethyl-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(4-fluoro-benzyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(2,2-dimethyl-propyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-isobutyl-piperidine-3-carboxylic acid (1-pyrimidin-2-yl-cyclopropyl)-amide;

(3S,4S)-1-Benzyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Cyclobutylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-isopropyl-piperidine-3-carboxylic acid (1-pyrimidin-2-yl-cyclopropyl)-amide;

(3S,4S)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide;

(3R,4R)-1-Cyclopentyl-4-{[5-(2,4-difluoro-phenyl)-isoxazole-3-carbonyl]-amino}-piperidine-3-carboxylic acid ethyl-methyl-amide;

(3R,4R)-1-Cyclopentyl-4-{[5-(2,4-difluoro-phenyl)-isoxazole-3-carbonyl]-amino}-piperidine-3-carboxylic acid methyl-(2-pyridin-2-yl-ethyl)-amide;

(3R,4R)-1-Cyclopropylmethyl-4-{[5-(2,4-difluoro-phenyl)-isoxazole-3-carbonyl]-amino}-piperidine-3-carboxylic acid methyl-(2-pyridin-2-yl-ethyl)-amide;

(3S,4S)-1-(2,2-Difluoro-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(3-fluoro-propyl)-piperidine-3-carboxylic acid (1-pyrimidin-2-yl-cyclopropyl)-amide;

(3R*,4R*)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino-}-1-(1-methyl-cyclopropylmethyl)-piperidine-3-carboxylic acid (1-pyrimidin-2-yl-cyclopropyl)-amide;

(3S,4S)-1-Cyclopropylmethyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Allyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Bicyclo[3.1.0]hex-3-yl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-propyl-piperidine-3-carboxylic acid (1-pyrimidin-2-yl-cyclopropyl)-amide;

(3S,4S)-1-Cyclopentyl-4-{[5-(2,4-difluoro-phenyl)-oxazole-2-carbonyl]-amino}-piperidine-3-carboxylic acid (1-pyrimidin-2-yl-cyclopropyl)-amide;

(3S,4S)-1-(3,3-Difluoro-cyclobutylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-spiro[2.3]hex-5-yl-piperidine-3-carboxylic acid (1-pyrimidin-2-yl-cyclopropyl)-amide;

(3S,4S)-1-Cyclobutyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide;

(3S,4S)-4-{[5-(2,4-difluoro-phenyl)-[1,3,4]thiadiazole-2-carbonyl]-amino}-1-(1-fluoro-cyclopropylmethyl)-piperidine-3-carboxylic acid (1-pyrimidin-2-yl-cyclopropyl)-amide;

(3S,4S)-1-(Cyclopropyl-($d_2$-methyl))-4-{[5-(2,4-difluoro-phenyl)-isoxazole-3-carbonyl]-amino}-piperidine-3-carboxylic acid (1-pyrimidin-2-yl-cyclopropyl)-amide;

(3R*,4R*)-1-Cyclopropylmethyl-4-{[4-fluoro-5-(4-fluoro-phenyl)-isoxazole-3-carbonyl]-amino}-piperidine-3-carboxylic acid (1-pyrimidin-2-yl-cyclopropyl)-amide;

(3R*,4R*)-1-Cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide;
(3S,4S)-1-cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;
(3S,4S)-4-{[5-(2,4-Difluoro-phenyl)-isoxazole-3-carbonyl]-amino-}-1-(1-fluoro-cyclopropylmethyl)-piperidine-3-carboxylic acid (1-pyrimidin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-phenyl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid (1-pyrimidin-4-yl-cyclopropyl)-amide;
1-[((3S,4S)-1-Cyclopropylmethyl-4-{[5-(2,4-difluoro-phenyl)-isoxazole-3-carbonyl]-amino}-piperidine-3-carbonyl)-amino]-cyclopropanecarboxylic acid ethyl ester;
(3S,4S)-1-Cyclopropylmethyl-4-{[5-(2,4-difluoro-phenyl)-isoxazole-3-carbonyl]-amino}-piperidine-3-carboxylic acid (1-phenyl-cyclobutyl)-amide;
(3S,4S)-1-Cyclopropylmethyl-4-{[5-(2,4-difluoro-phenyl)-isoxazole-3-carbonyl]-amino}-piperidine-3-carboxylic acid benzyl-(2-fluoro-ethyl)-amide;
(3S,4S)-1-Cyclopropylmethyl-4-{[5-(2,4-difluoro-phenyl)-isoxazole-3-carbonyl]-amino}-piperidine-3-carboxylic acid [1-(3-methoxy-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [1-(2-trifluoromethyl-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [1-(2-fluoro-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [2-(2-chloro-phenyl)-ethyl]-amide;
5-(2,4-Difluoro-phenyl)-isoxazole-3-carboxylic acid [(3S,4S)-1-cyclopropylmethyl-3-((R)-2-phenyl-azetidine-1-carbonyl)-piperidin-4-yl]-amide;
5-(2,4-difluoro-phenyl)-isoxazole-3-carboxylic acid [(3S,4S)-1-cyclopropylmethyl-3-((S)-2-phenyl-azetidine-1-carbonyl)-piperidin-4-yl]-amide;
(3S,4S)-1-Cyclopropylmethyl-4-{[5-(2,4-difluoro-phenyl)-isoxazole-3-carbonyl]-amino}-piperidine-3-carboxylic acid [1-(3-chloro-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [1-(4-methyl-thiazol-2-yl)-cyclobutyl]-amide;
(3S,4S)-1-Cyclopropylmethyl-4-{[5-(2,4-difluoro-phenyl)-isoxazole-3-carbonyl]-amino}-piperidine-3-carboxylic acid [1-(2-methoxy-phenyl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [(R)-1-(3-bromo-phenyl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [1-(2-hydroxy-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [1-(1-oxy-pyrimidin-2-yl)-cyclopropyl]-amide;
5-(2,4-Difluoro-phenyl)-isoxazole-3-carboxylic acid [(3S,4S)-1-cyclopropylmethyl-3-(2-pyrimidin-2-yl-pyrrolidine-1-carbonyl)-piperidin-4-yl]-amide;
5-(2,4-Difluoro-phenyl)-isoxazole-3-carboxylic acid [(3S,4S)-1-cyclopropylmethyl-3-((R)-2-pyrimidin-2-yl-azetidine-1-carbonyl)-piperidin-4-yl]-amide;
5-(2,4-difluoro-phenyl)-isoxazole-3-carboxylic acid [(3S,4S)-1-cyclopropylmethyl-3-((S)-2-pyrimidin-2-yl-azetidine-1-carbonyl)-piperidin-4-yl]-amide;
(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide;
(3S,4S)-1-Cyclobutyl-4-{[5-(2,4-difluoro-phenyl)-isoxazole-3-carbonyl]-amino}-piperidine-3-carboxylic acid (1-methyl-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid ((R)-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid ((S)-1-pyrimidin-2-yl-ethyl)-amide;
(3R,4R)-1-Cyclobutyl-4-{[5-(2,4-difluoro-phenyl)-isoxazole-3-carbonyl]-amino}-piperidine-3-carboxylic acid (3-benzyl-oxetan-3-yl)-amide;
(3R,4R)-1-Cyclobutyl-4-{[5-(2,4-difluoro-phenyl)-isoxazole-3-carbonyl]-amino}-piperidine-3-carboxylic acid (3-phenyl-oxetan-3-ylmethyl)-amide;
(3S,4S)-4-{[5-(2,4-Difluoro-phenyl)-isoxazole-3-carbonyl]-amino}-1-ethyl-piperidine-3-carboxylic acid [(R)-1-(6-methyl-pyridin-2-yl)-ethyl]-amide;
(3S,4S)-4-{[5-(2,4-Difluoro-phenyl)-isoxazole-3-carbonyl]-amino}-1-ethyl-piperidine-3-carboxylic acid (1-methyl-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid [3-(3-chloro-phenyl)-oxetan-3-yl]-amide;
(3S,4S)-1-Cyclobutyl-4-{[5-(2,4-difluoro-phenyl)-isoxazole-3-carbonyl]-amino}-piperidine-3-carboxylic acid [1-(3-fluoro-pyridin-2-yl)-ethyl]-amide;
(3S,4S)-1-Cyclobutyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide;
(3S,4S)-1-Cyclobutyl-4-{[5-(2,4-difluoro-phenyl)-isoxazole-3-carbonyl]-amino}-piperidine-3-carboxylic acid [(S)-1-(3-fluoro-pyridin-2-yl)-ethyl]-amide;
(3R*,4R*)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide;
(3R*,4R*)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide (enantiomer 1);
(3S,4S)-1-Cyclopropylmethyl-4-{[5-(2,4-difluoro-phenyl)-isoxazole-3-carbonyl]-amino}-piperidine-3-carboxylic acid (1-methyl-1-pyrimidin-2-yl-ethyl)-amide;
(3S,4S)-1-Cyclopropylmethyl-4-{[4-fluoro-5-(4-fluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[1-(2,4-difluoro-phenyl)-1H-[1,2,3]triazole-4-carbonyl]-amino}-piperidine-3-carboxylic acid (1-pyrimidin-2-yl-cyclopropyl)-amide;

(3S,4S)-1-Cyclopropylmethyl-4-{[5-(2,4-dimethyl-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[3-(2,4-difluoro-phenyl)-isoxazole-5-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-[1,2,4]oxadiazole-3-carbonyl]-amino}-piperidine-3-carboxylic acid (1-pyrimidin-2-yl-cyclopropyl)-amide;
(3S,4S)-1-Cyclopropylmethyl-4-{[4-(2,4-difluoro-phenyl)-oxazole-2-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-oxazole-2-carbonyl]-amino}-piperidine-3-carboxylic acid (1-pyrimidin-2-yl-cyclopropyl)-amide; and
(3S,4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide. 23) Another embodiment relates to preferred compounds according to embodiment 1) which are selected from the following compounds:
(3S,4S)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide;
(3R,4R)-1-Cyclohexyl-4-{[5-(2,4-difluoro-phenyl)-isoxazole-3-carbonyl]-amino}-piperidine-3-carboxylic acid dimethylamide;
(3S,4S)-1-Cyclohexyl-4-{[5-(2,4-difluoro-phenyl)-isoxazole-3-carbonyl]-amino}-piperidine-3-carboxylic acid dimethylamide;
(3R,4R)-1-Cyclohexyl-4-{[5-(2,4-difluoro-phenyl)-isoxazole-3-carbonyl]-amino}-piperidine-3-carboxylic acid methylamide;
(3S,4S)-1-Cyclohexyl-4-{[5-(2,4-difluoro-phenyl)-isoxazole-3-carbonyl]-amino}-piperidine-3-carboxylic acid methylamide;
(3R,4R)-1-Cyclohexyl-4-{[5-(2,4-difluoro-phenyl)-isoxazole-3-carbonyl]-amino}-piperidine-3-carboxylic acid ethylamide;
(3S,4S)-1-Cyclohexyl-4-{[5-(2,4-difluoro-phenyl)-isoxazole-3-carbonyl]-amino}-piperidine-3-carboxylic acid ethylamide;
(3R,4R)-1-Cyclohexyl-4-{[5-(2,4-difluoro-phenyl)-isoxazole-3-carbonyl]-amino}-piperidine-3-carboxylic acid (pyridin-2-ylmethyl)-amide;
(3S,4S)-1-Cyclohexyl-4-{[5-(2,4-difluoro-phenyl)-isoxazole-3-carbonyl]-amino}-piperidine-3-carboxylic acid (pyridin-2-ylmethyl)-amide;
(3R,4R)-1-Cyclohexyl-4-{[5-(2,4-difluoro-phenyl)-isoxazole-3-carbonyl]-amino}-piperidine-3-carboxylic acid ((1R)-1-pyridin-2-yl-ethyl)-amide;
(3R,4R)-1-Cyclohexyl-4-{[5-(2,4-difluoro-phenyl)-isoxazole-3-carbonyl]-amino}-piperidine-3-carboxylic acid ((1S)-1-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((1R)-1-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((1S)-1-pyridin-2-yl-ethyl)-amide;
(3R,4R)-1-Cyclohexyl-4-{[5-(2,4-difluoro-phenyl)-isoxazole-3-carbonyl]-amino}-piperidine-3-carboxylic acid [2-(2-oxo-pyrrolidin-1-yl)-ethyl]-amide;
(3S,4S)-1-Cyclohexyl-4-{[5-(2,4-difluoro-phenyl)-isoxazole-3-carbonyl]-amino}-piperidine-3-carboxylic acid [2-(2-oxo-pyrrolidin-1-yl)-ethyl]-amide;
(3R,4R)-1-Cyclohexyl-4-{[5-(2,4-difluoro-phenyl)-isoxazole-3-carbonyl]-amino}-piperidine-3-carboxylic acid methyl-phenethyl-amide;
(3S,4S)-1-Cyclohexyl-4-{[5-(2,4-difluoro-phenyl)-isoxazole-3-carbonyl]-amino}-piperidine-3-carboxylic acid methyl-phenethyl-amide;
(3R,4R)-1-Cyclohexyl-4-{[5-(2,4-difluoro-phenyl)-isoxazole-3-carbonyl]-amino}-piperidine-3-carboxylic acid (thiazol-2-ylmethyl)-amide;
(3S,4S)-1-Cyclohexyl-4-{[5-(2,4-difluoro-phenyl)-isoxazole-3-carbonyl]-amino}-piperidine-3-carboxylic acid (thiazol-2-ylmethyl)-amide;
(3R,4R)-1-Cyclohexyl-4-{[5-(2,4-difluoro-phenyl)-isoxazole-3-carbonyl]-amino}-piperidine-3-carboxylic acid (2-o-tolyl-ethyl)-amide;
(3S,4S)-1-Cyclohexyl-4-{[5-(2,4-difluoro-phenyl)-isoxazole-3-carbonyl]-amino}-piperidine-3-carboxylic acid (2-o-tolyl-ethyl)-amide;
(3R,4R)-1-Cyclohexyl-4-{[5-(2,4-difluoro-phenyl)-isoxazole-3-carbonyl]-amino}-piperidine-3-carboxylic acid [2-(2-methoxy-phenyl)-ethyl]-amide;
(3S,4S)-1-Cyclohexyl-4-{[5-(2,4-difluoro-phenyl)-isoxazole-3-carbonyl]-amino}-piperidine-3-carboxylic acid [2-(2-methoxy-phenyl)-ethyl]-amide;
(3R,4R)-1-Cyclohexyl-4-{[5-(2,4-difluoro-phenyl)-isoxazole-3-carbonyl]-amino}-piperidine-3-carboxylic acid [2-(2-chloro-phenyl)-ethyl]-amide;
(3S,4S)-1-Cyclohexyl-4-{[5-(2,4-difluoro-phenyl)-isoxazole-3-carbonyl]-amino}-piperidine-3-carboxylic acid [2-(2-chloro-phenyl)-ethyl]-amide;
(3R,4R)-1-Cyclohexyl-4-{[5-(2,4-difluoro-phenyl)-isoxazole-3-carbonyl]-amino}-piperidine-3-carboxylic acid ((1R,2S)-2-phenyl-cyclopropyl)-amide;
(3R,4R)-1-Cyclohexyl-4-{[5-(2,4-difluoro-phenyl)-isoxazole-3-carbonyl]-amino}-piperidine-3-carboxylic acid ((1S,2R)-2-phenyl-cyclopropyl)-amide;
(3S,4S)-1-Cyclohexyl-4-{[5-(2,4-difluoro-phenyl)-isoxazole-3-carbonyl]-amino}-piperidine-3-carboxylic acid ((1R,2S)-2-phenyl-cyclopropyl)-amide;
(3S,4S)-1-Cyclohexyl-4-{[5-(2,4-difluoro-phenyl)-isoxazole-3-carbonyl]-amino}-piperidine-3-carboxylic acid ((1S,2R)-2-phenyl-cyclopropyl)-amide;
(3R,4R)-1-Cyclohexyl-4-{[5-(2,4-difluoro-phenyl)-isoxazole-3-carbonyl]-amino}-piperidine-3-carboxylic acid (2-p-tolyl-ethyl)-amide;
(3S,4S)-1-Cyclohexyl-4-{[5-(2,4-difluoro-phenyl)-isoxazole-3-carbonyl]-amino}-piperidine-3-carboxylic acid (2-p-tolyl-ethyl)-amide;
(3R,4R)-1-Cyclohexyl-4-{[5-(2,4-difluoro-phenyl)-isoxazole-3-carbonyl]-amino}-piperidine-3-carboxylic acid (2-m-tolyl-ethyl)-amide;
(3S,4S)-1-Cyclohexyl-4-{[5-(2,4-difluoro-phenyl)-isoxazole-3-carbonyl]-amino}-piperidine-3-carboxylic acid (2-m-tolyl-ethyl)-amide;
(3R,4R)-1-Cyclohexyl-4-{[5-(2,4-difluoro-phenyl)-isoxazole-3-carbonyl]-amino}-piperidine-3-carboxylic acid (1-pyridin-2-yl-cyclopropyl)-amide;
(3S,4S)-1-Cyclohexyl-4-{[5-(2,4-difluoro-phenyl)-isoxazole-3-carbonyl]-amino}-piperidine-3-carboxylic acid (1-pyridin-2-yl-cyclopropyl)-amide;
(3R,4R)-1-Cyclohexyl-4-{[5-(2,4-difluoro-phenyl)-isoxazole-3-carbonyl]-amino}-piperidine-3-carboxylic acid ((R)-2-hydroxy-2-phenyl-ethyl)-amide;

(3S,4S)-1-Cyclohexyl-4-{[5-(2,4-difluoro-phenyl)-isoxazole-3-carbonyl]-amino}-piperidine-3-carboxylic acid ((R)-2-hydroxy-2-phenyl-ethyl)-amide;
(3R,4R)-1-Cyclohexyl-4-{[5-(2,4-difluoro-phenyl)-isoxazole-3-carbonyl]-amino}-piperidine-3-carboxylic acid (2-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid (2-pyridin-2-yl-ethyl)-amide;
(3R,4R)-1-Cyclohexyl-4-{[5-(2,4-difluoro-phenyl)-isoxazole-3-carbonyl]-amino}-piperidine-3-carboxylic acid methyl-(2-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid methyl-(2-pyridin-2-yl-ethyl)-amide;
(3R,4R)-1-Cyclohexyl-4-{[5-(2,4-difluoro-phenyl)-isoxazole-3-carbonyl]-amino}-piperidine-3-carboxylic acid ((1R)-2-ethoxy-1-methyl-ethyl)-amide;
(3R,4R)-1-Cyclohexyl-4-{[5-(2,4-difluoro-phenyl)-isoxazole-3-carbonyl]-amino}-piperidine-3-carboxylic acid ((1S)-2-ethoxy-1-methyl-ethyl)-amide;
(3S,4S)-1-Cyclohexyl-4-{[5-(2,4-difluoro-phenyl)-isoxazole-3-carbonyl]-amino}-piperidine-3-carboxylic acid ((1R)-2-ethoxy-1-methyl-ethyl)-amide;
(3S,4S)-1-Cyclohexyl-4-{[5-(2,4-difluoro-phenyl)-isoxazole-3-carbonyl]-amino}-piperidine-3-carboxylic acid ((1S)-2-ethoxy-1-methyl-ethyl)-amide;
(3R,4R)-1-Cyclohexyl-4-{[5-(2,4-difluoro-phenyl)-isoxazole-3-carbonyl]-amino}-piperidine-3-carboxylic acid ((R)-1-pyrazin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((R)-1-pyrazin-2-yl-ethyl)-amide;
(3R,4R)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide;
(3S,4S)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide;
(3R,4R)-1-Cyclohexyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide;
(3S,4S)-1-Cyclohexyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide;
(3R,4R)-1-Cyclohexyl-4-{[5-(2,4-difluoro-phenyl)-isoxazole-3-carbonyl]-amino}-piperidine-3-carboxylic acid [(R)-1-(5-fluoro-pyrimidin-2-yl)-ethyl]-amide;
(3S,4S)-1-Cyclohexyl-4-{[5-(2,4-difluoro-phenyl)-isoxazole-3-carbonyl]-amino}-piperidine-3-carboxylic acid [(R)-1-(5-fluoro-pyrimidin-2-yl)-ethyl]-amide;
(3R,4R)-1-((1R,2R)-2-Methyl-cyclopentyl)-4-{[5-(2,4,6-trifluoro-phenyl)-isoxazole-3-carbonyl]-amino}piperidine-3-carboxylic acid dimethylamide;
(3R,4R)-1-((1S,2S)-2-Methyl-cyclopentyl)-4-{[5-(2,4,6-trifluoro-phenyl)-isoxazole-3-carbonyl]-amino}-piperidine-3-carboxylic acid dimethylamide;
(3R,4R)-1-((1R,2S)-2-Methyl-cyclopentyl)-4-{[5-(2,4,6-trifluoro-phenyl)-isoxazole-3-carbonyl]-amino}-piperidine-3-carboxylic acid dimethylamide;
(3R,4R)-1-((1S,2R)-2-Methyl-cyclopentyl)-4-{[5-(2,4,6-trifluoro-phenyl)-isoxazole-3-carbonyl]-amino}-piperidine-3-carboxylic acid dimethylamide;
(3S,4S)-1-((1R,2R)-2-Methyl-cyclopentyl)-4-{[5-(2,4,6-trifluoro-phenyl)-isoxazole-3-carbonyl]-amino}piperidine-3-carboxylic acid dimethylamide;
(3S,4S)-1-((1S,2S)-2-Methyl-cyclopentyl)-4-{[5-(2,4,6-trifluoro-phenyl)-isoxazole-3-carbonyl]-amino}-piperidine-3-carboxylic acid dimethylamide;
(3S,4S)-1-((1R,2S)-2-Methyl-cyclopentyl)-4-{[5-(2,4,6-trifluoro-phenyl)-isoxazole-3-carbonyl]-amino}-piperidine-3-carboxylic acid dimethylamide;
(3S,4S)-1-((1S,2R)-2-Methyl-cyclopentyl)-4-{[5-(2,4,6-trifluoro-phenyl)-isoxazole-3-carbonyl]-amino}-piperidine-3-carboxylic acid dimethylamide;
(3S,4S)-1-Cyclopropylmethyl-4-{[5-(2,4,6-trifluoro-phenyl)-isoxazole-3-carbonyl]-amino}piperidine-3-carboxylic acid (2-methoxy-1,1-dimethyl-ethyl)-amide;
(3R,4R)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;
(3S,4S)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;
(3R,4R)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;
(3S,4S)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;
(3S,4S)-1-Cyclohexyl-4-{[5-(2,4,6-trifluoro-phenyl)-isoxazole-3-carbonyl]-amino}-piperidine-3-carboxylic acid ((R)-1-pyridin-2-yl-ethyl)-amide;
(3S,4S)-1-Cyclopentyl-4-{[5-(2,4,6-trifluoro-phenyl)-isoxazole-3-carbonyl]-amino}-piperidine-3-carboxylic acid ((R)-1-pyridin-2-yl-ethyl)-amide;
(3R,4R)-1-Cyclopropylmethyl-4-{[5-(2,4,6-trifluoro-phenyl)-isoxazole-3-carbonyl]-amino}piperidine-3-carboxylic acid ((R)-1-pyridin-2-yl-ethyl)-amide;
(3S,4S)-1-Cyclopropylmethyl-4-{[5-(2,4,6-trifluoro-phenyl)-isoxazole-3-carbonyl]-amino}-piperidine-3-carboxylic acid ((R)-1-pyridin-2-yl-ethyl)-amide;
(3R,4R)-1-(2-Methyl-cyclopentyl)-4-{[5-(2,4,6-trifluoro-phenyl)-isoxazole-3-carbonyl]-amino}-piperidine-3-carboxylic acid ((R)-1-pyridin-2-yl-ethyl)-amide;
(3S,4S)-1-(2-Methyl-cyclopentyl)-4-{[5-(2,4,6-trifluoro-phenyl)-isoxazole-3-carbonyl]-amino}-piperidine-3-carboxylic acid ((R)-1-pyridin-2-yl-ethyl)-amide;
(3R,4R)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide;
(3S,4S)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide;
(3R,4R)-1-Cyclopentyl-4-{[3-(2,4-difluoro-phenyl)-isoxazole-5-carbonyl]-amino}-piperidine-3-carboxylic acid ((R)-1-pyridin-2-yl-ethyl)-amide;
(3S,4S)-1-Cyclopentyl-4-{[3-(2,4-difluoro-phenyl)-isoxazole-5-carbonyl]-amino}-piperidine-3-carboxylic acid ((R)-1-pyridin-2-yl-ethyl)-amide;
(3S,4S)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3R,4R)-1-Cyclopropylmethyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3S,4S)-1-Cyclopropylmethyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3S,4S)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide;

(3S,4S)-1-Cyclopropylmethyl-4-{[5-(2,4,6-trifluoro-phenyl)-isoxazole-3-carbonyl]-amino}-piperidine-3-carboxylic acid ((R)-1-cyclobutyl-ethyl)-amide;

(3R,4R)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide;

(3S,4S)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide;

(3R,4R)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3S,4S)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3R,4R)-1-Cyclopropylmethyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3S,4S)-1-Cyclopropylmethyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;

(3S,4S)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3R,4R)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3R,4R)-1-Cyclohexyl-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-Cyclohexyl-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-Cyclopropylmethyl-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-((1R,2R)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-((1R,2S)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-((1S,2R)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-((1S,2S)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-((1R,2R)-2-Methyl-cyclopentyl)-4-{[5-(2,4,6-trifluoro-phenyl)-isoxazole-3-carbonyl]-amino}piperidine-3-carboxylic acid (1-pyridin-2-yl-cyclopropyl)-amide;

(3S,4S)-1-((1R,2S)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-((1S,2R)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3S,4S)-1-((1S,2S)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide;

(3R,4R)-1-Cyclopropylmethyl-4-{[3-(2,4-difluoro-phenyl)-isoxazole-5-carbonyl]-amino}-piperidine-3-carboxylic acid (1-pyridin-2-yl-cyclopropyl)-amide;

(3S,4S)-1-Cyclopropylmethyl-4-{[3-(2,4-difluoro-phenyl)-isoxazole-5-carbonyl]-amino}-piperidine-3-carboxylic acid (1-pyridin-2-yl-cyclopropyl)-amide;

(3R,4R)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide;

(3S,4S)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,4,6-trifluoro-phenyl)-isoxazole-3-carbonyl]-amino}piperidine-3-carboxylic acid (1-pyrimidin-2-yl-cyclopropyl)-amide;

(3S,4S)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid (1-pyrazin-2-yl-cyclopropyl)-amide;

(3S,4S)-1-Cyclopentyl-4-{[5-(2,4-difluoro-phenyl)-isoxazole-3-carbonyl]-amino}-piperidine-3-carboxylic acid (1-pyrazin-2-yl-cyclopropyl)-amide;

(3R,4R)-1-Cyclohexyl-4-{[5-(2,4-difluoro-phenyl)-isoxazole-3-carbonyl]-amino}-piperidine-3-carboxylic acid (cyano-dimethyl-methyl)-amide;

(3S,4S)-1-Cyclohexyl-4-{[5-(2,4-difluoro-phenyl)-isoxazole-3-carbonyl]-amino}-piperidine-3-carboxylic acid (cyano-dimethyl-methyl)-amide;

(3S,4S)-1-Cyclopentyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide;

(3R,4R)-1-Cyclohexyl-4-{[5-(2,4-difluoro-phenyl)-isoxazole-3-carbonyl]-amino}-piperidine-3-carboxylic acid dimethylamide;

(3S,4S)-1-Cyclohexyl-4-{[5-(2,4-difluoro-phenyl)-isoxazole-3-carbonyl]-amino}-piperidine-3-carboxylic acid ((R)-1-pyridin-2-yl-ethyl)-amide;

(3S,4S)-1-Cyclohexyl-4-{[5-(2,4-difluoro-phenyl)-isoxazole-3-carbonyl]-amino}-piperidine-3-carboxylic acid [(R)-1-(6-methyl-pyridin-2-yl)-ethyl]-amide;

(3R,4R)-4-{[5-(2,4-Difluoro-phenyl)-isoxazole-3-carbonyl]-amino}-1-isopropyl-piperidine-3-carboxylic acid methyl-phenethyl-amide;

(3S,4S)-4-{[5-(2,4-Difluoro-phenyl)-isoxazole-3-carbonyl]-amino}-1-isopropyl-piperidine-3-carboxylic acid methyl-phenethyl-amide;

(3R,4R)-1-Cyclopentyl-4-{[5-(2,4-difluoro-phenyl)-isoxazole-3-carbonyl]-amino}-piperidine-3-carboxylic acid methyl-phenethyl-amide;

(3S,4S)-1-Cyclopentyl-4-{[5-(2,4-difluoro-phenyl)-isoxazole-3-carbonyl]-amino}-piperidine-3-carboxylic acid methyl-phenethyl-amide;

(3R,4R)-1-Cyclopropylmethyl-4-{[5-(2,4-difluoro-phenyl)-isoxazole-3-carbonyl]-amino}-piperidine-3-carboxylic acid methyl-phenethyl-amide;

(3S,4S)-1-Cyclopropylmethyl-4-{[5-(2,4-difluoro-phenyl)-isoxazole-3-carbonyl]-amino}-piperidine-3-carboxylic acid methyl-phenethyl-amide;

(3R,4R)-4-{[5-(2,4-Difluoro-phenyl)-isoxazole-3-carbonyl]-amino}-1-isopropyl-piperidine-3-carboxylic acid ((1R)-1-pyridin-2-yl-ethyl)-amide;

(3R,4R)-4-{[5-(2,4-Difluoro-phenyl)-isoxazole-3-carbonyl]-amino}-1-isopropyl-piperidine-3-carboxylic acid ((1S)-1-pyridin-2-yl-ethyl)-amide;

(3S,4S)-4-{[5-(2,4-Difluoro-phenyl)-isoxazole-3-carbonyl]-amino}-1-isopropyl-piperidine-3-carboxylic acid ((1R)-1-pyridin-2-yl-ethyl)-amide;

(3S,4S)-4-{[5-(2,4-Difluoro-phenyl)-isoxazole-3-carbonyl]-amino}-1-isopropyl-piperidine-3-carboxylic acid ((1S)-1-pyridin-2-yl-ethyl)-amide;

(3R,4R)-1-Cyclopentyl-4-{[5-(2,4-difluoro-phenyl)-isoxazole-3-carbonyl]-amino}-piperidine-3-carboxylic acid ((1R)-1-pyridin-2-yl-ethyl)-amide;

(3R,4R)-1-Cyclopentyl-4-{[5-(2,4-difluoro-phenyl)-isoxazole-3-carbonyl]-amino}-piperidine-3-carboxylic acid ((1S)-1-pyridin-2-yl-ethyl)-amide;

(3S,4S)-1-Cyclopentyl-4-{[5-(2,4-difluoro-phenyl)-isoxazole-3-carbonyl]-amino}-piperidine-3-carboxylic acid ((1R)-1-pyridin-2-yl-ethyl)-amide;

(3S,4S)-1-Cyclopentyl-4-{[5-(2,4-difluoro-phenyl)-isoxazole-3-carbonyl]-amino}-piperidine-3-carboxylic acid ((1S)-1-pyridin-2-yl-ethyl)-amide;

(3R,4R)-1-Cyclopropylmethyl-4-{[5-(2,4-difluoro-phenyl)-isoxazole-3-carbonyl]-amino}-piperidine-3-carboxylic acid ((1R)-1-pyridin-2-yl-ethyl)-amide;

(3R,4R)-1-Cyclopropylmethyl-4-{[5-(2,4-difluoro-phenyl)-isoxazole-3-carbonyl]-amino}-piperidine-3-carboxylic acid ((1S)-1-pyridin-2-yl-ethyl)-amide;

(3S,4S)-1-Cyclopropylmethyl-4-{[5-(2,4-difluoro-phenyl)-isoxazole-3-carbonyl]-amino}-piperidine-3-carboxylic acid ((1R)-1-pyridin-2-yl-ethyl)-amide;

(3S,4S)-1-Cyclopropylmethyl-4-{[5-(2,4-difluoro-phenyl)-isoxazole-3-carbonyl]-amino}-piperidine-3-carboxylic acid ((1S)-1-pyridin-2-yl-ethyl)-amide;

(3R,4R)-1-((1R)-1-Cyclopropyl-ethyl)-4-{[5-(2,4-difluoro-phenyl)-isoxazole-3-carbonyl]-amino}-piperidine-3-carboxylic acid dimethylamide;

(3R,4R)-1-((1S)-1-Cyclopropyl-ethyl)-4-{[5-(2,4-difluoro-phenyl)-isoxazole-3-carbonyl]-amino}-piperidine-3-carboxylic acid dimethylamide;

(3S,4S)-1-((1R)-1-Cyclopropyl-ethyl)-4-{[5-(2,4-difluoro-phenyl)-isoxazole-3-carbonyl]-amino}-piperidine-3-carboxylic acid dimethylamide;

(3S,4S)-1-((1S)-1-Cyclopropyl-ethyl)-4-{[5-(2,4-difluoro-phenyl)-isoxazole-3-carbonyl]-amino}-piperidine-3-carboxylic acid dimethylamide;

(3R,4R)-4-{[5-(2,4-Difluoro-phenyl)-isoxazole-3-carbonyl]-amino}-1-((1R,2R)-2-ethyl-cyclopentyl)-piperidine-3-carboxylic acid dimethylamide;

(3R,4R)-4-{[5-(2,4-Difluoro-phenyl)-isoxazole-3-carbonyl]-amino}-1-((1R,2S)-2-ethyl-cyclopentyl)-piperidine-3-carboxylic acid dimethylamide;

(3R,4R)-4-{[5-(2,4-Difluoro-phenyl)-isoxazole-3-carbonyl]-amino}-1-((1S,2R)-2-ethyl-cyclopentyl)-piperidine-3-carboxylic acid dimethylamide;

(3R,4R)-4-{[5-(2,4-Difluoro-phenyl)-isoxazole-3-carbonyl]-amino}-1-((1S,2S)-2-ethyl-cyclopentyl)-piperidine-3-carboxylic acid dimethylamide;

(3S,4S)-4-{[5-(2,4-Difluoro-phenyl)-isoxazole-3-carbonyl]-amino}-1-((1R,2R)-2-ethyl-cyclopentyl)-piperidine-3-carboxylic acid dimethylamide;

(3S,4S)-4-{[5-(2,4-Difluoro-phenyl)-isoxazole-3-carbonyl]-amino}-1-((1R,2S)-2-ethyl-cyclopentyl)-piperidine-3-carboxylic acid dimethylamide;

(3S,4S)-4-{[5-(2,4-Difluoro-phenyl)-isoxazole-3-carbonyl]-amino}-1-((1S,2R)-2-ethyl-cyclopentyl)-piperidine-3-carboxylic acid dimethylamide;

(3S,4S)-4-{[5-(2,4-Difluoro-phenyl)-isoxazole-3-carbonyl]-amino}-1-((1S,2S)-2-ethyl-cyclopentyl)-piperidine-3-carboxylic acid dimethylamide;

(3R,4R)-4-{[5-(2,4-Difluoro-phenyl)-isoxazole-3-carbonyl]-amino}-1-((1R,2R)-2-methyl-cyclobutyl)-piperidine-3-carboxylic acid dimethylamide;

(3R,4R)-4-{[5-(2,4-Difluoro-phenyl)-isoxazole-3-carbonyl]-amino}-1-((1S,2S)-2-methyl-cyclobutyl)-piperidine-3-carboxylic acid dimethylamide;

(3R,4R)-4-{[5-(2,4-Difluoro-phenyl)-isoxazole-3-carbonyl]-amino}-1-((1R,2S)-2-methyl-cyclobutyl)-piperidine-3-carboxylic acid dimethylamide;

(3R,4R)-4-{[5-(2,4-Difluoro-phenyl)-isoxazole-3-carbonyl]-amino}-1-((1S,2R)-2-methyl-cyclobutyl)-piperidine-3-carboxylic acid dimethylamide;

(3S,4S)-4-{[5-(2,4-Difluoro-phenyl)-isoxazole-3-carbonyl]-amino}-1-((1R,2R)-2-methyl-cyclobutyl)-piperidine-3-carboxylic acid dimethylamide;

(3S,4S)-4-{[5-(2,4-Difluoro-phenyl)-isoxazole-3-carbonyl]-amino}-1-((1S,2S)-2-methyl-cyclobutyl)-piperidine-3-carboxylic acid dimethylamide;

(3S,4S)-4-{[5-(2,4-Difluoro-phenyl)-isoxazole-3-carbonyl]-amino}-1-((1R,2S)-2-methyl-cyclobutyl)-piperidine-3-carboxylic acid dimethylamide;

(3S,4S)-4-{[5-(2,4-Difluoro-phenyl)-isoxazole-3-carbonyl]-amino}-1-((1S,2R)-2-methyl-cyclobutyl)-piperidine-3-carboxylic acid dimethylamide;

(3R,4R)-4-{[5-(2,4-Difluoro-phenyl)-isoxazole-3-carbonyl]-amino}-(1R)-1-(2,2-dimethyl-cyclobutyl)-piperidine-3-carboxylic acid dimethylamide;

(3R,4R)-4-{[5-(2,4-Difluoro-phenyl)-isoxazole-3-carbonyl]-amino}-(1S)-1-(2,2-dimethyl-cyclobutyl)-piperidine-3-carboxylic acid dimethylamide;

(3S,4S)-4-{[5-(2,4-Difluoro-phenyl)-isoxazole-3-carbonyl]-amino}-(1R)-1-(2,2-dimethyl-cyclobutyl)-piperidine-3-carboxylic acid dimethylamide;

(3S,4S)-4-{[5-(2,4-Difluoro-phenyl)-isoxazole-3-carbonyl]-amino}-(1S)-1-(2,2-dimethyl-cyclobutyl)-piperidine-3-carboxylic acid dimethylamide;

(3R,4R)-1-Cyclopentyl-4-{[5-(2,4-difluoro-phenyl)-isoxazole-3-carbonyl]-amino}-piperidine-3-carboxylic acid dimethylamide;

(3R,4R)-4-{[5-(2,4-Difluoro-phenyl)-isoxazole-3-carbonyl]-amino}-1-((1R,2R)-2-methyl-cyclopentyl)-piperidine-3-carboxylic acid dimethylamide;

(3R,4R)-4-{[5-(2,4-Difluoro-phenyl)-isoxazole-3-carbonyl]-amino}-1-((1R,2S)-2-methyl-cyclopentyl)-piperidine-3-carboxylic acid dimethylamide;

(3R,4R)-4-{[5-(2,4-Difluoro-phenyl)-isoxazole-3-carbonyl]-amino}-1-((1S,2R)-2-methyl-cyclopentyl)-piperidine-3-carboxylic acid dimethylamide;

(3R,4R)-4-{[5-(2,4-Difluoro-phenyl)-isoxazole-3-carbonyl]-amino}-1-((1S,2S)-2-methyl-cyclopentyl)-piperidine-3-carboxylic acid dimethylamide;

(3S,4S)-4-{[5-(2,4-Difluoro-phenyl)-isoxazole-3-carbonyl]-amino}-1-((1R,2R)-2-methyl-cyclopentyl)-piperidine-3-carboxylic acid dimethylamide;

(3S,4S)-4-{[5-(2,4-Difluoro-phenyl)-isoxazole-3-carbonyl]-amino}-1-((1R,2S)-2-methyl-cyclopentyl)-piperidine-3-carboxylic acid dimethylamide;
(3S,4S)-4-{[5-(2,4-Difluoro-phenyl)-isoxazole-3-carbonyl]-amino}-1-((1S,2R)-2-methyl-cyclopentyl)-piperidine-3-carboxylic acid dimethylamide;
(3S,4S)-4-{[5-(2,4-Difluoro-phenyl)-isoxazole-3-carbonyl]-amino}-1-((1S,2S)-2-methyl-cyclopentyl)-piperidine-3-carboxylic acid dimethylamide;
(3R,4R)-4-{[5-(2,4-Difluoro-phenyl)-isoxazole-3-carbonyl]-amino}-1-((1R)-3,3-dimethyl-cyclohexyl)-piperidine-3-carboxylic acid dimethylamide;
(3R,4R)-4-{[5-(2,4-Difluoro-phenyl)-isoxazole-3-carbonyl]-amino}-1-((1S)-3,3-dimethyl-cyclohexyl)-piperidine-3-carboxylic acid dimethylamide;
(3S,4S)-4-{[5-(2,4-Difluoro-phenyl)-isoxazole-3-carbonyl]-amino}-1-((1R)-3,3-dimethyl-cyclohexyl)-piperidine-3-carboxylic acid dimethylamide;
(3S,4S)-4-{[5-(2,4-Difluoro-phenyl)-isoxazole-3-carbonyl]-amino}-1-((1S)-3,3-dimethyl-cyclohexyl)-piperidine-3-carboxylic acid dimethylamide;
(3R,4R)-1-Cyclobutyl-4-{[5-(2,4-difluoro-phenyl)-isoxazole-3-carbonyl]-amino}-piperidine-3-carboxylic acid dimethylamide;
(3S,4S)-1-Cyclobutyl-4-{[5-(2,4-difluoro-phenyl)-isoxazole-3-carbonyl]-amino}-piperidine-3-carboxylic acid dimethylamide;
(3R,4R)-1-Cyclopropylmethyl-4-{[5-(2,4-difluoro-phenyl)-isoxazole-3-carbonyl]-amino}-piperidine-3-carboxylic acid dimethylamide;
(3S,4S)-1-Cyclopropylmethyl-4-{[5-(2,4-difluoro-phenyl)-isoxazole-3-carbonyl]-amino}-piperidine-3-carboxylic acid dimethylamide;
(3R,4R)-1-Cyclopentylmethyl-4-{[5-(2,4-difluoro-phenyl)-isoxazole-3-carbonyl]-amino}-piperidine-3-carboxylic acid dimethylamide;
(3S,4S)-1-Cyclopentylmethyl-4-{[5-(2,4-difluoro-phenyl)-isoxazole-3-carbonyl]-amino}-piperidine-3-carboxylic acid dimethylamide;
(3R,4R)-4-{[5-(2,4-Difluoro-phenyl)-isoxazole-3-carbonyl]-amino}-1-(1-methyl-cyclopropylmethyl)-piperidine-3-carboxylic acid dimethylamide;
(3S,4S)-4-{[5-(2,4-Difluoro-phenyl)-isoxazole-3-carbonyl]-amino}-1-(1-methyl-cyclopropylmethyl)-piperidine-3-carboxylic acid dimethylamide;
(3R,4R)-1-Cyclobutylmethyl-4-{[5-(2,4-difluoro-phenyl)-isoxazole-3-carbonyl]-amino}-piperidine-3-carboxylic acid dimethylamide;
(3S,4S)-1-Cyclobutylmethyl-4-{[5-(2,4-difluoro-phenyl)-isoxazole-3-carbonyl]-amino}-piperidine-3-carboxylic acid dimethylamide;
(3R,4R)-1-(2-Cyclopropyl-ethyl)-4-{[5-(2,4-difluoro-phenyl)-isoxazole-3-carbonyl]-amino}-piperidine-3-carboxylic acid dimethylamide;
(3S,4S)-1-(2-Cyclopropyl-ethyl)-4-{[5-(2,4-difluoro-phenyl)-isoxazole-3-carbonyl]-amino}piperidine-3-carboxylic acid dimethylamide;
(3R,4R)-1-Cyclopropylmethyl-4-{[5-(2,4-difluoro-phenyl)-isoxazole-3-carbonyl]-amino}-piperidine-3-carboxylic acid dimethylamide;
(3R,4R)-1-((1R)-1-Cyclopropyl-ethyl)-4-{[5-(2,4-difluoro-phenyl)-isoxazole-3-carbonyl]-amino}-piperidine-3-carboxylic acid dimethylamide;
(3R,4R)-1-((1S)-1-Cyclopropyl-ethyl)-4-{[5-(2,4-difluoro-phenyl)-isoxazole-3-carbonyl]-amino}-piperidine-3-carboxylic acid dimethylamide;
(3R,4R)-4-{[5-(2,4-Difluoro-phenyl)-isoxazole-3-carbonyl]-amino}-1-((1R,2R)-2-hydroxy-cyclohexyl)-piperidine-3-carboxylic acid methyl-phenethyl-amide;
(3R,4R)-4-{[5-(2,4-Difluoro-phenyl)-isoxazole-3-carbonyl]-amino}-1-((1R,2S)-2-hydroxy-cyclohexyl)-piperidine-3-carboxylic acid methyl-phenethyl-amide;
(3R,4R)-4-{[5-(2,4-Difluoro-phenyl)-isoxazole-3-carbonyl]-amino}-1-((1S,2R)-2-hydroxy-cyclohexyl)-piperidine-3-carboxylic acid methyl-phenethyl-amide;
(3R,4R)-4-{[5-(2,4-Difluoro-phenyl)-isoxazole-3-carbonyl]-amino}-1-((1S,2S)-2-hydroxy-cyclohexyl)-piperidine-3-carboxylic acid methyl-phenethyl-amide;
(3S,4S)-4-{[5-(2,4-Difluoro-phenyl)-isoxazole-3-carbonyl]-amino}-1-((1R,2R)-2-hydroxy-cyclohexyl)-piperidine-3-carboxylic acid methyl-phenethyl-amide;
(3S,4S)-4-{[5-(2,4-Difluoro-phenyl)-isoxazole-3-carbonyl]-amino}-1-((1R,2S)-2-hydroxy-cyclohexyl)-piperidine-3-carboxylic acid methyl-phenethyl-amide;
(3S,4S)-4-{[5-(2,4-Difluoro-phenyl)-isoxazole-3-carbonyl]-amino}-1-((1S,2R)-2-hydroxy-cyclohexyl)-piperidine-3-carboxylic acid methyl-phenethyl-amide;
(3S,4S)-4-{[5-(2,4-Difluoro-phenyl)-isoxazole-3-carbonyl]-amino}-1-((1S,2S)-2-hydroxy-cyclohexyl)-piperidine-3-carboxylic acid methyl-phenethyl-amide;
(3R,4R)-4-{[5-(2,4-Difluoro-phenyl)-isoxazole-3-carbonyl]-amino-}-1-((1R,2R)-2-hydroxy-1-methyl-propyl)-piperidine-3-carboxylic acid methyl-phenethyl-amide;
(3R,4R)-4-{[5-(2,4-Difluoro-phenyl)-isoxazole-3-carbonyl]-amino}-1-((1R,2S)-2-hydroxy-1-methyl-propyl)-piperidine-3-carboxylic acid methyl-phenethyl-amide;
(3R,4R)-4-{[5-(2,4-Difluoro-phenyl)-isoxazole-3-carbonyl]-amino}-1-((1S,2R)-2-hydroxy-1-methyl-propyl)-piperidine-3-carboxylic acid methyl-phenethyl-amide;
(3R,4R)-4-{[5-(2,4-Difluoro-phenyl)-isoxazole-3-carbonyl]-amino}-1-((1S,2S)-2-hydroxy-1-methyl-propyl)-piperidine-3-carboxylic acid methyl-phenethyl-amide;
(3S,4S)-4-{[5-(2,4-Difluoro-phenyl)-isoxazole-3-carbonyl]-amino}-1-((1R,2R)-2-hydroxy-1-methyl-propyl)-piperidine-3-carboxylic acid methyl-phenethyl-amide;
(3S,4S)-4-{[5-(2,4-Difluoro-phenyl)-isoxazole-3-carbonyl]-amino}-1-((1R,2S)-2-hydroxy-1-methyl-propyl)-piperidine-3-carboxylic acid methyl-phenethyl-amide;
(3S,4S)-4-{[5-(2,4-Difluoro-phenyl)-isoxazole-3-carbonyl]-amino}-1-((1S,2R)-2-hydroxy-1-methyl-propyl)-piperidine-3-carboxylic acid methyl-phenethyl-amide;
(3S,4S)-4-{[5-(2,4-Difluoro-phenyl)-isoxazole-3-carbonyl]-amino}-1-((1S,2S)-2-hydroxy-1-methyl-propyl)-piperidine-3-carboxylic acid methyl-phenethyl-amide;
(3R,4R)-4-{[5-(2,4-Difluoro-phenyl)-isoxazole-3-carbonyl]-amino}-1-((1R,2R)-2-hydroxy-cyclohexyl)-piperidine-3-carboxylic acid ((1R)-1-pyridin-2-yl-ethyl)-amide;
(3R,4R)-4-{[5-(2,4-Difluoro-phenyl)-isoxazole-3-carbonyl]-amino}-1-((1R,2R)-2-hydroxy-cyclohexyl)-piperidine-3-carboxylic acid ((1S)-1-pyridin-2-yl-ethyl)-amide;
(3R,4R)-4-{[5-(2,4-Difluoro-phenyl)-isoxazole-3-carbonyl]-amino}-1-((1R,2S)-2-hydroxy-cyclohexyl)-piperidine-3-carboxylic acid ((1R)-1-pyridin-2-yl-ethyl)-amide;
(3R,4R)-4-{[5-(2,4-Difluoro-phenyl)-isoxazole-3-carbonyl]-amino}-1-((1R,2S)-2-hydroxy-cyclohexyl)-piperidine-3-carboxylic acid ((1S)-1-pyridin-2-yl-ethyl)-amide;
(3R,4R)-4-{[5-(2,4-Difluoro-phenyl)-isoxazole-3-carbonyl]-amino}-1-((1S,2R)-2-hydroxy-cyclohexyl)-piperidine-3-carboxylic acid ((1R)-1-pyridin-2-yl-ethyl)-amide;

(3R,4R)-4-{[5-(2,4-Difluoro-phenyl)-isoxazole-3-carbonyl]-amino}-1-((1S,2R)-2-hydroxy-cyclohexyl)-piperidine-3-carboxylic acid ((1S)-1-pyridin-2-yl-ethyl)-amide;
(3R,4R)-4-{[5-(2,4-Difluoro-phenyl)-isoxazole-3-carbonyl]-amino}-1-((1S,2S)-2-hydroxy-cyclohexyl)-piperidine-3-carboxylic acid ((1R)-1-pyridin-2-yl-ethyl)-amide;
(3R,4R)-4-{[5-(2,4-Difluoro-phenyl)-isoxazole-3-carbonyl]-amino}-1-((1S,2S)-2-hydroxy-cyclohexyl)-piperidine-3-carboxylic acid ((1S)-1-pyridin-2-yl-ethyl)-amide;
(3S,4S)-4-{[5-(2,4-Difluoro-phenyl)-isoxazole-3-carbonyl]-amino}-1-((1R,2R)-2-hydroxy-cyclohexyl)-piperidine-3-carboxylic acid ((1R)-1-pyridin-2-yl-ethyl)-amide;
(3S,4S)-4-{[5-(2,4-Difluoro-phenyl)-isoxazole-3-carbonyl]-amino}-1-((1R,2R)-2-hydroxy-cyclohexyl)-piperidine-3-carboxylic acid ((1S)-1-pyridin-2-yl-ethyl)-amide;
(3S,4S)-4-{[5-(2,4-Difluoro-phenyl)-isoxazole-3-carbonyl]-amino}-1-((1R,2S)-2-hydroxy-cyclohexyl)-piperidine-3-carboxylic acid ((1R)-1-pyridin-2-yl-ethyl)-amide;
(3S,4S)-4-{[5-(2,4-Difluoro-phenyl)-isoxazole-3-carbonyl]-amino}-1-((1R,2S)-2-hydroxy-cyclohexyl)-piperidine-3-carboxylic acid ((1S)-1-pyridin-2-yl-ethyl)-amide;
(3S,4S)-4-{[5-(2,4-Difluoro-phenyl)-isoxazole-3-carbonyl]-amino}-1-((1S,2R)-2-hydroxy-cyclohexyl)-piperidine-3-carboxylic acid ((1R)-1-pyridin-2-yl-ethyl)-amide;
(3S,4S)-4-{[5-(2,4-Difluoro-phenyl)-isoxazole-3-carbonyl]-amino}-1-((1S,2R)-2-hydroxy-cyclohexyl)-piperidine-3-carboxylic acid ((1S)-1-pyridin-2-yl-ethyl)-amide;
(3S,4S)-4-{[5-(2,4-Difluoro-phenyl)-isoxazole-3-carbonyl]-amino}-1-((1S,2S)-2-hydroxy-cyclohexyl)-piperidine-3-carboxylic acid ((1R)-1-pyridin-2-yl-ethyl)-amide;
(3S,4S)-4-{[5-(2,4-Difluoro-phenyl)-isoxazole-3-carbonyl]-amino}-1-((1S,2S)-2-hydroxy-cyclohexyl)-piperidine-3-carboxylic acid ((1S)-1-pyridin-2-yl-ethyl)-amide;
(3S,4S)-4-{[5-(2,4-Difluoro-phenyl)-isoxazole-3-carbonyl]-amino}-1-(2-methoxy-ethyl)-piperidine-3-carboxylic acid (1-pyrimidin-2-yl-cyclopropyl)-amide;
(3S,4S)-4-{[5-(2,4-Difluoro-phenyl)-isoxazole-3-carbonyl]-amino}-1-ethyl-piperidine-3-carboxylic acid (1-pyrimidin-2-yl-cyclopropyl)-amide;
(3S,4S)-4-{[5-(2,4-Difluoro-phenyl)-isoxazole-3-carbonyl]-amino}-1-(1,1,2,2,2-d-ethyl)-piperidine-3-carboxylic acid (1-pyrimidin-2-yl-cyclopropyl)-amide;
(3R,4R)-1-Cyclohexyl-4-{[5-(2,4-difluoro-phenyl)-[1,3,4]oxadiazole-2-carbonyl]-amino}-piperidine-3-carboxylic acid dimethylamide;
(3R,4R)-1-Cyclohexyl-4-{[5-(2,4,6-trifluoro-phenyl)-isoxazole-3-carbonyl]-amino}-piperidine-3-carboxylic acid dimethylamide;
(3S,4S)-1-Cyclohexyl-4-{[5-(2,4,6-trifluoro-phenyl)-isoxazole-3-carbonyl]-amino}-piperidine-3-carboxylic acid dimethylamide;
(3R,4R)-1-Cyclohexyl-4-{[5-(2,4-difluoro-phenyl)-[1,2,4]oxadiazole-3-carbonyl]-amino}-piperidine-3-carboxylic acid (1-pyridin-2-yl-cyclopropyl)-amide;
(3S,4S)-1-Cyclohexyl-4-{[5-(2,4-difluoro-phenyl)-[1,2,4]oxadiazole-3-carbonyl]-amino}-piperidine-3-carboxylic acid (1-pyridin-2-yl-cyclopropyl)-amide;
(3R,4R)-1-Cyclohexyl-4-{[5-(2,4-difluoro-phenyl)-oxazole-2-carbonyl]-amino}-piperidine-3-carboxylic acid (1-pyridin-2-yl-cyclopropyl)-amide;
(3S,4S)-1-Cyclohexyl-4-{[5-(2,4-difluoro-phenyl)-oxazole-2-carbonyl]-amino}-piperidine-3-carboxylic acid (1-pyridin-2-yl-cyclopropyl)-amide;
(3R,4R)-1-Cyclohexyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide;
(3S,4S)-1-Cyclohexyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide;
(3S,4S)-1-Cyclopropylmethyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide;
(3S,4S)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide;
(3S,4S)-1-Cyclohexyl-4-{[5-(2,4-difluoro-phenyl)-isoxazole-3-carbonyl]-amino}-piperidine-3-carboxylic acid (2-methoxy-1,1-dimethyl-ethyl)-amide;
(3S,4S)-1-Cyclohexyl-4-{[5-(2,4-difluoro-phenyl)-isoxazole-3-carbonyl]-amino}-piperidine-3-carboxylic acid ((1R)-1-[1,2,4]oxadiazol-3-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((1S)-1-[1,2,4]oxadiazol-3-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((R)-1-phenyl-ethyl)-amide;
(3S,4S)-1-Cyclohexyl-4-{[5-(2,4-difluoro-phenyl)-isoxazole-3-carbonyl]-amino}-piperidine-3-carboxylic acid ((S)-2-hydroxy-1-phenyl-ethyl)-amide;
(3S,4S)-1-Cyclohexyl-4-{[5-(2,4-difluoro-phenyl)-isoxazole-3-carbonyl]-amino}-piperidine-3-carboxylic acid benzylamide;
(3S,4S)-1-Cyclopropylmethyl-4-{[5-(2,4-difluoro-phenyl)-isoxazole-3-carbonyl]-amino}-piperidine-3-carboxylic acid [(1R)-1-(2H-pyrazol-3-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [(1S)-1-(2H-pyrazol-3-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid ((R)-1-pyridin-3-yl-ethyl)-amide;
(3S,4S)-1-Cyclopentyl-4-{[5-(2,4-difluoro-phenyl)-isoxazole-3-carbonyl]-amino}-piperidine-3-carboxylic acid (1-pyridin-4-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyridin-4-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyridin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyridin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-methyl-1-pyridin-2-yl-ethyl)-amide;

(3S,4S)-1-Cyclopentyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]-amide;

(3S,4S)-1-Cyclopentyl-4-{[5-(2,4-difluoro-phenyl)-isoxazole-3-carbonyl]-amino}-piperidine-3-carboxylic acid ((1R)-1-isoxazol-3-yl-ethyl)-amide;

(3S,4S)-1-Cyclopentyl-4-{[5-(2,4-difluoro-phenyl)-isoxazole-3-carbonyl]-amino}-piperidine-3-carboxylic acid ((1S)-1-isoxazol-3-yl-ethyl)-amide;

(3S,4S)-1-Cyclopentyl-4-{[5-(2,4-difluoro-phenyl)-isoxazole-3-carbonyl]-amino}-piperidine-3-carboxylic acid [(1R)-1-(2H-pyrazol-3-yl)-ethyl]-amide;

(3S,4S)-1-Cyclopentyl-4-{[5-(2,4-difluoro-phenyl)-isoxazole-3-carbonyl]-amino}-piperidine-3-carboxylic acid [(1S)-1-(2H-pyrazol-3-yl)-ethyl]-amide;

(3S,4S)-1-Cyclopentyl-4-{[5-(2,4-difluoro-phenyl)-isoxazole-3-carbonyl]-amino}-piperidine-3-carboxylic acid ((R)-1-pyridin-3-yl-ethyl)-amide; and (3S,4S)-1-Cyclopropylmethyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]-amide.

24) In addition to the compounds of embodiment 23), further preferred compounds according to embodiment 1) are selected from the following compounds:

(3R,4R)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,3,4-trifluoro-phenyl)-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,3,4-trifluoro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,4-difluoro-phenyl)-isoxazole-3-carbonyl]-amino}-piperidine-3-carboxylic acid (1-pyridin-2-yl-cyclobutyl)-amide;

(3S,4S)-1-Cyclopropylmethyl-4-{[5-(2,4-difluoro-phenyl)-isoxazole-3-carbonyl]-amino}-piperidine-3-carboxylic acid (1-pyridin-2-yl-cyclobutyl)-amide;

(3R,4R)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide;

(3R,4R)-4-{[5-(2,4-Difluoro-phenyl)-isoxazole-3-carbonyl]-amino}-1-((1R,2R)-2-hydroxy-cyclohexyl)-piperidine-3-carboxylic acid (1-pyrimidin-2-yl-cyclopropyl)-amide;

(3R,4R)-4-{[5-(2,4-Difluoro-phenyl)-isoxazole-3-carbonyl]-amino}-1-((1R,2S)-2-hydroxy-cyclohexyl)-piperidine-3-carboxylic acid (1-pyrimidin-2-yl-cyclopropyl)-amide;

(3R,4R)-4-{[5-(2,4-Difluoro-phenyl)-isoxazole-3-carbonyl]-amino}-1-((1S,2R)-2-hydroxy-cyclohexyl)-piperidine-3-carboxylic acid (1-pyrimidin-2-yl-cyclopropyl)-amide;

(3R,4R)-4-{[5-(2,4-Difluoro-phenyl)-isoxazole-3-carbonyl]-amino}-1-((1S,2S)-2-hydroxy-cyclohexyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-((1R,2R)-2-hydroxy-cyclohexyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-((1R,2S)-2-hydroxy-cyclohexyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-((1S,2R)-2-hydroxy-cyclohexyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-((1S,2S)-2-hydroxy-cyclohexyl)-piperidine-3-carboxylic acid (1-pyrimidin-2-yl-cyclopropyl)-amide;

(3R,4R)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3S,4S)-1-Cyclopentyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3R,4R)-1-Cyclopentyl-4-{[5-(2,4-difluoro-phenyl)-isoxazole-3-carbonyl]-amino}-piperidine-3-carboxylic acid (1-cyano-cyclobutyl)-amide;

(3S,4S)-1-Cyclopentyl-4-{[5-(2,4-difluoro-phenyl)-isoxazole-3-carbonyl]-amino}-piperidine-3-carboxylic acid (1-cyano-cyclobutyl)-amide;

(3S,4S)-1-Cyclopentylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-(1-Difluoromethyl-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(4-fluoro-benzyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(2,2-dimethyl-propyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-isobutyl-piperidine-3-carboxylic acid (1-pyrimidin-2-yl-cyclopropyl)-amide;

(3S,4S)-1-Benzyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Cyclobutylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-isopropyl-piperidine-3-carboxylic acid (1-pyrimidin-2-yl-cyclopropyl)-amide;

(3S,4S)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide;

(3R,4R)-1-Cyclopentyl-4-{[5-(2,4-difluoro-phenyl)-isoxazole-3-carbonyl]-amino}-piperidine-3-carboxylic acid ethyl-methyl-amide;

(3R,4R)-1-Cyclopentyl-4-{[5-(2,4-difluoro-phenyl)-isoxazole-3-carbonyl]-amino}-piperidine-3-carboxylic acid methyl-(2-pyridin-2-yl-ethyl)-amide;

(3R,4R)-1-Cyclopropylmethyl-4-{[5-(2,4-difluoro-phenyl)-isoxazole-3-carbonyl]-amino}-piperidine-3-carboxylic acid methyl-(2-pyridin-2-yl-ethyl)-amide;

(3S,4S)-1-((1R)-2,2-Difluoro-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-((1S)-2,2-Difluoro-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(3-fluoro-propyl)-piperidine-3-carboxylic acid (1-pyrimidin-2-yl-cyclopropyl)-amide;

(3R,4R)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino-}-1-(1-methyl-cyclopropylmethyl)-piperidine-3-carboxylic acid (1-pyrimidin-2-yl-cyclopropyl)-amide;

(3S,4S)-1-Cyclopropylmethyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Allyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Bicyclo[3.1.0]hex-3-yl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-propyl-piperidine-3-carboxylic acid (1-pyrimidin-2-yl-cyclopropyl)-amide;

(3S,4S)-1-Cyclopentyl-4-{[5-(2,4-difluoro-phenyl)-oxazole-2-carbonyl]-amino}-piperidine-3-carboxylic acid (1-pyrimidin-2-yl-cyclopropyl)-amide;

(3S,4S)-1-(3,3-Difluoro-cyclobutylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-spiro[2.3]hex-5-yl-piperidine-3-carboxylic acid (1-pyrimidin-2-yl-cyclopropyl)-amide;

(3S,4S)-1-Cyclobutyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide;

(3S,4S)-4-{[5-(2,4-difluoro-phenyl)-[1,3,4]thiadiazole-2-carbonyl]-amino}-1-(1-fluoro-cyclopropylmethyl)-piperidine-3-carboxylic acid (1-pyrimidin-2-yl-cyclopropyl)-amide;

(3S,4S)-1-(Cyclopropyl-($d_2$-methyl))-4-{[5-(2,4-difluoro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[4-fluoro-5-(4-fluoro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[4-fluoro-5-(4-fluoro-phenyl)-isoxazole-3-carbonyl]-amino}-piperidine-3-carboxylic acid (1-pyrimidin-2-yl-cyclopropyl)-amide;

(3R,4R)-1-Cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide;

(3S,4S)-1-cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3S,4S)-4-{[5-(2,4-Difluoro-phenyl)-isoxazole-3-carbonyl]-amino-}-1-(1-fluoro-cyclopropylmethyl)-piperidine-3-carboxylic acid (1-pyrimidin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid (1-phenyl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid (1-pyrimidin-4-yl-cyclopropyl)-amide;

1-[((3S,4S)-1-Cyclopropylmethyl-4-{[5-(2,4-difluoro-phenyl)-isoxazole-3-carbonyl]-amino}-piperidine-3-carbonyl)-amino]-cyclopropanecarboxylic acid ethyl ester;

(3S,4S)-1-Cyclopropylmethyl-4-{[5-(2,4-difluoro-phenyl)-isoxazole-3-carbonyl]-amino}-piperidine-3-carboxylic acid (1-phenyl-cyclobutyl)-amide;

(3S,4S)-1-Cyclopropylmethyl-4-{[5-(2,4-difluoro-phenyl)-isoxazole-3-carbonyl]-amino}-piperidine-3-carboxylic acid benzyl-(2-fluoro-ethyl)-amide;

(3S,4S)-1-Cyclopropylmethyl-4-{[5-(2,4-difluoro-phenyl)-isoxazole-3-carbonyl]-amino}-piperidine-3-carboxylic acid [1-(3-methoxy-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(2-trifluoromethyl-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(2-fluoro-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [2-(2-chloro-phenyl)-ethyl]-amide;

5-(2,4-Difluoro-phenyl)-isoxazole-3-carboxylic acid [(3S,4S)-1-cyclopropylmethyl-3-((R)-2-phenyl-azetidine-1-carbonyl)-piperidin-4-yl]-amide;

5-(2,4-difluoro-phenyl)-isoxazole-3-carboxylic acid [(3S,4S)-1-cyclopropylmethyl-3-((S)-2-phenyl-azetidine-1-carbonyl)-piperidin-4-yl]-amide;

(3S,4S)-1-Cyclopropylmethyl-4-{[5-(2,4-difluoro-phenyl)-isoxazole-3-carbonyl]-amino}-piperidine-3-carboxylic acid [1-(3-chloro-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(4-methyl-thiazol-2-yl)-cyclobutyl]-amide;

(3S,4S)-1-Cyclopropylmethyl-4-{[5-(2,4-difluoro-phenyl)-isoxazole-3-carbonyl]-amino}-piperidine-3-carboxylic acid [(R)-1-(2-methoxy-phenyl)-ethyl]-amide;

(3S,4S)-1-cyclopropylmethyl-4-{[5-(2,4-difluoro-phenyl)-isoxazole-3-carbonyl]-amino}-piperidine-3-carboxylic acid [(S)-1-(2-methoxy-phenyl)-ethyl]-amide;

(3S,4S)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [(R)-1-(3-bromo-phenyl)-ethyl]-amide;

(3S,4S)-1-Cyclopropylmethyl-4-{[5-(2,4-difluoro-phenyl)-isoxazole-3-carbonyl]-amino}-piperidine-3-carboxylic acid [1-(2-hydroxy-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(1-oxy-pyrimidin-2-yl)-cyclopropyl]-amide;
5-(2,4-Difluoro-phenyl)-isoxazole-3-carboxylic acid [(3S,4S)-1-cyclopropylmethyl-3-((R)-2-pyrimidin-2-yl-pyrrolidine-1-carbonyl)-piperidin-4-yl]-amide;
5-(2,4-Difluoro-phenyl)-isoxazole-3-carboxylic acid [(3S,4S)-1-cyclopropylmethyl-3-((S)-2-pyrimidin-2-yl-pyrrolidine-1-carbonyl)-piperidin-4-yl]-amide;
5-(2,4-Difluoro-phenyl)-isoxazole-3-carboxylic acid [(3S,4S)-1-cyclopropylmethyl-3-((R)-2-pyrimidin-2-yl-azetidine-1-carbonyl)-piperidin-4-yl]-amide;
5-(2,4-difluoro-phenyl)-isoxazole-3-carboxylic acid [(3S,4S)-1-cyclopropylmethyl-3-((S)-2-pyrimidin-2-yl-azetidine-1-carbonyl)-piperidin-4-yl]-amide;
(3S,4S)-1-Cyclopropylmethyl-4-{[5-(2,4-difluoro-phenyl)-isoxazole-3-carbonyl]-amino}-piperidine-3-carboxylic acid ((R)-1-pyrimidin-2-yl-ethyl)-amide;
(3S,4S)-1-Cyclopropylmethyl-4-{[5-(2,4-difluoro-phenyl)-isoxazole-3-carbonyl]-amino}-piperidine-3-carboxylic acid ((S)-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide;
(3S,4S)-1-Cyclobutyl-4-{[5-(2,4-difluoro-phenyl)-isoxazole-3-carbonyl]-amino}-piperidine-3-carboxylic acid (1-methyl-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid ((R)-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid ((S)-1-pyrimidin-2-yl-ethyl)-amide;
(3R,4R)-1-Cyclobutyl-4-{[5-(2,4-difluoro-phenyl)-isoxazole-3-carbonyl]-amino}-piperidine-3-carboxylic acid (3-benzyl-oxetan-3-yl)-amide;
(3R,4R)-1-Cyclobutyl-4-{[5-(2,4-difluoro-phenyl)-isoxazole-3-carbonyl]-amino}-piperidine-3-carboxylic acid (3-phenyl-oxetan-3-ylmethyl)-amide;
(3S,4S)-4-{[5-(2,4-Difluoro-phenyl)-isoxazole-3-carbonyl]-amino}-1-ethyl-piperidine-3-carboxylic acid [(R)-1-(6-methyl-pyridin-2-yl)-ethyl]-amide;
(3S,4S)-4-{[5-(2,4-Difluoro-phenyl)-isoxazole-3-carbonyl]-amino}-1-ethyl-piperidine-3-carboxylic acid (1-methyl-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid [3-(3-chloro-phenyl)-oxetan-3-yl]-amide;
(3S,4S)-1-Cyclobutyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide;
(3S,4S)-1-Cyclobutyl-4-{[5-(2,4-difluoro-phenyl)-isoxazole-3-carbonyl]-amino}-piperidine-3-carboxylic acid [(S)-1-(3-fluoro-pyridin-2-yl)-ethyl]-amide;
(3R,4R)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide;
(3R,4R)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide (enantiomer 1);
(3S,4S)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide (enantiomer 1);
(3S,4S)-1-Cyclopropylmethyl-4-{[5-(2,4-difluoro-phenyl)-isoxazole-3-carbonyl]-amino}-piperidine-3-carboxylic acid (1-methyl-1-pyrimidin-2-yl-ethyl)-amide;
(3S,4S)-1-Cyclopropylmethyl-4-{[4-fluoro-5-(4-fluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[1-(2,4-difluoro-phenyl)-1H-[1,2,3]triazole-4-carbonyl]-amino}-piperidine-3-carboxylic acid (1-pyrimidin-2-yl-cyclopropyl)-amide;
(3S,4S)-1-Cyclopropylmethyl-4-{[5-(2,4-dimethyl-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[3-(2,4-difluoro-phenyl)-isoxazole-5-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-[1,2,4]oxadiazole-3-carbonyl]-amino}-piperidine-3-carboxylic acid (1-pyrimidin-2-yl-cyclopropyl)-amide;
(3S,4S)-1-Cyclopropylmethyl-4-{[4-(2,4-difluoro-phenyl)-oxazole-2-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-oxazole-2-carbonyl]-amino}-piperidine-3-carboxylic acid (1-pyrimidin-2-yl-cyclopropyl)-amide; and
(3S,4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide.

25) Another embodiment relates to particularly preferred compounds according to embodiment 1) which are selected from the following compounds:
(3S,4S)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[5-(2,4,6-trifluoro-phenyl)-isoxazole-3-carbonyl]-amino}-piperidine-3-carboxylic acid (2-methoxy-1,1-dimethyl-ethyl)-amide;
(3S,4S)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;
(3S,4S)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide;
(3S,4S)-1-Cyclohexyl-4-{[5-(2,4,6-trifluoro-phenyl)-isoxazole-3-carbonyl]-amino}-piperidine-3-carboxylic acid ((R)-1-pyridin-2-yl-ethyl)-amide;
(3S,4S)-1-Cyclopentyl-4-{[5-(2,4,6-trifluoro-phenyl)-isoxazole-3-carbonyl]-amino}-piperidine-3-carboxylic acid ((R)-1-pyridin-2-yl-ethyl)-amide;
(3S,4S)-1-Cyclopropylmethyl-4-{[5-(2,4,6-trifluoro-phenyl)-isoxazole-3-carbonyl]-amino}-piperidine-3-carboxylic acid ((R)-1-pyridin-2-yl-ethyl)-amide;
(3S,4S)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide;
(3S,4S)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide;
(3S,4S)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide;
(3S,4S)-1-Cyclopropylmethyl-4-{[5-(2,4,6-trifluoro-phenyl)-isoxazole-3-carbonyl]-amino}-piperidine-3-carboxylic acid ((R)-1-cyclobutyl-ethyl)-amide;

(3S,4S)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide;
(3S,4S)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide;
(3S,4S)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;
(3S,4S)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide;
(3S,4S)-1-Cyclopropylmethyl-4-{[5-(2,4,6-trifluoro-phenyl)-isoxazole-3-carbonyl]-amino}-piperidine-3-carboxylic acid (1-pyridin-2-yl-cyclopropyl)-amide;
(3S,4S)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyrazin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyrazin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide;
(3S,4S)-1-Cyclohexyl-4-{[5-(2,4-difluoro-phenyl)-isoxazole-3-carbonyl]-amino}-piperidine-3-carboxylic acid ((R)-1-pyridin-2-yl-ethyl)-amide;
(3S,4S)-1-Cyclohexyl-4-{[5-(2,4-difluoro-phenyl)-isoxazole-3-carbonyl]-amino}-piperidine-3-carboxylic acid [(R)-1-(6-methyl-pyridin-2-yl)-ethyl]-amide;
(3S,4S)-4-{[5-(2,4-Difluoro-phenyl)-isoxazole-3-carbonyl]-amino}-1-(2-methoxy-ethyl)-piperidine-3-carboxylic acid (1-pyrimidin-2-yl-cyclopropyl)-amide;
(3S,4S)-4-{[5-(2,4-Difluoro-phenyl)-isoxazole-3-carbonyl]-amino}-1-ethyl-piperidine-3-carboxylic acid (1-pyrimidin-2-yl-cyclopropyl)-amide;
(3S,4S)-4-{[5-(2,4-Difluoro-phenyl)-isoxazole-3-carbonyl]-amino}-1-(1,1,2,2,2-d-ethyl)-piperidine-3-carboxylic acid (1-pyrimidin-2-yl-cyclopropyl)-amide;
(3S,4S)-1-Cyclopropylmethyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide;
(3S,4S)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide;
(3S,4S)-1-Cyclohexyl-4-{[5-(2,4-difluoro-phenyl)-isoxazole-3-carbonyl]-amino}-piperidine-3-carboxylic acid (2-methoxy-1,1-dimethyl-ethyl)-amide;
(3S,4S)-1-Cyclohexyl-4-{[5-(2,4-difluoro-phenyl)-isoxazole-3-carbonyl]-amino}-piperidine-3-carboxylic acid ((1R)-1-[1,2,4]oxadiazol-3-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((1S)-1-[1,2,4]oxadiazol-3-yl-ethyl)-amide;
(3S,4S)-1-Cyclohexyl-4-{[5-(2,4-difluoro-phenyl)-isoxazole-3-carbonyl]-amino}-piperidine-3-carboxylic acid ((R)-1-phenyl-ethyl)-amide;
(3S,4S)-1-Cyclohexyl-4-{[5-(2,4-difluoro-phenyl)-isoxazole-3-carbonyl]-amino}-piperidine-3-carboxylic acid ((S)-2-hydroxy-1-phenyl-ethyl)-amide;
(3S,4S)-1-Cyclohexyl-4-{[5-(2,4-difluoro-phenyl)-isoxazole-3-carbonyl]-amino}-piperidine-3-carboxylic acid benzylamide;
(3S,4S)-1-Cyclopropylmethyl-4-{[5-(2,4-difluoro-phenyl)-isoxazole-3-carbonyl]-amino}-piperidine-3-carboxylic acid [(1R)-1-(2H-pyrazol-3-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [(1S)-1-(2H-pyrazol-3-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid ((R)-1-pyridin-3-yl-ethyl)-amide;
(3S,4S)-1-Cyclopentyl-4-{[5-(2,4-difluoro-phenyl)-isoxazole-3-carbonyl]-amino}-piperidine-3-carboxylic acid (1-pyridin-4-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyridin-4-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyridin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopentyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyridin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-isoxazole-3-carbonyl]-amino}-piperidine-3-carboxylic acid (1-methyl-1-pyridin-2-yl-ethyl)-amide;
(3S,4S)-1-Cyclopentyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]-amide;
(3S,4S)-1-Cyclopentyl-4-{[5-(2,4-difluoro-phenyl)-isoxazole-3-carbonyl]-amino}-piperidine-3-carboxylic acid ((1R)-1-isoxazol-3-yl-ethyl)-amide;
(3S,4S)-1-Cyclopentyl-4-{[5-(2,4-difluoro-phenyl)-isoxazole-3-carbonyl]-amino}-piperidine-3-carboxylic acid ((1S)-1-isoxazol-3-yl-ethyl)-amide;
(3S,4S)-1-Cyclopentyl-4-{[5-(2,4-difluoro-phenyl)-isoxazole-3-carbonyl]-amino}-piperidine-3-carboxylic acid [(1R)-1-(2H-pyrazol-3-yl)-ethyl]-amide;
(3S,4S)-1-Cyclopentyl-4-{[5-(2,4-difluoro-phenyl)-isoxazole-3-carbonyl]-amino}-piperidine-3-carboxylic acid [(1S)-1-(2H-pyrazol-3-yl)-ethyl]-amide;
(3S,4S)-1-Cyclopentyl-4-{[5-(2,4-difluoro-phenyl)-isoxazole-3-carbonyl]-amino}-piperidine-3-carboxylic acid ((R)-1-pyridin-3-yl-ethyl)-amide; and
(3S,4S)-1-Cyclopropylmethyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]-amide.

26) In addition to the compounds of embodiment 25), further particularly preferred compounds according to embodiment 1) are selected from the following compounds:
(3S,4S)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,3,4-trifluoro-phenyl)-isoxazole-3-carbonyl]-amino}-piperidine-3-carboxylic acid (1-pyrimidin-2-yl-cyclopropyl)-amide;

(3S,4S)-1-Cyclopentyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3S,4S)-1-Cyclopentylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-(1-Difluoromethyl-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(4-fluoro-benzyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(2,2-dimethyl-propyl)-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-isobutyl-piperidine-3-carboxylic acid (1-pyrimidin-2-yl-cyclopropyl)-amide;

(3S,4S)-1-Benzyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Cyclobutylmethyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-isopropyl-piperidine-3-carboxylic acid (1-pyrimidin-2-yl-cyclopropyl)-amide;

(3S,4S)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-((1R)-2,2-Difluoro-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-((1S)-2,2-Difluoro-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-(3-fluoro-propyl)-piperidine-3-carboxylic acid (1-pyrimidin-2-yl-cyclopropyl)-amide;

(3S,4S)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino-}-1-(1-methyl-cyclopropylmethyl)-piperidine-3-carboxylic acid (1-pyrimidin-2-yl-cyclopropyl)-amide;

(3S,4S)-1-Cyclopropylmethyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide;

(3S,4S)-1-Allyl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-Bicyclo[3.1.0]hex-3-yl-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-propyl-piperidine-3-carboxylic acid (1-pyrimidin-2-yl-cyclopropyl)-amide;

(3S,4S)-1-Cyclopentyl-4-{[5-(2,4-difluoro-phenyl)-oxazole-2-carbonyl]-amino}-piperidine-3-carboxylic acid (1-pyrimidin-2-yl-cyclopropyl)-amide;

(3S,4S)-1-(3,3-Difluoro-cyclobutylmethyl)-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-4-{[5-(2,4-Difluoro-phenyl)-isoxazole-3-carbonyl]-amino}-1-spiro[2.3]hex-5-yl-piperidine-3-carboxylic acid (1-pyrimidin-2-yl-cyclopropyl)-amide;

(3S,4S)-1-Cyclobutyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide;

(3S,4S)-4-{[5-(2,4-difluoro-phenyl)-[1,3,4]thiadiazole-2-carbonyl]-amino}-1-(1-fluoro-cyclopropylmethyl)-piperidine-3-carboxylic acid (1-pyrimidin-2-yl-cyclopropyl)-amide;

(3S,4S)-1-(Cyclopropyl-(d$_2$-methyl))-4-{[5-(2,4-difluoro-phenyl)-isoxazole-3-carbonyl]-amino}-piperidine-3-carboxylic acid (1-pyrimidin-2-yl-cyclopropyl)-amide;

(3S,4S)-1-cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide;

(3S,4S)-4-{[5-(2,4-Difluoro-phenyl)-isoxazole-3-carbonyl]-amino-}-1-(1-fluoro-cyclopropylmethyl)-piperidine-3-carboxylic acid (1-pyrimidin-2-yl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid (1-phenyl-cyclopropyl)-amide;

(3S,4S)-1-Cyclopropylmethyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid (1-pyrimidin-4-yl-cyclopropyl)-amide;

1-[((3S,4S)-1-Cyclopropylmethyl-4-{[5-(2,4-difluoro-phenyl)-isoxazole-3-carbonyl]-amino}-piperidine-3-carbonyl)-amino]-cyclopropanecarboxylic acid ethyl ester;

(3S,4S)-1-Cyclopropylmethyl-4-{[5-(2,4-difluoro-phenyl)-isoxazole-3-carbonyl]-amino}-piperidine-3-carboxylic acid (1-phenyl-cyclobutyl)-amide;

(3S,4S)-1-Cyclopropylmethyl-4-{[5-(2,4-difluoro-phenyl)-isoxazole-3-carbonyl]-amino}-piperidine-3-carboxylic acid benzyl-(2-fluoro-ethyl)-amide;

(3S,4S)-1-Cyclopropylmethyl-4-{[5-(2,4-difluoro-phenyl)-isoxazole-3-carbonyl]-amino}-piperidine-3-carboxylic acid [1-(3-methoxy-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(2-trifluoromethyl-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(2-fluoro-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [2-(2-chloro-phenyl)-ethyl]-amide;

5-(2,4-Difluoro-phenyl)-isoxazole-3-carboxylic acid [(3S,4S)-1-cyclopropylmethyl-3-((R)-2-phenyl-azetidine-1-carbonyl)-piperidin-4-yl]-amide;

5-(2,4-difluoro-phenyl)-isoxazole-3-carboxylic acid [(3S,4S)-1-cyclopropylmethyl-3-((S)-2-phenyl-azetidine-1-carbonyl)-piperidin-4-yl]-amide;

(3S,4S)-1-Cyclopropylmethyl-4-{[5-(2,4-difluoro-phenyl)-isoxazole-3-carbonyl]-amino}-piperidine-3-carboxylic acid [1-(3-chloro-phenyl)-cyclopropyl]-amide;

(3S,4S)-1-Cyclopropylmethyl-4-{[5-(2,4-difluoro-phenyl)-isoxazole-3-carbonyl]-amino}-piperidine-3-carboxylic acid [1-(4-methyl-thiazol-2-yl)-cyclobutyl]-amide;
(3S,4S)-1-Cyclopropylmethyl-4-{[5-(2,4-difluoro-phenyl)-isoxazole-3-carbonyl]-amino}-piperidine-3-carboxylic acid [(R)-1-(2-methoxy-phenyl)-ethyl]-amide;
(3S,4S)-1-cyclopropylmethyl-4-{[5-(2,4-difluoro-phenyl)-isoxazole-3-carbonyl]-amino}-piperidine-3-carboxylic acid [(S)-1-(2-methoxy-phenyl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [(R)-1-(3-bromo-phenyl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid [1-(2-hydroxy-phenyl)-cyclopropyl]-amide;
(3S,4S)-1-Cyclopropylmethyl-4-{[5-(2,4-difluoro-phenyl)-isoxazole-3-carbonyl]-amino}-piperidine-3-carboxylic acid [1-(1-oxy-pyrimidin-2-yl)-cyclopropyl]-amide;
5-(2,4-Difluoro-phenyl)-isoxazole-3-carboxylic acid [(3S,4S)-1-cyclopropylmethyl-3-((R)-2-pyrimidin-2-yl-pyrrolidine-1-carbonyl)-piperidin-4-yl]-amide;
5-(2,4-Difluoro-phenyl)-isoxazole-3-carboxylic acid [(3S,4S)-1-cyclopropylmethyl-3-((S)-2-pyrimidin-2-yl-pyrrolidine-1-carbonyl)-piperidin-4-yl]-amide;
5-(2,4-Difluoro-phenyl)-isoxazole-3-carboxylic acid [(3S,4S)-1-cyclopropylmethyl-3-((R)-2-pyrimidin-2-yl-azetidine-1-carbonyl)-piperidin-4-yl]-amide;
5-(2,4-difluoro-phenyl)-isoxazole-3-carboxylic acid [(3S,4S)-1-cyclopropylmethyl-3-((S)-2-pyrimidin-2-yl-azetidine-1-carbonyl)-piperidin-4-yl]-amide;
(3S,4S)-1-Cyclopropylmethyl-4-{[5-(2,4-difluoro-phenyl)-isoxazole-3-carbonyl]-amino}-piperidine-3-carboxylic acid ((R)-1-pyrimidin-2-yl-ethyl)-amide;
(3S,4S)-1-Cyclopropylmethyl-4-{[5-(2,4-difluoro-phenyl)-isoxazole-3-carbonyl]-amino}-piperidine-3-carboxylic acid ((S)-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide;
(3S,4S)-1-Cyclobutyl-4-{[5-(2,4-difluoro-phenyl)-isoxazole-3-carbonyl]-amino}-piperidine-3-carboxylic acid (1-methyl-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid ((R)-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid ((S)-1-pyrimidin-2-yl-ethyl)-amide;
(3S,4S)-4-{[5-(2,4-Difluoro-phenyl)-isoxazole-3-carbonyl]-amino}-1-ethyl-piperidine-3-carboxylic acid [(R)-1-(6-methyl-pyridin-2-yl)-ethyl]-amide;
(3S,4S)-4-{[5-(2,4-Difluoro-phenyl)-isoxazole-3-carbonyl]-amino}-1-ethyl-piperidine-3-carboxylic acid (1-methyl-1-pyrimidin-2-yl-ethyl)-amide;
(3S,4S)-1-Cyclobutyl-4-{[5-(2,4-difluoro-phenyl)-isoxazole-3-carbonyl]-amino}-piperidine-3-carboxylic acid [3-(3-chloro-phenyl)-oxetan-3-yl]-amide;
(3S,4S)-1-Cyclobutyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide;
(3S,4S)-1-Cyclobutyl-4-{[5-(2,4-difluoro-phenyl)-isoxazole-3-carbonyl]-amino}-piperidine-3-carboxylic acid [(S)-1-(3-fluoro-pyridin-2-yl)-ethyl]-amide;
(3S,4S)-1-Cyclopropylmethyl-4-{[5-(2,4-difluoro-phenyl)-isoxazole-3-carbonyl]-amino}-piperidine-3-carboxylic acid (1-methyl-1-pyrimidin-2-yl-ethyl)-amide;
(3S,4S)-1-Cyclopropylmethyl-4-{[4-fluoro-5-(4-fluoro-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[1-(2,4-difluoro-phenyl)-1H-[1,2,3]triazole-4-carbonyl]-amino}-piperidine-3-carboxylic acid (1-pyrimidin-2-yl-cyclopropyl)-amide;
(3S,4S)-1-Cyclopropylmethyl-4-{[5-(2,4-dimethyl-phenyl)-isoxazole-3-carbonyl]-amino}-piperidine-3-carboxylic acid (1-pyrimidin-2-yl-cyclopropyl)-amide;
(3S,4S)-1-Cyclopropylmethyl-4-{[3-(2,4-difluoro-phenyl)-isoxazole-5-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-[1,2,4]oxadiazole-3-carbonyl]-amino}-piperidine-3-carboxylic acid (1-pyrimidin-2-yl-cyclopropyl)-amide;
(3S,4S)-1-Cyclopropylmethyl-4-{[4-(2,4-difluoro-phenyl)-oxazole-2-carbonyl]-amino}-piperidine-3-carboxylic acid (1-pyrimidin-2-yl-cyclopropyl)-amide;
(3S,4S)-1-Cyclopropylmethyl-4-{[5-(2,4-difluoro-phenyl)-oxazole-2-carbonyl]-amino}-piperidine-3-carboxylic acid (1-pyrimidin-2-yl-cyclopropyl)-amide; and
(3S,4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide.

27) A further aspect of the invention relates to novel piperidine derivatives of formula (II);

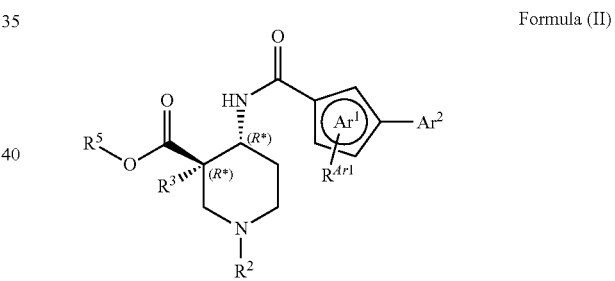

Formula (II)

wherein the two substituents of the piperidine ring: $R^1$—CO— and —NH—CO—$Ar^1$—$Ar^2$, are in relative trans-configuration (i.e. the relative configuration of the two chiral carbon atoms in position 3 and 4 of the piperidine ring is (3R*,4R*));

$Ar^1$ represents a 5-membered heteroarylene group (especially a 5-membered heteroarylene containing one to a maximum of three heteroatoms, each independently selected from oxygen and nitrogen; notably oxazol-diyl, isoxazol-diyl, oxadiazol-diyl, or triazol-diyl), wherein the —NH—CO— group and $Ar^2$ are attached in meta arrangement to ring atoms of $Ar^1$; wherein said 5-membered heteroarylene is unsubstituted, or mono-substituted with $R^{Ar1}$ wherein $R^{Ar1}$ represents $(C_{1-4})$alkyl, $(C_{1-4})$alkoxy, halogen, $(C_{1-3})$fluoroalkyl, or $(C_{1-3})$fluoroalkoxy (especially said 5-membered heteroarylene is unsubstituted);

$Ar^2$ represents phenyl which is mono-, di- or tri-substituted, wherein the substituents are independently fluoro or chloro (especially $Ar^2$ represents phenyl which is mono-, di- or tri-substituted with fluoro);

$R^5$ represents $(C_{1-6})$alkyl;
$R^2$ represents
- hydrogen;
- $(C_{1-6})$alkyl (especially ethyl, isopropyl, 2,2-dimethylpropyl, 3-methyl-butyl, 3,3-dimethylbutyl);
- $(C_{2-6})$alkyl which is mono-substituted with $(C_{1-3})$alkoxy (especially methoxy), or hydroxy (especially 2-hydroxyethyl, 2-methoxy-ethyl, 2-hydroxy-1-methylpropyl);
- $(C_{2-3})$fluoroalkyl;
- $(C_{3-8})$cycloalkyl-$(C_{0-3})$alkyl; wherein said $(C_{3-8})$cycloalkyl group may optionally contain one ring oxygen atom; wherein the $(C_{3-8})$cycloalkyl is unsubstituted, or mono- or di-substituted wherein the substituents are independently selected from $(C_{1-3})$alkyl (especially methyl), fluoro, hydroxy, hydroxy-$(C_{1-3})$alkyl (especially hydroxy-methyl), or $(C_{1-3})$alkoxy (especially methoxy);
- (especially cyclobutyl, 2-methylcyclobutyl, 2,2-dimethylcyclobutyl, 3,3-dimethylcyclobutyl, cyclopentyl, cyclohexyl, spiro[2.4]hept-4-yl, spiro[3.3]hept-2-yl, bicyclo[2.2.1]hept-2-yl, 2-methylcyclopentyl, 2-(hydroxymethyl)-cyclopentyl, 3,3-dimethylcyclopentyl, 2-ethylcyclopentyl, 3,3-dimethylcyclohexyl, 2-fluoro-cyclohexyl, 4-fluoro-cyclohexyl, 4,4-difluoro-cyclohexyl, 2-hydroxy-cyclohexyl, 2-methoxy-cyclohexyl, 3-methoxy-cyclohexyl, cyclopropylmethyl, cyclobutylmethyl, cyclopentylmethyl, 1-cyclopropylethyl, (1-methyl-cyclopropyl)-methyl, (1-methyl-cyclobutyl)-methyl, 2-cyclopropyl-ethyl); or
- $(C_{3-8})$cycloalkenyl-$(C_{1-3})$alkyl (especially cyclopenten-1-yl-methyl); and $R^3$ represents hydrogen, or methyl (especially hydrogen).

The compounds of formula (II) are important intermediates suitable for the preparation of the compounds of formula (I) as described in reaction scheme A below. In addition, such compounds of formula (II) may also act as CXCR7 receptor antagonists, and may, thus, be useful for the prevention or treatment of diseases which respond to the activation of the CXCL12 receptors and/or CXCL11 receptors, especially cancer.

It is understood that the characteristics of embodiments 2) to 10) and 15) to 19), especially as set out in embodiment 20), apply mutatis mutandis also to the compounds of formula (II).

The compounds of formula (I) according to embodiments 1) to 26) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or (II), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) as defined in any one of embodiments 1) to 26).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I) as defined in any one of embodiments 1) to 26) are useful for the prevention/prophylaxis or treatment of disorders relating to the CXCR7 receptor or its ligands which are especially to disorders relating to a dysfunction of the CXCR7 receptor, or dysfunction of ligands signalling through CXCR7, or dysfunction of CXCR7 ligands (CXCL12 and CXCL11) signalling through their other receptors (CXCR4 and CXCR3).

Diseases or disorders relating to the CXCR7 receptor or its ligands are especially selected from the group consisting of
- cancer (notably brain tumors including malignant gliomas, glioblastoma multiforme; neuroblastoma; pancreatic cancer including pancreatic adenocarcinoma/pancreatic ductal adenocarcinoma; gastro-intestinal cancers including colon carcinoma, hepatocellular carcinoma; Kaposi's sarcoma; leukemias including adult T-cell leukemia; lymphoma; lung cancer; breast cancer; rhabdomyosarcoma; prostate cancer; esophageal squamous cancer; oral squamous cell carcinoma; endometrial cancer; thyroid carcinoma including papillary thyroid carcinoma; metastatic cancers; lung metastasis; skin cancer including melanoma and metastatic melanoma; bladder cancer; multiple myelomas; osteosarcoma; head and neck cancer; and renal carcinomas including renal clear cell carcinoma, metastatic renal clear cell carcinoma);
- inflammatory diseases (notably chronic rhinosinusitis, asthma, chronic obstructive pulmonary disorder, atherosclerosis, myocarditis, and sarcoidosis; especially chronic rhinosinusitis, asthma, and atherosclerosis);
- autoimmune disorders (notably (inflammatory) demyelinating diseases; multiple sclerosis (MS); Guillain Barré syndrome; rheumatoid arthritis (RA); inflammatory bowel diseases (IBD, especially comprising Crohn's disease and ulcerative colitis); systemic lupus erythematosus (SLE); lupus nephritis; interstitial cystitis; celiac disease; autoimmune encephalomyelitis; osteoarthritis; and type I diabetes; especially autoimmune disorders which have an inflammatory component such as (inflammatory) demyelinating diseases, multiple sclerosis, Guillain Barré syndrome, rheumatoid arthritis, inflammatory bowel diseases, systemic lupus erythematosus, lupus nephritis, and auto-immune encephalomyelitis);

transplant rejection (notably renal allograft rejection, cardiac allograft rejection, and graft-versus-host diseases brought about by hematopoietic stem cell transplantation); and fibrosis (notably liver fibrosis, liver cirrhosis, lung fibrosis, especially idiopathic pulmonary fibrosis).

Notably such diseases or disorders relating to the CXCR7 receptor or its ligands are cancers, autoimmune disorders (especially autoimmune disorders which have an inflammatory component), and fibrosis.

In addition, further diseases or disorders relating to the CXCR7 receptor or its ligands are diseases involving CXCR7 and/or CXCL12 and/or CXCL11 mediated metastasis, chemotaxis, cell adhesion, trans-endothelial migration, cell proliferation and/or survival.

In addition, further particular diseases or disorders relating to the CXCR7 receptor or its ligands are proliferative diabetic retinopathy; West Nile virus encephalitis; pulmonary vascular diseases, acute renal failure, ischemia including cerebral ischemia, acute coronary syndrome, injured central nervous system, hypertension, pulmonary hypertension, Shiga-toxin-associated heomolytic uremic syndrome, preeclampsia, vascular injury, HIV/AIDS, angiogenesis, and brain and neuronal dysfunctions (such as inflammatory components of Alzheimer's disease), stress-related disorders (such as anxiety, depression, and posttraumatic stress disorder), and diseases involving opioid receptors. In a sub-embodiment, such a further particular disease or disorder relating to the CXCR7 receptor or its ligands is especially pulmonary hypertension.

The term "cancer" refers to all sorts of cancers such as carcinomas; adenocarcinomas; leukemias; sarcomas; lymphomas; myelomas; metastatic cancers; brain tumors; neuroblastomas; pancreatic cancers; gastro-intestinal cancers; lung cancers; breast cancers; prostate cancers; endometrial cancers; skin cancers; bladder cancers; head and neck cancers; neuroendocrine tumors; ovarian cancers; cervical cancers; oral tumors; nasopharyngeal tumors; thoracic cancers; and virally induced tumors.

Notably the term refers to brain tumors including brain metastases, malignant gliomas, glioblastoma multiforme, medulloblastoma, meningiomas; neuroblastoma; pancreatic cancer including pancreatic adenocarcinoma/pancreatic ductal adenocarcinoma; gastro-intestinal cancers including colon carcinoma, colorectal adenoma, colorectal adenocarcinoma, metastatic colorectal cancer, familial adenomatous polyposis (FAP), gastric cancer, gallbladder cancer, cholangiocarcinoma, hepatocellular carcinoma; Kaposi's sarcoma; leukemias including acute myeloid leukemia, adult T-cell leukemia; lymphomas including Burkitt's lymphoma, Hodgkin's lymphoma, MALT lymphoma, and primary intraocular B-Cell lymphoma; lung cancer including non-small cell lung cancer; breast cancer including triple negative breast carcinoma; rhabdomyosarcoma; prostate cancer including castrate-resistant prostate cancer; esophageal squamous cancer; (oral) squamous cell carcinoma; endometrial cancer; thyroid carcinoma including papillary thyroid carcinoma; metastatic cancers; lung metastasis; skin cancer including melanoma and metastatic melanoma; bladder cancer including urinary bladder cancer, urothelial cell carcinoma; multiple myelomas; osteosarcoma; head and neck cancer; and renal carcinomas including renal cell carcinoma renal clear cell carcinoma, metastatic renal cell carcinoma, metastatic renal clear cell carcinoma; as well as neuroendocrine tumors; ovarian cancer; cervical cancer; oral tumors; nasopharyngeal tumors; thoracic cancer; choriocarcinoma; Ewing's sarcoma; and virally induced tumors.

Especially the term "cancer" refers to malignant glioma in particular glioblastoma multiforme, neuroblastoma; pancreatic cancers in particular pancreatic ductal adenocarcinoma; Kaposi's sarcoma; adult T-cell leukemia, lymphoma; lung cancer; breast cancer; rhabdomyosarcoma; prostate cancer; esophageal squamous cancer; (oral) squamous cell carcinoma; endometrial cancer; papillary thyroid carcinoma; metastatic cancer; lung metastasis; melanoma; bladder cancer; multiple myelomas; osteosarcoma; gastro-intestinal cancers, in particular colon carcinoma, hepatocellular carcinoma; head and neck cancer; and renal clear cell carcinoma. Preferably the term "cancer" refers to malignant glioma, in particular glioblastoma multiforme; pancreatic cancers, in particular pancreatic ductal adenocarcinoma; papillary thyroid carcinoma; hepatocellular carcinoma; lung cancer; breast cancer; metastatic cancers; lung metastasis; melanoma; colon carcinoma; and head and neck cancer.

The compounds of formula (I) as defined in any one of embodiments 1) to 26) may in particular be useful as therapeutic agents for the prevention/prophylaxis or treatment of a cancer as defined before, which cancer is a metastatic cancer/a cancer which forms metastasis.

The compounds of formula (I) as defined in any one of embodiments 1) to 26) are in particular useful as therapeutic agents for the prevention/prophylaxis or treatment of a cancer. They can be used as single therapeutic agents or in combination with one or more chemotherapy agents and/or radiotherapy and/or targeted therapy. In a sub-embodiment, when a compound of formula (I) is used for the prevention/prophylaxis or treatment of a cancer in combination with one or more chemotherapy agents and/or radiotherapy and/or targeted therapy, such cancer is especially a malignant glioma, in particular a glioblastoma multiforme; pancreatic cancer, especially pancreatic ductal adenocarcinoma; papillary thyroid carcinoma; lung metastasis; melanoma; lung cancer; metastatic cancers; hepatocellular carcinoma; breast cancer; colorectal cancer; or head and neck cancer. Such combined treatment may be effected simultaneously, separately, or over a period of time.

The invention, thus, also relates to pharmaceutical compositions comprising a pharmaceutically acceptable carrier material, and:
a compound of formula (I) as defined in any one of embodiments 1) to 26);
and one or more cytotoxic chemotherapy agents.

The invention, thus, further relates to a kit comprising
a pharmaceutical composition, said composition comprising a pharmaceutically acceptable carrier material, and
a compound of formula (I) as defined in any one of embodiments 1) to 26);
and instructions how to use said pharmaceutical composition for the prevention or the treatment of a cancer (especially of a malignant glioma, in particular of a glioblastoma multiforme), in combination with chemotherapy and/or radiotherapy and/or targeted therapy.

The terms "radiotherapy" or "radiation therapy" or "radiation oncology", refer to the medical use of ionizing radiation in the prevention (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or deliver toxic substances directly to cancer cells and kill them. An example of a targeted therapy which is in particular suitable to be combined with the compounds of the present invention is immunotherapy, especially immunotherapy targeting the programmed cell death receptor 1 (PD-1 receptor) or its ligand PD-L1 (Feig C et al, PNAS 2013).

When used in combination with the compounds of formula (I), the term "targeted therapy" especially refers to agents such as:

a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab);

b) B-RAF inhibitors (for example Vemurafenib, Sorafenib, Dabrafenib, GDC-0879, PLX-4720, LGX818);

c) Aromatase inhibitors (for example Exemestane, Letrozole, Anastrozole, Vorozole, Formestane, Fadrozole);

d) Immune Checkpoint inhibitors (for example, anti-PD1 antibodies such as Pembrolizumab (Lambrolizumab, MK-3475), Nivolumab, Pidilizumab, AMP-514/MED10680; small molecule anti PD1 agents such as for example compounds disclosed in WO2015/033299, WO2015/044900 and WO2015/034820; anti-PD1L antibodies, such as BMS-936559, atezolizumab (MPDL3280A), MED14736, avelumab (MSB0010718C); anti-PDL2, such as AMP224, anti-CTLA-4 antibodies, such as ipilimumab, tremilmumab);

e) Vaccination approaches (for example dendritic cell vaccination, peptide or protein vaccination (for example with gp100 peptide or MAGE-A3 peptide);

f) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX);

g) T-cell based adoptive immunotherapies, including chimeric antigen receptor (CAR) engineered T-cells (for example CTL019);

h) Cytokine or immunocytokine based therapy (for example Interferon alpha, interferon beta, interferon gamma, interleukin 2, interleukin 15);

i) Toll-like receptor (TLR) agonists (for example resiquimod, imiquimod, glucopyranosyl lipid A, CpG oligodesoxynucleotides);

j) Thalidomide analogues (for example Lenalidomide, Pomalidomide);

k) Indoleamin-2,3-Dioxgenase (IDO) and/or Tryptophane-2,3-Dioxygenase (TDO) inhibitors (for example NLG919/Indoximod, 1MT (1-methyltryptophan), INCB024360);

l) Activators of T-cell co-stimulatory receptors (for example anti-Lymphocyte-activation gene 3 (LAG-3) antibodies (such as BMS-986016); anti T cell immunoglobulin mucin-3 (TIM-3) antibodies, anti-CD137/4-1BB antibodies (for example BMS-663513/urelumab), anti-Killer-cell immunoglobulin-like receptors (KIR) for example Lirilumab (IPH2102/BMS-986015); anti-OX40/CD134 (Tumor necrosis factor receptor superfamily, member 4), anti OX40-Ligand/CD252; anti-glucocorticoid-induced TNFR family related gene (GITR) (such as TRX518), anti-CD40 (TNF receptor superfamily member 5) antibodies (such as CP-870, 893); anti-CD40-Ligand antibodies (such as BG9588); anti-CD28 antibodies);

m) Molecules binding a tumor specific antigen as well as a T-cell surface marker such as bispecific antibodies or antibody fragments, antibody mimetic proteins such as designed ankyrin repeat proteins (DARPINS), bispecific T-cell engager (BITE, for example AMG103, AMG330);

n) Antibodies or small molecular weight inhibitors targeting colony-stimulating factor-1 receptor (CSF-1R) (for example RG7155 or PLX3397).

When used in combination with the compounds of formula (I), immune checkpoint inhibitors such as those listed under d), and especially those targeting the programmed cell death receptor 1 (PD-1 receptor) or its ligand PD-L1, are preferred.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy.

The term "cytotoxic chemotherapy agent" or "chemotherapy agent" as used herein refers to an active anti-neoplastic agent inducing apoptosis or necrotic cell death. When used in combination with the compounds of formula (I), the term especially refers to conventional cytotoxic chemotherapy agents such as:

a) alkylating agents (for example mechlorethamine, chlorambucil, cyclophosphamide, ifosfamide, streptozocin, carmustine, lomustine, melphalan, busulfan, dacarbazine, temozolomide, thiotepa or altretamine; in particular temozolomide);

b) platinum drugs (for example cisplatin, carboplatin or oxaliplatin);

c) antimetabolite drugs (for example 5-fluorouracil, capecitabine, 6-mercaptopurine, methotrexate, gemcitabine, cytarabine, fludarabine or pemetrexed);

d) anti-tumor antibiotics (for example daunorubicin, doxorubicin, epirubicin, idarubicin, actinomycin-D, bleomycin, mitomycin-C or mitoxantrone);

e) mitotic inhibitors (for example paclitaxel, docetaxel, ixabepilone, vinblastine, vincristine, vinorelbine, vindesine or estramustine); or f) topoisomerase inhibitors (for example etoposide, teniposide, topotecan, irinotecan, diflomotecan or elomotecan).

When used in combination with the compounds of formula (I), preferred cytotoxic chemotherapy agents are the above-mentioned alkylating agents (notably mechlorethamine, chlorambucil, cyclophosphamide, ifosfamide, streptozocin, carmustine, lomustine, melphalan, busulfan, dacarbazine, 3-methyl-(triazen-1-yl)imidazole-4-carboxamide (MTIC) and prodrugs thereof such as especially temozolomide, thiotepa, altretamine; or pharmaceutically acceptable salts of these compounds; in particular temozolomide); and mitotic inhibitors (notably paclitaxel, docetaxel, ixabepilone, vinblastine, vincristine, vinorelbine, vindesine, estramustine; or pharmaceutically acceptable salts of these compounds; in particular paclitaxel). Most preferred cytotoxic chemotherapy agents to be used in combination with the compounds of formula (I) are those routinely used in the treatment of glioblastoma multiforme, in particular temozolomide. Equally preferred is radiotherapy.

Chemotherapy may be given with a curative intent or it may aim to prolong life or to palliate symptoms.
a) Combined modality chemotherapy is the use of drugs with other cancer treatments, such as radiation therapy or surgery.
b) Induction chemotherapy is the first line treatment of cancer with a chemotherapeutic drug. This type of chemotherapy is used for curative intent.
c) Consolidation chemotherapy is the given after remission in order to prolong the overall disease free time and improve overall survival. The drug that is administered is the same as the drug that achieved remission.
d) Intensification chemotherapy is identical to consolidation chemotherapy but a different drug than the induction chemotherapy is used.
e) Combination chemotherapy involves treating a patient with a number of different drugs simultaneously. The drugs differ in their mechanism and side effects. The biggest advantage is minimising the chances of resistance developing to any one agent. Also, the drugs can often be used at lower doses, reducing toxicity.
f) Neoadjuvant chemotherapy is given prior to a local treatment such as surgery, and is designed to shrink the primary tumor. It is also given to cancers with a high risk of micrometastatic disease.
g) Adjuvant chemotherapy is given after a local treatment (radiotherapy or surgery). It can be used when there is little evidence of cancer present, but there is risk of recurrence. It is also useful in killing any cancerous cells that have spread to other parts of the body. These micrometastases can be treated with adjuvant chemotherapy and can reduce relapse rates caused by these disseminated cells.
h) Maintenance chemotherapy is a repeated low-dose treatment to prolong remission.
i) Salvage chemotherapy or palliative chemotherapy is given without curative intent, but simply to decrease tumor load and increase life expectancy. For these regimens, a better toxicity profile is generally expected.

When combined with the compounds of formula (I), preventive or curative forms of chemotherapy (or mutatis mutandis: radiotherapy) such as those listed under a), b) c), d), e), and especially g) and/or h) above are preferred.

"Simultaneously", when referring to an administration type, means in the present application that the administration type concerned consists in the administration of two or more active ingredients and/or treatments at approximately the same time; wherein it is understood that a simultaneous administration will lead to exposure of the subject to the two or more active ingredients and/or treatments at the same time. When administered simultaneously, said two or more active ingredients may be administered in a fixed dose combination, or in an equivalent non-fixed dose combination (e.g. by using two or more different pharmaceutical compositions to be administered by the same route of administration at approximately the same time), or by a non-fixed dose combination using two or more different routes of administration; wherein said administration leads to essentially simultaneous exposure of the subject to the two or more active ingredients and/or treatments.

"Fixed dose combination", when referring to an administration type, means in the present application that the administration type concerned consists in the administration of one single pharmaceutical composition comprising the two or more active ingredients.

"Separately", when referring to an administration type, means in the present application that the administration type concerned consists in the administration of two or more active ingredients and/or treatments at different points in time; wherein it is understood that a separate administration will lead to a treatment phase (e.g. at least 1 hour, notably at least 6 hours, especially at least 12 hours) where the subject is exposed to the two or more active ingredients and/or treatments at the same time; wherein such "separate administration" may under certain circumstances also encompass a treatment phase where for a certain period of time (e.g. at least 12 hours, especially at least one day) the subject is exposed to only one of the two or more active ingredients and/or treatments. Separate administration thus especially refers to situations wherein one active ingredient and/or treatment is given e.g. once a day, and another is given e.g. twice a day, thrice a day, every other day, wherein as a consequence of such administration type the subject is exposed to the two or more active ingredients and/or treatments the same time during essentially the whole treatment period. Separate administration also refers to situations wherein at least one of the active ingredients and/or treatments is given with a periodicity substantially longer than daily (such as once or twice daily) administration (e.g. wherein one active ingredient and/or treatment is given e.g. once or twice a day, and another is given once a week). For example when used in combination with (e.g. weekly or bi-weekly) radiotherapy the present CXCR7 modulators would possibly be used "separately".

By administration "over a period of time" is meant in the present application the subsequent administration of two or more active ingredients and/or treatments at different times. The term in particular refers to an administration method according to which the entire administration of one of the active ingredients and/or treatments is completed before the administration of the other/the others begins. In this way it is possible to administer one of the active ingredients and/or treatments for several months before administering the other active ingredient(s) and/or treatment(s).

Administration "over a period of time" also encompasses situations wherein the CXCR7 modulators of formula (I) or (II) would be used in a treatment that starts after termination of an initial chemotherapeutic or radiotherapeutic treatment or targeted therapy (for example an induction chemotherapy), wherein optionally said treatment would be in combination with a further/an ongoing chemotherapeutic or radiotherapeutic treatment or targeted therapy treatment (for example in combination with a consolidation chemotherapy, an intensification chemotherapy, an adjuvant chemotherapy, or a maintenance chemotherapy; or radiotherapeutic equivalents thereof); wherein such further/ongoing chemotherapeutic or radiotherapeutic treatment or targeted therapy would be simultaneously or separately with the treatment using the CXCR7 modulator.

Autoimmune disorders may be defined as comprising (inflammatory) demyelinating diseases; multiple sclerosis (MS); Guillain Barré syndrome; rheumatoid arthritis (RA); inflammatory bowel disease (IBD, especially comprising Crohn's disease and ulcerative colitis); systemic lupus erythematosus (SLE); lupus nephritis; interstitial cystitis; celiac disease; autoimmune encephalomyelitis; osteoarthritis; and type I diabetes. In addition, autoimmune diseases further comprise disorders such as psoriasis; psoriatic arthritis; antiphospholipid syndrome; thyroiditis such as Hashimoto's thyroiditis; lymphocytic thyroiditis; myasthenia gravis; uveitis; episcleritis; scleritis; Kawasaki's disease; uveoretinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis. In a sub-embodiment, autoimmune disorders especially refer to autoimmune disorders which have an inflammatory component wherein particular examples are (inflammatory) demyelinating diseases, multiple sclerosis (MS), Guillain Barré syndrome, rheumatoid arthritis (RA), inflammatory bowel disease (IBD, especially comprising Crohn's disease and ulcerative colitis), systemic lupus erythematosus (SLE), lupus nephritis, and auto-immune encephalomyelitis.

Inflammatory diseases may be defined as comprising especially chronic rhinusitis, as well as asthma, chronic obstructive pulmonary disorder (COPD), atherosclerosis, myocarditis, dry eye disease, sarcoidosis, inflammatory myopathies, and acute lung injury.

Transplant rejection may be defined as comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy.

Fibrosis may be defined as comprising especially liver fibrosis, liver cirrhosis, lung fibrosis, idiopathic pulmonary fibrosis, renal fibrosis, endomyocardial fibrosis, and arthrofibrosis.

The compounds of formula (I) according to embodiments 1) to 31) are also useful in method of prophylaxis or treating tumors comprising administering an effective amount of the compound of formula (I) wherein said effective amount leads to a change of tumor properties, and wherein said modification is achieved by modulating the CXCL11/CXCL12 receptor pathway; wherein said prophylaxis or treatment may optionally be effected in combination with a conventional chemotherapeutic or radiotherapeutic treatment (in which case the tumor is notably a malignant glioma, in particular a glioblastoma multiforme). Such combined treatment may be effected simultaneously, separately, and/or over a period of time.

The compounds of formula (I) are also useful in method of modulating an immune response comprising the administration of an effective amount of the compound of formula (I) wherein said effective amount modulates an inflammatory disease and wherein said response is mediated by the CXCL11/CXCL12 receptor pathway.

Preparation of Compounds of Formula (I)

The compounds of formula (I) can be prepared by the methods given below, by the methods given in the experimental part below or by analogous methods. Optimum reaction conditions may vary with the particular reactants or solvents used, but such conditions can be determined by a person skilled in the art by routine optimisation procedures. In the schemes below, the generic groups $Ar^1$, $Ar^2$, $R^1$, $R^2$, $R^3$, $R^{Ar1}$, $R^{N1}$, $R^{N2}$ are as defined for the compounds of formula (I). In some instances the generic groups $Ar^1$, $Ar^2$, $R^1$, $R^2$, $R^3$, $R^{Ar1}$, $R^{N1}$, $R^{N2}$ may be incompatible with the assembly illustrated in the schemes, or will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. The compounds obtained may also be converted into salts, especially pharmaceutically acceptable salts in a manner known per se.

Compounds of formula (I) of the present invention can be prepared according to the general sequence of reactions outlined below.

Compounds of formula (I) are prepared by reaction of an acid of Structure 1 ($L^1$=OH), or a salt such as a sodium or lithium salt thereof, with an amine of Structure 2 in the presence of an amide-coupling reagent such as TBTU, HATU, COMU, EDC, DCC, $T_3P$ or PyBOP and a base like DIPEA or TEA in a solvent such as DCM, MeCN or DMF.

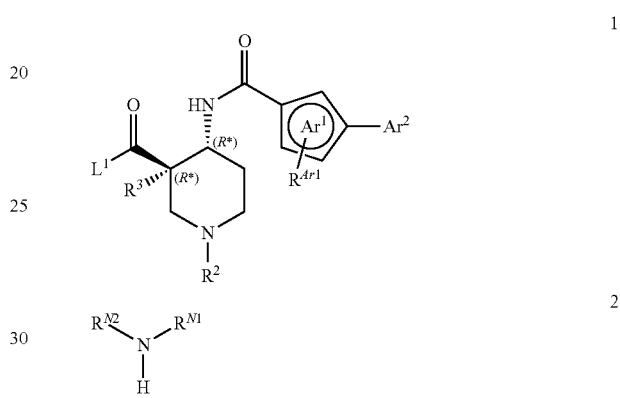

Compounds of Structure 1 may be prepared by one of the synthetic pathways described below.

Compounds of Structure 1 may be prepared by the procedure illustrated in Reaction Scheme A. A commercially available alkyl (3R*,4R*)-4-((tert-butoxycarbonyl)amino)piperidine-3-carboxylate A-1 ($R^5$=alkyl) is N-alkylated by treatment with an aldehyde or a ketone in the presence of a reductive reagent like $NaBH_4$, $NaBH_3CN$, $NaBH(OAc)_3$ in a solvent like DCM, MeOH, THF; or in the presence of a titanium salt like $TiCl_4$ or tetraisopropyl-orthotitanate, to give the tertiary amine A-2. The intermediate A-2 is Boc-deprotected by treatment with an acid, preferentially 4M HCl in dioxane or TFA in DCM, to give the corresponding amine A-3. The amine A-3 can be acylated by reaction with an acid A-4 in the presence of an amide-coupling reagent such as TBTU, HATU, COMU, EDC, DCC, $T_3P$ or PyBOP and a base like DIPEA or TEA in a solvent such as DCM, MeCN or DMF. Hydrolysis of the ester A-5 by treatment with a base like NaOH or LiOH in a solvent like methanol, ethanol or water/THF at temperature between RT and 60° C. gives the corresponding acid of Structure 1.

Reaction Scheme A

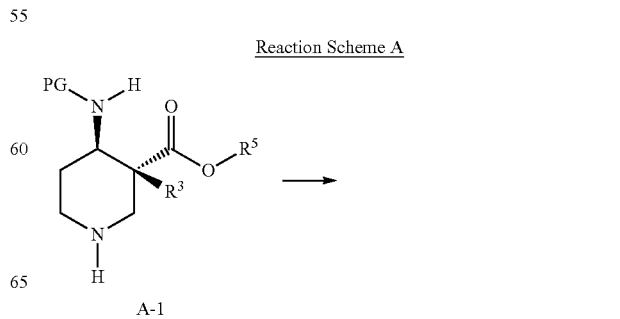

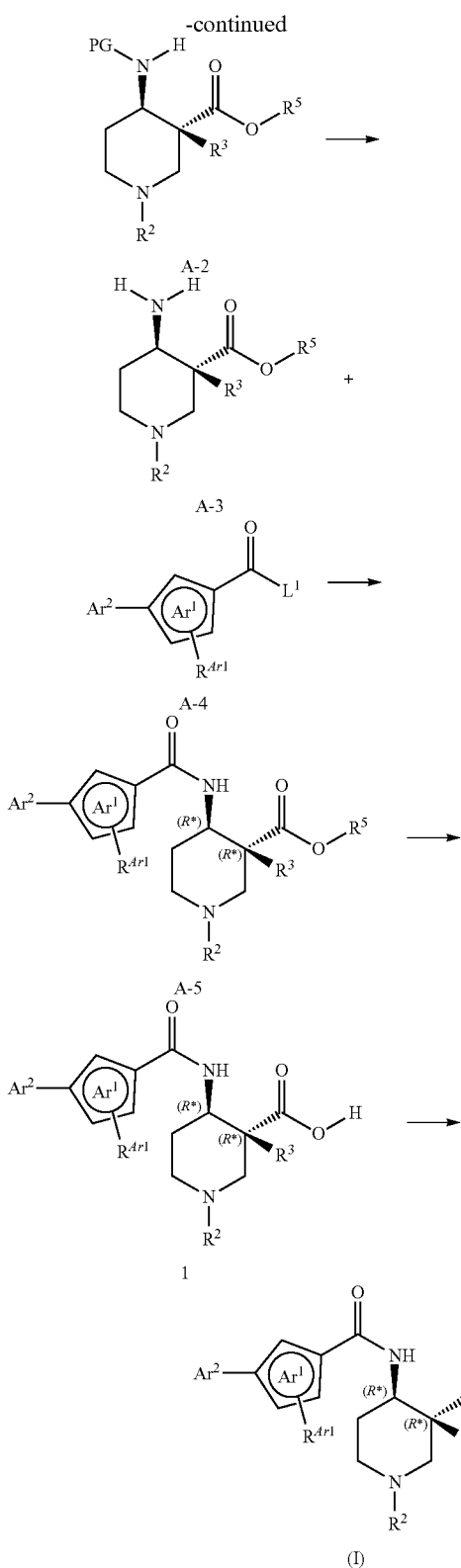

and a base like DIPEA or TEA in a solvent such as DCM, MeCN or DMF; or the corresponding acyl chloride (L¹=Cl) and a base like DIPEA or TEA in a solvent like DCM gives the corresponding amide B-2. The N-benzyl protective group is removed by catalytic hydrogenation in the presence of Pd on charcoal in a solvent like AcOEt preferably at atmospheric pressure of hydrogen, in the presence of di-tert-butyl dicarbonate in order to obtain the Boc-N-protected derivative B-3. Hydrolysis of the ester group of B-3 by treatment with a base like NaOH or LiOH in a solvent like methanol, ethanol or water/THF at temperature between RT and 60° C. gives the corresponding acid B-4. 3-Piperidine carboxamides of type B-5 are obtained by amidation of B-4 with an amine of Structure 2 in the presence of an amide-coupling reagent such as TBTU, HATU, COMU, EDC, DCC, T₃P or PyBOP and a base like DIPEA or TEA in a solvent such as DCM, MeCN or DMF. The carbamate B-5 is Boc-deprotected as described before to give the piperidine B-6. N-alkylation of B-6 by treatment with an aldehyde or a ketone in the presence of a reductive reagent like NaBH₄, NaBH₃CN, NaBH(OAc)₃ in a solvent like DCM, MeOH, THF, DMF; and in the case of $R^{3a}$=alkyl, in the presence of a titanium salt like TiCl₄ or tetraisopropyl-orthotitanate, to give compounds of formula (I). Alternatively compounds of formula (I) can be prepared by alkylation of intermediate B-6 with an alkyl halogenide or alkyl sulfonate in the presence of a base like DIPEA, TEA, or K₂CO₃ in a solvent like DMF, MeCN or EtOH. In the case where R² represents $(C_{1-6})$alkyl or a $(C_{3-8})$cycloalkyl which is mono-substituted with an hydroxyl group, compounds of formula (I) can be obtained by condensation of an amine of Structure B-6 and a mono or disubstituted epoxide in a polar aprotic solvent like MeCN in the presence of calcium trifluoromethane-sulfonate at RT or in water at temperature between RT and refluxing temperature.

Reaction Scheme B

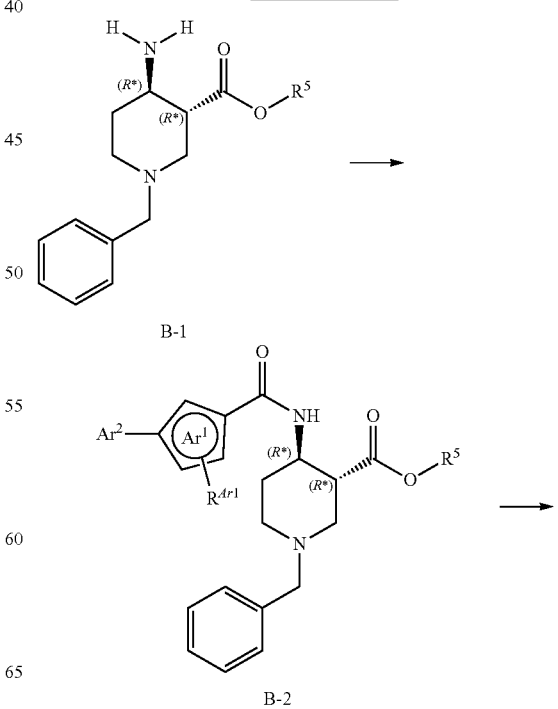

Compounds of formula (I) may alternatively be prepared as illustrated in Reaction Scheme B. Amidation of the commercially available alkyl (3R*,4R*)-4-amino-1-benzylpiperidine-3-carbon/late B-1 with an acid of Structure A-4 (L¹=OH) in the presence of an amide-coupling reagent such as TBTU, HATU, COMU, EDC, DCC, T₃P or PyBOP

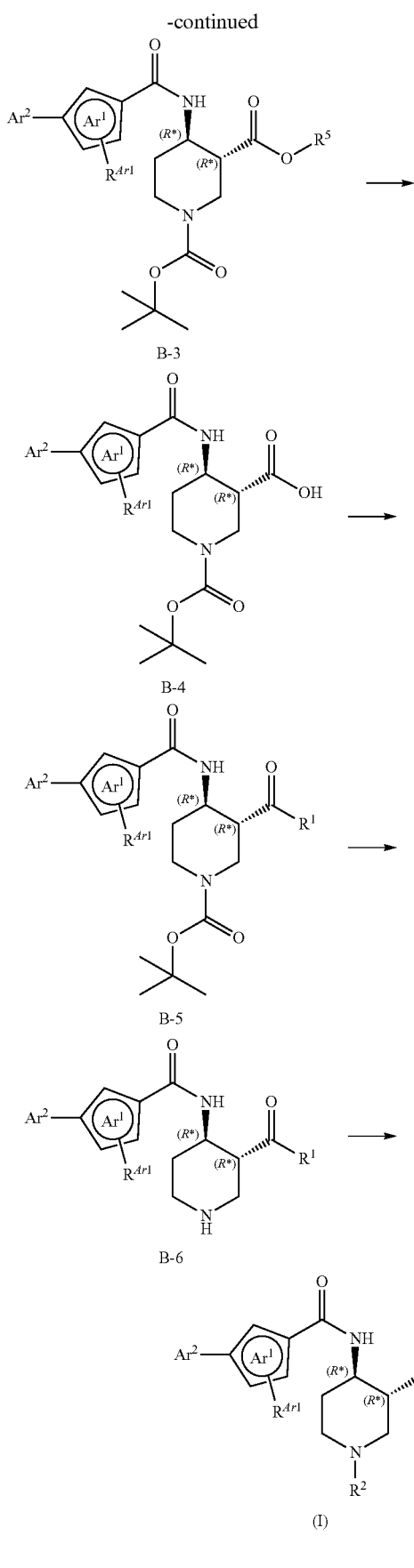

Compounds of formula (I) may alternatively be prepared as illustrated in Reaction Scheme C. A commercially available alkyl (3R*,4R*)-4-((tert-butoxycarbonyl)amino)piperidine-3-carboxylate A-1 ($R^5$=alkyl) is N-alkylated by treatment with an aldehyde or a ketone as described for B-6 before to give the tertiary amine A-2. The N-substituted alkyl (3R*,4R*)-4-((tert-butoxycarbonyl)amino)piperidine-3-carboxylate A-2 can be hydrolysed to the acid C-1 by treatment with a base like NaOH or LiOH in a solvent like methanol, ethanol or a mixture water/THF at temperature between RT and 60° C. Piperidinyl carboxamide C-2 are prepared by condensation of an amine of Structure 2 in the presence of an amide-coupling reagent such as TBTU, HATU, COMU, EDC, DCC, $T_3P$ or PyBOP and a base like DIPEA or TEA in a solvent such as DCM, MeCN or DMF. The intermediate C-2 is Boc-deprotected as described before to give the corresponding amine C-3. Acylation of 4-amino-3-carboxamide C-3 may be achieved by treatment of the in situ prepared 4-dimethylaluminum amide resulting from the reaction of a trialkyl aluminium compound like trimethyl aluminium with C-3 in a solvent like toluene, DCM or DCE at temperatures between RT and reflux followed by condensation with an ester or a carboxylic acid A-4 (L1=O-alkyl or OH) to give compound of formula (I).

Reaction Scheme C

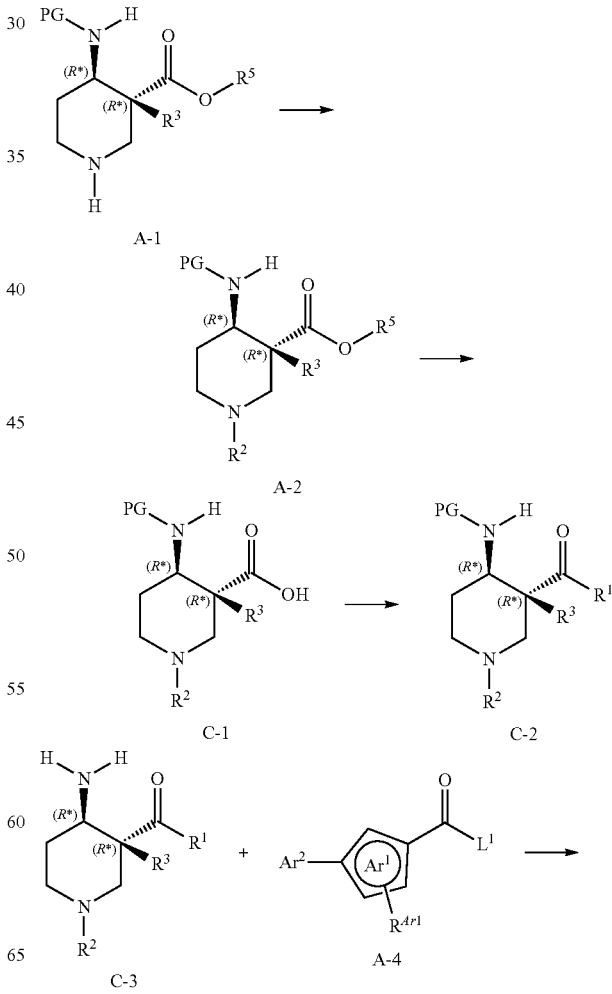

-continued

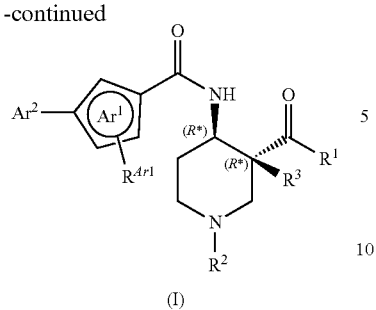
(I)

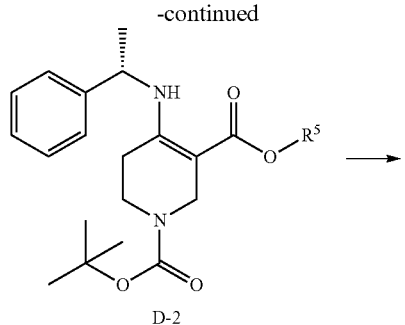
D-2

For the synthesis of [S,S] 3,4-disubstituted piperidines the sequence shown in Scheme D can be used, following the procedure described by S. Gellman et al. Eur. J. Org. Chem. 2003, 721. The enamine D-2 of the N-Boc protected 4-ketopiperidine D-1 can be prepared by heating with (S)-(−)-α-methyl benzylamine in toluene in presence of a catalytic amount of an acid, like p-toluenesulfonic acid with Dean-Stark trapping. Reduction of the enamine D-2 with a reducing agent like sodium triisobutyroxyborohydride, sodium trifluroacetoxyborohydride or with sodium triacetoxyborohydride in toluene, THF or dioxane at temperatures between −78° C. and RT gives predominantly the cis-amino ester D-3. Epimerization to the trans-amino ester D-4 can be done by treatment with a base like sodium ethoxyde, sodium methoxyde or potassium t-butoxyde in a solvent like EtOH, MeOH, t-BuOH in the presence of ethylacetate, methylacetate or t-butylacetate at temperature between 0° C. and reflux. Hydrogenolysis of the benzyl group by catalytic hydrogenation in the presence of Pd on charcoal or Pd hydroxide in a solvent like AcOEt, EtOH or MeOH, preferably at atmospheric pressure of hydrogen, gives the trans-amino ester D-5. Amidation with an acid of Structure A-4 (L$^1$=OH) in the presence of an amide-coupling reagent such as TBTU, HATU, COMU, EDC, DCC, T$_3$P or PyBOP and a base like DIPEA or TEA in a solvent such as DCM, MeCN or DMF; or the corresponding acyl chloride (L$^1$=Cl) and a base like DIPEA or TEA in a solvent like DCM gives the corresponding amide D-6. The [S,S] trans-amido ester D-6, which corresponds to the intermediate B-3 in Scheme B, can be transformed into the final compound of formula (I) by following the sequence ester hydrolysis, amide formation, cleavage of the Boc group and N-alkylation as described in scheme B. The same sequence can be used for the synthesis of [R,R] 3,4-disubstituted piperidines by starting with (R)-(+)-α-methyl benzylamine as a chiral auxiliary.

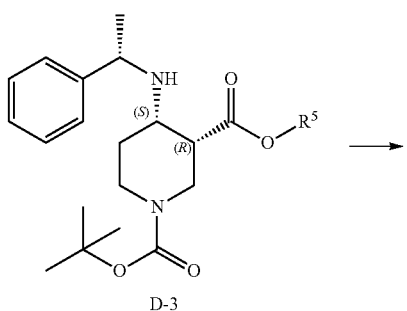
D-3

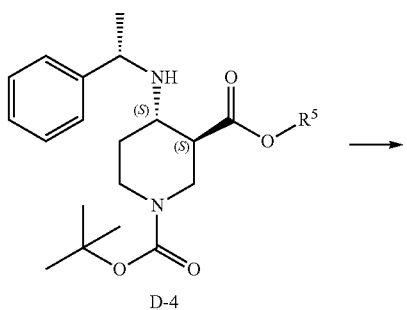
D-4

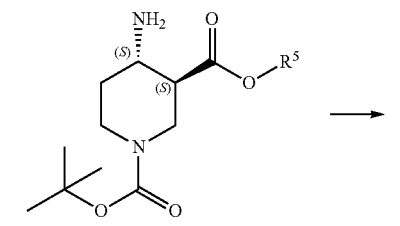
D-5

Reaction Scheme D

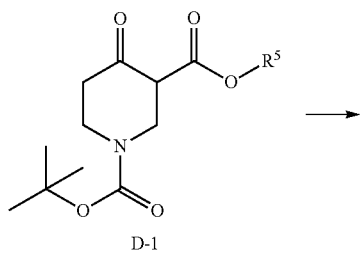
D-1

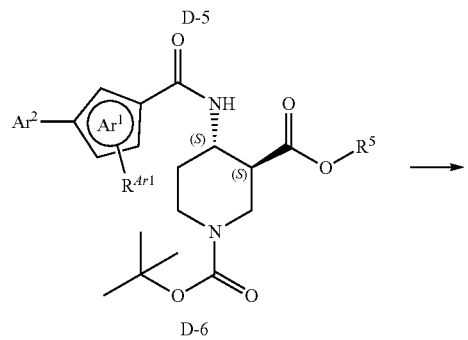
D-6

101

-continued

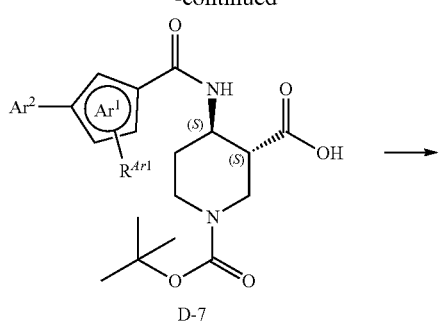

D-7

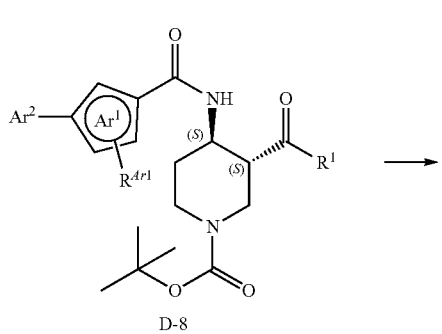

D-8

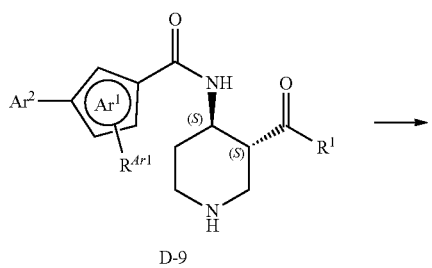

D-9

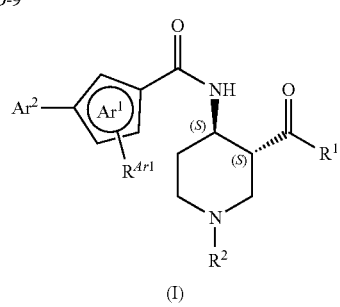

(I)

Alternatively [S,S] 3,4-disubstituted piperidines may be prepared as illustrated in Reaction Scheme E by changing the sequence of reactions shown in Scheme D. The predominantly cis-amino ester D-3 can be prepared as described before. Hydrogenolysis of the benzyl group as described before gives the predominantly cis-amino ester E-4. Amidation with an acid of Structure A-4 ($L^1$=OH) or the corresponding acyl chloride ($L^1$=Cl), using the conditions described before gives the corresponding predominantly cis amido ester E-5. Epimerization to the trans-amido ester B-3 can be done using the conditions described before. The trans-amido ester B-3 can be transformed into the final compound of formula (I) as described in scheme B. The same sequence can be used for the synthesis of [R,R] 3,4-disubstituted piperidines by starting with (R)-(+)-α-methyl benzylamine as a chiral auxiliary.

102

Reaction Scheme E

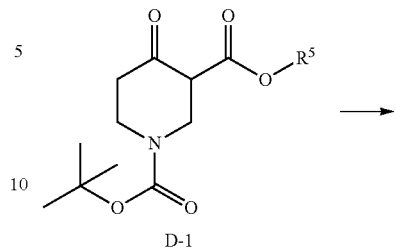

D-1

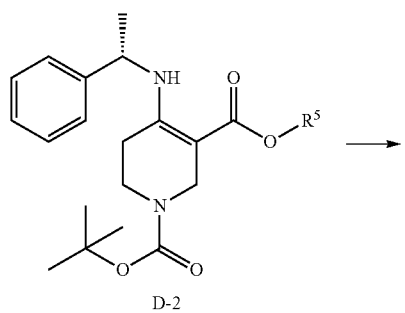

D-2

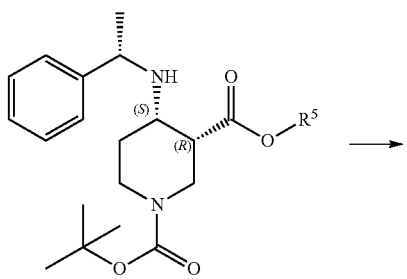

D-3

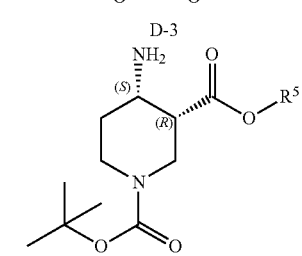

E-4

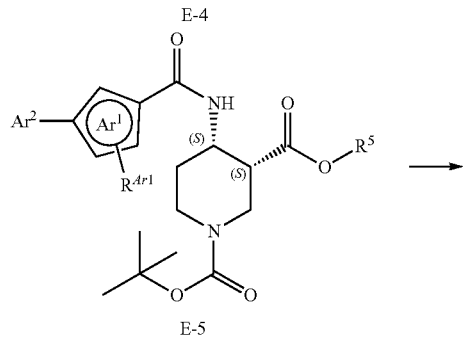

E-5

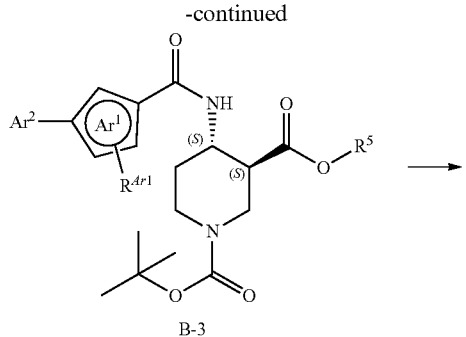

B-3

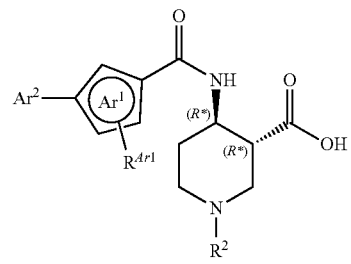

1

Compounds of Structure 1 may alternatively be prepared from the trans amido ester B-3. The intermediate B-3 is Boc-deprotected as described before to give the corresponding amine F-1 which is N-alkylated as described before for A-2, to give the N-alkyl piperidine F-2. The N-substituted alkyl (3R*,4R*)-4-amido-piperidine-3-carboxylate ester F-2 can be hydrolysed to the acid 1 by treatment with a base as described for C-1 before.

Compounds of formula (I) may alternatively be prepared as illustrated in Reaction Scheme G. A commercially available alkyl 4-((tert-butoxycarbonyl)amino)piperidine-3-carboxylate G-1 is C-alkylated at position 3 by treatment with an alkyl halogenide in the presence of a base like potassium carbonate in a solvent like acetone at temperature between 0° C. and reflux to give the keto ester G-2. The enamine G-3 can be prepared as described before. Reduction of the enamine G-3 as described before gives the trans-amino ester G-4. Hydrogenolysis of the benzyl group as described before gives the trans-amino ester G-5. Amidation with an acid of Structure A-4 ($L^1$=OH); or the corresponding acyl chloride ($L^1$=Cl), as described before gives the corresponding amide G-6, which can be transformed into the final compound of formula (I) by following the sequence described in scheme B. The ester G-6 is saponified into the acid G-7 which is condensed with an amine 2. The resulting bis amide G-8 can be deprotected to give the piperidine G-9 which is finally N-alkylated to give the compound of formula (I).

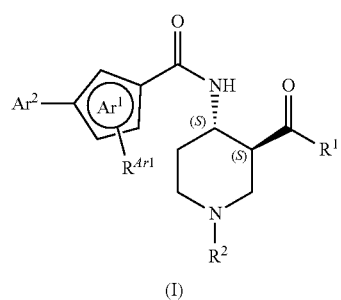

(I)

Reaction Scheme F

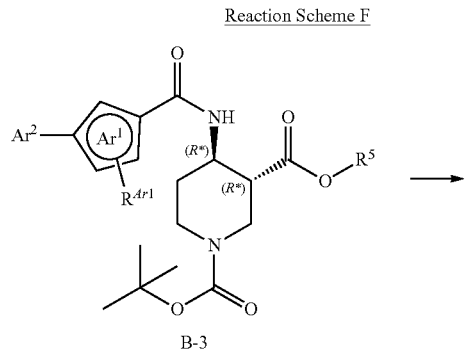

Reaction Scheme G

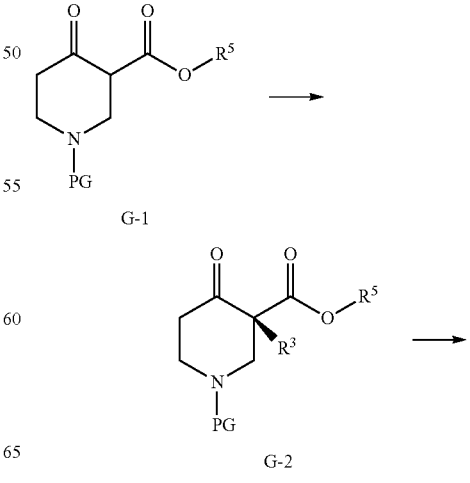

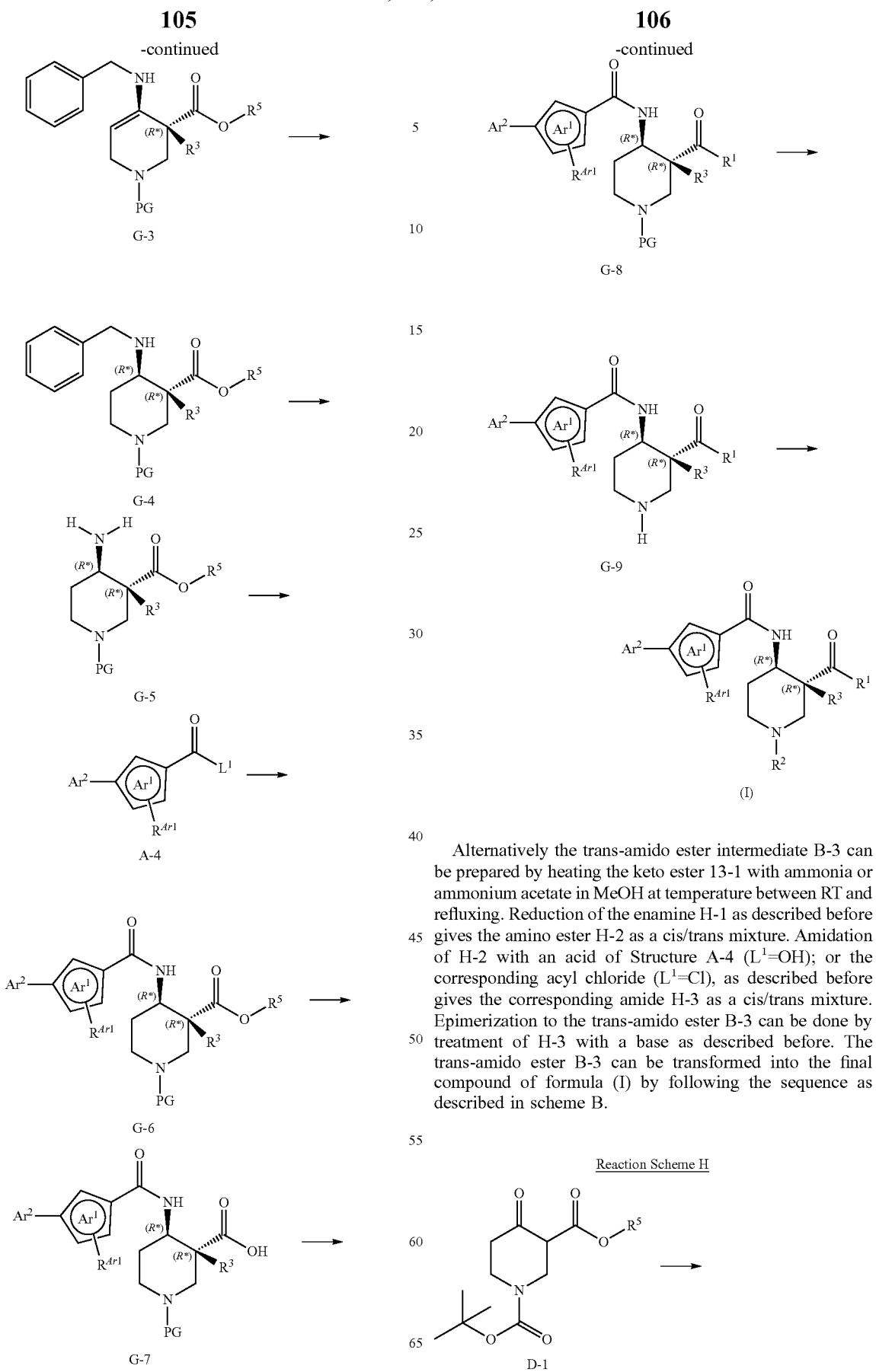

Alternatively the trans-amido ester intermediate B-3 can be prepared by heating the keto ester 13-1 with ammonia or ammonium acetate in MeOH at temperature between RT and refluxing. Reduction of the enamine H-1 as described before gives the amino ester H-2 as a cis/trans mixture. Amidation of H-2 with an acid of Structure A-4 ($L^1$=OH); or the corresponding acyl chloride ($L^1$=Cl), as described before gives the corresponding amide H-3 as a cis/trans mixture. Epimerization to the trans-amido ester B-3 can be done by treatment of H-3 with a base as described before. The trans-amido ester B-3 can be transformed into the final compound of formula (I) by following the sequence as described in scheme B.

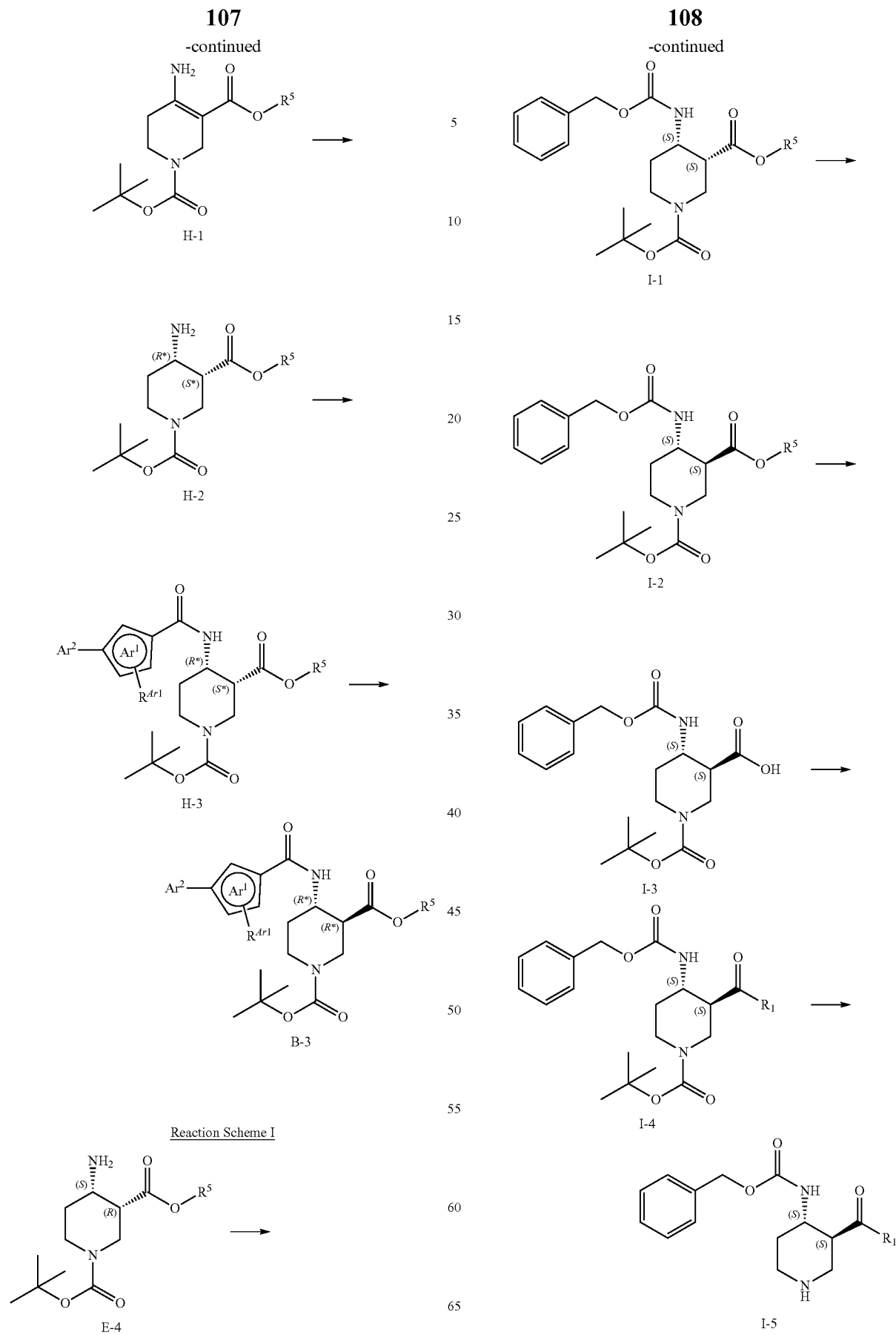

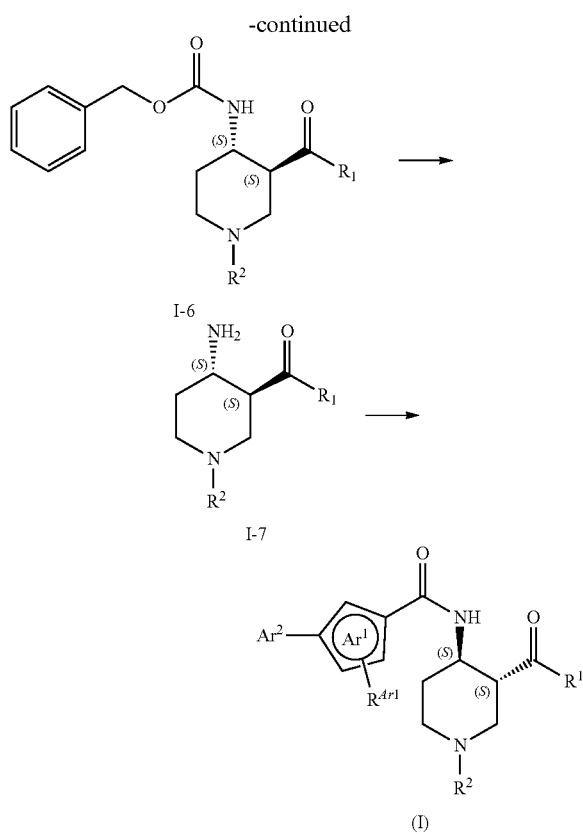

Alternatively [S,S] 3,4-disubstituted piperidines may be prepared as illustrated in Reaction Scheme I. The cis-amino ester E-4 can be transformed into the corresponding cis 4-benzylcarbamate derivative 1-1 by treatment with N-(benzyloxycarbonyloxy) succinimide in THF or DCM. Epimerization to the trans-amido ester 1-2 can be done using the conditions described before. 1-2 can be transformed into the intermediate 1-6 by following the sequence ester hydrolysis, amide formation, cleavage of the Boc group and N-alkylation as described in scheme B. The benzylcarbamate protecting group is removed by catalytic hydrogenation in the presence of Pd on charcoal or Pd hydroxide in a solvent like AcOEt, EtOH or MeOH, preferably at atmospheric pressure of hydrogen, to yield the 4-trans-amino-3-carboxamide I-7. Amidation of 1-7 with an acid of Structure A-4 ($L^1$=OH) or the corresponding acyl chloride ($L^1$=Cl), using the conditions described before gives the final compound of formula (I) as described in scheme B. The same sequence can be used for the synthesis of [R,R] 3,4-disubstituted piperidines by starting with (R)-(+)-α-methyl benzylamine as a chiral auxiliary.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm), IA, IB, IC, IE, or IF (5 μm) or AD-H (5 μm) column. Typical conditions of chiral HPLC are an isocratic mixture of eluent A (EtOH, in presence or absence of an amine such as triethylamine or diethylamine) and eluent B (heptane), at a flow rate of 0.8 to 150 mL/min.

The following examples are provided to illustrate the invention. These examples are illustrative only and should not be construed as limiting the invention in any way.

EXPERIMENTAL PART

I. Chemistry

All temperatures are stated in ° C. Commercially available starting materials were used as received without further purification. Unless otherwise specified, all reactions were carried out in oven-dried glassware under an atmosphere of nitrogen or argon. Compounds were purified by flash column chromatography on silica gel or by preparative HPLC. Compounds described in the invention are characterised by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.

NMR Spectroscopy

Bruker Avance II spectrometer equipped with a 400 MHz ($^1$H) Ultrashield™ Magnet and a BBO 5 mm probehead or a PAXTI 1 mm probehead, or a Bruker Avance III HD Ascend 500 MHz ('H), magnet equipped with DCH cryoprobe. Chemical shifts (δ) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm. The abbreviations s, d, t, q and m refer to singlet, doublet, triplet, quartet, multiplet and br to broad, respectively. Coupling constants J are reported in Hz. In case NMR spectra are measured using 1 mm Microprobe® tubes and a PAXTI 1 mm probehead, the compounds are dissolved in non-deuterated DMSO. The spectra are then measured with double irradiation for suppression of the DMSO and $H_2O$ peaks. In that case only a selection of representative NMR peaks of the compound is given.

Quality Control (QC) Analytical LC-MS:
Equipment and Conditions:

Pump: Waters Acquity Binary, Solvent Manager, MS: Waters SQ Detector, DAD: Acquity UPLC PDA Detector, ELSD: Acquity UPLC ELSD. Columns: Acquity UPLC CSH C18 1.7 μm 2.1×50 mm or Acquity UPLC HSS T3 C18 1.8 μm 2.1×50 mm from Waters, thermostated in the Acquity UPLC Column Manager at 60° C. Eluents: A1: H2O+0.05% FA; B1: AcCN+0.045% FA. Method: Gradient: 2% B 98% B over 2.0 min. Flow: 1.0 mL/min. Detection: UV 214 nm and ELSD, and MS, tR is given in min.

Analytical LC-MS
Equipment:

Binary gradient pump Agilent G4220A or equivalent with mass spectrometry detection (single quadrupole mass analyser, Thermo Finnigan MSQPlus or equivalent)

Conditions:

Method A (acidic conditions): Column: Zorbax SB-aq (3.5 μm, 4.6×50 mm); conditions: MeCN [eluent A]; water+ 0.04% TFA [eluent B]; gradient: 95% B→5% B over 1.5 min (flow: 4.5 mL/min). Detection: UV/Vis+MS.

Method B (acidic conditions): Column: Waters XBridge C18 (2.5 μm, 4.6×30 mm); conditions: MeCN [eluent A]; water+0.04% TFA [eluent B]; gradient: 95% B→5% B over 1.5 min (flow: 4.5 mL/min). Detection: UV/Vis+MS.

Method C (acidic conditions): Column: Waters BEH C18 (2.5 μm, 3.0×50 mm); conditions: MeCN [eluent A]; water+ 0.04% TFA [eluent B]; gradient: 95% B→5% B over 1.5 min (flow: 4.5 mL/min). Detection: UV/Vis+MS.

Method D (basic conditions): Column: Waters BEH C18 (2.5 μm, 3.0×50 mm); conditions: MeCN [eluent A]; H$_2$O+ 0.05% NH$_4$OH [eluent B]; gradient: 95% B→5% B over 1.9 min (flow 1.6 mL/min), Detection: UV/Vis+MS.

Preparative LC-MS

Equipment:

Binary gradient pump Gilson 333/334 or equivalent with mass spectrometry detection (single quadrupole mass analyser, Thermo Finnigan MSQPlus or equivalent)

Conditions:

Method E (basic conditions): Column: Waters XBridge C18 (10 μm, 30×75 mm); conditions: MeCN [eluent A]; water+0.5% NH$_4$OH (25% aq.) [eluent B]; gradient: 95% B→5% B, over 6.5 min (flow: 75 mL/min). Detection: UV/Vis+MS Method F (acidic conditions): column: Waters XBridge C18 (10 μm, 30×75 mm); conditions: MeCN [eluent A]; water+0.5% formic acid [eluent B]; gradient: 95% B→5% B, over 6.5 min (flow: 75 mL/min). Detection: UV/Vis+MS Chiral Analytical Chromatography Equipment:

HPLC: Dionex HPG-3200SD pump with a Dionex DAD-3000 UV detector.

SFC: CO$_2$ supply: Aurora Fusion A5 Evolution; pump: Agilent G4302A; UV detector: Agilent G1315C.

Conditions:

HPLC: Columns: ChiralPak AY-H, 5 μm, 250×4.6 mm or Regis (R,R) Whelk-01 250×4.6 mm, 5 μm; eluent: A: Hept, 0.05% DEA, B: Ethanol, 0.05% DEA, flow 0.8 to 1.2 mL/min.

SFC Column: Regis (R,R) Whelk-01, 4.6×250 mm, 5 μM; eluent: A: 60% CO$_2$, B: 40% DCM/EtOH/DEA 50:50:0.1

Chiral Preparative Chromatography

Equipment:

HPLC: 2 Varian SD1 pump with a Dionex DAD-3000 UV detector.

SFC: CO$_2$ supply: Maximator DLE15-GG-C; pumps: 2 SSI HF CP 300; UV detector: Dionex DAD-3000.

Conditions:

HPLC: Columns: ChiralPak IA, IB, IC, IE, or IF, 5 μm, 20×250 mm, or Regis (R,R) Whelk-01, 21.1×250 mm, 5 μm; eluent: appropriate mixture of A (0% to 90% Hept) and B (10% to 100% EtOH, 0.1% DEA), flow: appropriate flow of 16, 23 or 34 mL/min.

SFC: Columns: Regis (R,R) Whelk-01, 30×250 mm, 5 μm or ChiralPak IC, 30×250 mm, 5 μm; eluent: appropriate mixture of A (60% to 70% CO$_2$), and B (30% to 40% of DCM/EtOH/DEA 50:50:0.1), flow 160 mL/min.

Abbreviations (as Used Hereinbefore or Hereinafter)

aq. aqueous
atm atmosphere
BSA bovine serum albumin
Boc butyloxycarbonyl
BB building-block
CDI carbonyl diimidazole
COMU 1-Cyano-2-ethoxy-2-oxoethylidenaminooxy)dimethylamino-morpholino-carbenium hexafluorophosphate
d days
dba dibenzylidene acetone
DCC dicyclohexyl carbodiimide
DCM dichloromethane
DEA diethylamine
DIPEA diisopropyl-ethylamine, Hunig's base, ethyl-diisopropylamine
DMAP 4-dimethylaminopyridine
DMF dimethylformamide
DMSO dimethylsulfoxide
EDC N-(3-dimethylaminopropyl)-N'-ethyl-carbodiimide
eq. equivalent(s)
Et ethyl
EtOAc ethyl acetate
EtOH ethanol
Ex. example(s)
h hour(s)
HATU 2-(7-Aza-1H-benzotriazole-1-yl)-1,1,3,3-tetramethyluronium hexafluorophosphate
HBTU 0-(benzotriazol-1-yl)-N,N,N',N'-tetramethyluronium hexafluorophosphate
Hept heptane
HOBt 1-hydroxybenzotriazole
HOAT 7-Aza-1-hydroxybenzotriazole
HPLC high performance liquid chromatography
HV high vacuum conditions
$^i$Bu isobutyl
$^i$Pr isopropyl
KO$^t$Bu potassium tert-butoxide
LC-MS liquid chromatography mass spectrometry
LiHMDS Lithium bis(trimethylsilyl)amide
Lit. Literature
Me methyl
MeCN acetonitrile
MeOH methanol
mL milliliter
MTBE methyl-tert-butyl ether
min minute(s)
Nr number
NaOAc sodium acetate
NBS N-Bromosuccinimide
NMP N-methylpyrrolidone
$^n$Pr n-propyl
OAc acetate
Ph phenyl
PPh$_3$ triphenyl phosphine
POCl$_3$ Phosphorus (V) oxychloride
prep. Preparative
PyBOP benzotriazol-1-yl-oxy-tris-pyrrolidino-phosphonium-hexafluoro-phosphate
rac racemic
RT room temperature
s second(s)
sat. Saturated
Selectfluor® 1-Chloromethyl-4-fluoro-1,4-diazoniabicyclo[2.2.2]octane bis(tetrafluoroborate)
SFC: supercritical fluid chromatography
soln. solution
tBu tert-butyl=tertiary butyl
TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
T$_3$P Propylphosphonic anhydride
t$_R$ retention time Preparation of Esters and Carboxylic Acids of Structure A-4 Used for the Synthesis of Building-Blocks 1.07 to 1.17 and Examples 3.001 to 3.022

A-4.01:
5-(2,4,6-Trifluoro-phenyl)-isoxazole-3-carboxylic Acid

A-4.01a:
5-(2,4,6-Trifluoro-phenyl)-isoxazole-3-carboxylic Acid Ethyl Ester

The title compound A-4.01a is prepared in analogy to the procedure described in *Eur. J. Org. Chem.* 2006, 4852-4860, by stirring a solution of ethyl nitroacetate (1.36 mL, 12 mmol), 2-ethynyl-1,3,5-trifluorobenzene (312 mg, 2 mmol) and 1,4-diazabicyclo[2.2.2]octane (0.156 mL, 1.4 mmol) in NMP (1.2 mL), at 65° C. overnight. The solvent is evaporated and the product used in the next step without further purification, LC-MS method A: $t_R$=1.07 min.

A-4.01:
5-(2,4,6-Trifluoro-phenyl)-isoxazole-3-carboxylic Acid

To a solution of ester A-4.01a (542 mg, 2 mmol) in THF (4 mL) is added LiOH.H$_2$O (12 mmol) dissolved in 10 mL water. After stirring for 64 h, a 4M solution HCl (10 mmol) is added, followed by water (1.5 mL). The precipitated product is filtered, washed with water (2×2.5 mL) and DCM (2×2.5 mL) and dried under HV. The title compound is obtained as a white powder, LC-MS method A: $t_R$=0.83 min; [M+H]$^+$=407.05; $^1$H NMR (400 MHz, DMSO) δ: 14.3 (bs, 1H), 7.54 (t, J=9.3 Hz, 2H), 7.19 (s, 1H).

A-4.02: 5-(2-Chloro-4-fluoro-phenyl)-isoxazole-3-carboxylic Acid

A-4.02a: 5-(2-Chloro-4-fluoro-phenyl)-isoxazole-3-carboxylic Acid Ethyl Ester

The title compound is prepared according to the procedure A-4.01a, starting from 2-chloro-1-ethynyl-4-fluoro-benzene; LC-MS method A: $t_R$=1.15 min.

A-4.02: 5-(2-Chloro-4-fluoro-phenyl)-isoxazole-3-carboxylic Acid

The title compound is prepared according to the procedure A-4.01b, starting from ester A-4.02a; LC-MS method A: $t_R$=0.9 min; 1H NMR (500 MHz, DMSO) δ: 8.00 (m, 1H), 7.73 (m, 1H), 7.45 (m, 1H), 7.14 (s, 1H).

A-4.03: 5-(4-Chloro-2-fluoro-phenyl)-isoxazole-3-carboxylic Acid

A-4.03a: 5-(4-Chloro-2-fluoro-phenyl)-isoxazole-3-carboxylic Acid Ethyl Ester

The title compound is prepared according to the procedure A-4.01a, starting from 4-chloro-1-ethynyl-2-fluoro-benzene; LC-MS method A: $t_R$=1.18 min.

A-4.03: 5-(4-Chloro-2-fluoro-phenyl)-isoxazole-3-carboxylic Acid

The title compound is prepared according to the procedure A-4.01b, starting from ester A-4.03a; LC-MS method D: $t_R$=0.93 min; $^1$H NMR (500 MHz, DMSO) δ: 8.03 (m, 1H), 7.77 (m, 1H), 7.52-7.54 (m, 1H), 7.18-7.19 (m, 1H).

A-4.04:
5-(2,6-Difluoro-phenyl)-isoxazole-3-carboxylic Acid

A-4.04a:
5-(2,6-Difluoro-phenyl)-isoxazole-3-carboxylic Acid Ethyl Ester

The title compound is prepared according to the procedure A-4.01a, starting from 2-ethynyl-1,3-difluorobenzene; LC-MS method A: $t_R$=1.06 min.

A-4.04:
5-(2,6-Difluoro-phenyl)-isoxazole-3-carboxylic Acid

The title compound is prepared according to the procedure A-4.01b, starting from ester A-4.04a; LC-MS method A: $t_R$=0.84 min; $^1$H NMR (500 MHz, DMSO) δ: 7.65 (m, 1H), 7.35 (m, 2H), 6.91 (s, 1H).

A-4.05: 3-(2,4-Difluoro-phenyl)-[1,2,4]oxadiazole-5-carboxylic Acid Ethyl Ester

The title compound is prepared in analogy to the procedure described in *ChemMedChem* 2012, 7, 1020-1030. To a solution of 2,4-difluorobenzamidoxime (344 mg, 2 mmol) dissolved in THF (5 mL) is added ethyl 2-chloro-2-oxoacetate (0.279 mL, 2.5 mmol), followed by DIPEA (0.437 mL, 2.5 mmol). The reaction mixture is stirred at 75° C. for 3 h. The mixture is then quenched with water (25 mL) and extracted with EtOAc (25 mL). The organic layer is dried over MgSO$_4$, filtered and concentrated under reduced pressure to give the desired product as a yellow solid. LC-MS method C: $t_R$=1.01 min. 1H NMR (400 MHz, DMSO) δ: 8.15 (m, 1H), 7.62 (m, 1H), 7.37 (m, 1H), 4.49 (q, J=7.1 Hz, 2H), 1.39 (t, J=7.2 Hz, 3H).

A-4.06:
5-(2,4-Difluoro-phenyl)-oxazole-2-carboxylic Acid Lithium Salt

The title compound is prepared in analogy to the procedure described in *ChemMedChem* 2012, 7, 1020-1030.

A-4.06a: Ethyl 2-((2-(2,4-difluorophenyl)-2-oxo-ethyl)amino)-2-oxoacetate

To a solution of 2,4-difluorophenacylamine hydrochloride (415 mg, 2 mmol) in DCM (8 mL) and TEA (0.591 mL, 4.2 mmol), cooled to 0° C., is added ethyl chlorooxoacetate (0.226 mL, 2.02 mmol). The reaction mixture is stirred 1 h30 at 0° C. and then quenched with water (10 mL), extracted twice with DCM (2×10 mL). The combined organic layers are dried over MgSO$_4$, and the solvent is evaporated to give the title compound as a brown oil. LC-MS method C: $t_R$=0.82 min; [M+H]$^+$=272.20.

A-4.06b:
5-(2,4-Difluoro-phenyl)-oxazole-2-carboxylic Acid Ethyl Ester

POCl$_3$ (0.52 mL, 5.58 mmol) is added dropwise to a solution of A-4.06a (480 mg, 1.77 mmol), dissolved in toluene (5 mL). The mixture is stirred overnight at 110° C. After cooling the solution to 0° C., it is quenched by dropwise addition of water (2 mL) and then it is neutralized with sat. aq. NaHCO$_3$ and extracted with DCM (20 mL). The organic layer is evaporated and the product is purified by prep. LC-MS method F. LC-MS method D: $t_R$=1.01 min; [M+H]$^+$=253.98.

A-4.06:
5-(2,4-Difluoro-phenyl)-oxazole-2-carboxylic Acid Lithium Salt

To a solution of ester A-4.06b (574 mg, 2.13 mmol) in THF (10 mL) is added 1 M LiOH aq. sol. (6.4 mL, mg, 6.4 mmol). After stirring for 1 hour, the solvents are evaporated under reduced pressure to give the title compound as a beige powder, LC-MS method D: $t_R$=0.65 min; [M+H]$^+$=226.30.

A-4.07: 5-(2,4-Difluoro-phenyl)-[1,3,4]oxadiazole-2-carboxylic Acid Lithium Salt A-4.07a: 5-(2,4-Difluoro-phenyl)-[1,3,4]oxadiazole-2-carboxylic Acid Ethyl Ester The title compound is prepared in analogy to the procedure described in *ChemMedChem* 2012, 7, 1020-1030.

To a solution of 2,4-difluorobenzoic acid hydrazide (2.65 g, 15.4 mmol) in 50 mL DCM is added TEA (9.67 mL, 69.4 mmol). The mixture is cooled to 0° C. and ethyl chlorooxoacetate (2.44 mL, 21.2 mmol) is added. The mixture is stirred 2 h at 0° C. Then, toluene-4-sulfonyl chloride (4.40 g, 23.1 mmol) is added and stirring is continued overnight at RT. A sat. aq. NaHCO$_3$ solution (50 mL) is added and the reaction mixture is extracted twice with DCM (2×50 mL). The combined organic layers are dried over MgSO$_4$, filtered and evaporated. The residue is purified by flash chromatography using a gradient of eluent heptane/AcOEt (9:1 to 4:1) to give a light yellow solid. LC-MS method A: $t_R$=0.80 min; [M+H]$^+$=255.13, [M+H+MeCN]$^+$=296.10.

A-4.07: 5-(2,4-Difluoro-phenyl)-[1,3,4]oxadiazole-2-carboxylic Acid Lithium Salt To a solution of ester A-4.07a (25.4 mg, 0.1 mmol) in THF (0.2 mL) is added LiOH hydrate (5 mg, 0.1 mmol) dissolved in water (0.2 mL). After stirring for 1 hour, the solvents are evaporated under reduced pressure to give the title compound as a white powder, LC-MS method D: $t_R$=0.41 min; $^1$H NMR (400 MHz, DMSO) δ: 8.07 (m, 1H), 7.58 (m, 1H), 7.34 (m, 1H).

A-4.08: 1-(2,4-Difluoro-phenyl)-1H-[1,2,3]triazole-4-carboxylic Acid

A-4.08a: 1-(2,4-Difluoro-phenyl)-1H-[1,2,3]triazole-4-carboxylic Acid Ethyl Ester To a solution of ethyl 2-diazo-3-oxopropanoate (obtained according to procedure described in *Journal of the American Chemical Society*, 2011, 133(4), 1044-1051) (1.6 g, 8.85 mmol) in EtOH (3.15 mL) is added glacial acetic acid (1.27 mL, 22.1 mmol) followed by 2,4-difluoroaniline (1.22 g, 9.47 mmol). After stirring overnight, the reaction mixture is concentrated and the residue is diluted with cold water (40 mL). The precipitate is filtered, washed with cold water (10 mL) and dried under HV to afford the title compound as a beige solid. LC-MS method A: $t_R$=0.8 min; [M+H]$^+$=254.12.

A-4.08: 1-(2,4-Difluoro-phenyl)-1H-[1,2,3]triazole-4-carboxylic Acid

To a solution of ester A-4.08a (1.93 g, 7.62 mmol) in THF (16 mL) is added LiOH hydrate (11.4 mmol) dissolved in water (16 mL). After stirring for 45 min, THF is evaporated and the aq. residue is cooled to 0° C. A 1M HCl solution is added until pH=2. The precipitated product is filtered, washed with water (15 mL), and dried under HV. The title compound is obtained as a beige powder, LC-MS method A: $t_R$=0.61 min; [M+H]$^+$=225.96, [M+H+MeCN]$^+$=267.10.

A-4.09: 5-(2,4-Difluoro-phenyl)-[1,2,4]oxadiazole-3-carboxylic Acid

A-4.09a: 5-(2,4-Difluoro-phenyl)-[1,2,4]oxadiazole-3-carboxylic Acid Ethyl Ester The title compound is prepared following a procedure analogous to that described in WO 2012/168315. Ethyl 2-amino(hydroxyimino)acetate (2.27 g, 16.7 mmol) dissolved in 2,6-dimethylpyridine (5.88 mL, 50 mmol) is treated dropwise with a solution of 2,4-difluorobenzoyl chloride (1.39 mL, 11.1 mmol) in DCM (30 mL). The reaction mixture is stirred overnight. The beige suspension is dissolved with DCM (150 mL) and washed with water (50 mL), then 1M HCl (50 mL) and brine (50 mL). The organic layer is dried over MgSO$_4$, filtered and the solvent evaporated. The intermediate white powder ethyl 2-(2,4-difluorobenzamido)-2-(hydroxyimino)acetate is then heated 1 h at 200° C. in a DrySyn metal block (from Asynt Ltd.). After cooling down, the title compound is purified by flash chromatography using a gradient of 2% to 20% EtOAc in n-heptane as eluent. LC-MS method A: $t_R$=0.85 min; [M+H]$^+$=255.02.

A-4.09: 5-(2,4-Difluoro-phenyl)-[1,2,4]oxadiazole-3-carboxylic Acid

To compound A-4.09a (3.84 g, 14.1 mmol) dissolved in THF (25 mL) and water (25 mL), is added LiOH.H$_2$O (799 mg, 19 mmol) and the mixture is stirred for 1 h. THF is evaporated and the aq. phase is diluted with water (50 mL), cooled to 0° C. and acidified to pH 2-3 with an aq. 1M HCl solution. The precipitated product is filtered, washed with water (20 mL) and dried under HV. LC-MS method A: $t_R$=0.57; 1H NMR (400 MHz, DMSO) δ: 8.27 (m, 1H), 7.67 (m, 1H), 7.41 (m, 1H).

A-4.10:
3-(2,4-Difluoro-phenyl)-isoxazole-5-carboxylic Acid

A-4.10a:
3-(2,4-Difluoro-phenyl)-isoxazole-5-carboxylic Acid Ethyl Ester

The title compound is prepared in analogy to the preparation described in *Bioorganic & Medicinal Chemistry Letters* 18 (2008), 4521-4524.

2,4-Difluorobenzaldehyde oxime (prepared according to procedure described in *Bioorganic & Medicinal Chemistry Letters*, 20 (2010), 1272-1277) (4.25 g, 24.4 mmol) is dissolved in THF (50 mL). Then pyridine (2.46 mL, 30.5 mmol) is added. The mixture is heated up to 60° C. and N-chlorosuccinimide (3.58 g, 26.8 mmol) is added. The reaction mixture is stirred at 60° C. for 45 min and then TEA (4.11 mL, 29.2 mmol) and ethyl propiolate (2.72 mL, 26.8 mmol) are added. The reaction mixture is stirred overnight at 60° C. and then concentrated under HV. The residue is taken up in DCM (100 ml) and diluted with aq. 1M HCl (100 mL). The separated organic phase is washed with water (100 mL). The organic phase is dried over MgSO$_4$, filtered and the solvent is evaporated under HV. The crude is purified by flash chromatography using n-Heptan/EtOAc 9/1 as eluent to yield the title compound. LC-MS method A: $t_R$=0.92 min.

A-4.10: 3-(2,4-Difluoro-phenyl)-isoxazole-5-carboxylic Acid

The title compound is prepared according to the procedure A-4.09, starting from building block A-4.10a. LC-MS method A: $t_R$=0.68 min. 1H NMR (400 MHz, DMSO) δ: 14.48 (bs, 1H), 7.99-8.05 (m, 1H), 7.50-7.56 (m, 2H), 7.30 (m, 1H).

A-4.11: 4-Fluoro-5-(4-fluoro-phenyl)-isoxazole-3-carboxylic Acid

A-4.11a: 4-Fluoro-5-(4-fluoro-phenyl)-isoxazole-3-carboxylic Acid Methyl Ester

To a solution of methyl 5-(4-fluorophenyl)isoxazole-3-carboxylate (246 mg, 1.11 mmol) in tetramethylene sulfone (4 mL, 41.6 mmol) is added Selectfluor® (498 mg, 1.33 mmol). The reaction mixture is stirred at 150° C. overnight. DCM (20 mL) and water (20 mL) are added. After separation of the layers, the aq. phase is extracted with DCM (20 mL). The combined organic layer are washed with water (3×20 mL), dried over MgSO$_4$, filtered and evaporated. The crude product is purified by flash chromatography using n-heptane to n-heptane/ethyl acetate (7:3) as eluent to yield the title compound. LC-MS method A: $t_R$=1.01 min.

A-4.11: 4-Fluoro-5-(4-fluoro-phenyl)-isoxazole-3-carboxylic Acid

The title compound is prepared according to the procedure A-4.09, starting from building block A-4.11a. LC-MS method A: $t_R$=0.79 min.

A-4.12: 5-(2,4-Difluoro-phenyl)-4-fluoro-isoxazole-3-carboxylic Acid A-4.12a: 5-(2,4-Difluoro-phenyl)-4-fluoro-isoxazole-3-carboxylic Acid Ethyl Ester The title compound is prepared according to the procedure A-4.11, starting from 5-(2,4-Difluoro-phenyl)-isoxazole-3-carboxylic acid ethyl ester. LC-MS method A: $t_R$=1.01 min.

A-4.12: 5-(2,4-Difluoro-phenyl)-4-fluoro-isoxazole-3-carboxylic Acid

The title compound is prepared according to the procedure A-4.09, starting from building block A-4.12a. LC-MS method A: $t_R$=0.76 min.

A-4.13: 5-(2-Trifluoromethyl-phenyl)-isoxazole-3-carboxylic Acid

A-4.13a: 2,4-Dioxo-4-(2-trifluoromethyl-phenyl)-butyric Acid Ethyl Ester

To a solution of sodium ethoxide (21% in EtOH) (2.16 mL, 5.79 mmol) at RT is added diethyl oxalate (0.929 mL, 6.84 mmol) in one portion. A solution of 2-(trifluoromethyl) acetophenone (0.797 mL, 5.26 mmol) in THF (3 mL) is added dropwise to the reaction mixture. The brown RM is stirred 1 h at RT. The reaction is slowly quenched by dropwise addition of 1M HCl (8 mL). THF is evaporated. The residue is partitioned between DCM (10 mL) and sat. NaHCO3 solution (10 mL) and the aq. phase is extracted with DCM (2×10 mL), dried over MgSO4, filtered and evaporated to yield the title compound as an orange oil; LC-MS method A: $t_R$=1.00 min. [M+H]$^+$=289.16.

A-4.13b: 5-(2-Trifluoromethyl-phenyl)-isoxazole-3-carboxylic Acid Ethyl Ester

Hydroxylamine hydrochloride (0.372 mL, 5.46 mmol) is added to a solution of 2,4-dioxo-4-(2-trifluoromethyl-phenyl)-butyric acid ethyl ester (1500 mg, 5.2 mmol) in EtOH (20 mL). The mixture is heated to 70° C. overnight. To the hot mixture, water (10 mL) is added dropwise. After addition, the mixture is allowed to cool down to RT. DCM (10 mL) and sat. NaHCO3 solution (10 mL) are added and the aq. phase is extracted with DCM (2×10 mL), dried over MgSO4, filtered and evaporated. The crude product is purified by LC-MS method E. LC-MS method A: $t_R$=1.01 min. [M+H]$^+$=286.17.

A-4.13: 5-(2-Trifluoromethyl-phenyl)-isoxazole-3-carboxylic Acid

The title compound is prepared according to the procedure A-4.09, starting from building block A-4.13b. LC-MS method A: $t_R$=0.80 min. [M+H+MeCN]$^+$=299.13.

A-4.14: 5-(2,6-Difluoro-phenyl)-isoxazole-3-carboxylic Acid

A-4.14a: 4-(2,6-Difluoro-phenyl)-2,4-dioxo-butyric Acid Ethyl Ester

The title compound is prepared according to the procedure A-4.13a, starting from 1-(2,6-difluorophenyl)ethan-1-one. LC-MS method A: $t_R$=1.00 min.

A-4.14b: 5-(2,6-Difluoro-phenyl)-isoxazole-3-carboxylic Acid Ethyl Ester

The title compound is prepared according to the procedure A-4.13b, starting from building block A-4.14a. LC-MS method A: $t_R$=0.97 min. [M+H]$^+$=254.20.

A-4.14: 5-(2,6-Difluoro-phenyl)-isoxazole-3-carboxylic Acid

The title compound is prepared according to the procedure A-4.09, starting from building block A-4.14b. LC-MS method A: $t_R$=0.74 min. [M+H+MeCN]$^+$=267.14

A-4.15: 5-(4-Trifluoromethyl-phenyl)-isoxazole-3-carboxylic Acid

A-4.15a: 2,4-Dioxo-4-(4-trifluoromethyl-phenyl)-butyric Acid Ethyl Ester

The title compound is prepared according to the procedure A-4.13a, starting from 1-(4-(trifluoromethyl)phenyl) ethan-1-one. LC-MS method A: $t_R$=1.05 min. [M+H]$^+$= 288.96.

A-4.15b: 5-(4-Trifluoromethyl-phenyl)-isoxazole-3-carboxylic Acid Ethyl Ester The title compound is prepared according to the procedure A-4.13b, starting from building block A-4.15a. LC-MS method A: $t_R$=1.05 min. $[M+H+MeCN]^+$=327.06.

A-4.15: 5-(4-Trifluoromethyl-phenyl)-isoxazole-3-carboxylic Acid

The title compound is prepared according to the procedure A-4.09, starting from building block A-4.15b. LC-MS method A: $t_R$=0.85 min.

A-4.16: 5-(3-Trifluoromethyl-phenyl)-isoxazole-3-carboxylic Acid

A-4.16a: 2,4-Dioxo-4-(3-trifluoromethyl-phenyl)-butyric Acid Ethyl Ester

The title compound is prepared according to the procedure A-4.13a, starting from 1-(3-(trifluoromethyl)phenyl)ethan-1-one. LC-MS method A: $t_R$=1.05 min. $[M+H]^+$=289.17.

A-4.16b: 5-(3-Trifluoromethyl-phenyl)-isoxazole-3-carboxylic Acid Ethyl Ester The title compound is prepared according to the procedure A-4.13b, starting from building block A-4.16a. LC-MS method A: $t_R$=1.05 min. $[M+H]^+$=286.18.

A-4.16: 5-(3-Trifluoromethyl-phenyl)-isoxazole-3-carboxylic Acid

The title compound is prepared according to the procedure A-4.09, starting from building block A-4.16b. LC-MS method A: $t_R$=0.85 min.

A-4.17: 5-(2,3,4-Trifluoro-phenyl)-isoxazole-3-carboxylic Acid

A-4.17a: 2,4-Dioxo-4-(2,3,4-trifluoro-phenyl)-butyric Acid Ethyl Ester

The title compound is prepared according to the procedure A-4.13a, starting from 1-(2,3,4-trifluorophenyl)ethan-1-one. LC-MS method A: $t_R$=1.04 min. $[M+H]^+$=275.17.

A-4.17b: 5-(2,3,4-Trifluoro-phenyl)-isoxazole-3-carboxylic Acid Ethyl Ester

The title compound is prepared according to the procedure A-4.13b, starting from building block A-4.17a. LC-MS method A: $t_R$=1.02 min.

A-4.17: 5-(2,3,4-Trifluoro-phenyl)-isoxazole-3-carboxylic Acid

The title compound is prepared according to the procedure A-4.09, starting from building block A-4.17b. LC-MS method A: $t_R$=0.79 min.

A-4.18: 5-(5-Fluoro-pyridin-2-yl)-isoxazole-3-carboxylic Acid

A-4.18a: 4-(5-Fluoro-pyridin-2-yl)-2,4-dioxo-butyric Acid Ethyl Ester

The title compound is prepared according to the procedure A-4.13a, starting from 1-(5-fluoropyridin-2-yl)ethan-1-one. LC-MS method A: $t_R$=0.89 min. $[M+H]^+$=240.25.

A-4.18b: 5-(5-Fluoro-pyridin-2-yl)-isoxazole-3-carboxylic Acid Ethyl Ester

The title compound is prepared according to the procedure A-4.13b, starting from building block A-4.18a. LC-MS method A: $t_R$=0.85 min. $[M+H]^+$=237.28.

A-4.18: 5-(5-Fluoro-pyridin-2-yl)-isoxazole-3-carboxylic Acid

The title compound is prepared according to the procedure A-4.09, starting from building block A-4.18b. LC-MS method A: $t_R$=0.59 min. $[M+H]^+$=209.37.

A-4.19: 4-(2,4-Difluoro-phenyl)-oxazole-2-carboxylic Acid

A-4.19a: 4-(2,4-Difluoro-phenyl)-oxazole-2-carboxylic Acid Ethyl Ester

2-Acetoxy-2',4'-difluoroacetophenone (200 mg, 0.934 mmol) is dissolved in p-xylene (10 mL). Ethyl oxamate (437 mg, 3.74 mmol) and boron trifluoride diethyl etherate (0.248 mL, 0.934 mmol) are added. The reaction mixture is heated to 150° C. for 20 h.

The reaction mixture is diluted with EtOAc (40 mL) and washed with saturated NaHCO$_3$ solution (20 mL). After separation of the layers the aq. layer is extracted with EtOAc (2×20 mL). The combined organic layers are dried over MgSO$_4$, filtered and evaporated. The crude product is purified by LC-MS method E. LC-MS method A: $t_R$=0.96 min. $[M+H]^+$=254.11.

A-4.19: 4-(2,4-Difluoro-phenyl)-oxazole-2-carboxylic Acid

The title compound is prepared according to the procedure A-4.09, starting from building block A-4.19b. LC-MS method A: $t_R$=0.69 min. $[M+H]^+$=226.23.

A-4.20: 1-(2,4,6-Trifluoro-phenyl)-1H-[1,2,3]triazole-4-carboxylic Acid

A-4.20a: 1-(2,4,6-Trifluoro-phenyl)-1H-[1,2,3]triazole-4-carboxylic Acid Ethyl Ester The title compound is prepared according to the procedure A-4.08a, starting from ethyl 2-diazo-3-oxopropanoate and 2,4,6-trifluoroaniline. LC-MS method A: $t_R$=0.84 min. $[M+H]^+$=272.29.

A-4.20: 1-(2,4,6-Trifluoro-phenyl)-1H-[1,2,3]triazole-4-carboxylic Acid

The title compound is prepared according to the procedure A-4.08, starting from building block A-4.20a. LC-MS method A: $t_R$=0.65 min. [M+H]$^+$=244.24.

A-4.21: 5-(2,4-Difluoro-phenyl)-isothiazole-3-carboxylic Acid

A-4.21a: 5-(2,4-Difluorophenyl)-3-methylisothiazole

Pd(PPh$_3$)$_4$ (892 mg, 0.77 mmol) is added to a degassed solution of 5-bromo-3-methylisothiazole (1446 mg, 7.72 mmol), 2,4,difluorophenylboronic acid (1462 mg, 9.26 mmol) and K$_3$PO$_4$ (8355 mg, 748 mmol) in dioxane (64 mL) and water (10 mL). The resulting solution is stirred for 24 h at 90° C. under argon. The resulting mixture is diluted with DCM (100 mL) and washed with H$_2$O (100 mL). The organic layer is separated and the aq. phase is extracted twice with DCM (2×100 mL). The combined organic layers are dried over anhydrous sodium sulfate and filtered. The resulting mixture is concentrated under vacuum. The crude is purified by flash silicagel chromatography using n-heptan to n-heptan/EtOAc 85:15 as eluent to yield the title compound as a white powder. LC-MS method A: $t_R$=1.01 min. [M+H]$^+$=212.19.

A-4.21b: 3-Bromomethyl-5-(2,4-difluoro-phenyl)-isothiazole

A mixture of 5-(2,4-difluorophenyl)-3-methylisothiazole (1042 mg, 4.93 mmol), N-bromosuccinimide (966 mg, 5.43 mmol) and benzoyl peroxide (119 mg, 0.49 mmol) in trifluorotoluene (40 mL) is refluxed for 30 h. More NBS (500 mg, 2.8 mmol), benzoyl peroxide (80 mg, 0.33 mmol) are added and the mixture is then refluxed 2 h. It is diluted with DCM (100 mL) and water (100 mL). The organic layer is separated and the aq. layer is extracted with DCM (100 mL). The combined organic layers are dried over anhydrous sodium sulfate, concentrated, and purified by flash silicagel chromatography using DCM/n-heptan 1:1 as eluent to yield the title compound as a sticky oil. LC-MS method A: $t_R$=1.06 min. [M+H]$^+$=292.09.

A-4.21c: 5-(2,4-Difluoro-phenyl)-isothiazole-3-carboxylic Acid Ethyl Ester

A suspension of 3-bromomethyl-5-(2,4-difluoro-phenyl)-isothiazole (1150 mg, 3.96 mmol) in water (10 mL) at reflux is treated with small portions of potassium permanganate (860 mg, 5.39 mmol) over 30 minutes. The reaction mixture is stirred for 5 h. During this time the purple coloration turns to a colorless liquid with a black suspension, which is filtered through a Whatmann GF/A filtered and evaporated. The crude is diluted with DCM (25 mL) and sat. HCl 1N (25 mL) The aq. phase is extracted thrice with DCM (3×25 mL). The combined organic extracts are dried over MgSO$_4$, filtered and concentrated in vacuo. The crude contains mainly starting material. The black residue is diluted in ethanol (200 ml) and 4N HCl in dioxane (25 mL) is added. The reaction mixture is refluxed overnight. The black slurry turns to a clear solution and the corresponding ester has been formed. The solution is concentrated in vacuo. The crude is purified by flash silicagel chromatography using n-heptan to n-heptan/EtOAc 95:5 as eluent to yield the title compound as a white powder. LC-MS method A: $t_R$=1.06 min. [M+H]$^+$= 270.17.

A-4.21: 5-(2,4-Difluoro-phenyl)-isothiazole-3-carboxylic Acid

A solution of 5-(2,4-difluoro-phenyl)-isothiazole-3-carboxylic acid ethyl ester (216 mg, 0.8 mmol) in EtOH/1N aq. NaOH (4 mL) is stirred for 24 h at RT. The reaction mixture is washed with EtOAc (10 mL). The aq. phase is made acidic with 1N HCl (5 mL) and then extracted five times with DCM (5×10 mL). The combined extracts are dried over MgSO4, filtered and concentrated in vacuo to yield the title compound as a white powder. LC-MS method A: $t_R$=0.84 min. [M+H]$^+$=241.83.

General Method A for the Synthesis of Compounds of Formula (I)
Buildings Blocks:
Preparation of Building Blocks of Structure 1.

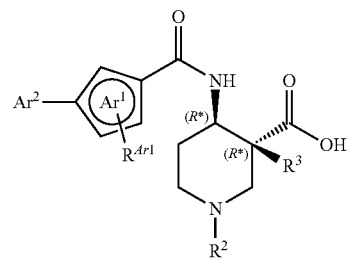

1

BB 1.01: rac-(3R*,4R*)-1-Cyclohexyl-4-{[5-(2,4-difluoro-phenyl)-isoxazole-3-carbonyl]-amino}-piperidine-3-carboxylic Acid

1.01a: rac-(3R*,4R*)-4-tert-Butoxycarbonylamino-1-cyclohexyl-piperidine-3-carboxylic Acid Methyl Ester To a solution of rac-(3R*,4R*)-4-tert-butoxycarbonylamino-piperidine-3-carboxylic acid methyl ester (3.0 g, 11.3 mmol) in DCM (56.4 mL) at RT is added cyclohexanone (1.42 mL, 13.5 mmol) followed by acetic acid (0.966 mL, 16.9 mmol) and sodium triacetoxyborohydride (3.39 g, 15.2 mmol). After stirring for 5 h, additional cyclohexanone (0.23 mL, 2.3 mmol), acetic acid (0.17 mL, 2.8 mmol) and sodium triacetoxyborohydride (590 mg, 2.8 mmol) are added. The reaction mixture is stirred overnight. The reaction mixture is diluted with DCM (200 mL) and treated with aq. sat. NaHCO$_3$ (250 mL). The organic phase is dried over MgSO$_4$ and evaporated. The crude title compound is used in the next step without further purification; LC-MS method D $t_R$=1.09 min; [M+H]$^+$=341.19.

1.01b: rac-(3R*,4R*)-4-Amino-1-cyclohexyl-piperidine-3-carboxylic Acid Methyl Ester rac-(3R*,4R*)-4-tert-Butoxycarbonylamino-1-cyclohexyl-piperidine-3-carboxylic acid methyl ester 1.01a (3.85 g, 11.3 mmol) is dissolved in MeOH (56.5 mL). A 4M solution of HCl in dioxane (56.5 mL, 226 mmol) is added and the reaction is stirred for 1 h. The reaction mixture is concentrated, dissolved in DCM (250 mL) and treated with aq. sat. NaHCO$_3$ (200 mL). The organic layer is separated and the aq. phase is extracted with DCM (150 mL). The combined organic layers are dried over MgSO$_4$ and evaporated. The crude title compound is obtained as a yellow oil; LC-MS method D $t_R$=0.79 min; [M+H]$^+$=241.20.

1.01c: rac-(3R*,4R*)-1-Cyclohexyl-4-{[5-(2,4-difluoro-phenyl)-isoxazole-3-carbonyl]-amino}-piperidine-3-carboxylic Acid Methyl Ester To a solution of rac-(3R*,4R*)-4-amino-1-cyclohexyl-piperidine-3-carboxylic acid methyl ester 1.01b (2.64 g, 10.4 mmol) in DMF (56.7 mL) at RT is added 5-(2,4-difluoro-phenyl)isoxazole-3-carboxylic Acid (2.42 g, 10.4 mmol). DIPEA (5.83 mL, 33.4 mmol) is then added followed by HATU (4.16 g, 10.9 mmol). The reaction mixture is stirred overnight (17 h). The reaction mixture is concentrated, dissolved in DCM (300 mL) and treated with aq. sat. NaHCO$_3$ (225 mL). The organic layer is dried over MgSO$_4$ and evaporated. The crude residue is purified by prep. LC-MS under basic conditions (method E). The title compound is obtained as white powder; LC-MS method D $t_R$=1.15 min; [M+H]$^+$=448.19.

1.01: rac-(3R*,4R*)-1-Cyclohexyl-4-{[5-(2,4-difluoro-phenyl)-isoxazole-3-carbonyl]-amino}-piperidine-3-carboxylic Acid rac-(3R*,4R*)-1-Cyclohexyl-4-{[5-(2,4-difluoro-phenyl)-isoxazole-3-carbonyl]-amino}-piperidine-3-carboxylic acid methyl ester 1.01c (2.24 g, 5 mmol) is dissolved in THF (30.6 mL) at RT. Aq. 1M NaOH solution (15 mL, 15 mmol) is then added and the mixture stirred for 6.5 h. The reaction mixture is acidified to around pH=3 with a 2M HCl solution (7.75 mL) and evaporated. The resulting suspension is filtered, washed twice with water (2×4 mL) and dried under HV. The title compound is obtained as a white powder; LC-MS method D $t_R$=0.61 min; [M+H]$^+$=433.89.

Preparation of Building-Blocks of Structure 1 Used as Intermediates in the Preparation of Examples 1.001 to 1.199

The following intermediates are prepared in analogy to BB 1.01:

BB 1.02: rac-(3R*,4R*)-1-Cyclohexyl-4-{[1-(2,4-difluoro-phenyl)-1H-[1,2,3]triazole-4-carbonyl]-amino}-piperidine-3-carboxylic Acid 1.02c: rac-(3R*,4R*)-1-Cyclohexyl-4-{[1-(2,4-difluoro-phenyl)-1H-[1,2,3]triazole-4-carbonyl]-amino}-piperidine-3-carboxylic Acid Methyl Ester The title compound is prepared according to the procedure 1.01c, starting from building block 1.01b and building block A-4.08; LC-MS method D: $t_R$=1.03 min; [M+H]$^+$=448.15.

1.02: rac-(3R*,4R*)-1-Cyclohexyl-4-{[1-(2,4-difluoro-phenyl)-1H-[1,2,3]triazole-4-carbonyl]-amino}-piperidine-3-carboxylic Acid The title compound is prepared according to the procedure 1.01, starting from building block 1.02c; LC-MS method D: $t_R$=0.54 min; [M+H]$^+$=433.88.

BB 1.03: rac-(3R*,4R*)-1-Cyclopentyl-4-{[1-(2,4-difluoro-phenyl)-1H-[1,2,3]triazole-4-carbonyl]-amino}-piperidine-3-carboxylic Acid 1.03a: rac-(3R*,4R*)-4-tert-Butoxycarbonylamino-1-cyclopentyl-piperidine-3-carboxylic Acid Methyl Ester The title compound is prepared according to the procedure 1.01a, starting from rac-(3R*,4R*)-4-tert-butoxycarbonylamino-piperidine-3-carboxylic acid methyl ester and cyclopentanone; LC-MS method D: $t_R$=1.0 min; [M+H]$^+$=327.18.

1.03b: rac-(3R*,4R*)-4-Amino-1-cyclopentyl-piperidine-3-carboxylic Acid Methyl Ester The title compound is prepared according to the procedure 1.01b, starting from building block 1.03a; LC-MS method D: $t_R$=0.71 min; [M+H]$^+$=227.18.

1.03c: rac-(3R*,4R*)-1-Cyclopentyl-4-{[1-(2,4-difluoro-phenyl)-1H-[1,2,3]triazole-4-carbonyl]-amino}-piperidine-3-carboxylic Acid Methyl Ester The title compound is prepared according to the procedure 1.01c, starting from building block 1.03b and building block A-4.08; LC-MS method D: $t_R$=0.95 min; [M+H]$^+$=433.9.

1.03: rac-(3R*,4R*)-1-Cyclopentyl-4-{[1-(2,4-difluoro-phenyl)-1H-[1,2,3]triazole-4-carbonyl]-amino}-piperidine-3-carboxylic Acid The title compound is prepared according to the procedure 1.01, starting from building block 1.03c; LC-MS method D: $t_R$=0.49 min; [M+H]$^+$=420.07.

BB 1.04: rac-(3R*,4R*)-1-Cyclopropylmethyl-4-{[1-(2,4-difluoro-phenyl)-1H-[1,2,3]triazole-4-carbonyl]-amino}-piperidine-3-carboxylic Acid 1.04a: rac-(3R*,4R*)-4-tert-Butoxycarbonylamino-1-cyclopropylmethyl-piperidine-3-carboxylic Acid Methyl Ester The title compound is prepared according to the procedure 1.01a, starting from rac-(3R*,4R*)-4-tert-Butoxycarbonylamino-piperidine-3-carboxylic acid methyl ester and cyclopropanecarbaldehyde; LC-MS method D: $t_R$=0.94 min; [M+H]$^+$=313.18.

1.04b: rac-(3R*,4R*)-4-Amino-1-cyclopropylmethyl-piperidine-3-carboxylic Acid Methyl Ester The title compound is prepared according to the procedure 1.01b, starting from building block 1.04a; LC-MS method D: $t_R$=0.64 min; [M+H]$^+$=213.21.

1.04c: rac-(3R*,4R*)-1-cyclopropylmethyl-4-{[1-(2,4-difluoro-phenyl)-1H-[1,2,3]triazole-4-carbonyl]amino}-piperidine-3-carboxylic Acid Methyl Ester The title compound is prepared according to the procedure 1.01c, starting from building block 1.04b and building block A-4.08; LC-MS method D: $t_R$=0.89 min; [M+H]$^+$=420.1.

1.04: rac-(3R*,4R*)-1-cyclopropylmethyl-4-{[1-(2,4-difluoro-phenyl)-1H-[1,2,3]triazole-4-carbonyl]amino}-piperidine-3-carboxylic Acid The title compound is prepared according to the procedure 1.01, starting from building block 1.04c; LC-MS method D: $t_R$=0.48 min; [M+H]$^+$=406.09.

BB 1.05: rac-(3R*,4R*)-4-{[1-(2,4-Difluoro-phenyl)-1H-[1,2,3]triazole-4-carbonyl]-amino}-1-(2-methyl-cyclopentyl)-piperidine-3-carboxylic Acid 1.05a: rac-(3R*,4R*)-4-tert-Butoxycarbonylamino-1-(2-methyl-cyclopentyl)-piperidine-3-carboxylic Acid Methyl Ester The title compound is prepared according to the procedure 1.01a, starting from rac-(3R*,4R*)-4-tert-Butoxycarbonylamino-piperidine-3-carboxylic acid methyl ester and 2-methyl-cyclopentanone; LC-MS method D: $t_R$=1.16 min; [M+H]$^+$=341.2.

1.05b: rac-(3R*,4R*)-4-Amino-1-(2-methyl-cyclobentyl)-piperidine-3-carboxylic acid methyl Ester The title compound is prepared according to the procedure 1.01b, starting from building block 1.05a; LC-MS method D: $t_R$=0.83 min; [M+H]$^+$=241.19.

1.05c: rac-(3R*,4R*)-1-(2-Methyl-cyclopentyl)-4-{[1-(2,4-difluoro-phenyl)-1H-[1,2,3]triazole-4-carbonyl]-amino}-piperidine-3-carboxylic Acid Methyl Ester The title compound is prepared according to the procedure 1.01c, starting from building block 1.05b and building block A-4.08; LC-MS method D: $t_R$=1.08 min; [M+H]$^+$=448.15.

1.05: rac-(3R*,4R*)-1-(2-Methyl-cyclopentyl)-4-{[1-(2,4-difluoro-phenyl)-1H-[1,2,3]triazole-4-carbonyl]-amino}-piperidine-3-carboxylic Acid The title compound is prepared according to the procedure 1.01, starting from building block 1.05c; LC-MS method D: $t_R$=0.53 min; [M+H]$^+$=433.82.

BB 1.06: rac-(3R*,4R*)-1-Cyclopentyl-4-{[5-(2,4,6-trifluoro-phenyl)-isoxazole-3-carbonyl]-amino}-piperidine-3-carboxylic Acid 1.06c: rac-(3R*,4R*)-1-Cyclopentyl-4-{[5-(2,4,6-trifluoro-phenyl)-isoxazole-3-carbonyl]-amino}-piperidine-3-carboxylic Acid Methyl Ester The title compound is prepared according to the procedure 1.01c, starting from building block 1.03b and building block A-4.01; LC-MS method D: $t_R$=1.06 min; [M+H]$^+$=452.13.

1.06: rac-(3R*,4R*)-1-Cyclopentyl-4-{[5-(2,4,6-trifluoro-phenyl)-isoxazole-3-carbonyl]-amino}-piperidine-3-carboxylic Acid The title compound is prepared according to the procedure 1.01, starting from building block 1.06c; LC-MS method D: $t_R$=0.55 min; [M+H]$^+$=438.1.

BB 1.07: rac-(3R*,4R*)-1-Cyclopropylmethyl-4-{[5-(2,4,6-trifluoro-phenyl)-isoxazole-3-carbonyl]-amino}-piperidine-3-carboxylic Acid 1.07c: rac-(3R*,4R*)-1-Cyclopropylmethyl-4-{[5-(2,4,6-trifluoro-phenyl)-isoxazole-3-carbonyl]-amino}-piperidine-3-carboxylic Acid Methyl Ester The title compound is prepared according to the procedure 1.01c, starting from building block 1.04b and building block A-4.01; LC-MS method D: $t_R$=1.0 min; [M+H]$^+$=438.11.

1.07: rac-(3R*,4R*)-1-Cyclopropylmethyl-4-{[5-(2,4,6-trifluoro-phenyl)-isoxazole-3-carbonyl]-amino}-piperidine-3-carboxylic Acid The title compound is prepared according to the procedure 1.01, starting from building block 1.07c; LC-MS method D: $t_R$=0.53 min; [M+H]$^+$=424.09.

BB 1.08: rac-(3R*,4R*)-1-(2-Methyl-cyclopentyl)-4-{[5-(2,4,6-trifluoro-phenyl)-isoxazole-3-carbonyl]-amino}-piperidine-3-carboxylic Acid 1.08c: rac-(3R*,4R*)-1-(2-Methyl-cyclopentyl)-4-{[5-(2,4,6-trifluoro-phenyl)-isoxazole-3-carbonyl]-amino}-piperidine-3-carboxylic Acid Methyl Ester The title compound is prepared according to the procedure 1.01c, starting from building block 1.05b and building block A-4.01; LC-MS method D: $t_R$=1.09 min; [M+H]$^+$=448.14.

1.08: rac-(3R*,4R*)-1-(2-Methyl-cyclopentyl)-4-{[5-(2,4,6-trifluoro-phenyl)-isoxazole-3-carbonyl]-amino}-piperidine-3-carboxylic Acid The title compound is prepared according to the procedure 1.01, starting from building block 1.08c; LC-MS method D: $t_R$=0.53 min; [M+H]$^+$=433.82.

BB 1.09: rac-(3R*,4R*)-1-Cyclohexyl-4-{[3-(2,4-difluoro-phenyl)-isoxazole-5-carbonyl]-amino}-piperidine-3-carboxylic Acid 1.09c: rac-(3R*,4R*)-1-Cyclohexyl-4-{[3-(2,4-difluoro-phenyl)-isoxazole-5-carbonyl]-amino}-piperidine-3-carboxylic Acid Methyl Ester The title compound is prepared according to the procedure 1.01c, starting from building block 1.01b and building block A-4.10; LC-MS method D: $t_R$=1.11 min; [M+H]$^+$=448.14.

1.09: rac-(3R*,4R*)-1-Cyclohexyl-4-{[3-(2,4-difluoro-phenyl)-isoxazole-5-carbonyl]-amino}-piperidine-3-carboxylic Acid The title compound is prepared according to the procedure 1.01, starting from building block 1.09c; LC-MS method D: $t_R$=0.58 min; [M+H]$^+$=433.88.

BB 1.10: rac-(3R*,4R*)-1-Cyclopentyl-4-{[3-(2,4-difluoro-phenyl)-isoxazole-5-carbonyl]-amino}-piperidine-3-carboxylic Acid 1.10c: rac-(3R*,4R*)-1-Cyclopentyl-4-{[3-(2,4-difluoro-phenyl)-isoxazole-5-carbonyl]-amino}-piperidine-3-carboxylic Acid Methyl Ester The title compound is prepared according to the procedure 1.01c, starting from building block 1.03b and building block A-4.10; LC-MS method D: $t_R$=1.03 min; [M+H]$^+$=433.88.

1.10: rac-(3R*,4R*)-1-Cyclopentyl-4-{[3-(2,4-difluoro-phenyl)-isoxazole-5-carbonyl]-amino}-piperidine-3-carboxylic Acid The title compound is prepared according to the procedure 1.01, starting from building block 1.10c; LC-MS method D: $t_R$=0.54 min; [M+H]$^+$=420.12.

BB 1.11: rac-(3R*,4R*)-1-Cyclohexyl-4-{[5-(2,4,6-trifluoro-phenyl)-isoxazole-3-carbonyl]-amino}-piperidine-3-carboxylic Acid 1.11c: rac-(3R*,4R*)-1-Cyclohexyl-4-{[5-(2,4,6-trifluoro-phenyl)-isoxazole-3-carbonyl]-amino}-piperidine-3-carboxylic Acid Methyl Ester The title compound is prepared according to the procedure 1.01c, starting from building block 1.01b and building block A-4.01; LC-MS method D: $t_R$=1.14 min; [M+H]$^+$=465.9.

1.11: rac-(3R*,4R*)-1-Cyclohexyl-4-{[5-(2,4,6-trifluoro-phenyl)-isoxazole-3-carbonyl]-amino}-piperidine-3-carboxylic Acid The title compound is prepared according to the procedure 1.01, starting from building block 1.11c; LC-MS method D: $t_R$=0.59 min; [M+H]$^+$=452.1.

BB 1.12: rac-(3R*,4R*)-1-Cyclopropylmethyl-4-{[3-(2,4-difluoro-phenyl)-isoxazole-5-carbonyl]-amino}-piperidine-3-carboxylic Acid 1.12c: rac-(3R*,4R*)-1-Cyclopropylmethyl-4-{[3-(2,4-difluoro-phenyl)-isoxazole-5-carbonyl]-amino}-piperidine-3-carboxylic Acid Methyl Ester The title compound is prepared according to the procedure 1.01c, starting from building block 1.04b and building block A-4.10; LC-MS method D: $t_R$=0.98 min; [M+H]$^+$=420.11.

1.12: rac-(3R*,4R*)-1-Cyclopropylmethyl-4-{[3-(2,4-difluoro-phenyl)-isoxazole-5-carbonyl]-amino}-piperidine-3-carboxylic Acid The title compound is prepared according to the procedure 1.01, starting from building block 1.12c; LC-MS method D: $t_R$=0.52 min; [M+H]$^+$=406.07.

BB 1.13: rac-(3R*,4R*)-1-(2-Methyl-cyclopentyl)-4-{[3-(2,4-difluoro-phenyl)-isoxazole-5-carbonyl]-amino}-piperidine-3-carboxylic Acid 1.13c: rac-(3R*,4R*)-1-(2-Methyl-cyclopentyl)-4-{[3-(2,4-difluoro-phenyl)-isoxazole-5-carbonyl]-amino}-piperidine-3-carboxylic Acid Methyl Ester The title compound is prepared according to the procedure 1.01c, starting from building block 1.05b and building block A-4.10; LC-MS method D: $t_R$=1.15 min; [M+H]$^+$=448.14.

1.13: rac-(3R*,4R*)-1-(2-Methyl-cyclopentyl)-4-{[3-(2,4-difluoro-phenyl)-isoxazole-5-carbonyl]-amino}-piperidine-3-carboxylic Acid The title compound is prepared according to the procedure 1.01, starting from building block 1.13c; LC-MS method D: $t_R$=0.59 min; [M+H]$^+$=433.87.

BB 1.14: rac-(3R*,4R*)-1-Cyclohexyl-4-{[5-(2,4-difluoro-phenyl)-[1,2,4]oxadiazole-3-carbonyl]-amino}-piperidine-3-carboxylic Acid 1.14c: rac-(3R*,4R*)-1-Cyclohexyl-4-{[5-(2,4-difluoro-phenyl)-[1,2,4]oxadiazole-3-carbonyl]-amino}-piperidine-3-carboxylic Acid Methyl Ester The title compound is prepared according to the procedure 1.01c, starting from building block 1.01b and building block A-4.09; LC-MS method D: $t_R$=1.07 min; [M+H]$^+$=449.03.

1.14: rac-(3R*,4R*)-1-Cyclohexyl-4-{[5-(2,4-difluoro-phenyl)-[1,2,4]oxadiazole-3-carbonyl]-amino}-piperidine-3-carboxylic Acid The title compound is prepared according to the procedure 1.01, starting from building block 1.14c; LC-MS method D: $t_R$=0.55 min; [M+H]$^+$=435.1.

BB 1.15: rac-(3R*,4R*)-1-Cyclopropylmethyl-4-{[5-(2,4-difluoro-phenyl)-[1,2,4]oxadiazole-3-carbonyl]-amino}-piperidine-3-carboxylic Acid 1.15c: rac-(3R*,4R*)-1-Cyclopropylmethyl-4-{[5-(2,4-difluoro-phenyl)-[1,2,4]oxadiazole-3-carbonyl]amino}-piperidine-3-carboxylic Acid Methyl Ester The title compound is prepared according to the procedure 1.01c, starting from building block 1.04b and building block A-4.09; LC-MS method D: $t_R$=0.93 min; [M+H]$^+$=421.1.

1.15: rac-(3R*,4R*)-1-Cyclopropylmethyl-4-{[5-(2,4-difluoro-phenyl)-[1,2,4]oxadiazole-3-carbonyl]-amino}-piperidine-3-carboxylic Acid The title compound is prepared according to the procedure 1.01, starting from building block 1.15c; LC-MS method D: $t_R$=0.49 min; [M+H]$^+$=407.05.

BB 1.16: rac-(3R*,4R*)-1-Cyclopentyl-4-{[5-(2,4-difluoro-phenyl)-[1,2,4]oxadiazole-3-carbonyl]-amino}-piperidine-3-carboxylic Acid 1.16c: rac-(3R*,4R*)-1-Cyclopentyl-4-{[5-(2,4-difluoro-phenyl)-[1,2,4]oxadiazole-3-carbonyl]-amino}-piperidine-3-carboxylic Acid Methyl Ester The title compound is prepared according to the procedure 1.01c, starting from building block 1.03b and building block A-4.09; LC-MS method D: $t_R$=0.99 min; [M+H]$^+$=435.1.

1.16: rac-(3R*,4R*)-1-Cyclopentyl-4-{[5-(2,4-difluoro-phenyl)-[1,2,4]oxadiazole-3-carbonyl]-amino}-piperidine-3-carboxylic Acid The title compound is prepared according to the procedure 1.01, starting from building block 1.16c; LC-MS method D: $t_R$=0.51 min; [M+H]$^+$=421.1.

BB 1.17: rac-(3R*,4R*)-1-(2-Methyl-cyclopentyl)-4-{[5-(2,4-difluoro-phenyl)-[1,2,4]oxadiazole-3-carbonyl]-amino}-piperidine-3-carboxylic Acid 1.17c: rac-(3R*,4R*)-1-(2-Methyl-cyclopentyl)-4-{[5-(2,4-difluoro-phenyl)-[1,2,4]oxadiazole-3-carbonyl]amino}-piperidine-3-carboxylic Acid Methyl Ester The title compound is prepared according to the procedure 1.01c, starting from building block 1.05b and building block A-4.09; LC-MS method D: $t_R$=1.12 min; [M+H]$^+$=449.02.

1.17: rac-(3R*,4R*)-1-(2-Methyl-cyclopentyl)-4-{[5-(2,4-difluoro-phenyl)-[1,2,4]oxadiazole-3-carbonyl]amino}-piperidine-3-carboxylic Acid The title compound is prepared according to the procedure 1.01, starting from building block 1.17c; LC-MS method D: $t_R$=0.56 min; [M+H]$^+$=435.1.

BB 1.18: rac-(3R*,4R*)-1-Cyclohexyl-4-{[5-(2,4-difluoro-phenyl)-[1,3,4]oxadiazole-2-carbonyl]-amino}-piperidine-3-carboxylic Acid Methyl Ester The title compound is prepared according to the procedure 1.01c, starting from building block 1.01b and building block A-4.07; LC-MS method D: $t_R$=1.05 min; [M+H]$^+$=449.08.

BB 1.19: rac-(3R*,4R*)-1-Cyclopropylmethyl-4-{[5-(2,4-dichloro-phenyl)-isoxazole-3-carbonyl]-amino}-piperidine-3-carboxylic Acid 1.19c: rac-(3R*,4R*)-1-Cyclopropylmethyl-4-{[5-(2,4-dichloro-phenyl)-isoxazole-3-carbonyl]-amino}-piperidine-3-carboxylic Acid Methyl Ester The title compound is prepared according to the procedure 1.01c, starting from building block 1.04b and 5-(2,4-dichlorophenyl)-1,2-oxazole-3-carboxylic acid; LC-MS method A: $t_R$=0.75 min; [M+H]$^+$=451.98.

1.19: rac-(3R*,4R*)-1-Cyclopropylmethyl-4-{[5-(2,4-dichloro-phenyl)-isoxazole-3-carbonyl]-amino}-piperidine-3-carboxylic Acid The title compound is prepared according to the procedure 1.01, starting from building block 1.19c; LC-MS method A: $t_R$=0.70 min; [M+H]$^+$=438.11.

BB 1.20: rac-(3R*,4R*)-1-Cyclopropylmethyl-4-{[5-(2-trifluoromethyl-phenyl)-isoxazole-3-carbonyl]-amino}-piperidine-3-carboxylic Acid 1.20c: rac-(3R*,4R*)-1-Cyclopropylmethyl-4-{[5-(2-trifluoromethyl-phenyl)-isoxazole-3-carbonyl]-amino}-piperidine-3-carboxylic Acid Methyl Ester The title compound is prepared according to the procedure 1.01c, starting from building block 1.04b and building block A-4.13; LC-MS method A: $t_R$=0.73 min; [M+H]$^+$=452.11.

1.20: rac-(3R*,4R*)-1-Cyclopropylmethyl-4-{[5-(2-trifluoromethyl-phenyl)-isoxazole-3-carbonyl]-amino}-piperidine-3-carboxylic Acid The title compound is prepared according to the procedure 1.01, starting from building block 1.20c; LC-MS method A: $t_R$=0.67 min; [M+H]$^+$=438.22.

BB 1.21: rac-(3R*,4R*)-1-Cyclopropylmethyl-4-{[5-(2,6-difluoro-phenyl)-isoxazole-3-carbonyl]-amino}-piperidine-3-carboxylic Acid 1.21c: rac-(3R*,4R*)-1-Cyclopropylmethyl-4-{[5-(2,6-difluoro-phenyl)-isoxazole-3-carbonyl]-amino}-piperidine-3-carboxylic Acid Methyl Ester The title compound is prepared according to the procedure 1.01c, starting from building block 1.04b and building block A-4.14; LC-MS method A: $t_R$=0.68 min; [M+H]$^+$=420.11.

1.21: rac-(3R*,4R*)-1-Cyclopropylmethyl-4-{[5-(2,6-difluoro-phenyl)-isoxazole-3-carbonyl]-amino}-piperidine-3-carboxylic Acid The title compound is prepared according to the procedure 1.01, starting from building block 1.21c; LC-MS method A: $t_R$=0.62 min; [M+H]$^+$=406.22.

BB 1.22: rac-(3R*,4R*)-1-Cyclopropylmethyl-4-{[5-(4-trifluoromethyl-phenyl)-isoxazole-3-carbonyl]-amino}-piperidine-3-carboxylic Acid 1.22c: rac-(3R*,4R*)-1-Cyclopropylmethyl-4-{[5-(4-trifluoromethyl-phenyl)-isoxazole-3-carbonyl]-amino}-piperidine-3-carboxylic Acid Methyl Ester The title compound is prepared according to the procedure 1.01c, starting from building block 1.04b and building block A-4.15; LC-MS method A: $t_R$=0.75 min; [M+H]$^+$=452.07.

1.22: rac-(3R*,4R*)-1-Cyclopropylmethyl-4-{[5-(4-trifluoromethyl-phenyl)-isoxazole-3-carbonyl]-amino}-piperidine-3-carboxylic Acid The title compound is prepared according to the procedure 1.01, starting from building block 1.22c; LC-MS method A: $t_R$=0.70 min; [M+H]$^+$=438.25.

BB 1.23: rac-(3R*,4R*)-1-Cyclopropylmethyl-4-{[5-(3-trifluoromethyl-phenyl)-isoxazole-3-carbonyl]-amino}-piperidine-3-carboxylic Acid 1.23c: rac-(3R*,4R*)-1-Cyclopropylmethyl-4-{[5-(4-trifluoromethyl-phenyl)-isoxazole-3-carbonyl]-amino}-piperidine-3-carboxylic Acid Methyl Ester The title compound is prepared according to the procedure 1.01c, starting from building block 1.04b and building block A-4.16; LC-MS method A: $t_R$=0.74 min; [M+H]$^+$=452.09.

1.23: rac-(3R*,4R*)-1-Cyclopropylmethyl-4-{[5-(3-trifluoromethyl-phenyl)-isoxazole-3-carbonyl]-amino}-piperidine-3-carboxylic Acid The title compound is prepared according to the procedure 1.01, starting from building block 1.23c; LC-MS method A: $t_R$=0.69 min; [M+H]$^+$=438.25.

BB 1.24: rac-(3R*,4R*)-1-Cyclopropylmethyl-4-{[5-(2,3,4-trifluoro-phenyl)-isoxazole-3-carbonyl]-amino}-piperidine-3-carboxylic Acid 1.24c: rac-(3R*,4R*)-1-Cyclopropylmethyl-4-{[5-(2,3,4-trifluoro-phenyl)-isoxazole-3-carbonyl]-amino}-piperidine-3-carboxylic Acid Methyl Ester The title compound is prepared according to the procedure 1.01c, starting from building block 1.04b and building block A-4.17; LC-MS method A: $t_R$=0.72 min; [M+H]$^+$=438.16.

1.24: rac-(3R*,4R*)-1-Cyclopropylmethyl-4-{[5-(2,3,4-trifluoro-phenyl)-isoxazole-3-carbonyl]-amino}-piperidine-3-carboxylic Acid The title compound is prepared according to the procedure 1.01, starting from building block 1.24c; LC-MS method A: $t_R$=0.66 min; [M+H]$^+$=424.15.

BB 1.25: rac-(3R*,4R*)-1-Cyclopropylmethyl-4-{[5-(2-fluoro-4-methoxy-phenyl)-isoxazole-3-carbonyl]-amino}-piperidine-3-carboxylic Acid 1.25c: rac-(R*,4R*)-1-Cyclopropylmethyl-4-{[5-(2-fluoro-4-methoxy-phenyl)-isoxazole-3-carbonyl]-amino}-piperidine-3-carboxylic Acid Methyl Ester The title compound is prepared according to the procedure 1.01c, starting from building block 1.04b and 5-(2-fluoro-4-methoxyphenyl)isoxazole-3-carboxylic acid; LC-MS method A: $t_R$=0.69 min; [M+H]$^+$=432.29.

1.25: rac-(3R*,4R*)-1-Cyclopropylmethyl-4-{[5-(2-fluoro-4-methoxy-phenyl)-isoxazole-3-carbonyl]-amino}-piperidine-3-carboxylic Acid The title compound is prepared according to the procedure 1.01, starting from building block 1.25c; LC-MS method A: $t_R$=0.67 min; [M+H]$^+$=418.07.

BB 1.26: rac-(3R*,4R*)-1-Cyclopropylmethyl-4-{[5-(5-fluoro-pyridin-2-yl)-isoxazole-3-carbonyl]-amino}-piperidine-3-carboxylic Acid 1.26c: rac-(3R*,4R*)-1-Cyclopropylmethyl-4-{[5-(5-fluoro-pyridin-2-yl)-isoxazole-3-carbonyl]-amino}-piperidine-3-carboxylic Acid Methyl Ester The title compound is prepared according to the procedure 1.01c, starting from building block 1.04b and building block A-4.18; LC-MS method A: $t_R$=0.59 min; [M+H]$^+$=403.16.

1.26: rac-(3R*,4R*)-1-Cyclopropylmethyl-4-{[5-(5-fluoro-pyridin-2-yl)-isoxazole-3-carbonyl]-amino}-piperidine-3-carboxylic Acid The title compound is prepared according to the procedure 1.01, starting from building block 1.26c; LC-MS method A: $t_R$=0.54 min; [M+H]$^+$=389.22.

General Procedures for the Preparation of Examples 1.001 to 1.199:

Method A:

To a solution of the respective carboxylic acid (BB 1.01 to BB 1.26) (0.1 mmol) in 1 mL DMF is added the respective amine (commercially available) (0.12 to 0.15 mmol). DIPEA (0.3 mmol; 0.6 mmol if the amine is an hydrochloride salt) is then added followed by HATU (0.105 mmol). The reaction mixture is stirred overnight at RT. The crude mixture is directly purified by prep. LC-MS with method E.

Method B:

To a solution of the respective carboxylic acid (BB 1.01 to BB 1.26) (0.05 mmol) in pyridine (1 mL) at RT is added the respective commercially available amine ((0.1 mmol). POCl$_3$ (0.1 mmol) is then added and the mixture is stirred at RT for 2 h. Water (50 µL) is added and the resulting solution is evaporated. The crude residue is purified by prep. LC-MS with method E.

Method C:

To a solution of the respective carboxylic acid (BB 1.01 to BB 1.26) (0.07 mmol) and a commercially available amine (0.067 mmol) in 2 mL DCM, is added TEA (0.29 mmol) and T3P 50% in DCM (0.08 mL, 0.135 mmol). The mixture is stirred 24 h at RT and then the reaction mixture is washed with aq. sat. NaHCO$_3$ and water. The organic solvent is evaporated and the residue is purified by prep HPLC using method E.

Example 1.001: rac-(3R*,4R*)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide To a solution of rac-(3R*,4R*)-1-cyclohexyl-4-{[5-(2,4-difluoro-phenyl)-isoxazole-3-carbonyl]-amino}-piperidine-3-carboxylic acid (43.3 mg, 0.1 mmol) in DMF (1 mL) is added 2-(2-pyridyl)-2-propylamine dihydrochloride (41.8 mg, 0.2 mmol). DIPEA (0.055 mL, 0.32 mmol) is then added followed by HATU (39.9 mg, 0.105 mmol). The reaction mixture is stirred overnight at RT. The crude mixture is directly purified by prep. LC-MS with method E. LC-MS method D: $t_R$=1.07 min; [M+H]$^+$=552.15.

Compounds of Examples 1.001a to 1.199 listed in Table 1 below are prepared by applying one of the above-mentioned general procedures A, B or C to the building blocks BB-1.01-BB-1.26 coupled with commercially available amines of Structure 2.

Enantiomerically pure compounds are obtained by using one of the above mentioned chiral preparative chromatography methods.

TABLE 1

Examples 1.001-1.199

| Example Nr | Substance Name | QC LC-MS $t_R$ (min) | Mass Found $[M + H]^+$ |
|---|---|---|---|
| 1.001 | rac-(3R*,4R*)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide | 0.65 | 552 |
| 1.001a | (3R*,4R*)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide (enantiomer 1) | 0.66 | 552.3 |
| 1.001b | (3R*,4R*)-1-Cyclohexyl-4-{[5-(2,4-difluoro-phenyl)-isoxazole-3-carbonyl]-amino}-piperidine-3-carboxylic acid (1-methyl-1-pyridin-2-yl-ethyl)-amide (enantiomer 2) | 0.66 | 552.2 |
| 1.002 | rac-(3R*,4R*)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide | 0.64 | 551 |
| 1.002a | (3R*,4R*)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide (enantiomer 1) | 0.64 | 551.2 |
| 1.002b | (3R*,4R*)-1-Cyclohexyl-4-{[5-(2,4-difluoro-phenyl)-isoxazole-3-carbonyl]-amino}-piperidine-3-carboxylic acid (1-pyrimidin-2-yl-cyclopropyl)-amide (enantiomer 2) | 0.64 | 551 |
| 1.003 | rac-(3R*,4R*)-1-Cyclohexyl-4-{[5-(2,4-difluoro-phenyl)-isoxazole-3-carbonyl]-amino}-piperidine-3-carboxylic acid cyclopentylamide | 0.71 | 501.1 |
| 1.004 | rac-5-(2,4-Difluoro-phenyl)-isoxazole-3-carboxylic acid [(3R*,4R*)-1-cyclohexyl-3-(pyrrolidine-1-carbonyl)-piperidin-4-yl]-amide | 0.67 | 487.4 |
| 1.005 | rac-(3R*,4R*)-1-Cyclohexyl-4-{[5-(2,4-difluoro-phenyl)-isoxazole-3-carbonyl]-amino}-piperidine-3-carboxylic acid (2-hydroxy-ethyl)-methyl-amide | 0.6 | 491.3 |
| 1.006 | rac-(3R*,4R*)-1-Cyclohexyl-4-{[5-(2,4-difluoro-phenyl)-isoxazole-3-carbonyl]-amino}-piperidine-3-carboxylic acid (2-methoxy-ethyl)-amide | 0.61 | 491.1 |
| 1.007 | rac-(3R*,4R*)-1-Cyclohexyl-4-{[5-(2,4-difluoro-phenyl)-isoxazole-3-carbonyl]-amino}-piperidine-3-carboxylic acid isobutyl-amide | 0.71 | 489.4 |
| 1.008 | rac-(3R*,4R*)-1-Cyclohexyl-4-{[5-(2,4-difluoro-phenyl)-isoxazole-3-carbonyl]-amino}-piperidine-3-carboxylic acid isopropylamide | 0.66 | 475.3 |
| 1.009 | rac-(3R*,4R*)-1-Cyclohexyl-4-{[5-(2,4-difluoro-phenyl)-isoxazole-3-carbonyl]-amino}-piperidine-3-carboxylic acid dimethylamide | 0.63 | 461.1 |
| 1.010 | rac-(3R*,4R*)-1-Cyclohexyl-4-{[5-(2,4-difluoro-phenyl)-isoxazole-3-carbonyl]-amino}-piperidine-3-carboxylic acid methylamide | 0.58 | 447.3 |
| 1.011 | rac-(3R*,4R*)-1-Cyclohexyl-4-{[5-(2,4-difluoro-phenyl)-isoxazole-3-carbonyl]-amino}-piperidine-3-carboxylic acid (2-fluoro-ethyl)-amide | 0.61 | 479.3 |
| 1.012 | rac-(3R*,4R*)-1-Cyclohexyl-4-{[5-(2,4-difluoro-phenyl)-isoxazole-3-carbonyl]-amino}-piperidine-3-carboxylic acid ethylamide | 0.62 | 461.3 |
| 1.013 | rac-(3R*,4R*)-1-Cyclohexyl-4-{[5-(2,4-difluoro-phenyl)-isoxazole-3-carbonyl]-amino}-piperidine-3-carboxylic acid cyclopropyl-methyl-amide | 0.68 | 487.3 |
| 1.014 | rac-(3R*,4R*)-1-Cyclohexyl-4-{[5-(2,4-difluoro-phenyl)-isoxazole-3-carbonyl]-amino}-piperidine-3-carboxylic acid carbamoylmethyl-amide | 0.54 | 490.1 |
| 1.015 | rac-(3R*,4R*)-1-Cyclohexyl-4-{[5-(2,4-difluoro-phenyl)-isoxazole-3-carbonyl]-amino}-piperidine-3-carboxylic acid (2-hydroxy-ethyl)-amide | 0.56 | 477.3 |
| 1.016 | rac-5-(2,4-Difluoro-phenyl)-isoxazole-3-carboxylic acid [(3R*,4R*)-1-cyclohexyl-3-(morpholine-4-carbonyl)-piperidin-4-yl]-amide | 0.63 | 503.1 |
| 1.017 | rac-(3R*,4R*)-1-Cyclohexyl-4-{[5-(2,4-difluoro-phenyl)-isoxazole-3-carbonyl]-amino}-piperidine-3-carboxylic acid isopropyl-methyl-amide | 0.72 | 489.1 |
| 1.018 | rac-(3R*,4R*)-1-Cyclohexyl-4-{[5-(2,4-difluoro-phenyl)-isoxazole-3-carbonyl]-amino}-piperidine-3-carboxylic acid (2-dimethylamino-ethyl)-methyl-amide | 0.42 | 518.2 |
| 1.019 | rac-(3R*,4R*)-1-Cyclohexyl-4-{[5-(2,4-difluoro-phenyl)-isoxazole-3-carbonyl]-amino}-piperidine-3-carboxylic acid (2-ethoxy-ethyl)-methyl-amide | 0.71 | 519.3 |
| 1.020 | rac-(3R*,4R*)-1-Cyclohexyl-4-{[5-(2,4-difluoro-phenyl)-isoxazole-3-carbonyl]-amino}-piperidine-3-carboxylic acid (5-methyl-thiazol-2-ylmethyl)-amide | 0.66 | 544.1 |
| 1.021 | rac-(3R*,4R*)-1-Cyclohexyl-4-{[5-(2,4-difluoro-phenyl)-isoxazole-3-carbonyl]-amino}-piperidine-3-carboxylic acid (2-methoxy-ethyl)-methyl-amide | 0.67 | 505.1 |

TABLE 1-continued

Examples 1.001-1.199

| Example Nr | Substance Name | QC LC-MS t_R (min) | Mass Found [M + H]+ |
|---|---|---|---|
| 1.022 | rac-(3R*,4R*)-1-Cyclohexyl-4-{[5-(2,4-difluoro-phenyl)-isoxazole-3-carbonyl]-amino}-piperidine-3-carboxylic acid (5-methyl-isoxazol-3-ylmethyl)-amide | 0.65 | 528.3 |
| 1.023 | rac-(3R*,4R*)-1-Cyclohexyl-4-{[5-(2,4-difluoro-phenyl)-isoxazole-3-carbonyl]-amino}-piperidine-3-carboxylic acid (2-dimethylamino-ethyl)-amide | 0.4 | 504.2 |
| 1.024 | rac-(3R*,4R*)-1-Cyclohexyl-4-{[5-(2,4-difluoro-phenyl)-isoxazole-3-carbonyl]-amino}-piperidine-3-carboxylic acid ethyl-methyl-amide | 0.67 | 475.3 |
| 1.025 | rac-(3R*,4R*)-1-Cyclohexyl-4-{[5-(2,4-difluoro-phenyl)-isoxazole-3-carbonyl]-amino}-piperidine-3-carboxylic acid (pyridin-2-ylmethyl)-amide | 0.58 | 524.1 |
| 1.026 | rac-(3R*,4R*)-1-Cyclohexyl-4-{[5-(2,4-difluoro-phenyl)-isoxazole-3-carbonyl]-amino}-piperidine-3-carboxylic acid (2,2-difluoro-ethyl)-amide | 0.64 | 497.3 |
| 1.027 | rac-(3R*,4R*)-1-Cyclohexyl-4-{[5-(2,4-difluoro-phenyl)-isoxazole-3-carbonyl]-amino}-piperidine-3-carboxylic acid (3-methoxy-propyl)-methyl-amide | 0.7 | 519.3 |
| 1.028 | 5-(2,4-Difluoro-phenyl)-isoxazole-3-carboxylic acid [(3R*,4R*)-1-cyclohexyl-3-((3RS)-3-hydroxy-pyrrolidine-1-carbonyl)-piperidin-4-yl]-amide (mixture of isomers) | 0.58 | 503.3 |
| 1.029 | rac-(3R*,4R*)-1-Cyclohexyl-4-{[5-(2,4-difluoro-phenyl)-isoxazole-3-carbonyl]-amino}-piperidine-3-carboxylic acid (3-methyl-isoxazol-5-ylmethyl)-amide | 0.63 | 528.3 |
| 1.030 | rac-5-(2,4-Difluoro-phenyl)-isoxazole-3-carboxylic acid [(3R*,4R*)-3-(azetidine-1-carbonyl)-1-cyclohexyl-piperidin-4-yl]-amide | 0.62 | 473.3 |
| 1.031 | rac-(3R*,4R*)-1-Cyclohexyl-4-{[5-(2,4-difluoro-phenyl)-isoxazole-3-carbonyl]-amino}-piperidine-3-carboxylic acid (2-methyl-thiazol-4-ylmethyl)-amide | 0.65 | 544.3 |
| 1.032 | rac-(3R*,4R*)-1-Cyclohexyl-4-{[5-(2,4-difluoro-phenyl)-isoxazole-3-carbonyl]-amino}-piperidine-3-carboxylic acid (pyrimidin-2-ylmethyl)-amide | 0.58 | 525.3 |
| 1.033 | rac-(3R*,4R*)-1-Cyclohexyl-4-{[5-(2,4-difluoro-phenyl)-isoxazole-3-carbonyl]-amino}-piperidine-3-carboxylic acid (4-methyl-thiazol-5-ylmethyl)-amide | 0.61 | 544.1 |
| 1.034 | rac-(3R*,4R*)-1-Cyclohexyl-4-{[5-(2,4-difluoro-phenyl)-isoxazole-3-carbonyl]-amino}-piperidine-3-carboxylic acid (pyrimidin-4-ylmethyl)-amide | 0.57 | 525.1 |
| 1.035 | rac-(3R*,4R*)-1-Cyclohexyl-4-{[5-(2,4-difluoro-phenyl)-isoxazole-3-carbonyl]-amino}-piperidine-3-carboxylic acid (oxazol-5-ylmethyl)-amide | 0.58 | 514.3 |
| 1.036 | rac-5-(2,4-Difluoro-phenyl)-isoxazole-3-carboxylic acid [(3R*,4R*)-1-cyclohexyl-3-(3-fluoro-azetidine-1-carbonyl)-piperidin-4-yl]-amide | 0.63 | 491.3 |
| 1.037 | rac-(3R*,4R*)-1-Cyclohexyl-4-{[5-(2,4-difluoro-phenyl)-isoxazole-3-carbonyl]-amino}-piperidine-3-carboxylic acid (pyrazin-2-ylmethyl)-amide | 0.58 | 525.3 |
| 1.038 | rac-(3R*,4R*)-1-Cyclohexyl-4-{[5-(2,4-difluoro-phenyl)-isoxazole-3-carbonyl]-amino}-piperidine-3-carboxylic acid (2-trifluoromethoxy-ethyl)-amide | 0.71 | 545.3 |
| 1.039 | rac-(3R*,4R*)-1-Cyclohexyl-4-{[5-(2,4-difluoro-phenyl)-isoxazole-3-carbonyl]-amino}-piperidine-3-carboxylic acid methyl-oxetan-3-ylmethyl-amide | 0.62 | 517.1 |
| 1.040 | (3R*,4R*)-1-Cyclohexyl-4-{[5-(2,4-difluoro-phenyl)-isoxazole-3-carbonyl]-amino}-piperidine-3-carboxylic acid ((1RS)-1-pyridin-2-yl-ethyl)-amide (mixture of isomers) | 0.62 | 539 |
| 1.041 | rac-(3R*,4R*)-1-Cyclohexyl-4-{[5-(2,4-difluoro-phenyl)-isoxazole-3-carbonyl]-amino}-piperidine-3-carboxylic acid [2-(2-oxo-pyrrolidin-1-yl)-ethyl]-amide | 0.61 | 544 |
| 1.042 | rac-(3R*,4R*)-1-Cyclohexyl-4-{[5-(2,4-difluoro-phenyl)-isoxazole-3-carbonyl]-amino}-piperidine-3-carboxylic acid (1-methyl-1H-pyrazol-3-ylmetyl)-amide | 0.61 | 527.2 |
| 1.043 | rac-(3R*,4R*)-1-Cyclohexyl-4-{[5-(2,4-difluoro-phenyl)-isoxazole-3-carbonyl]-amino}-piperidine-3-carboxylic acid (1H-imidazol-4-ylmethyl)-amide | 0.39 | 513.1 |
| 1.044 | (3R*,4R*)-1-Cyclohexyl-4-{[5-(2,4-difluoro-phenyl)-isoxazole-3-carbonyl]-amino}-piperidine-3-carboxylic acid ((2RS)-tetrahydro-furan-2-ylmethyl)-amide (mixture of isomers) | 0.64 | 517.1 |
| 1.045 | rac-(3R*,4R*)-1-Cyclohexyl-4-{[5-(2,4-difluoro-phenyl)-isoxazole-3-carbonyl]-amino}-piperidine-3-carboxylic acid (1,5-dimethyl-1H-pyrazol-3-ylmethyl)-amide | 0.63 | 541.2 |
| 1.046a | (3R,4R)-1-Cyclohexyl-4-{[5-(2,4,6-trifluoro-phenyl)-isoxazole-3-carbonyl]-amino}-piperidine-3-carboxylic acid ((1S,2R)-2-phenyl-cyclopropyl)-amide or (3R,4R)-1-Cyclohexyl-4-{[5-(2,4,6-trifluoro-phenyl)-isoxazole-3-carbonyl]-amino}-piperidine-3-carboxylic acid ((1R,2S)-2-phenyl-cyclopropyl)-amide or (3S,4S)-1-Cyclohexyl-4-{[5-(2,4,6-trifluoro-phenyl)-isoxazole-3-carbonyl]-amino}-piperidine-3-carboxylic acid ((1S,2R)-2-phenyl-cyclopropyl)-amide or (3S,4S)-1-Cyclohexyl-4-{[5-(2,4,6-trifluoro- | 0.78 | 567.3 |

TABLE 1-continued

Examples 1.001-1.199

| Example Nr | Substance Name | QC LC-MS $t_R$ (min) | Mass Found [M + H]+ |
|---|---|---|---|
| | phenyl)-isoxazole-3-carbonyl]-amino}-piperidine-3-carboxylic acid ((1R,2S)-2-phenyl-cyclopropyl)-amide (1st eluted enantiomer) | | |
| 1.047 | rac-(3R*,4R*)-1-Cyclohexyl-4-{[5-(2,4-difluoro-phenyl)-isoxazole-3-carbonyl]-amino}-piperidine-3-carboxylic acid (3-ethyl-[1,2,4]oxadiazol-5-ylmethyl)-amide | 0.66 | 543.3 |
| 1.048 | rac-(3R*,4R*)-1-Cyclohexyl-4-{[5-(2,4-difluoro-phenyl)-isoxazole-3-carbonyl]-amino}-piperidine-3-carboxylic acid (pyridin-3-ylmethyl)-amide | 0.5 | 524.1 |
| 1.049 | rac-(3R*,4R*)-1-Cyclohexyl-4-{[5-(2,4-difluoro-phenyl)-isoxazole-3-carbonyl]-amino}-piperidine-3-carboxylic acid methyl-phenethyl-amide | 0.82 | 551 |
| 1.050 | rac-(3R*,4R*)-1-Cyclohexyl-4-{[5-(2,4-difluoro-phenyl)-isoxazole-3-carbonyl]-amino}-piperidine-3-carboxylic acid (pyridin-4-ylmethyl)-amide | 0.46 | 524.1 |
| 1.051 | rac-(3R*,4R*)-1-Cyclohexyl-4-{[5-(2,4-difluoro-phenyl)-isoxazole-3-carbonyl]-amino}-piperidine-3-carboxylic acid (thiazol-2-ylmethyl)-amide | 0.63 | 530.3 |
| 1.052 | rac-5-(2,4-Difluoro-phenyl)-isoxazole-3-carboxylic acid [(3R*,4R*)-1-cyclohexyl-3-(3,3-difluoro-azetidine-1-carbonyl)-piperidin-4-yl]-amide | 0.67 | 509.3 |
| 1.053 | (3R*,4R*)-1-Cyclohexyl-4-{[5-(2,4-difluoro-phenyl)-isoxazole-3-carbonyl]-amino}-piperidine-3-carboxylic acid ((3RS)-tetrahydro-furan-3-ylmethyl)-amide (mixture of isomers) | 0.61 | 517.4 |
| 1.054 | rac-(3R*,4R*)-1-Cyclohexyl-4-{[5-(2,4-difluoro-phenyl)-isoxazole-3-carbonyl]-amino}-piperidine-3-carboxylic acid (2,5-dimethyl-2H-pyrazol-3-ylmethyl)-amide | 0.61 | 541.2 |
| 1.055 | rac-(3R*,4R*)-1-Cyclohexyl-4-{[5-(2,4-difluoro-phenyl)-isoxazole-3-carbonyl]-amino}-piperidine-3-carboxylic acid [2-(2-hydroxy-ethoxy)-ethyl]-isopropyl-amide | 0.46 | 563.2 |
| 1.056 | rac-(3R*,4R*)-1-Cyclohexyl-4-{[5-(2,4-difluoro-phenyl)-isoxazole-3-carbonyl]-amino}-piperidine-3-carboxylic acid (2-o-tolyl-ethyl)-amide | 0.8 | 551.2 |
| 1.057 | rac-(3R*,4R*)-1-Cyclohexyl-4-{[5-(2,4-difluoro-phenyl)-isoxazole-3-carbonyl]-amino}-piperidine-3-carboxylic acid [2-(2-methoxy-phenyl)-ethyl]-amide | 0.78 | 567.4 |
| 1.058 | rac-(3R*,4R*)-1-Cyclohexyl-4-{[5-(2,4-difluoro-phenyl)-isoxazole-3-carbonyl]-amino}-piperidine-3-carboxylic acid [2-(2-chloro-phenyl)-ethyl]-amide | 0.81 | 571 |
| 1.059 | rac-(3R*,4R*)-1-Cyclohexyl-4-{[5-(2,4-difluoro-phenyl)-isoxazole-3-carbonyl]-amino}-piperidine-3-carboxylic acid [2-(4-fluoro-phenyl)-ethyl]-amide | 0.77 | 555.1 |
| 1.060 | (3R*,4R*)-1-Cyclohexyl-4-{[5-(2,4-difluoro-phenyl)-isoxazole-3-carbonyl]-amino}-piperidine-3-carboxylic acid ((2RS)-2-phenyl-propyl)-amide (mixture of isomers) | 0.8 | 551.4 |
| 1.061 | (3R*,4R*)-1-Cyclohexyl-4-{[5-(2,4-difluoro-phenyl)-isoxazole-3-carbonyl]-amino}-piperidine-3-carboxylic acid ((1R*,2S*)-2-phenyl-cyclopropyl)-amide and (3R*,4R*)-1-Cyclohexyl-4-{[5-(2,4-difluoro-phenyl)-isoxazole-3-carbonyl]-amino}-piperidine-3-carboxylic acid ((1S*,2R*)-2-phenyl-cyclopropyl)-amide (mixture of isomers) | 0.79 | 549.4 |
| 1.062 | rac-(3R*,4R*)-1-Cyclohexyl-4-{[5-(2,4-difluoro-phenyl)-isoxazole-3-carbonyl]-amino}-piperidine-3-carboxylic acid (2-p-tolyl-ethyl)-amide | 0.82 | 551 |
| 1.063 | (3R*,4R*)-1-Cyclohexyl-4-{[5-(2,4-difluoro-phenyl)-isoxazole-3-carbonyl]-amino}-piperidine-3-carboxylic acid ((1RS)-1-(pyrimidin-4-yl)-ethyl)-amide (mixture of isomers) | 0.59 | 539 |
| 1.064 | rac-(3R*,4R*)-1-Cyclohexyl-4-{[5-(2,4-difluoro-phenyl)-isoxazole-3-carbonyl]-amino}-piperidine-3-carboxylic acid phenylamide | 0.74 | 509.3 |
| 1.065 | rac-(3R*,4R*)-1-Cyclohexyl-4-{[5-(2,4-difluoro-phenyl)-isoxazole-3-carbonyl]-amino}-piperidine-3-carboxylic acid (4,5-dimethyl-thiazol-2-yl)-amide | 0.77 | 544.1 |
| 1.066 | rac-(3R*,4R*)-1-Cyclohexyl-4-{[5-(2,4-difluoro-phenyl)-isoxazole-3-carbonyl]-amino}-piperidine-3-carboxylic acid (2-m-tolyl-ethyl)-amide | 0.81 | 551.2 |
| 1.067 | rac-(3R*,4R*)-1-Cyclohexyl-4-{[5-(2,4-difluoro-phenyl)-isoxazole-3-carbonyl]-amino}-piperidine-3-carboxylic acid pyridin-3-ylamide | 0.57 | 510.1 |
| 1.068 | rac-(3R*,4R*)-1-Cyclohexyl-4-{[5-(2,4-difluoro-phenyl)-isoxazole-3-carbonyl]-amino}-piperidine-3-carboxylic acid (4-methyl-thiazol-2-ylmethyl)-amide | 0.66 | 544.1 |
| 1.069 | (3R*,4R*)-1-Cyclohexyl-4-{[5-(2,4-difluoro-phenyl)-isoxazole-3-carbonyl]-amino}-piperidine-3-carboxylic acid ((1RS)-2,2,2-trifluoro-1-pyridin-2-yl-ethyl)-amide (mixture of isomers) | 0.73 | 592.3 |
| 1.070 | 5-(2,4-Difluoro-phenyl)-isoxazole-3-carboxylic acid [(3R*,4R*)-1-cyclohexyl-3-((3RS)-3-phenyl-pyrrolidine-1-carbonyl)-piperidin-4-yl]-amide (mixture of isomers) | 0.81 | 563 |
| 1.071 | rac-(3R*,4R*)-1-Cyclohexyl-4-{[5-(2,4-difluoro-phenyl)-isoxazole-3-carbonyl]-amino}-piperidine-3-carboxylic acid (1-pyridin-2-yl-cyclopropyl)-amide | 0.63 | 550.2 |
| 1.072 | (3R*,4R*)-1-Cyclohexyl-4-{[5-(2,4-difluoro-phenyl)-isoxazole-3-carbonyl]-amino}-piperidine-3-carboxylic acid ((R)-2-hydroxy-2-phenyl-ethyl)-amide (mixture of isomers) | 0.69 | 553 |

TABLE 1-continued

Examples 1.001-1.199

| Example Nr | Substance Name | $t_R$ (min) | Mass Found $[M + H]^+$ |
|---|---|---|---|
| 1.073 | (3R*,4R*)-1-Cyclohexyl-4-{[5-(2,4-difluoro-phenyl)-isoxazole-3-carbonyl]-amino}-piperidine-3-carboxylic acid ((S)-2-hydroxy-2-phenyl-ethyl)-amide (mixture of isomers) | 0.69 | 553.3 |
| 1.074 | rac-(3R*,4R*)-1-Cyclohexyl-4-{[5-(2,4-difluoro-phenyl)-isoxazole-3-carbonyl]-amino}-piperidine-3-carboxylic acid (2-pyridin-2-yl-ethyl)-amide | 0.52 | 538.3 |
| 1.075 | rac-(3R*,4R*)-1-Cyclohexyl-4-{[5-(2,4-difluoro-phenyl)-isoxazole-3-carbonyl]-amino}-piperidine-3-carboxylic acid methyl-(2-pyridin-2-yl-ethyl)-amide | 0.57 | 552.2 |
| 1.076 | (3R*,4R*)-1-Cyclohexyl-4-{[5-(2,4-difluoro-phenyl)-isoxazole-3-carbonyl]-amino}-piperidine-3-carboxylic acid ((1RS)-2-hydroxy-1-methyl-ethyl)-amide (mixture of isomers) | 0.58 | 491.1 |
| 1.077 | (3R*,4R*)-1-Cyclohexyl-4-{[5-(2,4-difluoro-phenyl)-isoxazole-3-carbonyl]-amino}-piperidine-3-carboxylic acid ((1RS)-2,2-difluoro-1-methyl-ethyl)-amide (mixture of isomers) | 0.67 | 511.3 |
| 1.078 | (3R*,4R*)-1-Cyclohexyl-4-{[5-(2,4-difluoro-phenyl)-isoxazole-3-carbonyl]-amino}-piperidine-3-carboxylic acid ((1RS)-1-cyclobutyl-ethyl)-amide (mixture of isomers) | 0.77 | 515.4 |
| 1.079 | rac-(3R*,4R*)-1-Cyclohexyl-4-{[5-(2,4-difluoro-phenyl)-isoxazole-3-carbonyl]-amino}-piperidine-3-carboxylic acid (2-fluoro-1,1-dimethyl-ethyl)-amide | 0.7 | 507 |
| 1.080 | rac-(3R*,4R*)-1-Cyclohexyl-4-{[5-(2,4-difluoro-phenyl)-isoxazole-3-carbonyl]-amino}-piperidine-3-carboxylic acid (3,3,3-trifluoro-1,1-dimethyl-propyl)-amide | 0.78 | 557.3 |
| 1.081 | rac-(3R*,4R*)-1-Cyclohexyl-4-{[5-(2,4-difluoro-phenyl)-isoxazole-3-carbonyl]-amino}-piperidine-3-carboxylic acid (2-methanesulfonyl-1,1-dimethyl-ethyl)-amide | 0.63 | 567.1 |
| 1.082 | (3R*,4R*)-1-Cyclohexyl-4-{[5-(2,4-difluoro-phenyl)-isoxazole-3-carbonyl]-amino}-piperidine-3-carboxylic acid ((1RS)-2-fluoro-1-methyl-ethyl)-amide (mixture of isomers) | 0.64 | 493.3 |
| 1.083 | (3R*,4R*)-1-Cyclohexyl-4-{[5-(2,4-difluoro-phenyl)-isoxazole-3-carbonyl]-amino}-piperidine-3-carboxylic acid ((1RS)-2-ethoxy-1-methyl-ethyl)-amide (mixture of isomers) | 0.69 | 519.4 |
| 1.084 | (3R*,4R*)-1-Cyclohexyl-4-{[5-(2,4-difluoro-phenyl)-isoxazole-3-carbonyl]-amino}-piperidine-3-carboxylic acid ((3RS)-3-methyl-tetrahydro-furan-3-yl)-amide (mixture of isomers) | 0.64 | 517.2 |
| 1.085 | (3R*,4R*)-1-Cyclohexyl-4-{[5-(2,4-difluoro-phenyl)-isoxazole-3-carbonyl]-amino}-piperidine-3-carboxylic acid [(1RS)-1-(5-methyl-[1,3,4]oxadiazol-2-yl)-ethyl]-amide (mixture of isomers) | 0.62 | 543 |
| 1.086 | (3R*,4R*)-1-Cyclohexyl-4-{[5-(2,4-difluoro-phenyl)-isoxazole-3-carbonyl]-amino}-piperidine-3-carboxylic acid [(1RS)-1-(3,5-difluoro-pyridin-2-yl)-ethyl]-amide (mixture of isomers) | 0.74 | 574 |
| 1.087 | rac-(3R*,4R*)-1-Cyclohexyl-4-{[5-(2,4-difluoro-phenyl)-isoxazole-3-carbonyl]-amino}-piperidine-3-carboxylic acid (3,3-difluoro-1-methyl-cyclobutyl)-amide (mixture of isomers) | 0.73 | 537.3 |
| 1.088 | rac-(3R*,4R*)-1-Cyclohexyl-4-{[5-(2,4-difluoro-phenyl)-isoxazole-3-carbonyl]-amino}-piperidine-3-carboxylic acid (2-hydroxy-1,1-dimethyl-ethyl)-amide | 0.63 | 505.2 |
| 1.089 | 5-(2,4-Difluoro-phenyl)-isoxazole-3-carboxylic acid [(3R*,4R*)-1-cyclohexyl-3-((3RS)-3-pyridin-2-yl-pyrrolidine-1-carbonyl)-piperidin-4-yl]-amide (mixture of isomers) | 0.64 | 564 |
| 1.090 | (3R*,4R*)-1-Cyclohexyl-4-{[5-(2,4-difluoro-phenyl)-isoxazole-3-carbonyl]-amino}-piperidine-3-carboxylic acid ((R)-1-pyrazin-2-yl-ethyl)-amide (mixture of isomers) | 0.61 | 539.4 |
| 1.091 | (3R*,4R*)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide (mixture of isomers) | 0.77 | 515.4 |
| 1.092 | (3R*,4R*)-1-Cyclohexyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide (mixture of isomers) | 0.72 | 556.4 |
| 1.093 | (3R*,4R*)-1-Cyclohexyl-4-{[5-(2,4-difluoro-phenyl)-isoxazole-3-carbonyl]-amino}-piperidine-3-carboxylic acid ((R)-1,2,2-trimethyl-propyl)-amide (mixture of isomers) | 0.79 | 517.4 |
| 1.094 | (3R*,4R*)-1-Cyclohexyl-4-{[5-(2,4-difluoro-phenyl)-isoxazole-3-carbonyl]-amino}-piperidine-3-carboxylic acid [(R)-1-(5-fluoro-pyrimidin-2-yl)-ethyl]-amide (mixture of isomers) | 0.66 | 557 |
| 1.095 | rac-(3R*,4R*)-1-Cyclohexyl-4-{[1-(2,4-difluoro-phenyl)-1H-[1,2,3]triazole-4-carbonyl]-amino}-piperidine-3-carboxylic acid dimethylamide | 0.55 | 461.3 |
| 1.095a | (3R,4R)-1-Cyclohexyl-4-{[1-(2,4-difluoro-phenyl)-1H-[1,2,3]triazole-4-carbonyl]-amino}-piperidine-3-carboxylic acid dimethylamide or (3S,4S)-1-Cyclohexyl-4-{[1-(2,4-difluoro-phenyl)-1H-[1,2,3]triazole-4-carbonyl]-amino}-piperidine-3-carboxylic acid dimethylamide (1st eluted enantiomer) | 0.55 | 461.3 |

TABLE 1-continued

Examples 1.001-1.199

| Example Nr | Substance Name | QC LC-MS t_R (min) | Mass Found [M + H]+ |
|---|---|---|---|
| 1.096 | rac-(3R*,4R*)-1-Cyclopentyl-4-{[1-(2,4-difluoro-phenyl)-1H-[1,2,3]triazole-4-carbonyl]-amino}-piperidine-3-carboxylic acid dimethylamide | 0.5 | 447.2 |
| 1.097 | rac-(3R*,4R*)-1-Cyclopropylmethyl-4-{[1-(2,4-difluoro-phenyl)-1H-[1,2,3]triazole-4-carbonyl]-amino}-piperidine-3-carboxylic acid dimethylamide | 1 | 433.3 |
| 1.098 | (3R*,4R*)-4-{[1-(2,4-Difluoro-phenyl)-1H-[1,2,3]triazole-4-carbonyl]-amino}-1-((1RS,2RS)-2-Methyl-cyclopentyl)-piperidine-3-carboxylic acid dimethylamide (mixture of isomers) | 0.55 | 461.3 |
| 1.099 | rac-(3R*,4R*)-1-Cyclopentyl-4-{[5-(2,4,6-trifluoro-phenyl)-isoxazole-3-carbonyl]-amino}-piperidine-3-carboxylic acid dimethylamide | 0.59 | 465.3 |
| 1.100 | rac-(3R*,4R*)-1-Cyclopropylmethyl-4-{[5-(2,4,6-trifluoro-phenyl)-isoxazole-3-carbonyl]-amino}-piperidine-3-carboxylic acid dimethylamide | 0.58 | 451.3 |
| 1.101 | (3R*,4R*)-1-((1RS,2RS)-2-Methyl-cyclopentyl)-4-{[5-(2,4,6-trifluoro-phenyl)-isoxazole-3-carbonyl]-amino}-piperidine-3-carboxylic acid dimethylamide (mixture of isomers) | 0.63 | 479.3 |
| 1.102 | rac-(3R*,4R*)-1-Cyclohexyl-4-{[3-(2,4-difluoro-phenyl)-isoxazole-5-carbonyl]-amino}-piperidine-3-carboxylic acid dimethylamide | 0.62 | 461 |
| 1.103 | rac-(3R*,4R*)-1-Cyclopentyl-4-{[3-(2,4-difluoro-phenyl)-isoxazole-5-carbonyl]-amino}-piperidine-3-carboxylic acid dimethylamide | 0.57 | 447 |
| 1.104 | rac-1-(2,4-Difluoro-phenyl)-1H-[1,2,3]triazole-4-carboxylic acid [(3R*,4R*)-3-(azetidine-1-carbonyl)-1-cyclohexyl-piperidin-4-yl]-amide | 0.54 | 473.3 |
| 1.105 | rac-5-(2,4,6-Trifluoro-phenyl)-isoxazole-3-carboxylic acid [(3R*,4R*)-3-(azetidine-1-carbonyl)-1-cyclohexyl-piperidin-4-yl]-amide | 0.62 | 491 |
| 1.106 | rac-5-(2,4,6-Trifluoro-phenyl)-isoxazole-3-carboxylic acid [(3R*,4R*)-3-(azetidine-1-carbonyl)-1-cyclopentyl-piperidin-4-yl]-amide | 0.58 | 477.1 |
| 1.107 | rac-5-(2,4,6-Trifluoro-phenyl)-isoxazole-3-carboxylic acid [(3R*,4R*)-3-(azetidine-1-carbonyl)-1-cyclopropylmethyl-piperidin-4-yl]-amide | 0.57 | 463.3 |
| 1.108 | 5-(2,4,6-Trifluoro-phenyl)-isoxazole-3-carboxylic acid [(3R*,4R*)-3-(azetidine-1-carbonyl)-1-((1RS,2RS)-2-methyl-cyclopentyl)-piperidin-4-yl]-amide (mixture of isomers) | 0.62 | 491.3 |
| 1.109 | rac-(3R*,4R*)-1-Cyclopentyl-4-{[1-(2,4-difluoro-phenyl)-1H-[1,2,3]triazole-4-carbonyl]-amino}-piperidine-3-carboxylic acid (2-methoxy-1,1-dimethyl-ethyl)-amide | 0.6 | 505 |
| 1.110 | rac-(3R*,4R*)-1-Cyclopropylmethyl-4-{[1-(2,4-difluoro-phenyl)-1H-[1,2,3]triazole-4-carbonyl]-amino}-piperidine-3-carboxylic acid (2-methoxy-1,1-dimethyl-ethyl)-amide | 1.1 | 491.3 |
| 1.111 | rac-(3R*,4R*)-1-Cyclohexyl-4-{[5-(2,4,6-trifluoro-phenyl)-isoxazole-3-carbonyl]-amino}-piperidine-3-carboxylic acid (2-methoxy-1,1-dimethyl-ethyl)-amide | 0.71 | 537.3 |
| 1.111a | (3R*,4R*)-1-Cyclohexyl-4-{[5-(2,4,6-trifluoro-phenyl)-isoxazole-3-carbonyl]-amino}-piperidine-3-carboxylic acid (2-methoxy-1,1-dimethyl-ethyl)-amide (enantiomer 1) | 0.71 | 537.3 |
| 1.111b | (3R*,4R*)-1-Cyclohexyl-4-{[5-(2,4,6-trifluoro-phenyl)-isoxazole-3-carbonyl]-amino}-piperidine-3-carboxylic acid (2-methoxy-1,1-dimethyl-ethyl)-amide (enantiomer 2) | 0.71 | 537.2 |
| 1.112 | rac-(3R*,4R*)-1-Cyclopentyl-4-{[5-(2,4,6-trifluoro-phenyl)-isoxazole-3-carbonyl]-amino}-piperidine-3-carboxylic acid (2-methoxy-1,1-dimethyl-ethyl)-amide | 0.68 | 523 |
| 1.113 | rac-(3R*,4R*)-1-Cyclopropylmethyl-4-{[5-(2,4,6-trifluoro-phenyl)-isoxazole-3-carbonyl]-amino}-piperidine-3-carboxylic acid (2-methoxy-1,1-dimethyl-ethyl)-amide | 0.67 | 509 |
| 1.113a | (3R*,4R*)-1-Cyclopropylmethyl-4-{[5-(2,4,6-trifluoro-phenyl)-isoxazole-3-carbonyl]-amino}-piperidine-3-carboxylic acid (2-methoxy-1,1-dimethyl-ethyl)-amide (enantiomer 1) | 0.67 | 509.1 |
| 1.113b | (3R*,4R*)-1-Cyclopropylmethyl-4-{[5-(2,4,6-trifluoro-phenyl)-isoxazole-3-carbonyl]-amino}-piperidine-3-carboxylic acid (2-methoxy-1,1-dimethyl-ethyl)-amide (enantiomer 2) | 0.67 | 509.3 |
| 1.114 | (3R*,4R*)-1-((1RS,2RS)-2-Methyl-cyclopentyl)-4-{[5-(2,4,6-trifluoro-phenyl)-isoxazole-3-carbonyl]-amino}-piperidine-3-carboxylic acid (2-methoxy-1,1-dimethyl-ethyl)-amide (mixture of isomers) | 0.7 | 537 |
| 1.115 | rac-(3R*,4R*)-1-Cyclohexyl-4-{[3-(2,4-difluoro-phenyl)-isoxazole-5-carbonyl]-amino}-piperidine-3-carboxylic acid (2-methoxy-1,1-dimethyl-ethyl)-amide | 0.69 | 519 |
| 1.116 | rac-(3R*,4R*)-1-Cyclopentyl-4-{[3-(2,4-difluoro-phenyl)-isoxazole-5-carbonyl]-amino}-piperidine-3-carboxylic acid (2-methoxy-1,1-dimethyl-ethyl)-amide | 0.67 | 505.3 |
| 1.117 | (3R*,4R*)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide (mixture of isomers) | 0.54 | 538.2 |
| 1.117a | (3S,4S)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)- | 0.54 | 538.1 |

TABLE 1-continued

Examples 1.001-1.199

| Example Nr | Substance Name | QC LC-MS $t_R$ (min) | Mass Found $[M + H]^+$ |
|---|---|---|---|
| | amide or (3R,4R)-1-Cyclohexyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide ($2^{nd}$ eluted enantiomer) | | |
| 1.118 | (3R*,4R*)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide (mixture of isomers) | 0.5 | 524.2 |
| 1.118a | (3S,4S)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide or (3R,4R)-1-Cyclopentyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide ($2^{nd}$ eluted enantiomer) | 0.51 | 524.1 |
| 1.119 | (3R*,4R*)-1-Cyclopropylmethyl-4-{[1-(2,4-difluoro-phenyl)-1H-[1,2,3]triazole-4-carbonyl]-amino}-piperidine-3-carboxylic acid ((R)-1-pyridin-2-yl-ethyl)-amide (mixture of isomers) | 0.49 | 510.1 |
| 1.120 | (3R*,4R*)-4-{[1-(2,4-Difluoro-phenyl)-1H-[1,2,3]triazole-4-carbonyl]-amino}-1-((1RS,2RS)-2-Methyl-cyclopentyl)-piperidine-3-carboxylic acid ((R)-1-pyridin-2-yl-ethyl)-amide (mixture of isomers) | 0.53 | 538.2 |
| 1.121 | (3R*,4R*)-1-Cyclohexyl-4-{[5-(2,4,6-trifluoro-phenyl)-isoxazole-3-carbonyl]-amino}-piperidine-3-carboxylic acid ((R)-1-pyridin-2-yl-ethyl)-amide (mixture of isomers) | 0.63 | 556.1 |
| 1.121a | (3R*,4R*)-1-Cyclohexyl-4-{[5-(2,4,6-trifluoro-phenyl)-isoxazole-3-carbonyl]-amino}-piperidine-3-carboxylic acid ((R)-1-pyridin-2-yl-ethyl)-amide (enantiomer 1) | 0.61 | 556.1 |
| 1.121b | (3R*,4R*)-1-Cyclohexyl-4-{[5-(2,4,6-trifluoro-phenyl)-isoxazole-3-carbonyl]-amino}-piperidine-3-carboxylic acid ((R)-1-pyridin-2-yl-ethyl)-amide (enantiomer 2) | 0.63 | 556.1 |
| 1.122 | (3R*,4R*)-1-Cyclopentyl-4-{[5-(2,4,6-trifluoro-phenyl)-isoxazole-3-carbonyl]-amino}-piperidine-3-carboxylic acid ((R)-1-pyridin-2-yl-ethyl)-amide (mixture of isomers) | 0.6 | 542.3 |
| 1.122a | (3R*,4R*)-1-Cyclopentyl-4-{[5-(2,4,6-trifluoro-phenyl)-isoxazole-3-carbonyl]-amino}-piperidine-3-carboxylic acid ((R)-1-pyridin-2-yl-ethyl)-amide (enantiomer 1) | 0.58 | 542.1 |
| 1.122b | (3R*,4R*)-1-Cyclopentyl-4-{[5-(2,4,6-trifluoro-phenyl)-isoxazole-3-carbonyl]-amino}-piperidine-3-carboxylic acid ((R)-1-pyridin-2-yl-ethyl)-amide (enantiomer 2) | 0.6 | 542.1 |
| 1.123 | (3R*,4R*)-1-Cyclopropylmethyl-4-{[5-(2,4,6-trifluoro-phenyl)-isoxazole-3-carbonyl]-amino}-piperidine-3-carboxylic acid ((R)-1-pyridin-2-yl-ethyl)-amide (mixture of isomers) | 0.57 | 528.1 |
| 1.123a | (3S,4S)-1-Cyclopropylmethyl-4-{[5-(2,4,6-trifluoro-phenyl)-isoxazole-3-carbonyl]-amino}-piperidine-3-carboxylic acid ((R)-1-pyridin-2-yl-ethyl)-amide or (3R,4R)-1-Cyclopropylmethyl-4-{[5-(2,4,6-trifluoro-phenyl)-isoxazole-3-carbonyl]-amino}-piperidine-3-carboxylic acid ((R)-1-pyridin-2-yl-ethyl)-amide ($2^{nd}$ eluted enantiomer) | 0.58 | 528 |
| 1.124 | (3R*,4R*)-1-((1RS,2RS)-2-Methyl-cyclopentyl)-4-{[5-(2,4,6-trifluoro-phenyl)-isoxazole-3-carbonyl]-amino}-piperidine-3-carboxylic acid ((R)-1-pyridin-2-yl-ethyl)-amide (mixture of isomers) | 0.62 | 556.1 |
| 1.125 | (3R*,4R*)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide (mixture of isomers) | 0.61 | 538.2 |
| 1.125a | (3S,4S)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide or (3R,4R)-1-Cyclohexyl-4-{[3-(2,4-difluoro-phenyl)-isoxazole-5-carbonyl]-amino}-piperidine-3-carboxylic acid ((R)-1-pyridin-2-yl-ethyl)-amide ($2^{nd}$ eluted enantiomer) | 0.62 | 538.2 |
| 1.126 | (3R*,4R*)-1-Cyclopentyl-4-{[3-(2,4-difluoro-phenyl)-isoxazole-5-carbonyl]-amino}-piperidine-3-carboxylic acid ((R)-1-pyridin-2-yl-ethyl)-amide (mixture of isomers) | 0.58 | 524.1 |
| 1.127 | (3R*,4R*)-1-Cyclohexyl-4-{[1-(2,4-difluoro-phenyl)-1H-[1,2,3]triazole-4-carbonyl]-amino}-piperidine-3-carboxylic acid ((R)-1-pyrazin-2-yl-ethyl)-amide (mixture of isomers) | 1 | 539.1 |
| 1.128 | (3R*,4R*)-1-Cyclopentyl-4-{[1-(2,4-difluoro-phenyl)-1H-[1,2,3]triazole-4-carbonyl]-amino}-piperidine-3-carboxylic acid ((R)-1-pyrazin-2-yl-ethyl)-amide (mixture of isomers) | 1 | 525.1 |
| 1.129 | (3R*,4R*)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide (mixture of isomers) | 0.6 | 557.2 |
| 1.129a | (3R*,4R*)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide (enantiomer 1) | 0.6 | 557.4 |
| 1.129b | (3R*,4R*)-1-Cyclohexyl-4-{[5-(2,4,6-trifluoro-phenyl)-isoxazole-3-carbonyl]-amino}-piperidine-3-carboxylic acid ((R)-1-pyrazin-2-yl-ethyl)-amide (enantiomer 2) | 0.63 | 557.2 |

TABLE 1-continued

Examples 1.001-1.199

| Example Nr | Substance Name | QC LC-MS $t_R$ (min) | Mass Found $[M + H]^+$ |
|---|---|---|---|
| 1.130 | (3R*,4R*)-1-Cyclopentyl-4-{[5-(2,4,6-trifluoro-phenyl)-isoxazole-3-carbonyl]-amino}-piperidine-3-carboxylic acid ((R)-1-pyrazin-2-yl-ethyl)-amide (mixture of isomers) | 0.59 | 543.3 |
| 1.131 | (3R*,4R*)-1-Cyclopropylmethyl-4-{[5-(2,4,6-trifluoro-phenyl)-isoxazole-3-carbonyl]-amino}-piperidine-3-carboxylic acid ((R)-1-pyrazin-2-yl-ethyl)-amide (mixture of isomers) | 0.59 | 529 |
| 1.132 | (3R*,4R*)-1-((1RS,2RS)-2-Methyl-cyclopentyl)-4-{[5-(2,4,6-trifluoro-phenyl)-isoxazole-3-carbonyl]-amino}-piperidine-3-carboxylic acid ((R)-1-pyrazin-2-yl-ethyl)-amide (mixture of isomers) | 0.62 | 557.3 |
| 1.133 | (3R*,4R*)-1-Cyclohexyl-4-{[3-(2,4-difluoro-phenyl)-isoxazole-5-carbonyl]-amino}-piperidine-3-carboxylic acid ((R)-1-pyrazin-2-yl-ethyl)-amide (mixture of isomers) | 0.59 | 539.3 |
| 1.134 | (3R*,4R*)-1-Cyclohexyl-4-{[1-(2,4-difluoro-phenyl)-1H-[1,2,3]triazole-4-carbonyl]-amino}-piperidine-3-carboxylic acid ((R)-1-cyclobutyl-ethyl)-amide (mixture of isomers) | 0.69 | 515.4 |
| 1.135 | (3R*,4R*)-1-Cyclopentyl-4-{[1-(2,4-difluoro-phenyl)-1H-[1,2,3]triazole-4-carbonyl]-amino}-piperidine-3-carboxylic acid ((R)-1-cyclobutyl-ethyl)-amide (mixture of isomers) | 0.66 | 501.4 |
| 1.136 | (3R*,4R*)-1-Cyclopropylmethyl-4-{[1-(2,4-difluoro-phenyl)-1H-[1,2,3]triazole-4-carbonyl]-amino}-piperidine-3-carboxylic acid ((R)-1-cyclobutyl-ethyl)-amide (mixture of isomers) | 0.64 | 487.3 |
| 1.137 | (3R*,4R*)-4-{[1-(2,4-Difluoro-phenyl)-1H-[1,2,3]triazole-4-carbonyl]-amino}-1-((1RS,2RS)-2-Methyl-cyclopentyl)-piperidine-3-carboxylic acid ((R)-1-cyclobutyl-ethyl)-amide (mixture of isomers) | 0.68 | 515.4 |
| 1.138 | (3R*,4R*)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide (mixture of isomers) | 0.74 | 519.3 |
| 1.138a | (3R*,4R*)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide (enantiomer 1) | 0.73 | 519.2 |
| 1.138b | (3R*,4R*)-1-Cyclopentyl-4-{[5-(2,4,6-trifluoro-phenyl)-isoxazole-3-carbonyl]-amino}-piperidine-3-carboxylic acid ((R)-1-cyclobutyl-ethyl)-amide (enantiomer 2) | 0.74 | 519.1 |
| 1.139 | (3R*,4R*)-1-Cyclopropylmethyl-4-{[5-(2,4,6-trifluoro-phenyl)-isoxazole-3-carbonyl]-amino}-piperidine-3-carboxylic acid ((R)-1-cyclobutyl-ethyl)-amide (mixture of isomers) | 0.72 | 505.3 |
| 1.139a | (3R*,4R*)-1-Cyclopropylmethyl-4-{[5-(2,4,6-trifluoro-phenyl)-isoxazole-3-carbonyl]-amino}-piperidine-3-carboxylic acid ((R)-1-cyclobutyl-ethyl)-amide (enantiomer 1) | 0.71 | 505.1 |
| 1.139b | (3R*,4R*)-1-Cyclopropylmethyl-4-{[5-(2,4,6-trifluoro-phenyl)-isoxazole-3-carbonyl]-amino}-piperidine-3-carboxylic acid ((R)-1-cyclobutyl-ethyl)-amide (enantiomer 2) | 0.73 | 505.3 |
| 1.140 | (3R*,4R*)-1-Cyclohexyl-4-{[3-(2,4-difluoro-phenyl)-isoxazole-5-carbonyl]-amino}-piperidine-3-carboxylic acid ((R)-1-cyclobutyl-ethyl)-amide (mixture of isomers) | 0.75 | 515.4 |
| 1.141 | (3R*,4R*)-1-Cyclopentyl-4-{[3-(2,4-difluoro-phenyl)-isoxazole-5-carbonyl]-amino}-piperidine-3-carboxylic acid ((R)-1-cyclobutyl-ethyl)-amide (mixture of isomers) | 0.73 | 501.3 |
| 1.142 | rac-(3R*,4R*)-1-Cyclohexyl-4-{[1-(2,4-difluoro-phenyl)-1H-[1,2,3]triazole-4-carbonyl]-amino}-piperidine-3-carboxylic acid [1-(5-fluoro-pyridin-2-yl)-cyclopropyl]-amide | 0.64 | 568.2 |
| 1.143 | rac-(3R*,4R*)-1-Cyclohexyl-4-{[5-(2,4,6-trifluoro-phenyl)-isoxazole-3-carbonyl]-amino}-piperidine-3-carboxylic acid [1-(5-fluoro-pyridin-2-yl)-cyclopropyl]-amide | 0.72 | 586.1 |
| 1.144 | rac-(3R*,4R*)-1-Cyclopropylmethyl-4-{[5-(2,4,6-trifluoro-phenyl)-isoxazole-3-carbonyl]-amino}-piperidine-3-carboxylic acid [1-(5-fluoro-pyridin-2-yl)-cyclopropyl]-amide | 0.68 | 558.3 |
| 1.145 | (3R*,4R*)-1-Cyclohexyl-4-{[1-(2,4-difluoro-phenyl)-1H-[1,2,3]triazole-4-carbonyl]-amino}-piperidine-3-carboxylic acid ((1R*,2S*)-2-phenyl-cyclopropyl)-amide and (3R*,4R*)-1-Cyclohexyl-4-{[1-(2,4-difluoro-phenyl)-1H-[1,2,3]triazole-4-carbonyl]-amino}-piperidine-3-carboxylic acid ((1S*,2R*)-2-phenyl-cyclopropyl)-amide (mixture of isomers) | 0.72 | 549.4 |
| 1.146 | (3R*,4R*)-1-Cyclopentyl-4-{[1-(2,4-difluoro-phenyl)-1H-[1,2,3]triazole-4-carbonyl]-amino}-piperidine-3-carboxylic acid ((1S*,2R*)-2-phenyl-cyclopropyl)-amide and (3R*,4R*)-1-Cyclopentyl-4-{[1-(2,4-difluoro-phenyl)-1H-[1,2,3]triazole-4-carbonyl]-amino}-piperidine-3-carboxylic acid ((1R*,2S*)-2-phenyl-cyclopropyl)-amide (mixture of isomers) | 0.69 | 535.3 |
| 1.147 | (3R*,4R*)-1-Cyclohexyl-4-{[3-(2,4-difluoro-phenyl)-isoxazole-5-carbonyl]-amino}-piperidine-3-carboxylic acid ((1S*,2R)-2-phenyl-cyclopropyl)-amide and (3R*,4R*)-1-Cyclohexyl-4-{[3-(2,4-difluoro-phenyl)-isoxazole-5-carbonyl]-amino}-piperidine-3-carboxylic acid ((1R*,2S*)-2-phenyl-cyclopropyl)-amide(mixture of isomers) | 0.77 | 549.4 |

TABLE 1-continued

Examples 1.001-1.199

| Example Nr | Substance Name | QC LC-MS $t_R$ (min) | Mass Found [M + H]+ |
|---|---|---|---|
| 1.148 | (3R*,4R*)-1-Cyclopentyl-4-{[3-(2,4-difluoro-phenyl)-isoxazole-5-carbonyl]-amino}-piperidine-3-carboxylic acid ((1S*,2R*)-2-phenyl-cyclopropyl)-amide and (3R*,4R*)-1-Cyclopentyl-4-{[3-(2,4-difluoro-phenyl)-isoxazole-5-carbonyl]-amino}-piperidine-3-carboxylic acid ((1R*,2S*)-2-phenyl-cyclopropyl)-amide (mixture of isomers) | 0.75 | 535.3 |
| 1.149 | rac-(3R*,4R*)-1-Cyclopropylmethyl-4-{[3-(2,4-difluoro-phenyl)-isoxazole-5-carbonyl]-amino}-piperidine-3-carboxylic acid dimethylamide | 0.56 | 433.2 |
| 1.150 | (3R*,4R*)-4-{[3-(2,4-Difluoro-phenyl)-isoxazole-5-carbonyl]-amino}-1-((1RS,2RS)-2-Methyl-cyclopentyl)-piperidine-3-carboxylic acid dimethylamide (mixture of isomers) | 0.61 | 461.3 |
| 1.151 | rac-(3R*,4R*)-1-Cyclopropylmethyl-4-{[3-(2,4-difluoro-phenyl)-isoxazole-5-carbonyl]-amino}-piperidine-3-carboxylic acid (2-methoxy-1,1-dimethyl-ethyl)-amide | 0.65 | 491.3 |
| 1.152 | rac-(3R*,4R*)-1-Cyclohexyl-4-{[5-(2,4-difluoro-phenyl)-[1,2,4]oxadiazole-3-carbonyl]-amino}-piperidine-3-carboxylic acid (2-methoxy-1,1-dimethyl-ethyl)-amide | 0.65 | 520.2 |
| 1.153 | rac-(3R*,4R*)-1-Cyclopropylmethyl-4-{[5-(2,4-difluoro-phenyl)-[1,2,4]oxadiazole-3-carbonyl]-amino}-piperidine-3-carboxylic acid (2-methoxy-1,1-dimethyl-ethyl)-amide | 0.61 | 492.3 |
| 1.154 | (3R*,4R*)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide (mixture of isomers) | 0.57 | 510 |
| 1.154a | (3S,4S)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide or (3R,4R)-1-Cyclopropylmethyl-4-{[3-(2,4-difluoro-phenyl)-isoxazole-5-carbonyl]-amino}-piperidine-3-carboxylic acid ((R)-1-pyridin-2-yl-ethyl)-amide (2nd eluted enantiomer) | 0.58 | 510 |
| 1.155 | (3R*,4R*)-4-{[3-(2,4-Difluoro-phenyl)-isoxazole-5-carbonyl]-amino}-1-((1RS,2RS)-2-methyl-cyclopentyl)-piperidine-3-carboxylic acid ((R)-1-pyridin-2-yl-ethyl)-amide (mixture of isomers) | 0.61 | 538.2 |
| 1.156 | (3R*,4R*)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide (mixture of isomers) | 0.56 | 539.2 |
| 1.156a | (3S,4S)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide or (3R,4R)-1-Cyclohexyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide (2nd eluted enantiomer) | 0.57 | 539.2 |
| 1.157 | (3R*,4R*)-1-Cyclopentyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide (mixture of isomers) | 0.53 | 525.1 |
| 1.158 | (3R*,4R*)-1-Cyclopropylmethyl-4-{[5-(2,4-difluoro-phenyl)-[1,2,4]oxadiazole-3-carbonyl]-amino}-piperidine-3-carboxylic acid ((R)-1-pyridin-2-yl-ethyl)-amide (mixture of isomers) | 0.52 | 511.1 |
| 1.159 | (3R*,4R*)-1-Cyclopropylmethyl-4-{[3-(2,4-difluoro-phenyl)-isoxazole-5-carbonyl]-amino}-piperidine-3-carboxylic acid ((R)-1-pyrazin-2-yl-ethyl)-amide (mixture of isomers) | 0.55 | 510.9 |
| 1.160 | (3R*,4R*)-1-Cyclohexyl-4-{[5-(2,4-difluoro-phenyl)-[1,2,4]oxadiazole-3-carbonyl]-amino}-piperidine-3-carboxylic acid ((R)-1-pyrazin-2-yl-ethyl)-amide (mixture of isomers) | 0.56 | 540.4 |
| 1.161 | (3R*,4R*)-1-Cyclopropylmethyl-4-{[3-(2,4-difluoro-phenyl)-isoxazole-5-carbonyl]-amino}-piperidine-3-carboxylic acid ((R)-1-cyclobutyl-ethyl)-amide (mixture of isomers) | 0.71 | 487.3 |
| 1.162 | (3R*,4R*)-4-{[3-(2,4-Difluoro-phenyl)-isoxazole-5-carbonyl]-amino}-1-((1RS,2RS)-2-Methyl-cyclopentyl)-piperidine-3-carboxylic acid ((R)-1-cyclobutyl-ethyl)-amide (mixture of isomers) | 0.74 | 515.4 |
| 1.163 | rac-(3R*,4R*)-1-Cyclopropylmethyl-4-{[3-(2,4-difluoro-phenyl)-isoxazole-5-carbonyl]-amino}-piperidine-3-carboxylic acid [1-(5-fluoro-pyridin-2-yl)-cyclopropyl]-amide | 0.66 | 540.3 |
| 1.164 | (3R*,4R*)-1-Cyclopropylmethyl-4-{[3-(2,4-difluoro-phenyl)-isoxazole-5-carbonyl]-amino}-piperidine-3-carboxylic acid ((1S*,2R*)-2-phenyl-cyclopropyl)-amide and (3R*,4R*)-1-Cyclopropylmethyl-4-{[3-(2,4-difluoro-phenyl)-isoxazole-5-carbonyl]-amino}-piperidine-3-carboxylic acid ((1R*,2S*)-2-phenyl-cyclopropyl)-amide (mixture of isomers) | 0.73 | 521.3 |
| 1.165 | rac-(3R*,4R*)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide | 0.55 | 550.5 |
| 1.165a | (3R*,4R*)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide (enantiomer 1) | 0.54 | 550.2 |

TABLE 1-continued

Examples 1.001-1.199

| Example Nr | Substance Name | t_R (min) | Mass Found [M + H]+ |
|---|---|---|---|
| 1.165b | (3R*,4R*)-1-Cyclohexyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide (enantiomer 2) | 0.55 | 550.1 |
| 1.166 | rac-(3R*,4R*)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide | 0.51 | 536.1 |
| 1.167 | rac-(3R*,4R*)-1-Cyclopropylmethyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide | 0.5 | 522 |
| 1.168 | (3R*,4R*)-4-{[1-(2,4-Difluoro-phenyl)-1H-[1,2,3]triazole-4-carbonyl]-amino}-1-((1RS,2RS)-2-Methyl-cyclopentyl)-piperidine-3-carboxylic acid (1-pyridin-2-yl-cyclopropyl)-amide (mixture of isomers) | 0.54 | 550.2 |
| 1.169 | rac-(3R*,4R*)-1-Cyclohexyl-4-{[5-(2,4,6-trifluoro-phenyl)-isoxazole-3-carbonyl]-amino}-piperidine-3-carboxylic acid (1-pyridin-2-yl-cyclopropyl)-amide | 0.65 | 568.3 |
| 1.170 | rac-(3R*,4R*)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide | 0.6 | 554.1 |
| 1.170a | (3S,4S)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide or (3R,4R)-1-Cyclopentyl-4-{[5-(2,4,6-trifluoro-phenyl)-isoxazole-3-carbonyl]-amino}-piperidine-3-carboxylic acid (1-pyridin-2-yl-cyclopropyl)-amide (1$^{st}$ eluted enantiomer) | 0.6 | 554.1 |
| 1.171 | rac-(3R*,4R*)-1-Cyclopropylmethyl-4-{[5-(2,4,6-trifluoro-phenyl)-isoxazole-3-carbonyl]-amino}-piperidine-3-carboxylic acid (1-pyridin-2-yl-cyclopropyl)-amide | 0.59 | 540.1 |
| 1.171a | (3R*,4R*)-1-Cyclopropylmethyl-4-{[5-(2,4,6-trifluoro-phenyl)-isoxazole-3-carbonyl]-amino}-piperidine-3-carboxylic acid (1-pyridin-2-yl-cyclopropyl)-amide (enantiomer 1) | 0.58 | 540.1 |
| 1.171b | (3R*,4R*)-1-Cyclopropylmethyl-4-{[5-(2,4,6-trifluoro-phenyl)-isoxazole-3-carbonyl]-amino}-piperidine-3-carboxylic acid (1-pyridin-2-yl-cyclopropyl)-amide (enantiomer 2) | 0.59 | 540.1 |
| 1.172 | (3R*,4R*)-1-((1RS,2RS)-2-Methyl-cyclopentyl)-4-{[5-(2,4,6-trifluoro-phenyl)-isoxazole-3-carbonyl]-amino}-piperidine-3-carboxylic acid (1-pyridin-2-yl-cyclopropyl)-amide (mixture of isomers) | 0.62 | 568.1 |
| 1.173 | rac-(3R*,4R*)-1-Cyclopentyl-4-{[3-(2,4-difluoro-phenyl)-isoxazole-5-carbonyl]-amino}-piperidine-3-carboxylic acid (1-pyridin-2-yl-cyclopropyl)-amide | 0.59 | 536.3 |
| 1.174 | rac-(3R*,4R*)-1-Cyclopropylmethyl-4-{[3-(2,4-difluoro-phenyl)-isoxazole-5-carbonyl]-amino}-piperidine-3-carboxylic acid (1-pyridin-2-yl-cyclopropyl)-amide | 0.57 | 522.1 |
| 1.175 | (3R*,4R*)-4-{[3-(2,4-Difluoro-phenyl)-isoxazole-5-carbonyl]-amino}-1-((1RS,2RS)-2-Methyl-cyclopentyl)-piperidine-3-carboxylic acid (1-pyridin-2-yl-cyclopropyl)-amide (mixture of isomers) | 0.61 | 550.2 |
| 1.176 | rac-(3R*,4R*)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide | 0.62 | 555.3 |
| 1.176a | (3S,4S)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide or (3R,4R)-1-Cyclopentyl-4-{[5-(2,4,6-trifluoro-phenyl)-isoxazole-3-carbonyl]-amino}-piperidine-3-carboxylic acid (1-pyrimidin-2-yl-cyclopropyl)-amide (2$^{nd}$ eluted enantiomer) | 0.61 | 555.1 |
| 1.177 | rac-(3R*,4R*)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide | 0.63 | 541.1 |
| 1.178 | rac-(3R*,4R*)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide | 0.61 | 523.1 |
| 1.179 | (3S,4S)-1-Cyclopropylmethyl-4-{[5-(2,4-difluoro-phenyl)-isoxazole-3-carbonyl]-amino}-piperidine-3-carboxylic acid (1-pyrazin-2-yl-cyclopropyl)-amide | 0.61 | 523 |
| 1.180 | (3S,4S)-1-Cyclopropylmethyl-4-{[5-(2,4-difluoro-phenyl)-isoxazole-3-carbonyl]-amino}-piperidine-3-carboxylic acid (1-pyridazin-3-yl-cyclopropyl)-amide | 0.56 | 523 |
| 1.181 | (3S,4S)-1-Cyclopentyl-4-{[5-(2,4-difluoro-phenyl)-isoxazole-3-carbonyl]-amino}-piperidine-3-carboxylic acid (1-pyrazin-2-yl-cyclopropyl)-amide | 0.62 | 537.1 |
| 1.182 | (3S,4S)-1-Cyclopentyl-4-{[5-(2,4-difluoro-phenyl)-isoxazole-3-carbonyl]-amino}-piperidine-3-carboxylic acid (1-pyridazin-3-yl-cyclopropyl)-amide | 0.57 | 537.1 |
| 1.183 | rac-(3R*,4R*)-1-Cyclohexyl-4-{[5-(2,4-difluoro-phenyl)-isoxazole-3-carbonyl]-amino}-piperidine-3-carboxylic acid (cyano-dimethyl-methyl)-amide | 0.65 | 500.3 |

TABLE 1-continued

Examples 1.001-1.199

| Example Nr | Substance Name | QC LC-MS $t_R$ (min) | Mass Found [M + H]+ |
|---|---|---|---|
| 1.184 | (3S,4S)-1-Cyclopentyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide | 0.71 | 565.4 |
| 1.185 | (3S,4S)-1-Cyclopropylmethyl-4-{[5-(2,4-difluoro-phenyl)-isoxazole-3-carbonyl]-amino}-piperidine-3-carboxylic acid [1-(4,6-dimethyl-pyrimidin-2-yl)-cyclopropyl]-amide | 0.7 | 551.4 |
| 1.186 | (3R,4R)-1-Cyclohexyl-4-{[5-(2,4-difluoro-phenyl)-isoxazole-3-carbonyl]-amino}-piperidine-3-carboxylic acid dimethylamide | 0.63 | 461.3 |
| 1.187a | (3R*,4R*)-1-Cyclohexyl-4-{[5-(2,4-difluoro-phenyl)-isoxazole-3-carbonyl]-amino}-piperidine-3-carboxylic acid ((S)-1-pyridin-2-yl-ethyl)-amide (enantiomer 1) | 0.63 | 538.4 |
| 1.187b | (3R*,4R*)-1-Cyclohexyl-4-{[5-(2,4-difluoro-phenyl)-isoxazole-3-carbonyl]-amino}-piperidine-3-carboxylic acid ((S)-1-pyridin-2-yl-ethyl)-amide (enantiomer 2) | 0.63 | 538.3 |
| 1.187c | (3R*,4R*)-1-Cyclohexyl-4-{[5-(2,4-difluoro-phenyl)-isoxazole-3-carbonyl]-amino}-piperidine-3-carboxylic acid ((R)-1-pyridin-2-yl-ethyl)-amide (enantiomer 1) | 0.63 | 538.3 |
| 1.187d | (3R*,4R*)-1-Cyclohexyl-4-{[5-(2,4-difluoro-phenyl)-isoxazole-3-carbonyl]-amino}-piperidine-3-carboxylic acid ((R)-1-pyridin-2-yl-ethyl)-amide (enantiomer 2) | 0.62 | 538.2 |
| 1.188a | (3R*,4R*)-1-Cyclohexyl-4-{[5-(2,4-difluoro-phenyl)-isoxazole-3-carbonyl]-amino}-piperidine-3-carboxylic acid [(R)-1-(6-methyl-pyridin-2-yl)-ethyl]-amide (enantiomer 1) | 0.6 | 552.2 |
| 1.188b | (3R*,4R*)-1-Cyclohexyl-4-{[5-(2,4-difluoro-phenyl)-isoxazole-3-carbonyl]-amino}-piperidine-3-carboxylic acid [(R)-1-(6-methyl-pyridin-2-yl)-ethyl]-amide (enantiomer 2) | 0.59 | 552.2 |
| 1.188c | (3R*,4R*)-1-Cyclohexyl-4-{[5-(2,4-difluoro-phenyl)-isoxazole-3-carbonyl]-amino}-piperidine-3-carboxylic acid [(S)-1-(6-methyl-pyridin-2-yl)-ethyl]-amide (enantiomer 1) | 0.6 | 552.2 |
| 1.188.d | (3R*,4R*)-1-Cyclohexyl-4-{[5-(2,4-difluoro-phenyl)-isoxazole-3-carbonyl]-amino}-piperidine-3-carboxylic acid [(S)-1-(6-methyl-pyridin-2-yl)-ethyl]-amide (enantiomer 2) | 0.59 | 552.2 |
| 1.189 | rac-(3R*,4R*)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide | 0.70 | 555 |
| 1.189a | (3S,4S)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide or (3R,4R)-1-Cyclopropylmethyl-4-{[5-(2,4-dichloro-phenyl)-isoxazole-3-carbonyl]-amino}-piperidine-3-carboxylic acid (1-pyrimidin-2-yl-cyclopropyl)-amide (1$^{st}$ eluted enantiomer) | 0.70 | 555.3 |
| 1.190 | rac-(3R*,4R*)-1-Cyclopropylmethyl-4-{[5-(2-trifluoromethyl-phenyl)-isoxazole-3-carbonyl]-amino}-piperidine-3-carboxylic acid (1-pyrimidin-2-yl-cyclopropyl)-amide | 0.7 | 555.2 |
| 1.191 | rac-(3R*,4R*)-1-Cyclopropylmethyl-4-{[5-(2,6-difluoro-phenyl)-isoxazole-3-carbonyl]-amino}-piperidine-3-carboxylic acid (1-pyrimidin-2-yl-cyclopropyl)-amide | 0.6 | 523.4 |
| 1.192 | rac-(3R*,4R*)-1-Cyclopropylmethyl-4-{[5-(4-trifluoromethyl-phenyl)-isoxazole-3-carbonyl]-amino}-piperidine-3-carboxylic acid (1-pyrimidin-2-yl-cyclopropyl)-amide | 0.70 | 555.4 |
| 1.192a | (3R*,4R*)-1-Cyclopropylmethyl-4-{[5-(4-trifluoromethyl-phenyl)-isoxazole-3-carbonyl]-amino}-piperidine-3-carboxylic acid (1-pyrimidin-2-yl-cyclopropyl)-amide (enantiomer 1) | 0.70 | 555.4 |
| 1.192b | (3R*,4R*)-1-Cyclopropylmethyl-4-{[5-(4-trifluoromethyl-phenyl)-isoxazole-3-carbonyl]-amino}-piperidine-3-carboxylic acid (1-pyrimidin-2-yl-cyclopropyl)-amide (enantiomer 2) | 0.70 | 555.4 |
| 1.193 | rac-(3R*,4R*)-1-Cyclopropylmethyl-4-{[5-(3-trifluoromethyl-phenyl)-isoxazole-3-carbonyl]-amino}-piperidine-3-carboxylic acid (1-pyrimidin-2-yl-cyclopropyl)-amide | 0.70 | 555 |
| 1.193a | (3R,4R)-1-Cyclopropylmethyl-4-{[5-(3-trifluoromethyl-phenyl)-isoxazole-3-carbonyl]-amino}-piperidine-3-carboxylic acid (1-pyrimidin-2-yl-cyclopropyl)-amide or (3S,4S)-1-cyclopropylmethyl-4-{[5-(3-trifluoromethyl-phenyl)-isoxazole-3-carbonyl]-amino}-piperidine-3-carboxylic acid (1-pyrimidin-2-yl-cyclopropyl)-amide (2$^{nd}$ eluted enantiomer) | 0.70 | 555.2 |
| 1.194a | (3R,4R)-1-Cyclopropylmethyl-4-{[5-(2,3,4-trifluoro-phenyl)-isoxazole-3-carbonyl]-amino}-piperidine-3-carboxylic acid (1-pyrimidin-2-yl-cyclopropyl)-amide or (3S,4S)-1-cyclopropylmethyl-4-{[5-(2,3,4-trifluoro-phenyl)-isoxazole-3-carbonyl]-amino}-piperidine-3-carboxylic acid (1-pyrimidin-2-yl-cyclopropyl)-amide (1st eluted enantiomer) | 0.60 | 541 |
| 1.195 | rac-(3R*,4R*)-1-Cyclopropylmethyl-4-{[5-(2-fluoro-4-methoxy-phenyl)-isoxazole-3-carbonyl]-amino}-piperidine-3-carboxylic acid (1-pyrimidin-2-yl-cyclopropyl)-amide | 0.60 | 535.1 |

TABLE 1-continued

Examples 1.001-1.199

| Example Nr | Substance Name | QC LC-MS $t_R$ (min) | Mass Found [M + H]+ |
|---|---|---|---|
| 1.196 | rac-(3R*,4R*)-1-Cyclopropylmethyl-4-{[5-(5-fluoro-pyridin-2-yl)-isoxazole-3-carbonyl]-amino}-piperidine-3-carboxylic acid (1-pyrimidin-2-yl-cyclopropyl)-amide | 0.50 | 506 |
| 1.197 | rac-(3R*,4R*)-1-Cyclopropylmethyl-4-{[5-(2,4-difluoro-phenyl)-isoxazole-3-carbonyl]-amino}-piperidine-3-carboxylic acid (1-pyridin-2-yl-cyclobutyl)-amide | 0.6 | 536.2 |
| 1.198 | rac-(3R*,4R*)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide | 0.8 | 551.2 |
| 1.199 | rac-(3R*,4R*)-1-Cyclopropylmethyl-4-{[5-(2,3-difluoro-phenyl)-isoxazole-3-carbonyl]-amino}-piperidine-3-carboxylic acid (1-pyrimidin-2-yl-cyclopropyl)-amide | 0.6 | 523.2 |

General Method B for the Synthesis of Compounds of Formula (I)
Buildings Blocks:
Preparation of Building Blocks of Structure B-6

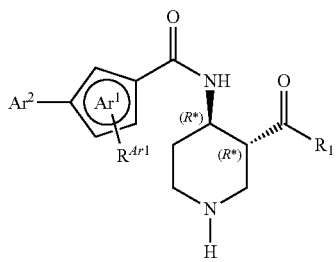

B-6

BB 2.01: rac-(3R*,4R*)-4-{[5-(2,4-Difluoro-phenyl)-isoxazole-3-carbonyl]-amino}-piperidine-3-carboxylic Acid Dimethylamide 2.01a: rac-(3R*,4R*)-1-Benzyl-4-{[5-(2,4-difluoro-phenyl)-isoxazole-3-carbonyl]-amino}-piperidine-3-carboxylic Acid Methyl Ester To a solution of rac-(3R*,4R*)-4-amino-1-benzyl-piperidine-3-carboxylic acid methyl ester (10.00 g, 33.4 mmol) in DMF (200 mL) is added 5-(2,4-difluorophenyl)isoxazole-3-carboxylic acid (7.74 g, 33.4 mmol). DIPEA (24.5 mL, 140 mmol) is then added followed by HATU (13.32 g, 35 mmol). The reaction mixture is stirred for 1 h. The reaction mixture is concentrated, diluted with DCM (750 mL) and treated with aq. sat. NaHCO$_3$ (600 mL). The organic layer is dried over MgSO$_4$ and evaporated. The crude residue is purified by prep. LC-MS in basic conditions to give the title compound; LC-MS method D $t_R$=1.14 min; [M+H]+=456.18.

2.01b: rac-(3R*,4R*)-4-{[5-(2,4-Difluoro-phenyl)-isoxazole-3-carbonyl]-amino}-piperidine-1,3-dicarboxylic Acid 1-tert-butyl ester 3-methyl Ester To a solution of rac-(3R*,4R*)-1-benzyl-4-{[5-(2,4-difluoro-phenyl)-isoxazole-3-carbonyl]-amino}-piperidine-3-carboxylic acid methyl ester 2.01a (11.33 g, 24.9 mmol) in ethyl acetate (250 mL) under argon is added 10% wet palladium on activated charcoal (2.647, 2.49 mmol) and di-tert-butyl-dicarbonate (6.03 g, 27.4 mmol). After degassing the reaction flask, the mixture is hydrogenated for 5 h at RT. The catalyst is filtered, washed with EtOAc and the solvent is evaporated. The crude residue is purified by prep. LC-MS with basic conditions to give the title compound; LC-MS method D $t_R$=1.11 min; [M+H]+=465.90.

2.01c: rac-(3R*,4R*)-4-{[5-(2,4-Difluoro-phenyl)-isoxazole-3-carbonyl]-amino}-piperidine-1,3-dicarboxylic Acid 1-tert-butyl Ester rac-(3R*,4R*)-4-{[5-(2,4-difluoro-phenyl)-isoxazole-3-carbonyl]-amino}-piperidine-1,3-dicarboxylic acid 1-tert-butyl ester 3-methyl ester 2.01b (8.71 g, 18.7 mmol) is dissolved in THF (114 mL). Aq. 1M NaOH solution (56.1 mL, 56.1 mmol) is then added and the mixture stirred at RT for 3 h. The reaction mixture is acidified to around pH=3 with 2M aq. HCl solution (30 mL) and concentrated. The resulting suspension is filtered, washed twice with water (2×14 mL) and dried under HV. The title compound is obtained as a white powder; LC-MS method D $t_R$=0.66 min; [M+H]+=452.17.

2.01d: rac-(3R*,4R*)-4-{[5-(2,4-Difluoro-phenyl)-isoxazole-3-carbonyl]-amino}-3-dimethylcarbamoyl-piperidine-1-carboxylic Acid Tert-Butyl Ester To a solution of rac-(3R*,4R*)-4-{[5-(2,4-difluoro-phenyl)-isoxazole-3-carbonyl]-amino}-piperidine-1,3-dicarboxylic acid 1-tert-butyl ester 2.01c (5 g, 11 mmol) in DMF (58 mL) at RT is added a 2M solution of dimethylamine in THF (22 mL, 44 mmol). DIPEA (6.15 mL, 35.2 mmol) is then added followed by HATU (4.4 g, 11.6 mmol). The reaction mixture is stirred at RT for 4 h. The volatiles are evaporated and the crude mixture is purified by prep. LC-MS with basic conditions to give the title compound; LC-MS method D $t_R$=1.01 min; [M+H]+=479.23.

2.01: rac-(3R*,4R*)-4-{[5-(2,4-Difluoro-phenyl)-isoxazole-3-carbonyl]-amino}-piperidine-3-carboxylic Acid Dimethylamide rac-(3R*,4R*)-4-{[5-(2,4-difluoro-phenyl)-isoxazole-3-carbonyl]-amino}-3-dimethylcarbamoyl-piperidine-1-carboxylic acid tert-butyl ester 2.01d (4.53 g, 9.47 mmol) is dissolved in MeOH (47.3 mL) at RT. A 4M solution of HCl in dioxane (47.3 mL, 189 mmol) is added and the reaction mixture is stirred at RT for 1 h. The solvents are evaporated to give the title compound; LC-MS method D $t_R$=0.75 min; $[M+H]^+$=379.11.

Preparation of Building-Blocks of General Formula (B-6) Used as Intermediates in the Preparation of Examples 2.001 to 2.108

The following intermediates are prepared in analogy to BB 2.01:

BB 2.02: rac-(3R*,4R*)-4-{[5-(2,4-Difluoro-phenyl)-isoxazole-3-carbonyl]-amino}-piperidine-3-carboxylic Acid Methyl-Phenethyl-Amide Hydrochloride 2.02b: rac-(3R*,4R*)-4-{[5-(2,4-Difluoro-phenyl)-isoxazole-3-carbonyl]-amino}-3-(methyl-phenethyl-carbamoyl)-piperidine-1-carboxylic Acid Tert-Butyl Ester The title compound is prepared according to the procedure 2.01d, starting from building block 2.01c and N-methyl-2-phenylethylamine; LC-MS method D: $t_R$=1.17 min; $[M+H]^+$=569.14.

2.02: rac-(3R*,4R*)-4-{[5-(2,4-Difluoro-phenyl)-isoxazole-3-carbonyl]-amino}-piperidine-3-carboxylic Acid Methyl-Phenethyl-Amide Hydrochloride The title compound is prepared according to the procedure 2.01, starting from building block 2.02b; LC-MS method D: $t_R$=0.92 min; $[M+H]^+$=469.18.

BB 2.03: rac-(3R*,4R*)-4-{[5-(2,4-Difluoro-phenyl)-isoxazole-3-carbonyl]-amino}-piperidine-3-carboxylic Acid (1-pyridin-2-yl-ethyl)-amide Hydrochloride 2.03b: rac-(3R*,4R*)-4-{[5-(2,4-Difluoro-phenyl)-isoxazole-3-carbonyl]-amino}-3-(1-pyridin-2-yl-ethylcarbamoyl)-piperidine-1-carboxylic Acid Tert-Butyl Ester The title compound is prepared according to the procedure 2.01d, starting from building block 2.01c and 1-(2-pyridyl)ethylamine; LC-MS method D: $t_R$=1.01 min; $[M+H]^+$=556.13.

2.03: rac-(3R*,4R*)-4-{[5-(2,4-Difluoro-phenyl)-isoxazole-3-carbonyl]-amino}-piperidine-3-carboxylic Acid (1-pyridin-2-yl-ethyl)-amide Hydrochloride The title compound is prepared according to the procedure 2.01, starting from building block 2.03b; LC-MS method D: $t_R$=0.77 min; $[M+H]^+$=456.09.

BB 2.04: (3S,4S)-4-{[5-(2,4-Difluoro-phenyl)-isoxazole-3-carbonyl]-amino}-piperidine-3-carboxylic Acid (1-pyrimidin-2-yl-cyclopropyl)-amide Hydrochloride 2.04a: (3S,4S)-4-{[5-(2,4-Difluoro-phenyl)-isoxazole-3-carbonyl]-amino}-piperidine-1,3-dicarboxylic Acid 1-tert-butyl Ester 3-methyl Ester The title compound is prepared by chiral preparative HPLC of rac-(3R*,4R*)-4-{[5-(2,4-Difluoro-phenyl)-isoxazole-3-carbonyl]-amino}-piperidine-1,3-dicarboxylic acid 1-tert-butyl ester 3-methyl ester using a column ChiralPak IC, 5 µm, 20×250 mm; with a mixture of A (25% Hept) and B (75% EtOH, 0.1% DEA) as eluent and a flow of 34 mL/min. Chiral HPLC: $t_R$=7.3 min.

2.04b: (3S,4S)-4-{[5-(2,4-Difluoro-phenyl)-isoxazole-3-carbonyl]-amino}-piperidine-1,3-dicarboxylic Acid 1-tert-butyl Ester The title compound is prepared according to the procedure 2.01c, starting from building block 2.04a; LC-MS method A: $t_R$=0.77 min; $[M+H]^+$=452.04.

2.04c: (3S,4S)-4-{[5-(2,4-Difluoro-phenyl)-isoxazole-3-carbonyl]-amino}-3-(1-pyrimidin-2-yl-cyclopropylcarbamoyl)-piperidine-1-carboxylic Acid Tert-Butyl Ester The title compound is prepared according to the procedure 2.01d, starting from 2.04b and 1-(pyrimidin-2-yl)cyclopropan-1-amine hydrochloride; LC-MS method A: $t_R$=0.94 min; $[M+H]^+$=569.19.

2.04: (3S,4S)-4-{[5-(2,4-Difluoro-phenyl)-isoxazole-3-carbonyl]-amino}-piperidine-3-carboxylic Acid (1-pyrimidin-2-yl-cyclopropyl)-amide Hydrochloride The title compound is prepared according to the procedure 2.01 described above, starting from building block 2.04c; LC-MS method A: $t_R$=0.62 min; $[M+H]^+$=469.23.

BB 2.05: (3R,4R)-4-{[5-(2,4-Difluoro-phenyl)-isoxazole-3-carbonyl]-amino}-piperidine-3-carboxylic Acid Dimethylamide Hydrochloride 2.05a: (3R,4R)-4-{[5-(2,4-Difluoro-phenyl)-isoxazole-3-carbonyl]-amino}-piperidine-1,3-dicarboxylic Acid 1-tert-butyl Ester 3-methyl Ester The title compound is prepared by chiral preparative HPLC of rac-(3R*,4R*)-4-{[5-(2,4-Difluoro-phenyl)-isoxazole-3-carbonyl]-amino}-piperidine-1,3-dicarboxylic acid 1-tert-butyl ester 3-methyl ester using a column ChiralPak IC, 5 µm, 20×250 mm; with a mixture of A (25% Hept) and B (75% EtOH, 0.1% DEA) as eluent and a flow of 34 mL/min. Chiral HPLC: $t_R$=5.9 min.

2.05b: (3R,4R)-4-{[5-(2,4-Difluoro-phenyl)-isoxazole-3-carbonyl]-amino}-piperidine-1,3-dicarboxylic Acid 1-tert-butyl Ester The title compound is prepared according to the procedure 2.01c, starting from building block 2.05a; LC-MS method D: $t_R$=0.62 min; $[M+H]^+$=452.17.

2.05c: (3R,4R)-4-{[5-(2,4-Difluoro-phenyl)-isoxazole-3-carbonyl]-amino}-3-dimethylcarbamoyl-piperidine-1-carboxylic Acid Tert-Butyl Ester The title compound is prepared according to the procedure 2.01d, starting from 2.05b and dimethylamine solution 2 M in THF; LC-MS method D: $t_R$=1.00 min; $[M+H]^+$=479.16.

2.05: (3R,4R)-4-{[5-(2,4-Difluoro-phenyl)-isoxazole-3-carbonyl]-amino}-piperidine-3-carboxylic Acid Dimethylamide Hydrochloride The title compound is prepared according to the procedure 2.01 described above, starting from building block 2.05c; LC-MS method D: $t_R$=0.75 min; [M+H]$^+$=379.15.

BB 2.06: rac-(3R*,4R*)-4-{[5-(2,4-Difluoro-phenyl)-isoxazole-3-carbonyl]-amino}-piperidine-3-carboxylic Acid [(R)-1-(1-oxy-pyridin-2-yl)-ethyl]-amide Hydrochloride

2.06b: rac-(3R*,4R*)-4-{[5-(2,4-Difluoro-phenyl)-isoxazole-3-carbonyl]-amino}-3-(1-pyridin-2-yl-ethylcarbamoyl)-piperidine-1-carboxylic Acid Tert-Butyl Ester The title compound is prepared according to the procedure 2.01d, starting from building block 2.01c and (R)-1-(pyridin-2-yl)ethanamine; LC-MS method A: $t_R$=0.87 min; [M+H]$^+$=556.26.

2.06c: 2-((R)-1-((3R*,4R*)-1-(tert-butoxycarbonyl)-4-(5-(2,4-difluorophenyl)isoxazole-3-carboxamido)piperidine-3-carboxamido)ethyl)pyridine-1-oxide To a solution of 2.06b (90 mg, 0.162 mmol) in DCM (3 mL) at 0° C. is added portionwise 3-chloroperbenzoic acid (47.2 mg, 0.211 mmol). The reaction mixture is stirred at RT for 1 h. The mixture is diluted with DCM and washed with aq. sat. NaHCO$_3$. The org phase is dried over MgSO4, filtered and concentrated to give the tittle compound as a white powder; LC-MS method A: $t_R$=0.96 min; [M+H]$^+$=572.28.

2.06: rac-(3R*,4R*)-4-{[5-(2,4-Difluoro-phenyl)-isoxazole-3-carbonyl]-amino}-piperidine-3-carboxylic Acid [(R)-1-(1-oxy-pyridin-2-yl)-ethyl]amide Hydrochloride The title compound is prepared according to the procedure 2.01, starting from building block 2.06c; LC-MS method A: $t_R$=0.63 min; [M+H]$^+$=472.19.

BB 2.07: rac-(3R*,4R*)-4-{[5-(2,4-Difluoro-phenyl)-isoxazole-3-carbonyl]-amino}-piperidine-3-carboxylic Acid [1-(1-oxy-pyridin-2-yl)-cyclopropyl]-amide Hydrochloride

2.07b: Rac-Tert-Butyl (3R*,4R*)-4-(5-(2,4-difluorophenyl)isoxazole-3-carboxamido)-3-((1-(pyridin-2-yl)cyclopropyl)carbamoyl)piperidine-1-carboxylate The title compound is prepared according to the procedure 2.01d, starting from building block 2.01c and 1-(pyridin-2-yl)cyclopropan-1-amine; LC-MS method A: $t_R$=0.88 min; [M+H]$^+$=568.26.

2.07c: rac-2-(1-((3R*,4R*)-1-(tert-butoxycarbonyl)-4-(5-(2,4-difluorophenyl)isoxazole-3-carboxamido)piperidine-3-carboxamido)cyclopropyl)pyridine 1-oxide The title compound is prepared according to the procedure 2.06c, starting from building block 2.07b; LC-MS method A: $t_R$=0.91 min; [M+H]$^+$=584.27.

2.07: (3R*,4R*)-4-{[5-(2,4-Difluoro-phenyl)-isoxazole-3-carbonyl]-amino}-piperidine-3-carboxylic Acid [1-(1-oxy-pyridin-2-yl)-cyclopropyl]-amide Hydrochloride The title compound is prepared according to the procedure 2.01, starting from building block 2.07c; LC-MS method A: $t_R$=0.63 min; [M+H]$^+$=484.19.

BB 2.08: (3S,4S)-4-{[5-(2,4-Difluoro-phenyl)-isoxazole-3-carbonyl]-amino}-piperidine-3-carboxylic Acid [1-(1-oxy-pyridin-2-yl)-cyclopropyl]-amide Hydrochloride

2.08b: tert-butyl (3S,4S)-4-(5-(2,4-difluorophenyl)isoxazole-3-carboxamido)-3-((1-(pyridin-2-yl)cyclopropyl)carbamoyl)piperidine-1-carboxylate The title compound is prepared according to the procedure 2.01d, starting from building block 2.04b and 1-(pyridin-2-yl)cyclopropan-1-amine; LC-MS method A: $t_R$=0.82 min; [M+H]$^+$=568.02.

2.08c: 2-(1-((3S,4S)-1-(tert-butoxycarbonyl)-4-(5-(2,4-difluorophenyl)isoxazole-3-carboxamido)piperidine-3-carboxamido)cyclopropyl)pyridine 1-oxide The title compound is prepared according to the procedure 2.06c, starting from building block 2.08b; LC-MS method A: $t_R$=0.87 min; [M+H]$^+$=583.99.

2.08: (3S,4S)-4-{[5-(2,4-Difluoro-phenyl)-isoxazole-3-carbonyl]-amino}-piperidine-3-carboxylic Acid [1-(1-oxy-pyridin-2-yl)-cyclopropyl]-amide Hydrochloride The title compound is prepared according to the procedure 2.01, starting from building block 2.08c; LC-MS method A: $t_R$=0.58 min; [M+H]$^+$=484.06.

BB 2.09: rac-(3R*,4R*)-4-{[5-(2,4-Difluoro-phenyl)-isoxazole-3-carbonyl]-amino}-piperidine-3-carboxylic Acid (1-cyano-cyclobutyl)-amide Hydrochloride

2.09b: rac-(3R*,4R*)-3-(1-Cyano-cyclobutylcarbamoyl)-4-{[5-(2,4-difluoro-phenyl)-isoxazole-3-carbonyl]-amino}-piperidine-1-carboxylic Acid Tert-Butyl Ester The title compound is prepared according to the procedure 2.01d, starting from building block 2.01c and 1aminocyclobutane carbonitrile; LC-MS method A: $t_R$=1.03 min; [M+H]$^+$=550.02.

2.09: rac-(3R*,4R*)-4-{[5-(2,4-Difluoro-phenyl)-isoxazole-3-carbonyl]-amino}-piperidine-3-carboxylic Acid (1-cyano-cyclobutyl)-amide Hydrochloride The title compound is prepared according to the procedure 2.01, starting from building block 2.09b; LC-MS method A: $t_R$=0.70 min; [M+H]$^+$=430.2.

BB 2.10: (3R,4R)-4-{[5-(2,4-Difluoro-phenyl)-isoxazole-3-carbonyl]-amino}-piperidine-3-carboxylic Acid (1-pyrimidin-2-yl-cyclopropyl)-amide Hydrochloride 2.10c: (3R,4R)-4-{[5-(2,4-Difluoro-phenyl)-isoxazole-3-carbonyl]-amino}-3-(1-pyrimidin-2-yl-cyclopropylcarbamoyl)-piperidine-1-carboxylic Acid Tert-Butyl Ester The title compound is prepared according to the procedure 2.01d, starting from 2.05b and 1-(pyrimidin-2-yl)cyclopropan-1-amine hydrochloride; LC-MS method A: $t_R$=0.86 min; [M+H]$^+$=569.19.

2.10: (3R,4R)-4-{[5-(2,4-Difluoro-phenyl)-isoxazole-3-carbonyl]-amino}-piperidine-3-carboxylic Acid (1-pyrimidin-2-yl-cyclopropyl)-amide Hydrochloride The title compound is prepared according to the procedure 2.01 described above, starting from building block 2.10c; LC-MS method A: $t_R$=0.61 min; [M+H]$^+$=469.19.

BB 2.11: (3R,4R)-4-{[5-(2,4-Difluoro-phenyl)-isoxazole-3-carbonyl]-amino}-piperidine-3-carboxylic Acid Ethyl-Methyl-Amide Hydrochloride 2.11c: (3R,4R)-4-{[5-(2,4-Difluoro-phenyl)-isoxazole-3-carbonyl]-amino}-3-(ethyl-methyl-carbamoyl)-piperidine-1-carboxylic Acid Tert-Butyl Ester The title compound is prepared according to the procedure 2.01d, starting from 2.05b and N-ethylmethylamine; LC-MS method A: $t_R$=0.99 min; [M+H]$^+$=493.18.

2.11: (3R,4R)-4-{[5-(2,4-Difluoro-phenyl)-isoxazole-3-carbonyl]-amino}-piperidine-3-carboxylic Acid Ethyl-Methyl-Amide Hydrochloride The title compound is prepared according to the procedure 2.01 described above, starting from building block 2.11c; LC-MS method A: $t_R$=0.69 min; [M+H]$^+$=393.18.

BB 2.12: (3R,4R)-4-{[5-(2,4-Difluoro-phenyl)-isoxazole-3-carbonyl]-amino}-piperidine-3-carboxylic Acid methyl-(2-pyridin-2-yl-ethyl)-amide Hydrochloride 2.12c: (3R,4R)-4-{[5-(2,4-Difluoro-phenyl)-isoxazole-3-carbonyl]-amino}-3-[methyl-(2-pyridin-2-yl-ethyl)-carbamoyl]-piperidine-1-carboxylic Acid Tert-Butyl Ester The title compound is prepared according to the procedure 2.01d, starting from 2.05b and N-methyl-2-(pyridin-2-yl)ethan-1-amine; LC-MS method A: $t_R$=0.78 min; [M+H]$^+$=570.17.

2.12: (3R,4R)-4-{[5-(2,4-Difluoro-phenyl)-isoxazole-3-carbonyl]-amino}-piperidine-3-carboxylic Acid methyl-(2-pyridin-2-yl-ethyl)-amide Hydrochloride The title compound is prepared according to the procedure 2.01 described above, starting from building block 2.12c; LC-MS method A: $t_R$=0.57 min; [M+H]$^+$=470.18.

BB 2.13: (3R,4R)-4-{[5-(2,4-Difluoro-phenyl)-isoxazole-3-carbonyl]-amino}-piperidine-3-carboxylic Acid (2-pyridin-2-yl-ethyl)-amide Hydrochloride 2.13c: (3R,4R)-4-{[5-(2,4-Difluoro-phenyl)-isoxazole-3-carbonyl]-amino}-3-(2-pyridin-2-yl-ethylcarbamoyl)-piperidine-1-carboxylic Acid Tert-Butyl Ester The title compound is prepared according to the procedure 2.01d, starting from 2.05b and 2-(pyridin-2-yl)ethan-1-amine; LC-MS method A: $t_R$=0.76 min; [M+H]$^+$=557.15.

2.13: (3R,4R)-4-{[5-(2,4-Difluoro-phenyl)-isoxazole-3-carbonyl]-amino}-piperidine-3-carboxylic Acid (2-pyridin-2-yl-ethyl)-amide Hydrochloride The title compound is prepared according to the procedure 2.01 described above, starting from building block 2.12c; LC-MS method A: $t_R$=0.56 min; [M+H]$^+$=456.18.

BB 2.14: (3S,4S)-4-{[5-(2,4-Difluoro-phenyl)-[1,3,4]thiadiazole-2-carbonyl]-amino}-piperidine-3-carboxylic Acid (1-pyrimidin-2-yl-cyclopropyl)-amide 2.14a: (3S,4S)-4-{[5-(2,4-Difluoro-phenyl)-[1,3,4]thiadiazole-2-carbonyl]amino}-piperidine-1,3-dicarboxylic Acid 1-tert-butyl Ester 3-ethyl Ester To a solution of (3R,4S)-4-amino-piperidine-1,3-dicarboxylic acid 1-tert-butyl ester 3-ethyl ester 4.06c (3.7 g, 13.6 mmol) in DMF (100 mL) is added 5-(2,4-difluoro-phenyl)-[1,3,4]thiadiazole-2-carboxylic acid sodium salt (3.73 g, 14.1 mmol). TEA (7.56 mL, 54.3 mmol) is then added followed by HATU (6.2 g, 16.3 mmol). The reaction mixture is stirred for 1 h. The reaction mixture is concentrated, diluted with DCM (250 mL) and treated with aq. sat. NaHCO$_3$ (250 mL). The organic layer is dried over MgSO$_4$ and evaporated. The crude residue is purified by flash chromatography using n-heptan/EtOAc 3:1 as eluent to deliver (3R,4S)-4-{[5-(2,4-Difluoro-phenyl)-[1,3,4]thiadiazole-2-carbonyl]amino}-piperidine-1,3-dicarboxylic acid 1-tert-butyl ester 3-ethyl ester as a white powder. This compound is dissolved in EtOH (40 mL) and EtOAc (20 mL). Sodium ethoxide 95% powder (3.44 g, 48 mmol) is added at once to and the resulting mixture is stirred under an argon atmosphere at RT for 4 d. The reaction mixture is quenched with sat. aq. NH$_4$Cl (100 mL) and extracted thrice with DCM (3×100 mL). The combined organic extracts are dried over MgSO$_4$, filtered and concentrated in vacuo. The crude is purified by prep-LC-MS, under basic conditions (method E) followed by chiral preparative SFC in order to remove traces of the [R,R]-isomer (Column: Regis (R,R) Whelk-01, 30×250 mm, 5 µm or ChiralPak IC, 30×250 mm, 5 µm; eluent: mixture of A (65% CO$_2$), and B (35% of DCM/EtOH/DEA 50:50:0.1), flow 160 mL/min. $t_R$=1.18 min.) The title product is obtained as a white powder; LC-MS method A: $t_R$=1.07 min; [M+H]$^+$=496.96.

2.14b: (3S,4S)-4-{[5-(2,4-Difluoro-phenyl)1,3,4-thiadiazole-2-carbonyl]-amino}-piperidine-1,3-dicarboxylic Acid 1-tert-butyl Ester The title compound is obtained by treatment of (3S,4S)-4-{[5-(2,4-Difluoro-phenyl)-[1,3,4]thiadiazole-2-carbonyl]amino}-piperidine-1,3-dicarboxylic acid 1-tert-butyl ester 3-ethyl ester with sodium hydroxide followed by HCl according to procedure 2.01c; LC-MS method A: $t_R$=0.94 min; [M+H]$^+$=468.88.

2.14c: (3S,4S)-4-{[5-(2,4-Difluoro-phenyl)-[1,3,4]thiadiazole-2-carbonyl]amino}-3-(1-pyrimidin-2-yl-cyclopropylcarbamoyl)-piperidine-1-carboxylic Acid Tert-Butyl Ester The title compound is prepared according to the procedure 2.01d, starting from 2.14b and 1-(pyrimidin-2-yl)cyclopropan-1-amine hydrochloride; LC-MS method D: $t_R$=0.94 min; [M+H]$^+$=585.34.

2.14: (3S,4S)-4-{[5-(2,4-Difluoro-phenyl)-[1,3,4]thiadiazole-2-carbonyl]amino}-piperidine-3-carboxylic Acid (1-pyrimidin-2-yl-cyclopropyl)-amide The title compound is prepared according to the procedure 2.01 described above, starting from building block 2.14c; LC-MS method A: $t_R$=0.67 min; [M+H]$^+$=486.24

General Procedures for the Preparation of Examples 2.001 to 2.109:

Method D:

To a solution of the respective amine (BB 2.01 to BB 2.14) (0.1 mmol) in DCM (mL) is added a commercially available aldehyde or ketone (0.12 to 1 mmol) followed by sodium triacetoxyborohydride (0.13 to 0.4 mmol). The reaction mixture is stirred overnight at RT. The reaction mixture is then diluted with DCM or chloroform (3 mL) and treated with aq. sat. NaHCO$_3$ (2 mL). The organic phase is dried over Na$_2$SO$_4$, filtered and the solvent is evaporated. The crude residue is purified by prep. LC-MS using method E.

Method E:

To a solution of the respective amine (BB 2.01 to BB 2.14) (0.1 mmol) in DMF (mL) is added a commercially available aldehyde or ketone (0.2 to 1 mmol) followed by sodium triacetoxyborohydride (0.23 mmol). The reaction mixture is stirred overnight at RT. 150 µL water are added and the product is purified by prep. LC-MS using method E.

Method F:

To the respective amine (BB 2.01 to BB 2.14) (0.5 mmol) and a commercially available ketone (0.6 mmol) and titanium(IV) isopropoxide (1 mmol) are stirred under argon at 80° C. for 4.5 h. Methanol (1.18 mL) is added followed by sodium borohydride (1.5 mmol) in one portion. The reaction mixture is stirred at RT for 1 h. Water (1.2 mL) is added. The resulting suspension is filtered, washed with 9 mL DCM/MeOH 3/1 and the solvents are evaporated. The crude residue is purified by prep. LC-MS using method E.

Method G:

The respective amine (BB 2.01 to BB 2.14) (0.1 mmol) is dissolved in water (0.7 mL). DIPEA (0.3 mmol) is added followed by a commercially available epoxide (0.4 mmol). The reaction mixture is stirred at 100° C. for 17 h. The solvent is evaporated and the crude mixture is dissolved in 1 mL MeOH/DMF and purified by prep. LC-MS using method E.

Method H:

To an ice cold solution of the respective amine (BB 2.01 to BB 2.14) (0.1 mmol) and K$_2$CO$_3$ (0.2 mmol) in acetone (5 mL) is added a commercially available alkyl bromide (0.11 mmol). The mixture is stirred 18 h at RT. Another equivalent of alkyl bromide is added and the mixture is stirred 18 h at 50° C. The reaction mixture is filtered and the solvent is evaporated under reduced pressure. The residue is purified by Prep HPLC using method E.

Example 2.001 rac-(3R*,4R*)-4-{[5-(2,4-Difluoro-phenyl)-isoxazole-3-carbonyl]-amino}-1-isopropyl-piperidine-3-carboxylic Acid Dimethylamide To a solution of rac-(3R*,4R*)-4-{[5-(2,4-difluoro-phenyl)-isoxazole-3-carbonyl]-amino}-piperidine-3-carboxylic acid dimethylamide (BB 2.01) (41.5 mg, 0.1 mmol) in DCM (0.5 mL) is added acetone (27.8 mg, 0.036 mL, 0.48 mmol) followed by sodium triacetoxyborohydride (61 mg, 0.27 mmol). The reaction mixture is stirred overnight at RT. The reaction mixture is then diluted with chloroform (3 mL) and treated with aq. sat. NaHCO$_3$ (2 mL). The organic phase is dried over Na$_2$SO$_4$, filtered and the solvent is evaporated. The crude residue is purified by prep. LC-MS using method E. LC-MS QC method: $t_R$=0.56 min; [M+H]$^+$=421.1.

Compounds of Examples 2.001 to 2.108 listed in Table 2 below are prepared by applying one of the above-mentioned general procedures D, E, F, G, or H to the building blocks BB-2.01 BB-2.14 or BB-8.01-BB-8.02 coupled with commercially available aldehydes, ketones, alkyl halogenides or epoxydes.

Enantiomerically pure compounds are obtained by using one of the above mentioned preparative chiral chromatography methods.

TABLE 2

Examples 2.001-2.108

| Example Nr | Substance Name | QC LC-MS $t_R$ (min) | Mass Found [M + H]$^+$ |
|---|---|---|---|
| 2.001 | rac-(3R*,4R*)-4-{[5-(2,4-Difluoro-phenyl)isoxazole-3-carbonyl]-amino}-1-isopropyl-piperidine-3-carboxylic acid dimethylamide | 0.56 | 421.1 |
| 2.002 | rac-(3R*,4R*)-4-{[5-(2,4-Difluoro-phenyl)isoxazole-3-carbonyl]-amino}-1-ethyl-piperidine-3-carboxylic acid dimethylamide | 0.54 | 407.3 |
| 2.003 | rac-(3R*,4R*)-4-{[5-(2,4-Difluoro-phenyl)isoxazole-3-carbonyl]-amino}-1-isopropyl-piperidine-3-carboxylic acid methyl-phenethyl-amide | 0.75 | 511 |
| 2.004 | rac-(3R*,4R*)-4-{[5-(2,4-Difluoro-phenyl)isoxazole-3-carbonyl]-amino}-1-ethyl-piperidine-3-carboxylic acid methyl-phenethyl-amide | 0.73 | 497.3 |
| 2.005 | rac-(3R*,4R*)-1-Cyclopentyl-4-{[5-(2,4-difluoro-phenyl)-isoxazole-3-carbonyl]-amino}-piperidine-3-carboxylic acid methyl-phenethyl-amide | 0.78 | 537.4 |
| 2.006 | rac-(3R*,4R*)-1-Cyclopropylmethyl-4-{[5-(2,4-difluoro-phenyl)-isoxazole-3-carbonyl]-amino}-piperidine-3-carboxylic acid methyl-phenethyl-amide | 0.77 | 523.3 |

TABLE 2-continued

Examples 2.001-2.108

| Example Nr | Substance Name | QC LC-MS $t_R$ (min) | Mass Found $[M + H]^+$ |
|---|---|---|---|
| 2.007 | (3R*,4R*)-4-{[5-(2,4-Difluoro-phenyl)-isoxazole-3-carbonyl]-amino}-1-isopropyl-piperidine-3-carboxylic acid ((1RS)-1-pyridin-2-yl-ethyl)-amide (mixture of isomers) | 0.57 | 498 |
| 2.008 | (3R*,4R*)-4-{[5-(2,4-Difluoro-phenyl)-isoxazole-3-carbonyl]-amino}-1-ethyl-piperidine-3-carboxylic acid ((1RS)-1-pyridin-2-yl-ethyl)-amide (mixture of isomers) | 0.55 | 484.1 |
| 2.009 | (3R*,4R*)-1-Cyclopentyl-4-{[5-(2,4-difluoro-phenyl)-isoxazole-3-carbonyl]-amino}-piperidine-3-carboxylic acid ((1RS)-1-pyridin-2-yl-ethyl)-amide (mixture of isomers) | 0.59 | 524.5 |
| 2.010 | (3R*,4R*)-1-Cyclopropylmethyl-4-{[5-(2,4-difluoro-phenyl)-isoxazole-3-carbonyl]-amino}-piperidine-3-carboxylic acid ((1RS)-1-pyridin-2-yl-ethyl)-amide (mixture of isomers) | 0.58 | 510.1 |
| 2.011 | (3R*,4R*)-1-Cyclopropylmethyl-4-{[5-(2,4-difluoro-phenyl)-isoxazole-3-carbonyl]-amino}-piperidine-3-carboxylic acid [(R)-1-(1-oxy-pyridin-2-yl)-ethyl]-amide (mixture of isomers) | 0.55 | 525.9 |
| 2.013 | (3R*,4R*)-1-((1RS)-1-Cyclopropyl-ethyl)-4-{[5-(2,4-difluoro-phenyl)-isoxazole-3-carbonyl]-amino}-piperidine-3-carboxylic acid dimethylamide (mixture of isomers) | 0.61 | 447.3 |
| 2.014 | (3R*,4R*)-4-{[5-(2,4-Difluoro-phenyl)-isoxazole-3-carbonyl]-amino}-1-((1RS,2RS)-2-hydroxymethyl-cyclopentyl)-piperidine-3-carboxylic acid dimethylamide (mixture of isomers) | 0.58 | 477.3 |
| 2.015 | (3R*,4R*)-4-{[5-(2,4-Difluoro-phenyl)-isoxazole-3-carbonyl]-amino}-1-((1RS,2RS)-2-ethyl-cyclopentyl)-piperidine-3-carboxylic acid dimethylamide (mixture of isomers) | 0.68 | 475.3 |
| 2.016 | (3R*,4R*)-4-{[5-(2,4-Difluoro-phenyl)-isoxazole-3-carbonyl]-amino}-1-((1RS,2RS)-2-methyl-cyclobutyl)-piperidine-3-carboxylic acid dimethylamide (mixture of isomers) | 0.61 | 447.3 |
| 2.016a | (3R,4R)-4-{[5-(2,4-Difluoro-phenyl)-isoxazole-3-carbonyl]-amino}-1-((1RS,2RS)-2-methyl-cyclobutyl)-piperidine-3-carboxylic acid dimethylamide, mixture of isomers 1 | 0.61 | 447.3 |
| 2.016b | (3R,4R)-4-{[5-(2,4-Difluoro-phenyl)-isoxazole-3-carbonyl]-amino}-1-((1RS,2RS)-2-methyl-cyclobutyl)-piperidine-3-carboxylic acid dimethylamide, mixture of isomers 2 | 0.6 | 447.3 |
| 2.017 | (3R*,4R*)-4-{[5-(2,4-Difluoro-phenyl)-isoxazole-3-carbonyl]-amino}-(1RS)-1-(2,2-dimethyl-cyclobutyl)-piperidine-3-carboxylic acid dimethylamide (mixture of isomers) | 0.65 | 461.1 |
| 2.018 | (3R*,4R*)-4-{[5-(2,4-Difluoro-phenyl)-isoxazole-3-carbonyl]-amino}-1-((1RS)-3,3-dimethyl-cyclopentyl)-piperidine-3-carboxylic acid dimethylamide (mixture of isomers) | 0.67 | 475.3 |
| 2.019 | rac-(3R*,4R*)-1-Cyclopentyl-4-{[5-(2,4-difluoro-phenyl)-isoxazole-3-carbonyl]-amino}-piperidine-3-carboxylic acid dimethylamide | 0.59 | 447.3 |
| 2.019a | (3R,4R)-1-Cyclopentyl-4-{[5-(2,4-difluoro-phenyl)-isoxazole-3-carbonyl]-amino}-piperidine-3-carboxylic acid dimethylamide or (3S,4S)-1-Cyclopentyl-4-{[5-(2,4-difluoro-phenyl)-isoxazole-3-carbonyl]-amino}-piperidine-3-carboxylic acid dimethylamide (1$^{st}$ eluted enantiomer) | 0.59 | 447.3 |
| 2.020 | rac-(3R*,4R*)-4-{[5-(2,4-Difluoro-phenyl)isoxazole-3-carbonyl]-amino}-1-(2,2-dimethyl-propyl)-piperidine-3-carboxylic acid dimethylamide | 0.65 | 449.1 |
| 2.021 | rac-(3R*,4R*)-4-{[5-(2,4-Difluoro-phenyl)isoxazole-3-carbonyl]-amino}-1-(3-methyl-butyl)-piperidine-3-carboxylic acid dimethylamide | 0.64 | 449 |
| 2.022 | rac-(3R*,4R*)-4-{[5-(2,4-Difluoro-phenyl)isoxazole-3-carbonyl]-amino}-1-(3,3-dimethyl-butyl)-piperidine-3-carboxylic acid dimethylamide | 0.68 | 463.4 |
| 2.023 | (3R*,4R*)-4-{[5-(2,4-Difluoro-phenyl)-isoxazole-3-carbonyl]-amino}-1-((1RS,2RS)-2-methyl-cyclopentyl)-piperidine-3-carboxylic acid dimethylamide (mixture of isomers) | 0.63 | 461.3 |
| 2.023a | (3R,4R)-4-{[5-(2,4-Difluoro-phenyl)-isoxazole-3-carbonyl]-amino}-1-((1RS,RS)-2-methyl-cyclopentyl)-piperidine-3-carboxylic acid dimethylamide, mixture of isomere 1 | 0.63 | 461.3 |
| 2.023b | (3R,4R)-4-{[5-(2,4-Difluoro-phenyl)-isoxazole-3-carbonyl]-amino}-1-((1RS,RS)-2-methyl-cyclopentyl)-piperidine-3-carboxylic acid dimethylamide, mixture of isomers 2 | 0.63 | 461.3 |
| 2.024 | (3R*,4R*)-4-{[5-(2,4-Difluoro-phenyl)-isoxazole-3-carbonyl]-amino}-1-((1RS)-3,3-dimethyl-cyclohexyl)-piperidine-3-carboxylic acid dimethylamide (mixture of isomers) | 0.72 | 489.3 |
| 2.025 | rac-(3R*,4R*)-4-{[5-(2,4-Difluoro-phenyl)isoxazole-3-carbonyl]-amino}-1-spiro[3.3]hept-2-yl-piperidine-3-carboxylic acid dimethylamide | 0.66 | 473.3 |
| 2.026 | (3R*,4R*)-4-{[5-(2,4-Difluoro-phenyl)-isoxazole-3-carbonyl]-amino}-1-((1RS,4RS)-4-fluoro-cyclohexyl)-piperidine-3-carboxylic acid dimethylamide (mixture of isomers) | 0.61 | 479.3 |
| 2.027 | rac-(3R*,4R*)-1-(4,4-Difluoro-cyclohexyl)-4-{[5-(2,4-difluoro-phenyl)-isoxazole-3-carbonyl]-amino}-piperidine-3-carboxylic acid dimethylamide | 0.63 | 497.3 |

TABLE 2-continued

Examples 2.001-2.108

| Example Nr | Substance Name | QC LC-MS $t_R$ (min) | Mass Found [M + H]+ |
|---|---|---|---|
| 2.028 | rac-(3R*,4R*)-1-Cyclobutyl-4-{[5-(2,4-difluoro-phenyl)-isoxazole-3-carbonyl]-amino}-piperidine-3-carboxylic acid dimethylamide | 0.56 | 433.4 |
| 2.029 | rac-(3R*,4R*)-1-Cyclopropylmethyl-4-{[5-(2,4-difluoro-phenyl)-isoxazole-3-carbonyl]-amino}-piperidine-3-carboxylic acid dimethylamide | 0.58 | 433 |
| 2.030 | rac-(3R*,4R*)-1-Cyclopentylmethyl-4-{[5-(2,4-difluoro-phenyl)-isoxazole-3-carbonyl]-amino}-piperidine-3-carboxylic acid dimethylamide | 0.66 | 461.3 |
| 2.031 | rac-(3R*,4R*)-4-{[5-(2,4-Difluoro-phenyl)isoxazole-3-carbonyl]-amino}-1-(3,3-dimethyl-cyclobutyl)-piperidine-3-carboxylic acid dimethylamide | 0.64 | 461.3 |
| 2.032 | (3R*,4R*)-4-{[5-(2,4-Difluoro-phenyl)-isoxazole-3-carbonyl]-amino}-1-((1RS,3RS)-3-methoxy-cyclohexyl)-piperidine-3-carboxylic acid dimethylamide (mixture of isomers) | 0.67 | 491 |
| 2.033 | (3R*,4R*)-4-{[5-(2,4-Difluoro-phenyl)-isoxazole-3-carbonyl]-amino}-1-((1RS,2RS)-2-methoxy-cyclohexyl)-piperidine-3-carboxylic acid dimethylamide (mixture of isomers) | 0.67 | 491 |
| 2.034 | rac-(3R*,4R*)-4-{[5-(2,4-Difluoro-phenyl)isoxazole-3-carbonyl]-amino}-1-(1-methyl-cyclopropylmethyl)-piperidine-3-carboxylic acid dimethylamide | 0.63 | 447.3 |
| 2.035 | rac-(3R*,4R*)-4-{[5-(2,4-Difluoro-phenyl)isoxazole-3-carbonyl]-amino}-1-(1-methyl-cyclobutylmethyl)-piperidine-3-carboxylic acid dimethylamide | 0.67 | 461 |
| 2.036 | rac-(3R*,4R*)-1-Cyclopent-1-enylmethyl-4-{[5-(2,4-difluoro-phenyl)-isoxazole-3-carbonyl]-amino}-piperidine-3-carboxylic acid dimethylamide | 0.66 | 459.1 |
| 2.037 | (3R*,4R*)-(1RS,2RS,4RS)-1-Bicyclo[2.2.1]hept-2-yl-4-{[5-(2,4-difluoro-phenyl)-isoxazole-3-carbonyl]-amino}-piperidine-3-carboxylic acid dimethylamide (mixture of isomers) | 0.64 | 473.3 |
| 2.038 | rac-(3R*,4R*)-1-Cyclobutylmethyl-4-{[5-(2,4-difluoro-phenyl)-isoxazole-3-carbonyl]-amino}-piperidine-3-carboxylic acid dimethylamide | 0.62 | 447.3 |
| 2.039 | rac-(3R*,4R*)-1-(2-Cyclopropyl-ethyl)-4-{[5-(2,4-difluoro-phenyl)-isoxazole-3-carbonyl]-amino}-piperidine-3-carboxylic acid dimethylamide | 0.62 | 447.1 |
| 2.040 | (3R*,4R*)-4-{[5-(2,4-Difluoro-phenyl)-isoxazole-3-carbonyl]-amino}-1-((1RS,2RS)-2-fluoro-cyclohexyl)-piperidine-3-carboxylic acid dimethylamide (mixture of isomers) | 0.63 | 479.3 |
| 2.045 | (3R,4R)-1-Cyclopropylmethyl-4-{[5-(2,4-difluoro-phenyl)-isoxazole-3-carbonyl]-amino}-piperidine-3-carboxylic acid dimethylamide | 0.58 | 433.3 |
| 2.046 | (3R,4R)-1-((1RS)-1-Cyclopropyl-ethyl)-4-{[5-(2,4-difluoro-phenyl)-isoxazole-3-carbonyl]-amino}-piperidine-3-carboxylic acid dimethylamide (mixture of isomers) | 0.62 | 447.3 |
| 2.047 | (3R,4R)-4-{[5-(2,4-Difluoro-phenyl)-isoxazole-3-carbonyl]-amino}-(1RS)-1-spiro[2.4]hept-4-yl-piperidine-3-carboxylic acid dimethylamide (mixture of isomers) | 0.68 | 473 |
| 2.048 | (3R*,4R*)-4-{[5-(2,4-Difluoro-phenyl)-isoxazole-3-carbonyl]-amino}-1-((1RS,2RS)-2-hydroxy-cyclohexyl)-piperidine-3-carboxylic acid dimethylamide (mixture of isomers) | 0.61 | 477.3 |
| 2.049 | (3R*,4R*)-4-{[5-(2,4-Difluoro-phenyl)-isoxazole-3-carbonyl]-amino}-1-((1RS,2RS)-2-hydroxy-1-methyl-propyl)-piperidine-3-carboxylic acid dimethylamide (mixture of isomers) | 0.56 | 451 |
| 2.050 | (3R*,4R*)-4-{[5-(2,4-Difluoro-phenyl)-isoxazole-3-carbonyl]-amino}-1-((1RS,2RS)-2-hydroxy-cyclohexyl)-piperidine-3-carboxylic acid methyl-phenethyl-amide (mixture of isomers) | 0.79 | 567.4 |
| 2.051 | (3R*,4R*)-4-{[5-(2,4-Difluoro-phenyl)-isoxazole-3-carbonyl]-amino}-1-((1RS,2RS)-2-hydroxy-1-methyl-propyl)-piperidine-3-carboxylic acid methyl-phenethyl-amide (mixture of isomers) | 0.75 | 541 |
| 2.052 | rac-(3R*,4R*)-4-{[5-(2,4-Difluoro-phenyl)isoxazole-3-carbonyl]-amino}-1-(2-hydroxy-ethyl)-piperidine-3-carboxylic acid methyl-phenethyl-amide | 0.72 | 513 |
| 2.053 | (3R*,4R*)-4-{[5-(2,4-Difluoro-phenyl)-isoxazole-3-carbonyl]-amino}-1-((1RS,2RS)-2-hydroxy-cyclohexyl)-piperidine-3-carboxylic acid ((1RS)-1-pyridin-2-yl-ethyl)-amide (mixture of isomers) | 0.59 | 554.2 |
| 2.054 | (3R*,4R*)-4-{[5-(2,4-Difluoro-phenyl)-isoxazole-3-carbonyl]-amino}-1-((1RS,2RS)-2-hydroxy-1-methyl-propyl)-piperidine-3-carboxylic acid ((1RS)-1-pyridin-2-yl-ethyl)-amide (mixture of isomers) | 0.57 | 528 |
| 2.055 | (3S,4S)-4-{[5-(2,4-Difluoro-phenyl)-isoxazole-3-carbonyl]-amino}-1-(2-methoxy-ethyl)-piperidine-3-carboxylic acid (1-pyrimidin-2-yl-cyclopropyl)-amide | 0.6 | 527.1 |
| 2.056 | (3S,4S)-4-{[5-(2,4-Difluoro-phenyl)-isoxazole-3-carbonyl]-amino}-1-ethyl-piperidine-3-carboxylic acid (1-pyrimidin-2-yl-cyclopropyl)-amide | 0.58 | 497 |

TABLE 2-continued

Examples 2.001-2.108

| Example Nr | Substance Name | t_R (min) | Mass Found [M + H]+ |
|---|---|---|---|
| 2.057 | (3S,4S)-4-{[5-(2,4-Difluoro-phenyl)-isoxazole-3-carbonyl]-amino}-1-((1,1,2,2,2-d_5-ethyl)-piperidine)-3-carboxylic acid (1-pyrimidin-2-yl-cyclopropyl)-amide | 0.58 | 502.2 |
| 2.058 (BB 2.02) | rac-(3R*,4R*)-4-{[5-(2,4-Difluoro-phenyl)isoxazole-3-carbonyl]-amino}-piperidine-3-carboxylic acid methyl-phenethyl-amide | 0.71 | 469 |
| 2.059 (BB 2.04) | (3S,4S)-4-{[5-(2,4-Difluoro-phenyl)-isoxazole-3-carbonyl]-amino}-piperidine-3-carboxylic acid (1-pyrimidin-2-yl-cyclopropyl)-amide | 0.58 | 469.27 |
| 2.060 | (3R*,4R*)-4-{[5-(2,4-Difluoro-phenyl)-isoxazole-3-carbonyl]-amino}-1-((1RS,2RS)-2-hydroxy-cyclohexyl)-piperidine-3-carboxylic acid (1-pyrimidin-2-yl-cyclopropyl)-amide (mixture of stereoisomers) | 0.60 | 567 |
| 2.061 | rac-(3R*,4R*)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide | 0.60 | 538.4 |
| 2.062 | rac-(3R*,4R*)-1-Cyclopentyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide | 0.65 | 552.2 |
| 2.062a | (3R*,4R*)-1-Cyclopentyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide (Enantiomer 1) | 0.65 | 552.2 |
| 2.062b | (3R*,4R*)-1-Cyclopentyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide (Enantiomer 2) | 0.65 | 552.17 |
| 2.063 | (3S,4S)-1-Cyclobutyl-4-{[5-(2,4-difluoro-phenyl)-isoxazole-3-carbonyl]-amino}-piperidine-3-carboxylic acid [1-(1-oxy-pyridin-2-yl)-cyclopropyl]-amide | 0.60 | 538.4 |
| 2.064 | rac-(3R*,4R*)-1-Cyclopentyl-4-{[5-(2,4-difluoro-phenyl)-isoxazole-3-carbonyl]-amino}-piperidine-3-carboxylic acid (1-cyano-cyclobutyl)-amide | 0.60 | 498 |
| 2.065 | (3S,4S)-1-Cyclopentylmethyl-4-{[5-(2,4-difluoro-phenyl)-isoxazole-3-carbonyl]-amino}-piperidine-3-carboxylic acid (1-pyrimidin-2-yl-cyclopropyl)-amide | 0.70 | 551 |
| 2.066 | (3R,4R)-1-Cyclopentyl-4-{[5-(2,4-difluoro-phenyl)-isoxazole-3-carbonyl]-amino}-piperidine-3-carboxylic acid (1-pyrimidin-2-yl-cyclopropyl)-amide | 0.60 | 537.1 |
| 2.067 | (3S,4S)-1-(1-Difluoromethyl-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide | 0.60 | 573 |
| 2.068 | (3S,4S)-4-{[5-(2,4-Difluoro-phenyl)-isoxazole-3-carbonyl]-amino}-1-(4-fluoro-benzyl)-piperidine-3-carboxylic acid (1-pyrimidin-2-yl-cyclopropyl)-amide | 0.70 | 577 |
| 2.069 | (3S,4S)-4-{[5-(2,4-Difluoro-phenyl)-isoxazole-3-carbonyl]-amino}-1-(2,2-dimethyl-propyl)-piperidine-3-carboxylic acid (1-pyrimidin-2-yl-cyclopropyl)-amide | 0.70 | 539.1 |
| 2.070 | (3S,4S)-4-{[5-(2,4-Difluoro-phenyl)-isoxazole-3-carbonyl]-amino}-1-isobutyl-piperidine-3-carboxylic acid (1-pyrimidin-2-yl-cyclopropyl)-amide | 0.60 | 525.2 |
| 2.071 | (3S,4S)-1-Benzyl-4-{[5-(2,4-difluoro-phenyl)-isoxazole-3-carbonyl]-amino}-piperidine-3-carboxylic acid (1-pyrimidin-2-yl-cyclopropyl)-amide | 0.70 | 559.1 |
| 2.072 | (3S,4S)-1-Cyclobutylmethyl-4-{[5-(2,4-difluoro-phenyl)-isoxazole-3-carbonyl]-amino}-piperidine-3-carboxylic acid (1-pyrimidin-2-yl-cyclopropyl)-amide | 0.60 | 537.4 |
| 2.073 | (3S,4S)-4-{[5-(2,4-Difluoro-phenyl)-isoxazole-3-carbonyl]-amino}-1-isopropyl-piperidine-3-carboxylic acid (1-pyrimidin-2-yl-cyclopropyl)-amide | 0.60 | 511.2 |
| 2.074 | (3S,4S)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide | 0.60 | 523.1 |
| 2.075 | (3S,4S)-1-Cyclopropyl-4-{[5-(2,4-difluoro-phenyl)-isoxazole-3-carbonyl]-amino}-piperidine-3-carboxylic acid (1-pyrimidin-2-yl-cyclopropyl)-amide | 0.60 | 509.1 |
| 2.076 | (3R,4R)-1-Cyclopentyl-4-{[5-(2,4-difluoro-phenyl)-isoxazole-3-carbonyl]-amino}-piperidine-3-carboxylic acid ethyl-methyl-amide | 0.60 | 461.3 |
| 2.077 | (3R,4R)-1-Cyclopropylmethyl-4-{[5-(2,4-difluoro-phenyl)-isoxazole-3-carbonyl]-amino}-piperidine-3-carboxylic acid ethyl-methyl-amide | 0.60 | 447 |
| 2.078 | (3R,4R)-1-Cyclopentyl-4-{[5-(2,4-difluoro-phenyl)-isoxazole-3-carbonyl]-amino}-piperidine-3-carboxylic acid methyl-(2-pyridin-2-yl-ethyl)-amide | 0.50 | 538.1 |
| 2.079 | (3R,4R)-1-Cyclopropylmethyl-4-{[5-(2,4-difluoro-phenyl)-isoxazole-3-carbonyl]-amino}-piperidine-3-carboxylic acid methyl-(2-pyridin-2-yl-ethyl)-amide | 0.50 | 524 |

TABLE 2-continued

Examples 2.001-2.108

| Example Nr | Substance Name | $t_R$ (min) | QC LC-MS Mass Found $[M + H]^+$ |
|---|---|---|---|
| 2.080 | (3R,4R)-1-Cyclopropylmethyl-4-{[5-(2,4-difluoro-phenyl)-isoxazole-3-carbonyl]-amino}-piperidine-3-carboxylic acid (2-pyridin-2-yl-ethyl)-amide | 0.50 | 510.2 |
| 2.081 | (3R,4R)-1-Benzyl-4-{[5-(2,4-difluoro-phenyl)-isoxazole-3-carbonyl]-amino}-piperidine-3-carboxylic acid dimethylamide | 0.70 | 469.3 |
| 2.082 | (3R,4R)-1-(2-Chloro-benzyl)-4-{[5-(2,4-difluoro-phenyl)-isoxazole-3-carbonyl]-amino}-piperidine-3-carboxylic acid dimethylamide | 0.70 | 503.3 |
| 2.083 | (3R,4R)-4-{[5-(2,4-Difluoro-phenyl)-isoxazole-3-carbonyl]-amino}-1-(2-fluoro-benzyl)-piperidine-3-carboxylic acid dimethylamide | 0.70 | 487.3 |
| 2.084 | (3S,4S)-1-((1RS)-2,2-Difluoro-cyclopropylmethyl)-4-{[5-(2,4-difluoro-phenyl)-isoxazole-3-carbonyl]-amino}-piperidine-3-carboxylic acid (1-pyrimidin-2-yl-cyclopropyl)-amide (mixture of isomers) | 0.60 | 559.1 |
| 2.085 | (3R,4R)-4-{[5-(2,4-Difluoro-phenyl)-isoxazole-3-carbonyl]-amino}-1-(1-methyl-1H-pyrrol-3-ylmethyl)-piperidine-3-carboxylic acid dimethylamide | 0.60 | 472.4 |
| 2.086 | (3S,4S)-4-{[5-(2,4-Difluoro-phenyl)-isoxazole-3-carbonyl]-amino}-1-methyl-piperidine-3-carboxylic acid (1-pyrimidin-2-yl-cyclopropyl)-amide | 0.60 | 483.4 |
| 2.087 | (3S,4S)-4-{[5-(2,4-Difluoro-phenyl)-isoxazole-3-carbonyl]-amino}-1-(3-fluoro-propyl)-piperidine-3-carboxylic acid (1-pyrimidin-2-yl-cyclopropyl)-amide | 0.60 | 529 |
| 2.088 | rac-(3R*,4R*)-1-Cyclobutyl-4-{[5-(2,4-difluoro-phenyl)-isoxazole-3-carbonyl]-amino}-piperidine-3-carboxylic acid (1-pyrimidin-2-yl-cyclopropyl)-amide | 0.60 | 523 |
| 2.089 | (3S,4S)-1-(3,3-Difluoro-cyclobutyl)-4-{[5-(2,4-difluoro-phenyl)-isoxazole-3-carbonyl]-amino}-piperidine-3-carboxylic acid (1-pyrimidin-2-yl-cyclopropyl)-amide | 0.7 | 559 |
| 2.090 | (3S,4S)-4-{[5-(2,4-Difluoro-phenyl)-isoxazole-3-carbonyl]-amino}-1-(1-methyl-cyclopropylmethyl)-piperidine-3-carboxylic acid (1-pyrimidin-2-yl-cyclopropyl)-amide | 0.6 | 537.1 |
| 2.091 | (3S,4S)-1-Cyclopropylmethyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide | 0.5 | 522 |
| 2.092 | (3S,4S)-1-Cyclopentyl-4-{[1-(2,4-difluoro-phenyl)-1H-[1,2,3]triazole-4-carbonyl]-amino}-piperidine-3-carboxylic acid (1-pyridin-2-yl-cyclopropyl)-amide | 0.5 | 536.2 |
| 2.093 | (3S,4S)-1-Allyl-4-{[5-(2,4-difluoro-phenyl)-isoxazole-3-carbonyl]-amino}-piperidine-3-carboxylic acid (1-pyrimidin-2-yl-cyclopropyl)-amide | 0.6 | 509.2 |
| 2.094 | (3S,4S)-1-Bicyclo[3.1.0]hex-3-yl-4-{[5-(2,4-difluoro-phenyl)-isoxazole-3-carbonyl]-amino}-piperidine-3-carboxylic acid (1-pyrimidin-2-yl-cyclopropyl)-amide | 0.6 | 549.2 |
| 2.095 | (3S,4S)-4-{[5-(2,4-Difluoro-phenyl)-isoxazole-3-carbonyl]-amino}-1-propyl-piperidine-3-carboxylic acid (1-pyrimidin-2-yl-cyclopropyl)-amide | 0.5 | 511.2 |
| 2.096 (BB 8.02) | (3S,4S)-4-{[5-(2,4-Difluoro-phenyl)-oxazole-2-carbonyl]-amino}-piperidine-3-carboxylic acid (1-pyrimidin-2-yl-cyclopropyl)-amide | 0.6 | 469 |
| 2.097 | (3S,4S)-1-Cyclobutyl-4-{[5-(2,4-difluoro-phenyl)-oxazole-2-carbonyl]-amino}-piperidine-3-carboxylic acid (1-pyrimidin-2-yl-cyclopropyl)-amide | 0.6 | 523.1 |
| 2.098 | (3S,4S)-1-Cyclopentyl-4-{[5-(2,4-difluoro-phenyl)-oxazole-2-carbonyl]-amino}-piperidine-3-carboxylic acid (1-pyrimidin-2-yl-cyclopropyl)-amide | 0.6 | 537.1 |
| 2.099 | (3S,4S)-4-{[5-(2,4-Difluoro-phenyl)-oxazole-2-carbonyl]-amino}-1-isopropyl-piperidine-3-carboxylic acid (1-pyrimidin-2-yl-cyclopropyl)-amide | 0.6 | 511.4 |
| 2.100 | (3S,4S)-4-{[5-(2,4-Difluoro-phenyl)-oxazole-2-carbonyl]-amino}-1-(1-fluoro-cyclopropylmethyl)-piperidine-3-carboxylic acid (1-pyrimidin-2-yl-cyclopropyl)-amide | 0.6 | 541.3 |
| 2.101 | (3S,4S)-1-(3,3-Difluoro-cyclobutylmethyl)-4-{[5-(2,4-difluoro-phenyl)-isoxazole-3-carbonyl]-amino}-piperidine-3-carboxylic acid (1-pyrimidin-2-yl-cyclopropyl)-amide | 0.6 | 573 |
| 2.102 | (3S,4S)-4-{[5-(2,4-Difluoro-phenyl)-isoxazole-3-carbonyl]-amino}-1-thietan-3-yl-piperidine-3-carboxylic acid (1-pyrimidin-2-yl-cyclopropyl)-amide | 0.6 | 541 |
| 2.103 | (3S,4S)-4-{[5-(2,4-Difluoro-phenyl)-isoxazole-3-carbonyl]-amino}-1-spiro[2.3]hex-5-yl-piperidine-3-carboxylic acid (1-pyrimidin-2-yl-cyclopropyl)-amide | 0.6 | 549 |
| 2.104 (BB 2.14) | (3S,4S)-4-{[5-(2,4-Difluoro-phenyl)-[1,3,4]thiadiazole-2-carbonyl]-amino}-piperidine-3-carboxylic acid (1-pyrimidin-2-yl-cyclopropyl)-amide | 1.0 | 486.4 |
| 2.105 | (3S,4S)-1-Cyclobutyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide | 0.6 | 540.1 |

TABLE 2-continued

Examples 2.001-2.108

| Example Nr | Substance Name | QC LC-MS $t_R$ (min) | Mass Found [M + H]$^+$ |
|---|---|---|---|
| 2.106 | (3S,4S)-4-{[5-(2,4-difluoro-phenyl)-[1,3,4]thiadiazole-2-carbonyl]-amino}-1-(1-fluoro-cyclopropylmethyl)-piperidine-3-carboxylic acid (1-pyrimidin-2-yl-cyclopropyl)-amide | 0.6 | 558.1 |
| 2.107 | (3S,4S)-4-{[5-(2,4-difluoro-phenyl)-[1,3,4]thiadiazole-2-carbonyl]-amino}-1-ethyl-piperidine-3-carboxylic acid (1-pyrimidin-2-yl-cyclopropyl)-amide | 0.6 | 514.1 |
| 2.108 | (3S,4S)-1-(Cyclopropyl-(d$_2$-methyl))-4-{[5-(2,4-difluoro-phenyl)-isoxazole-3-carbonyl]-amino}-piperidine-3-carboxylic acid (1-pyrimidin-2-yl-cyclopropyl)-amide | 0.6 | 525.3 |

General Method C for the Synthesis of Compounds of Formula (I)
Buildings Blocks:
Preparation of Building Blocks of Structure C-3

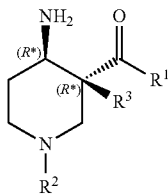

C-3

BB 3.01: rac-(3R*,4R*)-4-Amino-1-cyclohexyl-piperidine-3-carboxylic acid Dimethylamide 3.01a: rac-(3R*,4R*)-4-tert-Butoxycarbonylamino-1-cyclohexyl-piperidine-3-carboxylic Acid rac-(3R*,4R*)-4-tert-Butoxycarbonylamino-1-cyclohexyl-piperidine-3-carboxylic acid methyl ester 1.01a (2.85 g, 7.35 mmol) is dissolved in THF (45 mL) at RT. Aq. 1M NaOH solution (22.1 mL, 22.1 mmol) is then added and the mixture stirred at RT for 72 h. The reaction mixture is acidified to around pH=3 with a 2M HCl solution (12 mL) and evaporated. The resulting suspension is dissolved with DCM, the organic phase is dried over MgSO$_4$ and the solvents are evaporated to give the title compound; LC-MS method D $t_R$=0.54 min; [M+H]$^+$=327.23.

3.01b: rac-((3R*,4R*)-1-Cyclohexyl-3-dimethylcarbamoyl-piperidin-4-yl)-carbamic acid tert-butyl Ester To a solution of rac-(3R*,4R*)-4-tert-Butoxycarbonylamino-1-cyclohexyl-piperidine-3-carboxylic acid 3.01a (2.4 g, 7.35 mmol) in DMF (36.8 mL) is added a 40% solution of dimethylamine in water (2.79 mL, 22.1 mmol). DIPEA (4.11 mL, 23.5 mmol) is then added followed by HATU (2.93 g, 7.72 mmol). The reaction mixture is stirred for 2 h. The reaction mixture is concentrated, dissolved in DCM (150 mL) and treated with aq. sat. NaHCO$_3$ (150 mL). The organic layer is separated and the aq. phase is further extracted with DCM (3×150 mL). The combined organic phases are dried over MgSO$_4$ and evaporated. The crude residue is purified by prep. LC-MS with basic conditions (method E). The title compound is obtained; LC-MS method D $t_R$=0.91 min; [M+H]$^+$=353.96.

3.01: rac-(3R*,4R*)-4-Amino-1-cyclohexyl-piperidine-3-carboxylic Acid Dimethylamide rac-((3R*,4R*)-1-Cyclohexyl-3-dimethylcarbamoyl-piperidin-4-yl)-carbamic acid tert-butyl ester (2.08 g, 5.88 mmol) is dissolved in MeOH (29.5 mL) at RT. A 4M solution of HCl in dioxane (29.5 mL, 118 mmol) is added and the reaction is stirred at RT for 1 h. The reaction mixture is concentrated, dissolved in DCM (150 mL) and treated with aq. sat. NaHCO$_3$ (50 mL). The organic layer is separated and the aq. phase is extracted twice with DCM (2×100 mL) and twice with chloroform (2×100 mL). The combined organic phases are dried over MgSO$_4$, filtered and the solvent is evaporated to give the crude title compound; LC-MS method D $t_R$=0.68 min; [M+H]$^+$=254.24.

Preparation of Building-Blocks of General Formula (C-3) Used as Intermediates in the Preparation of Examples 3.001 to 3.022

The following intermediates are prepared in analogy to BB 3.01:

BB 3.02: rac-(3R*,4R*)-4-Amino-1-cyclohexyl-piperidine-3-carboxylic Acid (1-pyridin-2-yl-cyclopropyl)-amide, Dihydrochloride 3.02b: rac-[(3R*,4R*)-1-Cyclohexyl-3-(1-pyridin-2-yl-cyclopropylcarbamoyl)-piperidin-4-yl]-carbamic Acid Tert-Butyl Ester The title compound is prepared according to the procedure 3.01b, starting from building block 3.01a and 1-(2-pyridyl)cyclopropylamine dihydrochloride; LC-MS method D: $t_R$=0.97 min; [M+H]$^+$=443.21.

3.02: rac-(3R*,4R*)-4-Amino-1-cyclohexyl-piperidine-3-carboxylic Acid (1-pyridin-2-yl-cyclopropyl)-amide, Dihydrochloride The title compound is prepared according to the procedure 3.01, starting from building block 3.02b; LC-MS method D: $t_R$=0.77 min; [M+H]$^+$=343.17.

BB 3.03: rac-(3R*,4R*)-4-Amino-1-cyclopentyl-piperidine-3-carboxylic Acid Dimethylamide

3.03a: rac-(3R*,4R*)-4-tert-Butoxycarbonylamino-1-cyclopentyl-piperidine-3-carboxylic Acid The title compound is prepared according to the procedure 3.01a, starting from building block 1.03a; LC-MS method D: $t_R$=0.51 min; [M+H]$^+$=313.08.

3.03b: rac-((3R*,4R*)-1-Cyclopentyl-3-dimethylcarbamoyl-piperidin-4-yl)-carbamic Acid Tert-Butyl Ester The title compound is prepared according to the procedure 3.01b, starting from building block 3.03a and a 40% solution of dimethylamine in water; LC-MS method D: $t_R$=0.82 min; [M+H]$^+$=340.16.

3.02: rac-(3R*,4R*)-4-Amino-1-cyclopentyl-piperidine-3-carboxylic Acid Dimethylamide The title compound is prepared according to the procedure 3.01, starting from building block 3.03b; LC-MS method D: $t_R$=0.59 min; [M+H]$^+$=240.18.

BB 3.04: rac-(3R*,4R*)-4-Amino-1-cyclopropylmethyl-piperidine-3-carboxylic Acid (1-pyridin-2-yl-cyclopropyl)-amide, Dihydrochloride

3.04a: rac-(3R*,4R*)-4-tert-Butoxycarbonylamino-1-cyclopropylmethyl-piperidine-3-carboxylic Acid The title compound is prepared according to the procedure 3.01a, starting from building block 1.04a; LC-MS method D: $t_R$=0.47 min; [M+H]$^+$=299.13.

3.04b: rac-[(3R*,4R*)-1-Cyclopropylmethyl-3-(1-pyridin-2-yl-cyclopropylcarbamoyl)-piperidin-4-yl]-carbamic Acid Tert-Butyl Ester The title compound is prepared according to the procedure 3.01b, starting from building block 3.04a and 1-(2-pyridyl)cyclopropylamine dihydrochloride; LC-MS method D: $t_R$=0.85 min; [M+H]$^+$=415.17.

3.04 rac-(3R*,4R*)-4-Amino-1-cyclopropylmethyl-piperidine-3-carboxylic Acid (1-pyridin-2-yl-cyclopropyl)-amide, Dihydrochloride The title compound is prepared according to the procedure 3.01, starting from building block 3.04b; LC-MS method D: $t_R$=0.64 min; [M+H]$^+$=315.18.

BB 3.05: rac-(3R*,4R*)-4-Amino-1-cyclopropylmethyl-piperidine-3-carboxylic Acid (1-pyrimidin-2-yl-cyclopropyl)-amide Dihydrochloride

3.05b: rac-[(3R*,4R*)-1-Cyclopropylmethyl-3-(1-pyrimidin-2-yl-cyclopropylcarbamoyl)-piperidin-4-yl]-carbamic Acid Tert-Butyl Ester The title compound is prepared according to the procedure 3.01b, starting from building block 3.04a and 1-(2-pyrimidyl)cyclopropylamine hydrochloride; LC-MS method A: $t_R$=0.64 min; [M+H]$^+$=416.34.

3.05 rac-(3R*,4R*)-4-Amino-1-cyclopropylmethyl-piperidine-3-carboxylic Acid (1-pyrimidin-2-yl-cyclopropyl)-amide, Dihydrochloride The title compound is prepared according to the procedure 3.01, starting from building block 3.04b; LC-MS method A: $t_R$=0.38 min; [M+H]$^+$=316.34.

General Procedures for the Preparation of Compounds 3.001 to 3.022:

Method I:

To a solution of the respective amine (BB 3.01 to BB 3.05) (0.08 mmol) in 0.7 mL DMF is added the respective carboxylic acid (commercially available or of Structure A-4) (0.08 mmol). DIPEA (0.336 mmol) is then added followed by HATU (0.084 mmol). The reaction mixture is stirred 21 h at RT. Up to 0.28 mmol of a 2M HCl solution is added to the crude mixture to dissolve the precipitate, and the clear solution is directly purified by prep. LC-MS with method E.

Method J:

A solution of the respective amine (BB 3.01 to BB 3.05) (0.3 mmol) in toluene (0.4 mL) at 0° C. under argon is treated with a 2M solution of trimethylaluminium in toluene (0.3 mmol). After stirring for 30 min at 0° C., a solution of an ester of Structure A-4 (L1=O-alkyl) (0.1 mmol) in toluene (0.4 mL) is added and the mixture stirred at RT for 4 to 22 hours. The reaction mixture is quenched with a 1.25M solution of HCl in methanol (0.6 mmol) and the solvents are evaporated. The crude residue is purified by prep. LC-MS using method E.

Example 3.001: rac-(3R*,4R*)-1-Cyclohexyl-4-{[5-(2,6-difluoro-phenyl)-isoxazole-3-carbonyl]-amino}-piperidine-3-carboxylic Acid Dimethylamide To a solution of rac-(3R*,4R*)-4-amino-1-cyclohexyl-piperidine-3-carboxylic acid dimethylamide (20.3 mg, 0.08 mmol) in DMF (0.7 mL) is added 5-(2,6-difluoro-phenyl)-isoxazole-3-carboxylic acid (18 mg, 0.08 mmol). DIPEA (0.044 mL, 0.256 mmol) is then added followed by HATU (31.9 mg, 0.084 mmol). The reaction mixture is stirred 21 h at RT. Up to 0.28 mmol of a 2M HCl solution is added to the crude mixture to dissolve the precipitate, and the clear solution is directly purified by prep. LC-MS with method E. LC-MS method D: $t_R$=0.61 min; [M+H]$^+$=461.

Compounds of Examples 3.002 to 3.022 listed in Table 3 below are prepared by applying one of the above-mentioned general procedures I or J to the building blocks BB-3.01 BB-3.05 coupled with respective carboxylic acid or ester of Structure A-4 (L$^1$=OH or O-alkyl), which is commercially available or prepared according to/in analogy to the methods described above.

Enantiomerically pure compounds are obtained using one of the above mentioned chiral preparative chromatography methods.

TABLE 3

Examples 3.001a-3.022

| Example Nr | Substance Name | QC LC-MS $t_R$ (min) | Mass Found $[M + H]^+$ |
|---|---|---|---|
| 3.001 | rac-(3R*,4R*)-1-Cyclohexyl-4-{[5-(2,6-difluoro-phenyl)-isoxazole-3-carbonyl]-amino}-piperidine-3-carboxylic acid dimethylamide | 0.61 | 461 |
| 3.002 | rac-(3R*,4R*)-1-Cyclohexyl-4-{[5-(4-fluoro-phenyl)-isoxazole-3-carbonyl]-amino}-piperidine-3-carboxylic acid dimethylamide | 0.62 | 443 |
| 3.003 | rac-(3R*,4R*)-1-Cyclohexyl-4-{[5-(2,4-difluoro-phenyl)-[1,3,4]oxadiazole-2-carbonyl]-amino}-piperidine-3-carboxylic acid dimethylamide | 0.54 | 462.3 |
| 3.003a | (3R*,4R*)-1-Cyclohexyl-4-{[5-(2,4-difluoro-phenyl)-[1,3,4]oxadiazole-2-carbonyl]-amino}-piperidine-3-carboxylic acid dimethylamide (enantiomer 1) | 0.54 | 462.3 |
| 3.003b | (3R*,4R*)-1-Cyclohexyl-4-{[5-(2,4-difluoro-phenyl)-[1,3,4]oxadiazole-2-carbonyl]-amino}-piperidine-3-carboxylic acid dimethylamide (enantiomer 2) | 0.54 | 462 |
| 3.004 | rac-(3R*,4R*)-4-{[5-(2-Chloro-4-fluoro-phenyl)-isoxazole-3-carbonyl]-amino}-1-cyclohexyl-piperidine-3-carboxylic acid dimethylamide | 0.67 | 477.1 |
| 3.005 | rac-(3R*,4R*)-1-Cyclohexyl-4-{[5-(2,4,6-trifluoro-phenyl)-isoxazole-3-carbonyl]-amino}-piperidine-3-carboxylic acid dimethylamide | 0.63 | 479.3 |
| 3.006 | rac-(3R*,4R*)-4-{[5-(4-Chloro-2-fluoro-phenyl)-isoxazole-3-carbonyl]-amino}-1-cyclohexyl-piperidine-3-carboxylic acid dimethylamide | 0.69 | 477 |
| 3.007 | rac-(3R*,4R*)-1-Cyclohexyl-4-{[5-(2-difluoro-phenyl)-[1,2,4]oxadiazole-3-carbonyl]-amino}-piperidine-3-carboxylic acid dimethylamide | 0.56 | 462.3 |
| 3.009 | rac-(3R*,4R*)-1-Cyclohexyl-4-{[5-(2-fluoro-phenyl)-isoxazole-3-carbonyl]amino}-piperidine-3-carboxylic acid (1-pyridin-2-yl-cyclopropyl)-amide | 0.62 | 532.2 |
| 3.010 | rac-(3R*,4R*)-1-Cyclohexyl-4-{[5-(2,4-difluoro-phenyl)-[1,2,4]oxadiazole-3-carbonyl]-amino}-piperidine-3-carboxylic acid (1-pyridin-2-yl-cyclopropyl)-amide | 0.57 | 551 |
| 3.011 | rac-(3R*,4R*)-1-Cyclohexyl-4-{[5-(2-difluoro-phenyl)-oxazole-2-carbonyl]-amino}-piperidine-3-carboxylic acid (1-pyridin-2-yl-cyclopropyl)-amide | 0.61 | 550.3 |
| 3.012 | rac-(3R*,4R*)-1-Cyclohexyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide | 0.56 | 551.1 |
| 3.013 | rac-(3R*,4R*)-1-Cyclopropylmethyl-4-{[5-(2-fluoro-phenyl)-isoxazole-3-carbonyl]-amino}-piperidine-3-carboxylic acid (1-pyridin-2-yl-cyclopropyl)-amide | 0.56 | 504.1 |
| 3.014 | rac-(3R*,4R*)-1-Cyclopropylmethyl-4-{[5-(4-fluoro-phenyl)-isoxazole-3-carbonyl]-amino}-piperidine-3-carboxylic acid (1-pyridin-2-yl-cyclopropyl)-amide | 0.58 | 504.1 |
| 3.015 | rac-(3R*,4R*)-1-Cyclopropylmethyl-4-{[5-(2,4-difluoro-phenyl)-oxazole-2-carbonyl]-amino}-piperidine-3-carboxylic acid (1-pyridin-2-yl-cyclopropyl)-amide | 0.56 | 522.1 |
| 3.016 | rac-(3R*,4R*)-1-Cyclopropylmethyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide | 0.5 | 523.1 |
| 3.016a | (3S,4S)-1-Cyclopropylmethyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide or (3R,4R)-1-Cyclopropylmethyl-4-{[5-(2,4-difluoro-phenyl)-[1,3,4]oxadiazole-2-carbonyl]-amino}-piperidine-3-carboxylic acid (1-pyridin-2-yl-cyclopropyl)-amide (1$^{st}$ eluted enantiomer) | 0.51 | 523.1 |
| 3.017 | rac-(3R*,4R*)-1-Cyclopentyl-4-{[5-(2,4-difluoro-phenyl)-oxazole-2-carbonyl]-amino}-piperidine-3-carboxylic acid dimethylamide | 0.57 | 447.3 |
| 3.018 | rac-(3R*,4R*)-1-Cyclohexyl-4-{[5-(2,4-difluoro-phenyl)-oxazole-2-carbonyl]-amino}-piperidine-3-carboxylic acid dimethylamide | 0.61 | 461.3 |
| 3.019 | rac-(3R*,4R*)-1-Cyclohexyl-4-{[3-(2,4-difluoro-phenyl)-[1,2,4]oxadiazole-5-carbonyl]-amino}-piperidine-3-carboxylic acid dimethylamide | 0.59 | 462.3 |
| 3.020a | (3R*,4R*)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide (enantiomer 1) | 0.61 | 541.28 |
| 30.20b | (3R*,4R*)-1-Cyclopropylmethyl-4-{[5-(2,4,6-trifluoro-phenyl)-isoxazole-3-carbonyl]-amino}-piperidine-3-carboxylic acid (1-pyrimidin-2-yl-cyclopropyl)-amide (enantiomer 2) | 0.61 | 541.41 |
| 3.021 | rac-(3R*,4R*)-1-Cyclopropylmethyl-4-{[4-fluoro-5-(4-fluoro-phenyl)-isoxazole-3-carbonyl]-amino}-piperidine-3-carboxylic acid (1-pyrimidin-2-yl-cyclopropyl)-amide | 0.60 | 523.4 |
| 3.022 | rac-(3R*,4R*)-1-Cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide | 0.60 | 541 |
| 3.022a | (3R,4R)-1-Cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide or (3S,4S)-1-cyclopropylmethyl-4-{[5-(2,4-difluoro-phenyl)-4-fluoro-isoxazole-3-carbonyl]-amino}-piperidine-3-carboxylic acid (1-pyrimidin-2-yl-cyclopropyl)-amide (1$^{st}$ eluted enantiomer) | 0.60 | 541.4 |

General Method D for the Synthesis of Piperidines of Formula (I)
Buildings Blocks:
Preparation of Building Blocks of Structure 1

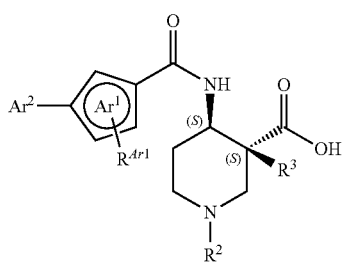

1

BB-4.01 (3S,4S)-1-Cyclohexyl-4-{[5-(2,4-difluoro-phenyl)-isoxazole-3-carbonyl]-amino}-piperidine-3-carboxylic Acid 4.01a: 4-((S)-1-Phenyl-ethylamino)-5,6-dihydro-2H-pyridine-1,3-dicarboxylic Acid 1-tert-butyl Ester 3-ethyl Ester In a dry flask equipped with a Dean-Stark trap and reflux condenser, 4-oxopiperidine-1,3-dicarboxylic acid-1-t-butyl ester 3-methyl ester (10 g, 35 mmol) is dissolved in toluene (500 mL). (S)-(−)-α-methylbenzylamine (6.36 g, 52.5 mmol) and p-toluenesulfonic acid monohydrate (0.34 g, 1.75 mmol) are added and the mixture is heated to reflux for 3 h. The mixture is then cooled to RT, washed three times with aq. sat. NaHCO$_3$ (3×100 mL) and dried over MgSO$_4$, filtered and concentrated under reduced pressure to yield the product as a thick yellow oil. LC-MS method A: $t_R$=1.01 min; [M+H]$^+$=375.18. $^1$H NMR (400 MHz, CDCl$_3$) δ: 9.28 (d, J=7.4 Hz, 1H), 7.25-7.38 (m, 5H), 4.63 (quint, J=6.7 Hz, 1H), 4.19 (q, J=7 Hz, 2H), 4.07 (s, 2H) 3.46-3.38 (m, 1H) 3.33-3.26 (m, 1H), 2.43-35 (m, 1H), 2.09-1.99 (m, 1H), 1.50 (d, J=7.4 Hz, 3H), 1.43 (s, 9H), 1.29 (t, J=7.0 Hz, 3H).

4.01b: (3S,4S)-4-((S)-1-Phenyl-ethylamino)-piperidine-1,3-dicarboxylic Acid 1-tert-butyl Ester 3-ethyl Ester Sodium borohydride (5.19 g, 137 mmol) is added portionwise under N$_2$ to a solution of isobutyric acid (68.1 mL, 734 mmol) in toluene (22 mL) at 0° C. The mixture is further stirred at RT for 20 min. The mixture is cooled again to 0° C. A solution of 4-((S)-1-Phenyl-ethylamino)-5,6-dihydro-2H-pyridine-1,3-dicarboxylic acid 1-tert-butyl ester 3-ethyl ester (13 g, 34.7 mmol) in toluene (50 mL) is slowly added and the resulting mixture is stirred for 60 min at 0° C. Additional sodium borohydride (817 mg, 21.6 mmol) is added in five portions over a 4 h period. Water (100 mL) is added carefully and the reaction mixture is stirred for 15 min at RT. A 3M aq.NaOH solution is added to bring the mixture to pH 10. The reaction mixture is extracted with EtOAc (3×150 mL), the combined organic layers are dried with MgSO$_4$ and the solvent is evaporated under reduced pressure. The resulting yellow oil is purified on a plug of silica gel and chromatographied with heptane/EtOAc 2:1 to give a yellowish oil. This oil is dissolved in dry ethanol (50 mL) under N$_2$ and the resulting solution is transferred to a solution prepared in advance by mixing sodium ethoxide in ethanol (20 mL of 21 w %, 52 mmol) and EtOAc (7.6 mL, 78 mmol). The resulting solution is stirred at 50° C. under N$_2$ for 15 h. The solvent is removed under reduced pressure, brine (150 mL) is added and the pH of the resulting solution is brought to pH=10 with 1 N aq. NaOH. The resulting mixture is extracted with EtOAc (3×100 mL). The combined organic layers are dried over MgSO$_4$ and concentrated under reduced pressure. The resulting oil is purified by flash chromatography over 100 g of silica gel with Heptane/EtOAc system (10:0 to 1:1 gradient) as eluent. The combined fractions are concentrated and dried under vacuum over night to obtain a pale yellow oil. This oil is dissolved in diethyl ether (10 mL) and 4 N HCl in dioxane (1.45 mL, 5.8 mmol) is added dropwise. The solution is stirred for 30 min and a precipitate is formed during this time. The precipitation is completed by adding heptane (28.7 mL) and storing the mixture at 0° C. for 1 h. The precipitate is isolated by filtration and washed with heptane to yield 2.57 g of an off-white solid. The solid is suspended in acetonitrile (4.6 mL) and heated to reflux until the solid has dissolved completely. The solution is then cooled to 0° C. overnight. The resulting crystals are isolated by filtration and washed 3× with 1.15 mL portions of cold acetonitrile to yield the hydrochloride salt as a colorless solid. The salt is then stirred in aq. 10% NaHCO$_3$ solution (25 mL) and extracted with DCM (2×20 mL). Evaporation of the organic layers under reduced pressure yields the title product as a colorless oil. LC-MS method A: $t_R$=0.73 min; [M+H]$^+$=377.29 $^1$H NMR (400 MHz, CDCl3) δ: 7.79-7.40 (m, 5H), 4.13-4.24 (m, 3H), 3.70-4.09 (m, 2H), 2.82-2.99 (m, 2H), 2.58-2.72 (m, 1H), 2.21-2.38 (m, 1H), 1.62-1.76 (m, 1H), 1.45 (m, 9H), 1.20-1.35 (m, 7H), 1.02-1.14 (m, 1H).

4.01c: (3S,4S)-4-Amino-piperidine-1,3-dicarboxylic Acid 1-tert-butyl Ester 3-methyl Ester A solution of (3S,4S)-4-((S)-1-phenyl-ethylamino)-piperidine-1,3-dicarboxylic acid 1-tert-butyl ester 3-ethyl ester (1.833 g, 5.06 mmol) in MeOH (7 mL) is added to a suspension of palladium on activated charcoal (10%) (183 mg, 0.172 mmol) and ammonium formate (2.63 g, 40.5 mmol) in MeOH (40 mL) under N$_2$. The mixture is refluxed for 6 h. After the reaction is complete (disappearance of the peak but also exchange of the ethyl- for the methyl ester) the cooled solution is filtered through Celite, and the filtrate is concentrated to obtain the title product as a slightly yellow oil. LC-MS method A: $t_R$=0.53 min; [M+H]$^+$=259.23. $^1$H NMR (400 MHz, CDCl3) δ: 3.87-3.49 (m, 4H), 3.70 (s, 3H), 3.31 (m, 1H), 2.43-1.75 (m, 5H), 1.43 (s, 9H).

4.01d: (3S,4S)-4-{[5-(2,4-Difluoro-phenyl)-isoxazole-3-carbonyl]-amino}-piperidine-1,3-dicarboxylic Acid 1-tert-butyl Ester 3-methyl Ester To a solution of (3S,4S)-4-amino-piperidine-1,3-dicarboxylic acid 1-tert-butyl ester 3-methyl ester (1 g, 3.87 mmol) in DMF (8 mL) at RT is added 5-(2,4-difluorophenyl) isoxazole-3-carboxylic acid (1.3 g, 5.81 mmol). DIPEA (2.12 mL, 12.4 mmol) is then added followed by HATU (1.55 g, 4.06 mmol). The reaction mixture is stirred overnight at RT. The reaction mixture is concentrated, dissolved in DCM (100 mL) and treated twice with aq. sat. NaHCO$_3$ (100 mL). The organic layer is dried over MgSO$_4$ and evaporated. The crude residue is purified by flash chromatography over 40 g of silica gel with heptane/EtOAc system (1:0 to 3:1) as eluent to yield the title compound as white powder; LC-MS method A: $t_R$=0.94 min; [M+H]$^+$=466.04.

¹H NMR (400 MHz, CDCl3) δ: 7.23-7.36 (m, 1H), 7.96 (m, 1H), 6.96-7.12 (m, 3H), 6.79-6.91 (m, 1H), 4.29-4.51 (m, 2H), 4.00-4.22 (m, 1H), 3.64-3.78 (m, 3H), 2.85-3.09 (m, 2H), 2.50-2.68 (m, 1H), 2.10-2.27 (m, 1H), 1.42-1.69 (m, 11H), 1.21-1.38 (m, 1H).

4.01e: (3S,4S)-4-{[5-(2,4-Difluoro-phenyl)-isoxazole-3-carbonyl]-amino}-piperidine-3-carboxylic Acid Methyl Ester Hydrochloride (3S,4S)-4-{[5-(2,4-Difluoro-phenyl)-isoxazole-3-carbonyl]-amino}-piperidine-1,3-dicarboxylic acid 1-tert-butyl ester 3-methyl ester (1152 mg, 2.48 mmol) is dissolved in DCM (15 mL). HCl in dioxane 4M (12.4 mL, 49.5 mmol) is added dropwise. The mixture is stirred at RT for 1 hour. The solvents are evaporated and the residue is dried on HV to deliver the title crude compound as a white powder. LC-MS method A: $t_R$=0.61 min; [M+H]⁺=366.18.

4.01f: (3S,4S)-1-Cyclohexyl-4-{[5-(2,4-difluoro-phenyl)-isoxazole-3-carbonyl]-amino}-piperidine-3-carboxylic Acid Methyl Ester To a suspension of (3S,4S)-4-{[5-(2,4-difluoro-phenyl)-isoxazole-3-carbonyl]-amino}-piperidine-3-carboxylic acid methyl ester hydrochloride (0.99 g, 2.48 mmol) in DCM (20 mL) at RT is added cyclohexanone (0.75 mL, 6.9 mmol) followed by acetic acid (0.44 mL, 7.7 mmol) and sodium triacetoxyborohydride (1.58 g, 7.45 mmol). The reaction mixture is stirred overnight at RT. The reaction mixture is diluted with DCM (30 mL) and treated with aq. sat. NaHCO₃ twice (50 mL). The organic phase is dried over MgSO₄ and evaporated. The crude title compound is obtained; LC-MS method A: $t_R$=0.71 min; [M+H]⁺=448.17.

4.01: (3S,4S)-1-Cyclohexyl-4-{[5-(2,4-difluoro-phenyl)-isoxazole-3-carbonyl]-amino}-piperidine-3-carboxylic Acid (3S,4S)-1-Cyclohexyl-4-{[5-(2,4-difluoro-phenyl)-isoxazole-3-carbonyl]-amino}-piperidine-3-carboxylic acid methyl ester (1214 mg, 2.71 mmol) is dissolved in THF (14 mL) and 1 M aq. LiOH solution (6.98 mL, 6.98 mmol) is added. The mixture is stirred overnight at RT. 1M aq. HCl solution (6.98 mL, 6.98 mmol) is added and the reaction is stirred for 5 min. The solvents are evaporated to give the title compound as a yellow solid. LC-MS method A: $t_R$=0.66 min; [M+H]⁺=434.06.

Preparation of Building Blocks of Structure 1 Used as Intermediates in the Preparation of Examples 4.001 to 4.102.

The following carboxylic acids are prepared in analogy to example BB-4.01:

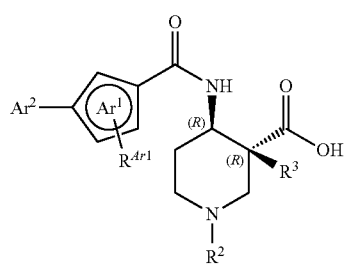

1

BB-4.02: (3R,4R)-1-Cyclohexyl-4-{[5-(2,4-difluoro-phenyl)-isoxazole-3-carbonyl]-amino}-piperidine-3-carboxylic Acid 4.02a: 4-((R)-1-Phenyl-ethylamino)-5,6-dihydro-2H-pyridine-1,3-dicarboxylic acid 1-tert-butyl Ester 3-ethyl Ester The title compound is prepared according to reaction 4.01a described above using 4-oxopiperidine-1,3-dicarboxylic acid-1-t-butyl ester 3-ethyl ester and (R)-(−)-α-methylbenzylamine; LC-MS method A: $t_R$=1.01 min; [M+H]⁺=375.28.

4.02b: (3R,4R)-4-(R)-1-Phenyl-ethylamino)-piperidine-1,3-dicarboxylic Acid 1-tert-butyl Ester 3-ethyl Ester The title compound is prepared according to reaction 4.01b described above by reduction of 4-((R)-1-phenylethylamino)-5,6-dihydro-2H-pyridine-1,3-dicarboxylic acid 1-tert-butyl ester 3-ethyl ester with a mixture of sodium borohydride and isobutyric acid followed by epimerisation with sodium ethoxide in EtOH and EtOAc; LC-MS method A: $t_R$=0.72 min; [M+H]⁺=377.27.

4.02c: (3R,4R)-4-amino-piperidine-1,3-dicarboxylic Acid 1-tert-butyl Ester 3-methyl Ester The title compound is prepared according to reaction 4.01c described above by treatment of (3R,4R)-4-(R)-1-phenyl-ethylamino)-piperidine-1,3-dicarboxylic acid 1-tert-butyl ester 3-ethyl ester with palladium on activated charcoal (10%)) and ammonium formate in MeOH; LC-MS method A: $t_R$=0.52 min; [M+H]⁺=259.22.

4.02d: (3R,4R)-4-{[5-(2,4-Difluoro-phenyl)-isoxazole-3-carbonyl]-amino}-piperidine-1,3-dicarboxylic Acid 1-tert-butyl Ester 3-methyl Ester The title compound is prepared according to reaction 4.01d by treatment of (3R,4R)-4-amino-piperidine-1,3-dicarboxylic acid 1-tert-butyl ester 3-methyl ester with 5-(2,4-difluorophenyl)isoxazole-3-carboxylic Acid; LC-MS A: $t_R$=0.94 min; [M+H]⁺=466.02.

4.02e: (3R,4R)-4-{[5-(2,4-Difluoro-phenyl)-isoxazole-3-carbonyl]-amino}-piperidine-3-carboxylic Acid Methyl Ester Hydrochloride The title compound is prepared according to reaction 4.01e by treatment of (3R,4R)-4-{[5-(2,4-difluoro-phenyl)-isoxazole-3-carbonyl]-amino}-piperidine-1,3-dicarboxylic acid 1-tert-butyl ester 3-methyl ester with HCl in Dioxane 4M; LC-MS method A: $t_R$=0.61 min; [M+H]⁺=366.14.

4.02f: (3R,4R)-1-Cyclohexyl-4-{[5-(2,4-difluoro-phenyl)-isoxazole-3-carbonyl]-amino}-piperidine-3-carboxylic Acid Methyl Ester The title compound is prepared according to reaction 4.01f by treatment of (3R,4R)-4-{[5-(2,4-difluoro-phenyl)-isoxazole-3-carbonyl]-amino}-piperidine-3-carboxylic Acid Methyl Ester hydrochloride with cyclohexanone and sodium triacetoxyborohydride; LC-MS method A: $t_R$=0.72 min; [M+H]⁺=448.19.

4.02: (3R,4R)-1-Cyclohexyl-4-{[5-(2,4-difluoro-phenyl)-isoxazole-3-carbonyl]-amino}-piperidine-3-carboxylic Acid The title compound is prepared according to reaction 4.01 by treatment of (3R,4R)-1-cyclohexyl-4-{[5-(2,4-difluoro-phenyl)-isoxazole-3-carbonyl]-amino}-piperidine-3-carboxylic acid methyl ester 1 M aq. LiOH solution. LC-MS method A: $t_R$=0.66 min; [M+H]$^+$=434.07.

BB-4.03: (3S,4S)-1-Cyclopropylmethyl-4-{[5-(2,4-difluoro-phenyl)-isoxazole-3-carbonyl]-amino}-piperidine-3-carboxylic Acid

4.03f: (3S,4S)-1-Cyclopropylmethyl-4-{[5-(2,4-difluoro-phenyl)-isoxazole-3-carbonyl]-amino}-piperidine-3-carboxylic Acid Methyl Ester The title compound is prepared according to reaction 4.01f by treatment of (3S,4S)-4-{[5-(2,4-difluoro-phenyl)-isoxazole-3-carbonyl]-amino}-piperidine-3-carboxylic Acid Methyl Ester hydrochloride with cyclopropanecarbaldehyde and sodium triacetoxyborohydride; LC-MS method D: $t_R$=1.02 min; [M+H]$^+$=420.12.

4.03: (3S,4S)-1-Cyclopropylmethyl-4-{[5-(2,4-difluoro-phenyl)-isoxazole-3-carbonyl]-amino}-piperidine-3-carboxylic Acid The title compound is prepared according to reaction 4.01 by treatment of (3S,4S)-1-cyclopropylmethyl-4-{[5-(2,4-difluoro-phenyl)-isoxazole-3-carbonyl]-amino}-piperidine-3-carboxylic acid methyl ester with 1 M aq. LiOH solution. LC-MS method D: $t_R$=0.54 min; [M+H]$^+$=405.79.

BB-4.04: (3S,4S)-1-Cyclopentyl-4-{[5-(2,4-difluoro-phenyl)-isoxazole-3-carbonyl]-amino}-piperidine-3-carboxylic Acid

4.04f: (3S,4S)-1-Cyclopentyl-4-{[5-(2,4-difluoro-phenyl)-isoxazole-3-carbonyl]-amino}-piperidine-3-carboxylic Acid Methyl Ester The title compound is prepared according to reaction 4.01f by treatment of (3S,4S)-4-{[5-(2,4-difluoro-phenyl)-isoxazole-3-carbonyl]-amino}-piperidine-3-carboxylic Acid Methyl Ester hydrochloride with cyclopentanone and sodium triacetoxyborohydride; LC-MS method D: $t_R$=1.04 min; [M+H]$^+$=434.14.

4.04g: (3S,4S)-1-Cyclopentyl-4-{[5-(2,4-difluoro-phenyl)-isoxazole-3-carbonyl]-amino}-piperidine-3-carboxylic Acid The title compound is prepared according to reaction 4.01 by treatment of (3S,4S)-1-cyclopentyl-4-{[5-(2,4-difluoro-phenyl)-isoxazole-3-carbonyl]-amino}-piperidine-3-carboxylic acid methyl ester with 1 M aq. LiOH solution. LC-MS method D: $t_R$=0.56 min; [M+H]$^+$=420.09.

BB-4.05: (3S,4S)-1-Cyanomethyl-4-{[5-(2,4-difluoro-phenyl)-isoxazole-3-carbonyl]-amino}-piperidine-3-carboxylic Acid

4.05f: (3S,4S)-1-Cyanomethyl-4-{[5-(2,4-difluoro-phenyl)-isoxazole-3-carbonyl]-amino}-piperidine-3-carboxylic Acid Ethyl Ester The title compound is prepared by treatment of (3S,4S)-4-{[5-(2,4-difluoro-phenyl)-isoxazole-3-carbonyl]-amino}-piperidine-3-carboxylic acid ethyl ester hydrochloride with bromoacetonitrile and DIPEA in EtOH; LC-MS method A: $t_R$=0.95 min; [M+H]$^+$=419.19.

4.05: (3S,4S)-1-Cyanomethyl-4-{[5-(2,4-difluoro-phenyl)-isoxazole-3-carbonyl]-amino}-piperidine-3-carboxylic Acid The title compound is prepared according to reaction 4.01 by treatment of (3S,4S)-1-cyanomethyl-4-{[5-(2,4-difluoro-phenyl)-isoxazole-3-carbonyl]-amino}-piperidine-3-carboxylic acid ethyl ester with 1 M aq. LiOH solution. LC-MS method D: $t_R$=0.81 min; [M+H]$^+$=391.20.

BB-4.06: (3S,4S)-4-{[5-(2,4-Difluoro-phenyl)-isoxazole-3-carbonyl]-amino}-1-(1-fluoro-cyclopropylmethyl)-piperidine-3-carboxylic Acid

4.06c: (3R,4S)-4-Amino-piperidine-1,3-dicarboxylic Acid 1-tert-butyl Ester 3-ethyl Ester The title compound is prepared according to reaction 4.01c described above by treatment of (3R,4S)-4-(R)-1-phenyl-ethylamino)-piperidine-1,3-dicarboxylic acid 1-tert-butyl ester 3-ethyl ester with palladium hydroxide on activated charcoal 20%)) and hydrogen in EtOH at 20 bar and 80° C.; LC-MS method D: $t_R$=0.81 min; [M+H]$^+$=273.21

4.06d: (3S,4S)-4-{[5-(2,4-Difluoro-phenyl)-isoxazole-3-carbonyl]-amino}-piperidine-1,3-dicarboxylic Acid 1-tert-butyl Ester 3-ethyl Ester The title compound is prepared according to reaction 4.01d by treatment of (3S,4R)-4-amino-piperidine-1,3-dicarboxylic acid 1-tert-butyl ester 3-ethyl ester with 5-(2,4-difluorophenyl)isoxazole-3-carboxylic Acid followed by epimerization with sodium ethoxyde in ethanol; LC-MS A: $t_R$=0.96 min; [M+H]$^+$=480.17.

4.06e: (3S,4S)-4-{[5-(2,4-Difluoro-phenyl)-isoxazole-3-carbonyl]-amino}-piperidine-3-carboxylic Acid Ethyl Ester Hydrochloride The title compound is prepared according to reaction 4.01e by treatment of (3S,4S)-4-{[5-(2,4-difluoro-phenyl)-isoxazole-3-carbonyl]-amino}-piperidine-1,3-dicarboxylic acid 1-tert-butyl ester 3-ethyl ester with HCl in dioxane 4M; LC-MS method A: $t_R$=0.70 min; [M+H]$^+$=380.18.

4.06f: (3S,4S)-4-{[5-(2,4-Difluoro-phenyl)-isoxa-zole-3-carbonyl]-amino}-1-(1-fluoro-cyclopropylmethyl)-piperidine-3-carboxylic Acid Ethyl Ester The title compound is prepared by treatment of (3S,4S)-4-{[5-(2,4-difluoro-phenyl)-isoxazole-3-carbonyl]-amino}-piperidine-3-carboxylic acid ethyl ester hydrochloride with 1-fluorocyclopropane-1-carbaldehyde and sodium triacetoxyborohydride; LC-MS method A: $t_R$=0.78 min; [M+H]$^+$= 452.19.

4.06: (3S,4S)-4-{[5-(2,4-Difluoro-phenyl)-isoxazole-3-carbonyl]-amino}-1-(1-fluoro-cyclopropylmethyl)-piperidine-3-carboxylic Acid The title compound is prepared according to reaction 4.01 by treatment of (3S,4S)-4-{[5-(2,4-difluoro-phenyl)-isoxazole-3-carbonyl]-amino}-1-(1-fluoro-cyclopropylmethyl)- piperidine-3-carboxylic acid ethyl ester with 1 M aq. LiOH solution. LC-MS method D: $t_R$=0.69 min; [M+H]$^+$=424.20.

BB-4.07: (3R,4R)-1-Cyclopropylmethyl-4-{[5-(2,4-difluoro-phenyl)-isoxazole-3-carbonyl]-amino}-piperidine-3-carboxylic Acid

4.07f: (3R,4R)-1-Cyclopropylmethyl-4-{[5-(2,4-difluoro-phenyl)-isoxazole-3-carbonyl]-amino}-piperidine-3-carboxylic Acid Methyl Ester The title compound is prepared according to reaction 4.01f by treatment of (3R,4R)-4-{[5-(2,4-difluoro-phenyl)-isoxazole-3-carbonyl]-amino}-piperidine-3-carboxylic Acid Methyl Ester hydrochloride with cyclopropanecarbaldehyde and sodium triacetoxyborohydride; LC-MS method A: $t_R$=0.7 min; [M+H]$^+$=420.14.

4.07: (3R,4R)-1-Cyclopropylmethyl-4-{[5-(2,4-difluoro-phenyl)-isoxazole-3-carbonyl]-amino}-piperidine-3-carboxylic Acid The title compound is prepared according to reaction 4.01 by treatment of (3R,4R)-1-cyclopropylmethyl-4-{[5-(2,4-difluoro-phenyl)-isoxazole-3-carbonyl]-amino}-piperidine-3-carboxylic acid methyl ester with 1 M aq. LiOH solution. LC-MS method A: $t_R$=0.64 min; [M+H]$^+$=406.06.

BB-4.08 (3S,4S)-1-Cyclobutyl-4-{[5-(2,4-difluoro-phenyl)-isoxazole-3-carbonyl]-amino}-piperidine-3-carboxylic Acid

4.08f: (3S,4S)-1-Cyclobutyl-4-{[5-(2,4-difluoro-phenyl)-isoxazole-3-carbonyl]-amino}-piperidine-3-carboxylic Acid Methyl Ester The title compound is prepared according to reaction 4.01f by treatment of (3S,4S)-4-{[5-(2,4-difluoro-phenyl)-isoxazole-3-carbonyl]-amino}-piperidine-3-carboxylic Acid Methyl Ester hydrochloride with cyclobutanone and sodium triacetoxyborohydride; LC-MS method A: $t_R$=0.76 min; [M+H]$^+$=420.21.

4.08: (3S,4S)-1-Cyclobutyl-4-{[5-(2,4-difluoro-phenyl)-isoxazole-3-carbonyl]-amino}-piperidine-3-carboxylic Acid The title compound is prepared according to reaction 4.01g by treatment of (3S,4S)-1-cyclobutyl-4-{[5-(2,4-difluoro-phenyl)-isoxazole-3-carbonyl]-amino}-piperidine-3-carboxylic acid methyl ester with 1 M aq. LiOH solution. LC-MS method A: $t_R$=0.64 min; [M+H]$^+$=406.33.

BB-4.09 (3R,4R)-1-Cyclobutyl-4-{[5-(2,4-difluoro-phenyl)-isoxazole-3-carbonyl]-amino}-piperidine-3-carboxylic Acid

4.09f: (3R,4R)-1-Cyclobutyl-4-{[5-(2,4-difluoro-phenyl)-isoxazole-3-carbonyl]-amino}-piperidine-3-carboxylic Acid Methyl Ester The title compound is prepared according to reaction 4.01f by treatment of (3R,4R)-4-{[5-(2,4-difluoro-phenyl)-isoxazole-3-carbonyl]-amino}-piperidine-3-carboxylic Acid Methyl Ester hydrochloride with cyclobutanone and sodium triacetoxyborohydride; LC-MS method A: $t_R$=0.77 min; [M+H]$^+$=419.83.

4.09: (3R,4R)-1-Cyclobutyl-4-{[5-(2,4-difluoro-phenyl)-isoxazole-3-carbonyl]-amino}-piperidine-3-carboxylic Acid The title compound is prepared according to reaction 4.01g by treatment of (3R,4R)-1-cyclobutyl-4-{[5-(2,4-difluoro-phenyl)-isoxazole-3-carbonyl]-amino}-piperidine-3-carboxylic acid methyl ester with 1 M aq. LiOH solution. LC-MS method A: $t_R$=0.69 min; [M+H]$^+$=406.22.

BB-4.10: (3S,4S)-4-{[5-(2,4-Difluoro-phenyl)-isoxazole-3-carbonyl]-amino}-1-ethyl-piperidine-3-carboxylic Acid

4.10f: (3S,4S)-4-{[5-(2,4-Difluoro-phenyl)-isoxazole-3-carbonyl]-amino}-1-ethyl-piperidine-3-carboxylic Acid Methyl Ester The title compound is prepared according to reaction 4.01f by treatment of (3S,4S)-4-{[5-(2,4-difluoro-phenyl)-isoxazole-3-carbonyl]-amino}-piperidine-3-carboxylic Acid Methyl Ester hydrochloride with acetaldehyde and sodium triacetoxyborohydride; LC-MS method A: $t_R$=0.66 min; [M+H]$^+$=394.35.

4.10: (3S,4S)-4-{[5-(2,4-Difluoro-phenyl)-isoxazole-3-carbonyl]-amino}-1-ethyl-piperidine-3-carboxylic Acid The title compound is prepared according to reaction 4.01g by treatment of (3S,4S)-1-cyclobutyl-4-{[5-(2,4-difluoro-phenyl)-isoxazole-3-carbonyl]-amino}-piperidine-3-carboxylic acid methyl ester with 1 M aq. LiOH solution. LC-MS method A: $t_R$=0.62 min; [M+H]$^+$=380.96.

BB-4.11: rac-(3R*,4R*)-1-tert-Butyl-4-{[5-(2,4-difluoro-phenyl)-isoxazole-3-carbonyl]-amino}-piperidine-3-carboxylic Acid

4.11a: 4-Amino-1-tert-butyl-1,2,5,6-tetrahydro-pyridine-3-carboxylic Acid Methyl Ester A solution of LiHMDS 1M in THF (6.73 mL, 6.73 mmol, 1.1 eq) is added dropwise at −78° C. to a solution of 1-tert-butylpiperidin-4-one (1000 mg, 6.12 mmol) in THF (10 mL) under argon. The mixture is stirred at this temperature for 1 h. Then methyl cyanoformate (0.486 mL, 6.12 mmol) is added and the reaction is stirred at −78° C. for 1 h. MeOH (30 mL) is added at −78° C., followed by ammonium acetate (4813 mg, 61.2 mmol). the mixture is stirred at this temperature for a 15 minutes and then allowed to warm to RT and stirred for 18 h. The solvents are evaporated under reduced pressure. The residue is taken up in DCM (25 mL) and washed with sat. aq. NaHCO$_3$ (25 mL). The aq. phase is extracted twice with DCM (2×25 mL). The organic phase is washed with brine (25 mL). The combined organic layers are dried over MgSO$_4$, filtered and concentrated to deliver the crude title compound as a yellowish oil; LC-MS method A: $t_R$=0.43 min; [M+H]$^+$=213.46.

4.11b: rac-[R*,R*]-Methyl-4-amino-1-(tert-butyl)piperidine-3-carboxylate and rac-[R*,S*]-methyl 4-amino-1-(tert-butyl)piperidine-3-carboxylate A solution of 4-amino-1-tert-butyl-1,2,5,6-tetrahydropyridine-3-carboxylic Acid Methyl Ester (1.29 g, 6.12 mmol) in methanol (10 mL) is treated with NaBH$_3$CN (774 mg, 12.3 mmol) and AcOH (1.06 mL, 9.25 mmol) at 0° C. Then the reaction is let to warm to RT. The reaction is stirred at 50° C. for 1 h. NaBH$_3$CN (387 mg, 6.15 mmol, 1 eq) is added and the reaction is heated at 50° C. for 18 h. MeOH is evaporated under reduced pressure and the residue is taken up in DCM (20 mL) and washed with sat. aq. NaHCO$_3$ (20 mL). The aq. phases are extracted twice (2×15 mL) with DCM and the organic phases are combined, dried over MgSO$_4$, filtered and concentrated under reduced pressure to yield the crude title product as a yellowish oil; LC-MS method A: t$_R$=0.21 min; [M+H]$^+$=215.34.

4.11c: rac-(3R*,4R*)-1-tert-Butyl-4-{[5-(2,4-difluoro-phenyl)-isoxazole-3-carbonyl]-amino}-piperidine-3-carboxylic Acid Methyl Ester A solution of rac-[R*,R*]-methyl 4-amino-1-(tert-butyl) piperidine-3-carboxylate and rac-[R*,S*]-methyl 4-amino-1-(tert-butyl)piperidine-3-carboxylate (659 mg, 3.08 mmol) in DCM (5 mL), is treated with 5-(2,4-difluorophenyl) isoxazole-3-carboxylic acid (714 mg, 3.08 mmol), HATU (2338 mg, 3.08 mmol), and DIPEA (0.526 mL, 3.08 mmol). The reaction mixture is stirred at RT for 1 h30. DCM (10 mL) and sat. aq. NaHCO$_3$ solution (10 mL) are added to the mixture. The organic phase is separated, the aq. phase is extracted with DCM (2×10 mL), the combined organic phases are dried over MgSO$_4$, filtered and evaporated. The crude is purified by prep. LC-MS with method E to obtain the title compound as a colorless oil; LC-MS method A: t$_R$=0.71 min; [M+H]$^+$=422.33.

4.11: rac-(3R*,4R*)-1-tert-Butyl-4-{[5-(2,4-difluoro-phenyl)-isoxazole-3-carbonyl]-amino}-piperidine-3-carboxylic Acid The title compound is prepared according to reaction 4.01g by treatment of rac-(3R*,4R*)-1-tert-butyl-4-{[5-(2,4-difluoro-phenyl)-isoxazole-3-carbonyl]-amino}-piperidine-3-carboxylic acid methyl ester with 1 M aq. LiOH solution. LC-MS method A: t$_R$=0.64 min; [M+H]$^+$=408.35.

Example 4.001: (3S,4S)-1-Cyclohexyl-4-{[5-(2,4-difluoro-phenyl)-isoxazole-3-carbonyl]-amino}-piperidine-3-carboxylic Acid (1-methyl-cyclopropyl)-amide To a solution of (3S,4S)-1-cyclohexyl-4-{[5-(2,4-difluoro-phenyl)-isoxazole-3-carbonyl]-amino}-piperidine-3-carboxylic acid (21.7 mg, 0.05 mmol) in DMF (0.55 mL) is added 1-methylcyclopropan-1-amine hydrochloride (11.3 mg, 0.1 mmol). DIPEA (0.028 mL, 0.16 mmol) is then added followed by HATU (20 mg, 0.052 mmol). The reaction mixture is stirred overnight at RT. The crude mixture is directly purified by prep. LC-MS with method E. LC-MS method D: t$_R$=0.66 min; [M+H]$^+$=487.2.

Compounds of Examples 4.001 to 4.102 listed in Table 4 below are prepared by applying one of the above-mentioned general procedures A, B or C to the building blocks BB-4.01 BB-4.11 coupled with commercially available amines or amine BB-9.01 of general structure 2. Enantiomerically pure compounds are obtained using one of the above mentioned chiral preparative chromatography methods.

TABLE 4

Examples 4.002-4.102

| Example Nr | Substance Name | QC LC-MS t$_R$ (min) | Mass Found [M + H]$^+$ |
|---|---|---|---|
| 4.001 | (3S,4S)-1-Cyclohexyl-4-{[5-(2,4-difluoro-phenyl)-isoxazole-3-carbonyl]-amino}-piperidine-3-carboxylic acid (1-methyl-cyclopropyl)-amide | 0.66 | 487.2 |
| 4.002 | (3S,4S)-1-Cyclohexyl-4-{[5-(2,4-difluoro-phenyl)-isoxazole-3-carbonyl]-amino}-piperidine-3-carboxylic acid (2-methoxy-1,1-dimethyl-ethyl)-amide | 0.71 | 519.2 |
| 4.003 | (3S,4S)-1-Cyclohexyl-4-{[5-(2,4-difluoro-phenyl)-isoxazole-3-carbonyl]-amino}-piperidine-3-carboxylic acid (3-methoxy-1,1-dimethyl-propyl)-amide | 0.72 | 533.4 |
| 4.004 | (3S,4S)-1-Cyclohexyl-4-{[5-(2,4-difluoro-phenyl)-isoxazole-3-carbonyl]-amino}-piperidine-3-carboxylic acid[1-(5-fluoro-pyridin-2-yl)-cyclopropyl]-amide | 0.72 | 568.1 |
| 4.005 | (3S,4S)-1-Cyclohexyl-4-{[5-(2,4-difluoro-phenyl)-isoxazole-3-carbonyl]-amino}-piperidine-3-carboxylic acid dimethylamide | 0.63 | 461 |
| 4.006 | (3S,4S)-1-Cyclohexyl-4-{[5-(2,4-difluoro-phenyl)-isoxazole-3-carbonyl]-amino}-piperidine-3-carboxylic acid (1-methyl-cyclobutyl)-amide | 0.73 | 501.3 |
| 4.007 | (3S,4S)-1-Cyclohexyl-4-{[5-(2,4-difluoro-phenyl)-isoxazole-3-carbonyl]-amino}-piperidine-3-carboxylic acid ((1RS)-1-[1,2,4]oxadiazol-3-yl-ethyl)-amide (mixture of isomers) | 0.63 | 529.3 |
| 4.008 | (3S,4S)-1-Cyclohexyl-4-{[5-(2,4-difluoro-phenyl)-isoxazole-3-carbonyl]-amino}-piperidine-3-carboxylic acid [(1RS)-1-(5-fluoro-pyridin-2-yl)-ethyl]-amide (mixture of isomers) | 0.71 | 556.3 |
| 4.009 | (3R,4R)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide | 0.76 | 515.2 |
| 4.010 | (3S,4S)-1-Cyclohexyl-4-{[5-(2,4-difluoro-phenyl)-isoxazole-3-carbonyl]-amino}-piperidine-3-carboxylic acid ((R)-1-phenyl-ethyl)-amide | 0.77 | 537.4 |
| 4.011 | (3S,4S)-1-Cyclohexyl-4-{[5-(2,4-difluoro-phenyl)-isoxazole-3-carbonyl]-amino}-piperidine-3-carboxylic acid ((S)-2-hydroxy-1-phenyl-ethyl)-amide | 0.67 | 553.4 |
| 4.012 | (3S,4S)-1-Cyclohexyl-4-{[5-(2,4-difluoro-phenyl)-isoxazole-3-carbonyl]-amino}-piperidine-3-carboxylic acid benzylamide | 0.72 | 523.4 |
| 4.013 | (3S,4S)-1-Cyclohexyl-4-{[5-(2,4-difluoro-phenyl)-isoxazole-3-carbonyl]-amino}-piperidine-3-carboxylic acid ((1RS)-2-hydroxy-1-pyridin-2-yl-ethyl)-amide (mixture of isomers) | 0.58 | 554.2 |
| 4.014 | (3S,4S)-1-Cyclohexyl-4-{[5-(2,4-difluoro-phenyl)-isoxazole-3-carbonyl]-amino}-piperidine-3-carboxylic acid ((R)-1-cyclobutyl-ethyl)-amide | 0.77 | 515.2 |

TABLE 4-continued

Examples 4.002-4.102

| Example Nr | Substance Name | QC LC-MS $t_R$ (min) | Mass Found $[M + H]^+$ |
|---|---|---|---|
| 4.015 | (3R,4R)-1-Cyclohexyl-4-{[5-(2,4-difluoro-phenyl)-isoxazole-3-carbonyl]-amino}-piperidine-3-carboxylic acid tert-butylamide | 0.73 | 489 |
| 4.016 | (3R,4R)-1-Cyclohexyl-4-{[5-(2,4-difluoro-phenyl)-isoxazole-3-carbonyl]-amino}-piperidine-3-carboxylic acid (1-methyl-cyclobutyl)-amide | 0.73 | 501.3 |
| 4.017 | (3R,4R)-1-Cyclohexyl-4-{[5-(2,4-difluoro-phenyl)-isoxazole-3-carbonyl]-amino}-piperidine-3-carboxylic acid amide | 0.56 | 433.3 |
| 4.018 | (3R,4R)-1-Cyclohexyl-4-{[5-(2,4-difluoro-phenyl)-isoxazole-3-carbonyl]-amino}-piperidine-3-carboxylic acid (1-methyl-cyclopropyl)-amide | 0.66 | 487 |
| 4.019 | (3R,4R)-1-Cyclohexyl-4-{[5-(2,4-difluoro-phenyl)-isoxazole-3-carbonyl]-amino}-piperidine-3-carboxylic acid (cyano-dimethyl-methyl)-amide | 0.65 | 500.3 |
| 4.020 | (3R,4R)-1-Cyclohexyl-4-{[5-(2,4-difluoro-phenyl)-isoxazole-3-carbonyl]-amino}-piperidine-3-carboxylic acid ((S)-2-hydroxy-1-phenyl-ethyl)-amide | 0.67 | 553.4 |
| 4.021 | (3R,4R)-1-Cyclohexyl-4-{[5-(2,4-difluoro-phenyl)-isoxazole-3-carbonyl]-amino}-piperidine-3-carboxylic acid ((R)-2-hydroxy-1-phenyl-ethylyamide | 0.68 | 553.3 |
| 4.022 | (3R,4R)-1-Cyclohexyl-4-{[5-(2,4-difluoro-phenyl)-isoxazole-3-carbonyl]-amino}-piperidine-3-carboxylic acid ((R)-1-phenyl-ethyl)-amide | 0.75 | 537.4 |
| 4.023 | (3S,4S)-1-Cyclopropylmethyl-4-{[5-(2,4-difluoro-phenyl)isoxazole-3-carbonyl]-amino}-piperidine-3-carboxylic acid [(1RS)-1-(2H-pyrazol-3yl)-ethyl]-amide (mixture of isomers) | 0.55 | 499.1 |
| 4.024 | (3S,4S)-1-Cyclopropylmethyl-4-{[5-(2,4-difluoro-phenyl)-isoxazole-3-carbonyl]-amino}-piperidine-3-carboxylic acid ((R)-1-pyridin-3-yl-ethyl)-amide | 0.49 | 510.1 |
| 4.025 | (3R,4R)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide | 0.61 | 523.3 |
| 4.026 | (3S,4S)-1-Cyclopentyl-4-{[5-(2,4-difluoro-phenyl)-isoxazole-3-carbonyl]-amino}-piperidine-3-carboxylic acid (1-pyridin-4-yl-cyclopropyl)-amide | 0.43 | 536.1 |
| 4.027 | (3S,4S)-1-Cyclopropylmethyl-4-{[5-(2,4-difluoro-phenyl)-isoxazole-3-carbonyl]-amino}-piperidine-3-carboxylic acid (1-pyridin-4-yl-cyclopropyl)-amide | 0.41 | 522.1 |
| 4.028 | (3S,4S)-1-Cyclopentyl-4-{[5-(2,4-difluoro-phenyl)-isoxazole-3-carbonyl]-amino}-piperidine-3-carboxylic acid (1-pyridin-2-yl-cyclopropyl)-amide | 0.61 | 536.1 |
| 4.029 | (3S,4S)-1-Cyclopentyl-4-{[5-(2,4-difluoro-phenyl)-isoxazole-3-carbonyl]-amino}-piperidine-3-carboxylic acid (1-pyrimidin-2-yl-cyclopropyl)-amide | 0.62 | 537.3 |
| 4.030 | (3S,4S)-1-Cyclopentyl-4-{[5-(2,4-difluoro-phenyl)-isoxazole-3-carbonyl]-amino}-piperidine-3-carboxylic acid (1-methyl-1-pyridin-2-yl-ethyl)-amide | 0.63 | 538.2 |
| 4.031 | (3S,4S)-1-Cyclopropylmethyl-4-{[5-(2,4-difluoro-phenyl)-isoxazole-3-carbonyl]-amino}-piperidine-3-carboxylic acid (1-pyridin-2-yl-cyclopropyl)-amide | 0.59 | 522.1 |
| 4.032 | (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide | 0.61 | 523.1 |
| 4.033 | (3S,4S)-1-Cyclopropylmethyl-4-{[5-(2,4-difluoro-phenyl)-isoxazole-3-carbonyl]-amino}-piperidine-3-carboxylic acid (1-methyl-1-pyridin-2-yl-ethyl)-amide | 0.61 | 524.1 |
| 4.034 | (3S,4S)-1-Cyclopentyl-4-{[5-(2,4-difluoro-phenyl)-isoxazole-3-carbonyl]-amino}-piperidine-3-carboxylic acid [1-methyl-1-methyl-1H-pyrazol-4yl)-ethyl]-amide | 0.64 | 541.1 |
| 4.035 | (3S,4S)-1-Cyclopentyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]-amide | 0.65 | 543.1 |
| 4.036 | (3S,4S)-1-Cyclopentyl-4-{[5-(2,4-difluoro-phenyl)-isoxazole-3-carbonyl]-amino}-piperidine-3-carboxylic acid bicyclopropyl-1-ylamide | 0.69 | 499.3 |
| 4.037 | (3S,4S)-1-Cyclopentyl-4-{[5-(2,4-difluoro-phenyl)-isoxazole-3-carbonyl]-amino}-piperidine-3-carboxylic acid [(1RS)-1-(tetrahydro-furan-2yl)-ethyl]-amide (mixture of isomers) | 0.65 | 517.4 |
| 4.038 | (3S,4S)-1-Cyclopentyl-4-{[5-(2,4-difluoro-phenyl)-isoxazole-3-carbonyl]-amino}-piperidine-3-carboxylic acid [(1RS)-1-(1H-[1,2,4]triazol-3-yl)-ethyl]-amide (mixture of isomers) | 0.55 | 514 |
| 4.039 | (3S,4S)-1-Cyclopentyl-4-{[5-(2,4-difluoro-phenyl)-isoxazole-3-carbonyl]-amino}-piperidine-3-carboxylic acid ((1RS)-1-methyl-prop-2-ynyl)-amide (mixture of isomers) | 0.63 | 471.3 |
| 4.04 | (3S,4S)-1-Cyclopentyl-4-{[5-(2,4-difluoro-phenyl)-isoxazole-3-carbonyl]-amino}-piperidine-3-carboxylic acid ((1RS)-1-isoxazol-3-yl-ethyl)-amide (mixture of isomers) | 0.63 | 514.3 |
| 4.041 | (3S,4S)-1-Cyclopentyl-4-{[5-(2,4-difluoro-phenyl)-isoxazole-3-carbonyl]-amino}-piperidine-3-carboxylic acid [(1RS)-1-(2H-pyrazol-3yl)-ethyl]amide (mixture of isomers) | 0.56 | 513.1 |
| 4.042 | (3S,4S)-1-Cyclopentyl-4-{[5-(2,4-difluoro-phenyl)-isoxazole-3-carbonyl]-amino}-piperidine-3-carboxylic acid ((R)-1-pyridin-3-yl-ethyl)-amide | 0.5 | 524.1 |

TABLE 4-continued

Examples 4.002-4.102

| Example Nr | Substance Name | QC LC-MS t$_R$ (min) | Mass Found [M + H]$^+$ |
|---|---|---|---|
| 4.043 | (3S,4S)-1-Cyclopropylmethyl-4-{[5-(2,4-difluoro-phenyl)-isoxazole-3-carbonyl]-amino}-piperidine-3-carboxylic acid [1-methyl-1-(1-methyl-1H-pyrazol-4-yl)-ethyl]amide | 0.63 | 527.2 |
| 4.044 | (3S,4S)-1-Cyclopropylmethyl-4-{[5-(2,4-difluoro-phenyl)-isoxazole-3-carbonyl]-amino}-piperidine-3-carboxylic acid [1-methyl-1-(5-methyl-[1,2,4]oxadiazol-3-yl)-ethyl]amide | 0.64 | 529.1 |
| 4.045 | (3S,4S)-1-Cyclopropylmethyl-4-{[5-(2,4-difluoro-phenyl)-isoxazole-3-carbonyl]-amino}-piperidine-3-carboxylic acid bicyclopropyl-1-ylamide | 0.67 | 485.3 |
| 4.046 | (3S,4S)-1-Cyclopropylmethyl-4-{[5-(2,4-difluoro-phenyl)-isoxazole-3-carbonyl]-amino}-piperidine-3-carboxylic acid [(1RS)-1-(tetrahydro-furan-2-yl)-ethyl]-amide (mixture of isomers) | 0.64 | 503.3 |
| 4.047 | (3S,4S)-1-Cyclopropylmethyl-4-{[5-(2,4-difluoro-phenyl)-isoxazole-3-carbonyl]-amino}-piperidine-3-carboxylic acid [(1RS)-1-(1H-[1,2,4]triazol-3-yl)-ethyl]-amide (mixture of isomers) | 0.53 | 500.1 |
| 4.048 | (3S,4S)-1-Cyclopropylmethyl-4-{[5-(2,4-difluoro-phenyl)-isoxazole-3-carbonyl]-amino}-piperidine-3-carboxylic acid ((1RS)-1-methyl-prop-2-ynyl)-amide (mixture of isomers) | 0.62 | 457.3 |
| 4.049 | (3S,4S)-1-Cyclopropylmethyl-4-{[5-(2,4-difluoro-phenyl)-isoxazole-3-carbonyl]-amino}-piperidine-3-carboxylic acid ((1RS)-1-isoxazol-3-yl-ethyl)-amide (mixture of isomers) | 0.61 | 500.3 |
| 4.050 | (3S,4S)-1-Cyclopropylmethyl-4-{[5-(2,4-difluoro-phenyl)-isoxazole-3-carbonyl]-amino}-piperidine-3-carboxylic acid [1-(1-oxy-pyridin-2-yl)-cyclopropyl]amide | 0.6 | 538.4 |
| 4.051 | (3S,4S)-1-Cyanomethyl-4-{[5-(2,4-difluoro-phenyl)-isoxazole-3-carbonyl]-amino}-piperidine-3-carboxylic acid (1-pyrimidin-2-yl-cyclopropyl)-amide | 0.9 | 508.3 |
| 4.052 | (3S,4S)-4-{[5-(2,4-Difluoro-phenyl)-isoxazole-3-carbonyl]-amino}-1-(1-fluoro-cyclopropylmethyl)-piperidine-3-carboxylic acid (1-pyrimidin-2-yl-cyclopropyl)-amide | 0.6 | 541 |
| 4.053 | (3S,4S)-1-Cyclopropylmethyl-4-{[5-(2,4-difluoro-phenyl)-isoxazole-3-carbonyl]-amino)-piperidine-3-carboxylic acid (1-phenyl-cyclopropyl)-amide | 0.7 | 521.4 |
| 4.054 | (3S,4S)-1-Cyclopropylmethyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide | 0.7 | 540.2 |
| 4.055 | (3S,4S)-1-Cyclopropylmethyl-4-{[5-(2,4-difluoro-phenyl)-isoxazole-3-carbonyl]-amino}-piperidine-3-carboxylic acid (1-pyrimidin-4-yl-cyclopropyl)-amide | 0.6 | 523.2 |
| 4.056 | 1-[((3S,4S)-1-Cyclopropylmethyl-4-{[5-(2,4-difluoro-phenyl)-isoxazole-3-carbonyl]-amino}-piperidine-3-carbonyl)-amino]-cyclopropanecarboxylic acid ethyl ester | 0.7 | 517.4 |
| 4.057 | (3S,4S)-1-Cyclopropylmethyl-4-{[5-(2,4-difluoro-phenyl)-isoxazole-3-carbonyl]-amino}-piperidine-3-carboxylic acid (1-phenyl-cyclobutyl)-amide | 0.8 | 535.1 |
| 4.058 | (3S,4S)-1-Cyclopropylmethyl-4-{[5-(2,4-difluoro-phenylyisoxazole-3-carbonyl]-amino}-piperidine-3-carboxylic acid benzyl-(2-fluoro-ethyl)-amide | 0.8 | 541.4 |
| 4.059 | (3S,4S)-1-Cyclopropylmethyl-4-{[5-(2,4-difluoro-phenyl)-isoxazole-3-carbonyl]-amino}-piperidine-3-carboxylic acid [1-(3-methoxy-phenyl)-cyclopropyl]-amide | 0.7 | 551.1 |
| 4.060 | (3S,4S)-1-Cyclopropylmethyl-4-{[5-(2,4-difluoro-phenyl)-isoxazole-3-carbonyl]-amino}-piperidine-3-carboxylic acid [1-(2-trifluoromethyl-phenyl)-cyclopropyl]-amide | 0.8 | 589.4 |
| 4.061 | (3S,4S)-1-Cyclopropylmethyl-4-{[5-(2,4-difluoro-phenyl)-isoxazole-3-carbonyl]-amino}-piperidine-3-carboxylic acid [1-(2-fluoro-phenyl)-cyclopropyl]-amide | 0.7 | 539.1 |
| 4.062 | (3S,4S)-1-Cyclopropylmethyl-4-{[5-(2,4-difluoro-phenyl)-isoxazole-3-carbonyl]-amino}-piperidine-3-carboxylic acid [1-(4-fluoro-phenyl)-cyclopropyl]-amide | 0.0 | 539 |
| 4.063 | (3S,4S)-1-Cyclopropylmethyl-4-{[5-(2,4-difluoro-phenyl)-isoxazole-3-carbonyl]-amino}-piperidine-3-carboxylic acid [1-(3-fluoro-phenyl)-cyclopropyl]-amide | 0.7 | 539 |
| 4.064 | (3S,4S)-1-Cyclopropylmethyl-4-{[5-(2,4-difluoro-phenyl)-isoxazole-3-carbonyl]-amino}-piperidine-3-carboxylic acid (6-methyl-pyridin-2-ylmethyl)-amide | 0.5 | 510 |
| 4.065 | (3S,4S)-1-Cyclopropylmethyl-4-{[5-(2,4-difluoro-phenyl)-isoxazole-3-carbonyl]-amino}-piperidine-3-carboxylic acid [2-(2-chloro-phenyl)-ethyl]-amide | 0.86 | 543.2 |
| 4.066 | (3S,4S)-1-Cyclopropylmethyl-4-{[5-(2,4-difluoro-phenyl)-isoxazole-3-carbonyl]-amino}-piperidine-3-carboxylic acid diethylamide | 0.7 | 461 |
| 4.067a | 5-(2,4-Difluoro-phenyl)-isoxazole-3-carboxylic acid [(3S,4S)-1-cyclopropylmethyl-3((R)-2-phenyl-azetidine-1-carbonyl)-piperidin-4-yl]-amide or 5-(2,4-Difluoro-phenyl)-isoxazole-3-carboxylic acid [(3S,4S)-1-cyclopropylmethyl-3((S)-2-phenyl-azetidine-1-carbonyl)-piperidin-4-yl]-amide (1$^{st}$ eluted epimer) | 0.7 | 521.1 |

TABLE 4-continued

Examples 4.002-4.102

| Example Nr | Substance Name | QC LC-MS t_R (min) | Mass Found [M + H]+ |
|---|---|---|---|
| 4.067b | 5-(2,4-Difluoro-phenyl)-isoxazole-3-carboxylic acid [(3S,4S)-1-cyclopropylmethyl-3-((R)-2-phenyl-azetidine-1-carbonyl)-piperidin-4-yl]-amide or 5-(2,4-Difluoro-phenyl)-isoxazole-3-carboxylic acid [(3S,4S)-1-cyclopropylmethyl-3-((S)-2-phenyl-azetidine-1-carbonyl)-piperidin-4-yl]-amide (2$^{nd}$ eluted epimer) | 0.7 | 521.1 |
| 4.068 | (3S,4S)-1-Cyclopropylmethyl-4-{[5-(2,4-difluoro-phenyl)-isoxazole-3-carbonyl]-amino}-piperidine-3-carboxylic acid [1-(3-chloro-phenyl)-cyclopropyl]-amide | 0.8 | 555 |
| 4.069 | (3R,4R)-1-Cyclopropylmethyl-4-{[5-(2,4-difluoro-phenyl)-isoxazole-3-carbonyl]-amino}-piperidine-3-carboxylic acid methoxy-methyl-amide | 0.6 | 449.2 |
| 4.070 | (3S,4S)-1-Cyclopropylmethyl-4-{[5-(2,4-difluoro-phenyl)-isoxazole-3-carbonyl]-amino)-piperidine-3-carboxylic acid [1-(4-methyl-thiazol-2-yl)-cyclobutyl]-amide | 0.7 | 556.1 |
| 4.071 | (3R,4R)-1-Cyclopropylmethyl-4-{[5-(2,4-difluoro-phenyl)-isoxazole-3-carbonyl]-amino}-piperidine-3-carboxylic acid diethylamide | 0.7 | 461.1 |
| 4.072 | (3S,4S)-1-Cyclopropylmethyl-4-{[5-(2,4-difluoro-phenyl)-isoxazole-3-carbonyl]-amino}-piperidine-3-carboxylic acid [(R,S)-1-(2-methoxy-phenyl)-ethyl]-amide | 0.7 | 539.4 |
| 4.072a | (3S,4S)-1-Cyclopropylmethyl-4-{[5-(2,4-difluoro-phenyl)-isoxazole-3-carbonyl]-amino}-piperidine-3-carboxylic acid [(R)-1-(2-methoxy-phenyl)-ethyl]-amide or (3S,4S)-1-cyclopropylmethyl-4-{[5-(2,4-difluoro-phenyl)-isoxazole-3-carbonyl]-amino}-piperidine-3-carboxylic acid [(S)-1-(2-methoxy-phenyl)-ethyl]-amide (1$^{st}$ eluted epimer) | 0.8 | 539.4 |
| 4.073 | (R,S)-[((3S,4S)-1-Cyclopropylmethyl-4-{[5-(2,4-difluoro-phenyl)-isoxazole-3-carbonyl]-amino}-piperidine-3-carbonyl)-amino]-phenyl-acetic acid ethyl ester | 0.8 | 567.2 |
| 4.074 | (3S,4S)-1-Cyclopropylmethyl-4-{[5-(2,4-difluoro-phenyl)-isoxazole-3-carbonyl]-amino}-piperidine-3-carboxylic acid [1-(2-methoxy-phenyl)-cyclopropyl]-amide | 0.8 | 551 |
| 4.075 | (3S,4S)-1-Cyclopropylmethyl-4-{[5-(2,4-difluoro-phenyl)-isoxazole-3-carbonyl]-amino}-piperidine-3-carboxylic acid [(R)-1-(3-bromo-phenyl)-ethyl]-amide | 0.8 | 587.1 |
| 4.076 | (3S,4S)-1-Cyclopropylmethyl-4-{[5-(2,4-difluoro-phenyl)-isoxazole-3-carbonyl]-amino}-piperidine-3-carboxylic acid [1-(2-hydroxy-phenyl)-cyclopropyl]-amide | 0.7 | 537 |
| 4.077 | (3S,4S)-1-Cyclopropylmethyl-4-{[5-(2,4-difluoro-phenyl)-isoxazole-3-carbonyl]-amino}-piperidine-3-carboxylic acid [1-(1-oxy-pyrimidin-2-yl)-cyclopropyl]-amide | 1.0 | 539.4 |
| 4.078 | 5-(2,4-Difluoro-phenyl)-isoxazole-3-carboxylic acid [(3S,4S)-1-cyclopropylmethyl-3-((R,S)-2-pyrimidin-2-yl-pyrrolidine-1-carbonyl)-piperidin-4-yl]-amide | 0.6 | 537 |
| 4.078b | 5-(2,4-Difluoro-phenyl)-isoxazole-3-carboxylic acid [(3S,4S)-1-cyclopropylmethyl-3-((R)-2-pyrimidin-2-yl-pyrrolidine-1-carbonyl)-piperidin-4-yl]-amide or 5-(2,4-difluoro-phenyl)-isoxazole-3-carboxylic acid [(3S,4S)-1-cyclopropylmethyl-3-((S)-2-pyrimidin-2-yl-pyrrolidine-1-carbonyl)-piperidin-4-yl]-amide (2$^{nd}$ eluted epimer) | 0.6 | 537.4 |
| 4.079a | 5-(2,4-Difluoro-phenyl)-isoxazole-3-carboxylic acid [(3S,4S)-1-cyclopropylmethyl-3-((R)-2-pyrimidin-2-yl-azetidine-1-carbonyl)-piperidin-4-yl]-amide or 5-(2,4-difluoro-phenyl)-isoxazole-3-carboxylic acid [(3S,4S)-1-cyclopropylmethyl-3-((S)-2-pyrimidin-2-yl-azetidine-1-carbonyl)-piperidin-4-yl]-amide (1st eluted epimer) | 0.6 | 523.4 |
| 4.079b | 5-(2,4-Difluoro-phenyl)-isoxazole-3-carboxylic acid [(3S,4S)-1-cyclopropylmethyl-3-((R)-2-pyrimidin-2-yl-azetidine-1-carbonyl)-piperidin-4-yl]-amide or 5-(2,4-difluoro-phenyl)-isoxazole-3-carboxylic acid [(3S,4S)-1-cyclopropylmethyl-3-((S)-2-pyrimidin-2-yl-azetidine-1-carbonyl)-piperidin-4-yl]-amide (2nd eluted epimer) | 0.6 | 523 |
| 4.080 | (3S,4S)-1-Cyclopropylmethyl-4-{[5-(2,4-difluoro-phenyl)-isoxazole-3-carbonyl]-amino}-piperidine-3-carboxylic acid ((R,S)-1-pyrimidin-2-yl-ethyl)-amide | 0.6 | 511.1 |
| 4.080a | (3S,4S)-1-Cyclopropylmethyl-4-{[5-(2,4-difluoro-phenyl)-isoxazole-3-carbonyl]-amino}-piperidine-3-carboxylic acid ((R)-1-pyrimidin-2-yl-ethyl)-amide or (3S,4S)-1-cyclopropylmethyl-4-{[5-(2,4-difluoro-phenyl)-isoxazole-3-carbonyl]-amino}-piperidine-3-carboxylic acid ((S)-1-pyrimidin-2-yl-ethyl)-amide (1st eluted epimer) | 0.6 | 511 |
| 4.080b | (3S,4S)-1-Cyclopropylmethyl-4-{[5-(2,4-difluoro-phenylyisoxazole-3-carbonyl]-amino}-piperidine-3-carboxylic acid ((R)-1-pyrimidin-2-yl-ethyl)-amide or (3S,4S)-1-cyclopropylmethyl-4-{[5-(2,4-difluoro-phenyl)-isoxazole-3-carbonyl]-amino}-piperidine-3-carboxylic acid ((S)-1-pyrimidin-2-yl-ethyl)-amide (2nd eluted epimer) | 0.6 | 511.4 |
| 4.081 | (3S,4S)-1-Cyclopropylmethyl-4-{[5-(2,4-difluoro-phenyl)-isoxazole-3-carbonyl]-amino}-piperidine-3-carboxylic acid (1-pyrimidin-5-yl-cyclopropyl)-amide | 0.6 | 523.1 |

TABLE 4-continued

Examples 4.002-4.102

| Example Nr | Substance Name | QC LC-MS $t_R$ (min) | Mass Found $[M + H]^+$ |
|---|---|---|---|
| 4.082 | (3S,4S)-1-Cyclobutyl-4-{[5-(2,4-difluoro-phenyl)-isoxazole-3-carbonyl]-amino}-piperidine-3-carboxylic acid [1-(3-fluoro-pyridin-2-yl)-cyclopropyl]-amide | 0.6 | 540.4 |
| 4.083 | (3S,4S)-1-Cyclobutyl-4-{[5-(2,4-difluoro-phenyl)-isoxazole-3-carbonyl]-amino}-piperidine-3-carboxylic acid (1-methyl-1-pyrimidin-2-yl-ethyl)-amide | 0.6 | 525.1 |
| 4.084 | (3S,4S)-1-Cyclobutyl-4-{[5-(2,4-difluoro-phenyl)-isoxazole-3-carbonyl]-amino}-piperidine-3-carboxylic acid ((R,S)-1-pyrimidin-2-yl-ethyl)-amide | 0.6 | 511 |
| 4.084b | (3S,4S)-1-Cyclobutyl-4-{[5-(2,4-difluoro-phenyl)-isoxazole-3-carbonyl]-amino}-piperidine-3-carboxylic acid ((R)-1-pyrimidin-2-yl-ethyl)-amide or (3S,4S)-1-cyclobutyl-4-{[5-(2,4-difluoro-phenyl)-isoxazole-3-carbonyl]-amino}-piperidine-3-carboxylic acid ((S)-1-pyrimidin-2-yl-ethyl)-amide (2nd eluted epimer) | 0.6 | 511 |
| 4.085 | (3R,4R)-1-Cyclobutyl-4-{[5-(2,4-difluoro-phenyl)-isoxazole-3-carbonyl]-amino}-piperidine-3-carboxylic acid (3-benzyl-oxetan-3-yl)-amide | 0.7 | 551.1 |
| 4.086 | (3R,4R)-1-Cyclobutyl-4-{[5-(2,4-difluoro-phenyl)-isoxazole-3-carbonyl]-amino}-piperidine-3-carboxylic acid [2-methyl-2-(3-methyl-pyridin-2-yl)-propyl]-amide | 0.6 | 552 |
| 4.087 | (3R,4R)-1-Cyclobutyl-4-{[5-(2,4-difluoro-phenyl)-isoxazole-3-carbonyl]-amino}-piperidine-3-carboxylic acid (2-methyl-2-pyridin-2-yl-propyl)-amide | 0.6 | 538.1 |
| 4.088 | (3S,4S)-1-Cyclobutyl-4-{[5-(2,4-difluoro-phenyl)-isoxazole-3-carbonyl]-amino}-piperidine-3-carboxylic acid (1-o-tolyl-cyclopropyl)-amide | 0.8 | 535 |
| 4.089 | (3R,4R)-1-Cyclobutyl-4-{[5-(2,4-difluoro-phenyl)-isoxazole-3-carbonyl]-amino}-piperidine-3-carboxylic acid [3-(4-fluoro-phenyl)-oxetan-3-yl]amide | 0.7 | 555.1 |
| 4.090 | (3R,4R)-1-Cyclobutyl-4-{[5-(2,4-difluoro-phenyl)-isoxazole-3-carbonyl]-amino}-piperidine-3-carboxylic acid (3-phenyl-oxetan-3-ylmethyl)-amide | 0.7 | 551 |
| 4.091 | (3R,4R)-1-Cyclobutyl-4-{[5-(2,4-difluoro-phenyl)-isoxazole-3-carbonyl]-amino}-piperidine-3-carboxylic acid [2-(2-chloro-phenyl)-2-methyl-propyl]-amide | 0.8 | 571.3 |
| 4.092 | (3R,4R)-1-Cyclobutyl-4-{[5-(2,4-difluoro-phenyl)-isoxazole-3-carbonyl]-amino}-piperidine-3-carboxylic acid [1-(4-chloro-phenyl)-cyclopropylmethyl]-amide | 0.8 | 569.4 |
| 4.093 | (3R,4R)-1-Cyclobutyl-4-{[5-(2,4-difluoro-phenyl)-isoxazole-3-carbonyl]-amino}-piperidine-3-carboxylic acid (1-pyridin-2-yl-cyclopropylmethyl)-amide | 0.6 | 536 |
| 4.094 | (3R,4R)-1-Cyclobutyl-4-{[5-(2,4-difluoro-phenyl)-isoxazole-3-carbonyl]-amino}-piperidine-3-carboxylic acid [3-(3-chloro-phenyl)-oxetan-3-yl]-amide | 0.7 | 571.1 |
| 4.095 | (3S,4S)-4-{[5-(2,4-Difluoro-phenyl)-isoxazole-3-carbonyl]-amino}-1-ethyl-piperidine-3-carboxylic acid [(R)-1-(6-methyl-pyridin-2-yl)-ethyl]-amide | 0.5 | 498 |
| 4.096 | (3S,4S)-4-{[5-(2,4-Difluoro-phenyl)-isoxazole-3-carbonyl]-amino}-1-ethyl-piperidine-3-carboxylic acid (1-methyl-1-pyrimidin-2-yl-ethyl)-amide | 0.6 | 499 |
| 4.097 | (3S,4S)-1-Cyclobutyl-4-{[5-(2,4-difluoro-phenyl)-isoxazole-3-carbonyl]-amino}-piperidine-3-carboxylic acid [3-(3-chloro-phenyl)-oxetan-3-yl]amide | 0.7 | 571.4 |
| 4.098 | (3S,4S)-1-Cyclobutyl-4-{[5-(2,4-difluoro-phenyl)-isoxazole-3-carbonyl]-amino}-piperidine-3-carboxylic acid [(R,S)-1-(3-fluoro-pyridin-2-yl)-ethyl]-amide | 0.6 | 528 |
| 4.098a | (3S,4S)-1-Cyclobutyl-4-{[5-(2,4-difluoro-phenyl)-isoxazole-3-carbonyl]-amino}-piperidine-3-carboxylic acid [(R)-1-(3-fluoro-pyridin-2-yl)-ethyl]-amide or (3S,4S)-1-Cyclobutyl-4-{[5-(2,4-difluoro-phenyl)-isoxazole-3-carbonyl]-amino}-piperidine-3-carboxylic acid [(S)-1-(3-fluoro-pyridin-2yl)-ethyl]-amide (2nd eluted epimer) | 0.6 | 528 |
| 4.099 | (3R,4R)-1-Cyclopropylmethyl-4-{[5-(2,4-difluoro-phenyl)-isoxazole-3-carbonyl]-amino)-piperidine-3-carboxylic acid (pyrimidin-2-ylmethyl)-amide | 0.5 | 497.2 |
| 4.100 | (3S,4S)-1-Cyclopropylmethyl-4-{[5-(2,4-difluoro-phenyl)-isoxazole-3-carbonyl]-amino)-piperidine-3-carboxylic acid (pyrimidin-2-ylmethyl)-amide | 0.5 | 497 |
| 4.101 | rac-(3R*,4R*)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide | 0.6 | 525.4 |
| 4.101a | (3R*,4R*)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide (enantiomer 1) | 0.6 | 525 |
| 4.101b | (3R*,4R*)-1-tert-Butyl-4-{[5-(2,4-difluoro-phenyl)-isoxazole-3-carbonyl]-amino}-piperidine-3-carboxylic acid (1-pyrimidin-2-yl-cyclopropyl)-amide (enantiomer 2) | 0.6 | 525 |
| 4.102 | (3S,4S)-1-Cyclopropylmethyl-4-{[5-(2,4-difluoro-phenyl)-isoxazole-3-carbonyl]-amino}-piperidine-3-carboxylic acid (1-methyl-1-pyrimidin-2-yl-ethyl)-amide | 0.6 | 525 |

General Method G for the Synthesis of Piperidines of Formula (I)
Buildings Blocks:
Preparation of building blocks of Structure G-9

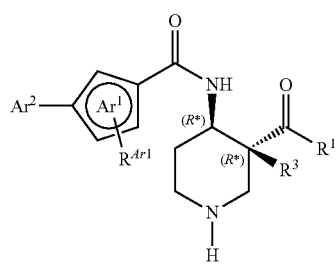

G-9

BB-5.01: rac-(3R*,4R*)-4-{[5-(2,4-Difluoro-phenyl)-isoxazole-3-carbonyl]-amino}-3-methyl-piperidine-3-carboxylic Acid Dimethylamide 5.01a: 3-Methyl-4-oxo-piperidine-1,3-dicarboxylic Acid 1-tert-butyl Ester 3-methyl Ester A mixture of 4-oxo-piperidine-1,3-dicarboxylic acid 1-tert-butyl ester 3-methyl ester (1 g, 4 mmol), potassium carbonate (1.1 g, 8 mmol) and iodomethane (1.13 g, 8 mmol) in acetone (12 mL) is heated under reflux for 7 h. The mixture is then cooled to RT and filtered through a fritted filter. The filtrate is concentrated under reduced pressure to yield the title compound as a yellowish oil. LC-MS method A: $t_R$=0.78 min; $[M+H]^+$=272.21.

5.01b: 4-Benzylamino-3-methyl-3,6-dihydro-2H-pyridine-1,3-dicarboxylic Acid 1-tert-butyl Ester 3-methyl Ester A solution of 3-methyl-4-oxo-piperidine-1,3-dicarboxylic acid 1-tert-butyl ester 3-methyl ester (1.02 g, 3.78 mmol) in toluene (30 mL) is treated with benzylamine (0.51 g, 4.76 mmol) and p-toluenesulfonic acid monohydrate (36 mg). The resulting mixture is heated under reflux for 2 h with a dean-stark condenser. The reaction mixture is extracted three times with aq. sat. NaHCO₃. The organic phase is collected, dried over MgSO₄, filtered and the solvents evaporated to yield the crude product as a yellow oil.

5.01c: rac-(3R*,4R*)-4-Benzylamino-3-methyl-piperidine-1,3-dicarboxylic Acid 1-tert-butyl Ester 3-methyl Ester The crude benzylamino-3-methyl-3,6-dihydro-2H-pyridine-1,3-dicarboxylic acid 1-tert-butyl ester 3-methyl ester (1.23 g, 3.3 mmol) is dissolved in MeCN (15 mL) and cooled to 0° C. AcOH (0.38 mL, 6.6 mmol) is added. Sodium triacetoxyborohydride (3.84 g, 18.1 mmol) is added portionwise. The resulting mixture is stirred at 0° C. for 30 min and at RT for 2 h. The reaction mixture is concentrated under reduced pressure. The residue is dissolved in DCM (50 mL) and sat. aq. sodium carbonate solution (50 mL) is added slowly. The organic layer is separated, the aq. phase extracted again with DCM (50 mL) and the combined organic layers are washed with brine (50 mL), dried over Na₂SO₄, filtered and evaporated. The two diastereomers are separated using silica gel column chromatography. Evaporation of the lower fraction delivers the trans isomer, as shown by 2D- and NOE NMR study, as a colorless oil. LC-MS method A: $t_R$=0.67 min; $[M+H]^+$=363.22.

5.01d: rac-(3R*,4R*)-4-Amino-3-methyl-piperidine-1,3-dicarboxylic Acid 1-tert-butyl Ester 3-methyl Ester Dry Pd on activated charcoal 10% (27 mg, 0.0254 mmol) is added to a solution of rac-(3R*,4R*)-4-benzylamino-3-methyl-piperidine-1,3-dicarboxylic acid 1-tert-butyl ester 3-methyl ester (0.3 g, 0.84 mmol) in MeOH (12 mL). After degassing the reaction flask, the mixture is hydrogenated for 1 h at ambient temperature. The reaction mixture is filtered to remove the catalyst, and then concentrated to give the crude product as a yellow oil. LC-MS method A: $t_R$=0.53 min; $[M+H]^+$=273.22.

5.01e: rac-(3R*,4R*)-4-{[5-(2,4-Difluoro-phenyl)-isoxazole-3-carbonyl]-amino}-3-methyl-piperidine-1,3-dicarboxylic Acid 1-tert-butyl Ester 3-methyl Ester To a solution of rac-(3R*,4R*)-4-amino-3-methyl-piperidine-1,3-dicarboxylic acid 1-tert-butyl ester 3-methyl ester (225 mg, 0.83 mmol) in DMF (5 mL) at RT is added 5-(2,4-difluorophenyl)isoxazole-3-carboxylic acid (205 mg, 0.91 mmol). DIPEA (0.283 mL, 1.65 mmol) is then added followed by HATU (346 mg, 0.91 mmol). The reaction mixture is stirred overnight at RT. The crude mixture is purified by prep. LC-MS in basic conditions. The title compound is obtained as a pale yellow solid. LC-MS method A: $t_R$=1.01 Min; $[M+H]^+$=480.14.

5.01f: rac-(3R*,4R*)-4-{[5-(2,4-Difluoro-phenyl)-isoxazole-3-carbonyl]-amino}-3-methyl-piperidine-1,3-dicarboxylic Acid 1-tert-butyl Ester rac-(3R*,4R*)-4-{[5-(2,4-Difluoro-phenyl)-isoxazole-3-carbonyl]-amino}-3-methyl-piperidine-1,3-dicarboxylic acid 1-tert-butyl ester 3-methyl ester (240 mg, 0.5 mmol) is dissolved in THF (4 mL) at RT. Aq. 1M LiOH solution (4 mL, 4 mmol) is then added and the mixture stirred at RT for 72 h. The reaction mixture is acidified with 1M HCl solution (5 mL). The resulting suspension is extracted twice with DCM (10 mL). The organic layer is dried over MgSO₄ and evaporated. The title compound is obtained as an off-white solid; LC-MS method A: $t_R$=0.91 min; $[M+H]^+$=465.91.

5.01q: rac-(3R*,4R*)-4-{[5-(2,4-Difluoro-phenyl)-isoxazole-3-carbonyl]-amino}-3-dimethylcarbamoyl-3-methyl-piperidine-1-carboxylic Acid Tert-Butyl Ester A solution of rac-(3R*,4R*)-4-{[5-(2,4-Difluoro-phenyl)-isoxazole-3-carbonyl]-amino}-3-methyl-piperidine-1,3-dicarboxylic acid 1-tert-butyl ester (200 mg, 0.43 mmol) in DMF (6 mL) is treated with dimethylamine 2M solution in THF (0.277 mL, 0.554 mmol) and DIPEA (0.158 mL, 0.924 mmol). Then, HATU (193 mg, 0.508 mmol) is added and the reaction is stirred overnight. DMF is evaporated and the crude is taken up in DCM (10 mL) and extracted three times with NaHCO3 sat sol. (10 mL). The combined organic layers are washed with brine (20 mL), dried over sodium sulfate, filtered and evaporated to yield the product as a slightly orange oil, used as crude for the next step. LC-MS method A: $t_R$=0.97 min; [M+H]$^+$=493.11.

5.01 h: rac-(3R*,4R*)-4-{[5-(2,4-Difluoro-phenyl)-isoxazole-3-carbonyl]-amino}-3-methyl-piperidine-3-carboxylic Acid Dimethylamide rac-(3R*,4R*)-4-{[5-(2,4-Difluoro-phenyl)-isoxazole-3-carbonyl]-amino}-3-dimethylcarbamoyl-3-methyl-piperidine-1-carboxylic acid tert-butyl ester (135 mg, 0.27 mmol) is dissolved in MeOH (5 mL) at RT. A 4M solution of HCl in dioxane (0.068 mL, 0.274 mmol) is added and the reaction stirred at RT for 1 h. The reaction mixture is concentrated, dissolved in DCM (10 mL) and treated with aq. sat. NaHCO$_3$ (10 mL). The organic layer is separated and the aq. phase is extracted twice with DCM (2×10 mL). The combined organic layers are dried over MgSO$_4$ and evaporated. The crude title compound is obtained; LC-MS A: $t_R$=0.64 min; [M+H]$^+$=393.15.

Preparation of Building Blocks of Substituted Piperidines of Structure 1 Used as Intermediates in the Preparation of Examples 5.002

In analogy to example BB-5.01 the following amide is prepared:

BB-5.02 (3R*,4R*)-4-{[5-(2,4-Difluoro-phenyl)-isoxazole-3-carbonyl]-amino}-3-methyl-piperidine-3-carboxylic Acid ((R)-1-pyridin-2-yl-ethyl)-amide 5.02a: (3R*,4R*)-4-{[5-(2,4-Difluoro-phenyl)-isoxazole-3-carbonyl]-amino}-3-methyl-3-((R)-1-pyridin-2-yl-ethylcarbamoyl)-piperidine-1-carboxylic Acid Tert-Butyl Ester The title compound is prepared according to the reaction 5.01g described above using rac-(3R*,4R*)-4-{[5-(2,4-difluoro-phenyl)-isoxazole-3-carbonyl]-amino}-3-methyl-piperidine-1,3-dicarboxylic acid 1-tert-butyl ester and ((R)-1-pyridin-2-yl-ethyl)-amine; LC-MS method A: $t_R$=0.78 min; [M+H]$^+$=570.12.

5.02: (3R*,4R*)-4-{[5-(2,4-Difluoro-phenyl)-isoxazole-3-carbonyl]-amino}-3-methyl-piperidine-3-carboxylic Acid ((R)-1-pyridin-2-yl-ethyl)-amide The title compound is prepared according to the reaction 5.01 h described above by treating (3R*,4R*)-4-{[5-(2,4-difluoro-phenyl)-isoxazole-3-carbonyl]-amino}-3-methyl-3-((R)-1-pyridin-2-yl-ethylcarbamoyl)-piperidine-1-carboxylic acid tert-butyl ester with 4M HCl in dioxane; LC-MS method A: $t_R$=0.56 min; [M+H]$^+$=470.09.

Example 5.001: (3R*,4R*)-1-Cyclohexyl-4-{[5-(2,4-difluoro-phenyl)-isoxazole-3-carbonyl]-amino}-3-methyl-piperidine-3-carboxylic Acid ((R)-1-pyridin-2-yl-ethyl)-amide A solution of rac-(3R*,4R*)-4-{[5-(2,4-difluoro-phenyl)-isoxazole-3-carbonyl]-amino}-3-methyl-piperidine-3-carboxylic acid ((R)-1-pyridin-2-yl-ethyl)-amide, cyclohexanone (0.046 mL, 0.45 mmol) and AcOH (0.032 mL, 0.56 mmol) in DCM (5 mL) at RT is treated by sodium triacetoxyborohydride (149 mg, 0.67 mmol). The reaction mixture is stirred overnight at RT. The reaction mixture is diluted with DCM (5 mL) and washed with aq. sat. NaHCO$_3$ (10 mL). The organic layer is dried over MgSO$_4$ and evaporated. The crude residue is purified by prep. LC-MS in basic conditions. The title compound is obtained as a colorless powder. LC-MS method A: $t_R$=0.69 Min; [M+H]$^+$=552.15.

Example 5.002: rac-(3R*,4R*)-1-Cyclohexyl-4-{[5-(2,4-difluoro-phenyl)-isoxazole-3-carbonyl]-amino}-3-methyl-piperidine-3-carboxylic Acid Dimethylamide The title compound is prepared according to Example 5.001 described above by treating rac-(3R*,4R*)-4-{[5-(2,4-Difluoro-phenyl)-isoxazole-3-carbonyl]-amino}-3-methyl-piperidine-3-carboxylic acid dimethylamide with cyclohexanone; LC-MS method A: $t_R$=0.76 min; [M+H]$^+$=475.13.

Buildings Blocks:
Preparation of Building Blocks of Structure B-3

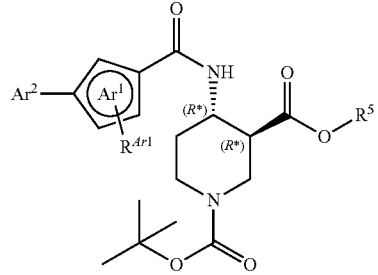

B-3

BB-6.01: rac-(3R*,4R*)-4-{[5-(2,4-Difluoro-phenyl)-isoxazole-3-carbonyl]-amino}-piperidine-1,3-dicarboxylic Acid 1-tert-butyl Ester 3-methyl Ester 6.01a: 4-Amino-5,6-dihydro-2H-pyridine-1,3-dicarboxylic Acid 1-tert-butyl Ester 3-methyl Ester A solution of 4-oxo-piperidine-1,3-dicarboxylic acid 1-tert-butyl ester 3-methyl ester (10 g, 36.9 mmol), in MeOH (140 mL) is treated with 7N ammonia solution in MeOH (25 mL, 1.14 mol) and the resulting solution is heated under reflux for 18 h. The mixture is then cooled to RT and concentrated under reduced pressure. The residue is taken up in DCM (100 mL) and washed twice with water (2×100 mL) and brine (2×100 mL). The organic layer is dried over MgSO$_4$, filtered and concentrated under reduced pressure to yield the crude product as a yellow solid. LC-MS method A: $t_R$=0.83 min; [M+H– t-Bu]$^+$=202.27.

6.01b: Mixture of rac-(3R*,4R*)-4-amino-piperidine-1,3-dicarboxylic Acid 1-tert-butyl Ester 3-methyl Ester and rac-(3S*,4R*)-4-amino-piperidine-1,3-dicarboxylic Acid 1-tert-butyl Ester 3-methyl Ester NaBH$_4$ (1.73 g, 45.7 mmol) is dissolved in THF (100 mL) and the resulting solution is cooled to –18° C. TFA (13 mL, 169 mmol) is added over 20 min. at –14° C. to –18° C. A solution of the crude 4-amino-5,6-dihydro-2H-pyridine-1,3-dicarboxylic acid 1-tert-butyl ester 3-methyl ester (9.53 g, 33.9 mmol) in THF (15 mL) is added dropwise over 10 min. The reaction is allowed to warm to 0° C. over 15 min and stirred at this temperature for 1 h. Water (50 mL) is poured onto the reaction mixture and stirring is continued for 10 min. The pH of the resulting solution is brought to pH=11 with 10 N aq. NaOH. The mixture is extracted with DCM (2×100 mL). The combined organic layers are washed with brine (2×100 mL), dried over Na$_2$SO$_4$, filtered and evaporated. The product is obtained as a cis-trans mixture of products, as a yellow foam: LC-MS method A: t$_R$=0.55 min; [M+H]$^+$=259.34 and 0.58 min; [M+H]$^+$=259.5.

6.01c: Mixture of rac-(3S*,4R*)-4-{[5-(2,4-Difluoro-phenyl)-isoxazole-3-carbonyl]-amino}-piperidine-1,3-dicarboxylic Acid 1-tert-butyl Ester 3-methyl Ester and rac-(3R*,4R*)-4-{[5-(2,4-Difluoro-phenyl)-isoxazole-3-carbonyl]-amino}-piperidine-1,3-dicarboxylic Acid 1-tert-butyl Ester 3-methyl Ester To a solution of rac-(3R*,4R*)-4-amino-3-methyl-piperidine-1,3-dicarboxylic acid 1-tert-butyl ester 3-methyl ester and rac-(3S*,4R*)-4-amino-piperidine-1,3-dicarboxylic acid 1-tert-butyl ester 3-methyl ester (7.1 g, 23.6 mmol) in DCM (75 mL) at RT is added 5-(2,4-difluorophenyl)isoxazole-3-carboxylic acid (6.673 g, 29.1 mmol). DIPEA (9.98 mL, 58.3 mmol) is then added followed by T$_3$P 50% solution in DCM (34.7 mL, 58.3 mmol). The reaction mixture is stirred for 1 h30 at RT. The pH of the resulting solution is brought to pH=11 with 1 N aq. NaOH and the mixture is washed twice with aq. 1 N NaOH solution (2×100 mL). The organic phase is dried over MgSO$_4$, filtered and concentrated under reduced pressure to deliver a mixture of cis-trans products (4:1 mixture) as a beige solid. LC-MS method A: t$_R$=1.07 Min; [M+H]$^+$=465.94 and t$_R$=1.10 Min; [M+H]$^+$= 465.94.

The pure cis isomer rac-(3S*,4R*)-4-{[5-(2,4-Difluoro-phenyl)-isoxazole-3-carbonyl]-amino}-piperidine-1,3-dicarboxylic acid 1-tert-butyl ester 3-methyl ester is obtained by suspending the cis-trans mixture in MeOH and then filtered off. LC-MS method A: t$_R$=1.07 Min; [M+H]$^+$= 465.96.

6.01d: rac-(3R*,4R*)-4-{[5-(2,4-Difluoro-phenyl)-isoxazole-3-carbonyl]-amino}-piperidine-1,3-dicarboxylic Acid 1-tert-butyl Ester 3-methyl Ester Sodium methoxide solution 25 wt. % in MeOH (7.43 mL, 0.0325 mol) is added to MeOH (15 mL) and methyl acetate (3.9 mL, 0.0488 mol). The mixture is refluxed for 30 min and cooled to RT. Then the mixture of rac-(3S*,4R*)-4-{[5-(2,4-difluoro-phenyl)-isoxazole-3-carbonyl]-amino}-3-methyl-piperidine-1,3-dicarboxylic acid 1-tert-butyl ester 3-methyl ester and rac-(3R*,4R*)-4-{[5-(2,4-difluoro-phenyl)-isoxazole-3-carbonyl]-amino}-3-methyl-piperidine-1,3-dicarboxylic acid 1-tert-butyl ester 3-methyl ester (8.37 g, 16.3 mmol) is suspended under nitrogen in dry MeOH (10 mL), and the resulting suspension is injected into the NaOMe solution prepared previously. The mixture is stirred at RT for 1 day. The reaction mixture is treated with aq. sat. NaHCO$_3$ (10 mL) and MeOH is evaporated at reduced pressure. DCM (25 mL) is added to the residue. The organic phase is separated and the aq. layer is extracted 3× with DCM (3×25 mL). The combined organic layers are dried over MgSO$_4$, filtered and concentrated. The crude residue is triturated with MeCN (10 mL) to afford the title compound as an off white solid. LC-MS method A: t$_R$=1.07 Min; [M+H]$^+$=465.94.

General Method I for the Synthesis of Piperidines of Formula (I)
Buildings Blocks:
Preparation of Building Blocks of Structure 1-7

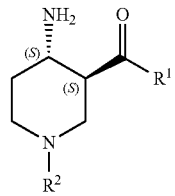

I-7

BB 7.01: (3S,4S)-4-Amino-1-cyclopropylmethyl-piperidine-3-carboxylic Acid (1-pyrimidin-2-yl-cyclopropyl)-amide 7.01a: (3R,4S)-4-Benzyloxycarbonylamino-piperidine-1,3-dicarboxylic Acid 1-tert-butyl Ester 3-ethyl Ester N-(Benzyloxycarbonyloxy)succinimide (12.2 g, 48.1 mmol) is added to a solution of (3R,4S)-4-amino-piperidine-1,3-dicarboxylic acid 1-tert-butyl ester 3-ethyl ester (13.1 g, 48.1 mmol) in THF (100 mL) at 0° C. The reaction mixture is stirred for 10 min at 0° C. and then at RT for 2 h. THF is evaporated and the residue is taken up in DCM (100 mL). The mixture is washed with aq.sat.NaHCO$_3$ (100 mL), dried over MgSO$_4$, filtered, concentrated and dried at HV to deliver the crude product as a yellowish oil. LC-MS method A t$_R$=1.01 min; [M+H]$^+$=407.15.

7.01b: (3S,4S)-4-Benzyloxycarbonylamino-piperidine-1,3-dicarboxylic Acid 1-tert-butyl Ester 3-ethyl Ester Sodium ethoxide solution 21 wt. % in EtOH (77.4 mL, 0.0465 mol) is added to EtOH (100 mL) and ethyl acetate (14.1 mL, 0.139 mol). The mixture is refluxed for 30 min and cooled to RT. A suspension of (3R,4S)-4-benzyloxycarbonylamino-piperidine-1,3-dicarboxylic acid 1-tert-butyl ester 3-ethyl ester in dry ethanol (20 mL) is added dropwise to the NaOEt solution at RT under nitrogen. The mixture is stirred at RT for 24 h. The reaction mixture is treated with water (10 mL) and EtOH is evaporated at reduced pressure. Water (100 mL) is added and the pH of the solution is adjusted to 5 by treatment with aq. 2N HCl. added to the residue. The aq. phase is extracted 3× with DCM (3×100 mL). The combined organic layers are dried over MgSO$_4$ and filtered. Evaporation of the solvent gives the crude title compound as a yellowish oil, contaminated by 15% of the acid 7.01c. LC-MS method A: t$_R$=1.01 Min; [M+H]$^+$= 407.13.

7.01c: (3S,4S)-4-Benzyloxycarbonylamino-piperidine-1,3-dicarboxylic Acid 1-tert-butyl Ester (3S,4S)-4-Benzyloxycarbonylamino-piperidine-1,3-dicarboxylic acid 1-tert-butyl ester 3-ethyl ester 7.01b (4.07 g, 10 mmol) is dissolved in THF (50 mL) at RT. Aq. 1M NaOH solution (20 mL, 20 mmol) is added and the mixture is stirred at RT for 18 h. The reaction mixture is acidified to around pH=3 with a 2M HCl solution (11 mL, 21 mmol) and evaporated. The resulting suspension is extracted twice with DCM (2×50 mL). The organic phase is dried over MgSO$_4$ and the solvent is evaporated to give the title compound; LC-MS method A $t_R$=0.86 min; [M+H]$^+$=379.18.

7.01d: (3S,4S)-4-Benzyloxycarbonylamino-3-(1-pyrimidin-2-yl-cyclopropylcarbamoyl)-piperidine-1-carboxylic Acid Tert-Butyl Ester A solution of (3S,4S)-4-benzyloxycarbonylamino-piperidine-1,3-dicarboxylic acid 1-tert-butyl ester (4.26 g, 11.3 mmol) in DMF (40 mL) is treated with 1-(pyrimidin-2-yl)cyclopropan-1-amine hydrochloride (2.17 g, 12.4 mmol), DIPEA (10.2 mL, 58.5 mmol) and HATU (5.136 g, 13.5 mmol). The mixture is stirred 2 h at RT. Aq. saturated NaHCO$_3$ solution (50 mL) and DCM (80 mL) are added and the aq. phase is extracted with DCM (2×70 mL), dried over MgSO4, filtered and evaporated. The crude is purified by Prep HPLC using basic conditions. The title compound is obtained as a yellowish foam. LC-MS method A: $t_R$=0.89 Min; [M+H]$^+$=496.11.

7.01e: [(3S,4S)-3-(1-Pyrimidin-2-yl-cyclopropylcarbamoyl)-piperidin-4-yl]-carbamic Acid Benzyl Ester (3S,4S)-4-Benzyloxycarbonylamino-3-(1-pyrimidin-2-yl-cyclopropylcarbamoyl)-piperidine-1-carboxylic acid tert-butyl ester (2622 mg, 5.29 mmol) in MeOH (35 mL) is treated with HCl 4M in dioxane (10.6 mL, 42.3 mmol). The reaction mixture is stirred at 50° C. for 2 h. After evaporation of the solvents, the crude is dried under HV to give the crude title compound; LC-MS method D $t_R$=0.56 min; [M+H]$^+$=396.07.

7.01f: [(3S,4S)-1-Cyclopropylmethyl-3-(1-pyrimidin-2-yl-cyclopropylcarbamoyl)-piperidin-4-yl]-carbamic Acid Benzyl Ester To a solution of [(3S,4S)-3-(1-pyrimidin-2-yl-cyclopropylcarbamoyl)-piperidin-4-yl]-carbamic acid benzyl ester (3.06 g, 7.09 mmol) in DCM (100 mL) at RT is added cyclopropanecarboxaldehyde (0.54 mL, 7.09 mmol) followed by DIPEA (3.64 mL, 21.3 mmol) and sodium triacetoxyborohydride (3.96 g, 17.7 mmol). The reaction mixture is stirred overnight. The reaction mixture is treated with aq. sat. NaHCO$_3$ (100 mL) and the resulting suspension is extracted twice with DCM (2×100 mL). The organic phase is dried over MgSO$_4$ and evaporated. The crude is purified by Prep HPLC using basic conditions. The title compound is obtained as a light yellowish solid. LC-MS method A: $t_R$=0.63 Min; [M+H]$^+$=450.17.

7.01: (3S,4S)-4-Amino-1-cyclopropylmethyl-piperidine-3-carboxylic Acid (1-pyrimidin-2-yl-cyclopropyl)-amide A flask is purged with nitrogen, then charged with Pd/C 10% (50% wet) (160 mg, 1.5 mmol) and dry MeOH (10 mL) is added. A nitrogen purged suspension of [(3S,4S)-1-cyclopropylmethyl-3-(1-pyrimidin-2-yl-cyclopropylcarbamoyl)-piperidin-4-yl]-carbamic acid benzyl ester (1349 mg, 3 mmol) in dry MeOH (20 mL) is added to the Pd suspension. The atmosphere is exchanged with hydrogen and the mixture is stirred at RT for 3 h. The mixture is filtered and evaporated. The crude is purified by Prep HPLC using basic conditions. The title compound is obtained as a light yellowish solid. LC-MS method A: $t_R$=0.34 Min; [M+H]$^+$=316.34.

BB 7.02: rac-(3R*,4R*)-4-Amino-1-cyclopropylmethyl-piperidine-3-carboxylic Acid (1-pyrimidin-2-yl-cyclopropyl)-amide

7.02a: rac-(3R*,4R*)-4-Benzyloxycarbonylamino-piperidine-1,3-dicarboxylic Acid 1-tert-butyl Ester 3-methyl Ester The title compound is prepared according to the procedure 7.01a starting from building block rac-(3S*,4R*)-4-amino-piperidine-1,3-dicarboxylic acid 1-tert-butyl ester 3-methyl ester. LC-MS method A $t_R$=1.00 min; [M+H]$^+$=393.26.

7.02b: rac-(3R*,4R*)-4-Benzyloxycarbonylamino-piperidine-1,3-dicarboxylic Acid 1-tert-butyl Ester 3-ethyl Ester The title compound is prepared according to the procedure 7.01b starting from building block 7.0a. LC-MS method A: $t_R$=0.96 Min; [M+H]$^+$=393.23.

7.02c: rac-(3R*,4R*)-4-Benzyloxycarbonylamino-piperidine-1,3-dicarboxylic Acid 1-tert-butyl Ester The title compound is prepared according to the procedure 7.01c starting from building block 7.02b; LC-MS method A $t_R$=0.86 min; [M+H]$^+$=379.25.

7.02d: rac-(3R*,4R*)-4-Benzyloxycarbonylamino-3-(1-pyrimidin-2-yl-cyclopropylcarbamoyl)-piperidine-1-carboxylic Acid Tert-Butyl Ester The title compound is prepared according to the procedure 7.01d starting from building block 7.02c; LC-MS method A: $t_R$=0.88 Min; [M+H]$^+$=496.25.

7.02e: rac-[(3R*,4R*)-3-(1-Pyrimidin-2-yl-cyclopropylcarbamoyl)-piperidin-4-yl]-carbamic Acid Benzyl Ester The title compound is prepared according to the procedure 7.01e starting from building block 7.02d. LC-MS method D $t_R$=0.56 min; [M+H]$^+$=396.27.

7.02f: rac-[(3R*,4*)-1-Cyclopropylmethyl-3-(1-pyrimidin-2-yl-cyclopropylcarbamoyl)-piperidin-4-yl]-carbamic Acid Benzyl Ester The title compound is prepared according to the procedure 7.01f starting from building block 7.02e. LC-MS method A: $t_R$=0.66 Min; [M+H]$^+$=450.09.

7.02: rac-(3R*,4R*)-4-Amino-1-cyclopropylmethyl-piperidine-3-carboxylic Acid (1-pyrimidin-2-yl-cyclopropyl)-amide The title compound is prepared according to the procedure 7.01 starting from building block 7.02f. LC-MS method A: $t_R$=0.37 Min; [M+H]$^+$=316.29.

Example 7.001: (3S,4S)-1-Cyclopropylmethyl-4-{[4-fluoro-5-(4-fluoro-phenyl)-isoxazole-3-carbonyl]-amino}-piperidine-3-carboxylic Acid (1-pyrimidin-2-yl-cyclopropyl)-amide To a solution of (3S,4S)-4-Amino-1-cyclopropylmethyl-piperidine-3-carboxylic acid (1-pyrimidin-2-yl-cyclopropyl)-amide (50 mg, 0.16 mmol) in DMF (5 mL) is added 4-fluoro-5-(4-fluoro-phenyl)-isoxazole-3-carboxylic acid (35.7 mg, 0.08 mmol). DIPEA (0.067 mL, 0.396 mmol) is then added followed by HATU (72.3 mg, 0.19 mmol). The reaction mixture is stirred 21 h at RT. Up to 0.28 mmol of a 2M HCl solution is added to the crude mixture to dissolve the precipitate, and the clear solution is directly purified by prep. LC-MS with method E. LC-MS QC method: $t_R$=0.60 min; [M+H]$^+$=523.1.

Compounds of Examples 7.002 to 7.016 listed in Table 5 below are prepared by applying one of the above-mentioned general procedures I or J to the building blocks BB-7.01 BB-7.02 coupled with respective carboxylic acid or ester of Structure A-4 (L$^1$=OH or O-alkyl), which is commercially available or prepared according to/in analogy to the methods described above.

Enantiomerically pure compounds are obtained using one of the above mentioned chiral preparative chromatography methods.

TABLE 5

Examples 7.002-7.016

| Example Nr | Substance Name | LC-MS $t_R$ (min) | Mass Found [M + H]$^+$ |
|---|---|---|---|
| 7.002 | (3S,4S)-1-Cyclopropylmethyl-4-[(5-o-tolyl-isoxazole-3-carbonyl)-amino]-piperidine-3-carboxylic acid (1-pyrimidin-2-yl-cyclopropyl)-amide | 0.60 | 501.4 |
| 7.003 | (3S,4S)-1-Cyclopropylmethyl-4-{[5-(3,4-dimethyl-phenyl)-isoxazole-3-carbonyl]-amino}-piperidine-3-carboxylic acid (1-pyrimidin-2-yl-cyclopropyl)-amide | 0.70 | 515.1 |
| 7.004 | (3S,4S)-1-Cyclopropylmethyl-4-{[1-(2,4-difluoro-phenyl)-1H-[1,2,3]triazole-4-carbonyl]-amino}-piperidine-3-carboxylic acid (1-pyrimidin-2-yl-cyclopropyl)-amide | 1.0 | 523.2 |
| 7.005 | (3S,4S)-1-Cyclopropylmethyl-4-{[5-(2,4-dimethyl-phenyl)-isoxazole-3-carbonyl]-amino}-piperidine-3-carboxylic acid (1-pyrimidin-2-yl-cyclopropyl)-amide | 0.70 | 515.1 |
| 7.006 | (3S,4S)-1-Cyclopropylmethyl-4-{[3-(2,4-difluoro-phenyl)-isoxazole-5-carbonyl]-amino}-piperidine-3-carboxylic acid (1-pyrimidin-2-yl-cyclopropyl)-amide | 0.60 | 523.1 |
| 7.007 | (3S,4S)-1-Cyclopropylmethyl-4-{[5-(4-fluoro-phenyl)-oxazole-2-carbonyl]-amino}-piperidine-3-carboxylic acid (1-pyrimidin-2-yl-cyclopropyl)-amide | 0.6 | 505 |
| 7.008 | (3S,4S)-1-Cyclopropylmethyl-4-{[5-(2,4-difluoro-phenyl)-[1,2,4]oxadiazole-3-carbonyl]-amino}-piperidine-3-carboxylic acid (1-pyrimidin-2-yl-cyclopropyl)-amide | 0.5 | 524 |
| 7.009 | (3S,4S)-4-{[5-(4-Cyano-phenyl)-isoxazole-3-carbonyl]-amino}-1-cyclopropylmethyl-piperidine-3-carboxylic acid (1-pyrimidin-2-yl-cyclopropyl)-amide | 0.5 | 512 |
| 7.010 | (3S,4S)-1-Cyclopropylmethyl-4-{[4-(2,4-difluoro-phenyl)-oxazole-2-carbonyl]-amino}-piperidine-3-carboxylic acid (1-pyrimidin-2-yl-cyclopropyl)-amide | 0.6 | 523.4 |
| 7.011 | (3S,4S)-1-Cyclopropylmethyl-4-{[5-(2,4-difluoro-phenyl)-oxazole-2-carbonyl]-amino}-piperidine-3-carboxylic acid (1-pyrimidin-2-yl-cyclopropyl)-amide | 0.6 | 523 |
| 7.012 | (3S,4S)-1-Cyclopropylmethyl-4-{[1-(2,4,6-trifluoro-phenyl)-1H-[1,2,3]triazole-4-carbonyl]-amino}-piperidine-3-carboxylic acid (1-pyrimidin-2-yl-cyclopropyl)-amide | 1.0 | 541.4 |
| 7.013 | (3S,4S)-1-Cyclopropylmethyl-4-{[5-(3,4-difluoro-phenyl)-isoxazole-3-carbonyl]-amino}-piperidine-3-carboxylic acid (1-pyrimidin-2-yl-cyclopropyl)-amide | 0.6 | 523 |
| 7.014 | (3S,4S)-1-Cyclopropylmethyl-4-{[3-(2,4-difluoro-phenyl)-isothiazole-5-carbonyl]-amino}-piperidine-3-carboxylic acid (1-pyrimidin-2-yl-cyclopropyl)-amide | 0.6 | 539 |
| 7.015 | (3S,4S)-1-Cyclopropylmethyl-4-{[5-(2,4-difluoro-phenyl)-isothiazole-3-carbonyl]-amino}-piperidine-3-carboxylic acid (1-pyrimidin-2-yl-cyclopropyl)-amide | 0.6 | 539.1 |
| 7.016 | (3S,4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide | 0.6 | 540.1 |

General Method I for the Synthesis of Piperidines of Formula (I)
Buildings Blocks:
Preparation of Building Blocks of Structure D-9

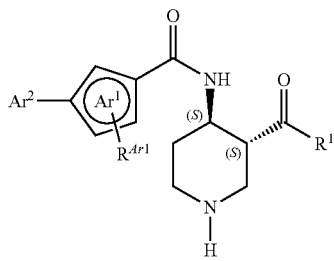

D-9

BB 8.01: (3S,4S)-4-{[1-(2,4-Difluoro-phenyl)-1H-[1,2,3]triazole-4-carbonyl]-amino}-piperidine-3-carboxylic Acid (1-pyridin-2-yl-cyclopropyl)-amide 8.01a: (3R,4S)-4-{[1-(2,4-Difluoro-phenyl)-1H-[1,2,3]triazole-4-carbonyl]amino}-piperidine-1,3-dicarboxylic Acid 1-tert-butyl Ester 3-ethyl Ester To a solution of (3R,4S)-4-amino-piperidine-1,3-dicarboxylic acid 1-tert-butyl ester 3-ethyl ester (1400 mg, 5.14 mmol)) in DMF (50 mL) at RT is added 1-(2,4-difluoro-phenyl)-1H-[1,2,3]triazole-4-carboxylic acid (1157 mg, 5.14 mmol). DIPEA (4.67 mL, 26.7 mmol) is then added followed by HATU (2346 mg, 6.17 mmol). The reaction mixture is stirred overnight at RT. The crude mixture is purified by prep. LC-MS in basic conditions. The title compound is obtained as a pale yellow solid. LC-MS method A: $t_R$=1.01 Min; [M+H]$^+$=480.11.

8.01b: (3S,4S)-4-{[1-(2,4-Difluoro-phenyl)-1H-[1,2,3]triazole-4-carbonyl]amino}-piperidine-1,3-dicarboxylic Acid 1-tert-butyl Ester 3-ethyl Ester To a solution of (3R,4S)-4-{[1-(2,4-difluoro-phenyl)-1H-[1,2,3]triazole-4-carbonyl]amino}-piperidine-1,3-dicarboxylic acid 1-tert-butyl ester 3-ethyl ester (1587 mg, 3.41 mmol) in EtOH (14.9 mL, 256 mmol) and EtOAc (7.36 mL, 75 mmol) is added in one portion sodium methoxide powder (776 mg, 13.6 mmol) at RT under an argon atmosphere. The reaction mixture is stirred at RT overnight. The reaction mixture is quenched with sat. aq. NH$_4$Cl (200 mL) and extracted twice with DCM (2×250 mL). The combined organic extracts are dried over MgSO4, filtered and concentrated in vacuo. The crude is purified by prep. LC-MS in basic conditions. LC-MS method A: $t_R$=0.98 Min; [M+H]$^+$=480.13.

8.01c (3S,4S)-4-{[1-(2,4-Difluoro-phenyl)-1H-[1,2,3]triazole-4-carbonyl]amino}-piperidine-1,3-dicarboxylic Acid 1-tert-butyl Ester To a solution of (3S,4S)-4-{[1-(2,4-difluoro-phenyl)-1H-[1,2,3]triazole-4-carbonyl]amino}-piperidine-1,3-dicarboxylic acid 1-tert-butyl ester 3-ethyl ester (1000 mg, 2.09 mmol) in THF (30 mL) is added 1 M NaOH (7 mL, 6.26 mmol). The mixture is stirred 4 h at RT. 2 M HCl (3.7 mL, 6.47 mmol, 3.1 eq) is added to reach pH 3 and THF is evaporated until dryness.

The white solid is dried under high vacuum overnight. LC-MS method A: $t_R$=0.85 min; [M+H]$^+$=451.8.

8.01d: (3S,4S)-4-{[1-(2,4-Difluoro-phenyl)-1H-[1,2,3]triazole-4-carbonyl]amino}-3-(1-pyridin-2-yl-cyclopropylcarbamoyl)-piperidine-1-carboxylic Acid Tert-Butyl Ester A solution of (3S,4S)-4-{[1-(2,4-difluoro-phenyl)-1H-[1,2,3]triazole-4-carbonyl]amino}-piperidine-1,3-dicarboxylic acid 1-tert-butyl ester (500 mg, 1.11 mmol) in DMF (12 mL) is treated with 1-(pyridin-2-yl)cyclopropan-1-amine dihydrochloride (226 mg, 1.11 mmol), DIPEA (1.01 mL, 5.76 mmol) and HATU (5.35 mg, 1.33 mmol). The mixture is stirred 2 h at RT. Saturated NaHCO$_3$ solution (20 mL) and DCM (20 mL) are added and the aq. phase is extracted twice with DCM (2×20 mL), dried over MgSO$_4$, filtered and evaporated. The crude is purified by Prep HPLC using basic conditions. The title compound is obtained as a white solid. LC-MS method A: $t_R$=0.77 Min; [M+H]$^+$=568.29.

8.01: (3S,4S)-4-{[1-(2,4-Difluoro-phenyl)-1H-[1,2,3]triazole-4-carbonyl]amino}-piperidine-3-carboxylic Acid (1-pyridin-2-yl-cyclopropyl)-amide Hydrochloride (3S,4S)-4-{[1-(2,4-Difluoro-phenyl)-1H-[1,2,3]triazole-4-carbonyl]amino}-3-(1-pyridin-2-yl-cyclopropylcarbamoyl)-piperidine-1-carboxylic acid tert-butyl ester (205 mg, 0.361 mmol) is dissolved in dioxane (8 mL) at RT. A 4M solution of HCl in dioxane (1 mL, 4 mmol) is added and the reaction stirred at RT for 1 h. The reaction mixture is concentrated. The white solid is dried under high vacuum overnight LC-MS A: $t_R$=0.50 min; [M+H]$^+$=467.83.

BB 8.02: (3S,4S)-4-{[5-(2,4-Difluoro-phenyl)-oxazole-2-carbonyl]-amino}-piperidine-3-carboxylic Acid (1-pyrimidin-2-yl-cyclopropyl)-amide Hydrochoride 8.02a: (3R,4S)-4-{[5-(2,4-Difluoro-phenyl)-oxazole-2-carbonyl]-amino}-piperidine-1,3-dicarboxylic Acid 1-tert-butyl Ester 3-ethyl Ester The title compound is prepared by treatment of (3R,4S)-4-amino-piperidine-1,3-dicarboxylic acid 1-tert-butyl ester 3-ethyl ester and 5-(2,4-Difluoro-phenyl)-oxazole-2-carboxylic Acid lithium salt according to procedure 8.01a. LC-MS method A: $t_R$=1.07 Min; [M+H]$^+$=480.16.

8.02b: (3S,4S)-4-{[5-(2,4-Difluoro-phenyl)-oxazole-2-carbonyl]-amino}-piperidine-1,3-dicarboxylic Acid 1-tert-butyl Ester 3-ethyl Ester The title compound is prepared according to the procedure 8.01b, starting from building block 8.02a; LC-MS method A: $t_R$=1.04 Min; [M+H]$^+$=480.16.

8.02c (3S,4S)-4-{[5-(2,4-Difluoro-phenyl)-oxazole-2-carbonyl]-amino}-piperidine-1,3-dicarboxylic Acid 1-tert-butyl Ester The title compound is prepared according to the procedure 8.01c, starting from building block 8.02b; LC-MS method A: $t_R$=0.91 min; [M+H]$^+$=452.18.

8.02d: (3S,4S)-4-{[5-(2,4-Difluoro-phenyl)-oxazole-2-carbonyl]-amino}-3-(1-pyrimidin-2-yl-cyclopropylcarbamoyl)-piperidine-1-carboxylic Acid Tert-Butyl Ester The title compound is prepared according to the procedure 8.01d, starting from 8.02c and 1-(pyrimidin-2-yl)cyclopropan-1-amine hydrochloride; LC-MS method A: $t_R$=0.93 Min; [M+H]$^+$=569.24.

8.02: (3S,4S)-4-{[5-(2,4-Difluoro-phenyl)-oxazole-2-carbonyl]-amino}-piperidine-3-carboxylic acid (1-pyrimidin-2-yl-cyclopropyl)-amide hydrochoride The title compound is prepared according to the procedure 8.01 described above, starting from building block 2.04c; LC-MS method A: $t_R$=0.62 min; [M+H]$^+$=469.16.
Buildings Blocks:
Preparation of Amines of Structure 2

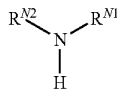

2

BB-9.01
1-(1-Oxy-pyrimidin-2-yl)-cyclopropylamine Hydrochoride

9.01a: [1-(1-Oxy-pyrimidin-2-yl)-cyclopropyl]-carbamic Acid Tert-Butyl Ester To a solution of (1-Pyrimidin-2-yl-cyclopropyl)-carbamic acid tert-butyl ester (200 mg, 0.834 mmol) in DCM (5 mL) at 0° C. is added portionwise 3-chloroperbenzoic acid (226 mg, 0.917 mmol). The reaction mixture is stirred at RT for 72 h. The mixture is diluted with DCM (20 mL) and washed with aq. sat. NaHCO$_3$ (20 mL). The organic phase is separated and the aq. phase is extracted with DCM (20 mL). The combined organic are dried over MgSO$_4$, filtered and concentrated. The crude is purified by Prep HPLC using basic conditions. The title compound is obtained as a white solid. LC-MS method A: $t_R$=0.77 Min; [M+H]$^+$=568.29. to give the tittle compound as a yellowish powder; LC-MS method A: $t_R$=0.60 min; [M+H]$^+$=252.27.

9.01: 1-(1-Oxy-pyrimidin-2-yl)-cyclopropylamine Hydrochloride

[1-(1-Oxy-pyrimidin-2-yl)-cyclopropyl]-carbamic acid tert-butyl ester (74 mg, 0.29 mmol) is dissolved in MeOH (3 mL) at RT. A 4M solution of HCl in dioxane (0.44 mL, 1.77 mmol) is added and the reaction mixture is stirred at RT for 18 h. The solvents are evaporated to give the title compound as a yellowish solid; LC-MS method A: $t_R$=0.21 min; [M+H]$^+$=152.31.

REFERENCE EXAMPLES

Reference Example 1 rac-(3R*,4R*)-4-[(5-Cyclopropyl-isoxazole-3-carbonyl)-amino]-1-cyclopropylmethyl-piperidine-3-carboxylic Acid (1-pyrimidin-2-yl-cyclopropyl)-amide The title compound is prepared according to the procedure described for the preparation of Example 7.001 starting from building block 7.02 and 5-cyclopropyl-isoxazole-3-carboxylic acid. LC-MS method A: $t_R$=0.61 Min; [M+H]$^+$=451.27.

Chiral preparative SFC of rac-(3R*,4R*)-4-[(5-cyclopropyl-isoxazole-3-carbonyl)-amino]-1-cyclopropylmethyl-piperidine-3-carboxylic acid (1-pyrimidin-2-yl-cyclopropyl)-amide using a column ChiralPak IC, 5 μm, 4.6×250 mm; with a mixture of A (CO$_2$) and B (DCM/MeOH/DEA 50:50:01)) as eluent yields both enantiomers:

Reference Compound 1a: (3R,4R)-4-[(5-Cyclopropyl-isoxazole-3-carbonyl)-amino]-1-cyclopropylmethyl-piperidine-3-carboxylic acid (1-pyrimidin-2-yl-cyclopropyl)-amide or (3S,4S)-4-[(5-cyclopropyl-isoxazole-3-carbonyl)-amino]-1-cyclopropylmethyl-piperidine-3-carboxylic Acid (1-pyrimidin-2-yl-cyclopropyl)-amide Chiral HPLC $t_R$=1.80 min.; QC LC-MS method: $t_R$=0.5 min; [M+H]$^+$=451;
IC$_{50}$: >10000 nM.

Reference Compound 1b: (3R,4R)-4-[(5-Cyclopropyl-isoxazole-3-carbonyl)-amino]-1-cyclopropylmethyl-piperidine-3-carboxylic acid (1-pyrimidin-2-yl-cyclopropyl)-amide or (3S,4S)-4-[(5-cyclopropyl-isoxazole-3-carbonyl)-amino]-1-cyclopropylmethyl-piperidine-3-carboxylic Acid (1-pyrimidin-2-yl-cyclopropyl)-amide Chiral HPLC $t_R$=2.48 min.; QC LC-MS method: $t_R$=0.5 min; [M+H]$^+$=451.3;
IC$_{50}$: >10000 nM.

Reference Example 2

(3R,4S)-1-Cyclopropylmethyl-4-{[5-(2,4-difluoro-phenyl)-isoxazole-3-carbonyl]-amino}-piperidine-3-carboxylic Acid (1-pyrimidin-2-yl-cyclopropyl)-amide and (3S,4R)-1-Cyclopropylmethyl-4-{[5-(2,4-difluoro-phenyl)-isoxazole-3-carbonyl]-amino}-piperidine-3-carboxylic Acid (1-pyrimidin-2-yl-cyclopropyl)-amide

Step 1: rac-(3R*,4S*)-4-{[5-(2,4-Difluoro-phenyl)-isoxazole-3-carbonyl]-amino}-piperidine-1,3-dicarboxylic Acid 1-tert-butyl Ester The title compound is prepared according to the procedure 2.01c, starting from building block 6.01c by treatment with NaOH in THF/H$_2$O, followed by aq. HCl; LC-MS method A: $t_R$=1.01 min; [M+H]$^+$=452.22.

Step 2: rac-(3R*,4S*)-4-{[5-(2,4-Difluoro-phenyl)-isoxazole-3-carbonyl]-amino}-3-(1-pyrimidin-2-yl-cyclopropylcarbamoyl)-piperidine-1-carboxylic Acid Tert-Butyl Ester The title compound is prepared according to the procedure 2.01d, starting from step 1 and 1-(pyrimidin-2-yl)cyclopropan-1-amine hydrochloride; LC-MS method A: $t_R$=1.06 min; [M+H]$^+$=569.33.

Step 3: rac-(3R*,4S*)-4-{[5-(2,4-Difluoro-phenyl)-isoxazole-3-carbonyl]-amino}-piperidine-3-carboxylic Acid (1-pyrimidin-2-yl-cyclopropyl)-amide The title compound is prepared according to the procedure 2.01, starting from step 2; LC-MS method A: $t_R$=0.74 min; [M+H]$^+$=469.14.

Step 4: rac-(3R*,4S*)-1-Cyclopropylmethyl-4-{[5-(2,4-difluoro-phenyl)-isoxazole-3-carbonyl]-amino}-piperidine-3-carboxylic Acid (1-pyrimidin-2-yl-cyclopropyl)-amide The title compound is prepared according to the method D, starting from step 3; LC-MS method A: $t_R$=0.71 min; [M+H]$^+$=523.18.

Chiral preparative HPLC of rac-(3R*,4S*)-1-cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide using a column ChiralPak IC, 5 µm, 4.6×250 mm; with a mixture of A (10% Heptan, 0.05% DEA)) and B (90% EtOH, 0.05% DEA) as eluent and a flow of 1.2 mL/min. Chiral HPLC: yields both enantiomers:

Reference Example 2a: (3R,4S)-1-Cyclopropylmethyl-4-{[5-(2,4-difluoro-phenyl)-isoxazole-3-carbonyl]-amino}-piperidine-3-carboxylic Acid (1-pyrimidin-2-yl-cyclopropyl)-amide Chiral HPLC $t_R$=12.01 min.; QC LC-MS method: $t_R$=0.7 min; [M+H]$^+$=523.1;
IC$_{50}$: >10000 nM.

Reference Example 2b: (3S,4R)-1-Cyclopropylmethyl-4-{[5-(2,4-difluoro-phenyl)-isoxazole-3-carbonyl]-amino}-piperidine-3-carboxylic Acid (1-pyrimidin-2-yl-cyclopropyl)-amide Chiral HPLC $t_R$=18.35 min.; QC LC-MS method: $t_R$=0.7 min; [M+H]$^+$=523.4;
IC$_{50}$: 2250 nM.

Reference Example 3

(3S,4S)-1-Cyclopropylmethyl-4-[(5-phenyl-isoxazole-3-carbonyl)-amino]-piperidine-3-carboxylic Acid (1-pyrimidin-2-yl-cyclopropyl)-amide Reference example 3 is prepared according to example 7.001, starting from (3S,4S)-4-amino-1-cyclopropylmethyl-piperidine-3-carboxylic acid (1-pyrimidin-2-yl-cyclopropyl)-amide and 4-phenyl-isoxazole-3-carboxylic acid. LC-MS method A: $t_R$=0.66 min; [M+H]$^+$=487.13.

IC$_{50}$: 1330 nM.

Table 6 summarizes NMR characterization data of particular example compounds.

TABLE 6

$^1$H NMR data of particular example compounds

| Example | Chemical shift (δ) in part per million (ppm) | Solvent |
|---|---|---|
| 1.004 | (400 MHz) δ: 8.72 (d, J = 8.6 Hz, 1H), 8.08-8.01 (m, 1H), 7.60-7.54 (m, 1H), 7.36-7.30 (m, 1H), 7.08 (d, J = 2.7 Hz, 1H), 4.10-4.05 (m, 1H), 3.78-3.72 (m, 2H), 3.22-3.15 (m, 1H), 2.93-2.81 (m, 4H), 2.29-2.19 (m, 3H), 1.90-1.68 (m, 9H), 1.61-1.54 (m, 2H), 1.20-1.15 (m, 5H). | DMSO-d6 |
| 1.095 | (400 MHz) δ: 8.93 (s, 1H), 8.54 (d, J = 8.6 Hz, 1H), 7.94-7.86 (m, 1H), 7.71-7.64 (m, 1H), 7.39-7.33 (m, 1H), 4.15-4.05 (m, 1H), 3.25-3.17 (m, 1H), 3.07 (s, 3H), 2.88-2.81 (m, 2H), 2.75 (s, 3H), 2.32-2.16 (m, 3H), 1.80-1.72 (m, 5H), 1.63-1.55 (m, 2H), 1.18-1.14 (m, 5H). | DMSO-d6 |
| 1.107 | (400 MHz) δ: 8.80 (d, J = 8.8 Hz, 1H), 7.51 (dd, J = 9.2, 9.2 Hz, 2H), 7.15 (s, 1H), 4.38-4.31 (m, 1H), 4.17-4.11 (m, 1H), 4.05-3.91 (m, 1H), 3.83-3.69 (m, 2H), 3.02-2.96 (m, 2H), 2.77-2.68 (m, 1H), 2.27 (dd, J = 6.4, 12.7 Hz, 1H), 2.19-1.98 (m, 5H), 1.83-1.76 (m, 1H), 1.69-1.59 (m, 1H), 0.83 (dd, J = 6.2, 6.2 Hz, 1H), 0.48-0.44 (m, 2H), 0.10-0.05 (m, 2H). | DMSO-d6 |
| 1.113b | (400 MHz) δ: 8.57 (d, J = 8.8 Hz, 1H), 7.53-7.45 (m, 2H), 7.14 (d, J = 1.2 Hz, 2H), 3.95-3.87 (m, 2H), 3.12 (s, 3H), 2.97 (d, J = 11.2 Hz, 2H), 2.62-2.54 (m, 1H), 2.21-2.17 (m, 2H), 2.13-1.95 (m, 2H), 1.82 (dd, J = 3.4, 13.0 Hz, 1H), 1.57-1.48 (m, 1H), 1.11 (s, J = 5.1 Hz, 6H), 0.87-0.77 (m, 1H), 0.45 (d, J = 7.1 Hz, 2H), 0.09-0.05 (m, 2H). | DMSO-d6 |
| 1.118a | (400 MHz) δ: 8.99 (s, 1H), 8.57-8.47 (m, 2H), 8.22 (d, J = 8.1 Hz, 1H), 7.94-7.87 (m, 1H), 7.72-7.64 (m, 2H), 7.39-7.35 (m, 1H), 7.31-7.22 (m, 2H), 4.93-4.87 (m, 1H), 4.06-4.01 (m, 1H), 2.95-2.91 (m, 2H), 2.80-2.73 (m, 1H), 2.15-1.97 (m, 2H), 1.88-1.74 (m, 1H), 1.59-1.45 (m, 5H), 1.34-1.27 (m, 2H), 1.23 (s, 1H), 1.17-1.13 (m, 3H). | DMSO-d6 |
| 1.189 | (400 MHz) δ: 8.43-8.51 (m, 4 H), 7.99 (s, 1 H), 7.97 (s, 1 H), 7.92 (d, J = 2.1 Hz, 1 H), 7.66 (dd, J$_1$ = 2.2 Hz, J$_2$ = 8.5 Hz, 1 H), 7.38 (s, 1 H), 7.18 (t, J = 4.9 Hz, 1 H), 3.99 (m, 1H), 2.70-3.18 (m, 3 H), 1.80-2.23 (m, 6 H), 1.48 (d, J = 3.8 Hz, 1 H), 1.36-1.40 (m, 2 H), 1.16 (m, 1 H), 0.83 (m, 1H) 0.49-0.50 (m, 2 H), 0.10 (d, J = 0.7 Hz, 2 H). | DMSO-d6 |
| 2.019a | (400 MHz) δ: 8.72 (d, J = 8.6 Hz, 1H), 8.07-8.00 (m, 1H), 7.58-7.51 (m, 1H), 7.35-7.29 (m, 1H), 7.08 (d, J = 2.9 Hz, 1H), 4.14-4.05 (m, 1H), 3.19-3.15 (m, 1H), 3.05 (s, 3H), 2.98-2.92 (m, 2H), 2.76 (s, 3H), 2.51 (s, 1H), 2.00-1.92 (m, 2H), 1.80-1.76 (m, 3H), 1.62-1.59 (m, 3H), 1.48 (t, J = 5.5 Hz, 2H), 1.38-1.29 (m, 2H). | DMSO-d6 |
| 2.031 | (400 MHz) δ: 8.73 (d, J = 8.6 Hz, 1H), 8.08-8.01 (m, 1H), 7.60-7.53 (m, 1H), 7.36 - 7.30 (m, 1H), 7.09 (d, J = 2.9 Hz, 1H), 4.11-4.04 (m, 1H), 3.20-3.14 (m, 2H), 3.06 (s, 3 H), 2.82-2.80 (m, 1H), 2.76 (s, 3H), 2.71-2.63 (m, 1H), 1.88-1.53 (m, 8H), 1.08 (d, J = 19.3 Hz, 6H). | DMSO-d6 |
| 2.073 | (400 MHz) δ: 8.49-8.55 (m, 3 H), 8.44 (s, 1 H), 8.05-8.09 (m, 1 H), 7.62 (d, J = 2.5 Hz, 1 H), 7.57-7.60 (m, 1 H), 7.32-7.37 (m, 1 H), 7.16-7.19 (m, 2 H), 3.96 (dd, J$_1$ = 4.2 Hz, J$_2$ = 8.5 Hz, 1 H), 2.92 (d, J = 9.7 Hz, 1 H), 2.74-2.80 (m, 2 H), 2.62-2.68 (m, 1 H), 2.32 (m, 1 H), 2.29 (s, 1 H), 2.17-2.19 (m, 1 H), 1.85-1.89 (m, 1 H), 1.46-1.56 (m, 1 H), 1.36-1.40 (m, 1 H), 1.09 (m, 2 H), 0.99 (d, J = 6.5 Hz, 6 H). | DMSO-d6 |

TABLE 6-continued

¹H NMR data of particular example compounds

| Example | Chemical shift (δ) in part per million (ppm) | Solvent |
| --- | --- | --- |
| 2.074 | (400 MHz) □: 8.57 (d, J = 8.5 Hz, 1 H), 8.45-8.50 (m, 3 H), 8.08 (m, 1 H), 7.60 (m, 1 H), 7.34 (td, J$_1$ = 2.2 Hz, J$_2$ = 8.5 Hz, 1 H), 7.16-7.19 (m, 2 H), 3.98 (dd, J$_1$ = 3.6 Hz, J$_2$ = 8.1 Hz, 1 H), 2.92 (d, J = 9.1 Hz, 1 H), 2.63-2.82 (m, 3 H), 1.74-1.99 (m, 7 H), 1.46-1.65 (m, 4 H), 1.35-1.39 (m, 1 H), 1.06-1.10 (m, 2 H). | DMSO-d6 |
| 3.003b | (500 MHz) δ: 9.26 (d, J = 8.5 Hz, 1 H), 8.18-8.13 (m, 1 H), 7.64 (m, 1 H), 7.39 (td, J$_1$ = 8.3 Hz, J$_2$ = 2.1 Hz, 1 H), 4.10 (m, 1 H), 3.21-3.15 (m, 1 H), 3.07 (s, 3 H), 2.90-2.78 (m, 2 H), 2.76 (s, 3 H), 2.38-2.25 (m, 2 H), 2.17 (t, J = 11.2 Hz, 1 H), 1.85-1.82 (m, 1 H), 1.76-1.68 (m, 4 H), 1.63-1.56 (m, 2 H), 1.30-1.15 (m, 4 H), 1.07 (m, 1 H). | DMSO-d6 |
| 3.015 | (400 MHz) δ: 8.98 (d, J = 8.8 Hz, 1 H), 8.56 (s, 1 H), 8.32 (d, J = 4.6 Hz, 1 H), 7.99-7.93 (m, 1 H), 7.78 (d, J = 3.3 Hz, 1 H), 7.52 (m, 1 H), 7.34-7.20 (m, 3 H), 7.01-6.98 (m, 1 H), 4.05-4.02 (m, 1 H), 3.11-3.01 (m, 2 H), 2.86-2.80 (m, 1 H), 2.51 (s), 2.29-2.01 (m, 4 H), 1.85-1.82 (m, 1 H), 1.68-1.64 (m, 1 H), 1.49-1.44 (m, 1 H), 1.31 (m, 1 H), 0.87-0.82 (m, 1 H), 0.48 (m, 2 H), 0.09 (m, 2 H). | DMSO-d6 |
| 3.019 | (400 MHz) δ: 9.35 (d, J = 8.3 Hz, 1H), 8.15-8.07 (m, 1H), 7.60-7.53 (m, 1H), 7.39-7.33 (m, 1H), 4.15-4.04 (m, 1H), 3.06 (s, 3H), 2.93-2.80 (m, 3H), 2.77 (s, 3H), 2.34-2.12 (m, 3H), 1.87-1.81 (m, 1H), 1.76-1.72 (m, 4H), 1.65-1.52 (m, 2H), 1.24-1.18 (m, 4H), 1.14-1.04 (m, 1H). | DMSO-d6 |
| 4.005 | (400 MHz) δ: 8.70 (d, J = 8.5 Hz, 1 H), 7.61 (d, J = 2.3 Hz, 1 H), 7.58-7.56 (m, 1 H), 7.33 (td, J$_1$ = 8.5 Hz, J$_2$ = 1.9 Hz, 1 H), 7.09 (d, J = 2.8 Hz, 1 H), 4.12-4.03 (m, 1 H), 3.13 (td, J$_1$ = 10.7 Hz, J$_2$ = 3.3 Hz, 1 H), 3.06 (s, 3 H), 2.88-2.77 (m, 5 H), 2-38-2.12 (m, 2 H), 1.83 (dd, J$_1$ = 12.5 Hz, J$_2$ = 3.9 Hz, 1 H), 1.73 (d, J = 7.3 Hz, 4 H), 1.57 (m, 2 H), 1.25-1.02 (m, 6 H). | DMSO-d6 |
| 4.032 | (400 MHz) δ: 8.57 (d, J = 8.5 Hz, 1 H), 8.51 (d, J = 4.8 Hz, 2 H), 8.47 (s, 1 H), 8.05-8.11 (m, 1 H), 7.59-7.62 (m, 1 H), 7.35 (m, 1 H), 7.14-7.21 (m, 2 H), 3.94-4.04 (m, 1 H), 3.32-3.40 (m, 1 H), 3.13-3.19 (m, 1 H), 2.95-3.03 (m, 1 H), 2.67-2.77 (m, 1 H), 2.45-2.60 (m, 19 H), 2.16-2.27 (m, 2 H), 2.09-2.14 (m, 1 H), 1.98-2.04 (m, 1 H), 1.84-1.90 (m, 1 H), 1.55-1.66 (m, 1 H), 1.48-1.52 (m, 1 H), 1.35-1.40 (m, 1 H), 1.04-1.14 (m, 2 H), 0.81-0.89 (m, 1 H), 0.45-0.52 (m, 2 H), 0.04-0.14 (m, 2 H) | DMSO-d6 |
| 4.033 | (400 MHz) δ: 8.76 (d, J = 8.6 Hz, 1H), 8.37 (d, J = 4.4 Hz, 1H), 8.09-8.02 (m, 2H), 7.59-7.51 (m, 1H), 7.40-7.29 (m, 3H), 7.15-7.06 (m, 2H), 3.99-3.89 (m, 1H), 3.07-2.99 (m, 2H), 2.81-2.73 (m, 1H), 2.24-2.16 (m, 2H), 2.12-1.98 (m, 2H), 1.88-1.82 (m, 1H), 1.62-1.55 (m, 1H), 1.51 (s, 3H), 1.43 (s, 3H), 0.86-0.82 (m, 1H), 0.51-0.45 (m, 2H), 0.10-0.05 (m, 2H). | DMSO-d6 |
| 4.052 | (400 MHz) δ: 8.57 (d, J = 8.5 Hz, 1 H), 8.48-8.51 (m, 3 H), 8.08 (m, 1 H), 7.59 (m, 1 H), 7.34 (m, 1 H), 7.16-7.20 (m, 2 H), 4.00 (d, J = 11.8 Hz, 1 H), 3.15-3.18 (m, 1 H), 3.00-3.03 (m, 1 H), 2.72-2.78 (m, 3 H), 2.32 (d, J = 11.6 Hz, 1 H), 2.21 (m, 1 H), 1.84-1.87 (m, 1 H), 1.62-1.65 (m, 1 H), 1.49 (d, J = 6.0 Hz, 1 H), 1.35-1.39 (m, 1 H), 0.99-1.10 (m, 4 H), 0.66-0.70 (m, 2 H). | DMSO-d6 |
| 4.055 | (400 MHz) δ: 8.94-9.02 (m, 2 H), 8.81 (d, J = 0.7 Hz, 1 H), 8.34 (m, 1 H), 8.09-8.14 (m, 2 H), 7.59-7.60 (m, 1 H), 7.26-7.37 (m, 3 H), 4.18 (s, 1 H), 3.26-3.46 (m, 7 H), 1.96-1.98 (m, 1 H), 1.47-1.52 (m, 2 H), 1.15-1.19 (m, 2 H), 1.00-1.03 (m, 1 H), 0.56-0.58 (m, 2 H), 0.25-0.25 (m, 2 H) . | DMSO-d6 |
| 4.081 | (400 MHz) δ: 8.88 (s, 1 H), 8.73 (d, J = 8.6 Hz, 1 H), 8.58 (s, 1 H), 8.48 (s, 2 H), 8.06-8.12 (m, 1 H), 7.57-7.63 (m, 1 H), 7.35 (td, J$_1$ = 2.0 Hz, J$_2$ = 8.3 Hz, 1 H), 7.12 (d, J = 3.0 Hz, 1 H), 4.00-4.03 (m, 1 H), 3.34 (s, 4 H), 2.99-3.08 (m, 2 H), 2.68-2.72 (m, 1 H), 2.01-2.25 (m, 4 H), 1.81-1.85 (m, 1 H), 1.61-1.62 (m, 1 H), 1.05-1.30 (m, 1 H), 0.74-0.86 (m, 3 H), 0.47 (d, J = 7.8 Hz, 2 H), 0.08 (s, 2 H) | DMSO-d6 |
| 4.101 | (400 MHz) δ: 8.54 (d, J = 8.0 Hz, 1 H), 8.50 (d, J = 4.7 Hz, 2 H), 8.47 (s, 1 H), 8.05-8.11 (m, 1 H), 7.57-7.63 (m, 1 H), 7.32-7.36 (m, 1 H), 7.17 (m, 2 H), 3.90-4.00 (m, 1 H), 3.30-3.38 (m, 3 H), 3.12-3.18 (m, 1 H), 2.97-3.03 (m, 1 H), 2.68 (ddd, J$_1$ = 2.5 Hz, J$_2$ = 6.3 Hz, 1 H), 2.51 (s, 46 H), 2.18-2.23 (m, 1 H), 2.08-2.14 (m, 1 H), 1.86-1.93 (m, 1 H), 1.47-1.57 (m, 2 H), 1.36-1.40 (m, 1 H), 1.05-1.15 (m, 11 H) | DMSO-d6 |
| 4.102 | (400 MHz) δ: 8.59-8.63 (m, 3 H), 8.04-8.10 (m, 2 H), 7.61 (d, J = 2.5 Hz, 1 H), 7.56-7.59 (m, 1 H), 7.31-7.35 (m, 1 H), 7.25 (t, J = 4.8 Hz, 1 H), 7.16 (d, J = 3.0 Hz, 1 H), 3.87 (d, J = 11.9 Hz, 1 H), 3.34 (s, 2 H), 2.96-3.01 (m, 1 H), 2.67-2.71 (m, 2 H), 2.19 (d, J = 5.8 Hz, 2 H), 1.97-2.05 (m, 1 H), 1.82-1.86 (m, 1 H), 1.51-1.58 (m, 6 H), 0.81-0.83 (m, 1 H), 0.45-0.48 (m, 2 H), 0.07 (q, J = 4.7 Hz, 2 H) | DMSO-d6 |

II. Biological Assays

In Vitro Assay

The antagonistic effect of the compounds of formula (I) on the CXCR7 receptor are determined in accordance with the following experimental method.

The assay is using the Tango CXCR7-bla U2OS cell line from invitrogen. These cells contain the human chemokine receptor CXCR7 linked to a TEV protease site and a Gal4-VP16 transcription factor stably integrated into the Tango GPCR-bla U2OS parental cell line. This parental cell line stably express a beta-arrestin/TEV protease fusion protein and the beta-lactamase reporter gene under the control of a UAS response element. Upon ligand binding and receptor activation, the protease-tagged beta-arrestin molecule is recruited to CXCR7 which is linked at the C-terminus by a protease cleavage site to a transcription factor. The protease cleaves the transcription factor from CXCR7, which translocates to the nucleus and activates the expression of beta-lactamase. A FRET-enabled substrate allows to detect beta-lactamase expression.

Tango CXCR7-bla U2OS cells are detached from culture dishes with 0.05% trypsin-EDTA and collected in growing medium (McCoy's 5A 90% (v/v), dialyzed FCS 10% (v/v), 0.1 mM NEAA, 25 mM HEPES (pH7.3), 1 mM sodium pyruvate, P/S 1% (v/v) 50 μg/ml Hygromycin, 100 μg/ml Geneticin, 200 μg/ml Zeocin), spinned down and resuspended in assay medium (McCoy's 5A 90% (v/v), dialyzed FCS 1% (v/v), 0.1 mM NEAA, 25 mM HEPES (pH7.3), P/S 1% (v/v)). 10'000 cells per well (in 30 μl) are seeded in a 384 well plate (black-walled, clear bottom). The plate is incubated at 37° C./5% $CO_2$ for 24 hours. Test compounds are dissolved to 10 mM in DMSO and serially diluted in DMSO to 500× of the final concentration for dose response curves. Compounds are then diluted 1:100 in assay medium to 5× of the final concentration. 10 μl/well of diluted compounds are added to the assay plate and incubated for 15 minutes at 37° C. Thereafter CXCL12/SDF1-α is diluted in assay medium to 5× of the final concentration (its EC80 value for receptor activation) and 10 μl/well are added to the assay plate. The agonist leads to activation of the receptor and therefore to b-arrestin recruitment. Compounds acting as antagonists reduce this activation. The plate is incubated for 22 hrs at 37° C. 10 μl/well of detection reagent (LiveBLAzer™-FRET BIG (CCF4-AM) substrate) is transferred to the assay plate and the plate is incubated for 2 hours at room temperature protected from light. Fluorescent counts are determined (Scan1: Ex 409/20 nm, Em 460/30 nm, Scan 2: Ex 409/20 nm, Em 530/30 nm). The calculated emission ratio is used for IC50 determination. The calculated $IC_{50}$ values may fluctuate depending on the daily cellular assay performance. Fluctuations of this kind are known to those skilled in the art. Average $IC_{50}$ values from several measurements are given as geometric mean values.

TABLE 7

| Example Nr | $IC_{50}$ [nmol/l] |
|---|---|
| 1.001 | 1 |
| 1.001a | 0.3 |
| 1.001b | 302 |
| 1.002 | 2 |
| 1.002a | 359 |
| 1.002b | 1 |
| 1.003 | 564 |
| 1.004 | 764 |
| 1.005 | 198 |
| 1.006 | 414 |
| 1.007 | 780 |
| 1.008 | 394 |
| 1.009 | 66 |
| 1.01 | 82 |
| 1.011 | 282 |
| 1.012 | 58 |
| 1.013 | 238 |
| 1.014 | 289 |
| 1.015 | 429 |
| 1.016 | 275 |
| 1.017 | 489 |
| 1.018 | 317 |
| 1.019 | 145 |
| 1.02 | 198 |
| 1.021 | 282 |
| 1.022 | 198 |
| 1.023 | 743 |
| 1.024 | 118 |
| 1.025 | 51 |
| 1.026 | 627 |
| 1.027 | 117 |
| 1.028 | 916 |
| 1.029 | 315 |
| 1.03 | 201 |
| 1.031 | 855 |
| 1.032 | 154 |
| 1.033 | 591 |
| 1.034 | 772 |
| 1.035 | 520 |
| 1.036 | 693 |
| 1.037 | 295 |
| 1.038 | 490 |
| 1.039 | 492 |
| 1.04 | 7 |
| 1.041 | 91 |
| 1.042 | 532 |
| 1.043 | 843 |
| 1.044 | 556 |
| 1.045 | 565 |
| 1.046a | 474 |
| 1.047 | 127 |
| 1.048 | 275 |
| 1.049 | 10 |
| 1.05 | 223 |
| 1.051 | 49 |
| 1.052 | 630 |
| 1.053 | 703 |
| 1.054 | 311 |
| 1.055 | 232 |
| 1.056 | 4 |
| 1.057 | 1 |
| 1.058 | 1 |
| 1.059 | 140 |
| 1.06 | 727 |
| 1.061 | 49 |
| 1.062 | 16 |
| 1.063 | 107 |
| 1.064 | 968 |
| 1.065 | 567 |
| 1.066 | 16 |
| 1.067 | 319 |
| 1.068 | 512 |
| 1.069 | 556 |
| 1.07 | 559 |
| 1.071 | 4 |
| 1.072 | 32 |
| 1.073 | 118 |
| 1.074 | 9 |
| 1.075 | 44 |
| 1.076 | 604 |
| 1.077 | 443 |
| 1.078 | 193 |
| 1.079 | 510 |
| 1.08 | 564 |
| 1.081 | 118 |
| 1.082 | 445 |
| 1.083 | 76 |
| 1.084 | 223 |
| 1.085 | 268 |
| 1.086 | 154 |
| 1.087 | 943 |
| 1.088 | 244 |
| 1.089 | 472 |
| 1.09 | 35 |
| 1.091 | 103 |
| 1.092 | 1 |
| 1.093 | 867 |
| 1.094 | 100 |
| 1.095 | 254 |
| 1.095a | 129 |
| 1.096 | 667 |
| 1.097 | 442 |
| 1.098 | 276 |
| 1.099 | 131 |
| 1.1 | 128 |
| 1.101 | 45 |
| 1.102 | 111 |
| 1.103 | 274 |
| 1.104 | 964 |
| 1.105 | 430 |
| 1.106 | 248 |
| 1.107 | 520 |
| 1.108 | 581 |
| 1.109 | 902 |
| 1.11 | 535 |
| 1.111 | 332 |
| 1.111a | 944 |
| 1.111b | 114 |
| 1.112 | 227 |
| 1.113 | 118 |
| 1.113a | 561 |

TABLE 7-continued

| Example Nr | IC$_{50}$ [nmol/l] |
|---|---|
| 1.113b | 48 |
| 1.114 | 626 |
| 1.115 | 566 |
| 1.116 | 614 |
| 1.117 | 68 |
| 1.117a | 39 |
| 1.118 | 36 |
| 1.118a | 75 |
| 1.119 | 146 |
| 1.12 | 789 |
| 1.121 | 4 |
| 1.121a | 742 |
| 1.121b | 2 |
| 1.122 | 10 |
| 1.122a | 525 |
| 1.122b | 17 |
| 1.123 | 15 |
| 1.123a | 4 |
| 1.124 | 16 |
| 1.125 | 81 |
| 1.125a | 30 |
| 1.126 | 49 |
| 1.127 | 360 |
| 1.128 | 124 |
| 1.129 | 105 |
| 1.129a | 647 |
| 1.129b | 35 |
| 1.13 | 140 |
| 1.131 | 102 |
| 1.132 | 410 |
| 1.133 | 594 |
| 1.134 | 266 |
| 1.135 | 592 |
| 1.136 | 202 |
| 1.137 | 919 |
| 1.138 | 816 |
| 1.138a | 437 |
| 1.138b | 83 |
| 1.139 | 50 |
| 1.139a | 790 |
| 1.139b | 29 |
| 1.14 | 358 |
| 1.141 | 379 |
| 1.142 | 472 |
| 1.143 | 719 |
| 1.144 | 178 |
| 1.145 | 363 |
| 1.146 | 904 |
| 1.147 | 443 |
| 1.148 | 769 |
| 1.149 | 276 |
| 1.15 | 155 |
| 1.151 | 554 |
| 1.152 | 569 |
| 1.153 | 803 |
| 1.154 | 54 |
| 1.154a | 46 |
| 1.155 | 315 |
| 1.156 | 92 |
| 1.156a | 19 |
| 1.157 | 131 |
| 1.158 | 82 |
| 1.159 | 818 |
| 1.16 | 526 |
| 1.161 | 105 |
| 1.162 | 638 |
| 1.163 | 953 |
| 1.164 | 267 |
| 1.165 | 92 |
| 1.165a | 43 |
| 1.165b | 537 |
| 1.166 | 52 |
| 1.167 | 134 |
| 1.168 | 728 |
| 1.169 | 5 |
| 1.17 | 16 |
| 1.170a | 33 |

TABLE 7-continued

| Example Nr | IC$_{50}$ [nmol/l] |
|---|---|
| 1.171 | 16 |
| 1.171a | 7 |
| 1.171b | 446 |
| 1.172 | 72 |
| 1.173 | 110 |
| 1.174 | 36 |
| 1.175 | 673 |
| 1.176 | 6 |
| 1.176a | 5 |
| 1.177 | 5 |
| 1.178 | 7 |
| 1.179 | 50 |
| 1.18 | 235 |
| 1.181 | 104 |
| 1.182 | 218 |
| 1.183 | 79 |
| 1.184 | 3 |
| 1.185 | 9 |
| 1.186 | 37 |
| 1.187a | 410 |
| 1.187b | 981 |
| 1.187c | 3 |
| 1.187d | 353 |
| 1.188a | 3 |
| 1.188b | 519 |
| 1.188c | 179 |
| 1.188d | 362 |
| 1.189 | 36 |
| 1.189a | 15 |
| 1.19 | 294 |
| 1.191 | 186 |
| 1.192 | 389 |
| 1.192a | 854 |
| 1.192b | 122 |
| 1.193 | 191 |
| 1.193a | 97 |
| 1.194a | 13 |
| 1.195 | 759 |
| 1.196 | 575 |
| 1.197 | 11 |
| 1.198 | 52 |
| 1.199 | 273 |
| 2.001 | 209 |
| 2.002 | 670 |
| 2.003 | 34 |
| 2.004 | 118 |
| 2.005 | 25 |
| 2.006 | 15 |
| 2.007 | 88 |
| 2.008 | 405 |
| 2.009 | 10 |
| 2.01 | 42 |
| 2.011 | 114 |
| 2.013 | 28 |
| 2.014 | 269 |
| 2.015 | 54 |
| 2.016 | 80 |
| 2.016a | 49 |
| 2.016b | 63 |
| 2.017 | 73 |
| 2.018 | 145 |
| 2.019 | 126 |
| 2.019a | 44 |
| 2.02 | 248 |
| 2.021 | 293 |
| 2.022 | 155 |
| 2.023 | 37 |
| 2.023a | 9 |
| 2.023b | 26 |
| 2.024 | 101 |
| 2.025 | 435 |
| 2.026 | 249 |
| 2.027 | 745 |
| 2.028 | 60 |
| 2.029 | 60 |
| 2.03 | 74 |
| 2.031 | 558 |

TABLE 7-continued

| Example Nr | IC$_{50}$ [nmol/l] |
|---|---|
| 2.032 | 192 |
| 2.033 | 132 |
| 2.034 | 87 |
| 2.035 | 121 |
| 2.036 | 165 |
| 2.037 | 161 |
| 2.038 | 99 |
| 2.039 | 83 |
| 2.04 | 475 |
| 2.045 | 114 |
| 2.046 | 16 |
| 2.047 | 145 |
| 2.048 | 501 |
| 2.049 | 709 |
| 2.05 | 15 |
| 2.051 | 42 |
| 2.052 | 267 |
| 2.053 | 26 |
| 2.054 | 138 |
| 2.055 | 49 |
| 2.056 | 48 |
| 2.057 | 50 |
| 2.058 | 347 |
| 2.059 | 169 |
| 2.06 | 4 |
| 2.061 | 41 |
| 2.062 | 23 |
| 2.062a | 298 |
| 2.062b | 14 |
| 2.063 | 219 |
| 2.064 | 84 |
| 2.065 | 1 |
| 2.066 | 359 |
| 2.067 | 18 |
| 2.068 | 12 |
| 2.069 | 6 |
| 2.07 | 11 |
| 2.071 | 8 |
| 2.072 | 1 |
| 2.073 | 20 |
| 2.074 | 25 |
| 2.075 | 554 |
| 2.076 | 71 |
| 2.077 | 112 |
| 2.078 | 72 |
| 2.079 | 38 |
| 2.08 | 311 |
| 2.081 | 118 |
| 2.082 | 342 |
| 2.083 | 777 |
| 2.084 | 8 |
| 2.085 | 179 |
| 2.086 | 111 |
| 2.087 | 84 |
| 2.088 | 45 |
| 2.089 | 975 |
| 2.09 | 3 |
| 2.091 | 62 |
| 2.092 | 95 |
| 2.093 | 26 |
| 2.094 | 2 |
| 2.095 | 18 |
| 2.096 | 634 |
| 2.097 | 650 |
| 2.098 | 94 |
| 2.099 | 343 |
| 2.1 | 396 |
| 2.101 | 29 |
| 2.102 | 411 |
| 2.103 | 4 |
| 2.104 | 195 |
| 2.105 | 60 |
| 2.106 | 13 |
| 2.107 | 114 |
| 2.108 | 3 |
| 3.001 | 965 |
| 3.002 | 435 |

TABLE 7-continued

| Example Nr | IC$_{50}$ [nmol/l] |
|---|---|
| 3.003 | 105 |
| 3.003a | 771 |
| 3.003b | 54 |
| 3.004 | 338 |
| 3.005 | 38 |
| 3.006 | 108 |
| 3.007 | 162 |
| 3.009 | 286 |
| 3.01 | 69 |
| 3.011 | 22 |
| 3.012 | 26 |
| 3.013 | 153 |
| 3.014 | 158 |
| 3.015 | 170 |
| 3.016 | 105 |
| 3.016a | 90 |
| 3.017 | 661 |
| 3.018 | 198 |
| 3.019 | 778 |
| 3.020a | 271 |
| 3.020b | 4 |
| 3.021 | 40 |
| 3.022 | 28 |
| 3.022a | 25 |
| 4.001 | 133 |
| 4.002 | 60 |
| 4.003 | 333 |
| 4.004 | 319 |
| 4.005 | 388 |
| 4.006 | 149 |
| 4.007 | 52 |
| 4.008 | 150 |
| 4.009 | 573 |
| 4.01 | 6 |
| 4.011 | 43 |
| 4.012 | 49 |
| 4.013 | 145 |
| 4.014 | 363 |
| 4.015 | 783 |
| 4.016 | 463 |
| 4.017 | 114 |
| 4.018 | 343 |
| 4.019 | 151 |
| 4.02 | 222 |
| 4.021 | 126 |
| 4.022 | 369 |
| 4.023 | 69 |
| 4.024 | 56 |
| 4.025 | 439 |
| 4.026 | 15 |
| 4.027 | 8 |
| 4.028 | 32 |
| 4.029 | 2 |
| 4.03 | 1 |
| 4.031 | 4 |
| 4.032 | 3 |
| 4.033 | 0.3 |
| 4.034 | 255 |
| 4.035 | 56 |
| 4.036 | 127 |
| 4.037 | 280 |
| 4.038 | 522 |
| 4.039 | 393 |
| 4.04 | 86 |
| 4.041 | 96 |
| 4.042 | 74 |
| 4.043 | 158 |
| 4.044 | 75 |
| 4.045 | 164 |
| 4.046 | 290 |
| 4.047 | 318 |
| 4.048 | 247 |
| 4.049 | 148 |
| 4.05 | 21 |
| 4.051 | 356 |
| 4.052 | 24 |
| 4.053 | 1 |

TABLE 7-continued

| Example Nr | IC$_{50}$ [nmol/l] |
|---|---|
| 4.054 | 1 |
| 4.055 | 16 |
| 4.056 | 64 |
| 4.057 | 13 |
| 4.058 | 90 |
| 4.059 | 61 |
| 4.06 | 60 |
| 4.061 | 1 |
| 4.062 | 141 |
| 4.063 | 142 |
| 4.064 | 753 |
| 4.065 | 14 |
| 4.066 | 320 |
| 4.067a | 20 |
| 4.067b | 2 |
| 4.068 | 1 |
| 4.069 | 153 |
| 4.07 | 73 |
| 4.071 | 212 |
| 4.072 | 16 |
| 4.072a | 8 |
| 4.073 | 173 |
| 4.074 | 27 |
| 4.075 | 2 |
| 4.076 | 97 |
| 4.077 | 4 |
| 4.078 | 64 |
| 4.078b | 15 |
| 4.079a | 186 |
| 4.079b | 18 |
| 4.08 | 46 |
| 4.080a | 851 |
| 4.080b | 15 |
| 4.081 | 426 |
| 4.082 | 20 |
| 4.083 | 11 |
| 4.084 | 232 |
| 4.084b | 77 |
| 4.085 | 61 |
| 4.086 | 472 |
| 4.087 | 342 |
| 4.088 | 138 |
| 4.089 | 299 |
| 4.09 | 34 |
| 4.091 | 134 |
| 4.092 | 126 |
| 4.093 | 165 |
| 4.094 | 201 |
| 4.095 | 57 |
| 4.096 | 33 |
| 4.097 | 80 |
| 4.098 | 18 |
| 4.098a | 12 |
| 4.099 | 852 |
| 4.1 | 159 |
| 4.101 | 71 |
| 4.101a | 18 |
| 4.101b | 712 |
| 4.102 | 1 |
| 5.001 | 368 |
| 5.002 | 857 |
| 7.001 | 32 |
| 7.002 | 308 |
| 7.003 | 210 |
| 7.004 | 64 |
| 7.005 | 36 |
| 7.006 | 8 |
| 7.007 | 140 |
| 7.008 | 51 |
| 7.009 | 240 |
| 7.01 | 60 |
| 7.011 | 78 |
| 7.012 | 356 |
| 7.013 | 252 |
| 7.014 | 629 |
| 7.015 | 201 |
| 7.016 | 2 |
| BB 1.01c | 206 |
| BB 1.18c | 119 |

Compounds of the present invention may be further characterized with regard to their general pharmacokinetic and pharmacological properties using conventional assays well known in the art; for example relating to their bioavailability in different species (such as rat or dog); or for their properties with regard to drug safety and/or toxicological properties using conventional assays well known in the art, for example relating to cytochrome P450 enzyme inhibition and time dependent inhibition, pregnane X receptor (PXR) activation, glutathione binding, or phototoxic behavior.

The invention claimed is:

1. A compound of formula (I)

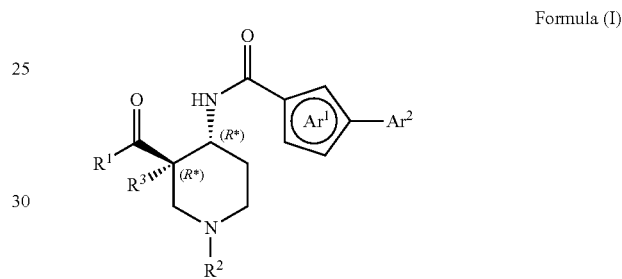

Formula (I)

wherein
the two substituents of the piperidine ring: $R^1$—CO— and —NH—CO—$Ar^1$—$Ar^2$, are in relative trans-configuration;
$Ar^1$ represents an unsubstituted 5-membered heteroarylene group containing one sulfur ring atom and one or two nitrogen ring atoms, wherein the —NH—CO— group and $Ar^2$ are attached in meta arrangement to ring atoms of $Ar^1$;
$Ar^2$ represents phenyl, or 6-membered heteroaryl; wherein said phenyl or 6-membered heteroaryl independently is mono-, di- or tri-substituted, wherein the substituents are independently selected from fluoro, chloro, methyl, cyano, methoxy, or $(C_1)$fluoroalkyl;
$R^1$ represents $R^{N1}R^{N2}N$—, wherein
  $R^{N1}$ represents
    hydrogen;
    $(C_{1-6})$alkyl;
    $(C_{1-6})$alkyl which is mono-substituted with
      hydroxy;
      $(C_{1-3})$alkoxy;
      2-hydroxy-ethoxy;
      —CO—NH$_2$;
      —SO$_2$—$(C_{1-3})$alkyl;
      cyano;
      $(C_{1-3})$fluoroalkoxy;
      —NR$^{N3}$R$^{N4}$, wherein R$^{N3}$ and R$^{N4}$ independently represent hydrogen or $(C_{1-4})$alkyl;
    $(C_{2-6})$alkynyl;
    $(C_{2-5})$fluoroalkyl;
    $(C_{1-4})$alkoxy;
    2-(2-oxo-pyrrolidin-1-yl)-ethyl;
    a group -L$^1$-Cy$^1$; wherein L¹ represents a direct bond, —(C₁₋₃)alkylene-, or —(C₃₋₅)cycloalkylene-; and Cy¹ represents (C₃₋₆)cycloalkyl, wherein said (C₃₋₆)cycloalkyl optionally contains one ring oxygen atom; wherein said (C₃₋₆)cycloalkyl independently is unsubstituted; or mono-substituted with fluoro, methyl, or hydroxy, —CO—(C₁₋₄)alkoxy, or cyano; or di-substituted with fluoro, or tri-substituted with methyl and two fluoro;

a group -L²-Ar³, wherein

L² represents a direct bond, —(C₁₋₄)alkylene-; *—(C₃₋₅)cycloalkylene-(C₀₋₂)alkylene- wherein said (C₃₋₅)cycloalkylene optionally contains one ring oxygen atom, wherein the asterisk indicates the bond to which Ar³ is attached; *—(C₁₋₂)alkylene-(C₃₋₅)cycloalkylene- wherein said (C₃₋₅)cycloalkylene optionally contains one ring oxygen atom, wherein the asterisk indicates the bond to which Ar³ is attached;

or —(C₁₋₃)alkylene- which is mono-substituted with hydroxy, trifluoromethyl, or —CO—(C₁₋₄)alkoxy; and Ar³ represents phenyl, or 5- or 6-membered heteroaryl; wherein said phenyl or 5- or 6-membered heteroaryl independently is unsubstituted, or mono-, or di-substituted; wherein the substituents are independently selected from (C₁₋₄)alkyl, (C₁₋₄)alkoxy, halogen, hydroxy, (C₁₋₃)fluoroalkyl, or (C₁₋₃)fluoroalkoxy; wherein, in case Ar³ represents 6-membered heteroaryl which is pyridyl or pyrimidinyl, such pyridyl or pyrimidinyl may additionally be present in form of the respective N-oxide;

and R^N2 independently represents hydrogen, (C₁₋₄)alkyl, or (C₂₋₃)fluoroalkyl;

or R^N1 and R^N2 together with the nitrogen atom to which they are attached to form a 4- to 6-membered ring selected from azetidinyl, pyrrolidinyl or piperidinyl; each independently unsubstituted;

or mono-substituted with fluoro, methyl, or hydroxy;

or di-substituted with fluoro;

or mono-substituted with Ar⁴, wherein Ar⁴ represents phenyl, or 5- or 6-membered heteroaryl; wherein said phenyl or 5- or 6-membered heteroaryl independently is unsubstituted, or mono-, or di-substituted; wherein the substituents are independently selected from (C₁₋₄)alkyl, (C₁₋₄)alkoxy, halogen, (C₁₋₃)fluoroalkyl, or (C₁₋₃)fluoroalkoxy; or morpholinyl;

R² represents hydrogen;

(C₁₋₆)alkyl;

(C₂₋₆)alkyl which is mono-substituted with (C₁₋₃)alkoxy, or hydroxy;

(C₃₋₅)alkenyl;

cyano-methyl;

(C₂₋₃)fluoroalkyl;

(C₃₋₈)cycloalkyl-(C₀₋₃)alkyl; wherein the (C₃₋₈)cycloalkyl is unsubstituted, or mono- or di-substituted wherein the substituents are independently selected from (C₁₋₃)alkyl, fluoro, hydroxy, hydroxy-(C₁₋₃)alkyl, (C₁₋₃)alkoxy, or (C₁₋₃)fluoroalkyl;

thietan-3-yl;

(C₃₋₈)cycloalkenyl-(C₁₋₃)alkyl; or

Ar⁵—CH₂— wherein Ar⁵ represents phenyl, or 5- or 6-membered heteroaryl, wherein the phenyl or 5- or 6-membered heteroaryl independently is unsubstituted, or mono- or di-substituted wherein the substituents are independently selected from (C₁₋₄)alkyl, (C₁₋₄)alkoxy, halogen, (C₁₋₃)fluoroalkyl, or (C₁₋₃)fluoroalkoxy; and R³ represents hydrogen, or methyl;

or a pharmaceutically acceptable salt thereof.

2. The compound of formula (I) as defined for claim 1 which are also compounds of Formula (I_S), wherein the two substituents of the piperidine ring: R¹—CO— and —NH—CO—Ar¹—Ar², are in relative trans-configuration, wherein the absolute configuration of the two chiral carbon atoms in position 3 and 4 of the piperidine ring is (3S,4S):

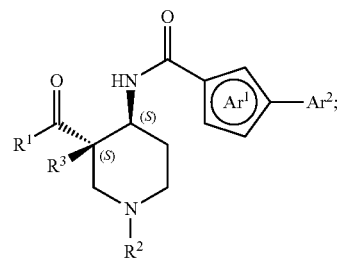

Formula (I_S)

or a pharmaceutically acceptable salt thereof.

3. The compound according to claim 2; wherein R³ represents hydrogen;

or a pharmaceutically acceptable salt thereof.

4. The compound according to claim 3; wherein Ar¹ represents [1,3,4]thiadiazol-2,5-diyl or isothiazol-3,5-diyl;

or a pharmaceutically acceptable salt thereof.

5. The compound according to claim 4; wherein Ar² represents phenyl which is mono-, di- or tri-substituted; wherein one or two of said substituents is/are independently selected from fluoro, chloro, and methyl, and the remaining, if present, is/are fluoro;

or a pharmaceutically acceptable salt thereof.

6. The compound according to claim 1; wherein R¹ represents R^N1R^N2N—, wherein

R^N1 represents (C₁₋₆)alkyl;

(C₁₋₆)alkyl which is mono-substituted with hydroxy;

(C₁₋₃)alkoxy;

2-hydroxy-ethoxy;

—CO—NH₂;

—SO₂—(C₁₋₃)alkyl;

cyano;

(C₁₋₃)fluoroalkoxy;

—NR^N3R^N4, wherein R^N3 and R^N4 independently represent hydrogen or (C₁₋₄)alkyl;

(C₂₋₆)alkynyl;

(C₂₋₅)fluoroalkyl;

2-(2-oxo-pyrrolidin-1-yl)-ethyl;

a group -L¹-Cy¹; wherein

L¹ represents a direct bond, —(C₁₋₃)alkylene-, or —(C₃₋₅)cycloalkylene-; and

Cy¹ represents (C₃₋₆)cycloalkyl, wherein said (C₃₋₆)cycloalkyl optionally contains one ring oxygen atom; wherein said (C₃₋₆)cycloalkyl independently is unsubstituted; or mono-substituted with fluoro, methyl, hydroxy, CO—$(C_{1-4})$alkoxy, or cyano; or di-substituted with fluoro, or tri-substituted with methyl and two fluoro;

a group -$L^2$-$Ar^3$, wherein
$L^2$ represents a —$(C_{1-4})$alkylene-; —$(C_{3-5})$cycloalkylene- wherein said $(C_{3-5})$cycloalkylene optionally contains one ring oxygen atom; *—$(C_{3-5})$cycloalkylene-$(C_{1-2})$alkylene- wherein said $(C_{3-5})$cycloalkylene optionally contains one ring oxygen atom, wherein the asterisk indicates the bond to which $Ar^3$ is attached; *—$(C_{1-2})$alkylene-$(C_{3-5})$cycloalkylene- wherein said $(C_{3-5})$cycloalkylene optionally contains one ring oxygen atom, wherein the asterisk indicates the bond to which $Ar^3$ is attached;
or —$(C_{1-3})$alkylene- which is mono-substituted with hydroxy or trifluoromethyl; and
$Ar^3$ represents phenyl, or 5-membered heteroaryl containing one oxygen atom and one or two nitrogen atoms, or 6-membered heteroaryl containing one or two nitrogen atoms; wherein said phenyl or 5- or 6-membered heteroaryl independently is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; wherein, in case $Ar^3$ represents 6-membered heteroaryl which is pyridyl or pyrimidinyl, such pyridyl or pyrimidinyl may additionally be present in form of the respective N-oxide;

and $R^{N2}$ independently represents hydrogen, or $(C_{1-4})$alkyl;
or a pharmaceutically acceptable salt thereof.

7. The compound according to claim 1; wherein $R^1$ represents $R^{N1}R^{N2}N$—, wherein
$R^{N1}$ represents
$(C_{3-6})$cycloalkyl, wherein said $(C_{3-6})$cycloalkyl optionally contains one ring oxygen atom; wherein said $(C_{3-6})$cycloalkyl independently is unsubstituted, or mono-substituted with fluoro, methyl, or hydroxy, or di-substituted with fluoro, or tri-substituted with methyl and two fluoro;
$(C_{3-6})$cycloalkyl-$(C_{1-3})$alkylene-, wherein said $(C_{3-6})$cycloalkyl optionally contains one ring oxygen atom;
$(C_{3-6})$cycloalkyl-$(C_{3-5})$cycloalkylene-;
phenyl-$(C_{1-4})$alkylene- wherein said phenyl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy;
phenyl-$(C_{1-3})$alkylene- wherein said —$(C_{1-3})$alkylene- is mono-substituted with hydroxy;
phenyl-$(C_{3-5})$cycloalkylene-; wherein said $(C_{3-5})$cycloalkylene optionally contains one ring oxygen atom, and wherein said phenyl is unsubstituted, or mono-, or di-substituted; wherein the substituents are independently selected from $(C_{1-4})$alkyl, $(C_{1-4})$alkoxy, halogen, hydroxy, $(C_{1-3})$fluoroalkyl, or $(C_{1-3})$fluoroalkoxy;
phenyl-$(C_{3-5})$cycloalkylene-$(C_{1-2})$alkylene- wherein said $(C_{3-5})$cycloalkylene optionally contains one ring oxygen atom, and wherein said phenyl is unsubstituted, or mono-substituted with halogen;
phenyl-$(C_{1-2})$alkylene-$(C_{3-5})$cycloalkylene- wherein said $(C_{3-5})$cycloalkylene optionally contains one ring oxygen atom;
5-membered heteroaryl-$(C_{1-3})$alkylene-, wherein said 5-membered heteroaryl contains one oxygen atom and one or two nitrogen atoms; and wherein said 5-membered heteroaryl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy;
6-membered heteroaryl-$(C_{1-4})$alkylene-, wherein said 6-membered heteroaryl contains one or two nitrogen atoms; and wherein said 6-membered heteroaryl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; wherein, in case $Ar^3$ represents pyridyl or pyrimidinyl, such pyridyl or pyrimidinyl may additionally be present in form of the respective N-oxide;
6-membered heteroaryl-$(C_{1-3})$alkylene-, wherein said —$(C_{1-3})$alkylene- is mono-substituted with hydroxy or trifluoromethyl; wherein said 6-membered heteroaryl contains one or two nitrogen atoms; or
6-membered heteroaryl-$(C_{3-5})$cycloalkylene-, wherein said 6-membered heteroaryl contains one or two nitrogen atoms; and wherein said 6-membered heteroaryl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; wherein, in case $Ar^3$ represents pyridyl or pyrimidinyl, such pyridyl or pyrimidinyl may additionally be present in form of the respective N-oxide;
6-membered heteroaryl-$(C_{3-5})$cycloalkylene-$(C_{1-2})$alkylene- wherein said 6-membered heteroaryl contains one or two nitrogen atoms; and wherein said 6-membered heteroaryl is unsubstituted;
and $R^{N2}$ independently represents hydrogen, or $(C_{1-4})$alkyl;
or $R^{N1}$ represents $(C_{1-3})$alkyl; and $R^{N2}$ represents hydrogen, or methyl;
or a pharmaceutically acceptable salt thereof.

8. The compound according to claim 5; wherein $R^1$ represents $R^{N1}R^{N2}N$—, wherein
$R^{N1}$ represents
$(C_{3-6})$cycloalkyl-$(C_{1-3})$alkylene-, wherein said $(C_{3-6})$ cycloalkyl optionally contains one ring oxygen atom;
phenyl-$(C_{1-4})$alkylene- wherein said phenyl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy;
phenyl-$(C_{3-5})$cycloalkylene- wherein said $(C_{3-5})$cycloalkylene optionally contains one ring oxygen atom, and wherein said phenyl is unsubstituted, or mono-, or di-substituted; wherein the substituents are independently selected from $(C_{1-4})$alkyl, $(C_{1-4})$alkoxy, halogen, hydroxy, $(C_{1-3})$fluoroalkyl, or $(C_{1-3})$fluoroalkoxy;
6-membered heteroaryl-$(C_{1-4})$alkylene-, wherein said 6-membered heteroaryl contains one or two nitrogen atoms; and wherein said 6-membered heteroaryl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; wherein, in case $Ar^3$ represents pyridyl or pyrimidinyl, such pyridyl or pyrimidinyl may additionally be present in form of the respective N-oxide;

6-membered heteroaryl-$(C_{3-5})$cycloalkylene-, wherein said 6-membered heteroaryl contains one or two nitrogen atoms; and wherein said 6-membered heteroaryl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; wherein, in case $Ar^3$ represents pyridyl or pyrimidinyl, such pyridyl or pyrimidinyl may additionally be present in form of the respective N-oxide;

and $R^{N2}$ independently represents hydrogen, or $(C_{1-4})$alkyl; or a pharmaceutically acceptable salt thereof.

9. The compound according to claim 5; wherein $R^1$ represents $R^{N1}R^{N2}N$—, wherein $R^{N1}$ represents 6-membered heteroaryl-$(C_{1-4})$alkylene-, wherein said 6-membered heteroaryl contains one or two nitrogen atoms; and wherein said 6-membered heteroaryl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; wherein, in case $Ar^3$ represents pyridyl or pyrimidinyl, such pyridyl or pyrimidinyl may additionally be present in form of the respective N-oxide;

6-membered heteroaryl-$(C_{3-5})$cycloalkylene-, wherein said 6-membered heteroaryl contains one or two nitrogen atoms; and wherein said 6-membered heteroaryl is unsubstituted, or mono-, or di-substituted; wherein the substituents are independently selected from $(C_{1-4})$alkyl, $(C_{1-4})$alkoxy, halogen, $(C_{1-3})$fluoroalkyl, or $(C_{1-3})$fluoroalkoxy; wherein, in case $Ar^3$ represents pyridyl or pyrimidinyl, such pyridyl or pyrimidinyl may additionally be present in form of the respective N-oxide;

and $R^{N2}$ independently represents hydrogen or methyl; or a pharmaceutically acceptable salt thereof.

10. The compound according to claim 7; wherein $R^2$ represents $(C_{3-8})$cycloalkyl-$(C_{1-3})$alkyl, wherein the $(C_{3-8})$cycloalkyl is unsubstituted; or mono-substituted wherein the substituent is $(C_{1-3})$alkyl, fluoro, or $(C_{1-3})$fluoroalkyl; or di-substituted with fluoro; or $(C_{3-8})$cycloalkyl, wherein the $(C_{3-8})$cycloalkyl is unsubstituted, or mono- or di-substituted wherein the substituents are independently selected from $(C_{1-3})$alkyl, or fluoro;

or a pharmaceutically acceptable salt thereof.

11. The compound according to claim 8; wherein $R^2$ represents unsubstituted $(C_{3-8})$cycloalkyl-$(C_{1-3})$alkyl; or
unsubstituted $(C_{3-6})$cycloalkyl; or
$(C_{3-8})$cycloalkyl, wherein the $(C_{3-8})$cycloalkyl is di-substituted with fluoro; or
$(C_{3-8})$cycloalkyl-$(C_{1-3})$alkyl; wherein the $(C_{3-8})$cycloalkyl is mono-substituted with methyl, fluoro, or $(C_1)$ fluoroalkyl; or di-substituted with fluoro;
or a pharmaceutically acceptable salt thereof.

12. The compound according to claim 1 which is:
(3S,4S)-1-Cyclobutyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide;

(3S,4S)-4-{[5-(2,4-difluoro-phenyl)-[1,3,4]thiadiazole-2-carbonyl]-amino}-1-(1-fluoro-cyclopropylmethyl)-piperidine-3-carboxylic acid (1-pyrimidin-2-yl-cyclopropyl)-amide; or (3S,4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide; or a pharmaceutically acceptable salt thereof.

13. The compound according to claim 1 which is (3S, 4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide; or a pharmaceutically acceptable salt thereof.

14. The compound according to claim 1 which is (3S, 4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide; wherein said compound is in free form.

15. The compound according to claim 1 which is (3S, 4S)-1-Cyclopropylmethyl-4-{[5-(2,4-difluoro-phenyl)-[1,3,4]thiadiazole-2-carbonyl]-amino}-piperidine-3-carboxylic acid (1-pyrimidin-2-yl-cyclopropyl)-amide; wherein said compound is in pharmaceutically acceptable salt form.

16. A pharmaceutical composition comprising, as active principle, one or more compounds according to claim 1, or a pharmaceutically acceptable salt thereof, and at least one therapeutically inert excipient.

17. A pharmaceutical composition comprising, as active principle, one or more compounds according to claim 11, or a pharmaceutically acceptable salt thereof, and at least one therapeutically inert excipient.

18. A pharmaceutical composition comprising, as active principle, one or more compounds according to claim 12, or a pharmaceutically acceptable salt thereof, and at least one therapeutically inert excipient.

19. A pharmaceutical composition comprising, as active principle, one or more compounds according to claim 13, or a pharmaceutically acceptable salt thereof, and at least one therapeutically inert excipient.

20. A method for the treatment of cancer; comprising administering to a subject in need thereof an effective amount of a compound of formula (I) as defined in claim 11, or a pharmaceutically acceptable salt thereof.

21. A method of treating tumors comprising administering an effective amount of the compound of formula (Ia) according to claim 11, or a pharmaceutically acceptable salt thereof, wherein said effective amount leads to a change of tumor properties, and wherein said modification is achieved by modulating the CXCL11/CXCL12 receptor pathway.

22. A method for the treatment of fibrosis; comprising administering to a subject in need thereof an effective amount of a compound of formula (I) as defined in claim 11, or a pharmaceutically acceptable salt thereof.

23. A method for the treatment of autoimmune disorders which have an inflammatory component selected from inflammatory demyelinating diseases, multiple sclerosis (MS), Guillain Barré syndrome, rheumatoid arthritis (RA), inflammatory bowel disease (IBD), systemic lupus erythematosus (SLE), lupus nephritis, and auto-immune encephalomyelitis; comprising administering to a subject in need thereof an effective amount of a compound of formula (I) as defined in claim 11, or a pharmaceutically acceptable salt thereof.

24. A method for the treatment of inflammatory diseases selected from
   lung inflammatory diseases selected from asthma, chronic obstructive pulmonary disorder (COPD), and acute lung injury; and
   atherosclerosis;
comprising administering to a subject in need thereof an effective amount of a compound of formula (I) as defined in claim 11, or a pharmaceutically acceptable salt thereof.

25. A method for the treatment of cancer; comprising administering to a subject in need thereof an effective amount of a compound of formula (I) as defined in claim 13, or a pharmaceutically acceptable salt thereof.

26. A method of treating tumors comprising administering an effective amount of the compound of claim 13, or a pharmaceutically acceptable salt thereof, wherein said effective amount leads to a change of tumor properties, and wherein said modification is achieved by modulating the CXCL11/CXCL12 receptor pathway.

27. A method for the treatment of fibrosis; comprising administering to a subject in need thereof an effective amount of a compound of formula (I) as defined in claim 13, or a pharmaceutically acceptable salt thereof.

28. A method for the treatment of autoimmune disorders which have an inflammatory component selected from inflammatory demyelinating diseases, multiple sclerosis (MS), Guillain Barré syndrome, rheumatoid arthritis (RA), inflammatory bowel disease (IBD), systemic lupus erythematosus (SLE), lupus nephritis, and auto-immune encephalomyelitis; comprising administering to a subject in need thereof an effective amount of a compound of formula (I) as defined in claim 13, or a pharmaceutically acceptable salt thereof.

29. A method for the treatment of inflammatory diseases selected from
   lung inflammatory diseases selected from asthma, chronic obstructive pulmonary disorder (COPD), and acute lung injury; and
   atherosclerosis;
comprising administering to a subject in need thereof an effective amount of a compound of formula (I) as defined in claim 13, or a pharmaceutically acceptable salt thereof.

\* \* \* \* \*